(12) United States Patent
Shipps, Jr. et al.

(10) Patent No.: US 9,206,142 B2
(45) Date of Patent: *Dec. 8, 2015

(54) ANILINOPIPERAZINE DERIVATIVES AND METHODS OF USE THEREOF

(75) Inventors: Gerald W. Shipps, Jr., Stoneham, MA (US); Cliff C. Cheng, Cambridge, MA (US); Xiaohua Huang, Malden, MA (US); Thierry O. Fischmann, Scotch Plains, NJ (US); Jose S. Duca, Cranford, NJ (US); Matthew Richards, Somerville, MA (US); Hongbo Zeng, Westford, MA (US); Binyuan Sun, Chestnut Hill, MA (US); Panduranga Adulla Reddy, Walpole, MA (US); Tzu T. Wong, Belmont, MA (US); Praveen K. Tadikonda, Norwood, MA (US); M. Arshad Siddiqui, Newton, MA (US); Marc A. Labroli, Moorestown, NJ (US); Cory S. Poker, Bridgewater, NJ (US); Timothy J. Guzi, Sudbury, MA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 1974 days.

This patent is subject to a terminal disclaimer.

(21) Appl. No.: 12/447,712

(22) PCT Filed: Oct. 29, 2007

(86) PCT No.: PCT/US2007/022829
§ 371 (c)(1),
(2), (4) Date: Jan. 26, 2010

(87) PCT Pub. No.: WO2008/054702
PCT Pub. Date: May 8, 2008

(65) Prior Publication Data
US 2012/0328691 A1    Dec. 27, 2012

Related U.S. Application Data

(60) Provisional application No. 60/855,654, filed on Oct. 31, 2006.

(51) Int. Cl.
| | | |
|---|---|---|
| *C07D 401/14* | (2006.01) | |
| *C07D 403/14* | (2006.01) | |
| *C07D 413/14* | (2006.01) | |
| *A61K 31/5355* | (2006.01) | |
| *A61K 31/496* | (2006.01) | |
| *C07D 277/56* | (2006.01) | |
| *C07D 417/04* | (2006.01) | |
| *C07D 417/12* | (2006.01) | |
| *C07D 417/14* | (2006.01) | |
| *C07D 471/10* | (2006.01) | |

(52) U.S. Cl.
CPC ............ *C07D 277/56* (2013.01); *C07D 417/04* (2013.01); *C07D 417/12* (2013.01); *C07D 417/14* (2013.01); *C07D 471/10* (2013.01)

(58) Field of Classification Search
CPC .. C07D 277/56; C07D 417/04; C07D 417/12; C07D 417/14
USPC ................................................ 514/235.8, 365
See application file for complete search history.

(56) References Cited

U.S. PATENT DOCUMENTS

| | | | |
|---|---|---|---|
| 6,107,305 A | 8/2000 | Misra et al. | |
| 6,413,974 B1 | 7/2002 | Dumont et al. | |
| 8,318,735 B2 * | 11/2012 | Shipps et al. | 514/235.8 |

FOREIGN PATENT DOCUMENTS

| | | |
|---|---|---|
| WO | WO 00/62778 | 10/2000 |
| WO | WO 02/10162 | 2/2002 |
| WO | WO 02/22610 | 3/2002 |
| WO | WO 03/097048 | 11/2003 |

(Continued)

OTHER PUBLICATIONS

F. Al-Khodairy, et al., "Identification and Characterization of New Elements Involved in Checkpoint and Feedback Controls in Fission Yeast", Molecular Biology of the Cell, vol. 5, pp. 147-160 (1994).

(Continued)

*Primary Examiner* — Barbara P Badio
*Assistant Examiner* — Sara E Townsley
(74) *Attorney, Agent, or Firm* — Richard S. Parr; Laura M. Ginkel

(57) ABSTRACT

The present invention relates to novel Anilinopiperazine Derivatives of Formula (I), compositions comprising the Anilinopiperazine Derivatives, and methods for using the Anilinopiperazine Derivatives for treating or preventing a proliferative disorder, cancer, an anti-proliferative disorder, inflammation, arthritis, a central nervous system disorder, a cardiovascular disease, alopecia, a neuronal disease, an ischemic injury, a viral disease, a fungal infection, or a disorder related to the activity of a protein kinase.

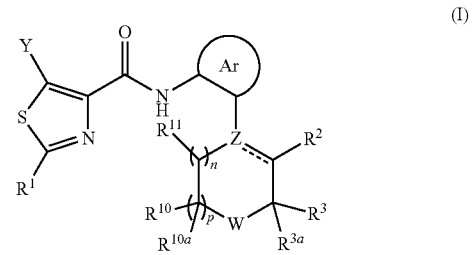

21 Claims, No Drawings

(56) References Cited

FOREIGN PATENT DOCUMENTS

| WO | WO 2004/039789 | | 5/2004 |
|---|---|---|---|
| WO | WO2005/003128 | * | 1/2005 |
| WO | WO 2006/081172 | | 8/2006 |
| WO | WO 2007/123269 | | 11/2007 |
| WO | WO 2008/106692 | | 9/2008 |

OTHER PUBLICATIONS

Stephen M. Berge, et al., "Pharmaceutical Salts", Journal of Pharmaceutical Sciences, vol. 66, No. 1, pp. 1-19 (1977).
Ann L. Bingham, et al., "Over one hundred solvates of sulfathiazole", Chem. Commun., pp. 603-604 (2001).
Carmen Birchmeier, et al., "Met, Metastasis, Motility and More", Nature Reviews, Molecular Cell Biology, vol. 4, pp. 915-925 (2003).
James R. Bischoff, et al., "A homologue of *Drosophila aurora* kinase is oncogenic and amplified in human colorectal cancers", The EMBO Journal, vol. 17, No. 11, pp. 3052-3065 (1998).
Joseph B. Bolen, "Nonreceptor tyrosine protein kinases", Oncogene, vol. 8, pp. 2025-2031 (1993).
Mino R. Caira, et al., "Preparation and Crystal Characterization of a Polymorph, a Monohydrate, and an Ethyl Acetate Solvate of the Antifungal Fluconazole", Journal of Pharmaceutical Sciences, vol. 93, No. 3, pp. 601-611 (2004).
Jagabandhu Das, et al., "2-Aminothiazole as a Novel Kinase Inhibitor Template. Structure—Activity Relationship Studies toward the Discovery of *N*-(2-Chloro-6-methylphenyl)-2-[[6-[4-(2-hydroxyethyl)-1-piperazinyl)]-2-methyl-4-pyrimidinyl]amino)]-1,3-thiazole-5-carboxamide (Dasatinib, BMS-354825) as a Potent *pan*-Src Kinase Inhibitor", J. Med. Chem., vol. 49, pp. 6819-6832 (2006).
Maria Deak, et al., "Mitogen- and stress-activated protein kinase-1 (MSK1) is directly activated by MAPK and SAPK2/p38, and may mediate activation of CREB", The EMBO Journal, vol. 17, No. 15, pp. 4426-4441 (1998).
Philip L. Gould, "Salt selection for basic drugs", International Journal of Pharmaceutics, vol. 33, pp. 201-217 (1986).
Tomoko Hosoi, et al., "Evidence for cdk5 as a Major Activity Phosphorylating Tau Protein in Porcine Brain Extract", J. Biochem. vol. 117, pp. 741-749 (1995).
Kyoung Soon Kim, et al., "Discovery of Aminothiazole Inhibitors of Cyclin-Dependent Kinase 2: Synthesis, X-ray Crystallographic Analysis, and Biological Activities", J. Med. Chem., vol. 45, pp. 3905-3927 (2002).
Masahi Kimura, et al., "Cell Cycle-dependent Expression and Spindle Pole Localization of a Novel Human Protein Kinase, Aik, Related to Aurora of *Drosophila* and Yeast Ipl1", The Journal of Biological Chemistry, vol. 272, No. 21, pp. 13766-13771 (1997).
Peter C. Maisonpierre, et al. "Angiopoietin-2, a Natural Antagonist for Tie2 that Disrupts in vivo Angiogenesis", Science, vol. 277, pp. 55-60 (1997).
Shuhei Matsuoka, et al., "Linkage of ATM to Cell Cycle Regulation by the CHk2 Protein Kinase", Science, vol. 282, pp. 1893-1897 (1998).
Laurent Meijer, et at., "Biochemical and cellular effects of roscovitine, a potent and selective inhibitor of the cyclin-dependent kinases cdc2, cdk2 and cdk5", Eur. J. Biochem, vol. 243, pp. 527-536 (1997).
Yvette Mettey, et al., "Aloisines, a New Family of CDK/GSK-3 Inhibitors. SAR Study, Crystal Structure in Complex with CDK2, Enzyme Selectivity, and Cellular Effects", J. Med. Chem. vol. 46, pp. 222-236 (2003).
Birgit Millauer, et al., "Dominant-Negative Inhibition of Flk-1 Suppresses the Growth of Many Tumor Types in Vivo", Cancer Research, vol. 56, pp. 1615-1620 (1996).

Moosa Mohammadi, et al., "Crystal structure of an angiogenesis inhibitor bound to the FGF receptor tyrosine kinase domain", The EMBO Journal, vol. 17, No. 20, pp. 5896-5904 (1998).
Paul Nurse, "Checkpoint Pathways Come of Age", Cell, vol. 91, pp. 865-867 (1997).
Rejane Paumelle, et al., "Hepatocyte growth factor/scatter factor activates the ETS1 transcription factor by a RAS-RAF-MEK-ERK signaling pathway", Oncogene, vol. 21, pp. 2309-2319 (2002).
Cheng-Yuan Peng, et al., "Mitotic and G2 Checkpoint Control: Regulation of 14-3-3 Protein Binding by Phosphorylation of Cdc25C on Serine-216", Science, vol. 277, pp. 1501-1505 (1997).
Gregory D. Plowman, "Receptor Tyrosine Kinases as Targets for Drug Intervention", DN&P, vol. 7, No. 6, pp. 334-339 (1994).
Jeremy Saklatvala, "The p38 MAP kinase pathway as a therapeutic target in inflammatory disease", Current Opinion in Pharmacology, vol. 4, pp. 372-377 (2004).
Yolanda Sanchez et al., "Conservation of the Chk1 Checkpoint Pathway in Mammals: Linkage of DNA Damage to Cdk Regulation Through Cdc25", Science, vol. 277, pp. 1497-1501 (1997).
Jill M. Schumacher, et al., "AIR-2: An Aurora/Ipl1-related Protein Kinase Associated with Chromosomes and Midbody Microtubules Is Required for Polar Body Extrusion and Cytokinesis in *Caenorhabditis elegans* Embryos", The Journal of Cell Biology, vol. 143, No. 6, pp. 1635-1646 (1998).
Adrian M. Senderowicz, et al. "Phase I Trial of Continuous Infusion Flavopiridol, a Novel Cyclin-Dependent Kinase Inhibitor, in Patients with Refractory Neoplasms", Journal of Clinical Oncology, vol. 16, No. 9, pp. 2986-2999 (1998).
Kate Petersen Shay, et al., "Pim-1 Kinase Stability is Regulated by Heat Shock Proteins and the Ubiquitin-Proteasome Pathway", Mol. Cancer Res., vol. 3, No. 3, pp. 170-181 (2005).
Yu Shi, et al., "In the Cellular Garden of Forking Paths: How p38 MAPKs Signal for Downstream Assistance", Biol. Chem., vol. 383, pp. 1519-1536 (2002).
Keisuke Shiroto, et al., "MK2-/-gene knockout mouse hearts carry anti-apoptotic signal and are resistant to ischemia reperfusion injury", Journal of Molecular and Cellular Cardiology, vol. 38, pp. 93-97 (2005).
P. Heinrich Stahl, et al., "Handbook of Pharmaceutical Salts—Properties, Selection, and Use", International Union of Pure and Applied Chemistry, 4 pages (2002).
Laurie M. Strawn, et al., "Flk-1 as a Target for Tumor Growth Inhibition", Cancer Research, vol. 56, pp. 3540-3545 (1996).
Elsa C. Van Tonder, et al., "Preparation and Physicochemical Characterization of 5 Niclosamide Solvates and 1 Hemisolvate", AAPS PharmSciTech, vol. 5, No. 1, Article 12 (2004).
Jaroslav Vesely, et al., "Inhibition of cyclin-dependent kinases by purine analogues", Eur. J. Biochem, vol. 224, pp. 771-786 (1994).
Nancy Walworth, et al., "Fission yeast chk1 protein kinase links the *rad* checkpoint pathway to *cdc2*", Nature, vol. 363, pp. 368-371 (1993).
Ted Weinert, "A DNA Damage Checkpoint Meets the Cell Cycle Engine", Science, vol. 277, No. 5331, pp. 1450-1451 (1997).
Hitoshi Yoshiji, et al., "Vascular Endothelial Growth Factor is Essential for Initial but not Continued in Vivo Growth of Human Breast Carcinoma Cells", Cancer Research, vol. 57, pp. 3924-3928 (1997).
Yan Zeng, et al., "Replication checkpoint requires phosphorylation of the phosphatase Cdc25 by Cds1 or Chk1", Nature, vol. 395, pp. 507-510 (1998).
Yu-Wein Zhang, et al., "HGF/SF-Met Signaling in the Control of Branching Morphogenesis and Invasion", Journal of Cellular Biochemistry, vol. 88, pp. 408-417 (2003).
PCT Written Opinion for corresponding International Application PCT/US2007/022829; (8 pages).
International Search Report for corresponding International Application PCT/US2007/022829, mailed Apr. 17, 2008 (6 pages).

* cited by examiner

ANILINOPIPERAZINE DERIVATIVES AND METHODS OF USE THEREOF

FIELD OF THE INVENTION

The present invention relates to novel Anilinopiperazine Derivatives, compositions comprising the Anilinopiperazine Derivatives, and methods for using the Anilinopiperazine Derivatives for treating or preventing a proliferative disorder, an anti-proliferative disorder, inflammation, arthritis, a central nervous system disorder, a cardiovascular disease, alopecia, a neuronal disease, an ischemic injury, a viral disease, a fungal infection, or a disorder related to the activity of a protein kinase.

BACKGROUND OF THE INVENTION

Protein kinases are a family of enzymes that catalyze phosphorylation of proteins, in particular the hydroxyl group of specific tyrosine, serine, or threonine residues in proteins. Protein kinases are pivotal in the regulation of a wide variety of cellular processes, including metabolism, cell proliferation, cell differentiation, and cell survival. Uncontrolled proliferation is a hallmark of cancer cells, and can be manifested by a deregulation of the cell division cycle in one of two ways—making stimulatory genes hyperactive or inhibitory genes inactive. Protein kinase inhibitors, regulators or modulators alter the function of kinases such as cyclin-dependent kinases (CDKs), mitogen activated protein kinase (MAPK/ERK), glycogen synthase kinase 3 (GSK3beta), Checkpoint (Chk) (e.g., CHK-1, CHK-2 etc.) kinases, AKT kinases, JNK, and the like. Examples of protein kinase inhibitors are described in WO02/22610 A1 and by Y. Mettey et al., in *J. Med. Chem.*, 46:222-236 (2003).

The cyclin-dependent kinases are serine/threonine protein kinases, which are the driving force behind the cell cycle and cell proliferation. Misregulation of CDK function occurs with high frequency in many important solid tumors. Individual CDK's, such as, CDK1, CDK2, CDK3, CDK4, CDK5, CDK6 and CDK7, CDK8 and the like, perform distinct roles in cell cycle progression and can be classified as either G1S, or G2M phase enzymes. CDK2 and CDK4 are of particular interest because their activities are frequently misregulated in a wide variety of human cancers. CDK2 activity is required for progression through G1 to the S phase of the cell cycle, and CDK2 is one of the key components of the G1 checkpoint. Checkpoints serve to maintain the proper sequence of cell cycle events and allow the cell to respond to insults or to proliferative signals, while the loss of proper checkpoint control in cancer cells contributes to tumorgenesis. The CDK2 pathway influences tumorgenesis at the level of tumor suppressor function (e.g. p52, RB, and p27) and oncogene activation (cyclin E). Many reports have demonstrated that both the coactivator, cyclin E, and the inhibitor, p27, of CDK2 are either over—or underexpressed, respectively, in breast, colon, nonsmall cell lung, gastric, prostate, bladder, non-Hodgkin's lymphoma, ovarian, and other cancers. Their altered expression has been shown to correlate with increased CDK2 activity levels and poor overall survival. This observation makes CDK2 and its regulatory pathways compelling targets for the development of cancer treatments.

A number of adenosine 5'-triphosphate (ATP) competitive small organic molecules as well as peptides have been reported in the literature as CDK inhibitors for the potential treatment of cancers. U.S. Pat. No. 6,413,974, col. 1, line 23-col. 15, line 10 offers a good description of the various CDKs and their relationship to various types of cancer. Flavopiridol (shown below) is a nonselective CDK inhibitor that is currently undergoing human clinical trials, A. M. Sanderowicz et al., *J. Clin. Oncol.* 16:2986-2999 (1998).

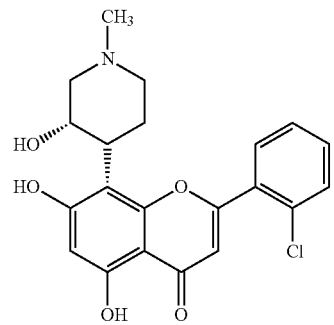

Other known inhibitors of CDKs include, for example, olomoucine (J. Vesely et al., *Eur. J. Biochem.*, 224:771-786 (1994)) and roscovitine (I. Meijer et al., *Eur. J. Biochem.*, 243:527-536 (1997)). U.S. Pat. No. 6,107,305 describes certain pyrazolo[3,4-b]pyridine compounds as CDK inhibitors. An illustrative compound from the '305 patent is:

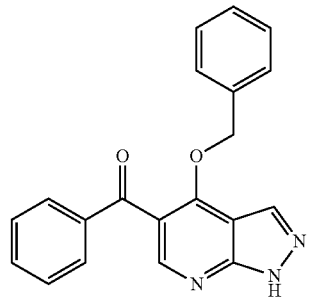 [SMILES: O=C(c1ccccc1)c1cnc2[nH]ncc2c1OCc1ccccc1]

K. S. Kim et al., *J. Med. Chem.* 45:3905-3927 (2002) and WO 02/10162 disclose certain aminothiazole compounds as CDK inhibitors.

Another series of protein kinases are those that play an important role as a checkpoint in cell cycle progression. Checkpoints prevent cell cycle progression at inappropriate times, such as in response to DNA damage, and maintain the metabolic balance of cells while the cell is arrested, and in some instances can induce apoptosis (programmed cell death) when the requirements of the checkpoint have not been met. Checkpoint control can occur in the G1 phase (prior to DNA synthesis) and in G2, prior to entry into mitosis.

One series of checkpoints monitors the integrity of the genome and, upon sensing DNA damage, these "DNA damage checkpoints" block cell cycle progression in $G_1$ & $G_2$ phases, and slow progression through S phase. This action enables DNA repair processes to complete their tasks before replication of the genome and subsequent separation of this genetic material into new daughter cells takes place. Inactivation of CHK1 has been shown to transduce signals from the DNA-damage sensory complex to inhibit activation of the cyclin B/Cdc2 kinase, which promotes mitotic entry, and abrogate G.sub.2 arrest induced by DNA damage inflicted by either anticancer agents or endogenous DNA damage, as well as result in preferential killing of the resulting checkpoint defective cells. See, e.g., Peng et al., *Science,* 277:1501-1505 (1997); Sanchez et al., *Science,* 277:1497-1501 (1997), Nurse, *Cell,* 91:865-867 (1997); Weinert, *Science,* 277:1450-

1451 (1997); Walworth et al., *Nature*, 363:368-371 (1993); and Al-Khodairy et al., *Molec. Biol. Cell.*, 5:147-160 (1994).

Selective manipulation of checkpoint control in cancer cells could afford broad utilization in cancer chemotherapeutic and radiotherapy regimens and may, in addition, offer a common hallmark of human cancer "genomic instability" to be exploited as the selective basis for the destruction of cancer cells. A number of factors place CHK1 as a pivotal target in DNA-damage checkpoint control. The elucidation of inhibitors of this and functionally related kinases such as CDS1/CHK2, a kinase recently discovered to cooperate with CHK1 in regulating S phase progression (see Zeng et al., *Nature*, 395:507-510 (1998); Matsuoka, *Science*, 282:1893-1897 (1998)), could provide valuable new therapeutic entities for the treatment of cancer.

Another group of kinases are the tyrosine kinases. Tyrosine kinases can be of the receptor type (having extracellular, transmembrane and intracellular domains) or the non-receptor type (being wholly intracellular). Receptor-type tyrosine kinases are comprised of a large number of transmembrane receptors with diverse biological activity. In fact, about 20 different subfamilies of receptor-type tyrosine kinases have been identified. One tyrosine kinase subfamily, designated the HER subfamily, is comprised of EGFR (HER1), HER2, HER3 and HER4. Ligands of this subfamily of receptors identified so far include epithelial growth factor, TGF-alpha, amphiregulin, HB-EGF, betacellulin and heregulin. Another subfamily of these receptor-type tyrosine kinases is the insulin subfamily, which includes INS-R, IGF-IR, IR, and IR-R. The PDGF subfamily includes the PDGF-alpha and beta receptors, CSFIR, c-kit and FLK-II. The FLK family is comprised of the kinase insert domain receptor (KDR), fetal liver kinase-1 (FLK-1), fetal liver kinase-4 (FLK-4) and the fms-like tyrosine kinase-1 (flt-1). For detailed discussion of the receptor-type tyrosine kinases, see Plowman et al., *DN&P* 7(6):334-339, 1994.

At least one of the non-receptor protein tyrosine kinases, namely, LCK, is believed to mediate the transduction in T-cells of a signal from the interaction of a cell-surface protein (Cd4) with a cross-linked anti-Cd4 antibody. A more detailed discussion of non-receptor tyrosine kinases is provided in Bolen, *Oncogene*, 8:2025-2031 (1993). The non-receptor type of tyrosine kinases is also comprised of numerous subfamilies, including Src, Frk, Btk, Csk, Abl, Zap70, Fes/Fps, Fak, Jak, Ack, and LIMK. Each of these subfamilies is further sub-divided into varying receptors. For example, the Src subfamily is one of the largest and includes Src, Yes, Fyn, Lyn, Lck, Blk, Hck, Fgr, and Yrk. The Src subfamily of enzymes has been linked to oncogenesis. For a more detailed discussion of the non-receptor type of tyrosine kinases, see Bolen, *Oncogene*, 8:2025-2031 (1993).

In addition to its role in cell-cycle control, protein kinases also play a crucial role in angiogenesis, which is the mechanism by which new capillaries are formed from existing vessels. When required, the vascular system has the potential to generate new capillary networks in order to maintain the proper functioning of tissues and organs. In the adult, however, angiogenesis is fairly limited, occurring only in the process of wound healing and neovascularization of the endometrium during menstruation. On the other hand, unwanted angiogenesis is a hallmark of several diseases, such as retinopathies, psoriasis, rheumatoid arthritis, age-related macular degeneration, and cancer (solid tumors). Protein kinases which have been shown to be involved in the angiogenic process include three members of the growth factor receptor tyrosine kinase family; VEGF-R2 (vascular endothelial growth factor receptor 2, also known as KDR (kinase insert domain receptor) and as FLK 1); FGF-R (fibroblast growth factor receptor); and TEK (also known as Tie-2).

VEGF-R2, which is expressed only on endothelial cells, binds the potent angiogenic growth factor VEGF and mediates the subsequent signal transduction through activation of its intracellular kinase activity. Thus, it is expected that direct inhibition of the kinase activity of VEGF-R2 will result in the reduction of angiogenesis even in the presence of exogenous VEGF (see Strawn et al, *Cancer Res.*, 56:3540-3545 (1996)), as has been shown with mutants of VEGF-R2 which fail to mediate signal transduction. Millauer et al, *Cancer Res.*, 56:1615-1620 (1996). Furthermore, VEGF-R2 appears to have no function in the adult beyond that of mediating the angiogenic activity of VEGF. Therefore, a selective inhibitor of the kinase activity of VEGF-R2 would be expected to exhibit little toxicity.

Similarly, FGFR binds the angiogenic growth factors aFGF and bFGF and mediates subsequent intracellular signal transduction. Recently, it has been suggested that growth factors such as bFGF may play a critical role in inducing angiogenesis in solid tumors that have reached a certain size. Yoshiji et al., *Cancer Research*, 57: 3924-3928 (1997). Unlike VEGF-R2, however, FGF-R is expressed in a number of different cell types throughout the body and may or may not play important roles in other normal physiological processes in the adult. Nonetheless, systemic administration of a small molecule inhibitor of the kinase activity of FGF-R has been reported to block bFGF-induced angiogenesis in mice without apparent toxicity. Mohammad et al., *EMBO Journal*, 17:5996-5904 (1998).

TEK (also known as Tie-2) is another receptor tyrosine kinase expressed only on endothelial cells which has been shown to play a role in angiogenesis. The binding of the factor angiopoietin-1 results in autophosphorylation of the kinase domain of TEK and results in a signal transduction process which appears to mediate the interaction of endothelial cells with peri-endothelial support cells, thereby facilitating the maturation of newly formed blood vessels. The factor angiopoietin-2, on the other hand, appears to antagonize the action of angiopoietin-1 on TEK and disrupts angiogenesis. Maisonpierre et al., *Science*, 277:55-60 (1997).

The kinase, JNK, belongs to the mitogen-activated protein kinase (MAPK) superfamily. JNK plays a crucial role in inflammatory responses, stress responses, cell proliferation, apoptosis, and tumorigenesis. JNK kinase activity can be activated by various stimuli, including the proinflammatory cytokines (TNF-alpha and interleukin-1), lymphocyte costimulatory receptors (CD28 and CD40), DNA-damaging chemicals, radiation, and Fas signaling. Results from the JNK knockout mice indicate that JNK is involved in apoptosis induction and T helper cell differentiation.

Pim-1 is a small serine/threonine kinase. Elevated expression levels of Pim-1 have been detected in lymphoid and myeloid malignancies, and recently Pim-1 was identified as a prognostic marker in prostate cancer. K. Peltola, "Signaling in Cancer: Pim-1 Kinase and its Partners", Annales Universitatis Turkuensis, Sarja—Ser. D Osa—Tom. 616, (Aug. 30, 2005), http://kirjasto.utu/fi/julkaisupalvelut/annaalit/2004/D616.html. Pim-1 acts as a cell survival factor and may prevent apoptosis in malignant cells. K. Petersen Shay et al., *Molecular Cancer Research* 3:170-181 (2005).

Aurora kinases (Aurora-A, Aurora-B, Aurora-C) are serine/threonine protein kinases that have been implicated in human cancer, such as colon, breast and other solid tumors. Aurora-A (also sometimes referred to as AIK) is believed to be involved in protein phosphorylation events that regulate the cell cycle. Specifically, Aurora-A may play a role in controlling the accurate segregation of chromosomes during mitosis. Misregulation of the cell cycle can lead to cellular proliferation and other abnormalities. In human colon cancer tissue, Aurora-A, Aurora-B, Aurora-C have been found to be overexpressed (see Bischoff et al., EMBO J., 17:3052-3065

(1998); Schumacher et al., *J. Cell Biol.* 143:1635-1646 (1998); Kimura et al., *J. Biol. Chem.*, 272:13766-13771 (1997)).

c-Met is a proto-oncogene that encodes for a tyrosine kinase receptor for hepatocyte growth factor/scatter factor (HGF/SF). The c-Met protein is expressed mostly in epithelial cells, and due to its function it is also known as hepatocyte growth factor receptor, or HGFR. When HGF/SF activates c-Met, the latter in turn may activate a number of kinase pathways, including the pathway from Ras to Raf to Mek to the mitogen-activated protein kinase ERK1 to the transcription factor ETS1. Met signaling has been implicated in the etiology and malignant progression of human cancers (see Birchmeier et al., *Nature Reviews Molecular Cell Biology*, 4.915-925 (2003); Zhang et al., *Journal of Cellular Biochemistry*, 88:408-417 (2003); and Paumelle et al., *Oncogene*, 21:2309-2319 (2002)).

Mitogen-activated protein kinase-activated protein kinase 2 (MAPKAP K2 or MK2) mediates multiple p38 MAPK-dependent cellular responses. MK2 is an important intracellular regulator of the production of cytokines, such as tumor necrosis factor alpha (TNFa), interleukin 6 (IL-6) and interferon gamma (IFNg), that are involved in many acute and chronic inflammatory diseases, e.g. rheumatoid arthritis and inflammatory bowel disease. MK2 resides in the nucleus of non-stimulated cells and upon stimulation, it translocates to the cytoplasm and phosphorylates and activates tuberin and HSP27. MK2 is also implicated in heart failure, brain ischemic injury, the regulation of stress resistance and the production of TNF-α (see Deak et al., *EMBO.* 17:4426-4441 (1998); Shi et al., *Biol. Chem.* 383:1519-1536 (2002); Staklatvala., *Curr. Opin. Pharmacol.* 4:372-377 (2004); and Shiroto et al., *J. Mol. Cell. Cardiol.* 38:93-97 (2005)).

There is a need for effective inhibitors of protein kinases in order to treat or prevent disease states associated with abnormal cell proliferation. Moreover, it is desirable for kinase inhibitors to possess both high affinities for the target kinase as well as high selectivity versus other protein kinases. Small-molecule compounds that may be readily synthesized and are potent inhibitors of cell proliferation are those, for example, that are inhibitors of one or more protein kinases, such as CHK1, CHK2, VEGF (VEGF-R2), Pim-1, CDKs or CDK/cyclin complexes and both receptor and non-receptor tyrosine kinases.

SUMMARY OF THE INVENTION

In one aspect, the present invention provides compounds of Formula (I):

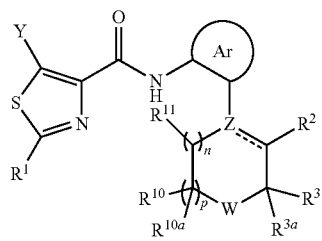

(I)

and pharmaceutically acceptable salts, solvates, esters, prodrugs and stereoisomers thereof, wherein the dashed line indicates an optional and additional bond and wherein:

$R^1$ is H, alkyl, alkenyl, alkynyl, halo, -(alkylene)$_m$-aryl, -alkenylene-aryl, -alkynylene-aryl, -(alkylene)$_m$cycloalkyl, -(alkylene)$_m$-heteroaryl, -(alkylene)$_m$-heterocyclyl, -(alkylene)$_m$-heterocyclenyl, wherein any aryl, cycloalkyl, heteroaryl, heterocyclyl or heterocyclenyl group can be optionally substituted with up to 5 substituents, which may be the same or different, and are independently selected from halo, alkyl, cycloalkyl, -(alkylene)$_m$-N(R$^9$)$_2$, -(alkylene)$_m$-O-alkyl, —O-aryl, —C(O)R$^8$, —S-alkyl, —O-aryl, -(alkylene)$_m$-CN, alkynyl, alkenyl, hydroxyalkyl, haloalkyl, —O-haloalkyl, —C(O)OR$^7$, —NHC(O)R$^7$, —C(O)N(R$^7$)$_2$, —S(O)$_2$N(R$^8$)$_2$, —NHS(O)$_2$R$^8$, -(alkylene)$_m$-heteroaryl, -(alkylene)$_m$-heterocyclyl and -(alkylene)$_m$-aryl; wherein an alkyl, alkenyl or alkynyl group can be substituted with one or more substituents, which may be the same or different, and are independently selected from halo, alkyl, —N(R$^7$)$_2$, —C(O)OH, aryl, and —O-alkyl; wherein any cyclic R$^1$ group can be optionally fused to a cycloalkyl, aryl, heteroaryl or heterocyclyl group; such that when R$^1$ is heteroaryl, heterocyclyl or heterocyclenyl, these groups are attached to the rest of the compound of formula (I) by a ring carbon atom;

$R^2$ is H, alkyl, haloalkyl, hydroxyalkyl, -(alkylene)$_m$-C(O)N(R$^8$)$_2$, -(alkylene)$_m$-NHC(O)—R$^9$ or -(alkylene)$_m$-N(R$^9$)$_2$, or R$^2$ and the ring carbon atom to which it is attached, form a carbonyl group;

$R^3$ is H, -alkyl, haloalkyl, hydroxyalkyl, -(alkylene)$_m$-C(O)N(R$^8$)$_2$, -(alkylene)$_m$-NHC(O)—R$^9$ or -(alkylene)$_m$-N(R$^9$)$_2$, or $R^3$ and $R^{3a}$, together with the common carbon atom to which each are attached, join to form a carbonyl, cycloalkyl or heterocyclyl group;

$R^{3a}$ is H, -alkyl, haloalkyl, hydroxyalkyl, -(alkylene)$_m$-C(O)N(R$^8$)$_2$, -(alkylene)$_m$-NHC(O)—R$^9$ or -(alkylene)$_m$-N(R$^9$)$_2$;

each occurrence of $R^4$ is independently H, -alkyl, -(alkylene)$_m$-aryl, -(alkylene)$_m$-heteroaryl, -(alkylene)$_m$-heterocyclyl, -(alkylene)$_m$-N(R$^8$)$_2$, -(alkylene)$_m$-OH, -(alkylene)$_m$-NHC(O)R$^8$, hydroxyalkyl, haloalkyl, —CH$_2$NH$_2$, —C(O)R$^5$, —C(O)OR$^8$, —C(O)-(alkylene)$_m$-N(R$^8$)$_2$, —C(O)NH-alkyl, —C(O)N(alkyl)$_2$, -(alkylene)$_m$-NHC(O)R$^6$, —NHC(O)OR$^8$, —CR$^2$C(O)NH$_2$, —CR$^2$C(O)NH(alkyl), —CR$^2$C(O)NH(alkyl)$_2$ or —NHS(O)$_2$R$^6$;

$R^5$ is H, alkyl, aryl, -heteroaryl or —NHOH;

each occurrence of $R^6$ is independently H, alkyl, aryl or haloalkyl;

each occurrence of $R^7$ is H, —OH, alkyl, —O-alkyl, cycloalkyl or haloalkyl;

each occurrence of $R^8$ is independently H, alkyl, -(alkylene)$_m$-aryl, -(alkylene)$_m$-heterocyclyl, -(alkylene)$_m$-heteroaryl or -(alkylene)$_m$-cycloalkyl;

each occurrence of $R^9$ is H, alkyl, haloalkyl, hydroxyalkyl, -(alkylene)$_m$-aryl, -(alkylene)$_m$-heterocyclyl, -(alkylene)$_m$-heteroaryl or -(alkylene)$_m$-cycloalkyl;

$R^{10}$ is H, -alkyl, haloalkyl, hydroxyalkyl, -(alkylene)$_m$-C(O)N(R$^8$)$_2$, -(alkylene)$_m$-NHC(O)—R$^9$ or -(alkylene)$_m$-N(R$^9$)$_2$, or $R^{10}$ and $R^{10a}$, together with the common carbon atom to which each are attached, join to form a carbonyl, cycloalkyl or heterocyclyl group;

$R^{10a}$ is H, -alkyl, haloalkyl, hydroxyalkyl, -(alkylene)$_m$-C(O)N(R$^8$)$_2$, -(alkylene)$_m$-NHC(O)—R$^9$ or -(alkylene)$_m$-N(R$^9$)$_2$;

each occurrence of $R^{11}$ is independently H, alkyl, haloalkyl, hydroxyalkyl, -(alkylene)$_m$-C(O)N(R$^8$)$_2$, -(alkylene)$_m$-NHC(O)—R$^9$ or -(alkylene)$_m$-N(R$^9$)$_2$, or any $R^{11}$ and the ring carbon atom to which it is attached, form a carbonyl group;

each occurrence of $R^{12}$ is independently H, alkyl, -(alkylene)$_m$-aryl, -(alkylene)$_m$-heteroaryl, -(alkylene)$_m$-heterocyclyl, —S(O)$_2$-alkyl, —S(O)$_2$-aryl, —S(O)$_2$-heteroaryl, hydroxyalkyl, —C(O)R$^8$, or —C(O)OR$^8$;

Ar is arylene or heteroarylene, wherein the arylene or heteroarylene is joined via any 2 of its adjacent ring carbon atoms, and wherein the arylene or heteroarylene group can be optionally substituted with up to 4 substituents, which may be the same or different, and are independently selected from halo, alkyl, —OH, —OR$^9$, -(alkylene)$_m$-N(R$^6$)$_2$—N(alkyl)$_2$, —SR$^9$, —S(O)R$^8$, —S(O)$_2$R$^8$, —S(O)$_2$NHR$^9$, —C(O)R$^8$, —C(O)OR$^9$, -(alkylene)$_m$-C(O)N(R$^8$)$_2$, —NHC(O)R$^9$, haloalkyl, hydroxyalkyl, —CN and NO$_2$, such that when Ar is tetrahydronaphthylene, R$^2$ and R$^3$ are each other than hydrogen;

W is —N(R$^{12}$)—, —S—, —O— or —C(R$^4$)$_2$—, wherein both R$^4$ groups and the common carbon atom to which they are attached can combine to form a cycloalkyl or heterocyclyl group, each of which can be further substituted;

Y is H, halo, alkyl or —CN;

Z is —C(R$^7$)— or —N—, such that when the optional additional bond is present, Z is —C(R$^7$)—;

each occurrence of m is independently 0 or 1;

n is an integer ranging from 0 to 2; and p is 0 or 1.

In one aspect, the compounds of Formula (I) (the "Anilinopiperazine Derivatives") can be useful as protein kinase inhibitors.

In another aspect, the Anilinopiperazine Derivatives can be useful for treating or preventing a proliferative disorder, an anti-proliferative disorder, inflammation, arthritis, a central nervous system disorder, a cardiovascular disease, alopecia, a neuronal disease, an ischemic injury, a viral disease, a fungal infection, or a disorder related to the activity of a protein kinase (each being a "Condition").

In another aspect, the present invention provides pharmaceutical compositions comprising an effective amount of at least one Anilinopiperazine Derivative and a pharmaceutically acceptable carrier. The compositions can be useful for treating or preventing a Condition in a patient.

In still another aspect, the present invention provides methods for treating pr preventing a Condition in a patient, the method comprising administering to the patient an effective amount of at least one Anilinopiperazine Derivative.

In another aspect, the present invention provides methods for treating a cancer in a patient, the method comprising administering to the patient an effective amount of at least one Anilinopiperazine Derivative.

In another aspect, the present invention provides methods for treating a cancer in a patient, the method comprising administering to the patient an at least one Anilinopiperazine Derivative and at least one additional anticancer agent which is not an Anilinopiperazine Derivative, wherein the amounts administered are together effective to treat the cancer.

DETAILED DESCRIPTION OF THE INVENTION

In an embodiment, the present invention provides Anilinopiperazine Derivatives of Formula (I) and or pharmaceutically acceptable salts, solvates, esters and prodrugs thereof. The Anilinopiperazine Derivatives can be useful for treating or preventing a Condition in a patient.

DEFINITIONS AND ABBREVIATIONS

As used above, and throughout this disclosure, the following terms, unless otherwise indicated, shall be understood to have the following meanings:

"Acyl" means an H—C(O)—, alkyl-C(O)— or cycloalkyl-C(O)—, group in which the various groups are as previously described. The bond to the parent moiety is through the carbonyl. In one embodiment, acyls contain a lower alkyl. Non-limiting examples of suitable acyl groups include formyl, acetyl and propanoyl.

"Alkoxy" means an alkyl-O— group in which the alkyl group is as previously described. Non-limiting examples of suitable alkoxy groups include methoxy, ethoxy, n-propoxy, isopropoxy and n-butoxy. The bond to the parent moiety is through the ether oxygen.

"Alkoxycarbonyl" means an alkyl-O—CO— group. Non-limiting examples of suitable alkoxycarbonyl groups include methoxycarbonyl and ethoxycarbonyl. The bond to the parent moiety is through the carbonyl.

"Alkyl" means an aliphatic hydrocarbon group which may be straight or branched and comprising about 1 to about 20 carbon atoms in the chain. In one embodiment, an alkyl group contains from about 1 to about 12 carbon atoms in the chain. In another embodiment, an alkyl group contains from about 1 to about 6 carbon atoms in the chain. Branched means that one or more lower alkyl groups such as methyl, ethyl or propyl, are attached to a linear alkyl chain. Lower alkyl refers to a group having about 1 to about 6 carbon atoms in the chain which may be straight or branched. An alkyl group may be unsubstituted or optionally substituted by one or more substituents which may be the same or different, each substituent being independently selected from the group consisting of halo, alkyl, aryl, cycloalkyl, cyano, hydroxy, alkoxy, —S-alkyl, amino, —NH(alkyl), —NH(cycloalkyl), —N(alkyl)$_2$, —O—C(O)-alkyl, —O—C(O)-aryl, —O—C(O)-cycloalkyl, carboxy and —C(O)O-alkyl. Non-limiting examples of suitable alkyl groups include methyl, ethyl, n-propyl, isopropyl, n-butyl, sec-butyl, isobutyl, t-butyl, n-pentyl, isopentyl, neopentyl, n-hexyl, n-heptyl and n-octyl. In one embodiment, an alkyl group is a "$C_1$-$C_6$ alkyl group," having from 1 to 6 carbon atoms.

"Alkylaryl" means an alkyl-arylene-group in which the alkyl and arylene are as previously described. In one embodiment, alkylaryls comprise a lower alkyl group. Non-limiting example of a suitable alkylaryl group is tolyl. The bond to the parent moiety is through the arylene group.

"Alkylsulfonyl" means an alkyl-S(O$_2$)— group. In one embodiment, groups are those in which the alkyl group is lower alkyl. The bond to the parent moiety is through the sulfonyl.

"Alkylthio" means an alkyl-S— group in which the alkyl group is as previously described. Non-limiting examples of suitable alkylthio groups include methylthio and ethylthio. An alkylthio group is bound to the parent moiety via its sulfur atom.

"Alkenyl" means an aliphatic hydrocarbon group containing at least one carbon-carbon double bond and which may be straight or branched and comprising about 2 to about 15 carbon atoms in the chain. In one embodiment, an alkenyl group has from about 2 to about 12 carbon atoms in the chain; in another embodiment, an alkenyl group has from about 2 to about 6 carbon atoms in the chain. Branched means that one or more lower alkyl groups such as methyl, ethyl or propyl, are attached to a linear alkenyl chain. Lower alkenyl refers to about 2 to about 6 carbon atoms in the chain which may be straight or branched. An alkenyl group may be unsubstituted or optionally substituted by one or more substituents which may be the same or different, each substituent being independently selected from the group consisting of halo, alkyl. aryl, cycloalkyl, cyano, alkoxy and —S(alkyl). Non-limiting examples of suitable alkenyl groups include ethenyl, propenyl, n-butenyl, 3-methylbut-2-enyl, n-pentenyl, octenyl and decenyl.

"Alkylene" means an alkyl group, as defined above, wherein one of the alkyl group's hydrogen atoms has been replaced with a bond. Non-limiting examples of alkylene groups include —$CH_2$—, —$CH_2CH_2$—, —$CH_2CH_2CH_2$—, —$CH_2CH_2CH_2CH_2$—, —$CH(CH_3)CH_2CH_2$—, —$CH(CH_3)$— and —$CH_2CH(CH_3)CH_2$—. In one embodiment, an alkylene group has from 1 to about 6 carbon atoms. In another embodiment, an alkylene group is branched. In another embodiment, an alkylene group is linear.

"Alkenylene" means a difunctional group obtained by removal of a hydrogen from an alkenyl group that is defined above. Non-limiting examples of alkenylene include —CH=CH—, —C($CH_3$)=CH—, and —CH=CH$CH_2$—.

"Alkynyl" means an aliphatic hydrocarbon group containing at least one carbon-carbon triple bond and which may be straight or branched and comprising about 2 to about 15 carbon atoms in the chain. In one embodiment, an alkynyl group has from about 2 to about 12 carbon atoms in the chain; and in another embodiment, an alkynyl group has from about 2 to about 4 carbon atoms in the chain. Branched means that one or more lower alkyl groups such as methyl, ethyl or propyl, are attached to a linear alkynyl chain. Lower alkynyl refers to about 2 to about 6 carbon atoms in the chain which may be straight or branched. Non-limiting examples of suitable alkynyl groups include ethynyl, propynyl, 2-butynyl and 3-methylbutynyl. An alkynyl group may be unsubstituted or optionally substituted by one or more substituents which may be the same or different, each substituent being independently selected from the group consisting of alkyl, aryl and cycloalkyl.

"Alkynylalkyl" means an alkynyl-alkyl-group in which the alkynyl and alkyl are as previously described. In one embodiment, alkynylalkyls contain a lower alkynyl and a lower alkyl group. The bond to the parent moiety is through the alkyl. Non-limiting examples of suitable alkynylalkyl groups include propargylmethyl.

"Aralkloxy" means an aralkyl-O— group in which the aralkyl group is as previously described. Non-limiting examples of suitable aralkyloxy groups include benzyloxy and 1- or 2-naphthalenemethoxy. The bond to the parent moiety is through the ether oxygen.

"Aralkoxycarbonyl" means an aralkyl-O—C(O)— group. Non-limiting example of a suitable aralkoxycarbonyl group is benzyloxycarbonyl. The bond to the parent moiety is through the carbonyl.

"Aralkyl" or "arylalkyl" means an aryl-alkylene-group in which the aryl and alkylene are as previously described. In one embodiment, aralkyls comprise a lower alkylene group. Non-limiting examples of suitable aralkyl groups include benzyl, 2-phenethyl and naphthalenylmethyl. The bond to the parent moiety is through the alkylene group.

"Aralkylthio" means an aralkyl-S— group in which the aralkyl group is as previously described. Non-limiting example of a suitable aralkylthio group is benzylthio. The bond to the parent moiety is through the sulfur.

"Aryl" means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl.

"Arylene," means an aryl group, wherein a hydrogen atom connected to one of the aryl group's ring carbon atoms is replaced with a single bond.

"Aryloxy" means an aryl-O— group in which the aryl group is as previously described. Non-limiting examples of suitable aryloxy groups include phenoxy and naphthoxy. The bond to the parent moiety is through the ether oxygen.

"Aryloxycarbonyl" means an aryl-O—C(O)— group. Non-limiting examples of suitable aryloxycarbonyl groups include phenoxycarbonyl and naphthoxycarbonyl.

The bond to the parent moiety is through the carbonyl.

"Arylsulfonyl" means an aryl-S($O_2$)— group. The bond to the parent moiety is through the sulfonyl.

"Arylthio" means an aryl-S— group in which the aryl group is as previously described. Non-limiting examples of suitable arylthio groups include phenylthio and naphthylthio. The bond to the parent moiety is through the sulfur.

"Benzofused cycloalkyl" means a cycloalkyl moiety as defined above which is fused to a benzene ring. Non-limiting examples of a benzofused cycloalkyl are indanyl and tetrahydronaphthylenyl.

"Benzofused cycloalkenyl" means a cycloalkenyl moiety as defined above which is fused to a benzene ring. Non-limiting examples of a benzofused cycloalkyl include indenyl.

"Benzofused heterocyclyl" means a heterocyclyl moiety as defined above which is fused to a benzene ring. Non-limiting examples of a benzofused heterocyclyl include indolinyl and 2,3-dihydrobenzofuran.

"Benzofused heteroaryl" means a heteroaryl moiety as defined above which is fused to a benzene ring. Non-limiting examples of a benzofused heteroaryl are indolyl, indazolyl, benzofuranyl, quinolinyl, isoquinolinyl, benzthiazolyl, indolyl, benzimidazolyl and benzothiophenyl.

"Composition" means a product comprising the specified ingredients in the specified amounts, as well as any product which results, directly or indirectly, from combination of the specified ingredients in the specified amounts.

"Cycloalkyl" means a non-aromatic mono- or multicyclic ring system comprising about 3 to about 10 carbon atoms, preferably about 5 to about 10 carbon atoms. In one embodiment, cycloalkyl rings contain about 5 to about 7 ring atoms. A cycloalkyl group can be optionally substituted with one or more "ring system substituents" which may be the same or different, and are as defined above. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantyl and the like.

"Cycloalkylalkyl" means a cycloalkyl moiety as defined above linked via an alkyl moiety (defined above) to a parent core. Non-limiting examples of suitable cycloalkylalkyls include cyclohexylmethyl, adamantylmethyl and the like.

"Cycloalkenyl" means a non-aromatic mono or multicyclic ring system comprising from 3 to about 10 carbon atoms and having at least one endocyclic carbon-carbon double bond. In one embodiment, a cycloalkenyl group has from about 5 to about 10 ring carbon atoms. In another embodiment, a cycloalkenyl group has from about 5 to about 7 ring carbon atoms. A cycloalkenyl group can be optionally substituted with one or more "ring system substituents" which may be the same or different, and are as defined above. Non-limiting examples of suitable monocyclic cycloalkenyls include cyclopentenyl, cyclohexenyl, cyclohepta-1,3-dienyl, and the like. Non-limiting example of a suitable multicyclic cycloalkenyl is norbornylenyl.

"Cycloalkenylalkyl" means a cycloalkenyl moiety as defined above linked via an alkyl moiety (defined above) to a parent core. Non-limiting examples of suitable cycloalkenylalkyls include cyclopentenylmethyl, cyclohexenylmethyl and the like.

"Effective amount" or "therapeutically effective amount" means an amount of Anilinopiperazine Derivative and/or an additional therapeutic agent, or a composition thereof that is effective in producing the desired therapeutic, ameliorative, inhibitory or preventative effect when administered to a patient suffering from a Condition. In the combination therapies of the present invention, an effective amount can refer to each individual agent or to the combination as a whole, wherein the amounts of all agents administered are together effective, but wherein the component agent of the combination may not be present individually in an effective amount.

"Halo" means —F, —Cl, —Br or —I. In one embodiment, halo refers to —Cl or —Br. In another embodiment, halo refers to —F.

"Haloalkyl" means an alkyl group as defined above, wherein one or more of the alkyl group's hydrogen atoms has been replaced with a halogen. In one embodiment, a haloalkyl group has from 1 to 6 carbon atoms. In another embodiment, a haloalkyl group is substituted with from 1 to 3 F atoms. Non-limiting examples of haloalkyl groups include —CH$_2$F, —CHF$_2$, —CF$_3$, —CH$_2$Cl and —CCl$_3$.

"Heteroaryl" means an aromatic monocyclic or multicyclic ring system comprising about 5 to about 14 ring atoms, wherein from 1 to 4 of the ring atoms is independently O, N or S and the remaining ring atoms are carbon atoms. In one embodiment, a heteroaryl group has 5 to 10 ring atoms. In another embodiment, a heteroaryl group is monocyclic and has 5 or 6 ring atoms. A heteroaryl group can be optionally substituted by one or more "ring system substituents" which may be the same or different, and are as defined herein below. A heteroaryl group is joined via a ring carbon atom, and any nitrogen atom of a heteroaryl can be optionally oxidized to the corresponding N-oxide. The term "heteroaryl" also encompasses a heteroaryl group, as defined above, that is fused to a benzene ring. Non-limiting examples of heteroaryls include pyridyl, pyrazinyl, furanyl, thienyl, pyrimidinyl, pyridone (including N-substituted pyridones), isoxazolyl, isothiazolyl, oxazolyl, thiazolyl, pyrazolyl, furazanyl, pyrrolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like. The term "heteroaryl" also refers to partially saturated heteroaryl moieties such as, for example, tetrahydroisoquinolyl, tetrahydroquinolyl and the like. In one embodiment, a heteroaryl group is unsubstituted. In another embodiment, a heteroaryl group is a 5-membered heteroaryl. In another embodiment, a heteroaryl group is a 6-membered heteroaryl.

The term "heteroarylene," as used herein, refers to a heteroaryl group, wherein a hydrogen atom connected to one of the heteroaryl group's ring atoms is replaced with a single bond.

"Heteroarylalkyl" means a heteroaryl moiety as defined above linked via an alkyl moiety (defined above) to a parent core. Non-limiting examples of suitable heteroaryls include 2-pyridinylmethyl, quinolinylmethyl and the like.

"Heterocyclyl" means a non-aromatic saturated monocyclic or multicyclic ring system comprising 3 to about 10 ring atoms, wherein from 1 to 4 of the ring atoms are independently O, S or N and the remainder of the ring atoms are carbon atoms. In one embodiment, a heterocyclyl group has from about 5 to about 10 ring atoms. In another embodiment, a heterocyclyl group has 5 or 6 ring atoms. There are no adjacent oxygen and/or sulfur atoms present in the ring system. Any —NH group in a heterocyclyl ring may exist protected such as, for example, as an —N(BOC), —N(Cbz), —N(Tos) group and the like; such protected heterocyclyl groups are considered part of this invention. The term "heterocyclyl" also encompasses a heterocyclyl group, as defined above, that is fused to an aryl (e.g., benzene) or heteroaryl ring. A heterocyclyl group can be optionally substituted by one or more "ring system substituents" which may be the same or different, and are as defined herein below. The nitrogen or sulfur atom of the heterocyclyl can be optionally oxidized to the corresponding N-oxide, S-oxide or S,S-dioxide. Non-limiting examples of monocyclic heterocyclyl rings include piperidyl, pyrrolidinyl, piperazinyl, morpholinyl, thiomorpholinyl, thiazolidinyl, 1,4-dioxanyl, tetrahydrofuranyl, tetrahydrothiophenyl, lactam, lactone, and the like. A ring carbon atom of a heterocyclyl group may be functionalized as a carbonyl group. An illustrative example of such a heterocyclyl group is pyrrolidonyl:

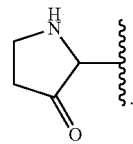

In one embodiment, a heterocyclyl group is unsubstituted. In another embodiment, a heterocyclyl group is a 5-membered heterocyclyl. In another embodiment, a heterocyclyl group is a 6-membered heterocyclyl.

"Heterocyclylalkyl" means a heterocyclyl moiety as defined above linked via an alkyl moiety (defined above) to a parent core. Non-limiting examples of suitable heterocyclylalkyls include piperidinylmethyl, piperazinylmethyl and the like.

"Heterocyclenyl" means a heterocyclyl group, as defined above, wherein the heterocyclyl group contains from 3 to 10 ring atoms, and at least one endocyclic carbon-carbon or carbon-nitrogen double bond. In one embodiment, a heterocyclenyl group has from 5 to 10 ring atoms. In another embodiment, a heterocyclenyl group is monocyclic and has 5 or 6 ring atoms. A heterocyclenyl group can optionally substituted by one or more ring system substituents, wherein "ring system substituent" is as defined above. The nitrogen or sulfur atom of the heterocyclenyl can be optionally oxidized to the corresponding N-oxide, S-oxide or S,S-dioxide. Non-limiting examples of heterocyclenyl groups include 1,2,3,4-tetrahydropyridinyl, 1,2-dihydropyridinyl, 1,4-dihydropyridinyl, 1,2,3,6-tetrahydropyridinyl, 1,4,5,6-tetrahydropyrimidinyl, 2-pyrrolinyl, 3-pyrrolinyl, 2-imidazolinyl, 2-pyrazolinyl, dihydroimidazolyl, dihydrooxazolyl, dihydrooxadiazolyl, dihydrothiazolyl, 3,4-dihydro-2H-pyranyl, dihydrofuranyl, fluoro-substituted dihydrofuranyl, 7-oxabicyclo[2.2.1]heptenyl, dihydrothiophenyl, dihydrothiopyranyl, and the like. A ring carbon atom of a heterocyclenyl group may be functionalized as a carbonyl group. An illustrative example of such a heterocyclenyl group is:

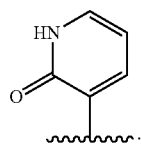

In one embodiment, a heterocyclenyl group is unsubstituted. In another embodiment, a heterocyclenyl group is a 5-membered heterocyclenyl.

"Heterocyclenylalkyl" means a heterocyclenyl moiety as defined above linked via an alkyl moiety (defined above) to a parent core.

It should be noted that in hetero-atom containing ring systems of this invention, there are no hydroxyl groups on carbon atoms adjacent to a N, O or S, as well as there are no N or S groups on carbon adjacent to another heteroatom. Thus, for example, in the ring:

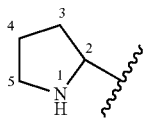

there is no —OH attached directly to carbons marked 2 and 5.

It should also be noted that tautomeric forms such as, for example, the moieties:

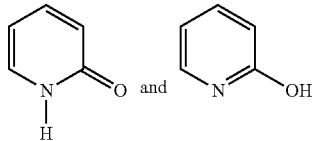 [SMILES: O=c1cccc[nH]1 ; "and" ; Oc1ccccn1]

are considered equivalent in certain embodiments of this invention.

"Heteroaralkyl" means a heteroaryl-alkyl-group in which the heteroaryl and alkyl are as previously described. In one embodiment, heteroaralkyls contain a lower alkyl group. Non-limiting examples of suitable aralkyl groups include pyridylmethyl, and quinolin-3-ylmethyl. The bond to the parent moiety is through the alkyl.

"Hydroxyalkyl" means an alkyl group as defined above, wherein one or more of the alkyl group's hydrogen atoms has been replaced with an —OH group. In one embodiment, a hydroxyalkyl group has from 1 to 6 carbon atoms. Non-limiting examples of hydroxyalkyl groups include —CH$_2$OH, —CH$_2$CH$_2$OH, —CH$_2$CH$_2$CH$_2$OH and —CH$_2$CH(OH)CH$_3$.

A "patient" is a human or non-human mammal. In one embodiment, a patient is a human. In another embodiment, a patient is a non-human mammal, including, but not limited to, a monkey, dog, baboon, rhesus, mouse, rat, horse, cat or rabbit. In another embodiment, a patient is a companion animal, including but not limited to a dog, cat, rabbit, horse or ferret. In one embodiment, a patient is a dog. In another embodiment, a patient is a cat.

The term "purified", "in purified form" or "in isolated and purified form" for a compound refers to the physical state of said compound after being isolated from a synthetic process (e.g. from a reaction mixture), or natural source or combination thereof. Thus, the term "purified", "in purified form" or "in isolated and purified form" for a compound refers to the physical state of said compound after being obtained from a purification process or processes described herein or well known to the skilled artisan (e.g., chromatography, recrystallization and the like), in sufficient purity to be characterizable by standard analytical techniques described herein or well known to the skilled artisan.

"Ring system substituent" means a substituent group attached to an aromatic or non-aromatic ring system which, for example, replaces an available hydrogen on the ring system. Ring system substituents may be the same or different, each being independently selected from the group consisting of alkyl, alkenyl, alkynyl, aryl, heteroaryl, -alkyl-aryl, -aryl-alkyl, -alkylene-heteroaryl, -alkenylene-heteroaryl, -alkynylene-heteroaryl, hydroxy, hydroxyalkyl, haloalkyl, —O-alkyl, —O-haloalkyl, -alkylene-O-alkyl, —O-aryl, aralkoxy, acyl, —C(O)-aryl, halo, nitro, cyano, carboxy, —C(O)O-alkyl, —C(O)O-aryl, —C(O)O-alkelene-aryl, —S(O)-alkyl, —S(O)$_2$-alkyl, —S(O)-aryl, —S(O)$_2$-aryl, —S(O)-heteroaryl, —S(O)$_2$-heteroaryl, —S-alkyl, —S-aryl, —S-heteroaryl, —S-alkylene-aryl, —S-alkylene-heteroaryl, cycloalkyl, heterocyclyl, —O—C(O)-alkyl, —O—C(O)-aryl, —O—C(O)-cycloalkyl, —C(=N—CN)—NH$_2$, —C(=NH)—NH$_2$, —C(=NH)—NH(alkyl), Y$_1$Y$_2$N—, Y$_1$Y$_2$N-alkyl-, Y$_1$Y$_2$NC(O)— and Y$_1$Y$_2$NSO$_2$—, wherein Y$_1$ and Y$_2$ can be the same or different and are independently selected from the group consisting of hydrogen, alkyl, aryl, cycloalkyl, and -alkylene-aryl. "Ring system substituent" may also mean a single moiety which simultaneously replaces two available hydrogens on two adjacent carbon atoms (one H on each carbon) on a ring system. Examples of such moiety are methylenedioxy, ethylenedioxy, —C(CH$_3$)$_2$—, —O-alkylene-O—, and the like which form moieties such as, for example:

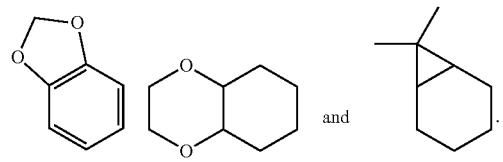

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound' or "stable structure" is meant a compound that is sufficiently robust to survive isolation to a useful degree of purity from a reaction mixture, and formulation into an efficacious therapeutic agent.

The term "optionally substituted" means optional substitution with the specified groups, radicals or moieties.

It should also be noted that any carbon atom or heteroatom with unsatisfied valences in the text, schemes, examples and tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in Organic Synthesis* (1991), Wiley, New York.

When any variable (e.g., aryl, heterocycle, $R^2$, etc.) occurs more than one time in any constituent or any chemical structure or formula herein, its definition on each occurrence is independent of its definition at every other occurrence.

Prodrugs and solvates of the compounds of the invention are also contemplated herein. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" means a compound (e.g., a drug precursor) that is transformed in vivo to yield an Anilinopiperazine Derivative or a pharmaceutically acceptable salt, hydrate or solvate of the compound. The transformation may occur by various mechanisms (e.g., by metabolic or chemical processes), such as, for example, through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

For example, if an Anilinopiperazine Derivative or a pharmaceutically acceptable salt, hydrate or solvate of the compound contains a carboxylic acid functional group, a prodrug can comprise an ester formed by the replacement of the hydrogen atom of the acid group with a group such as, for example, $(C_1-C_8)$alkyl, $(C_2-C_{12})$alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—$(C_1-C_2)$alkylamino$(C_2-C_3)$alkyl (such as β-dimethylaminoethyl), carbamoyl-$(C_1-C_2)$alkyl, N,N-di$(C_1-C_2)$alkylcarbamoyl-$(C_1-C_2)$alkyl and piperidino-, pyrrolidino- or morpholino$(C_2-C_3)$alkyl, and the like.

Similarly, if an Anilinopiperazine Derivative contains an alcohol functional group, a prodrug can be formed by the replacement of the hydrogen atom of the alcohol group with a group such as, for example, $(C_1-C_6)$alkanoyloxymethyl, 1-($(C_1-C_6)$alkanoyloxy)ethyl, 1-methyl-1-($(C_1-C_6)$alkanoyloxy)ethyl, $(C_1-C_6)$alkoxycarbonyloxymethyl, N—$(C_1-C_6)$alkoxycarbonylaminomethyl, succinoyl, $(C_1-C_6)$alkanoyl, α-amino$(C_1-C_4)$alkanyl, arylacyl and α-aminoacyl, or α-aminoacyl-α-aminoacyl, where each α-aminoacyl group is independently selected from the naturally occurring L-amino acids, $P(O)(OH)_2$, —$P(O)(O(C_1-C_6)alkyl)_2$ or glycosyl (the radical resulting from the removal of a hydroxyl group of the hemiacetal form of a carbohydrate), and the like.

If an Anilinopiperazine Derivative incorporates an amine functional group, a prodrug can be formed by the replacement of a hydrogen atom in the amine group with a group such as, for example, R-carbonyl, RO-carbonyl, NRR'-carbonyl where R and R' are each independently $(C_1-C_{10})$alkyl, $(C_3-C_7)$cycloalkyl, benzyl, or R-carbonyl is a natural α-aminoacyl or natural α-aminoacyl, —C(OH)C(O)OY$^1$ where in Y$^1$ is H, $(C_1-C_6)$alkyl or benzyl, —C(OY$^2$)Y$^3$ wherein Y$^2$ is $(C_1-C_4)$alkyl and Y$^3$ is $(C_1-C_6)$alkyl, carboxy$(C_1-C_6)$alkyl, amino $(C_1-C_4)$alkyl or mono-N- or di-N,N—$(C_1-C_6)$alkylaminoalkyl, —C(Y$^4$)Y$^5$ wherein Y$^4$ is H or methyl and Y$^5$ is mono-N- or di-N,N—$(C_1-C_6)$alkylamino morpholino, piperidin-1-yl or pyrrolidin-1-yl, and the like.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

One or more compounds of the invention may optionally be converted to a solvate. Preparation of solvates is generally known. Thus, for example, M. Caira et al, *J. Pharmaceutical Sci.*, 93(3), 601-611 (2004) describes the preparation of the solvates of the antifungal fluconazole in ethyl acetate as well as from water. Similar preparations of solvates, hemisolvate, hydrates and the like are described by E. C. van Tonder et al, *AAPS PharmSciTech.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example I. R. spectroscopy, show the presence of the solvent (or water) in the crystals as a solvate (or hydrate).

The Anilinopiperazine Derivatives can form salts which are also within the scope of this invention. Reference to an Anilinopiperazine Derivative herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when an Anilinopiperazine Derivative contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the Formula I may be formed, for example, by reacting an Anilinopiperazine Derivative with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quaternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Pharmaceutically acceptable esters of the present compounds include the following groups: (1) carboxylic acid esters obtained by esterification of the hydroxy groups, in which the non-carbonyl moiety of the carboxylic acid portion of the ester grouping is selected from straight or branched chain alkyl (for example, acetyl, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted with, for example, halogen, $C_{1-4}$alkyl, or $C_{1-4}$alkoxy or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di($C_{6-24}$)acyl glycerol.

Anilinopiperazine Derivatives, and salts, solvates, esters and prodrugs thereof, may exist in their tautomeric form (for example, as an amide or imino ether). All such tautomeric forms are contemplated herein as part of the present invention.

The Anilinopiperazine Derivatives may contain asymmetric or chiral centers, and, therefore, exist in different stereoisomeric forms. It is intended that all stereoisomeric forms of the Anilinopiperazine Derivatives as well as mixtures thereof, including racemic mixtures, form part of the present invention. In addition, the present invention embraces all geometric and positional isomers. For example, if an Anilinopiperazine Derivative incorporates a double bond or a fused ring, both the cis- and trans-forms, as well as mixtures, are embraced within the scope of the invention.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the Anilinopiperazine Derivatives may be atropisomers (e.g., substituted biaryls) and are considered as part of this invention. Enantiomers can also be separated by use of chiral HPLC column.

It is also possible that the Anilinopiperazine Derivatives may exist in different tautomeric forms, and all such forms are embraced within the scope of the invention. Also, for example, all keto-enol and imine-enamine forms of the compounds are included in the invention.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). (For example, if an Anilinopiperazine Derivative incorporates a double bond or a fused ring, both the cis- and trans-forms, as well as mixtures, are embraced within the scope of the invention. Also, for example, all keto-enol and imine-enamine forms of the compounds are included in the invention.).

Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate", "ester", "prodrug" and the like, is intended to equally apply to the salt, solvate, ester and prodrug of enantiomers, stereoisomers, rotamers, tautomers, positional isomers, racemates or prodrugs of the inventive compounds.

The present invention also embraces isotopically-labelled compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively.

Certain isotopically-labelled Anilinopiperazine Derivatives (e.g., those labeled with $^{3}H$ and $^{14}C$) are useful in compound and/or substrate tissue distribution assays. Tritiated (i.e., $^{3}H$) and carbon-14 (i.e., $^{14}C$) isotopes are particularly preferred for their ease of preparation and detectability. Further, substitution with heavier isotopes such as deuterium (i.e., $^{2}H$) may afford certain therapeutic advantages resulting from greater metabolic stability (e.g., increased in vivo half-life or reduced dosage requirements) and hence may be preferred in some circumstances. Isotopically labelled Anilinopiperazine Derivatives can generally be prepared by following procedures analogous to those disclosed in the Schemes and/or in the Examples hereinbelow, by substituting an appropriate isotopically labelled reagent for a non-isotopically labelled reagent.

Polymorphic forms of the Anilinopiperazine Derivatives, and of the salts, solvates, esters, prodrugs and stereoisomers of the Anilinopiperazine Derivatives, are intended to be included in the present invention.

The following abbreviations are used below and have the following meanings: Boc is tert-butoxycarbonyl, dba is dibenzylideneacetone, DMF is N,N-dimethylformamide, DMSO is dimethylsulfoxide, EtOAc is ethyl acetate, LCMS is liquid chromatography mass spectrometry, MeOH is methanol, NMR is nuclear magnetic resonance, PBS is phosphate buffered saline, S-phos is 2-dicyclohexylphosphino-2', 6'-dimethoxybiphenyl; SPA is scintillation proximity assay, Tf is triflate, TFA is trifluoroacetic acid, X-phos is 5-bromo-4-chloro-3-indolyl phosphate; and Xantphos is 9,9-Dimethyl-4,5-bis(diphenylphosphino) xanthene.

The Anilinopiperazine Derivatives of Formula (I)

The present invention provides Anilinopiperazine Derivatives of Formula (I):

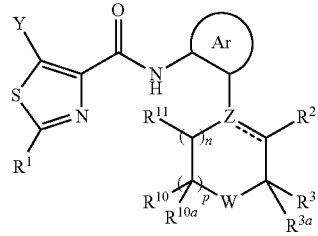
(I)

and pharmaceutically acceptable salts, solvates, esters, prodrugs and stereoisomers thereof, wherein the dashed line indicates an optional and additional bond and wherein $R^1$, $R^2$, $R^3$, $R^{3a}$, $R^{10}$, $R^{10a}$, $R^{11}$, n, p, Ar, W, Y and Z are defined above for formula (I).

In one embodiment, $R^1$ is H, alkyl, alkenyl, aryl, alkenylene-aryl, -alkylene-aryl, heteroaryl or heterocyclyl, wherein a heteroaryl or heterocyclyl group can be optionally fused to a benzene ring.

In another embodiment, $R^1$ is H.
In another embodiment, $R^1$ is alkyl.
In still another embodiment, $R^1$ is halo.
In yet another embodiment, $R^1$ is cycloalkyl.
In another embodiment, $R^1$ is benzofused cycloalkyl.
In yet another embodiment, $R^1$ is heteroaryl.
In a further embodiment, $R^1$ is benzofused heteroaryl.
In another embodiment, $R^1$ is heterocyclyl.
In another embodiment, $R^1$ is heterocyclenyl.
In still another embodiment, $R^1$ is benzofused heterocyclyl.
In yet another embodiment, $R^1$ is benzofused heterocyclenyl.
In one embodiment, $R^1$ is methyl
In one embodiment, $R^1$ is phenyl.
In another embodiment, $R^1$ is pyridyl.
In still another embodiment, $R^1$ is thiophenyl.
In yet another embodiment, $R^1$ is benzofuranyl.
In a further embodiment, $R^1$ is 2,3-dihydrobenzofuranyl.
In one embodiment, $R^1$ is isoxazolyl.
In another embodiment, $R^1$ is alkynyl.
In yet another embodiment, $R^1$ is —C≡C-phenyl
In another embodiment, $R^1$ is cycloalkyl.
In still another embodiment, $R^1$ is cyclopropyl, cyclopentyl or cyclohexyl.
In another embodiment, $R^1$ is pyrazolyl.
In a further embodiment, $R^1$ is pyrimidinyl.
In one embodiment, $R^1$ is biphenyl.
In one embodiment, $R^1$ is -phenyl-O-phenyl.
In another embodiment, $R^1$ is furanyl.
In another embodiment, $R^1$ is pyrrolyl.
In still another embodiment, $R^1$ is indolyl.
In yet another embodiment, $R^1$ is N-alkyl indolyl.

In one embodiment, $R^1$ is:

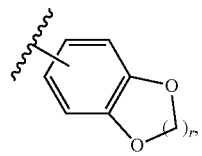

wherein r is 1, 2 or 3.

In specific embodiments, $R^1$ is:

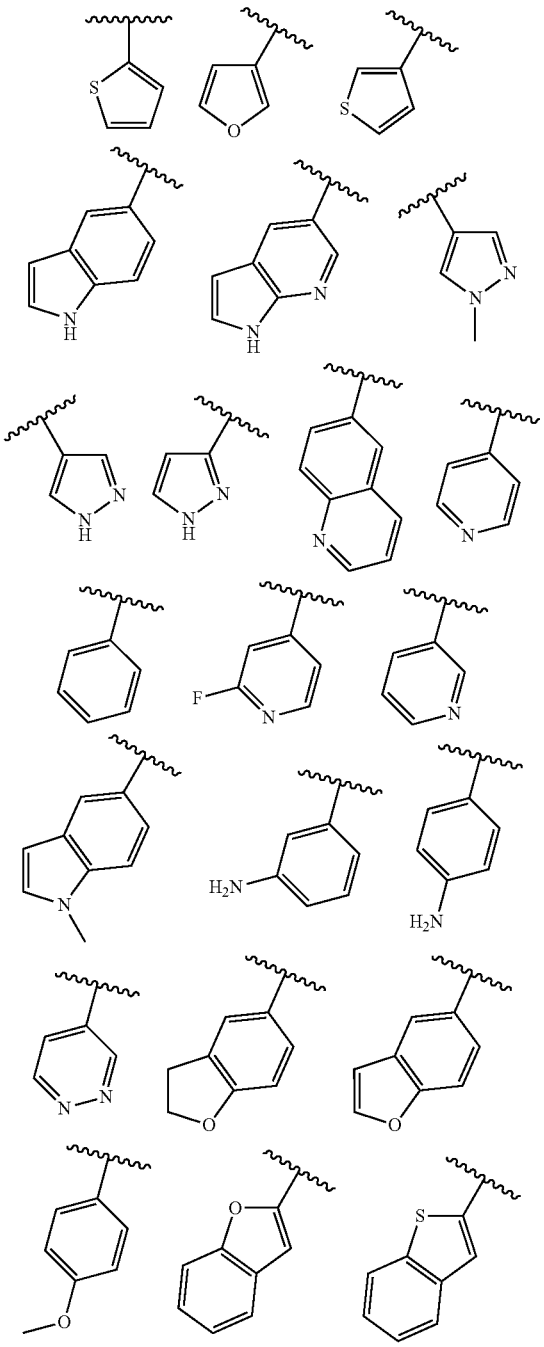

In one embodiment, R¹ is phenyl, wherein the phenyl has 1 or 2 substituents independently selected from alkyl, alkoxy, —N(alkyl)₂, —CH₂N(alkyl)₂, —NH₂, —NHSO₂alkyl, —NHC(O)H, —NHC(O)alkyl, —SO₂N(alkyl)₂, SO₂NHalkyl, —S-alkyl, —CH₂—O—CH₃ or —CH₂OH.

In one embodiment, R¹ is heteroaryl, wherein the heteroaryl has 1 or 2 substituents independently selected from alkyl, —C(O)O-alkyl, —C(O)NH-alkyl, —C(O)NH-cycloalkyl, —C(O)-heterocyclyl, —C(O)OH, —CN, phenyl or -5-membered heteroaryl.

In another embodiment, R¹ is:

wherein $R^a$ is one substituent chosen from —H, -alkyl, —COOH, —CN, phenyl or thiophenyl.

In one embodiment, R² is —H.
In another embodiment, R² is -alkyl.
In one embodiment, R² is —CH₃.
In another embodiment, R² is -α-CH₃.
In another embodiment, R² is -β-CH₃.
In a further embodiment, R² is -alkylene-NH₂.
In one embodiment, R² is —NH₂.
In another embodiment, R² is -α-NH₂.
In another embodiment, R² is -β-NH₂.
In a further embodiment, R² is -alkylene-NH₂.
In yet another embodiment, R² is —CH₂NH₂.
In one embodiment, R² and the carbon atom to which it is attached, form a carbonyl group.
In one embodiment, R³ is —H.
In another embodiment, $R^{3a}$ is —H.
In another embodiment, R³ and $R^{3a}$ are each —H.
In still another embodiment, R³ is -alkyl.
In another embodiment, R³ is haloalkyl.
In yet another embodiment, R³ is hydroxyalkyl.
In one embodiment, R³ is -(alkylene)$_m$-C(O)N(R⁸)₂.
In another embodiment, R³ is -(alkylene)$_m$-NHC(O)—R⁹.
In another embodiment, R³ is -(alkylene)$_m$-N(R⁹)₂.
In one embodiment, R³ is —CH₃.
In another embodiment, R³ is -α-CH₃.
In another embodiment, R³ is -β-CH₃.
In one embodiment, R³ is —NH₂.
In another embodiment, R³ is -α-NH₂.
In another embodiment, R³ is -β-NH₂.
In a further embodiment, R³ is -alkylene-NH₂.

In yet another embodiment, $R^3$ is —CH$_2$NH$_2$.

In one embodiment, $R^3$ and $R^{3a}$ and the common carbon atom to which they are attached, join to form a carbonyl group.

In another embodiment, $R^3$ and $R^{3a}$ and the common carbon atom to which they are attached, join to form a cycloalkyl group.

In another embodiment, $R^3$ and $R^{3a}$ and the common carbon atom to which they are attached, join to form a heterocycyl group.

In one embodiment, $R^2$ and $R^3$ are each —H.
In another embodiment, $R^2$ is alkyl and $R^3$ is —H.
In another embodiment, $R^2$ is —H and $R^3$ is alkyl.
In one embodiment, $R^{10}$ is —H.
In another embodiment, $R^{10a}$ is —H.
In another embodiment, $R^{10}$ and $R^{10a}$ are each —H.
In still another embodiment, $R^{10}$ is -alkyl.
In another embodiment, $R^{10}$ is haloalkyl.
In yet another embodiment, $R^{10}$ is hydroxyalkyl.
In one embodiment, $R^{10}$ is -(alkylene)$_m$-C(O)N(R$^8$)$_2$.
In another embodiment, $R^{10}$ is -(alkylene)$_m$-NHC(O)—R$^9$.
In another embodiment, $R^{19}$ is -(alkylene)$_m$-N(R$^9$)$_2$.
In one embodiment, $R^{10}$ is —CH$_3$.
In another embodiment, $R^{10}$ is -α-CH$_3$.
In another embodiment, $R^{10}$ is -β-CH$_3$.
In one embodiment, $R^{10}$ is —NH$_2$.
In another embodiment, $R^{10}$ is -α-NH$_2$.
In another embodiment, $R^{10}$ is -β-NH$_2$.
In a further embodiment, $R^{10}$ is -alkylene-NH$_2$.
In yet another embodiment, $R^{10}$ is —CH$_2$NH$_2$.

In one embodiment, $R^{10}$ and $R^{10a}$ and the common carbon atom to which they are attached, join to form a carbonyl group.

In another embodiment, $R^{10}$ and $R^{10a}$ and the common carbon atom to which they are attached, join to form a cycloalkyl group.

In another embodiment, $R^{10}$ and $R^{10a}$ and the common carbon atom to which they are attached, join to form a heterocycyl group.

In one embodiment, $R^{11}$ is —H.
In another embodiment, $R^{11}$ is -alkyl.
In one embodiment, $R^{11}$ is —CH$_3$.
In another embodiment, $R^{11}$ is -α-CH$_3$.
In another embodiment, $R^{11}$ is -β-CH$_3$.
In a further embodiment, $R^{11}$ is -alkylene-NH$_2$.
In one embodiment, $R^{11}$ is —NH$_2$.
In another embodiment, $R^{11}$ is -α-NH$_2$.
In another embodiment, $R^{11}$ is -β-NH$_2$.
In a further embodiment, $R^{11}$ is -alkylene-NH$_2$.
In yet another embodiment, $R^{11}$ is —CH$_2$NH$_2$.
In another embodiment, $R^{11}$ and the carbon atom to which it is attached, form a carbonyl group.

In one embodiment, n and p are each 1 and $R^{10}$, $R^{10a}$ and $R^{11}$ are each H.

In another embodiment, n and p are each 1 and $R^2$, $R^{10}$, $R^{10a}$ and $R^{11}$ are each H In still another embodiment, n and p are each 1 and $R^2$, $R^{3a}$, $R^{10}$, $R^{10a}$ and $R^{11}$ are each H.

In one embodiment, Z is —N—; n and p are each 1; and $R^{10}$, $R^{10a}$ and $R^{11}$ are each H.

In another embodiment, Z is —N—; n and p are each 1; and $R^2$, $R^{10}$, $R^{10a}$ and $R^{11}$ are each H In still another embodiment, Z is —N—; n and p are each 1; and $R^2$, $R^{3a}$, $R^{10}$, $R^{10a}$ and $R^{11}$ are each H.

In one embodiment, Ar is -arylene-.
In another embodiment, Ar is -heteroarylene-.

In another embodiment, Ar is:

In yet another embodiment, Ar is:

In one embodiment, W is —C(R$^4$)$_2$—.
In another embodiment, W is —N(R$^{12}$)—.
In another embodiment, W is —O—.
In still another embodiment, W is —S—.

In one embodiment, W is —C(R$^4$)$_2$— and both R$^4$ groups, together with the common carbon atom to which they are attached, join to form a cycloalkyl group.

In another embodiment, W is —C(R$^4$)$_2$— and both R$^4$ groups, together with the common carbon atom to which they are attached, join to form a heterocyclyl group.

In another embodiment, W is —C(R$^4$)$_2$— and both R$^4$ groups, together with the common carbon atom to which they are attached, join to form a group having the formula:

In one embodiment, W is —C(R$^4$)$_2$—, wherein each R$^4$ group is independently selected from H, -(alkylene)$_m$-NH$_2$, —NH-alkyl, —N(alkyl)$_2$, —C(O)NH$_2$, —OH, —C(O)O-alkyl, 5 or 6 membered heteroaryl or hydroxyalkyl.

In another embodiment, W is —C(R⁴)₂—, wherein each R⁴ group is independently selected from H, -(alkylene)$_m$-NH₂, —NH-alkyl, —N(alkyl)₂ or —C(O)NH₂.

In one embodiment, W is —C(NH₂)(C(O)NH₂)—.
In another embodiment, W is —C(NH₂)(alkyl)-.
In another embodiment, W is —C(NH₂)(CH₃)—.
In still another embodiment, W is —C(NH₂)(—C(O)NHOH)—.
In one embodiment, W is —CH(—NC(O)CF₃)—.
In another embodiment, W is —CH(—NS(O)₂alkyl)-.
In still another embodiment, W is —C(NH₂)(—C(O)NHOH)—.
In one embodiment, W is —CH(—CH₂NH₂)—.
In another embodiment, W is —C(—C(O)NH₂)(—NHalkyl)-.
In another embodiment, W is —CH(—C(O)NH₂)—.
In still another embodiment, W is —CH₂—.
In yet another embodiment, W is —NH—.
In still another embodiment, W is —CH(OH)—.
In a further embodiment, W is —CH(NH₂)—.
In one embodiment, W is —CH(CH₃)—.
In another embodiment, W is —CH(—C(O)CH₃)—.
In another embodiment, W is —C(OH)(alkyl)-.
In another embodiment, W is —C(OH)(-alkylene-OH)—.
In another embodiment, n is 0; p is 1 or 2; Z is —N—; R², R³, R³ª, R¹⁰, R¹⁰ª and R¹¹ are each H; W is —C(R⁴)₂—; and both R⁴ groups, together with the common carbon atom to which they are attached, join to form a group having the formula:

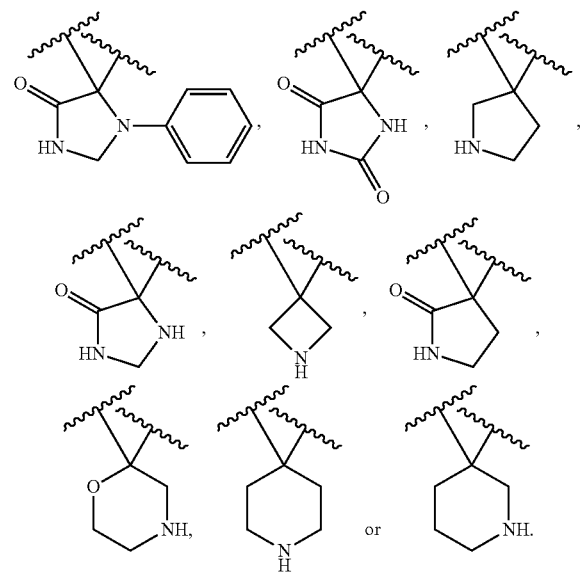

In one embodiment, n is 0; p is 1 or 2; Z is —N—; R², R³, R³ª, R¹⁰, R¹⁰ª and R¹¹ are each H; W is —C(R⁴)₂—, wherein each R⁴ group is independently selected from H, -(alkylene)$_m$-NH₂, —NH-alkyl, —N(alkyl)₂, —C(O)NH₂, —OH, —C(O)O-alkyl, 5 or 6 membered heteroaryl or hydroxyalkyl.

In another embodiment, n is 0; p is 1 or 2; Z is —N—; R², R³, R³ª, R¹⁰, R¹⁰ª and R¹¹ are each H; W is —C(R⁴)₂—, wherein each R⁴ group is independently selected from H, -(alkylene)$_m$-NH₂, —NH-alkyl, —N(alkyl)₂ or —C(O)NH₂.

In one embodiment, Y is —H.
In another embodiment, Y is -halo, -alkyl or —CN.
In another embodiment, Y is methyl.
In one embodiment, Z is —C(R⁷)—.

In another embodiment, Z is —C— and the optional and additional bond is present.
In another embodiment, Z is —CH—.
In still another embodiment, Z is —C(alkyl)-.
In yet another embodiment, Z is —C(OH)—.
In another embodiment, Z is —C(—O-alkyl)-.
In still another embodiment, Z is —C(—CF₃)—.
In a further embodiment, Z is —N—.
In one embodiment, n is 0.
In another embodiment, n is 1 and p is 1
In another embodiment, n is 2 and p is 1.
In one embodiment, n is 0, W is —CH₂— and Z is —N—.
In another embodiment, n is 1, W is —CH₂— and Z is —N—.
In another embodiment, n is 1, W is —NH— and Z is —N—.
In another embodiment, n is 0, W is —CH₂—, Z is —N—, R³ is —H and R³ª is —H.
In still another embodiment, n is 1, W is —C(NH₂)(C(O)NH₂)—, Z is —N—, R³ is —H and R³ª is —H.
In yet another embodiment, n is 1, W is —CH₂—, Z is —N—, R³ is —H and R³ª is —NH₂.
In another embodiment, n is 1, W is —CH₂—, Z is —N—, R³ is —H and R³ª is -β-NH₂.
In a further embodiment, n is 0, W is —CH₂—, Z is —N—, R³ is —H and R³ª is —NH₂.
In a further embodiment, n is 0, W is —CH₂—, Z is —N—, R³ is —H and R³ª is -α-NH₂.
In another embodiment, n is 1, W is —CH(NH₂)—, Z is —N—, R³ is —H and R³ª is —H.
In another embodiment, n is 1, W is —CH(OH)—, Z is —N—, R³ is —H and R³ª is —H.
In still another embodiment, n is 1, W is —CH(NH₂)(alkyl)-, Z is —N—, R³ is —H and R³ª is —H.
In one embodiment, Z is —N—.
In another embodiment, Y is —H and Z is —N—.
In still another embodiment, R² is —H, R³ is —H, R³ª is —H, Y is —H and Z is —N—.
In another embodiment, R² is -alkyl, R³ is —H, Y is —H and Z is —N—.
In yet another embodiment, R² is —CH₃, R³ is —H, Y is —H and Z is —N—.
In one embodiment, Ar is phenyl, R³ is —H and Z is —CH—.
In another embodiment, Ar is pyridyl, R³ is —H and Z is —CH—.
In specific embodiments, the group

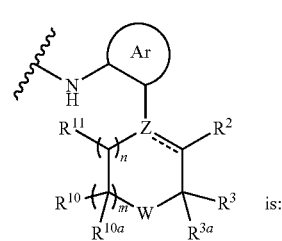

is:

27
-continued
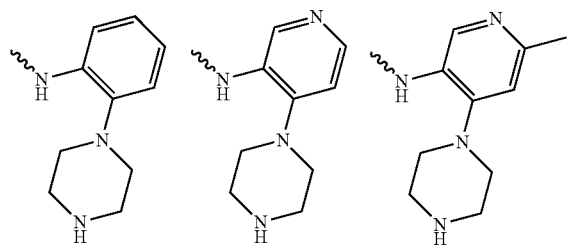
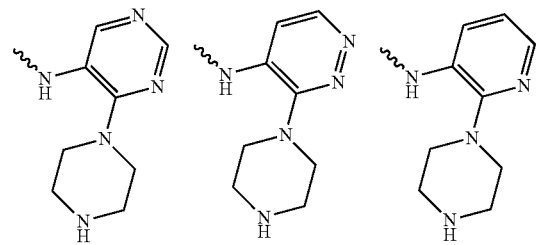
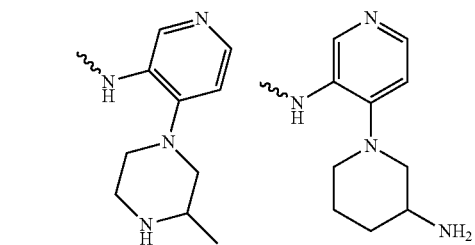
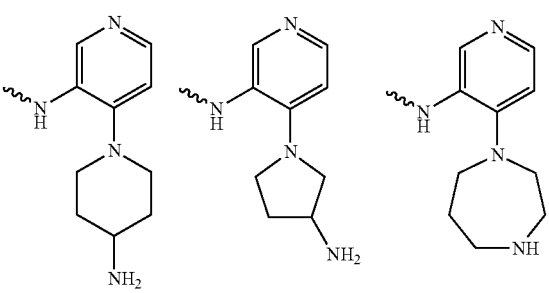
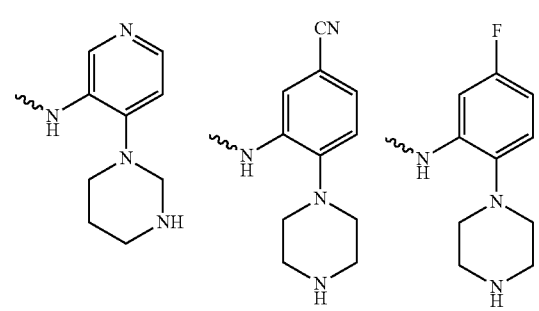
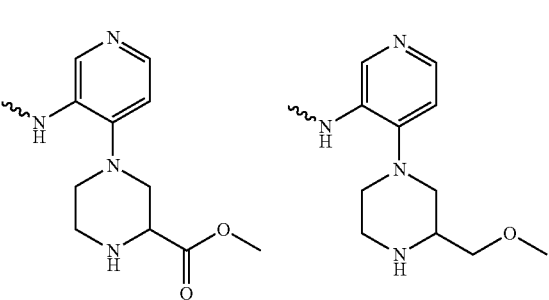
28
-continued
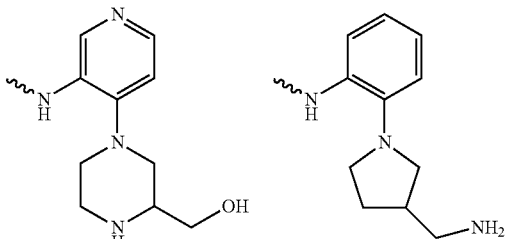
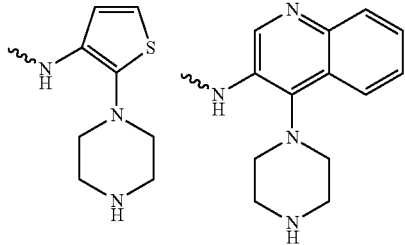
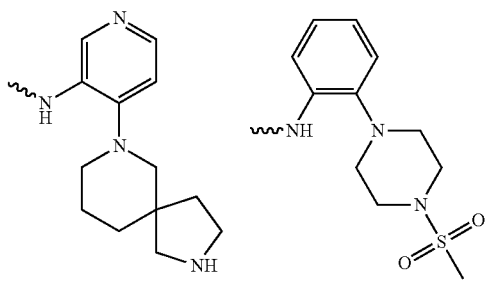
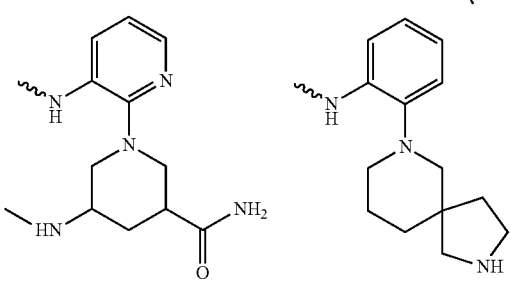
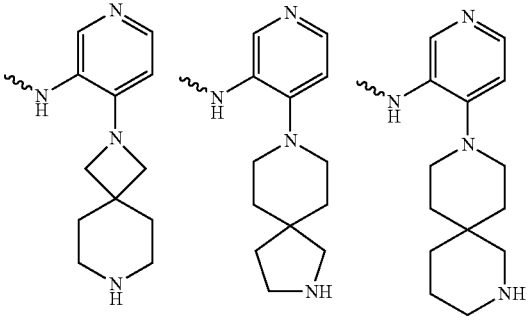
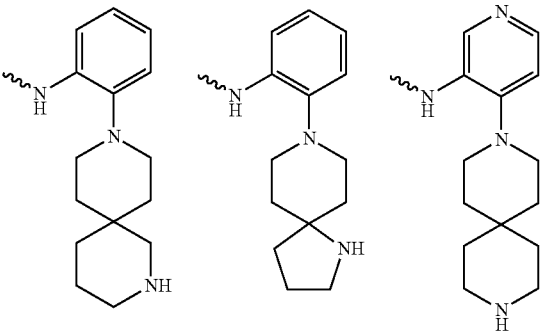

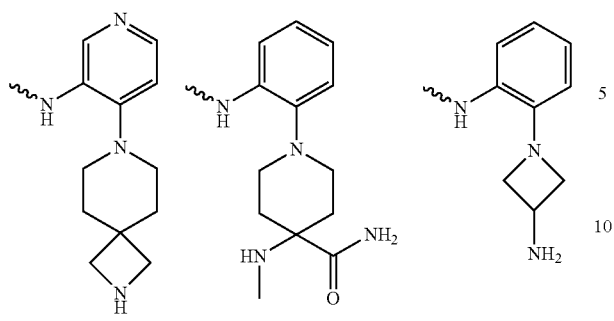
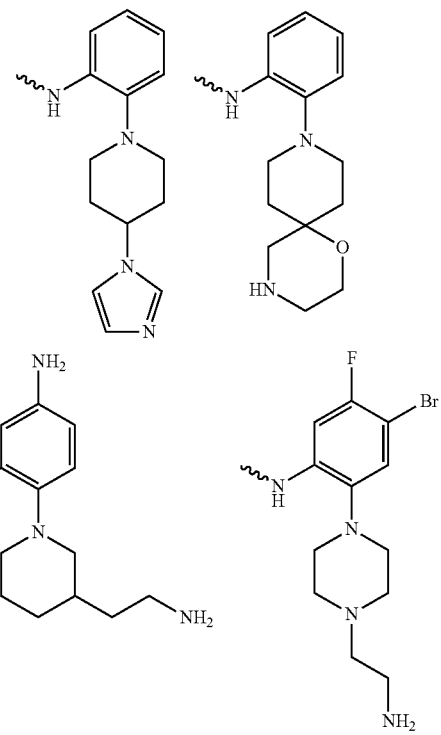
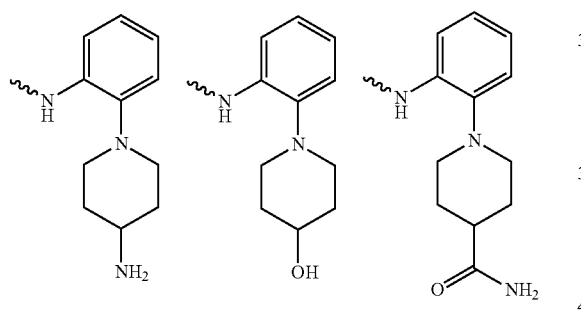
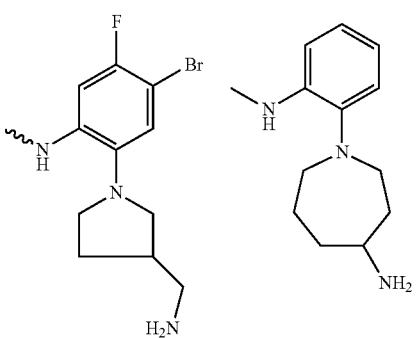
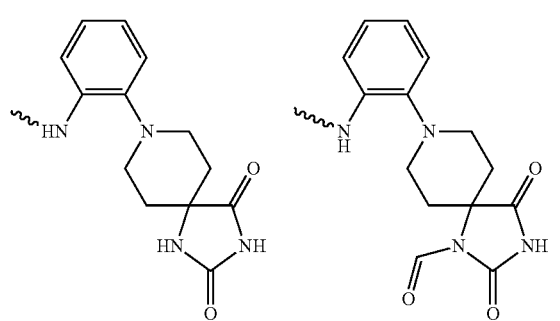
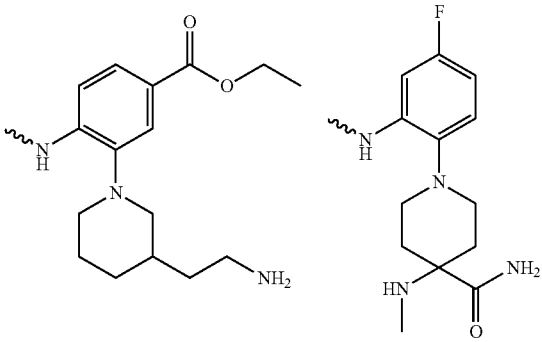
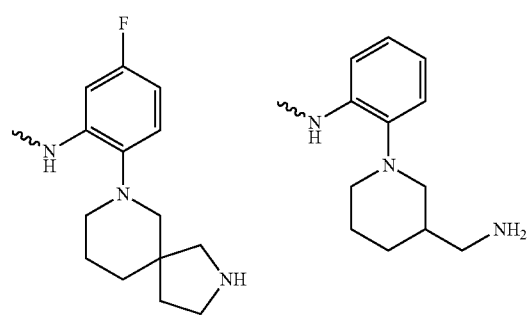
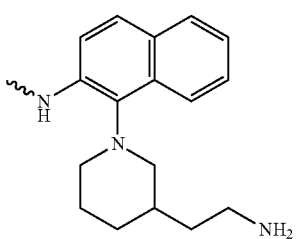

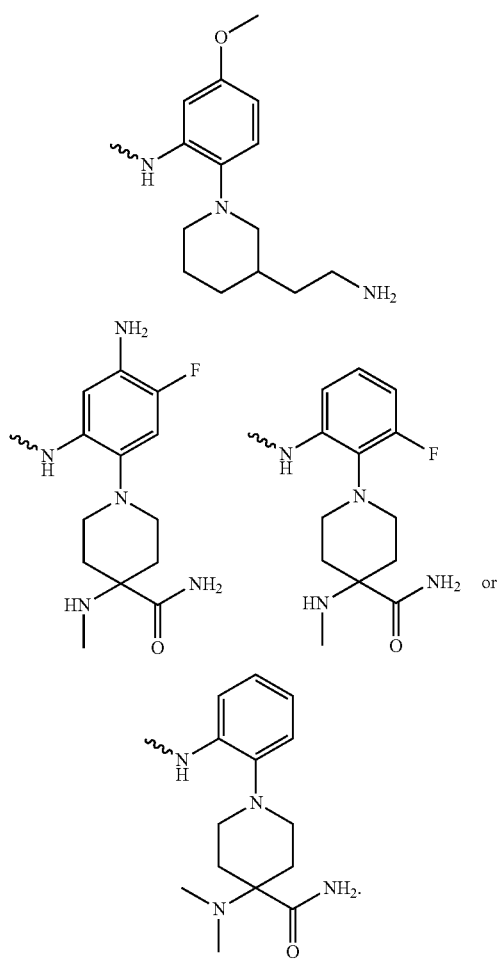
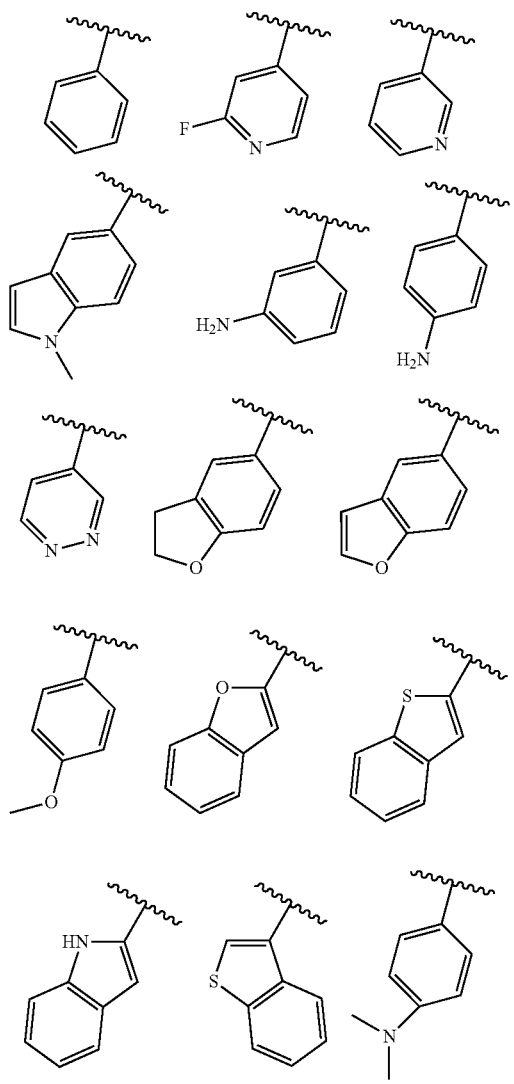
In one embodiment, R¹ is:
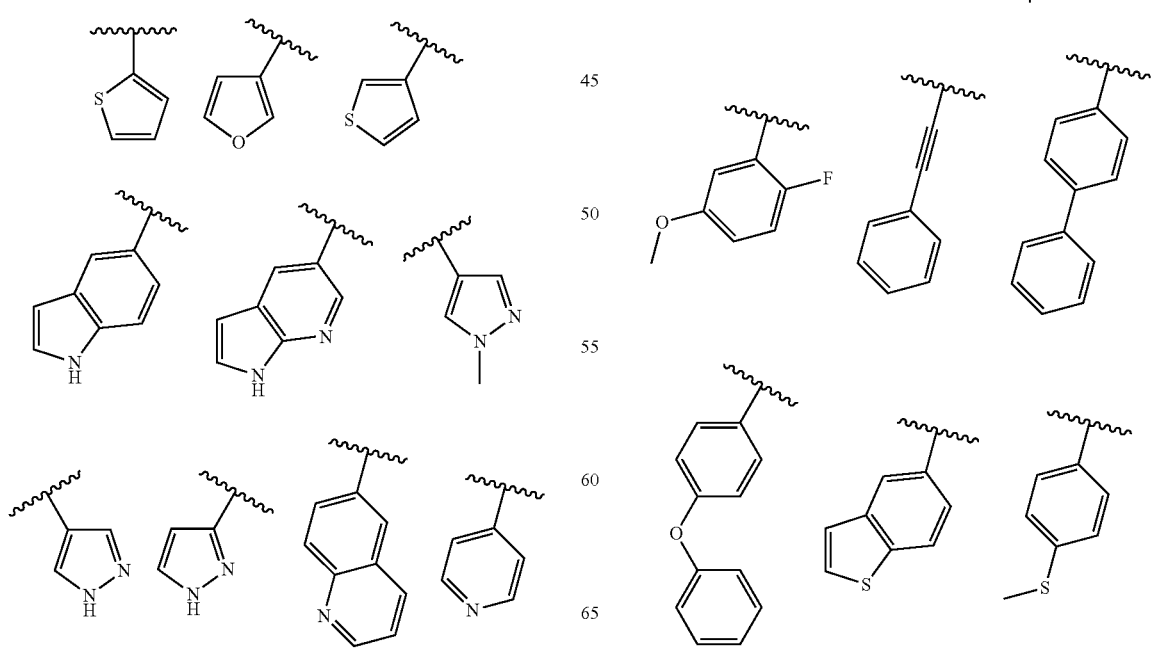

-continued
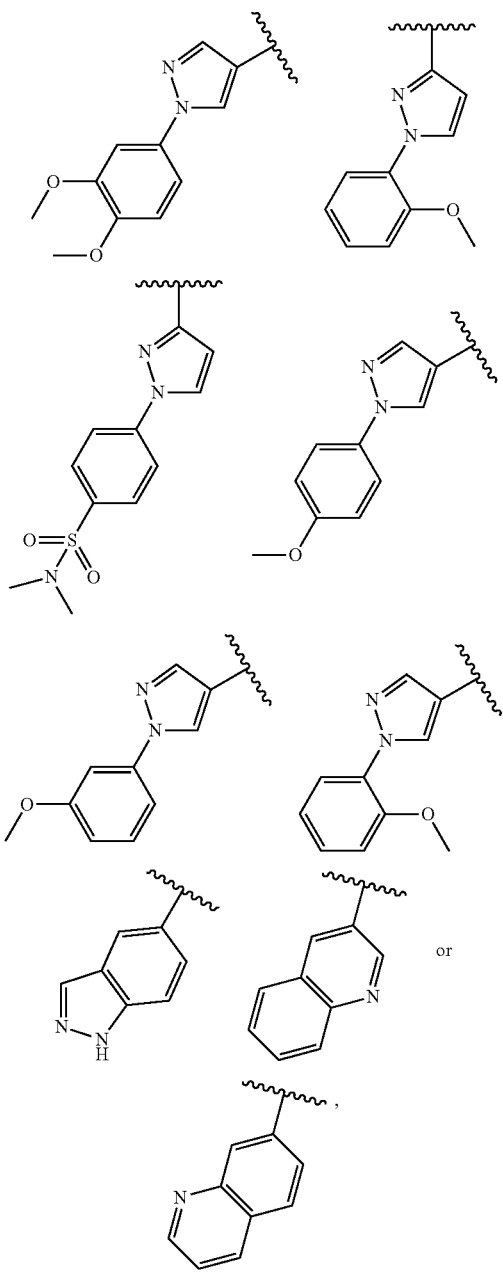
and the group
is:
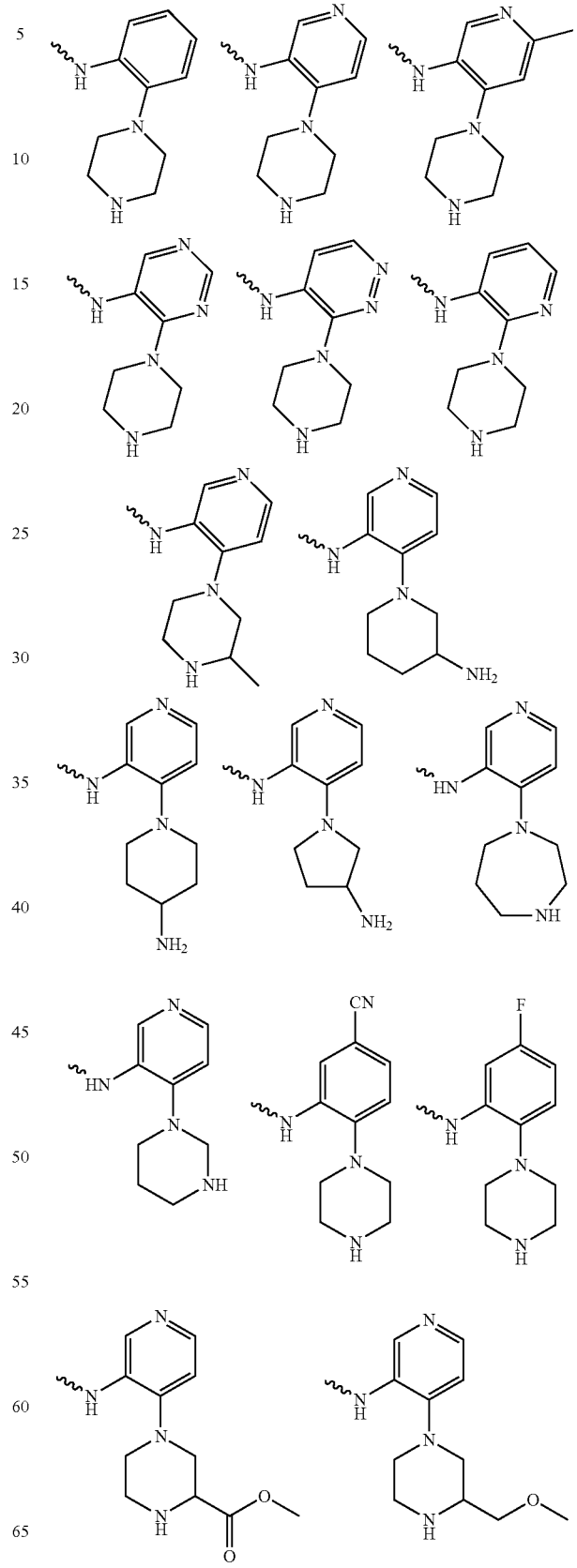

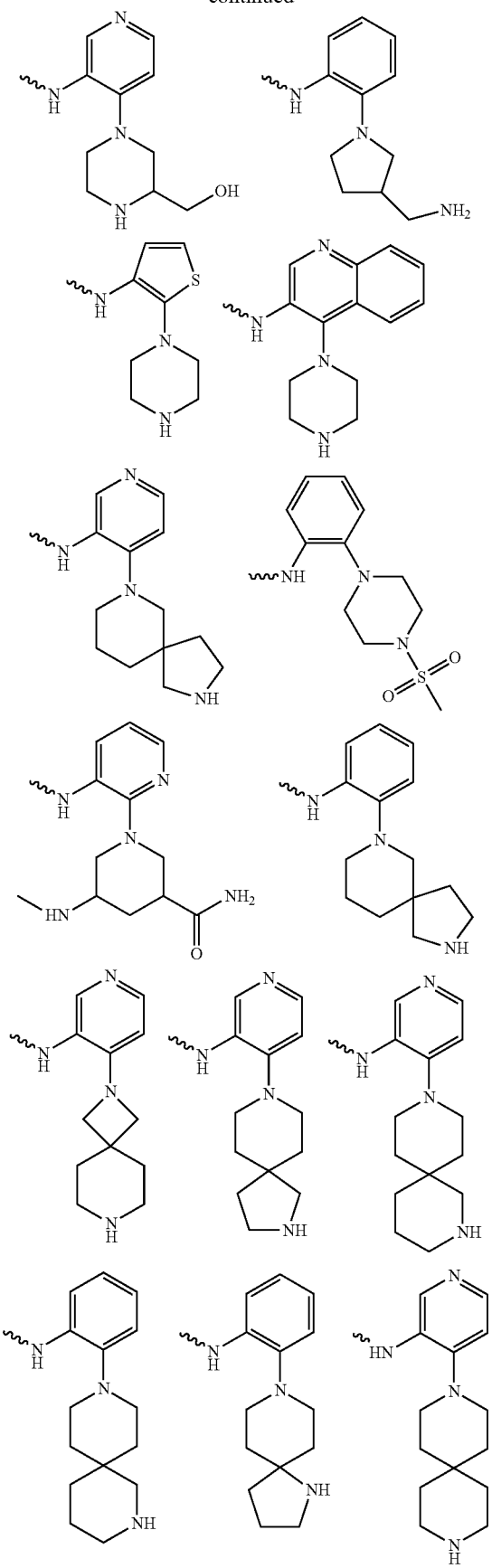
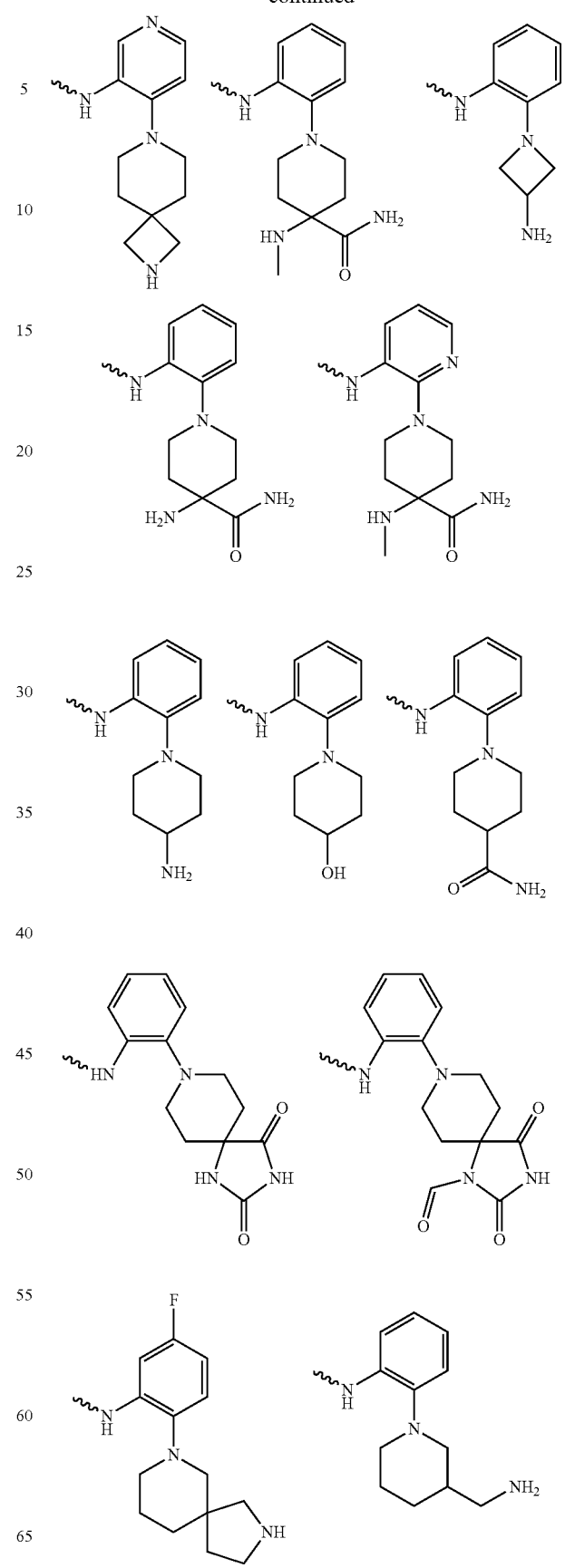

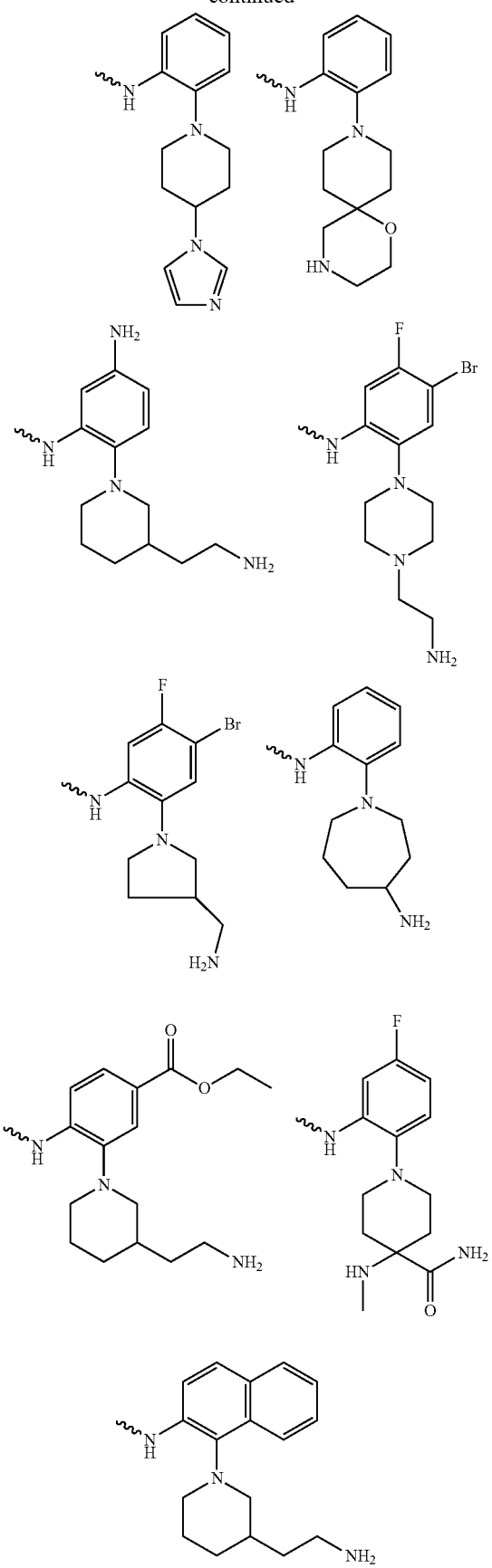
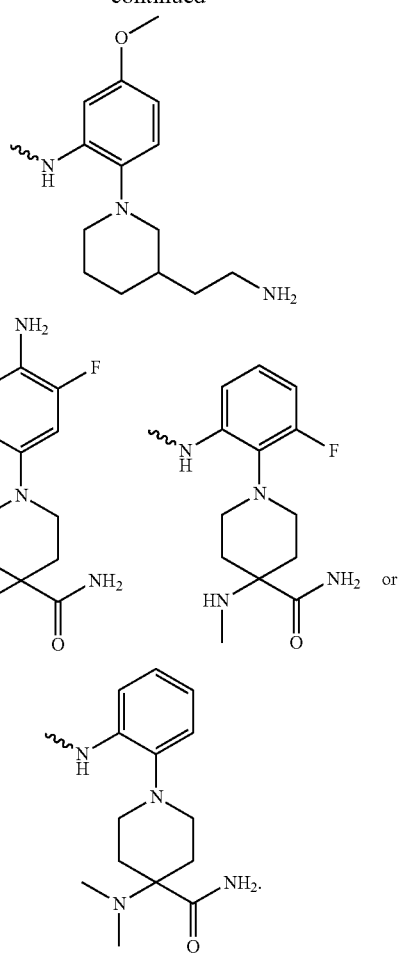

In one embodiment, the present invention provides a compound of formula (I) or a pharmaceutically acceptable salt, solvate, ester, prodrug or stereoisomer thereof, wherein $R^1$, $R^2$, $R^3$, $R^{3a}$, $R^{10}$, $R^{10a}$, $R^{11}$, Ar, n, p, W, X, Y and Z are selected independently of each other.

In one embodiment, the Anilinopiperazine Derivatives have the formula (IA):

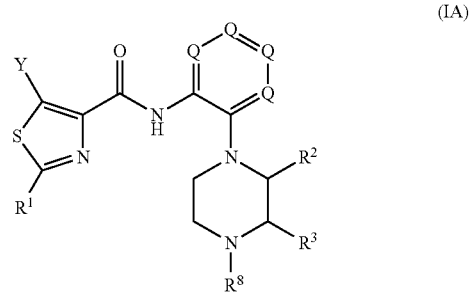

wherein $R^1$, $R^2$ and $R^3$ are is as defined above for the compounds of formula (I);

each Q is independently CH or N, such at least three occurrences of Q must be CH; and $R^8$ is H, alkyl or —C(O)-alkyl.

In one embodiment, $R^1$ is aryl.
In one embodiment, $R^1$ is phenyl.
In one embodiment, $R^1$ is alkynyl.
In another embodiment, $R^1$ is -alkynylene-aryl.
In another embodiment, $R^1$ is heteroaryl.
In still another embodiment, $R^1$ is benzofused heteroaryl.
In yet another embodiment, $R^1$ is heterocyclyl.
In a further embodiment, $R^1$ is benzofused heterocyclyl.
In one embodiment, $R^1$ is heterocyclenyl.
In another embodiment, $R^1$ is benzofused heterocyclenyl.
In one embodiment, $R^8$ is H.
In another embodiment, $R^8$ is alkyl.
In still another embodiment, $R^8$ is —C(O)alkyl.
In another embodiment, $R^8$ is methyl.
In still another embodiment, $R^8$ is —C(O)CH$_3$.

In one embodiment, the present invention provides a compound of formula (IA) or a pharmaceutically acceptable salt, solvate, ester, prodrug or stereoisomer thereof, wherein $R^1$, $R^2$, $R^3$, $R^8$, Y, and each occurrence of Q are selected independently of each other.

In one embodiment, the Anilinopiperazine Derivatives have the formula (IB):

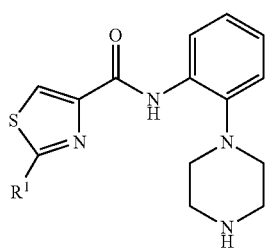

(IB)

wherein $R^1$ is as defined above for the compounds of formula (I);
In one embodiment, $R^1$ is aryl.
In one embodiment, $R^1$ is phenyl.
In one embodiment, $R^1$ is alkynyl.
In another embodiment, $R^1$ is -alkynylene-aryl.
In another embodiment, $R^1$ is heteroaryl.
In still another embodiment, $R^1$ is benzofused heteroaryl.
In yet another embodiment, $R^1$ is heterocyclyl.
In a further embodiment, $R^1$ is benzofused heterocyclyl.
In one embodiment, $R^1$ is heterocyclenyl.
In another embodiment, $R^1$ is benzofused heterocyclenyl.

Additional Illustrative examples of Anilinopiperazine Derivatives of formula (I) include, but are not limited to the compounds of formula (IB) listed below:

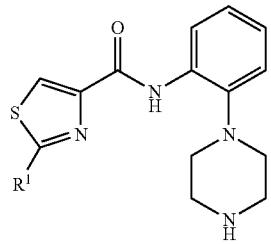

(IB)

| Compound | $R^1$ |
|---|---|
| 1 | 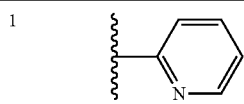 |
| 2 | H |
| 3 | methyl |
| 4 | 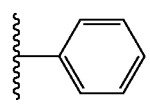 |
| 5 | Br |
| 6 | 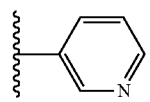 [SMILES: *c1cccnc1] |
| 7 | 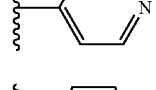 |
| 8 | 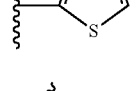 |
| 9 | 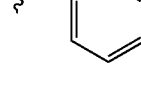 |
| 10 | 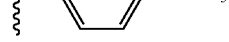 |
| 12 | 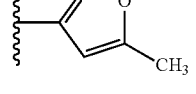 |
| 16 | 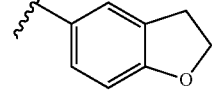 |
| 29 | 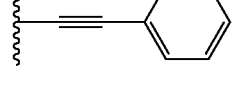 |

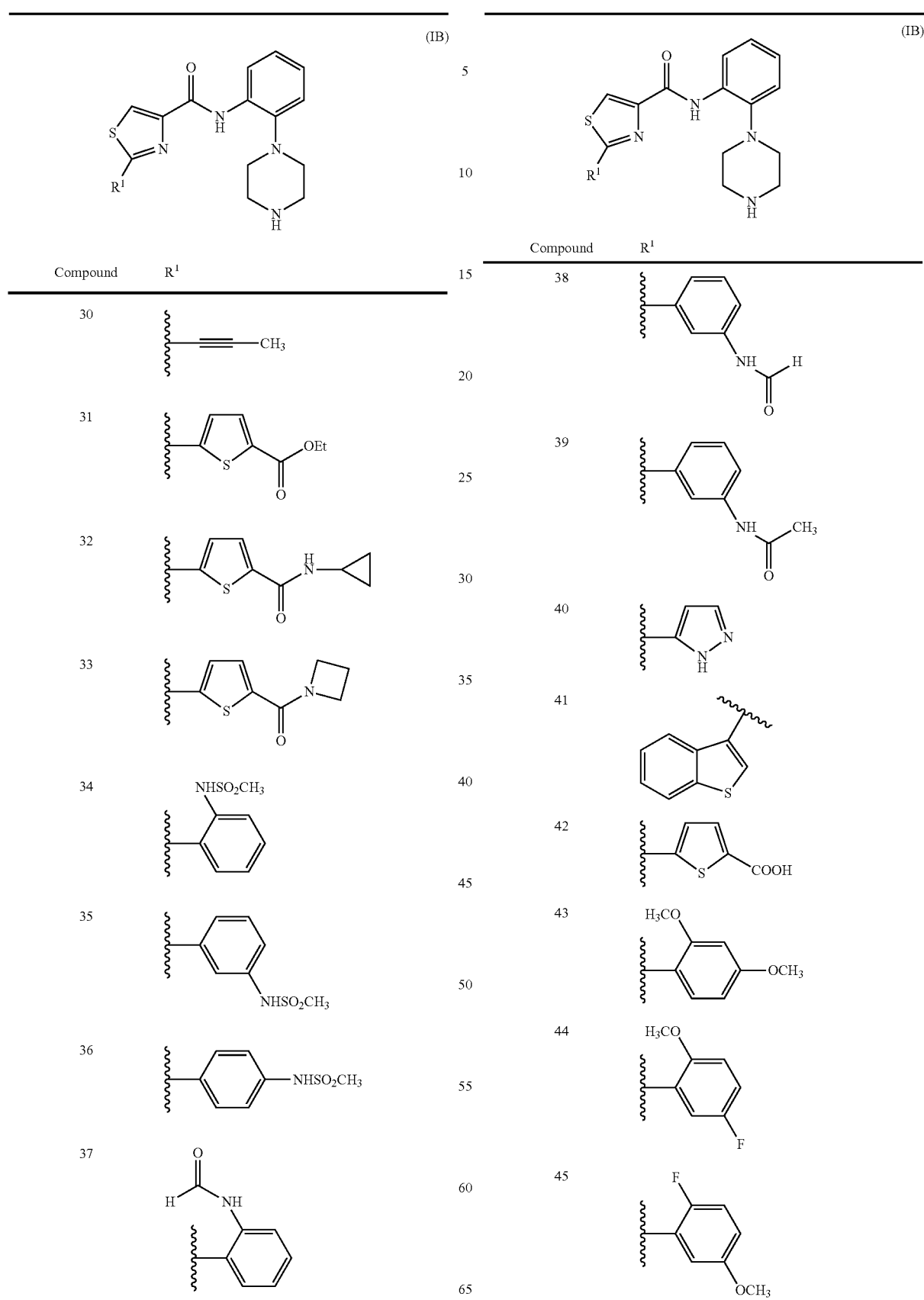

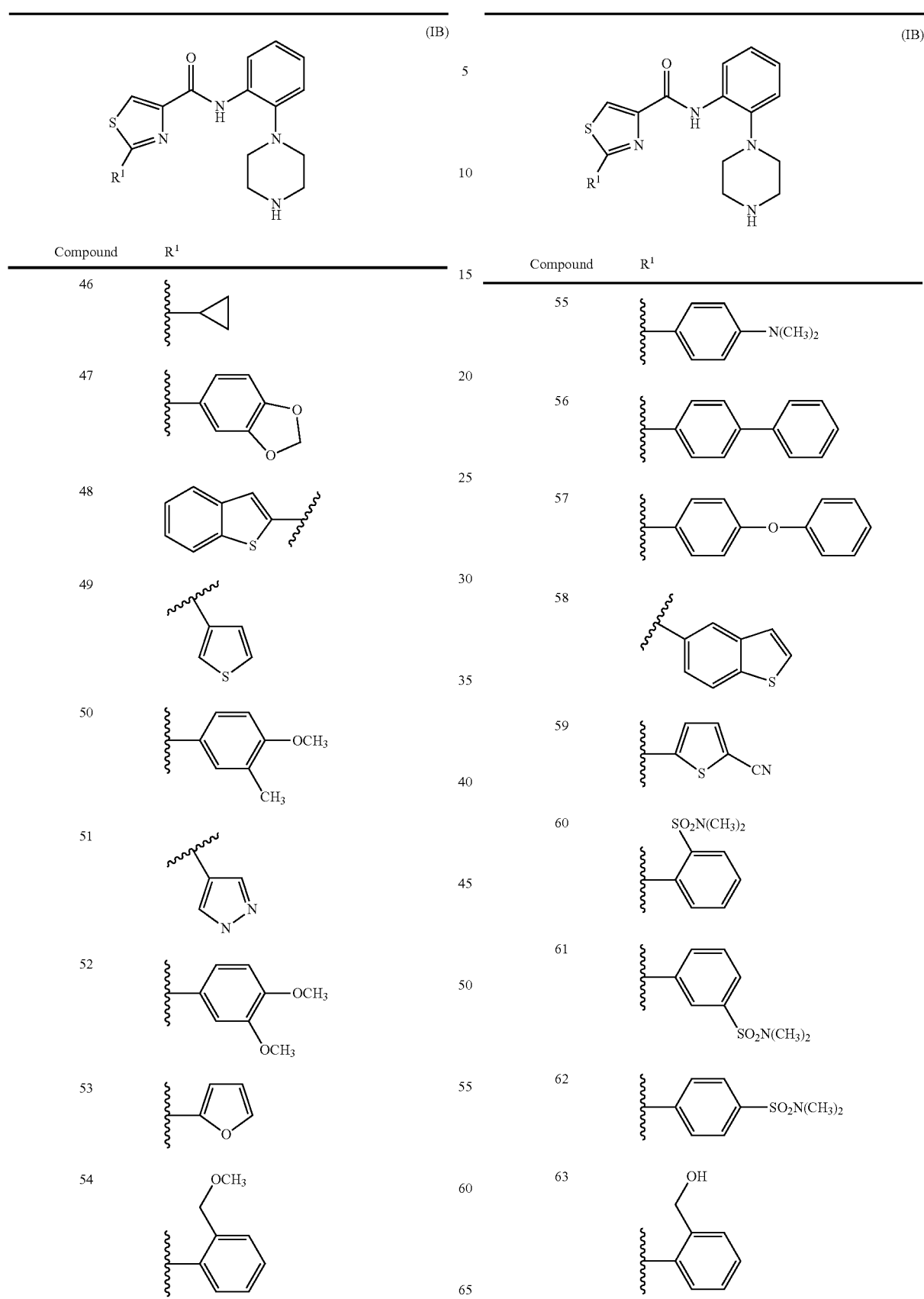

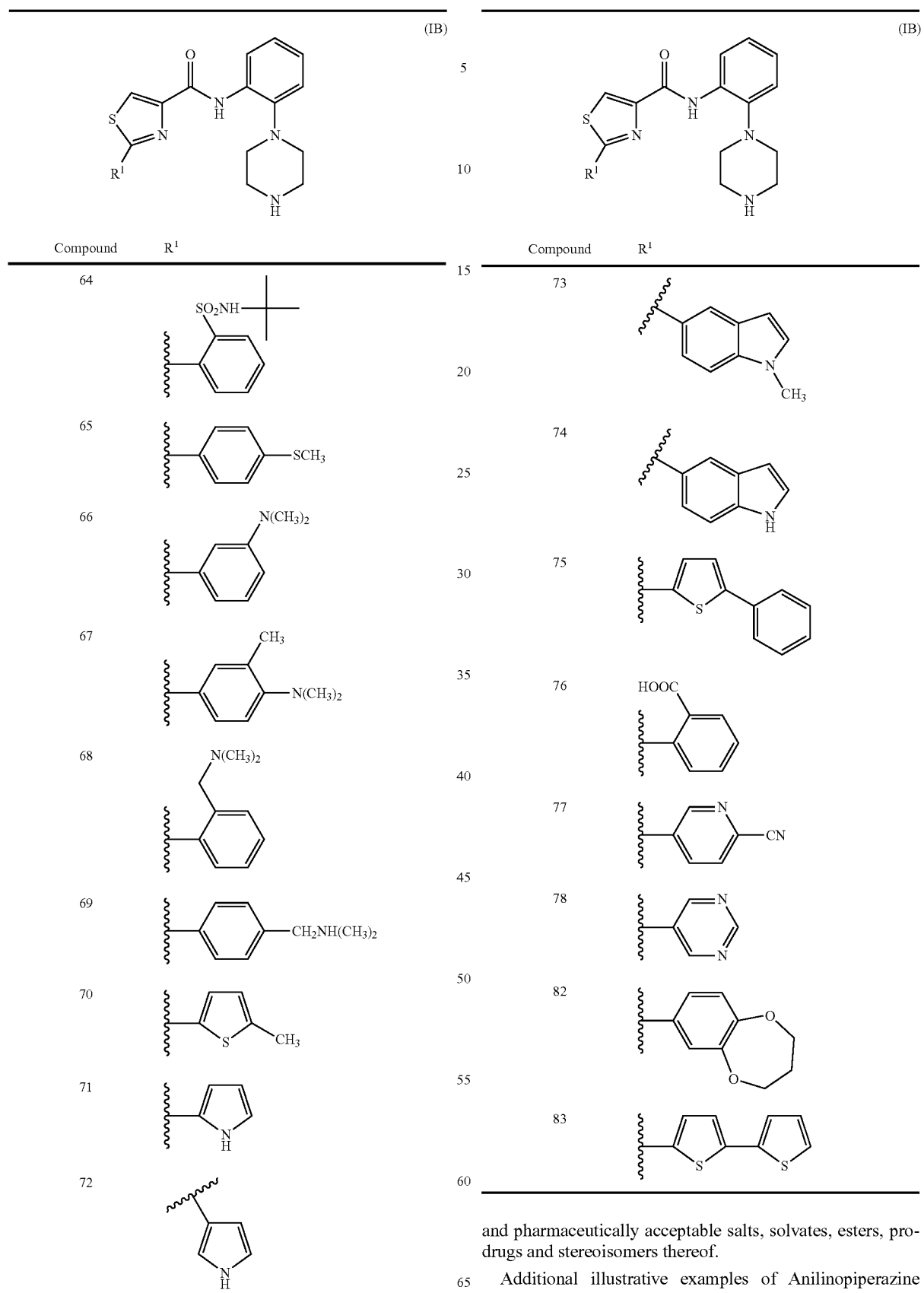
and pharmaceutically acceptable salts, solvates, esters, prodrugs and stereoisomers thereof.
Additional illustrative examples of Anilinopiperazine Derivatives of formula (I) include, but are not limited to the following compounds:

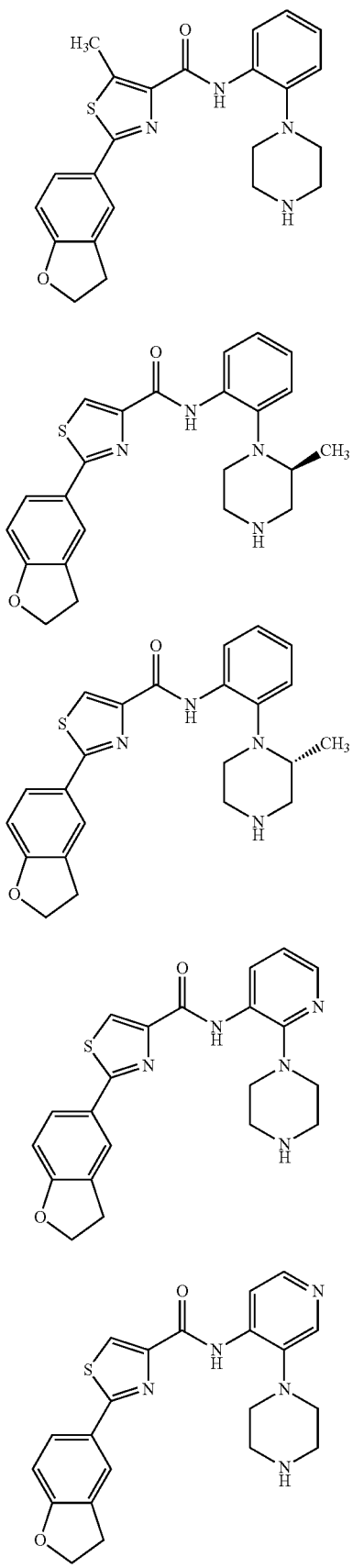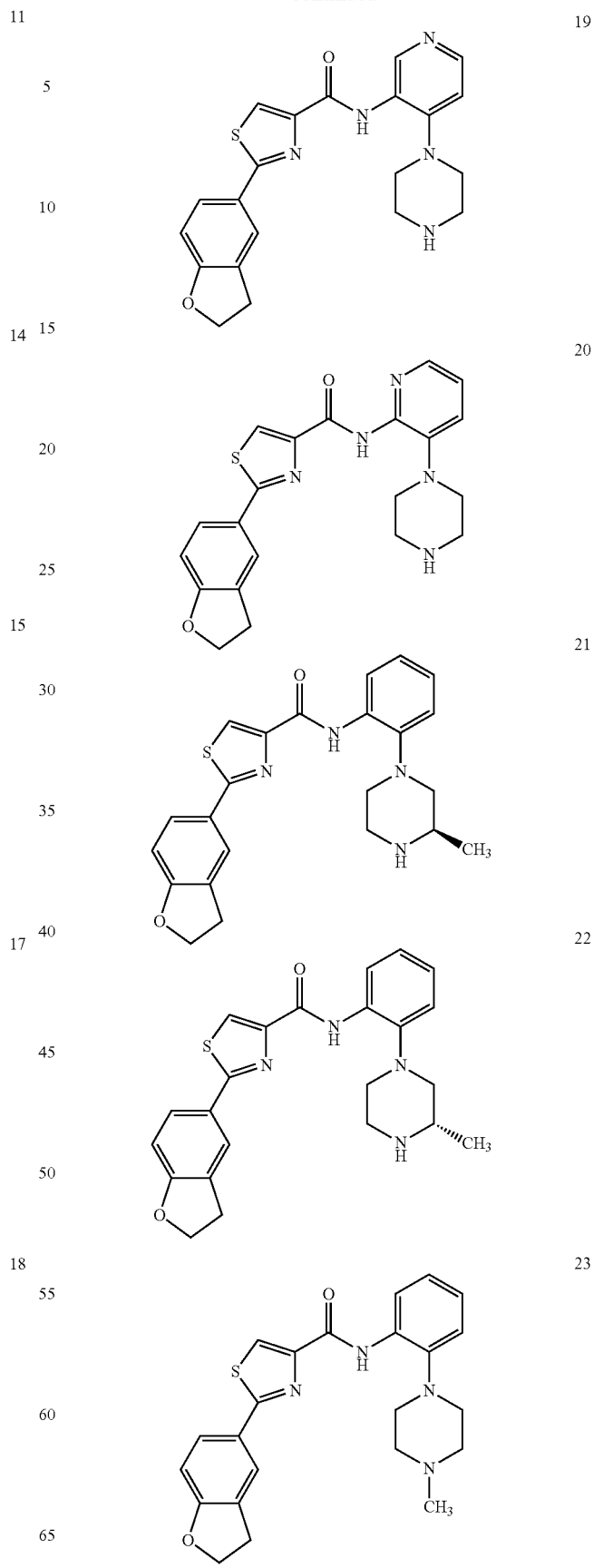

-continued
24
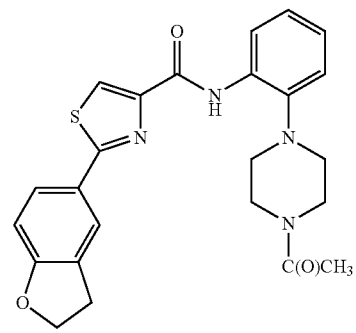
25
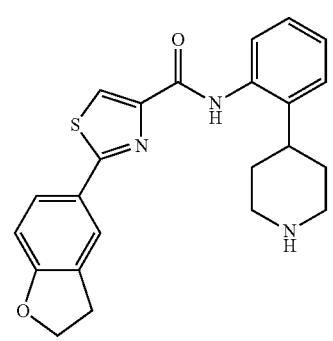
26
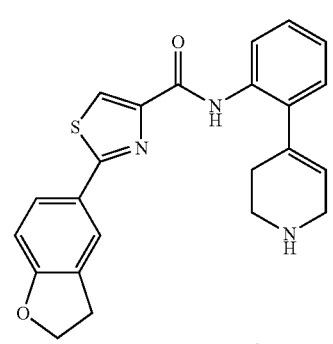
27
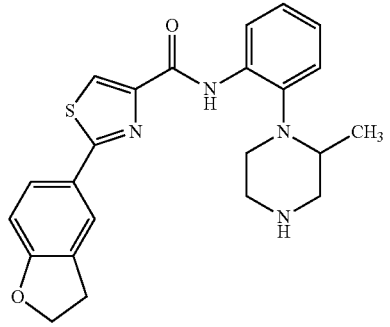
28
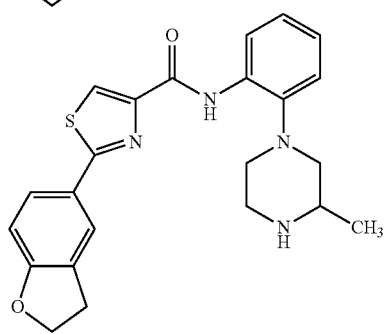
-continued
79
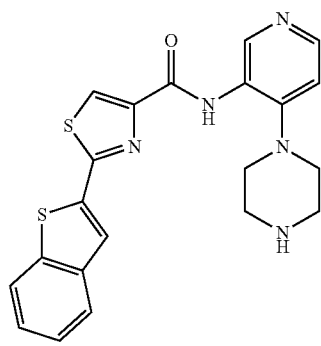
80
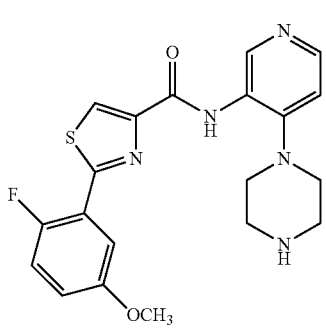
81
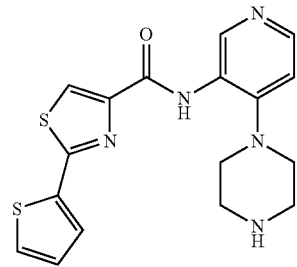
84
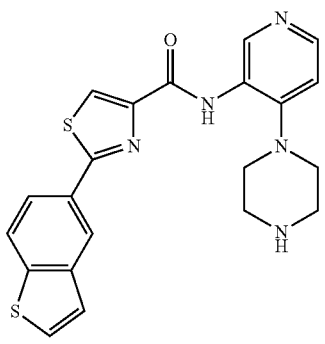
85
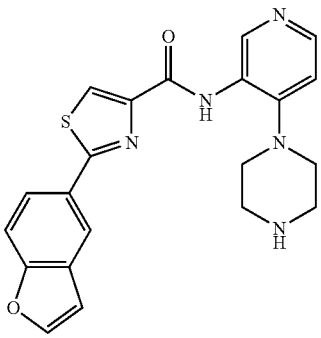

| No. | Structure |
|---|---|
| 86 | 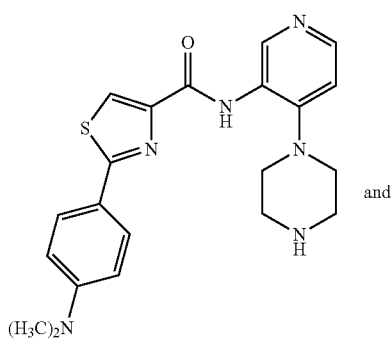 and |
| 87 | 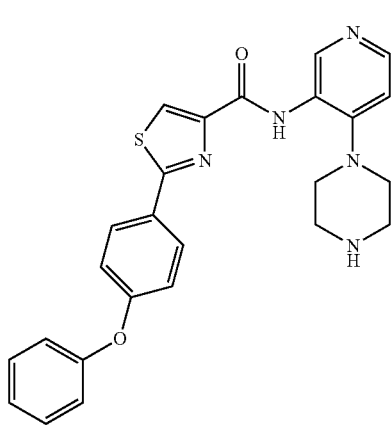 |
and pharmaceutically acceptable salts, solvates, esters, prodrugs and stereoisomers thereof.
Further non-limiting examples of Anilinopiperazine Derivatives of formula (I) include the following compounds:
| No. | Structure |
|---|---|
| 88 | 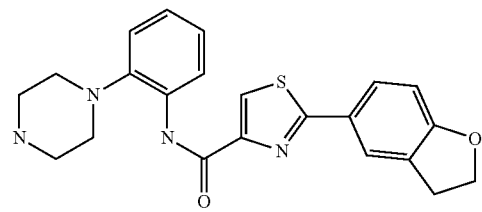 [SMILES: O=C(Nc1ccccc1N1CCNCC1)c1csc(-c2ccc3c(c2)CCO3)n1] |
| 89 | 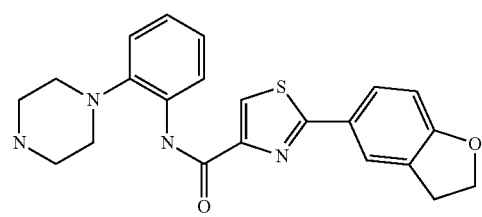 [SMILES: O=C(Nc1ccccc1N1CCNCC1)c1csc(-c2ccc3c(c2)CCO3)n1] |
| 90 | 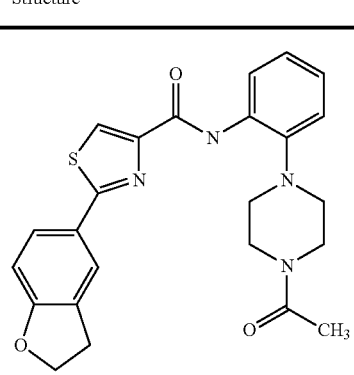 |
| 91 | 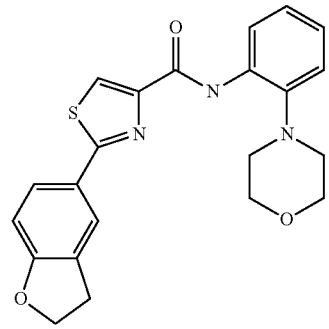 [SMILES: O=C(Nc1ccccc1N1CCOCC1)c1csc(-c2ccc3c(c2)CCO3)n1] |
| 92 | 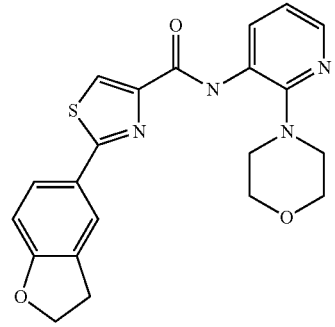 |
| 93 | 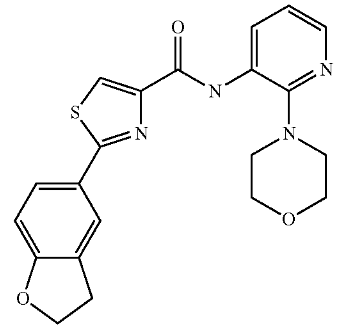 [SMILES: O=C(Nc1cccnc1N1CCOCC1)c1csc(-c2ccc3c(c2)CCO3)n1] |

| No. | Structure |
|---|---|
| 94 | 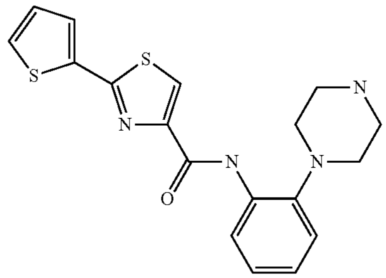 [SMILES: O=C(Nc1ccccc1N1CCNCC1)c1csc(-c2cccs2)n1] |
| 95 | 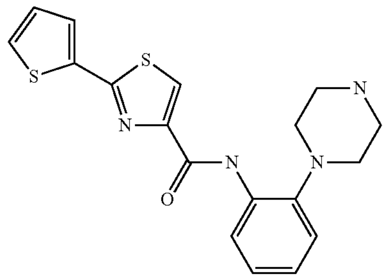 [SMILES: O=C(Nc1ccccc1N1CCNCC1)c1csc(-c2cccs2)n1] |
| 96 | 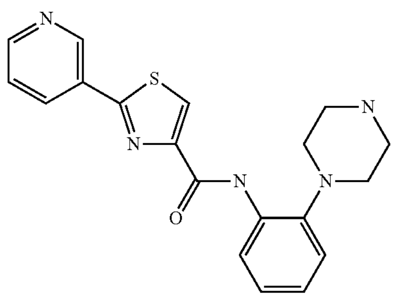 [SMILES: O=C(Nc1ccccc1N1CCNCC1)c1csc(-c2cccnc2)n1] |
| 97 | 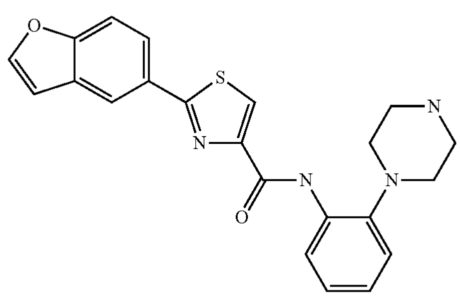 [SMILES: O=C(Nc1ccccc1N1CCNCC1)c1csc(-c2ccc3occc3c2)n1] |
| 98 | 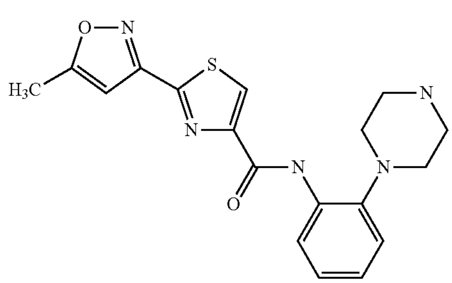 [SMILES: Cc1cc(-c2nc(C(=O)Nc3ccccc3N3CCNCC3)cs2)no1] |
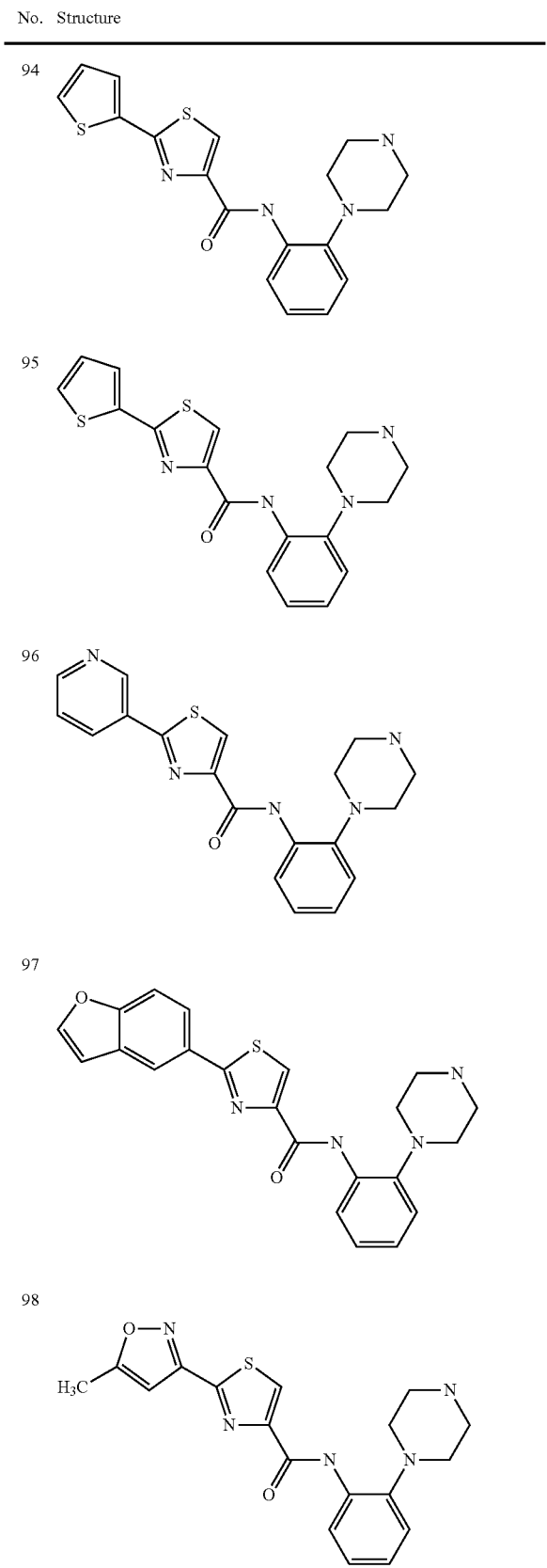
| No. | Structure |
|---|---|
| 99 | 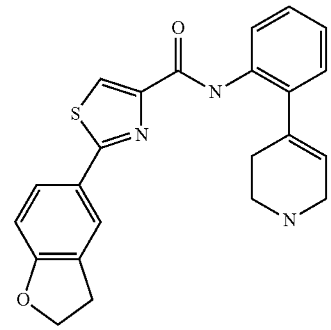 [SMILES: O=C(Nc1ccccc1C1=CCNCC1)c1csc(-c2ccc3c(c2)CCO3)n1] |
| 100 | 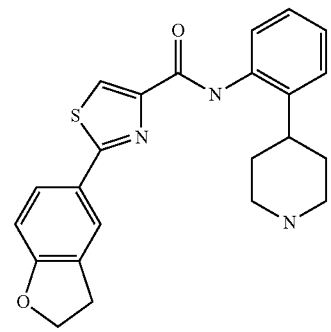 [SMILES: O=C(Nc1ccccc1C1CCNCC1)c1csc(-c2ccc3c(c2)CCO3)n1] |
| 101 | 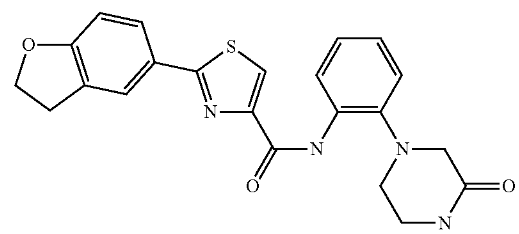 [SMILES: O=C1CN(c2ccccc2NC(=O)c2csc(-c3ccc4c(c3)CCO4)n2)CCN1] |
| 102 | 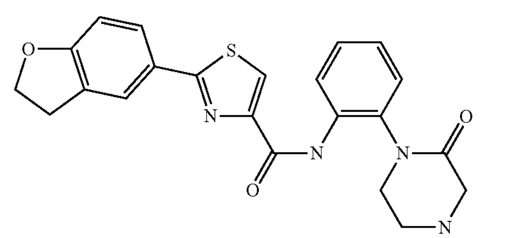 [SMILES: O=C(Nc1ccccc1N1CCNCC1=O)c1csc(-c2ccc3c(c2)CCO3)n1] |
| 103 | 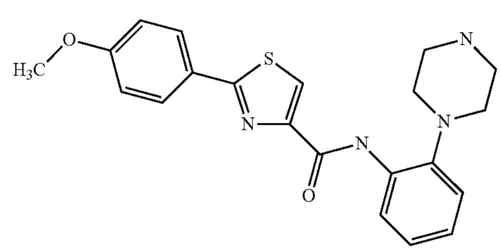 [SMILES: COc1ccc(-c2nc(C(=O)Nc3ccccc3N3CCNCC3)cs2)cc1] |
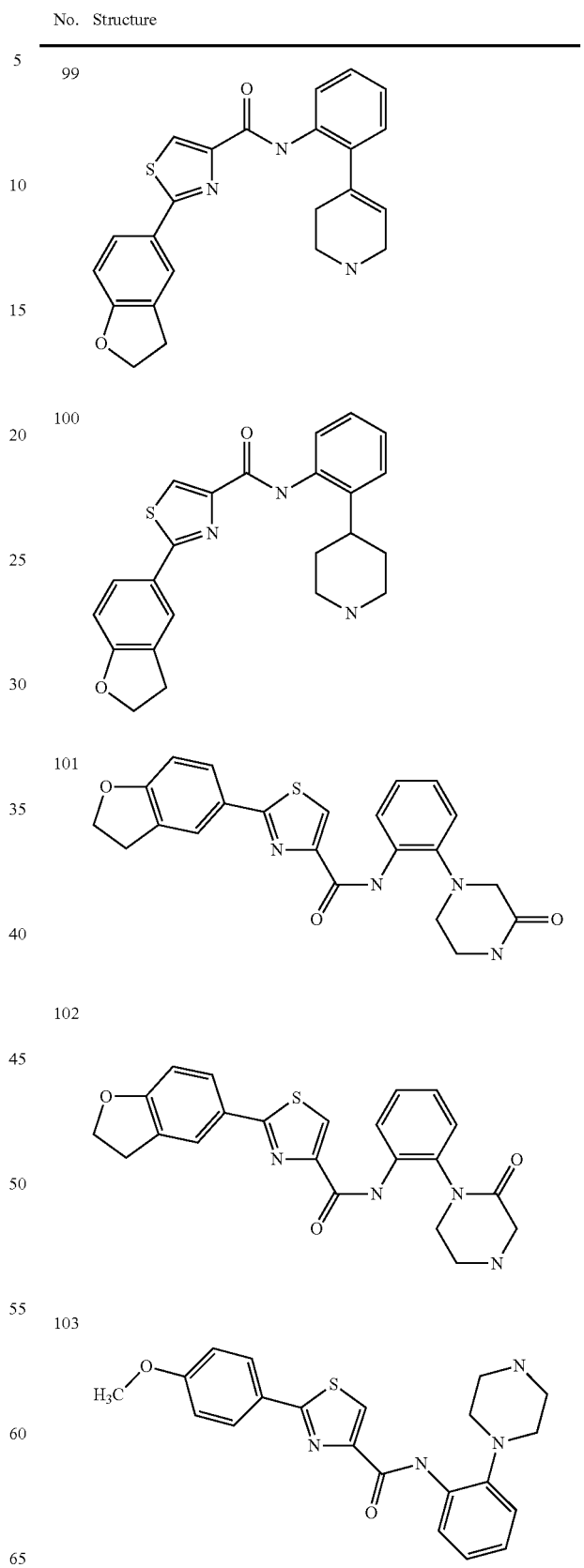

| No. | Structure |
|---|---|
| 104 | 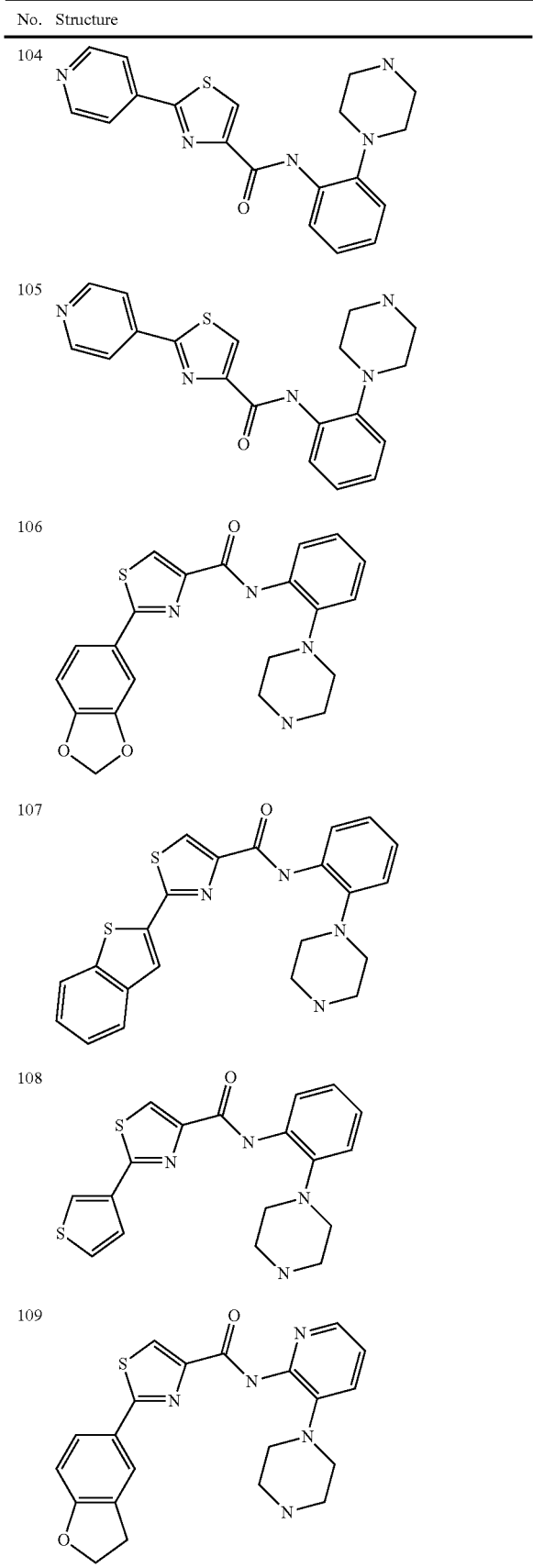 |
| 105 | |
| 106 | |
| 107 | |
| 108 | |
| 109 | |
| No. | Structure |
|---|---|
| 110 | 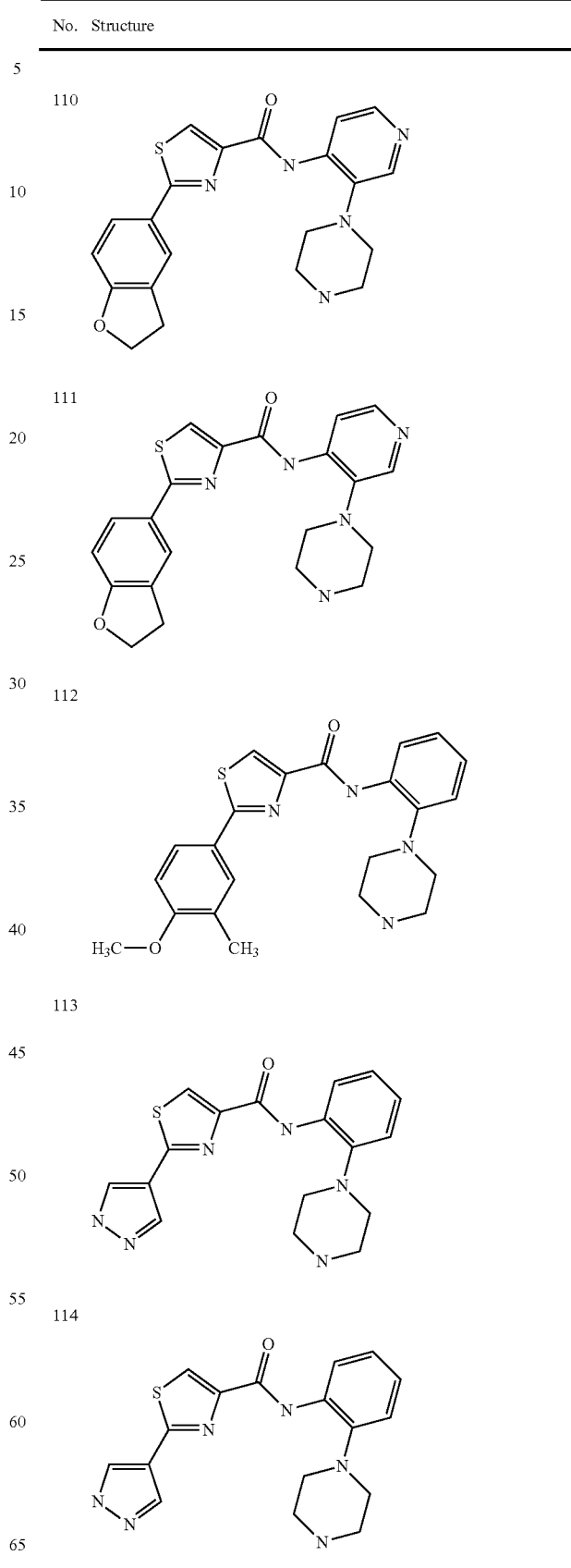 |
| 111 | |
| 112 | |
| 113 | |
| 114 | |

| No. | Structure |
|---|---|
| 115 | 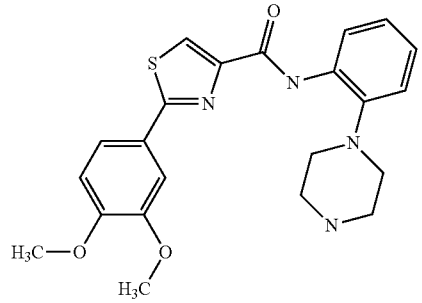 [SMILES: COc1ccc(-c2nc(C(=O)Nc3ccccc3N3CCNCC3)cs2)cc1OC] |
| 116 | 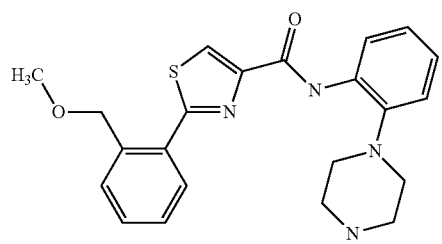 [SMILES: COCc1ccccc1-c1nc(C(=O)Nc2ccccc2N2CCNCC2)cs1] |
| 117 | 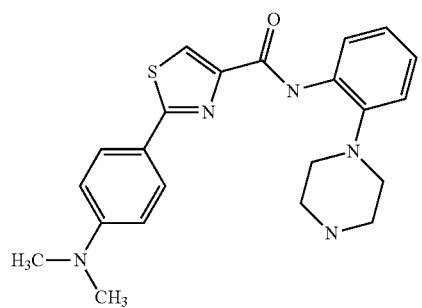 [SMILES: CN(C)c1ccc(-c2nc(C(=O)Nc3ccccc3N3CCNCC3)cs2)cc1] |
| 118 | 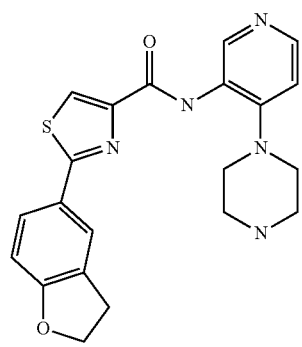 [SMILES: O=C(Nc1cnccc1N1CCNCC1)c1csc(-c2ccc3c(c2)CCO3)n1] |
| 119 | 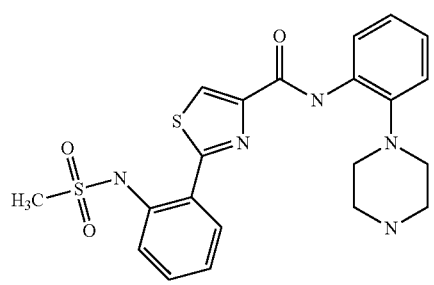 [SMILES: CS(=O)(=O)Nc1ccccc1-c1nc(C(=O)Nc2ccccc2N2CCNCC2)cs1] |
| No. | Structure |
|---|---|
| 120 | 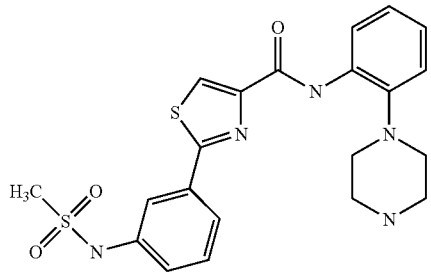 [SMILES: CS(=O)(=O)Nc1cccc(-c2nc(C(=O)Nc3ccccc3N3CCNCC3)cs2)c1] |
| 121 | 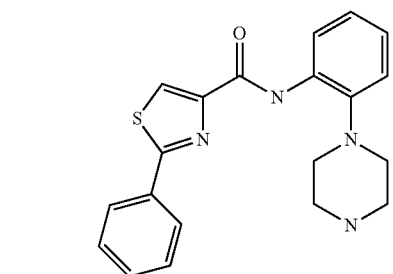 |
| 122 | 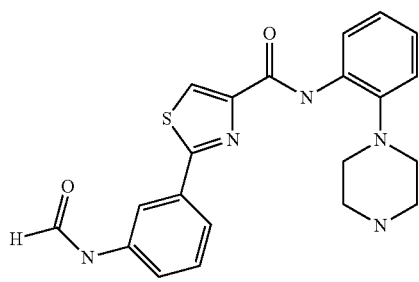 [SMILES: O=CNc1cccc(-c2nc(C(=O)Nc3ccccc3N3CCNCC3)cs2)c1] |
| 123 | 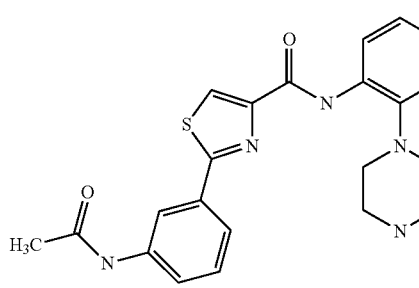 |
| 124 | 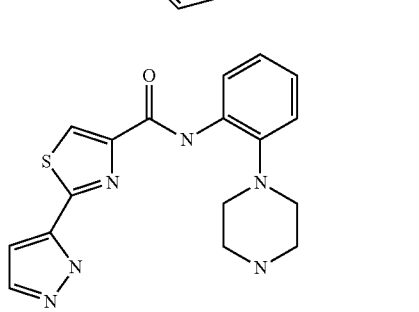 |

| No. | Structure |
|---|---|
| 125 | 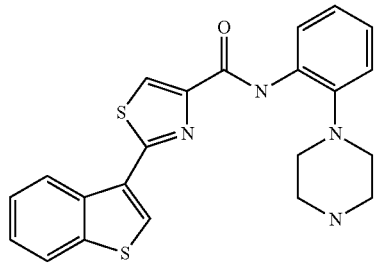 [SMILES: O=C(Nc1ccccc1N1CCNCC1)c1csc(-c2csc3ccccc23)n1] |
| 126 | 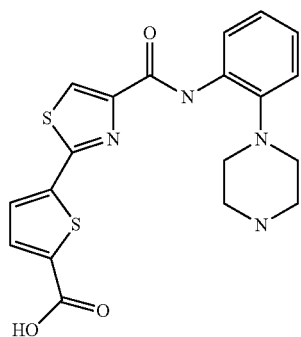 [SMILES: O=C(Nc1ccccc1N1CCNCC1)c1csc(-c2ccc(C(=O)O)s2)n1] |
| 127 | 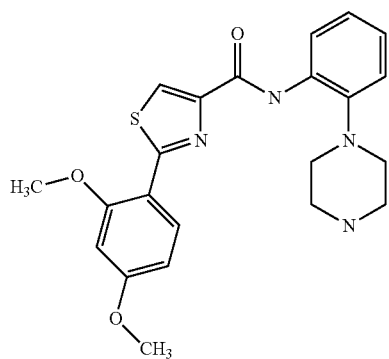 [SMILES: COc1ccc(-c2nc(C(=O)Nc3ccccc3N3CCNCC3)cs2)c(OC)c1] |
| 128 | 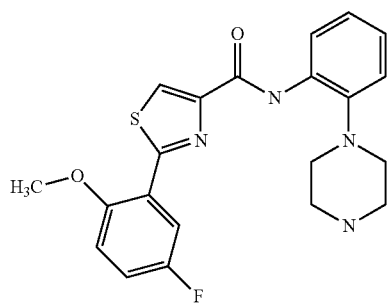 [SMILES: COc1ccc(F)cc1-c1nc(C(=O)Nc2ccccc2N2CCNCC2)cs1] |
| 129 | 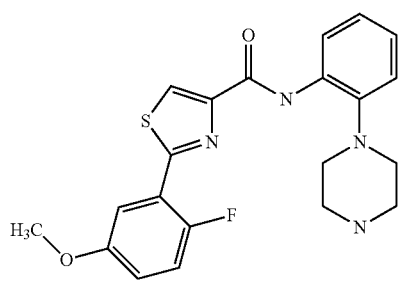 [SMILES: COc1ccc(F)c(-c2nc(C(=O)Nc3ccccc3N3CCNCC3)cs2)c1] |
| No. | Structure |
|---|---|
| 130 | 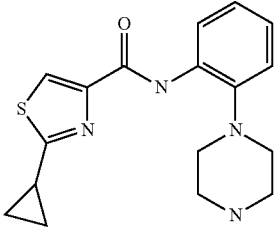 [SMILES: O=C(Nc1ccccc1N1CCNCC1)c1csc(C2CC2)n1] |
| 131 | 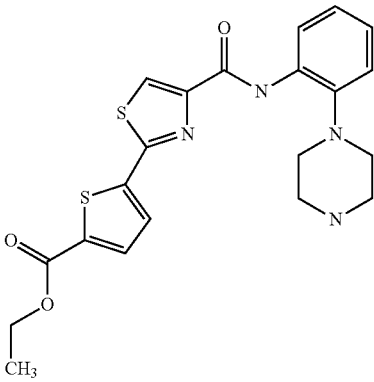 [SMILES: CCOC(=O)c1ccc(-c2nc(C(=O)Nc3ccccc3N3CCNCC3)cs2)s1] |
| 132 | 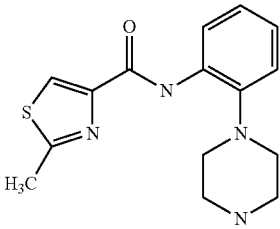 [SMILES: Cc1nc(C(=O)Nc2ccccc2N2CCNCC2)cs1] |
| 133 | 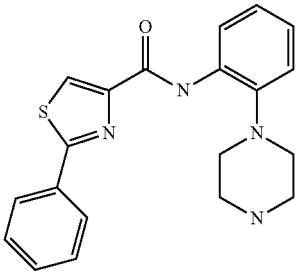 [SMILES: O=C(Nc1ccccc1N1CCNCC1)c1csc(-c2ccccc2)n1] |
| 134 | 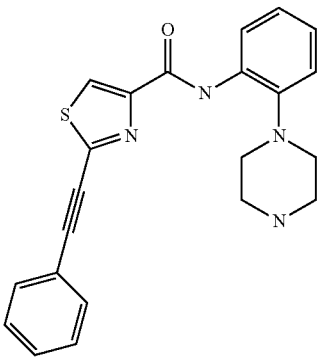 [SMILES: O=C(Nc1ccccc1N1CCNCC1)c1csc(C#Cc2ccccc2)n1] |

-continued
| No. | Structure |
|---|---|
| 135 | 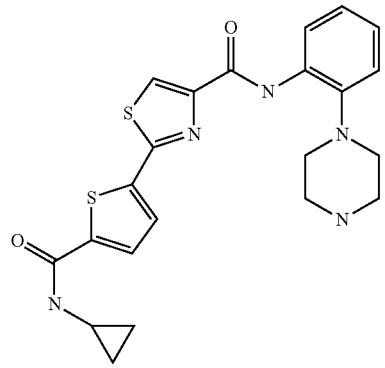 [SMILES: O=C(Nc1ccccc1N1CCNCC1)c1csc(-c2ccc(C(=O)NC3CC3)s2)n1] |
| 136 | 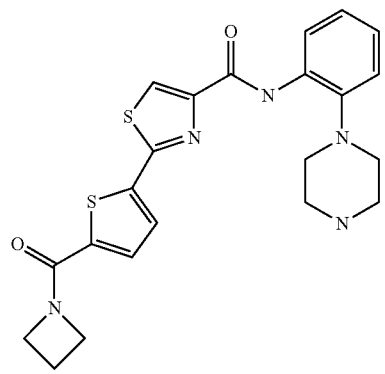 [SMILES: O=C(Nc1ccccc1N1CCNCC1)c1csc(-c2ccc(C(=O)N3CCC3)s2)n1] |
| 137 | 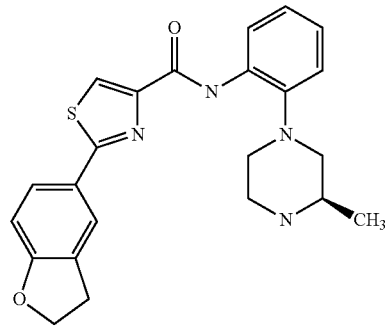 [SMILES: C[C@@H]1CN(c2ccccc2NC(=O)c2csc(-c3ccc4c(c3)CCO4)n2)CCN1] |
| 138 | 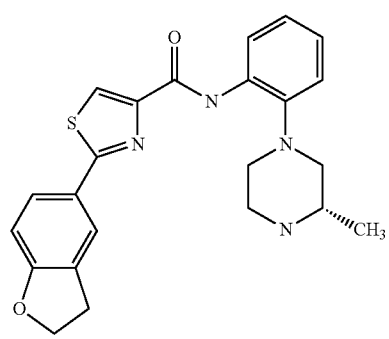 [SMILES: C[C@H]1CN(c2ccccc2NC(=O)c2csc(-c3ccc4c(c3)CCO4)n2)CCN1] |
-continued
| No. | Structure |
|---|---|
| 139 | 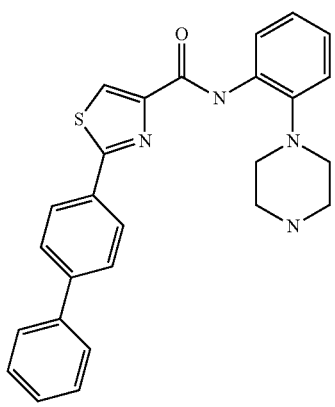 [SMILES: O=C(Nc1ccccc1N1CCNCC1)c1csc(-c2ccc(-c3ccccc3)cc2)n1] |
| 140 | 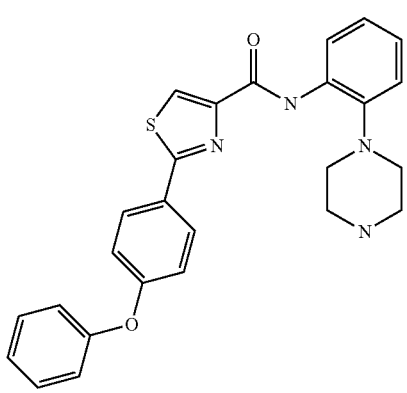 [SMILES: O=C(Nc1ccccc1N1CCNCC1)c1csc(-c2ccc(Oc3ccccc3)cc2)n1] |
| 141 | 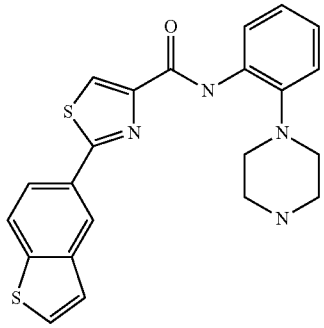 [SMILES: O=C(Nc1ccccc1N1CCNCC1)c1csc(-c2ccc3sccc3c2)n1] |
| 142 | 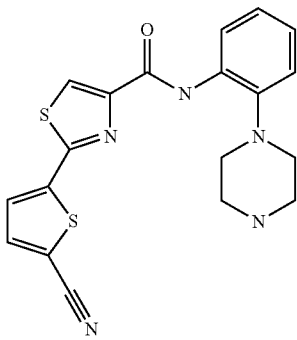 [SMILES: N#Cc1ccc(-c2nc(C(=O)Nc3ccccc3N3CCNCC3)cs2)s1] |

| No. | Structure |
|---|---|
| 143 | 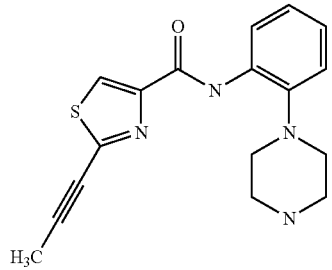 [SMILES: CC#Cc1nc(C(=O)Nc2ccccc2N2CCNCC2)cs1] |
| 144 | 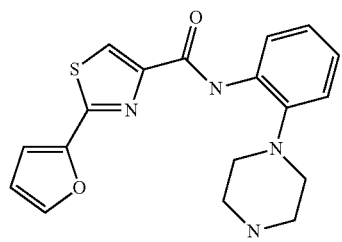 [SMILES: O=C(Nc1ccccc1N1CCNCC1)c1csc(-c2ccco2)n1] |
| 145 | 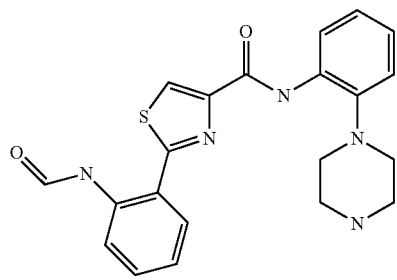 [SMILES: O=CNc1ccccc1-c1nc(C(=O)Nc2ccccc2N2CCNCC2)cs1] |
| 146 | 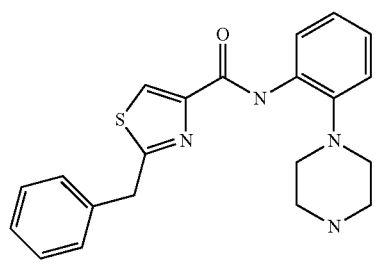 [SMILES: O=C(Nc1ccccc1N1CCNCC1)c1csc(Cc2ccccc2)n1] |
| 147 | 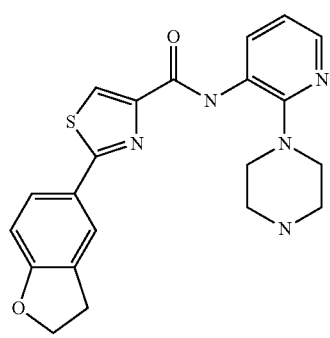 [SMILES: O=C(Nc1cccnc1N1CCNCC1)c1csc(-c2ccc3c(c2)CCO3)n1] |
| No. | Structure |
|---|---|
| 148 | 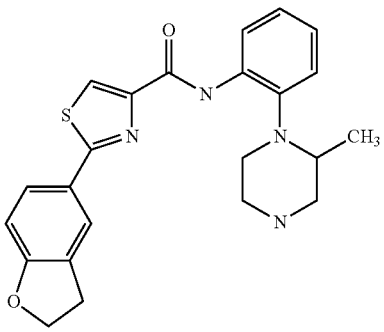 [SMILES: CC1CNCCN1c1ccccc1NC(=O)c1csc(-c2ccc3c(c2)CCO3)n1] |
| 149 | 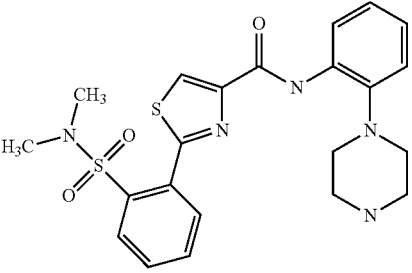 [SMILES: CN(C)S(=O)(=O)c1ccccc1-c1nc(C(=O)Nc2ccccc2N2CCNCC2)cs1] |
| 150 | 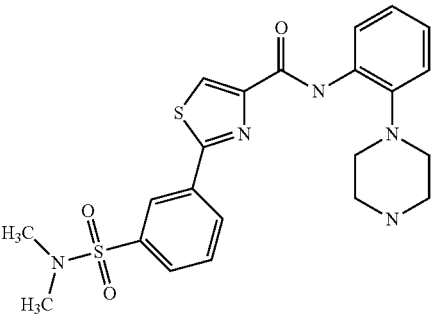 [SMILES: CN(C)S(=O)(=O)c1cccc(-c2nc(C(=O)Nc3ccccc3N3CCNCC3)cs2)c1] |
| 151 | 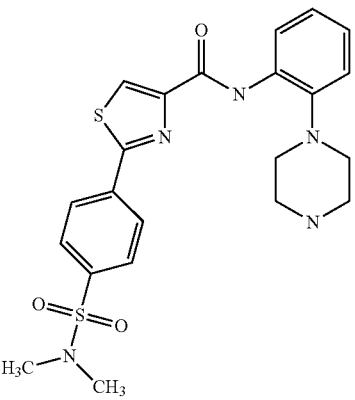 [SMILES: CN(C)S(=O)(=O)c1ccc(-c2nc(C(=O)Nc3ccccc3N3CCNCC3)cs2)cc1] |

-continued
| No. | Structure |
|---|---|
| 152 | 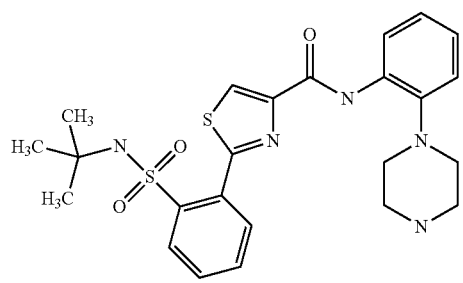 [SMILES: CC(C)(C)NS(=O)(=O)c1ccccc1-c1nc(C(=O)Nc2ccccc2N2CCNCC2)cs1] |
| 153 | 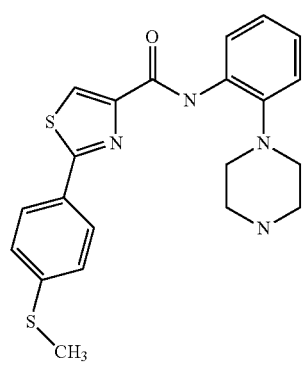 [SMILES: CSc1ccc(-c2nc(C(=O)Nc3ccccc3N3CCNCC3)cs2)cc1] |
| 154 | 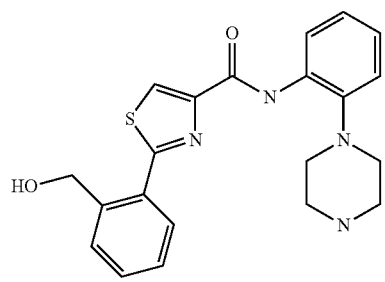 [SMILES: O=C(Nc1ccccc1N1CCNCC1)c1csc(-c2ccccc2CO)n1] |
| 155 | 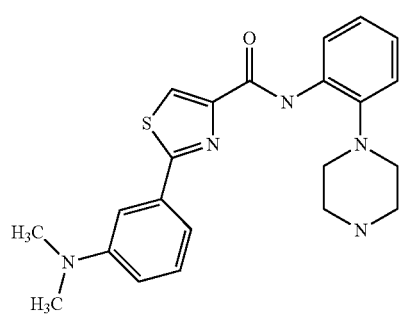 [SMILES: CN(C)c1cccc(-c2nc(C(=O)Nc3ccccc3N3CCNCC3)cs2)c1] |
| 156 | 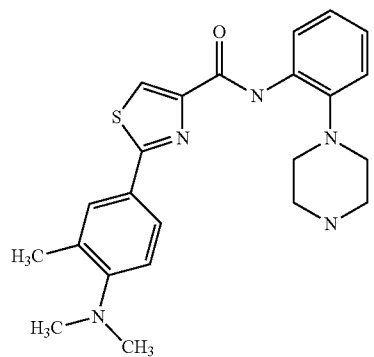 [SMILES: Cc1cc(-c2nc(C(=O)Nc3ccccc3N3CCNCC3)cs2)ccc1N(C)C] |
-continued
| No. | Structure |
|---|---|
| 157 | 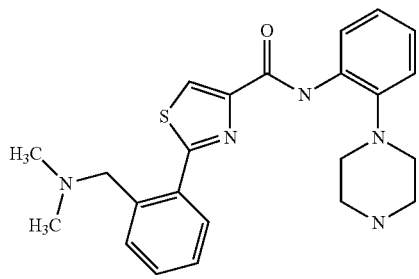 [SMILES: CN(C)Cc1ccccc1-c1nc(C(=O)Nc2ccccc2N2CCNCC2)cs1] |
| 158 | 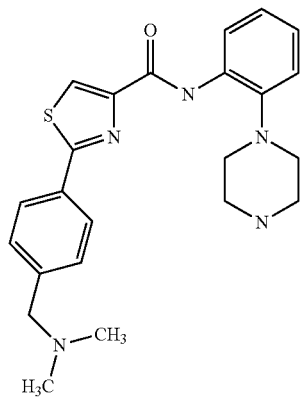 [SMILES: CN(C)Cc1ccc(-c2nc(C(=O)Nc3ccccc3N3CCNCC3)cs2)cc1] |
| 159 | 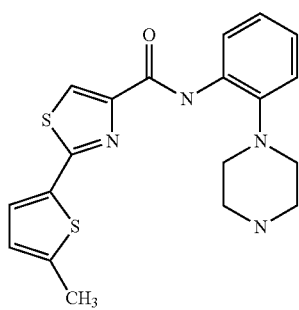 [SMILES: Cc1ccc(-c2nc(C(=O)Nc3ccccc3N3CCNCC3)cs2)s1] |
| 160 | 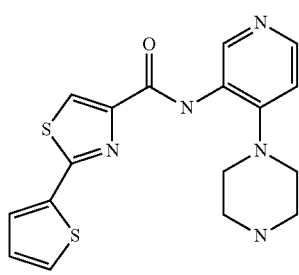 [SMILES: O=C(Nc1cnccc1N1CCNCC1)c1csc(-c2cccs2)n1] |

67
-continued
| No. | Structure |
|---|---|
| 161 | 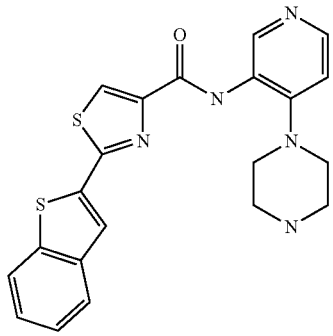 [SMILES: O=C(Nc1cnccc1N1CCNCC1)c1csc(-c2cc3ccccc3s2)n1] |
| 162 | 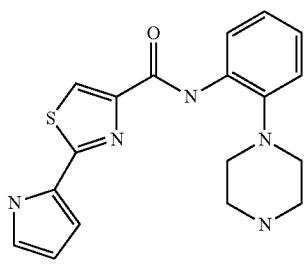 [SMILES: O=C(Nc1ccccc1N1CCNCC1)c1csc(-c2ccc[nH]2)n1] |
| 163 | 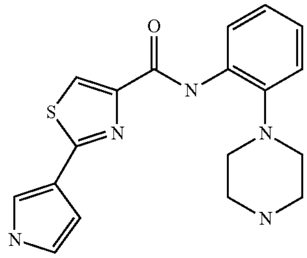 [SMILES: O=C(Nc1ccccc1N1CCNCC1)c1csc(-c2cc[nH]c2)n1] |
| 164 | 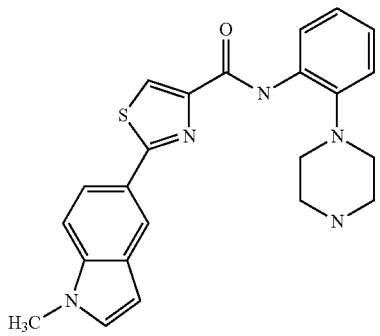 [SMILES: Cn1ccc2cc(-c3nc(C(=O)Nc4ccccc4N4CCNCC4)cs3)ccc21] |
| 165 | 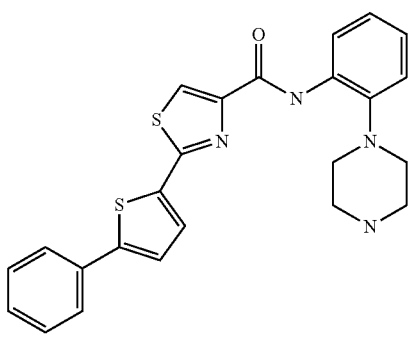 [SMILES: O=C(Nc1ccccc1N1CCNCC1)c1csc(-c2ccc(-c3ccccc3)s2)n1] |
68
-continued
| No. | Structure |
|---|---|
| 166 | 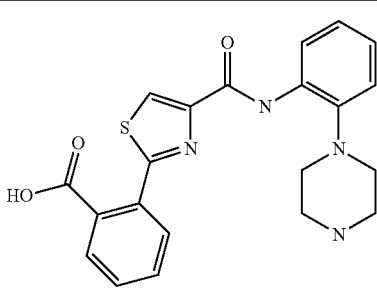 |
| 167 | 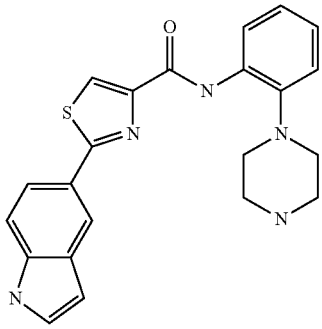 |
| 168 | 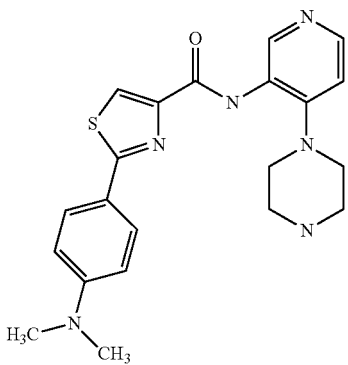 [SMILES: CN(C)c1ccc(-c2nc(C(=O)Nc3cnccc3N3CCNCC3)cs2)cc1] |
| 169 | 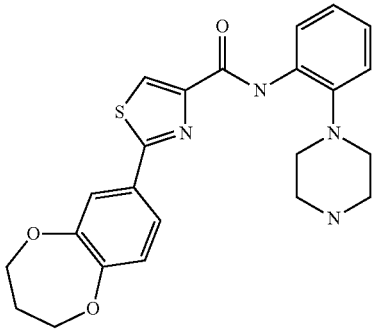 [SMILES: O=C(Nc1ccccc1N1CCNCC1)c1csc(-c2ccc3c(c2)OCCCO3)n1] |

| No. | Structure |
|---|---|
| 170 | 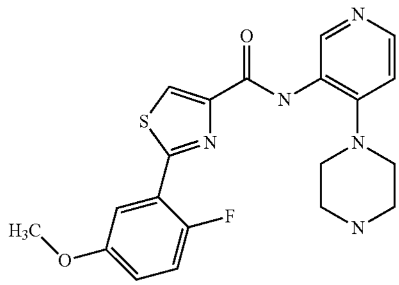 [SMILES: COc1ccc(F)c(-c2nc(C(=O)Nc3cnccc3N3CCNCC3)cs2)c1] |
| 171 | 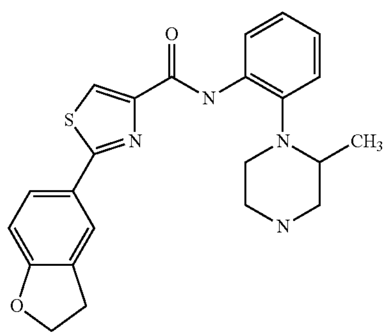 [SMILES: CC1CNCCN1c1ccccc1NC(=O)c1csc(-c2ccc3c(c2)CCO3)n1] |
| 172 | 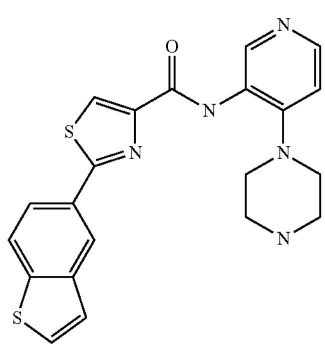 |
| 173 | 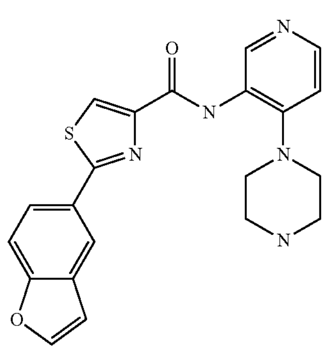 [SMILES: O=C(Nc1cnccc1N1CCNCC1)c1csc(-c2ccc3occc3c2)n1] |

| No. | Structure |
|---|---|
| 174 | 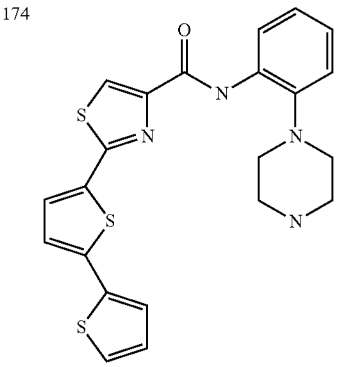 |
| 175 | 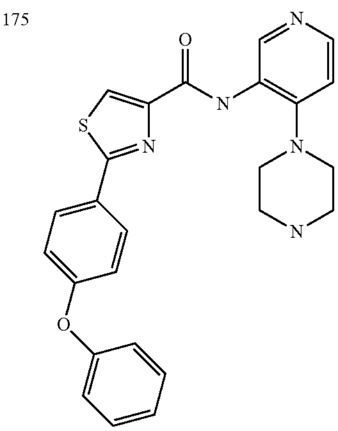 |
| 176 | 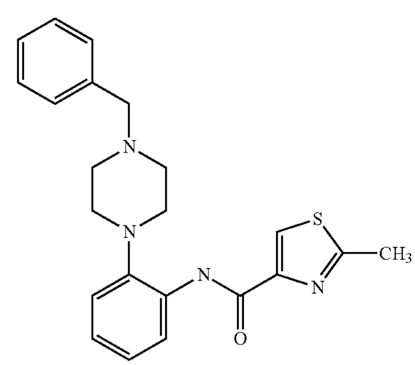 [SMILES: Cc1nc(C(=O)Nc2ccccc2N2CCN(Cc3ccccc3)CC2)cs1] |
| 177 | 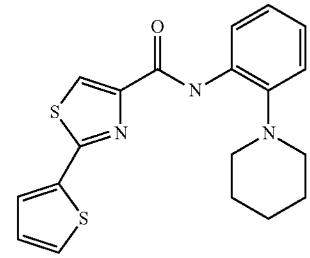 [SMILES: O=C(Nc1ccccc1N1CCCCC1)c1csc(-c2cccs2)n1] |

| No. | Structure |
|---|---|
| 178 | 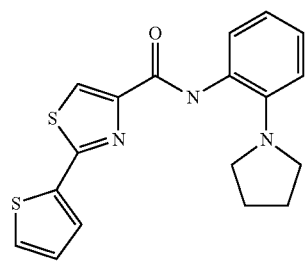 [SMILES: O=C(Nc1ccccc1N1CCCC1)c1csc(-c2cccs2)n1] |
| 179 | 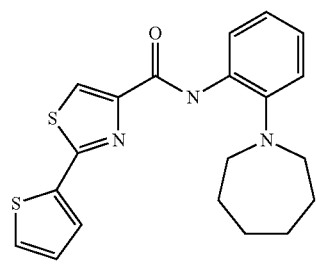 [SMILES: O=C(Nc1ccccc1N1CCCCCC1)c1csc(-c2cccs2)n1] |
| 180 | 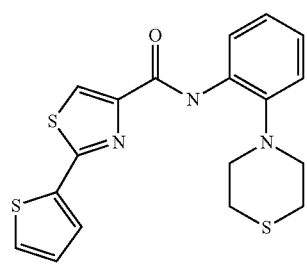 [SMILES: O=C(Nc1ccccc1N1CCSCC1)c1csc(-c2cccs2)n1] |
| 181 | 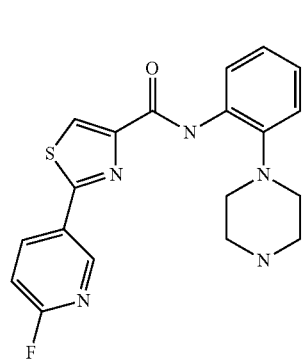 [SMILES: O=C(Nc1ccccc1N1CCNCC1)c1csc(-c2ccc(F)nc2)n1] |
| 182 | 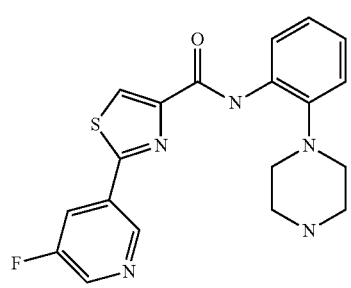 [SMILES: O=C(Nc1ccccc1N1CCNCC1)c1csc(-c2cncc(F)c2)n1] |
| 183 | 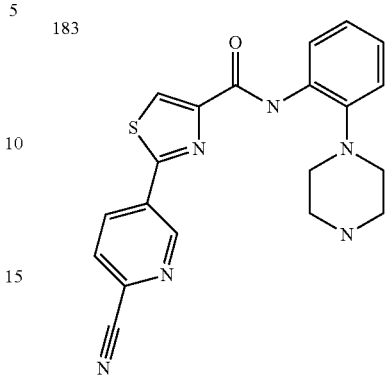 |
| 184 | 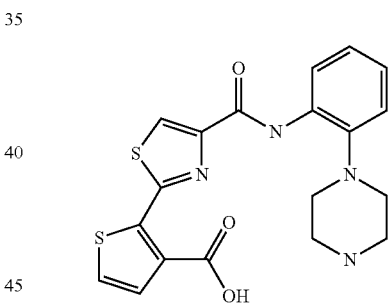 |
| 185 | 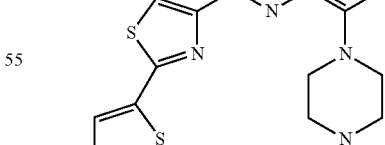 |
| 186 |  |

| No. | Structure |
|---|---|
| 187 | 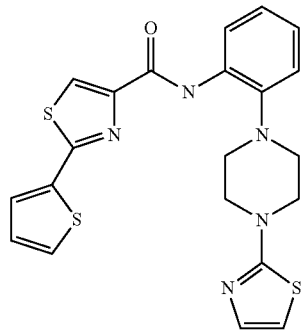 [SMILES: O=C(Nc1ccccc1N1CCN(c2nccs2)CC1)c1csc(-c2cccs2)n1] |
| 188 | 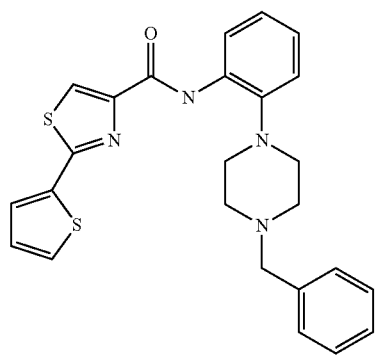 [SMILES: O=C(Nc1ccccc1N1CCN(Cc2ccccc2)CC1)c1csc(-c2cccs2)n1] |
| 189 | 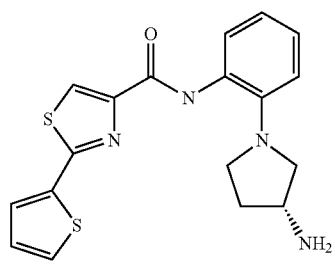 [SMILES: N[C@@H]1CCN(c2ccccc2NC(=O)c2csc(-c3cccs3)n2)C1] |
| 190 | 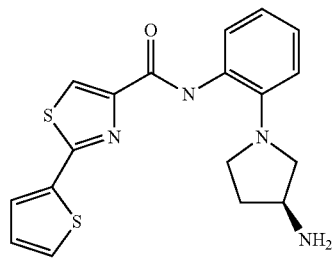 [SMILES: N[C@H]1CCN(c2ccccc2NC(=O)c2csc(-c3cccs3)n2)C1] |
| 191 | 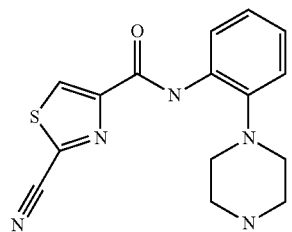 [SMILES: N#Cc1nc(C(=O)Nc2ccccc2N2CCNCC2)cs1] |
| No. | Structure |
|---|---|
| 192 | 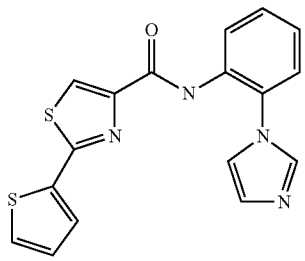 [SMILES: O=C(Nc1ccccc1-n1ccnc1)c1csc(-c2cccs2)n1] |
| 193 | 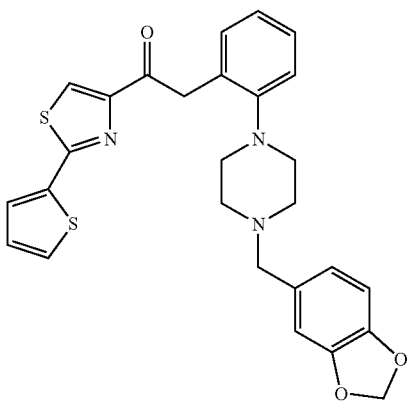 [SMILES: O=C(Cc1ccccc1N1CCN(Cc2ccc3c(c2)OCO3)CC1)c1csc(-c2cccs2)n1] |
| 194 | 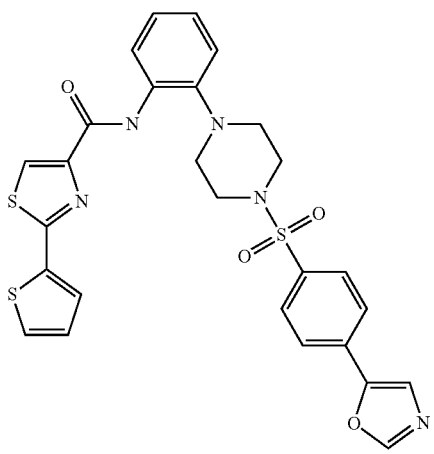 [SMILES: O=C(Nc1ccccc1N1CCN(S(=O)(=O)c2ccc(-c3cnco3)cc2)CC1)c1csc(-c2cccs2)n1] |
| 195 | 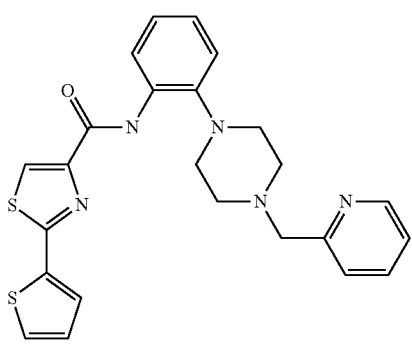 [SMILES: O=C(Nc1ccccc1N1CCN(Cc2ccccn2)CC1)c1csc(-c2cccs2)n1] |

| No. | Structure |
|---|---|
| 196 | 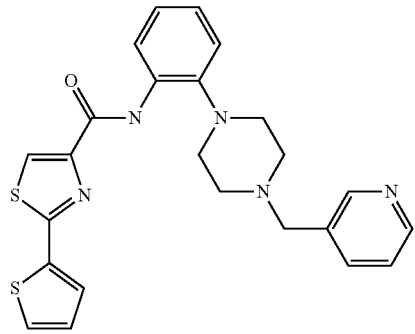 [SMILES: O=C(Nc1ccccc1N1CCN(Cc2cccnc2)CC1)c1csc(-c2cccs2)n1] |
| 197 | 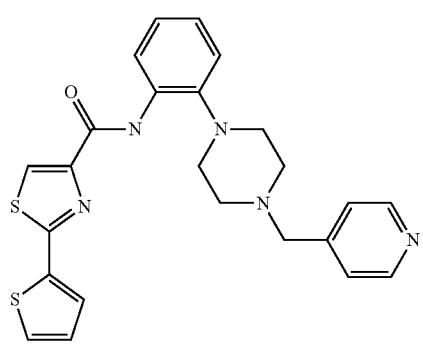 [SMILES: O=C(Nc1ccccc1N1CCN(Cc2ccncc2)CC1)c1csc(-c2cccs2)n1] |
| 198 | 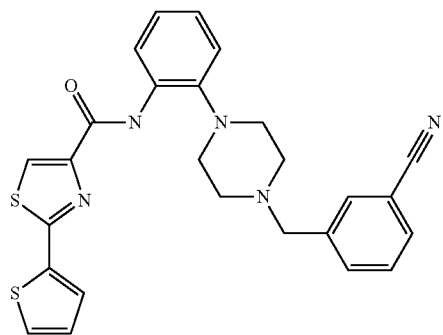 [SMILES: N#Cc1cccc(CN2CCN(c3ccccc3NC(=O)c3csc(-c4cccs4)n3)CC2)c1] |
| 199 | 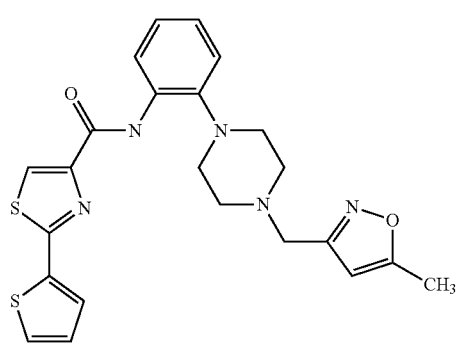 [SMILES: Cc1cc(CN2CCN(c3ccccc3NC(=O)c3csc(-c4cccs4)n3)CC2)no1] |
| 200 | 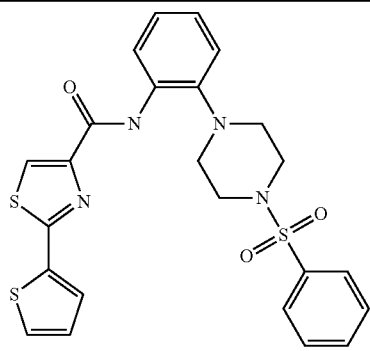 |
| 201 | 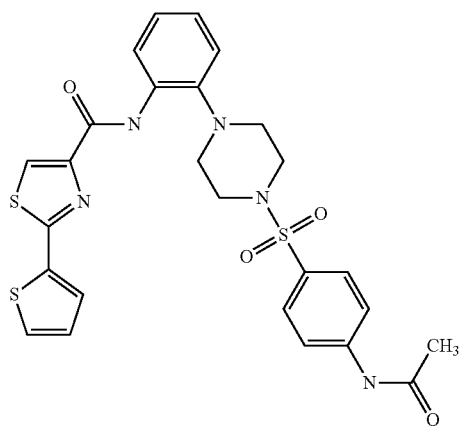 [SMILES: CC(=O)Nc1ccc(S(=O)(=O)N2CCN(c3ccccc3NC(=O)c3csc(-c4cccs4)n3)CC2)cc1] |
| 202 | 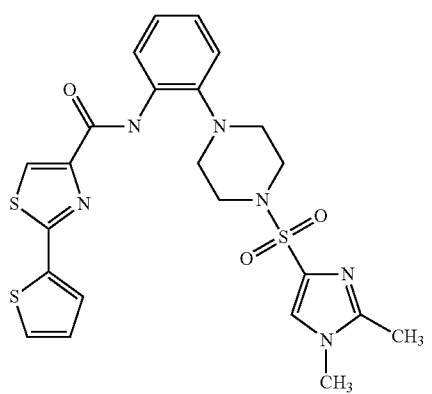 [SMILES: Cc1nc(S(=O)(=O)N2CCN(c3ccccc3NC(=O)c3csc(-c4cccs4)n3)CC2)cn1C] |
| 203 | 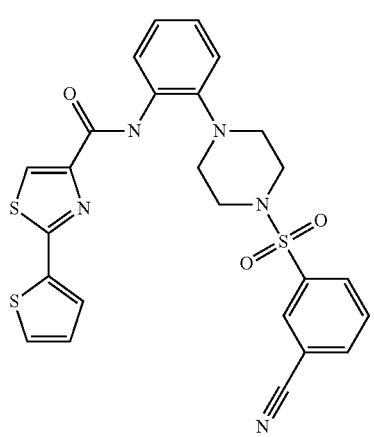 [SMILES: N#Cc1cccc(S(=O)(=O)N2CCN(c3ccccc3NC(=O)c3csc(-c4cccs4)n3)CC2)c1] |

| No. | Structure |
|---|---|
| 204 | 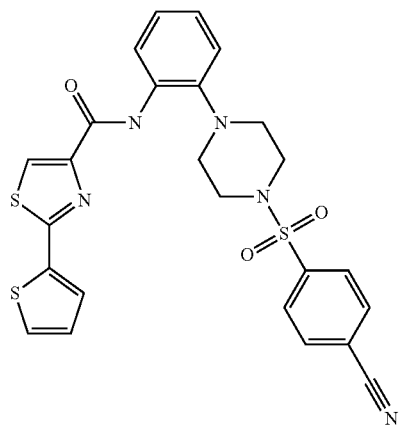 [SMILES: N#Cc1ccc(S(=O)(=O)N2CCN(c3ccccc3NC(=O)c3csc(-c4cccs4)n3)CC2)cc1] |
| 205 | 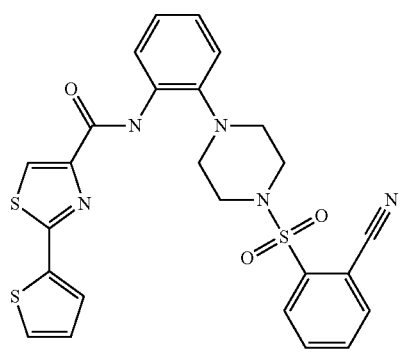 [SMILES: N#Cc1ccccc1S(=O)(=O)N1CCN(c2ccccc2NC(=O)c2csc(-c3cccs3)n2)CC1] |
| 206 | 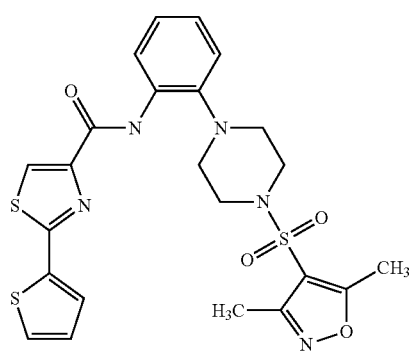 [SMILES: Cc1noc(C)c1S(=O)(=O)N1CCN(c2ccccc2NC(=O)c2csc(-c3cccs3)n2)CC1] |
| 207 | 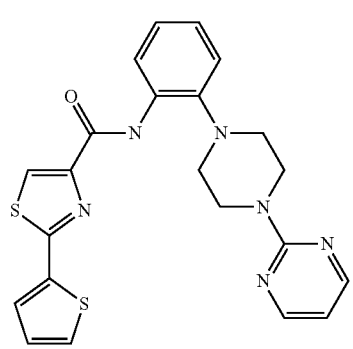 [SMILES: O=C(Nc1ccccc1N1CCN(c2ncccn2)CC1)c1csc(-c2cccs2)n1] |
| No. | Structure |
|---|---|
| 208 | 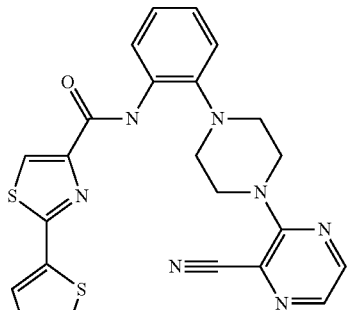 |
| 209 | 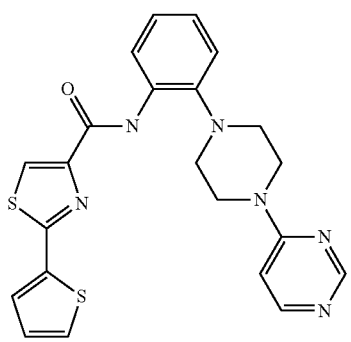 [SMILES: O=C(Nc1ccccc1N1CCN(c2ccncn2)CC1)c1csc(-c2cccs2)n1] |
| 210 | 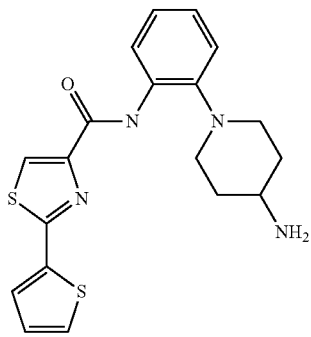 [SMILES: NC1CCN(c2ccccc2NC(=O)c2csc(-c3cccs3)n2)CC1] |
| 211 | 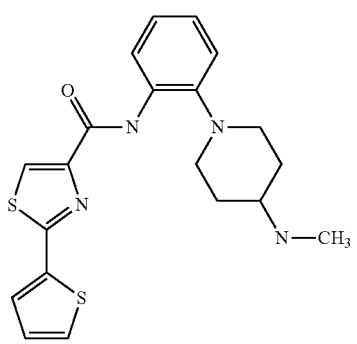 [SMILES: CNC1CCN(c2ccccc2NC(=O)c2csc(-c3cccs3)n2)CC1] |

| No. | Structure |
|---|---|
| 212 | 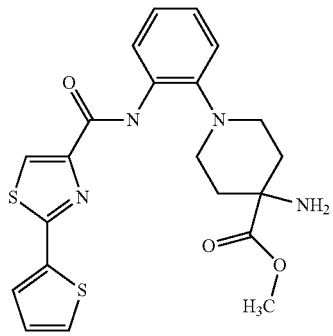 [SMILES: COC(=O)C1(N)CCN(c2ccccc2NC(=O)c2csc(-c3cccs3)n2)CC1] |
| 213 | 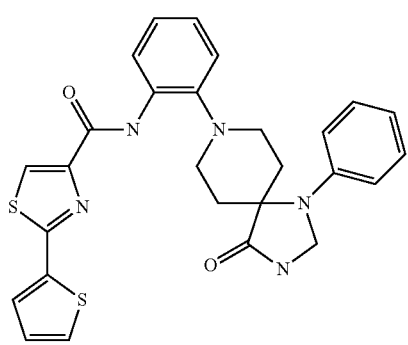 [SMILES: O=C(Nc1ccccc1N1CCC2(CC1)C(=O)NCN2c1ccccc1)c1csc(-c2cccs2)n1] |
| 214 | 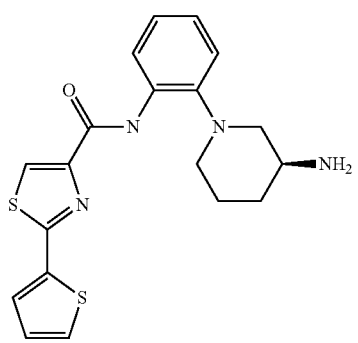 [SMILES: N[C@H]1CCCN(c2ccccc2NC(=O)c2csc(-c3cccs3)n2)C1] |
| 215 | 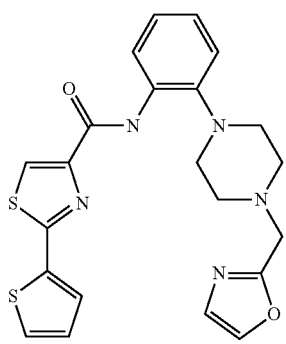 [SMILES: O=C(Nc1ccccc1N1CCN(Cc2ncco2)CC1)c1csc(-c2cccs2)n1] |
| No. | Structure |
|---|---|
| 216 | 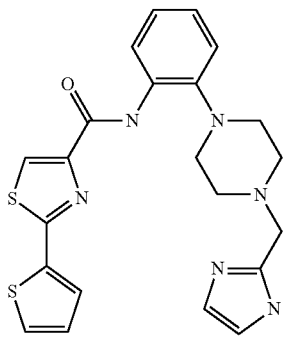 [SMILES: O=C(Nc1ccccc1N1CCN(Cc2ncc[nH]2)CC1)c1csc(-c2cccs2)n1] |
| 217 | 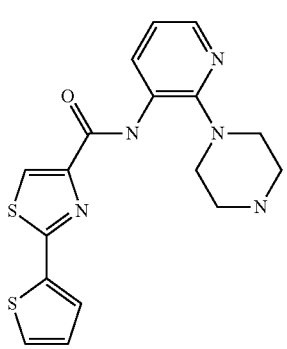 [SMILES: O=C(Nc1cccnc1N1CCNCC1)c1csc(-c2cccs2)n1] |
| 218 | 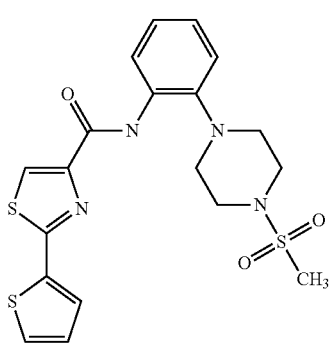 [SMILES: CS(=O)(=O)N1CCN(c2ccccc2NC(=O)c2csc(-c3cccs3)n2)CC1] |
| 219 | 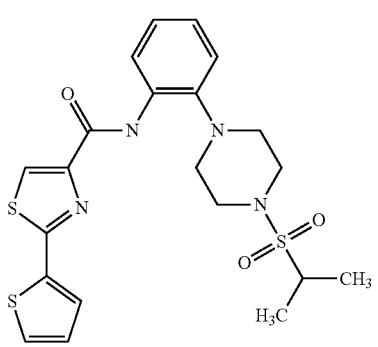 [SMILES: CC(C)S(=O)(=O)N1CCN(c2ccccc2NC(=O)c2csc(-c3cccs3)n2)CC1] |

| No. | Structure |
|---|---|
| 220 | 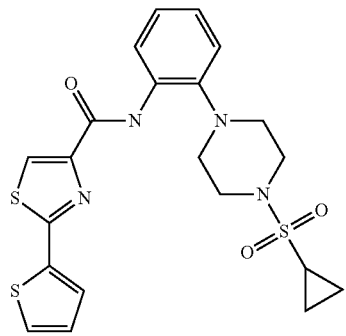 [SMILES: O=C(Nc1ccccc1N1CCN(S(=O)(=O)C2CC2)CC1)c1csc(-c2cccs2)n1] |
| 221 | 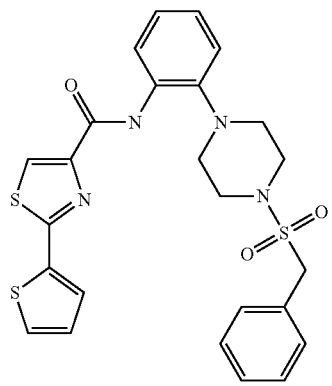 [SMILES: O=C(Nc1ccccc1N1CCN(S(=O)(=O)Cc2ccccc2)CC1)c1csc(-c2cccs2)n1] |
| 222 | 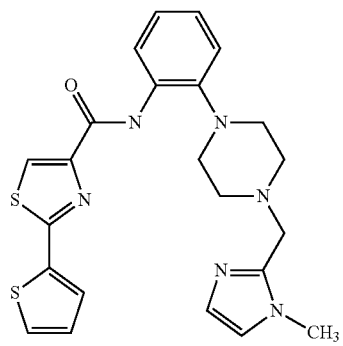 [SMILES: Cn1ccnc1CN1CCN(c2ccccc2NC(=O)c2csc(-c3cccs3)n2)CC1] |
| 223 | 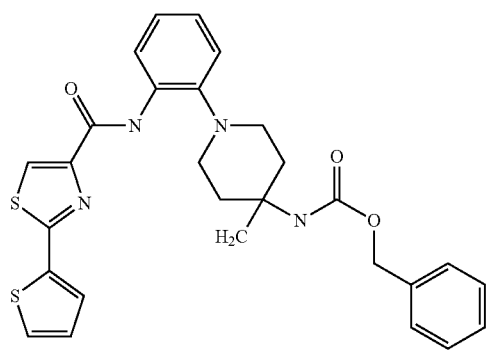 [SMILES: CC1(NC(=O)OCc2ccccc2)CCN(c2ccccc2NC(=O)c2csc(-c3cccs3)n2)CC1] |
| No. | Structure |
|---|---|
| 224 | 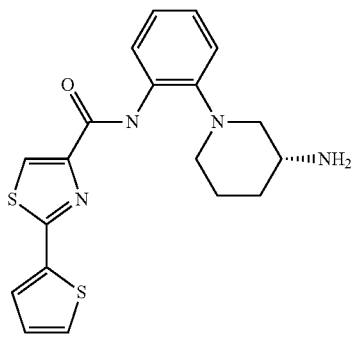 [SMILES: N[C@@H]1CCCN(c2ccccc2NC(=O)c2csc(-c3cccs3)n2)C1] |
| 225 | 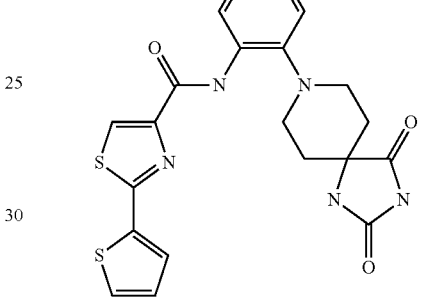 |
| 226 | 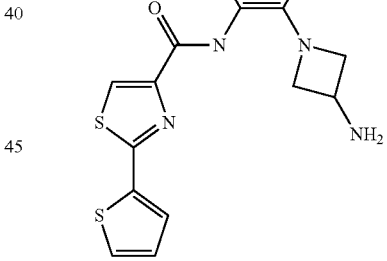 |
| 227 | 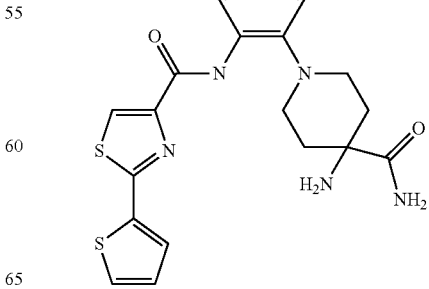 |

-continued
| No. | Structure |
|---|---|
| 228 | 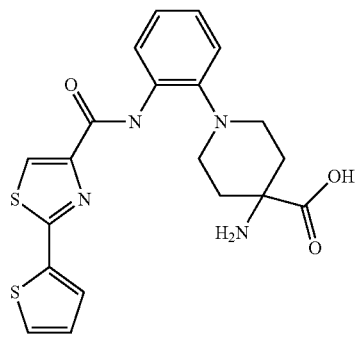 [SMILES: NC1(C(=O)O)CCN(c2ccccc2NC(=O)c2csc(-c3cccs3)n2)CC1] |
| 229 | 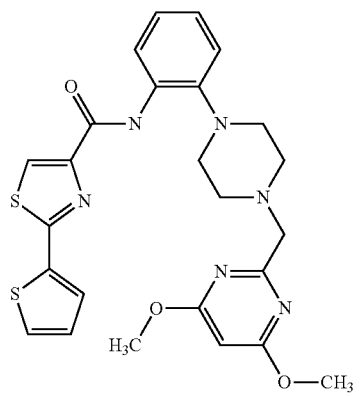 [SMILES: COc1cc(OC)nc(CN2CCN(c3ccccc3NC(=O)c3csc(-c4cccs4)n3)CC2)n1] |
| 230 | 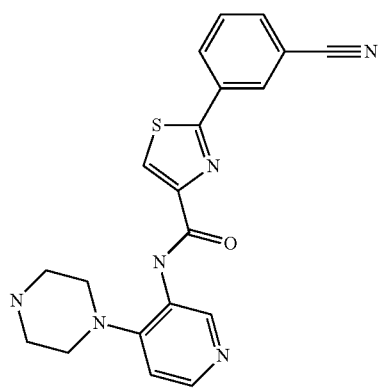 [SMILES: N#Cc1cccc(-c2nc(C(=O)Nc3cnccc3N3CCNCC3)cs2)c1] |
| 231 | 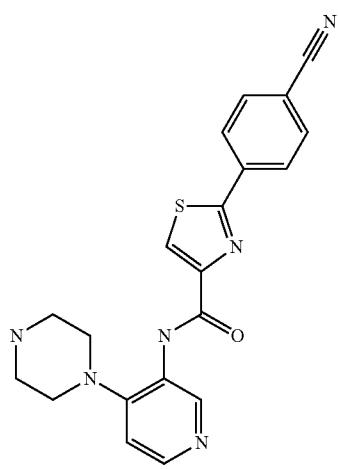 [SMILES: N#Cc1ccc(-c2nc(C(=O)Nc3cnccc3N3CCNCC3)cs2)cc1] |
-continued
| No. | Structure |
|---|---|
| 232 | 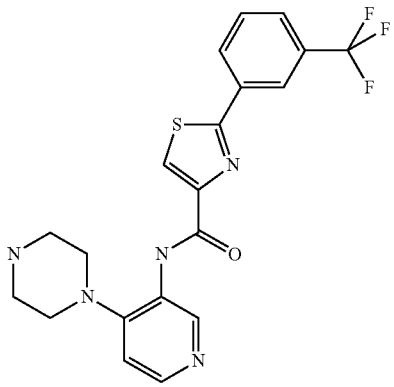 [SMILES: O=C(Nc1cnccc1N1CCNCC1)c1csc(-c2cccc(C(F)(F)F)c2)n1] |
| 233 | 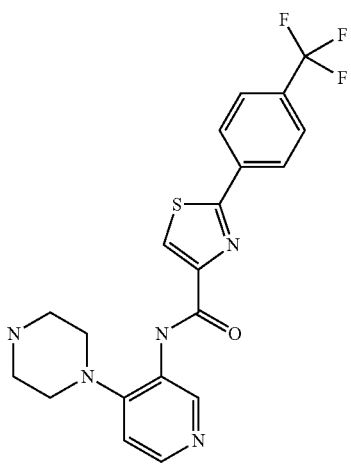 [SMILES: O=C(Nc1cnccc1N1CCNCC1)c1csc(-c2ccc(C(F)(F)F)cc2)n1] |
| 234 | 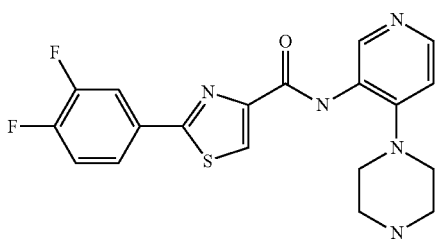 [SMILES: O=C(Nc1cnccc1N1CCNCC1)c1csc(-c2ccc(F)c(F)c2)n1] |
| 235 | 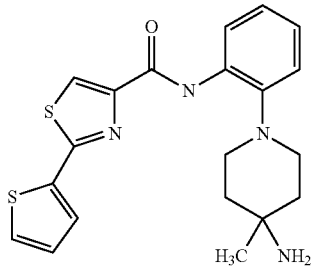 [SMILES: CC1(N)CCN(c2ccccc2NC(=O)c2csc(-c3cccs3)n2)CC1] |

| No. | Structure |
|---|---|
| 236 | 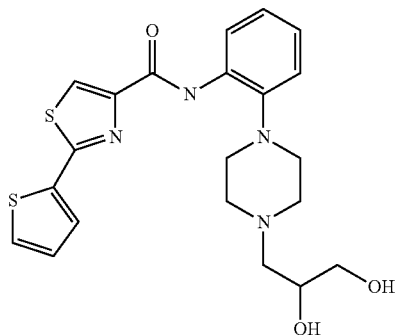 [SMILES: O=C(Nc1ccccc1N1CCN(CC(O)CO)CC1)c1csc(-c2cccs2)n1] |
| 237 | 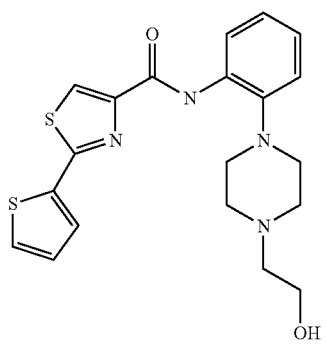 [SMILES: O=C(Nc1ccccc1N1CCN(CCO)CC1)c1csc(-c2cccs2)n1] |
| 238 | 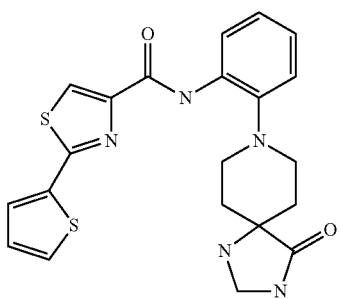 [SMILES: O=C(Nc1ccccc1N1CCC2(CC1)NCNC2=O)c1csc(-c2cccs2)n1] |
| 239 | 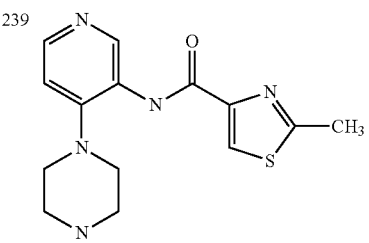 |
| 240 | 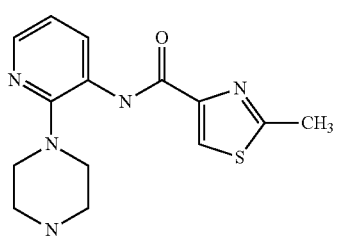 [SMILES: Cc1nc(C(=O)Nc2cccnc2N2CCNCC2)cs1] |
| No. | Structure |
|---|---|
| 241 | 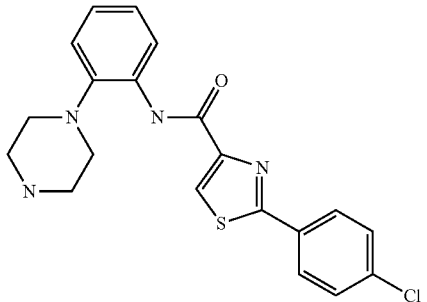 |
| 242 | 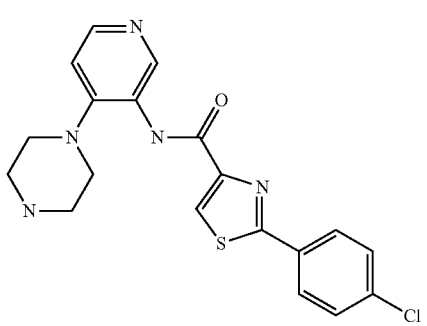 [SMILES: O=C(Nc1cnccc1N1CCNCC1)c1csc(-c2ccc(Cl)cc2)n1] |
| 243 | 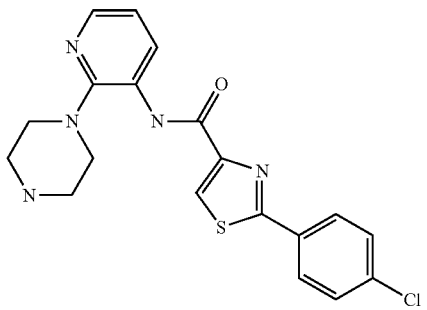 [SMILES: O=C(Nc1cccnc1N1CCNCC1)c1csc(-c2ccc(Cl)cc2)n1] |
| 244 | 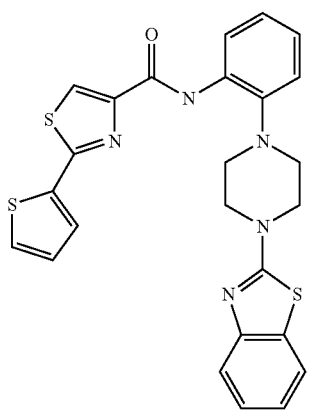 [SMILES: O=C(Nc1ccccc1N1CCN(c2nc3ccccc3s2)CC1)c1csc(-c2cccs2)n1] |

87
-continued
| No. | Structure |
|---|---|
| 245 | 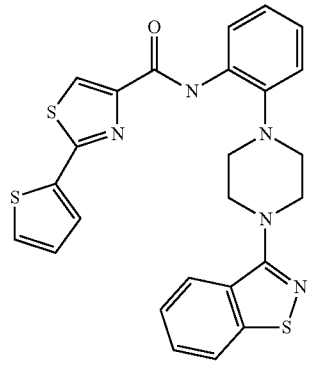 [SMILES: O=C(Nc1ccccc1N1CCN(c2nsc3ccccc23)CC1)c1csc(-c2cccs2)n1] |
| 246 | 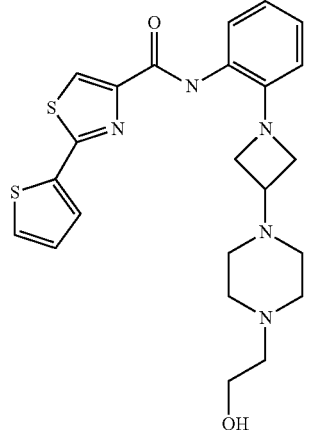 [SMILES: O=C(Nc1ccccc1N1CC(N2CCN(CCO)CC2)C1)c1csc(-c2cccs2)n1] |
| 247 | 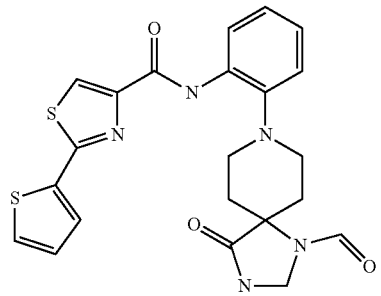 [SMILES: O=CN1CNC(=O)C12CCN(c1ccccc1NC(=O)c1csc(-c3cccs3)n1)CC2] |
| 248 | 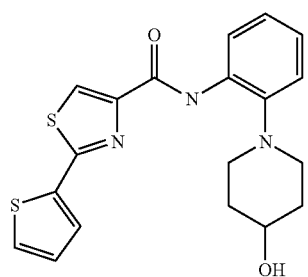 [SMILES: O=C(Nc1ccccc1N1CCC(O)CC1)c1csc(-c2cccs2)n1] |
88
-continued
| No. | Structure |
|---|---|
| 249 | 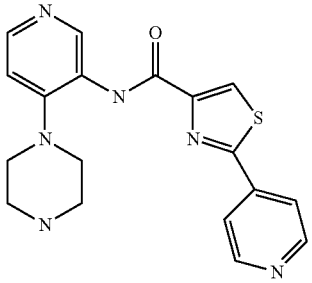 [SMILES: O=C(Nc1cnccc1N1CCNCC1)c1csc(-c2ccncc2)n1] |
| 250 | 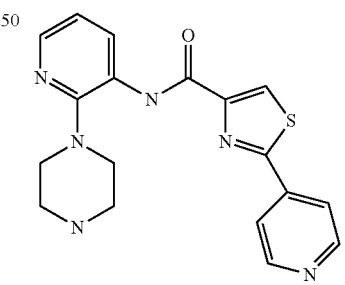 |
| 251 | 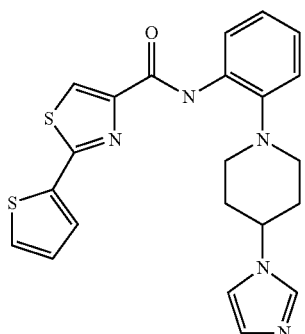 |
| 252 | 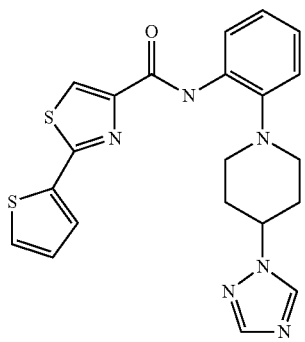 [SMILES: O=C(Nc1ccccc1N1CCC(n2cncn2)CC1)c1csc(-c2cccs2)n1] |
| 253 | 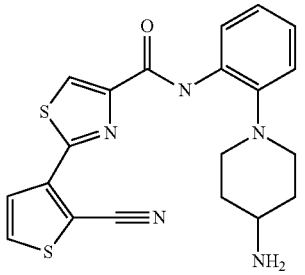 [SMILES: N#Cc1sccc1-c1nc(C(=O)Nc2ccccc2N2CCC(N)CC2)cs1] |

-continued
| No. | Structure |
|---|---|
| 254 | 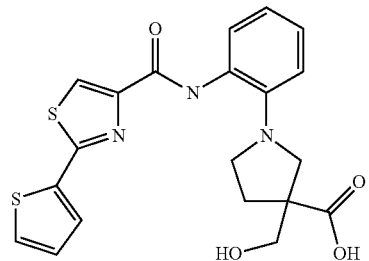 [SMILES: O=C(Nc1ccccc1N1CCC(CO)(C(=O)O)C1)c1csc(-c2cccs2)n1] |
| 255 | 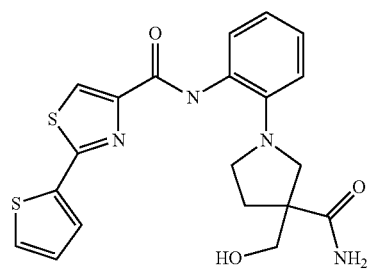 [SMILES: NC(=O)C1(CO)CCN(c2ccccc2NC(=O)c2csc(-c3cccs3)n2)C1] |
| 256 | 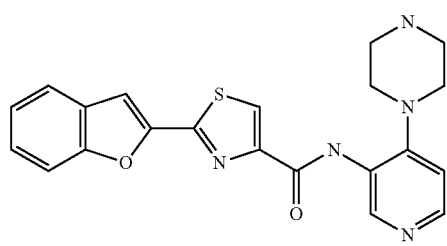 [SMILES: O=C(Nc1cnccc1N1CCNCC1)c1csc(-c2cc3ccccc3o2)n1] |
| 257 | 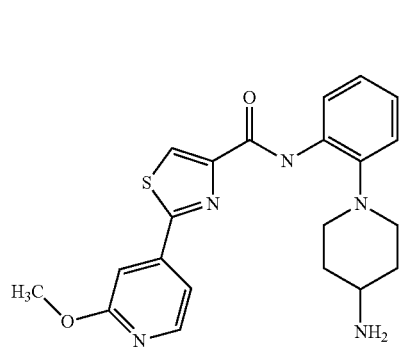 [SMILES: COc1cc(-c2nc(C(=O)Nc3ccccc3N3CCC(N)CC3)cs2)ccn1] |
| 258 | 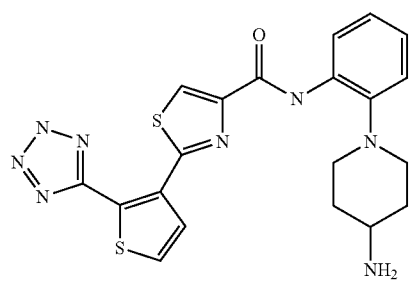 [SMILES: NC1CCN(c2ccccc2NC(=O)c2csc(-c3ccsc3-c3nn[nH]n3)n2)CC1] |
-continued
| No. | Structure |
|---|---|
| 259 | 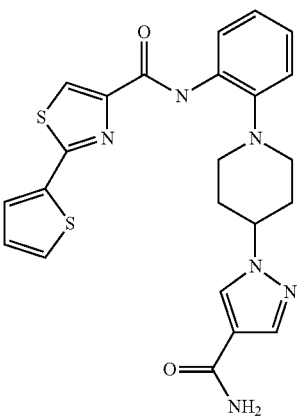 [SMILES: NC(=O)c1cnn(C2CCN(c3ccccc3NC(=O)c3csc(-c4cccs4)n3)CC2)c1] |
| 260 | 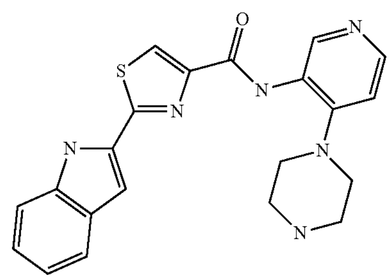 [SMILES: O=C(Nc1cnccc1N1CCNCC1)c1csc(-c2cc3ccccc3[nH]2)n1] |
| 261 | 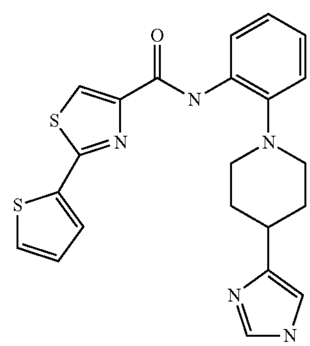 [SMILES: O=C(Nc1ccccc1N1CCC(c2c[nH]cn2)CC1)c1csc(-c2cccs2)n1] |
| 262 | 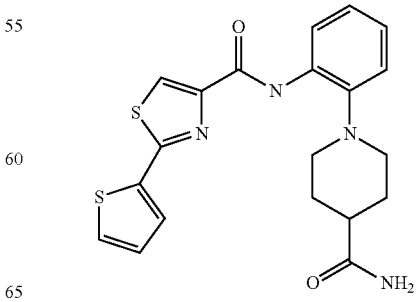 |

| No. | Structure |
|---|---|
| 263 | 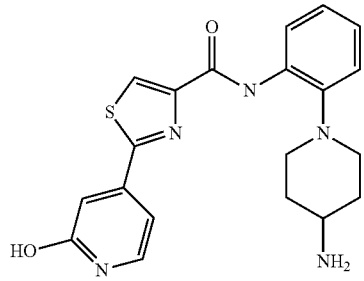 [SMILES: NC1CCN(c2ccccc2NC(=O)c2csc(-c3ccnc(O)c3)n2)CC1] |
| 264 | 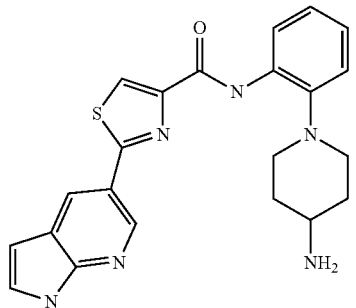 [SMILES: NC1CCN(c2ccccc2NC(=O)c2csc(-c3cnc4[nH]ccc4c3)n2)CC1] |
| 265 | 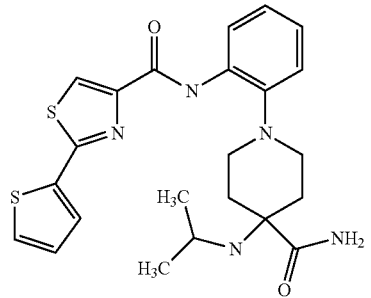 [SMILES: CC(C)NC1(C(N)=O)CCN(c2ccccc2NC(=O)c2csc(-c3cccs3)n2)CC1] |
| 266 | 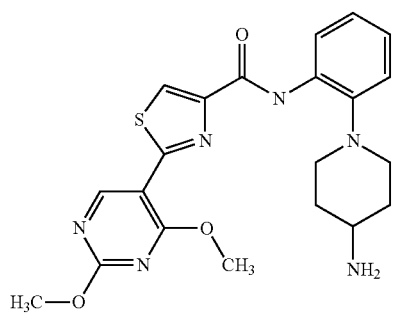 [SMILES: COc1ncc(-c2nc(C(=O)Nc3ccccc3N3CCC(N)CC3)cs2)c(OC)n1] |
| 267 | 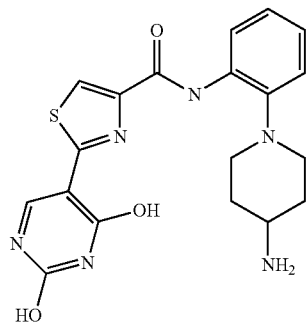 [SMILES: NC1CCN(c2ccccc2NC(=O)c2csc(-c3cnc(O)nc3O)n2)CC1] |
| No. | Structure |
|---|---|
| 268 | 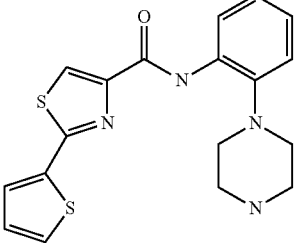 |
| 269 |  |
| 270 | 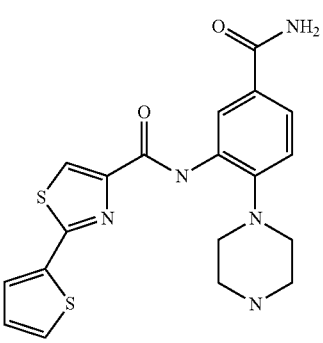 [SMILES: NC(=O)c1ccc(N2CCNCC2)c(NC(=O)c2csc(-c3cccs3)n2)c1] |
| 271 | 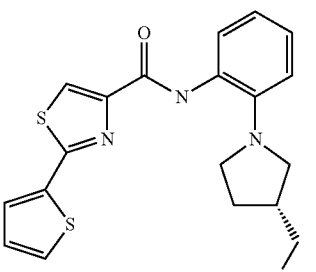 |
| 272 | 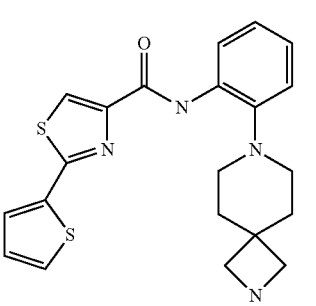 [SMILES: O=C(Nc1ccccc1N1CCC2(CC1)CNC2)c1csc(-c2cccs2)n1] |

| No. | Structure |
|---|---|
| 273 | 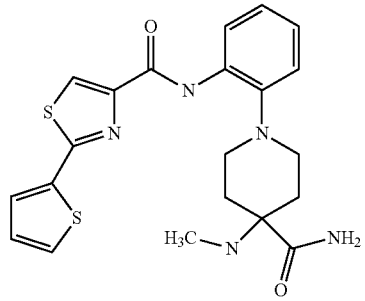 [SMILES: CNC1(C(N)=O)CCN(c2ccccc2NC(=O)c2csc(-c3cccs3)n2)CC1] |
| 274 | 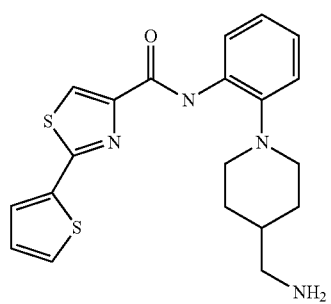 [SMILES: NCC1CCN(c2ccccc2NC(=O)c2csc(-c3cccs3)n2)CC1] |
| 275 | 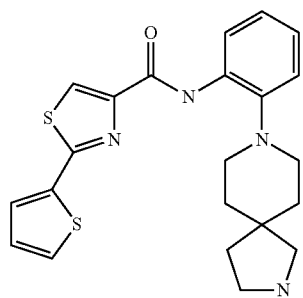 [SMILES: O=C(Nc1ccccc1N1CCC2(CCNC2)CC1)c1csc(-c2cccs2)n1] |
| 276 | 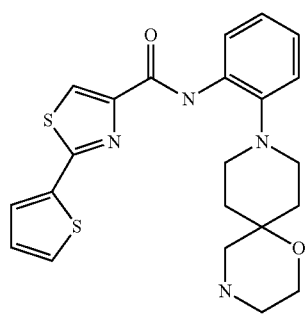 [SMILES: O=C(Nc1ccccc1N1CCC2(CC1)CNCCO2)c1csc(-c2cccs2)n1] |
| 277 | 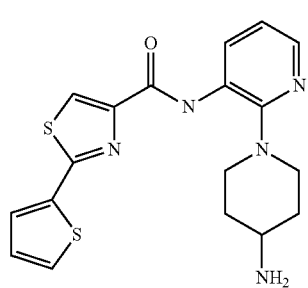 [SMILES: NC1CCN(c2ncccc2NC(=O)c2csc(-c3cccs3)n2)CC1] |
| 278 | 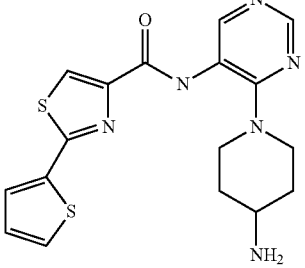 |
| 279 | 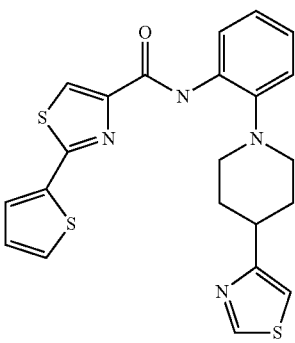 [SMILES: O=C(Nc1ccccc1N1CCC(c2cscn2)CC1)c1csc(-c2cccs2)n1] |
| 280 | 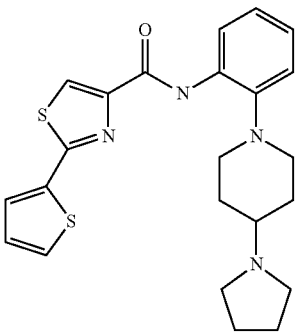 [SMILES: O=C(Nc1ccccc1N1CCC(N2CCCC2)CC1)c1csc(-c2cccs2)n1] |
| 281 | 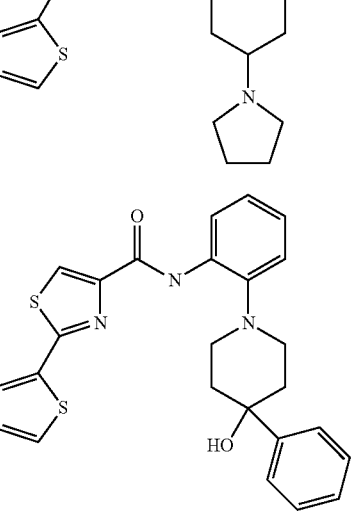 |
| 282 | 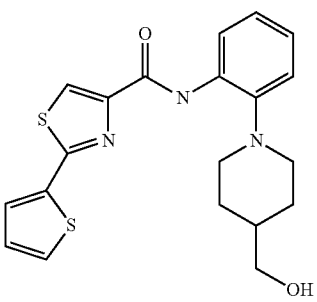 [SMILES: O=C(Nc1ccccc1N1CCC(CO)CC1)c1csc(-c2cccs2)n1] |

| No. | Structure |
|---|---|
| 283 | 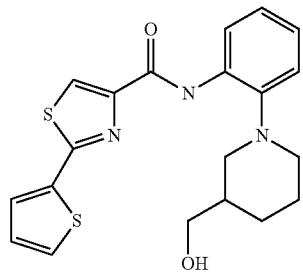 [SMILES: O=C(Nc1ccccc1N1CCCC(CO)C1)c1csc(-c2cccs2)n1] |
| 284 | 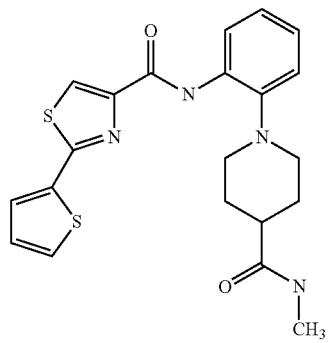 [SMILES: CNC(=O)C1CCN(c2ccccc2NC(=O)c2csc(-c3cccs3)n2)CC1] |
| 285 | 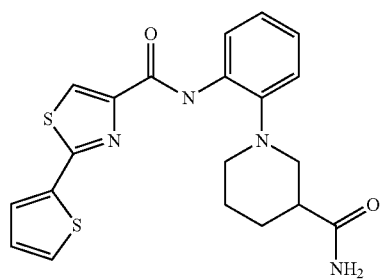 [SMILES: NC(=O)C1CCCN(c2ccccc2NC(=O)c2csc(-c3cccs3)n2)C1] |
| 286 | 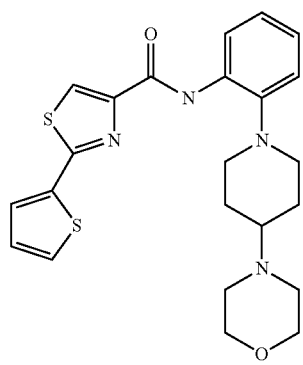 [SMILES: O=C(Nc1ccccc1N1CCC(N2CCOCC2)CC1)c1csc(-c2cccs2)n1] |
| 287 | 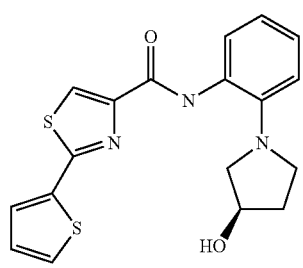 [SMILES: O=C(Nc1ccccc1N1CC[C@@H](O)C1)c1csc(-c2cccs2)n1] |
| 288 | 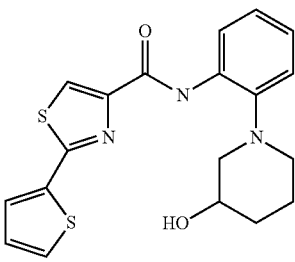 [SMILES: O=C(Nc1ccccc1N1CCCC(O)C1)c1csc(-c2cccs2)n1] |
| 289 | 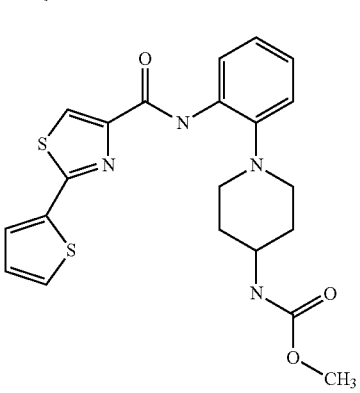 |
| 290 | 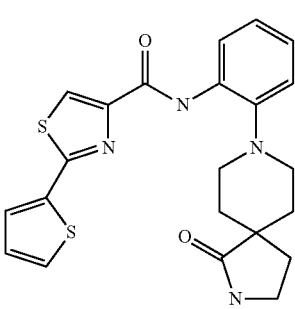 [SMILES: O=C(Nc1ccccc1N1CCC2(CCNC2=O)CC1)c1csc(-c2cccs2)n1] |
| 291 | 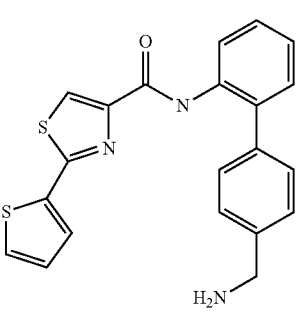 [SMILES: NCc1ccc(-c2ccccc2NC(=O)c2csc(-c3cccs3)n2)cc1] |
| 292 | 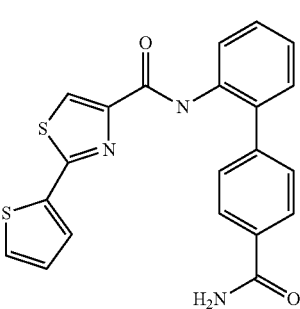 [SMILES: NC(=O)c1ccc(-c2ccccc2NC(=O)c2csc(-c3cccs3)n2)cc1] |

| No. | Structure |
|---|---|
| 293 | 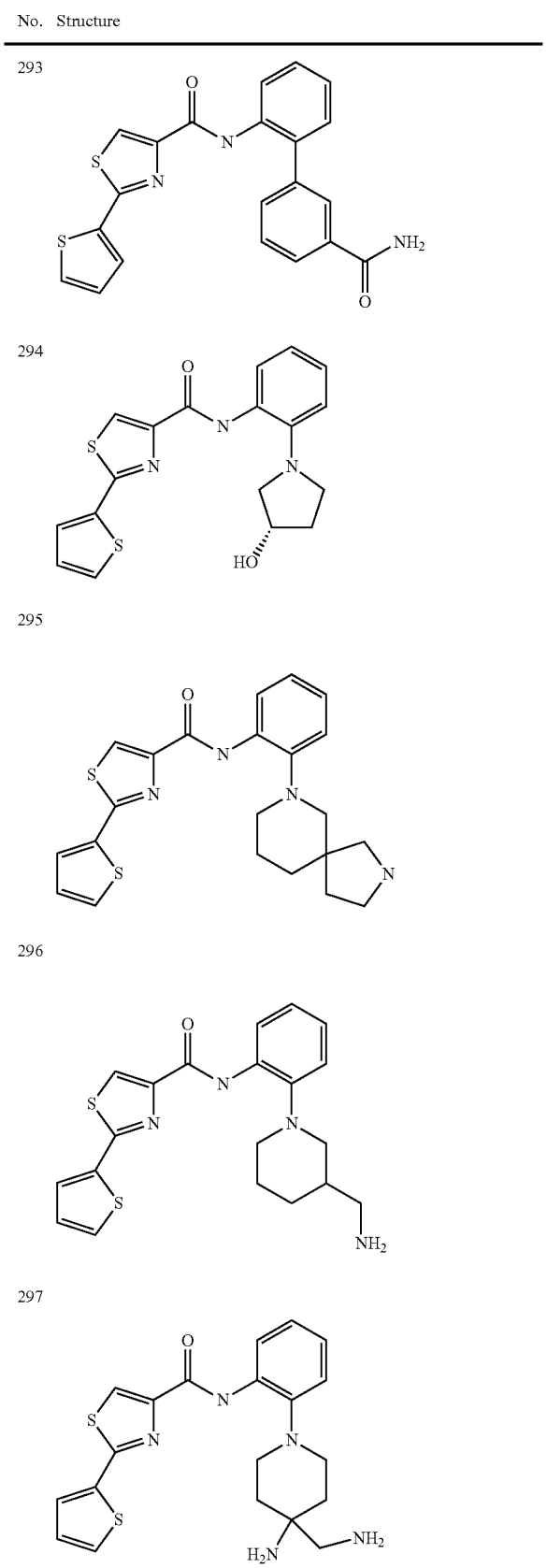 |
| 294 | |
| 295 | |
| 296 | |
| 297 | |
| No. | Structure |
|---|---|
| 298 | 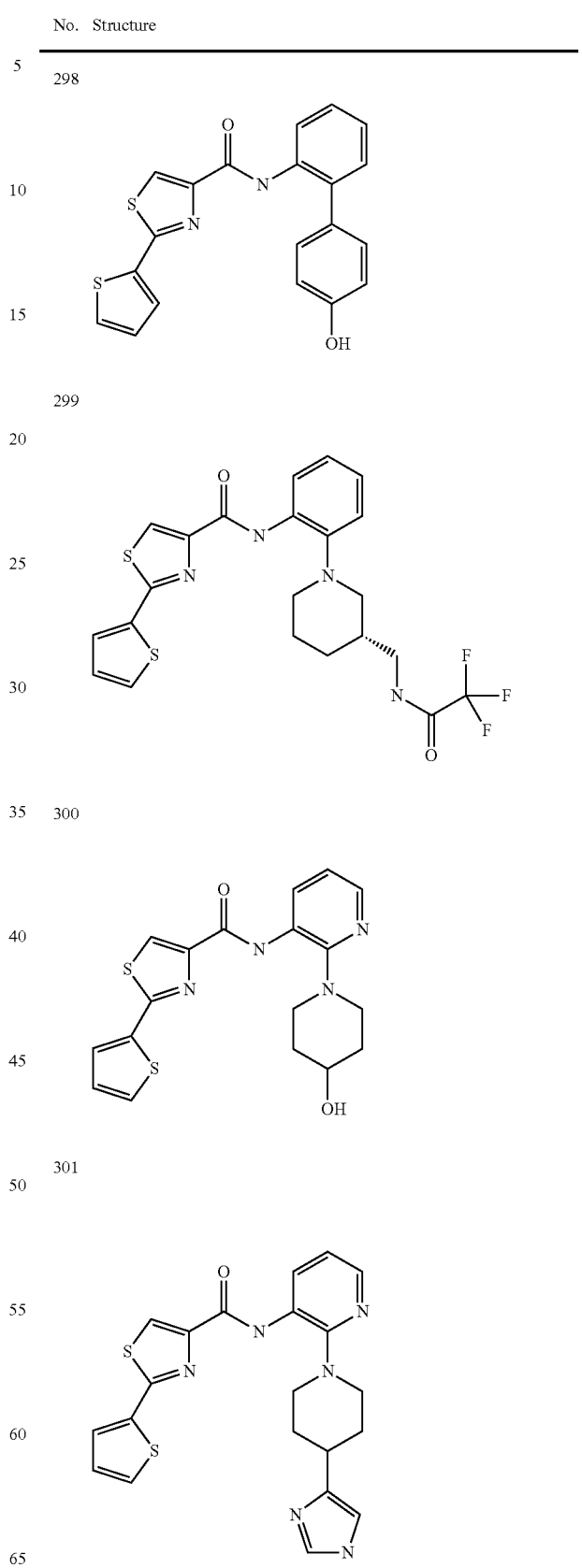 |
| 299 | |
| 300 | |
| 301 | |

| No. | Structure |
|---|---|
| 302 | 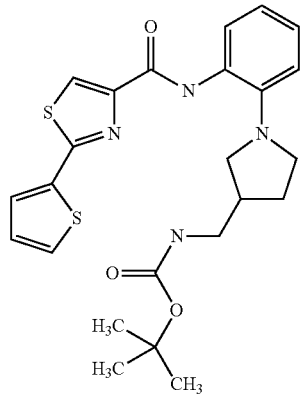 [SMILES: CC(C)(C)OC(=O)NCC1CCN(c2ccccc2NC(=O)c2csc(-c3cccs3)n2)C1] |
| 303 | 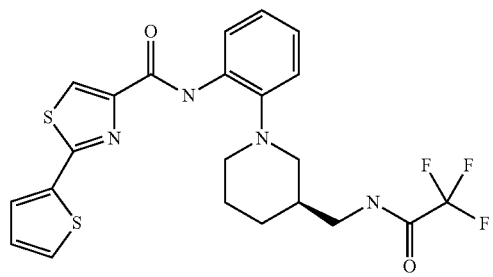 [SMILES: O=C(Nc1ccccc1N1CCC[C@H](CNC(=O)C(F)(F)F)C1)c1csc(-c2cccs2)n1] |
| 304 | 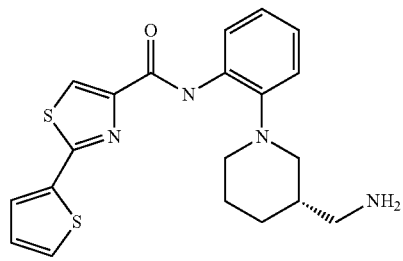 [SMILES: NC[C@@H]1CCCN(c2ccccc2NC(=O)c2csc(-c3cccs3)n2)C1] |
| 305 | 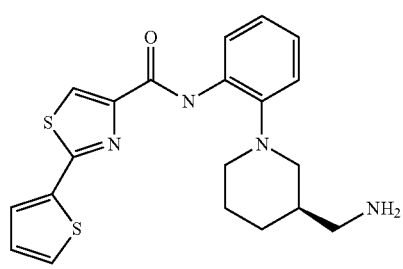 [SMILES: NC[C@H]1CCCN(c2ccccc2NC(=O)c2csc(-c3cccs3)n2)C1] |
| 306 | 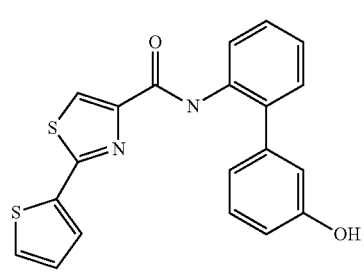 [SMILES: O=C(Nc1ccccc1-c1cccc(O)c1)c1csc(-c2cccs2)n1] |
| No. | Structure |
|---|---|
| 307 | 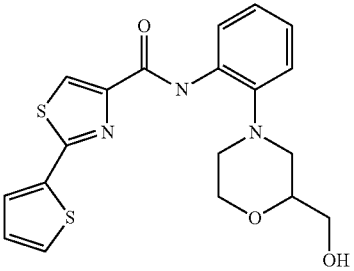 [SMILES: O=C(Nc1ccccc1N1CCOC(CO)C1)c1csc(-c2cccs2)n1] |
| 308 | 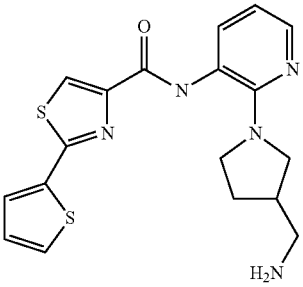 |
| 309 | 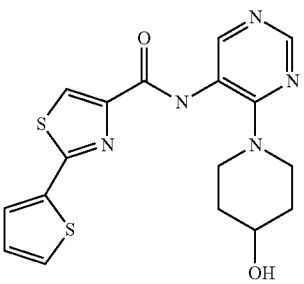 [SMILES: O=C(Nc1cncnc1N1CCC(O)CC1)c1csc(-c2cccs2)n1] |
| 310 | 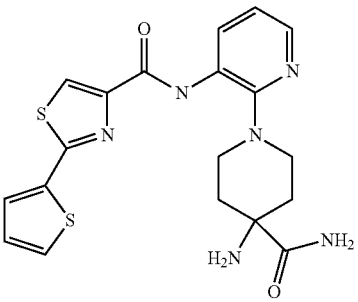 [SMILES: NC(=O)C1(N)CCN(c2ncccc2NC(=O)c2csc(-c3cccs3)n2)CC1] |
| 311 | 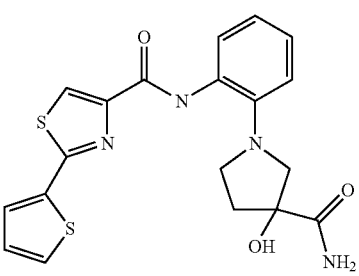 |

| No. | Structure |
|---|---|
| 312 | 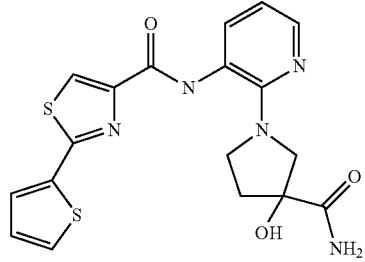 [SMILES: NC(=O)C1(O)CCN(c2ncccc2NC(=O)c2csc(-c3cccs3)n2)C1] |
| 313 | 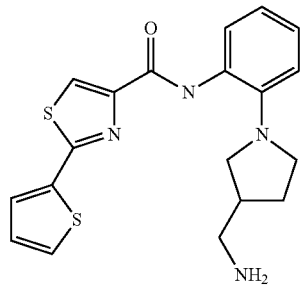 [SMILES: NCC1CCN(c2ccccc2NC(=O)c2csc(-c3cccs3)n2)C1] |
| 314 | 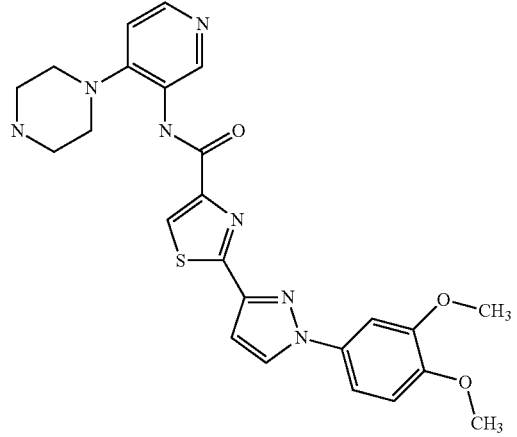 [SMILES: COc1ccc(-n2ccc(-c3nc(C(=O)Nc4cnccc4N4CCNCC4)cs3)n2)cc1OC] |
| 315 | 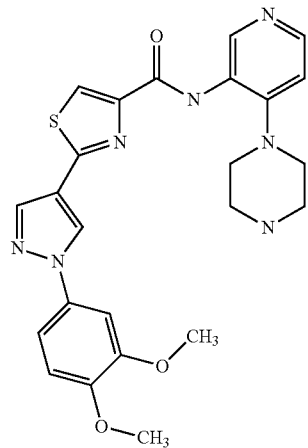 [SMILES: COc1ccc(-n2cc(-c3nc(C(=O)Nc4cnccc4N4CCNCC4)cs3)cn2)cc1OC] |
| No. | Structure |
|---|---|
| 316 | 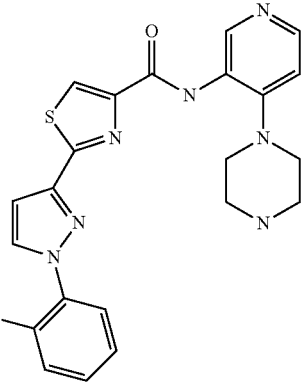 |
| 317 |  |
| 318 | 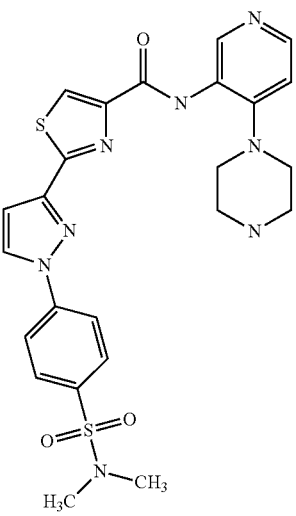 [SMILES: CN(C)S(=O)(=O)c1ccc(-n2ccc(-c3nc(C(=O)Nc4cnccc4N4CCNCC4)cs3)n2)cc1] |

| No. | Structure |
|---|---|
| 319 | 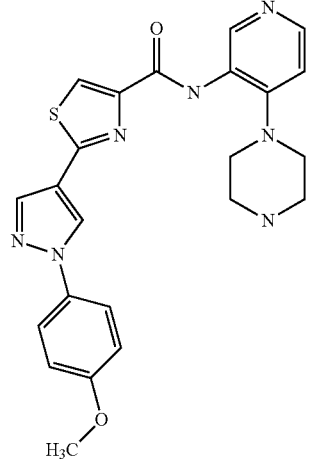 [SMILES: COc1ccc(-n2cc(-c3nc(C(=O)Nc4cnccc4N4CCNCC4)cs3)cn2)cc1] |
| 320 | 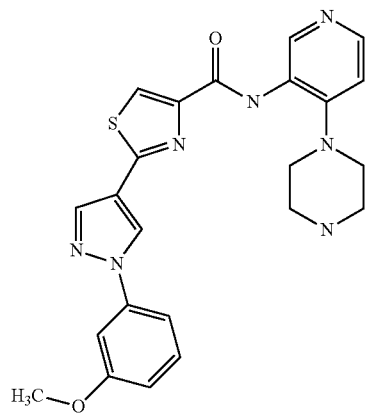 [SMILES: COc1cccc(-n2cc(-c3nc(C(=O)Nc4cnccc4N4CCNCC4)cs3)cn2)c1] |
| 321 | 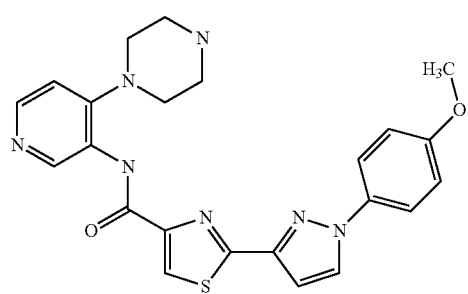 [SMILES: COc1ccc(-n2ccc(-c3nc(C(=O)Nc4cnccc4N4CCNCC4)cs3)n2)cc1] |
| 322 | 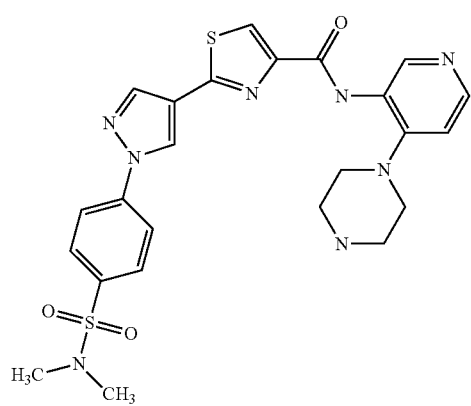 [SMILES: CN(C)S(=O)(=O)c1ccc(-n2cc(-c3nc(C(=O)Nc4cnccc4N4CCNCC4)cs3)cn2)cc1] |
| No. | Structure |
|---|---|
| 323 | 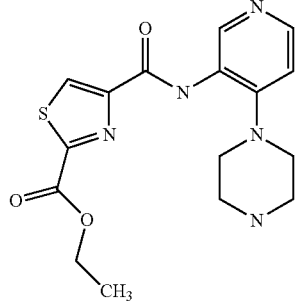 [SMILES: CCOC(=O)c1nc(C(=O)Nc2cnccc2N2CCNCC2)cs1] |
| 324 | 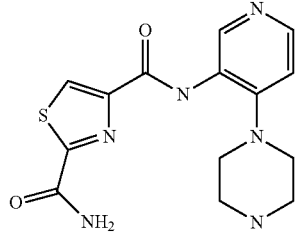 [SMILES: NC(=O)c1nc(C(=O)Nc2cnccc2N2CCNCC2)cs1] |
| 325 | 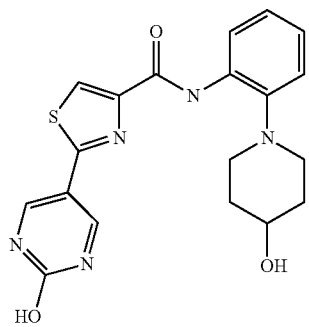 [SMILES: O=C(Nc1ccccc1N1CCC(O)CC1)c1csc(-c2cnc(O)nc2)n1] |
| 326 | 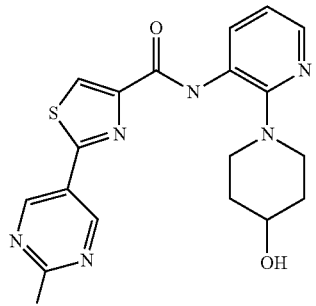 |
| 327 | 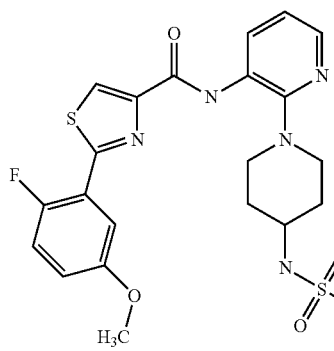 |

-continued
| No. | Structure |
|---|---|
| 328 | 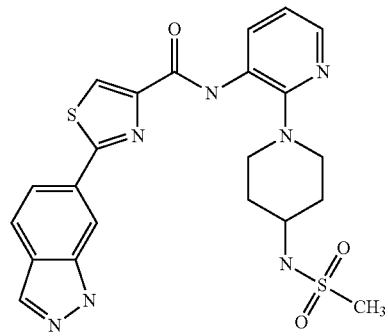 |
| 329 | 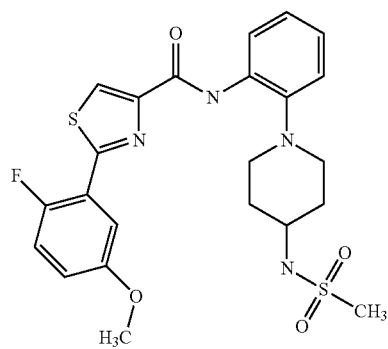 [SMILES: COc1ccc(F)c(-c2nc(C(=O)Nc3cccnc3N3CCC(NS(C)(=O)=O)CC3)cs2)c1] |
| 330 | 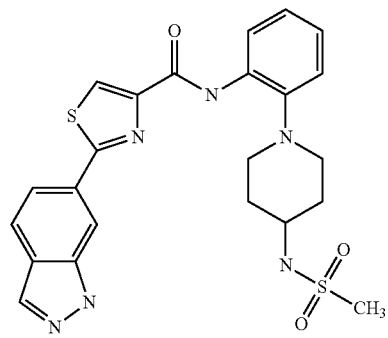 [SMILES: CS(=O)(=O)NC1CCN(c2ncccc2NC(=O)c2csc(-c3ccc4cn[nH]c4c3)n2)CC1] |
| 331 | 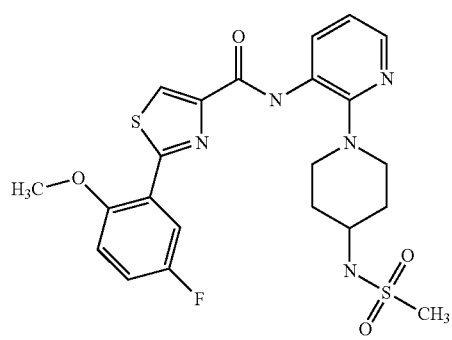 |
-continued
| No. | Structure |
|---|---|
| 332 | 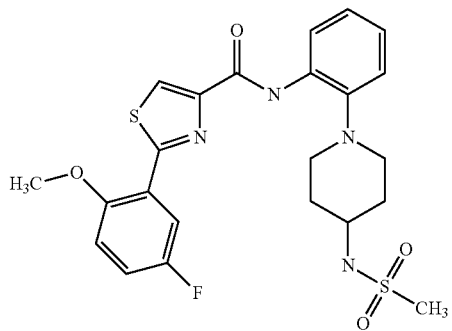 |
| 333 | 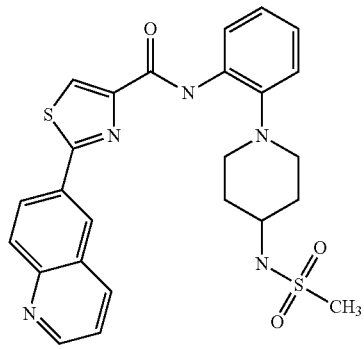 [SMILES: CS(=O)(=O)NC1CCN(c2ccccc2NC(=O)c2csc(-c3ccc4ncccc4c3)n2)CC1] |
| 334 | 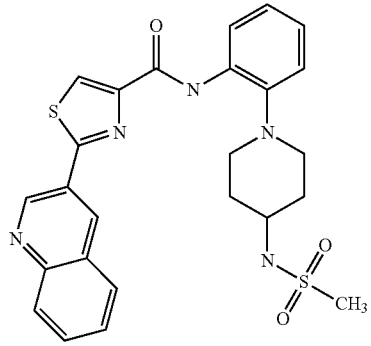 [SMILES: CS(=O)(=O)NC1CCN(c2ccccc2NC(=O)c2csc(-c3cnc4ccccc4c3)n2)CC1] |
| 335 | 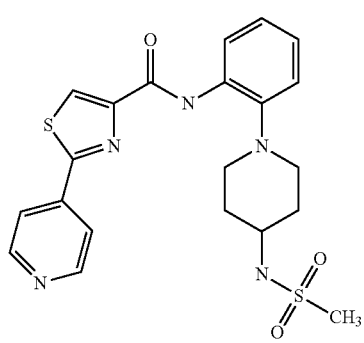 [SMILES: CS(=O)(=O)NC1CCN(c2ccccc2NC(=O)c2csc(-c3ccncc3)n2)CC1] |

107
-continued
| No. | Structure |
|---|---|
| 336 | 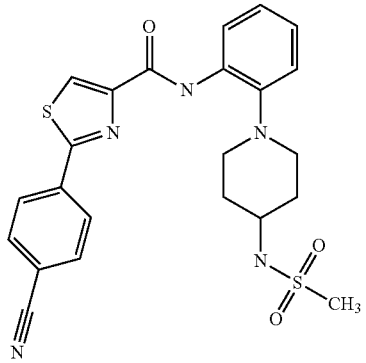 [SMILES: CS(=O)(=O)NC1CCN(c2ccccc2NC(=O)c2csc(-c3ccc(C#N)cc3)n2)CC1] |
| 337 | 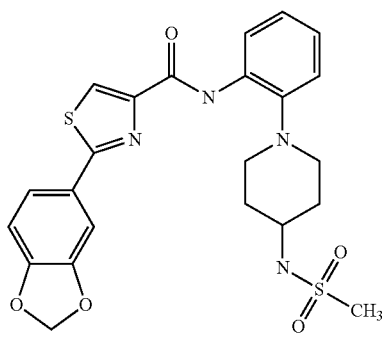 |
| 338 | 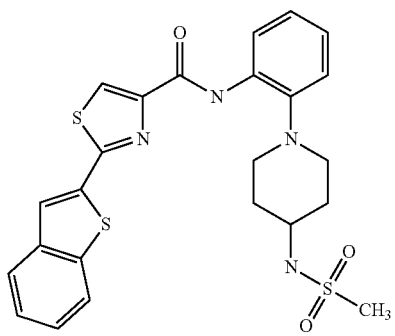 [SMILES: CS(=O)(=O)NC1CCN(c2ccccc2NC(=O)c2csc(-c3cc4ccccc4s3)n2)CC1] |
| 339 | 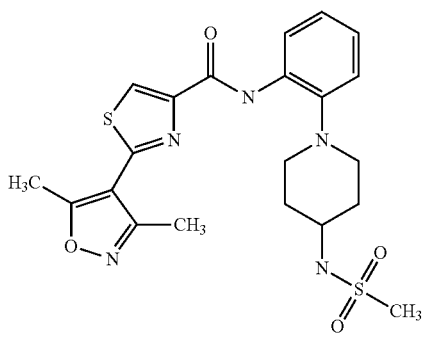 |
108
-continued
| No. | Structure |
|---|---|
| 340 | 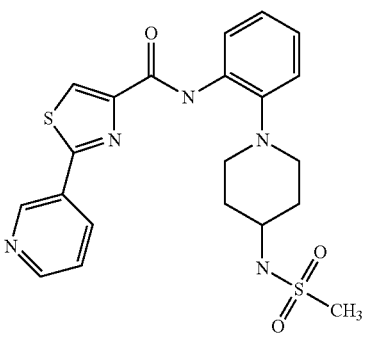 [SMILES: CS(=O)(=O)NC1CCN(c2ccccc2NC(=O)c2csc(-c3cccnc3)n2)CC1] |
| 341 | 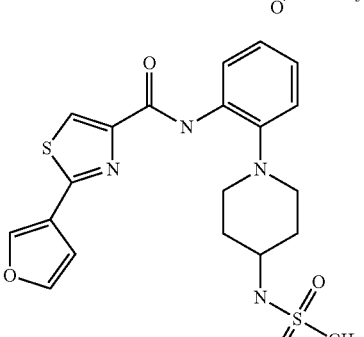 |
| 342 | 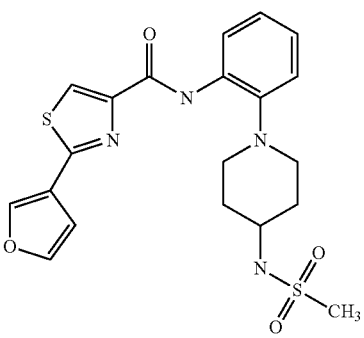 |
| 343 | 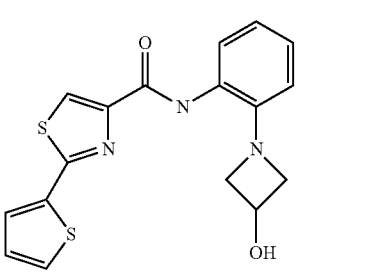 [SMILES: O=C(Nc1ccccc1N1CC(O)C1)c1csc(-c2cccs2)n1] |
| 344 | 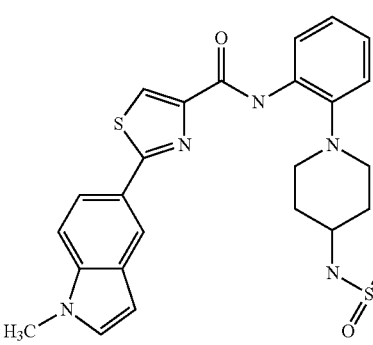 |

| No. | Structure |
|---|---|
| 345 | 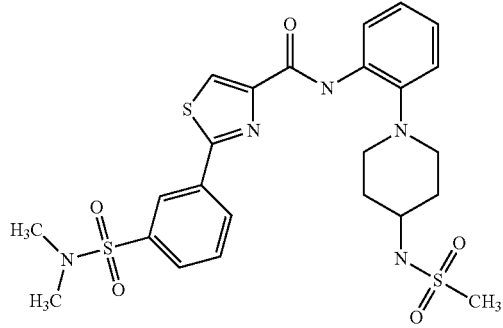 |
| 346 | 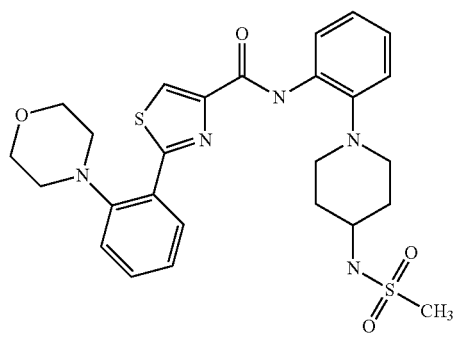 [SMILES: CS(=O)(=O)NC1CCN(c2ccccc2NC(=O)c2csc(-c3ccccc3N3CCOCC3)n2)CC1] |
| 347 | 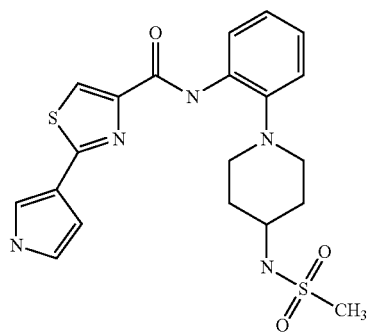 [SMILES: CS(=O)(=O)NC1CCN(c2ccccc2NC(=O)c2csc(-c3cc[nH]c3)n2)CC1] |
| 348 | 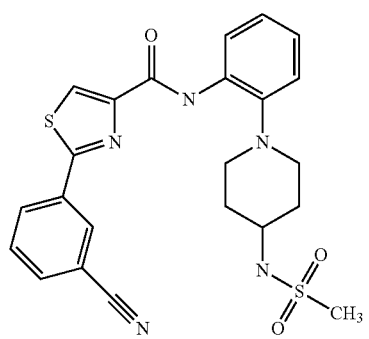 [SMILES: CS(=O)(=O)NC1CCN(c2ccccc2NC(=O)c2csc(-c3cccc(C#N)c3)n2)CC1] |
| No. | Structure |
|---|---|
| 349 | 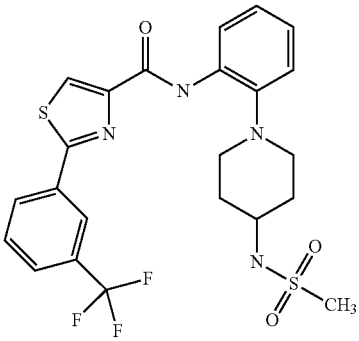 [SMILES: CS(=O)(=O)NC1CCN(c2ccccc2NC(=O)c2csc(-c3cccc(C(F)(F)F)c3)n2)CC1] |
| 350 | 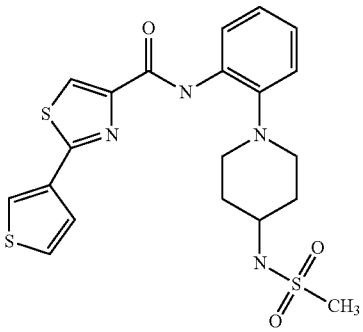 [SMILES: CS(=O)(=O)NC1CCN(c2ccccc2NC(=O)c2csc(-c3ccsc3)n2)CC1] |
| 351 | 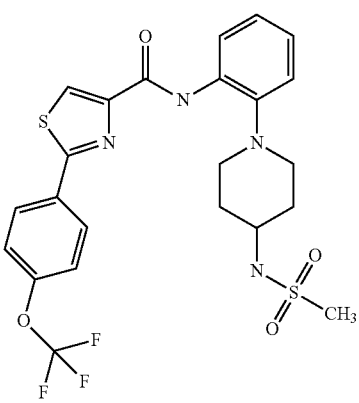 [SMILES: CS(=O)(=O)NC1CCN(c2ccccc2NC(=O)c2csc(-c3ccc(OC(F)(F)F)cc3)n2)CC1] |
| 352 | 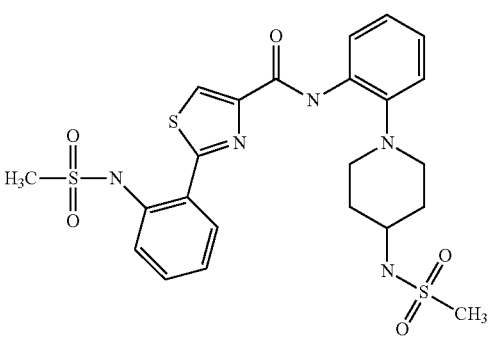 |

111
-continued
| No. | Structure |
|---|---|
| 353 | 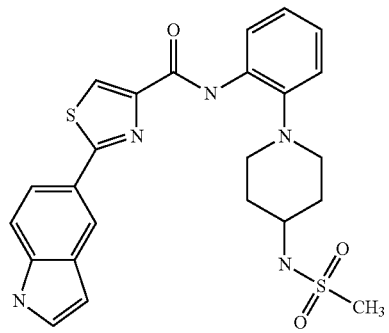 [SMILES: CS(=O)(=O)NC1CCN(c2ccccc2NC(=O)c2csc(-c3ccc4[nH]ccc4c3)n2)CC1] |
| 354 | 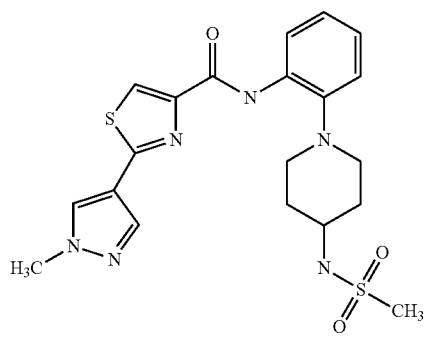 |
| 355 | 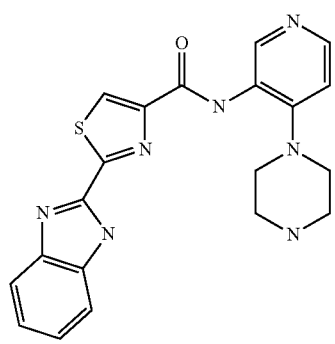 [SMILES: O=C(Nc1cnccc1N1CCNCC1)c1csc(-c2nc3ccccc3[nH]2)n1] |
| 356 | 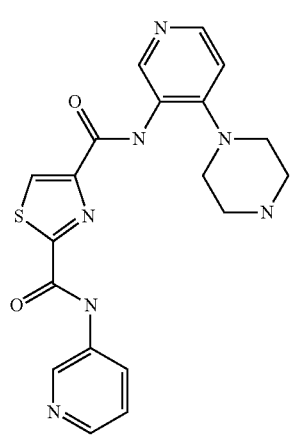 [SMILES: O=C(Nc1cnccc1N1CCNCC1)c1csc(C(=O)Nc2cccnc2)n1] |
112
-continued
| No. | Structure |
|---|---|
| 357 | 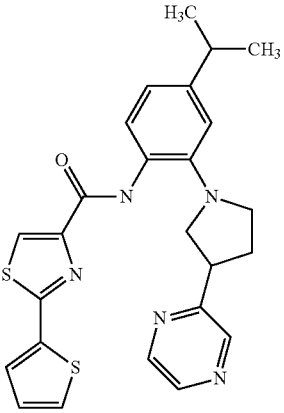 [SMILES: CC(C)c1ccc(NC(=O)c2csc(-c3cccs3)n2)c(N2CCC(c3cnccn3)C2)c1] |
| 358 | 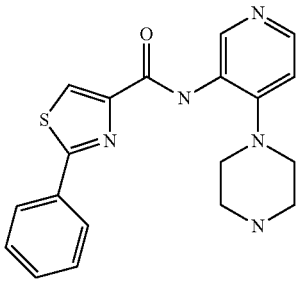 [SMILES: O=C(Nc1cnccc1N1CCNCC1)c1csc(-c2ccccc2)n1] |
| 359 | 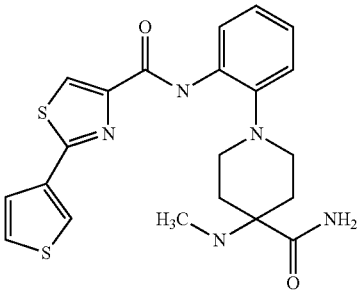 |
| 360 | 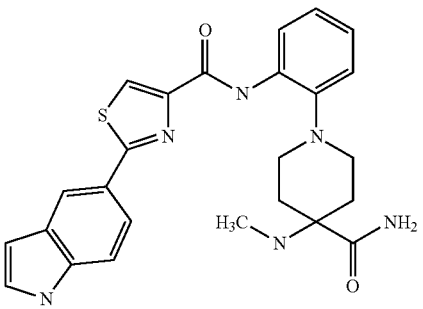 [SMILES: CNC1(C(N)=O)CCN(c2ccccc2NC(=O)c2csc(-c3ccc4[nH]ccc4c3)n2)CC1] |

-continued
| No. | Structure |
|---|---|
| 361 | 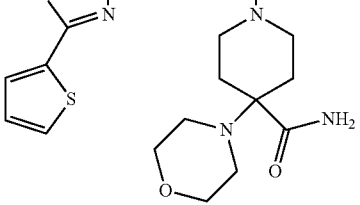 |
| 362 | 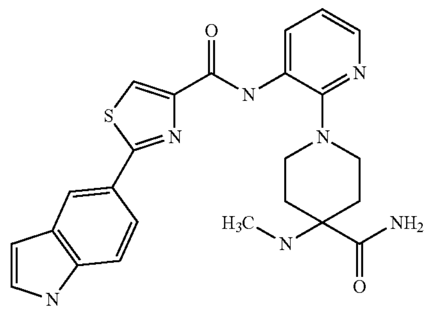 [SMILES: CNC1(C(N)=O)CCN(c2ncccc2NC(=O)c2csc(-c3ccc4[nH]ccc4c3)n2)CC1] |
| 363 | 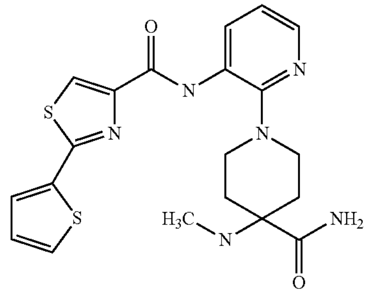 [SMILES: CNC1(C(N)=O)CCN(c2ncccc2NC(=O)c2csc(-c3cccs3)n2)CC1] |
| 364 | 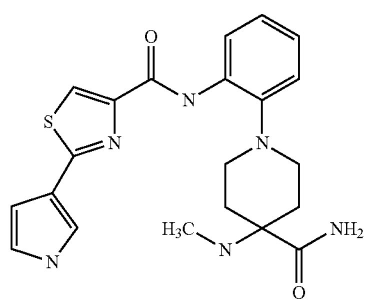 [SMILES: CNC1(C(N)=O)CCN(c2ccccc2NC(=O)c2csc(-c3cc[nH]c3)n2)CC1] |
| 365 | 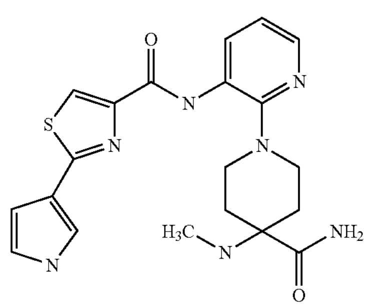 |
-continued
| No. | Structure |
|---|---|
| 366 | 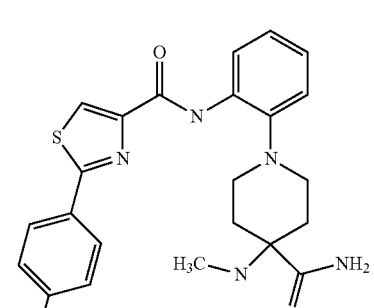 |
| 367 | 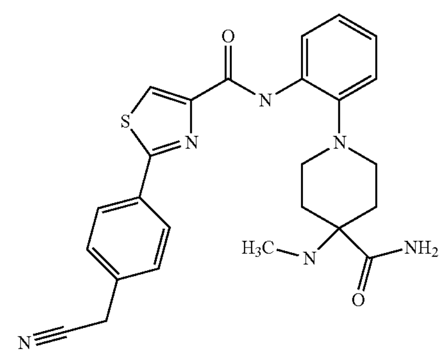 [SMILES: CNC1(C(N)=O)CCN(c2ccccc2NC(=O)c2csc(-c3ccc(CC#N)cc3)n2)CC1] |
| 368 | 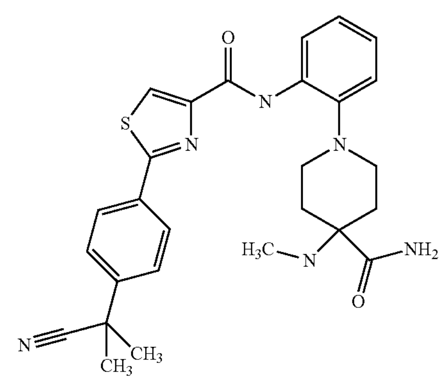 [SMILES: CNC1(C(N)=O)CCN(c2ccccc2NC(=O)c2csc(-c3ccc(C(C)(C)C#N)cc3)n2)CC1] |
| 369 | 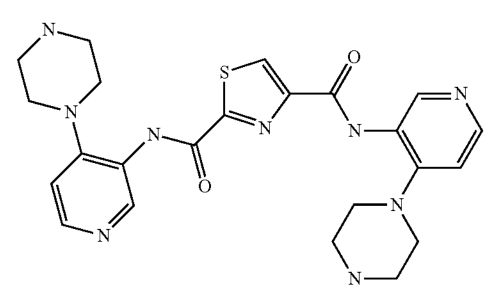 [SMILES: O=C(Nc1cnccc1N1CCNCC1)c1csc(C(=O)Nc2cnccc2N2CCNCC2)n1] |

| No. | Structure |
|---|---|
| 370 | 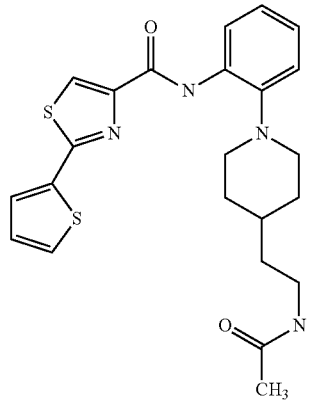 [SMILES: CC(=O)NCCC1CCN(c2ccccc2NC(=O)c2csc(-c3cccs3)n2)CC1] |
| 371 | 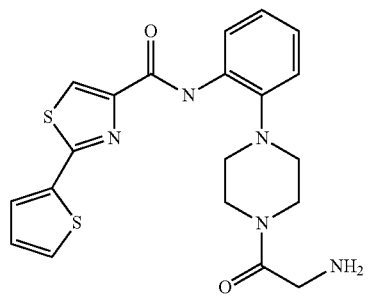 [SMILES: NCC(=O)N1CCN(c2ccccc2NC(=O)c2csc(-c3cccs3)n2)CC1] |
| 372 | 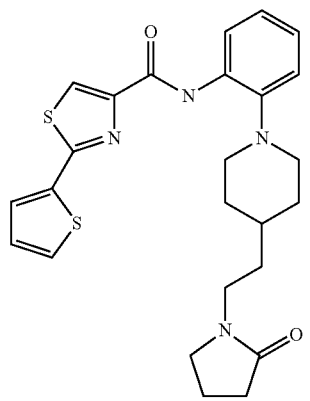 [SMILES: O=C(Nc1ccccc1N1CCC(CCN2CCCC2=O)CC1)c1csc(-c2cccs2)n1] |
| 373 | 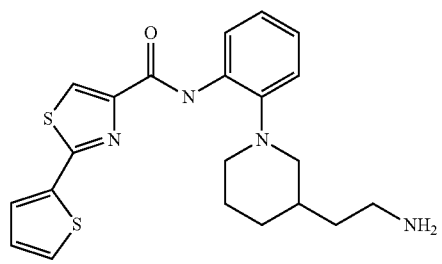 [SMILES: NCCC1CCCN(c2ccccc2NC(=O)c2csc(-c3cccs3)n2)C1] |
| No. | Structure |
|---|---|
| 374 | 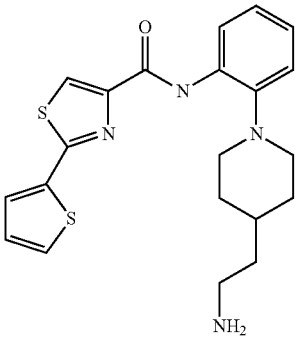 [SMILES: NCCC1CCN(c2ccccc2NC(=O)c2csc(-c3cccs3)n2)CC1] |
| 375 | 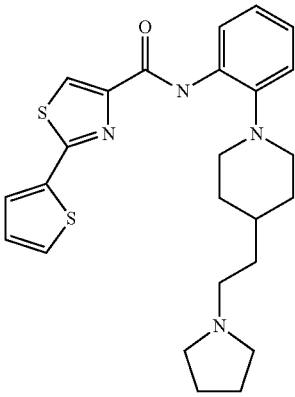 [SMILES: O=C(Nc1ccccc1N1CCC(CCN2CCCC2)CC1)c1csc(-c2cccs2)n1] |
| 376 | 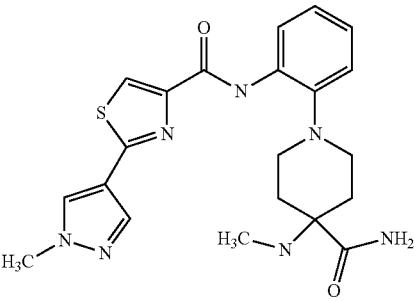 [SMILES: CNC1(C(N)=O)CCN(c2ccccc2NC(=O)c2csc(-c3cnn(C)c3)n2)CC1] |
| 377 | 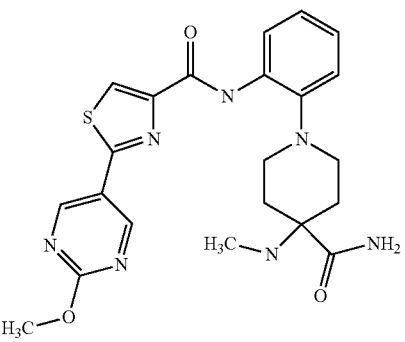 [SMILES: CNC1(C(N)=O)CCN(c2ccccc2NC(=O)c2csc(-c3cnc(OC)nc3)n2)CC1] |

117
-continued
| No. | Structure |
|---|---|
| 378 | 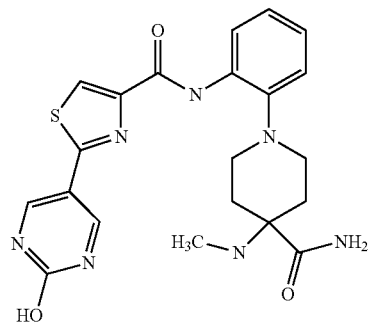 [SMILES: CNC1(C(N)=O)CCN(c2ccccc2NC(=O)c2csc(-c3cnc(O)nc3)n2)CC1] |
| 379 | 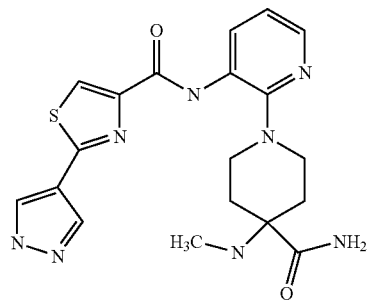 [SMILES: CNC1(C(N)=O)CCN(c2ncccc2NC(=O)c2csc(-c3cn[nH]c3)n2)CC1] |
| 380 | 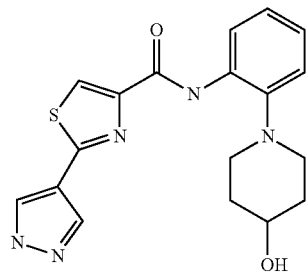 [SMILES: O=C(Nc1ccccc1N1CCC(O)CC1)c1csc(-c2cn[nH]c2)n1] |
| 381 | 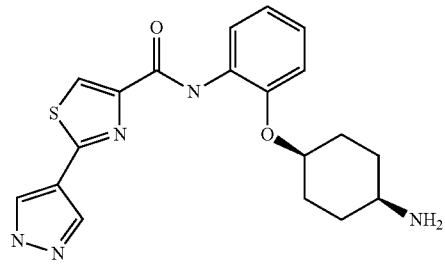 [SMILES: N[C@H]1CC[C@@H](Oc2ccccc2NC(=O)c2csc(-c3cn[nH]c3)n2)CC1] |
| 382 | 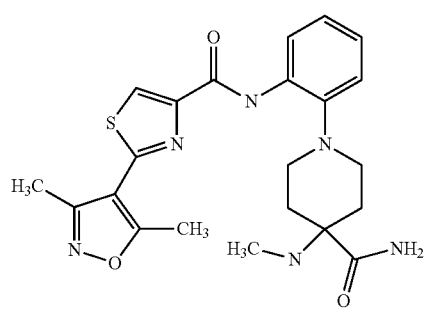 [SMILES: CNC1(C(N)=O)CCN(c2ccccc2NC(=O)c2csc(-c3c(C)noc3C)n2)CC1] |
118
-continued
| No. | Structure |
|---|---|
| 383 | 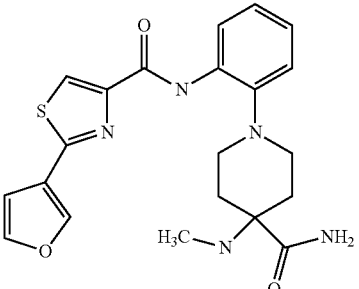 |
| 384 | 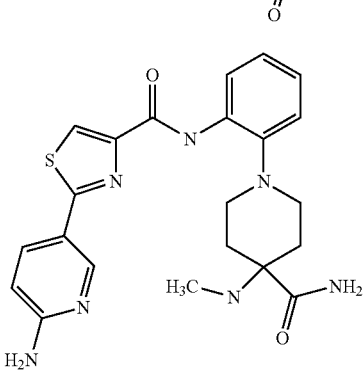 |
| 385 | 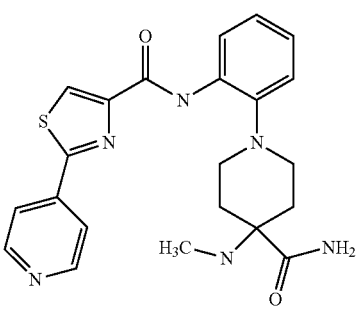 [SMILES: CNC1(C(N)=O)CCN(c2ccccc2NC(=O)c2csc(-c3ccncc3)n2)CC1] |
| 386 | 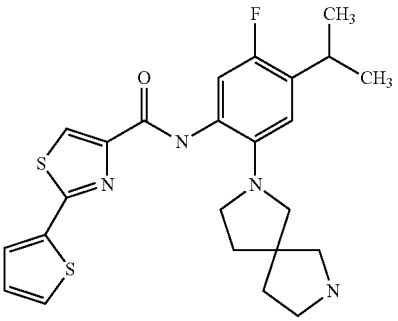 [SMILES: CC(C)c1cc(N2CCC3(CCNC3)C2)c(NC(=O)c2csc(-c3cccs3)n2)cc1F] |
| 387 | 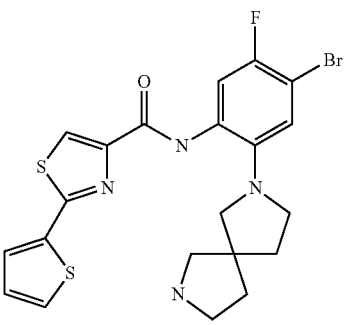 [SMILES: O=C(Nc1cc(F)c(Br)cc1N1CCC2(CCNC2)C1)c1csc(-c2cccs2)n1] |

| No. | Structure |
|---|---|
| 388 | 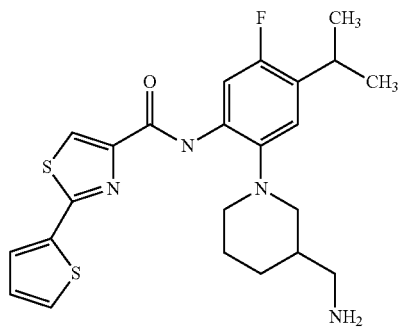 [SMILES: CC(C)c1cc(N2CCCC(CN)C2)c(NC(=O)c2csc(-c3cccs3)n2)cc1F] |
| 389 | 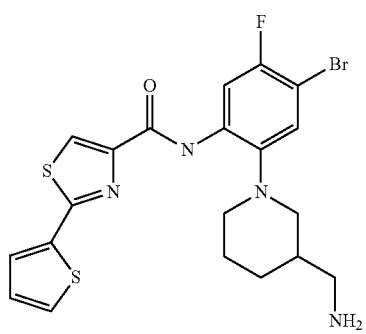 [SMILES: NCC1CCCN(c2cc(Br)c(F)cc2NC(=O)c2csc(-c3cccs3)n2)C1] |
| 390 | 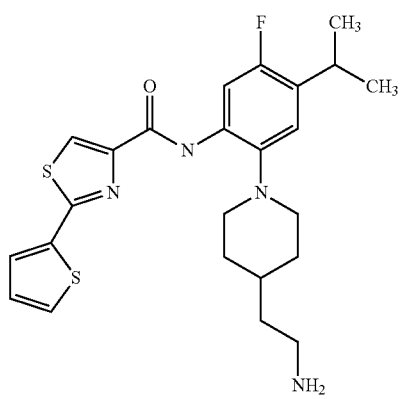 [SMILES: CC(C)c1cc(N2CCC(CCN)CC2)c(NC(=O)c2csc(-c3cccs3)n2)cc1F] |
| 391 | 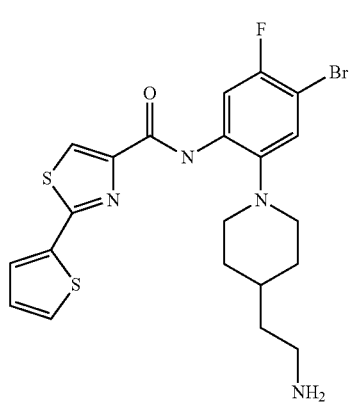 [SMILES: NCCC1CCN(c2cc(Br)c(F)cc2NC(=O)c2csc(-c3cccs3)n2)CC1] |
| No. | Structure |
|---|---|
| 392 | 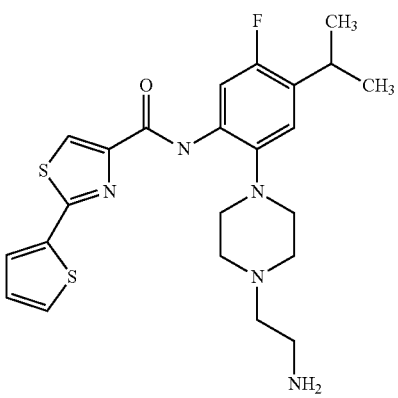 [SMILES: CC(C)c1cc(N2CCN(CCN)CC2)c(NC(=O)c2csc(-c3cccs3)n2)cc1F] |
| 393 | 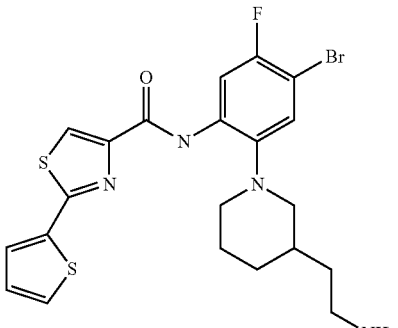 |
| 394 | 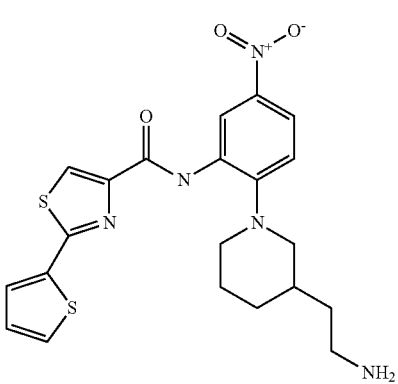 [SMILES: NCCC1CCCN(c2ccc([N+](=O)[O-])cc2NC(=O)c2csc(-c3cccs3)n2)C1] |
| 395 | 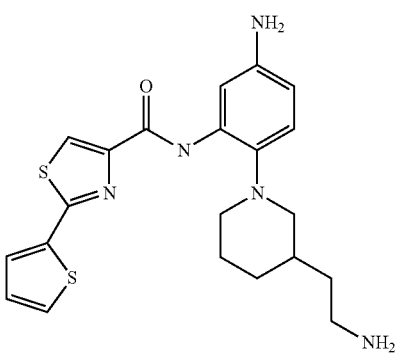 [SMILES: NCCC1CCCN(c2ccc(N)cc2NC(=O)c2csc(-c3cccs3)n2)C1] |

| No. | Structure |
|---|---|
| 396 | 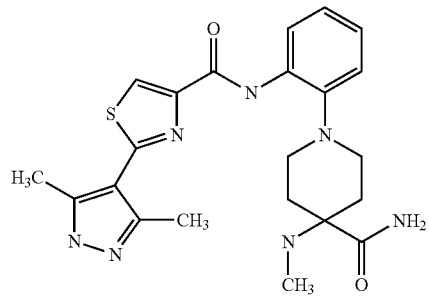 [SMILES: CNC1(C(N)=O)CCN(c2ccccc2NC(=O)c2csc(-c3c(C)n[nH]c3C)n2)CC1] |
| 397 | 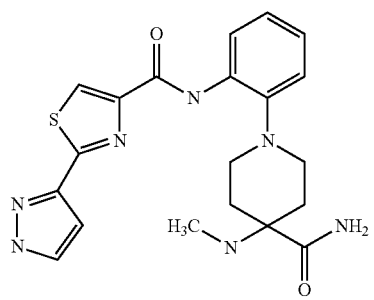 [SMILES: CNC1(C(N)=O)CCN(c2ccccc2NC(=O)c2csc(-c3cc[nH]n3)n2)CC1] |
| 398 | 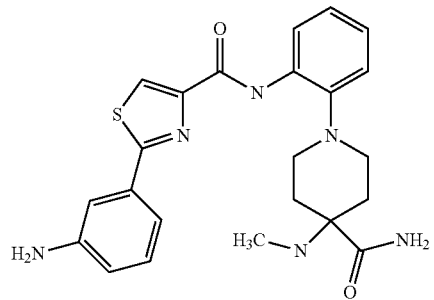 [SMILES: CNC1(C(N)=O)CCN(c2ccccc2NC(=O)c2csc(-c3cccc(N)c3)n2)CC1] |
| 399 | 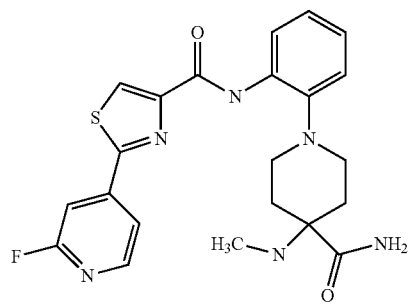 [SMILES: CNC1(C(N)=O)CCN(c2ccccc2NC(=O)c2csc(-c3ccnc(F)c3)n2)CC1] |
| 400 | 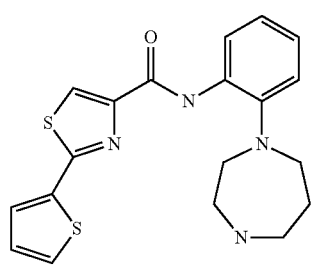 [SMILES: O=C(Nc1ccccc1N1CCCNCC1)c1csc(-c2cccs2)n1] |
| No. | Structure |
|---|---|
| 401 | 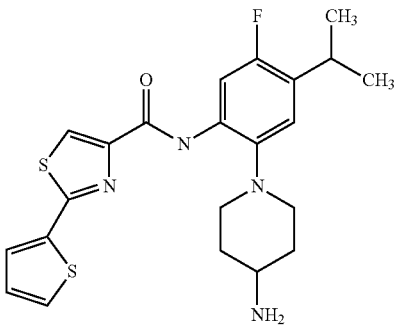 [SMILES: CC(C)c1cc(N2CCC(N)CC2)c(NC(=O)c2csc(-c3cccs3)n2)cc1F] |
| 402 | 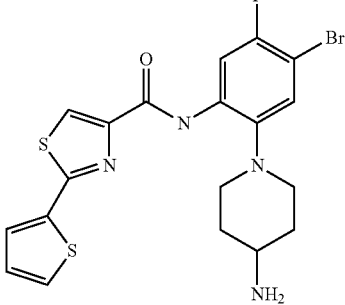 |
| 403 | 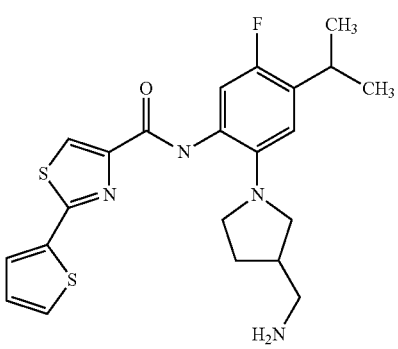 [SMILES: CC(C)c1cc(N2CCC(CN)C2)c(NC(=O)c2csc(-c3cccs3)n2)cc1F] |
| 404 | 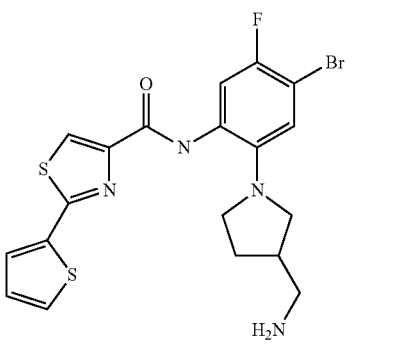 [SMILES: NCC1CCN(c2cc(Br)c(F)cc2NC(=O)c2csc(-c3cccs3)n2)C1] |
| 405 | 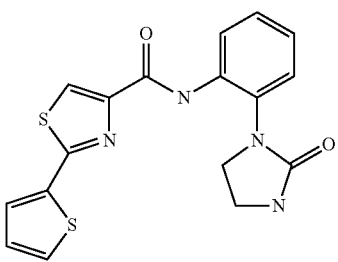 [SMILES: O=C(Nc1ccccc1N1CCNC1=O)c1csc(-c2cccs2)n1] |

| No. | Structure |
|---|---|
| 406 | 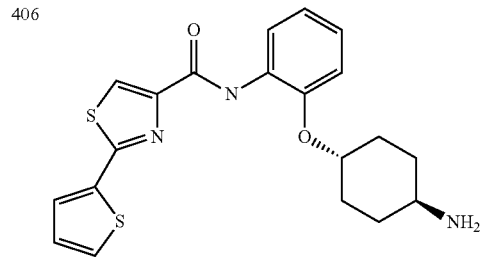 |
| 407 | 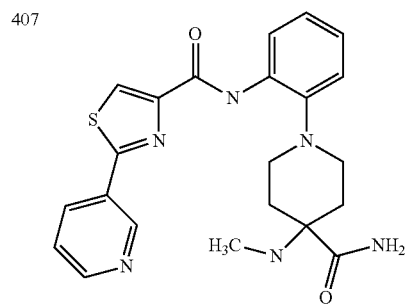 |
| 408 | 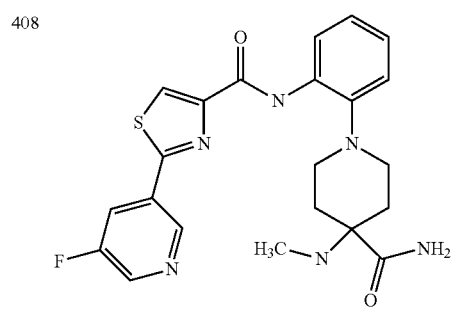 |
| 409 | 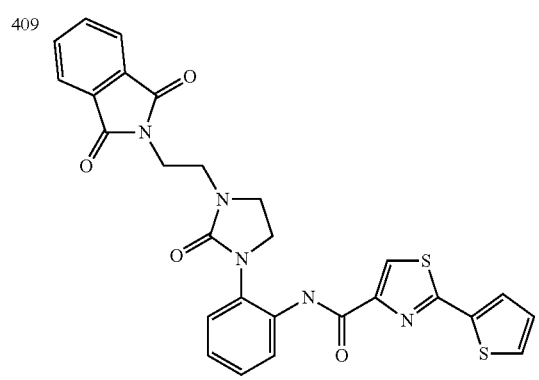 |
| 410 | 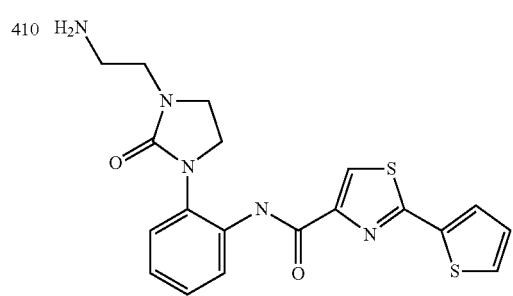 |
| No. | Structure |
|---|---|
| 411 | 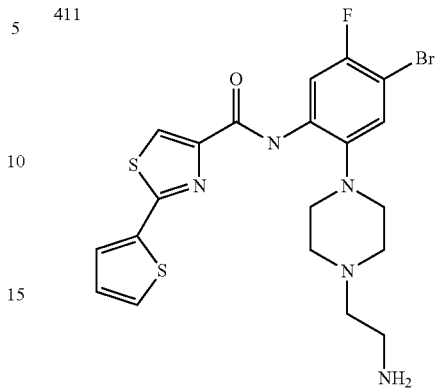 |
| 412 | 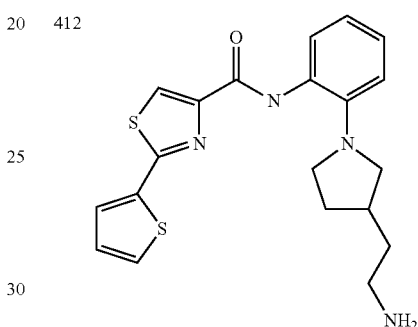 |
| 413 | 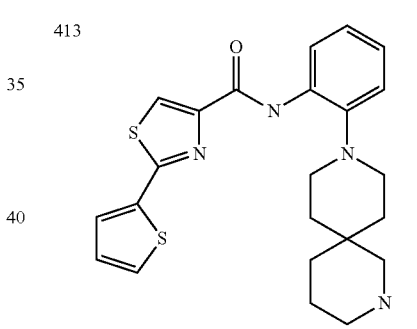 |
| 414 | 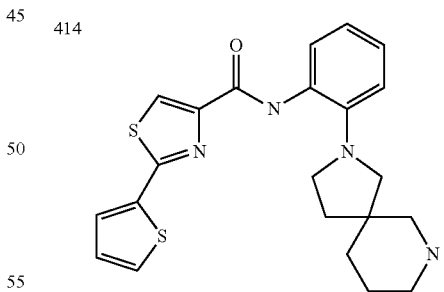 |
| 415 | 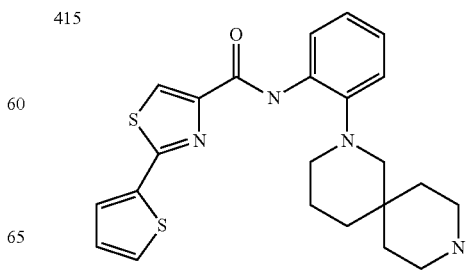 |

| No. | Structure |
|---|---|
| 416 | (structure) |
| 417 | (structure) |
| 418 | (structure) |
| 419 | (structure) |
| 420 | (structure) |
| 421 | (structure) |
| 422 | (structure) |
| 423 | (structure) |
| 424 | (structure) |

-continued
| No. | Structure |
|---|---|
| 425 | 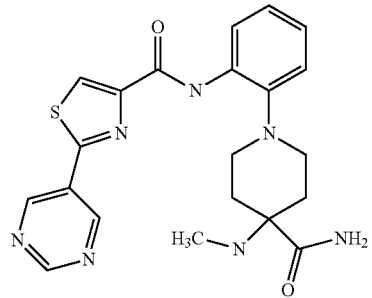 [SMILES: CNC1(C(N)=O)CCN(c2ccccc2NC(=O)c2csc(-c3cncnc3)n2)CC1] |
| 426 | 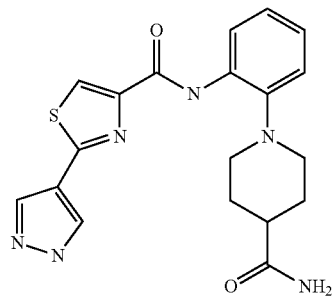 [SMILES: NC(=O)C1CCN(c2ccccc2NC(=O)c2csc(-c3cn[nH]c3)n2)CC1] |
| 427 | 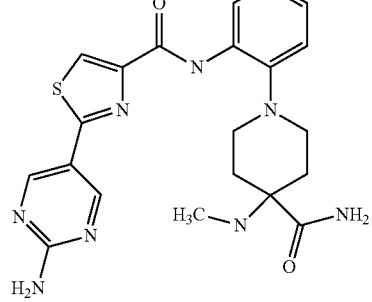 |
| 428 | 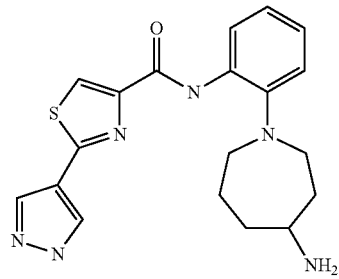 [SMILES: NC1CCCN(c2ccccc2NC(=O)c2csc(-c3cn[nH]c3)n2)CC1] |
| 429 | 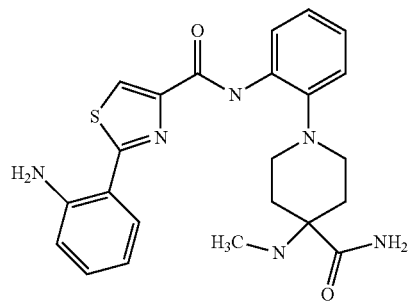 [SMILES: CNC1(C(N)=O)CCN(c2ccccc2NC(=O)c2csc(-c3ccccc3N)n2)CC1] |
-continued
| No. | Structure |
|---|---|
| 430 | 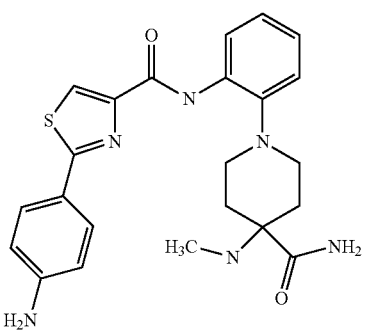 [SMILES: CNC1(C(N)=O)CCN(c2ccccc2NC(=O)c2csc(-c3ccc(N)cc3)n2)CC1] |
| 431 | 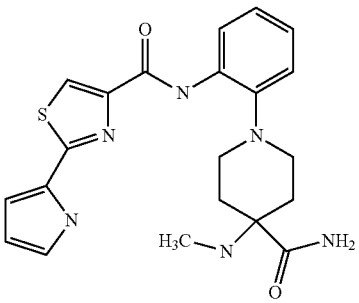 [SMILES: CNC1(C(N)=O)CCN(c2ccccc2NC(=O)c2csc(-c3ccc[nH]3)n2)CC1] |
| 432 | 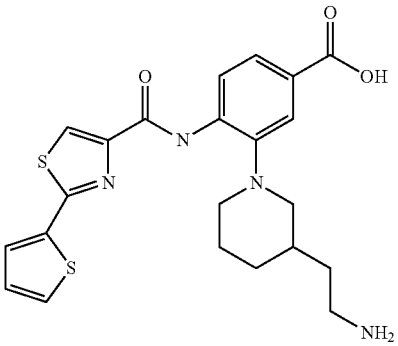 [SMILES: NCCC1CCCN(c2cc(C(=O)O)ccc2NC(=O)c2csc(-c3cccs3)n2)C1] |
| 433 | 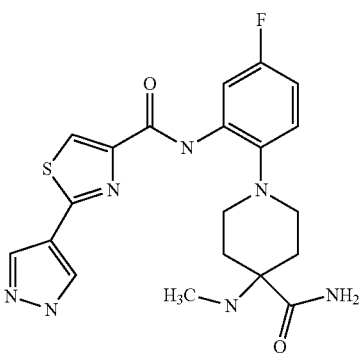 [SMILES: CNC1(C(N)=O)CCN(c2ccc(F)cc2NC(=O)c2csc(-c3cn[nH]c3)n2)CC1] |

-continued
| No. | Structure |
|---|---|
| 434 | 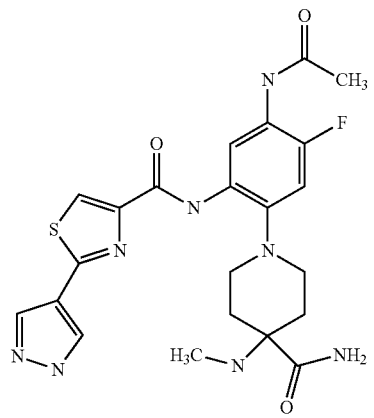 [SMILES: CNC1(C(N)=O)CCN(c2cc(F)c(NC(C)=O)cc2NC(=O)c2csc(-c3cn[nH]c3)n2)CC1] |
| 435 | 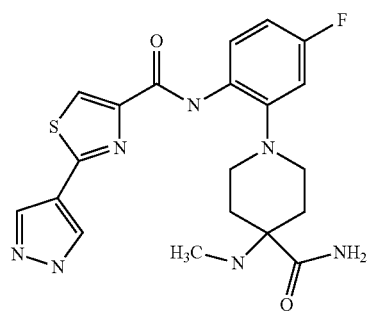 [SMILES: CNC1(C(N)=O)CCN(c2cc(F)ccc2NC(=O)c2csc(-c3cn[nH]c3)n2)CC1] |
| 436 | 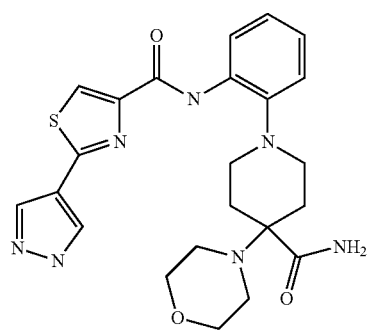 [SMILES: NC(=O)C1(N2CCOCC2)CCN(c2ccccc2NC(=O)c2csc(-c3cn[nH]c3)n2)CC1] |
| 437 | 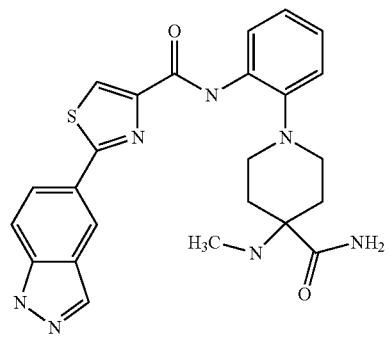 [SMILES: CNC1(C(N)=O)CCN(c2ccccc2NC(=O)c2csc(-c3ccc4[nH]ncc4c3)n2)CC1] |
-continued
| No. | Structure |
|---|---|
| 438 | 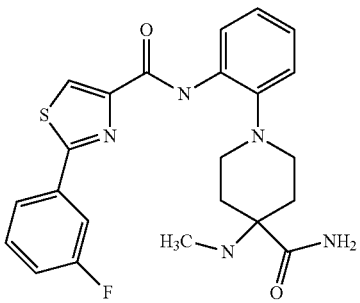 [SMILES: CNC1(C(N)=O)CCN(c2ccccc2NC(=O)c2csc(-c3cccc(F)c3)n2)CC1] |
| 439 | 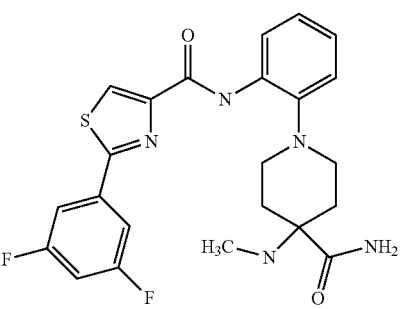 [SMILES: CNC1(C(N)=O)CCN(c2ccccc2NC(=O)c2csc(-c3cc(F)cc(F)c3)n2)CC1] |
| 440 | 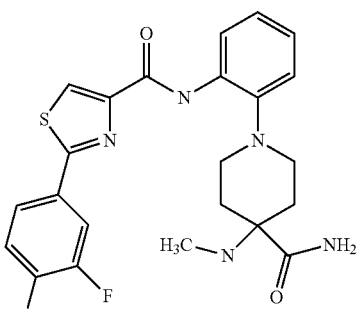 |
| 441 | 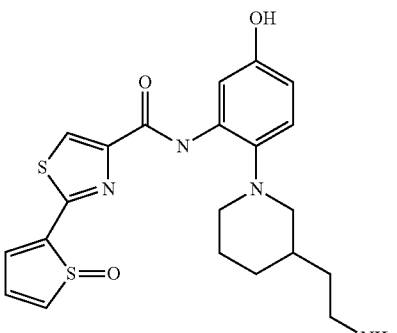 |
| 442 | 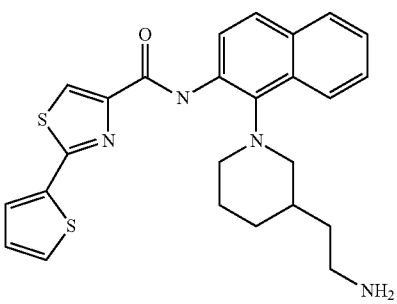 [SMILES: NCCC1CCCN(c2c(NC(=O)c3csc(-c4cccs4)n3)ccc3ccccc23)C1] |

| No. | Structure |
|---|---|
| 443 | 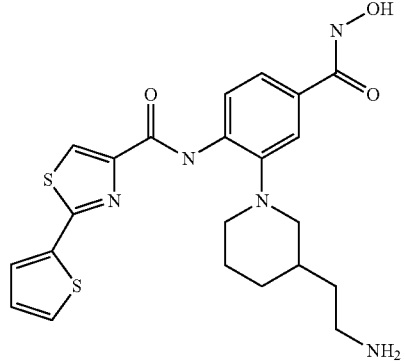 [SMILES: NCCC1CCCN(c2cc(C(=O)NO)ccc2NC(=O)c2csc(-c3cccs3)n2)C1] |
| 444 | 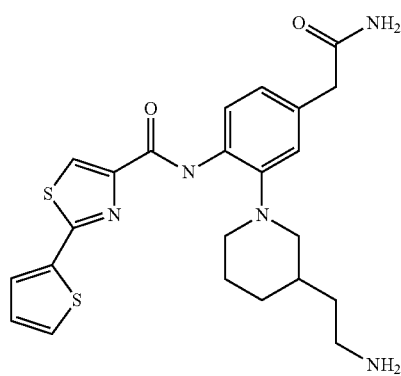 [SMILES: NCCC1CCCN(c2cc(CC(N)=O)ccc2NC(=O)c2csc(-c3cccs3)n2)C1] |
| 445 | 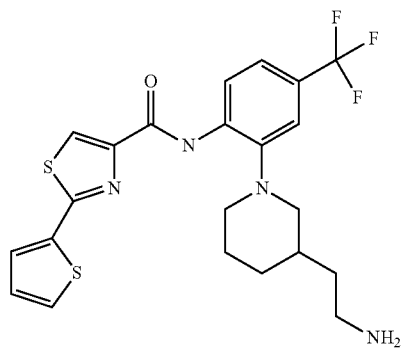 [SMILES: NCCC1CCCN(c2cc(C(F)(F)F)ccc2NC(=O)c2csc(-c3cccs3)n2)C1] |
| 446 | 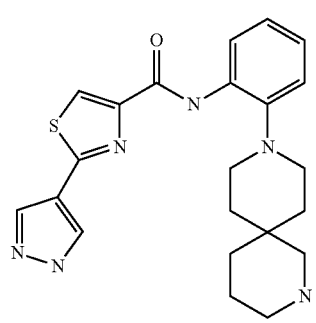 [SMILES: O=C(Nc1ccccc1N1CCC2(CCCNC2)CC1)c1csc(-c2cn[nH]c2)n1] |
| No. | Structure |
|---|---|
| 447 | 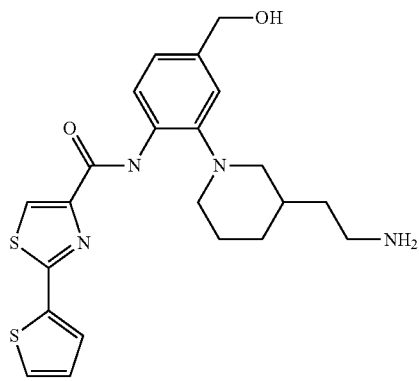 [SMILES: NCCC1CCCN(c2cc(CO)ccc2NC(=O)c2csc(-c3cccs3)n2)C1] |
| 448 | 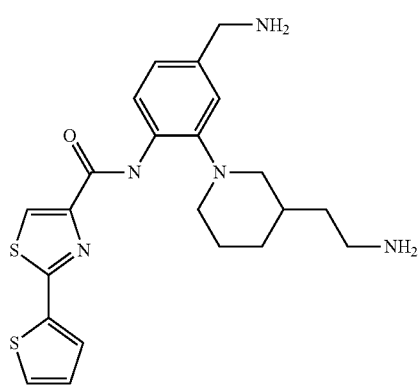 |
| 449 | 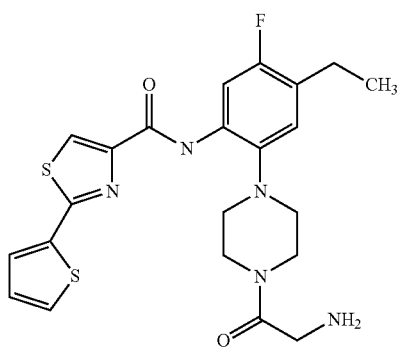 [SMILES: CCc1cc(N2CCN(C(=O)CN)CC2)c(NC(=O)c2csc(-c3cccs3)n2)cc1F] |
| 450 | 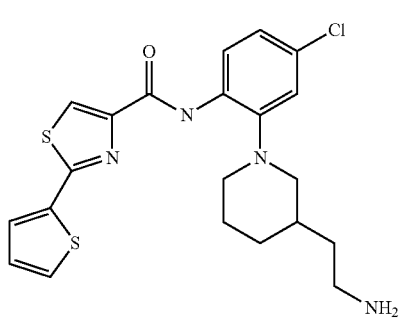 [SMILES: NCCC1CCCN(c2cc(Cl)ccc2NC(=O)c2csc(-c3cccs3)n2)C1] |

| No. | Structure |
|---|---|
| 451 | 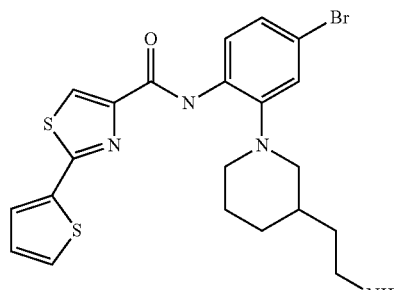 |
| 452 | 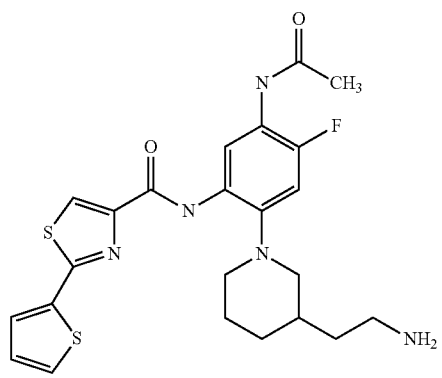 [SMILES: CC(=O)Nc1cc(NC(=O)c2csc(-c3cccs3)n2)c(N2CCCC(CCN)C2)cc1F] |
| 453 | 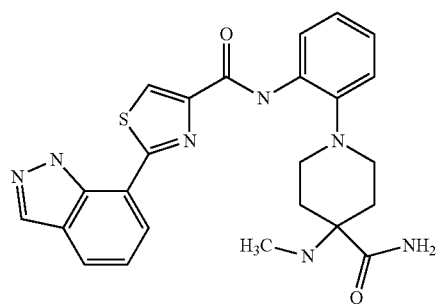 [SMILES: CNC1(C(N)=O)CCN(c2ccccc2NC(=O)c2csc(-c3cccc4cn[nH]c34)n2)CC1] |
| 454 | 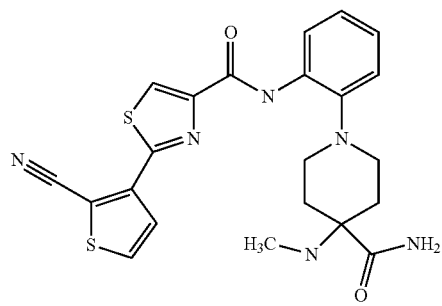 [SMILES: CNC1(C(N)=O)CCN(c2ccccc2NC(=O)c2csc(-c3ccsc3C#N)n2)CC1] |
| 455 | 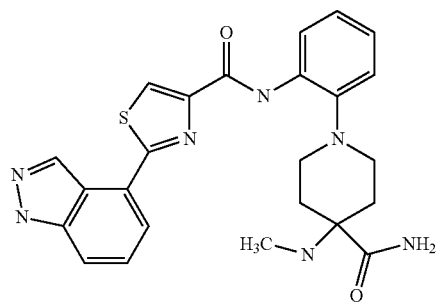 [SMILES: CNC1(C(N)=O)CCN(c2ccccc2NC(=O)c2csc(-c3cccc4[nH]ncc34)n2)CC1] |
| No. | Structure |
|---|---|
| 456 | 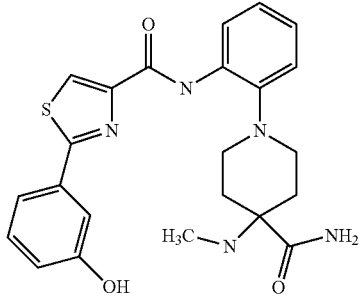 [SMILES: CNC1(C(N)=O)CCN(c2ccccc2NC(=O)c2csc(-c3cccc(O)c3)n2)CC1] |
| 457 | 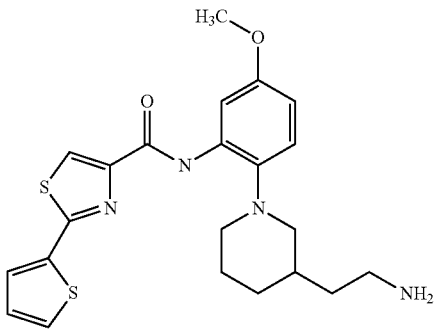 [SMILES: COc1ccc(N2CCCC(CCN)C2)c(NC(=O)c2csc(-c3cccs3)n2)c1] |
| 458 | 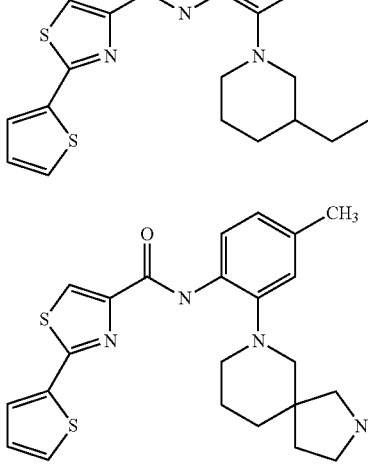 |
| 459 | 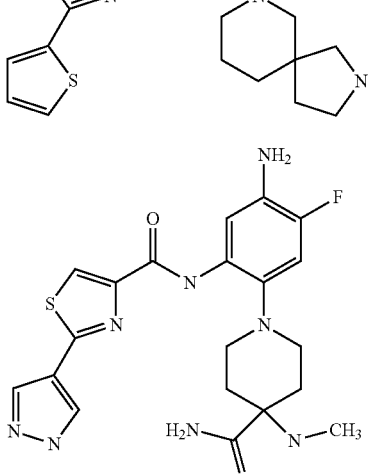 |
| 460 | 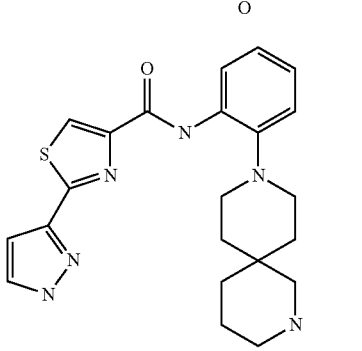 |

TABLE-continued

| No. | Structure |
|---|---|
| 461 | 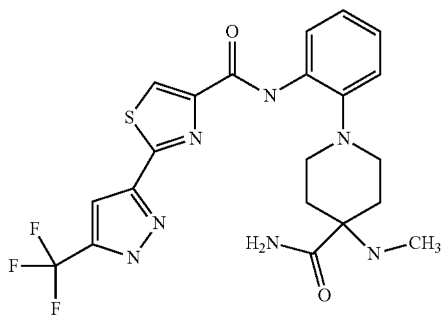 [SMILES: CNC1(C(N)=O)CCN(c2ccccc2NC(=O)c2csc(-c3cc(C(F)(F)F)[nH]n3)n2)CC1] |
| 462 | 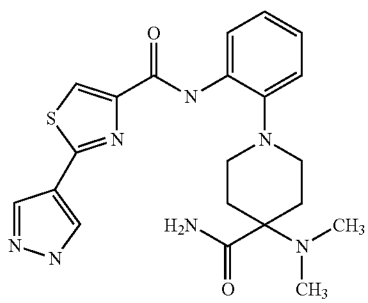 [SMILES: CN(C)C1(C(N)=O)CCN(c2ccccc2NC(=O)c2csc(-c3cn[nH]c3)n2)CC1] |
| 463 | 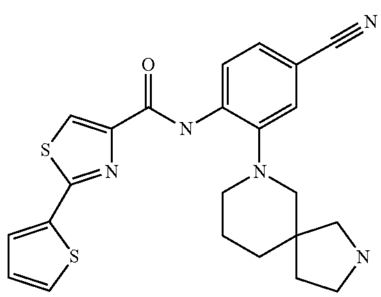 [SMILES: N#Cc1ccc(NC(=O)c2csc(-c3cccs3)n2)c(N2CCCC3(CCNC3)C2)c1] |
| 464 | 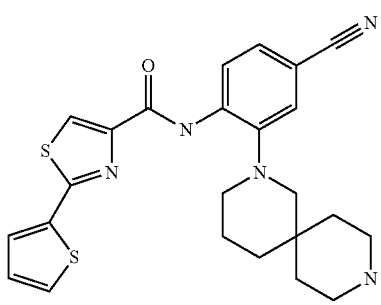 [SMILES: N#Cc1ccc(NC(=O)c2csc(-c3cccs3)n2)c(N2CCCC3(CCNCC3)C2)c1] |
| 465 | 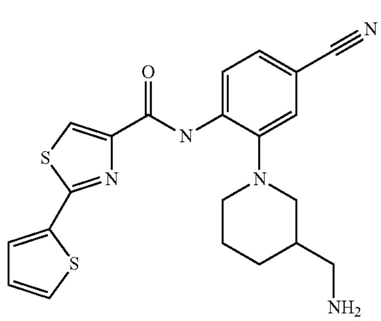 [SMILES: N#Cc1ccc(NC(=O)c2csc(-c3cccs3)n2)c(N2CCCC(CN)C2)c1] |
| 466 | |
| 467 | |
| 468 | |
| 469 | |

| No. | Structure |
|---|---|
| 470 | 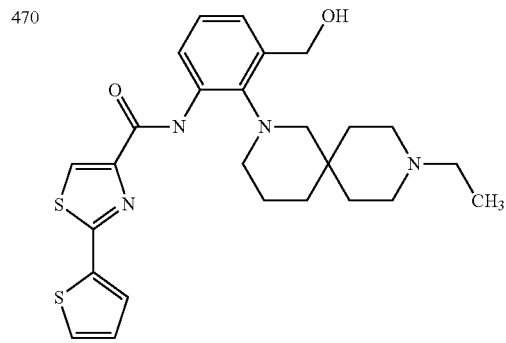 |
| 471 | 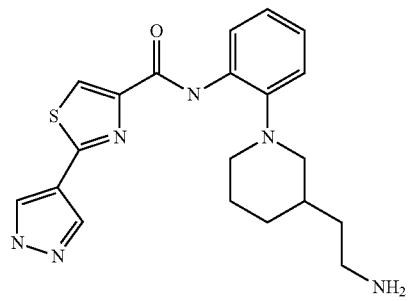 [SMILES: NCCC1CCCN(c2ccccc2NC(=O)c2csc(-c3cn[nH]c3)n2)C1] |
| 472 | 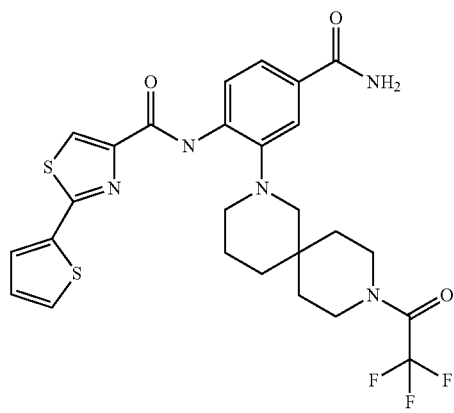 [SMILES: NC(=O)c1ccc(NC(=O)c2csc(-c3cccs3)n2)c(N2CCCC3(CCN(C(=O)C(F)(F)F)CC3)C2)c1] |
| 473 | 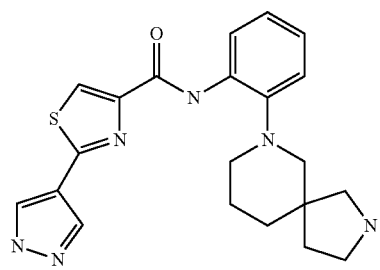 [SMILES: O=C(Nc1ccccc1N1CCCC2(CCNC2)C1)c1csc(-c2cn[nH]c2)n1] |
| No. | Structure |
|---|---|
| 474 | 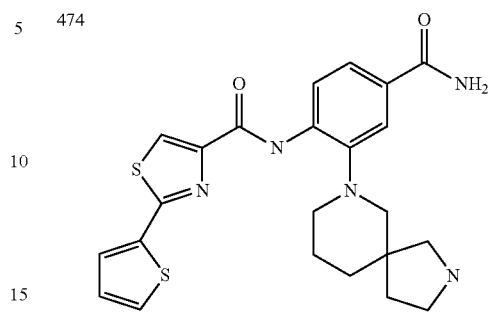 |
| 475 | 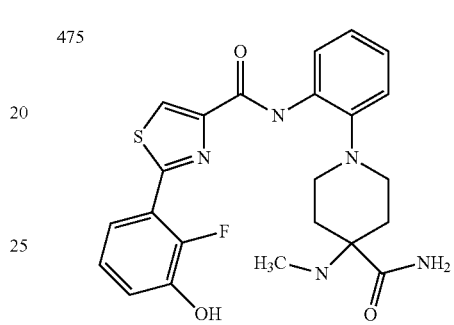 |
| 476 | 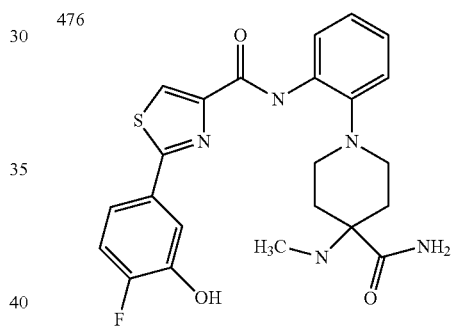 |
| 477 | 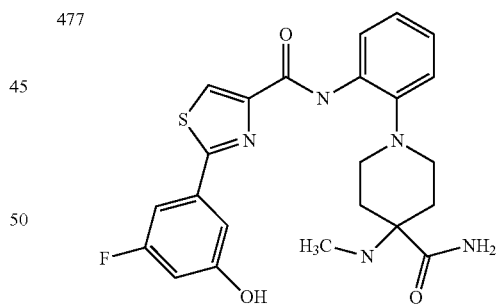 |
| 478 | 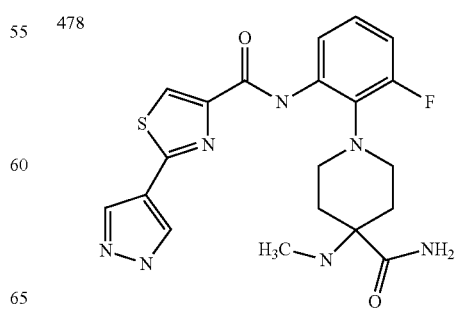 |

| No. | Structure |
|---|---|
| 479 | 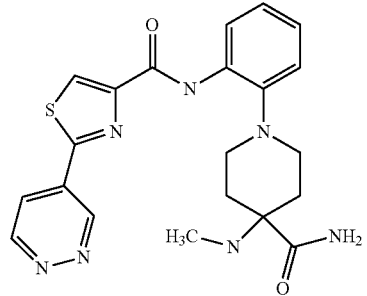 [SMILES: CNC1(C(N)=O)CCN(c2ccccc2NC(=O)c2csc(-c3ccnnc3)n2)CC1] |
| 480 | 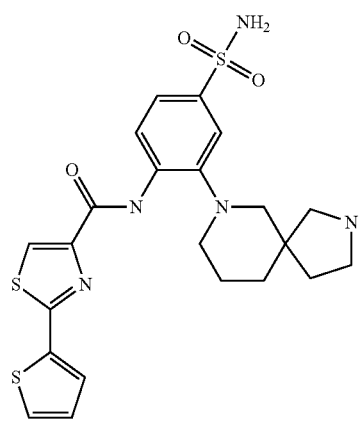 [SMILES: NS(=O)(=O)c1ccc(NC(=O)c2csc(-c3cccs3)n2)c(N2CCCC3(CCNC3)C2)c1] |
| 481 | 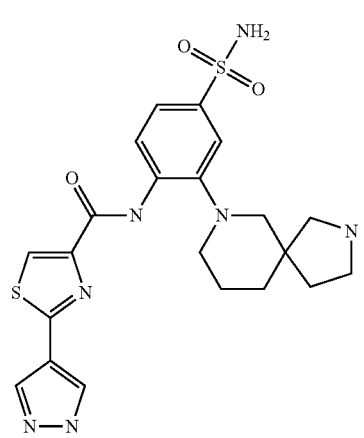 [SMILES: NS(=O)(=O)c1ccc(NC(=O)c2csc(-c3cn[nH]c3)n2)c(N2CCCC3(CCNC3)C2)c1] |
| 482 | 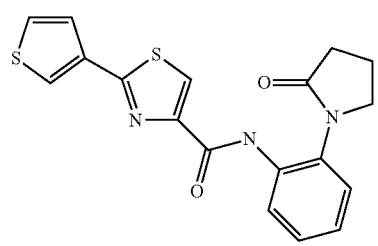 [SMILES: O=C(Nc1ccccc1N1CCCC1=O)c1csc(-c2ccsc2)n1] |
| 483 | 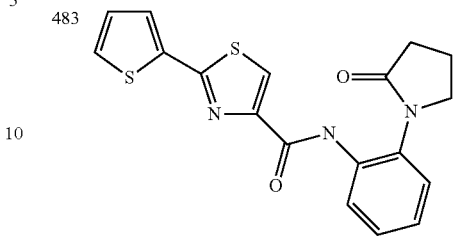 |
| 484 | 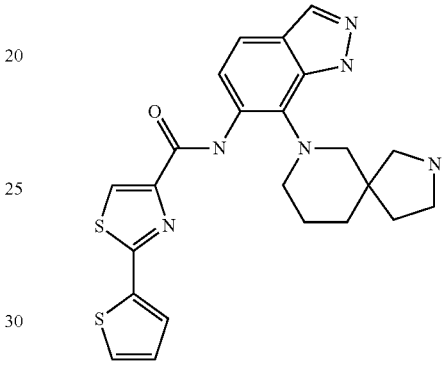 |
| 485 | 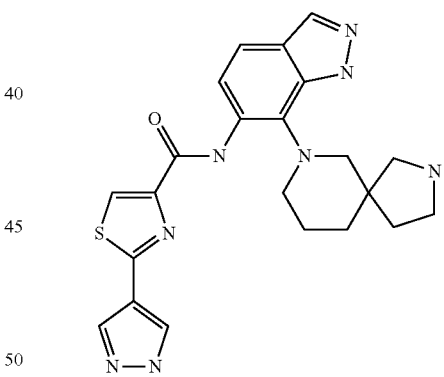 |
| 486 | 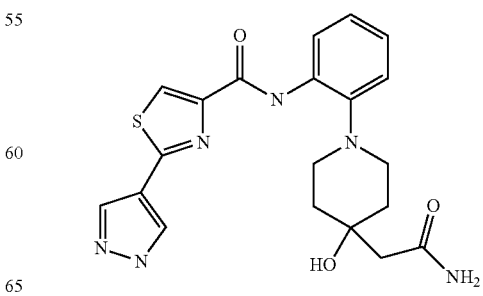 |

| No. | Structure |
|---|---|
| 487 | 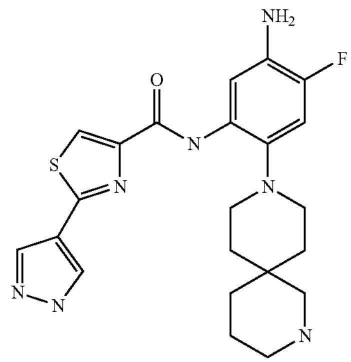 [SMILES: Nc1cc(NC(=O)c2csc(-c3cn[nH]c3)n2)c(N2CCC3(CCCNC3)CC2)cc1F] |
| 488 | 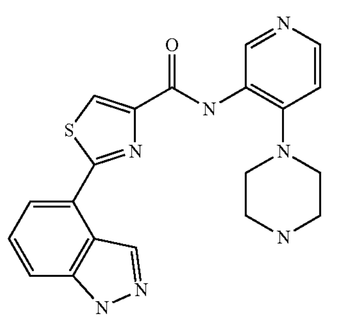 [SMILES: O=C(Nc1cnccc1N1CCNCC1)c1csc(-c2cccc3[nH]ncc23)n1] |
| 489 | 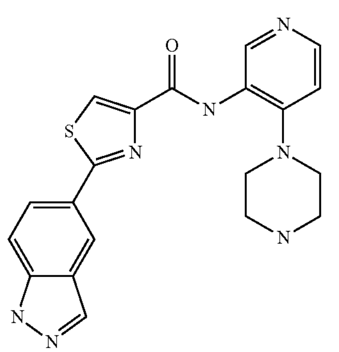 [SMILES: O=C(Nc1cnccc1N1CCNCC1)c1csc(-c2ccc3[nH]ncc3c2)n1] |
| 490 | 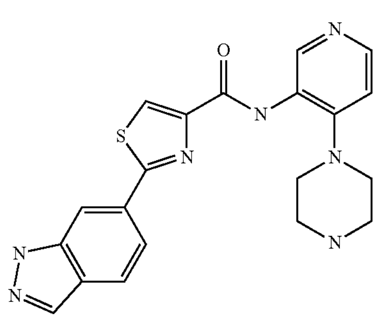 [SMILES: O=C(Nc1cnccc1N1CCNCC1)c1csc(-c2ccc3cn[nH]c3c2)n1] |

| No. | Structure |
|---|---|
| 491 | 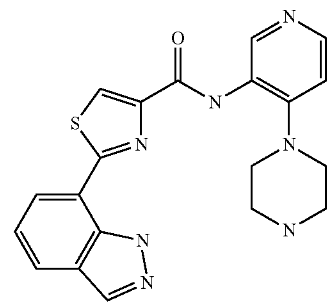 [SMILES: O=C(Nc1cnccc1N1CCNCC1)c1csc(-c2cccc3cn[nH]c23)n1] |
| 492 | 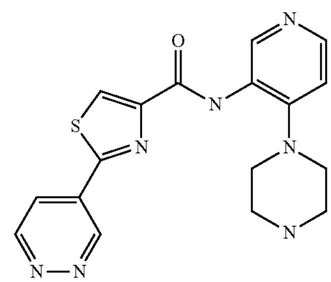 [SMILES: O=C(Nc1cnccc1N1CCNCC1)c1csc(-c2ccnnc2)n1] |
| 493 | 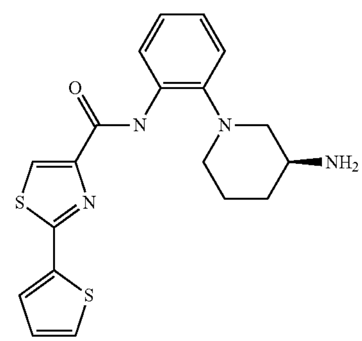 [SMILES: N[C@H]1CCCN(c2ccccc2NC(=O)c2csc(-c3cccs3)n2)C1] |
| 494 | 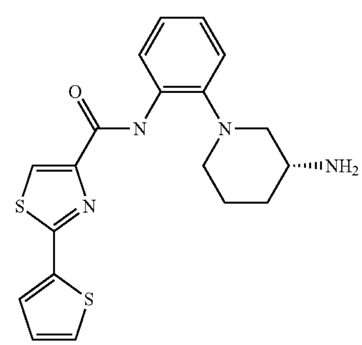 [SMILES: N[C@@H]1CCCN(c2ccccc2NC(=O)c2csc(-c3cccs3)n2)C1] |
| 495 | 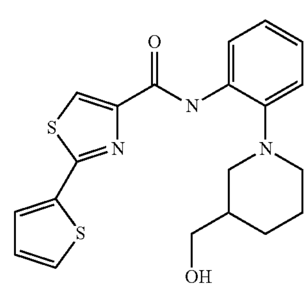 [SMILES: O=C(Nc1ccccc1N1CCCC(CO)C1)c1csc(-c2cccs2)n1] |

| No. | Structure |
|---|---|
| 496 | 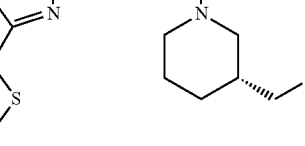 |
| 497 | |
| 498 | |
| 499 | |
| 500 | |
| No. | Structure |
|---|---|
| 501 | 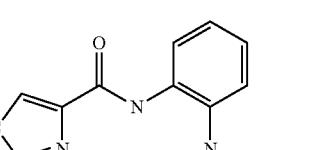 |
| 502 | |
| 503 | |
| 504 | |
| 505 | |

145
-continued
| No. | Structure |
|---|---|
| 506 | 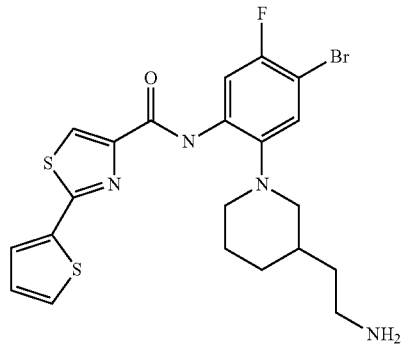 [SMILES: NCCC1CCCN(c2cc(Br)c(F)cc2NC(=O)c2csc(-c3cccs3)n2)C1] |
| 507 | 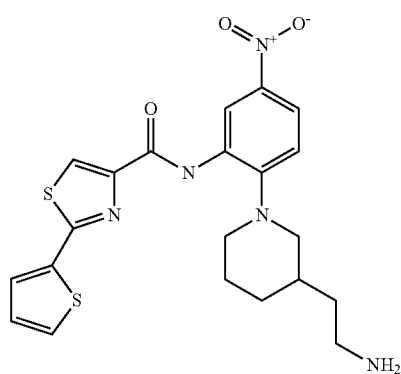 [SMILES: NCCC1CCCN(c2ccc([N+](=O)[O-])cc2NC(=O)c2csc(-c3cccs3)n2)C1] |
| 508 | 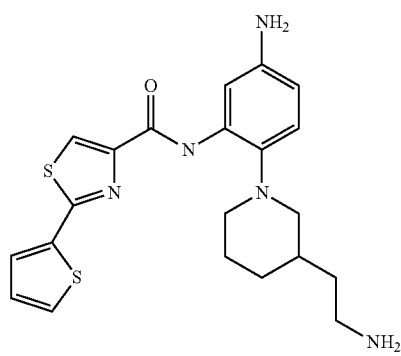 [SMILES: NCCC1CCCN(c2ccc(N)cc2NC(=O)c2csc(-c3cccs3)n2)C1] |
| 509 | 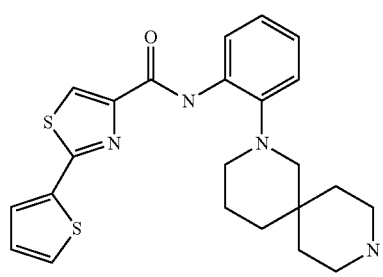 [SMILES: O=C(Nc1ccccc1N1CCCC2(CCNCC2)C1)c1csc(-c2cccs2)n1] |
146
-continued
| No. | Structure |
|---|---|
| 510 | 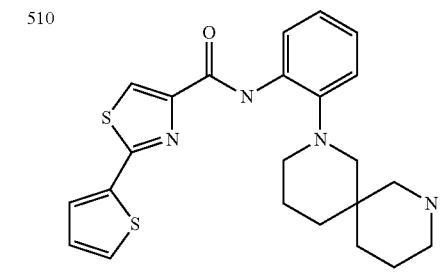 |
| 511 | 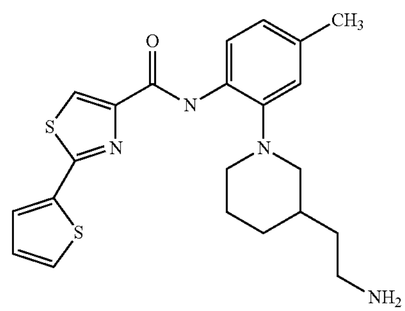 |
| | 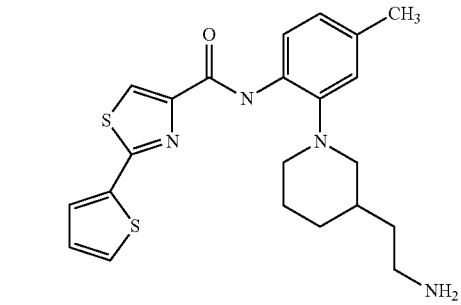 |
| 512 | 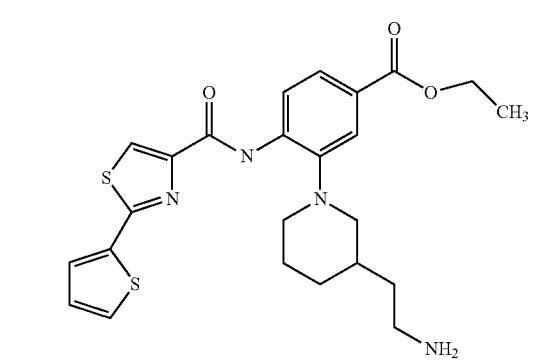 [SMILES: CCOC(=O)c1ccc(NC(=O)c2csc(-c3cccs3)n2)c(N2CCCC(CCN)C2)c1] |
| 513 | 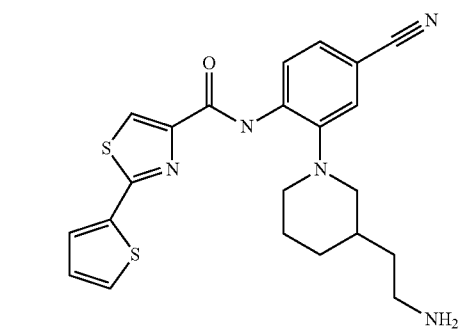 [SMILES: N#Cc1ccc(NC(=O)c2csc(-c3cccs3)n2)c(N2CCCC(CCN)C2)c1] |

-continued
| No. | Structure |
|---|---|
| 514 | 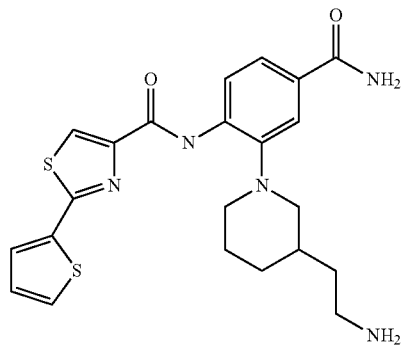 [SMILES: NCCC1CCCN(c2cc(C(N)=O)ccc2NC(=O)c2csc(-c3cccs3)n2)C1] |
| 515 | 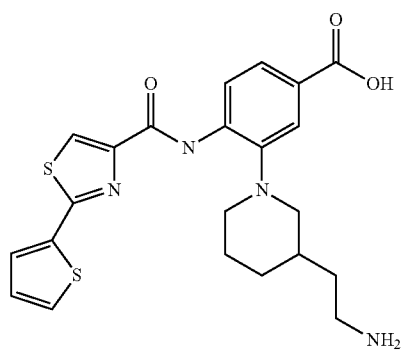 |
| 516 | 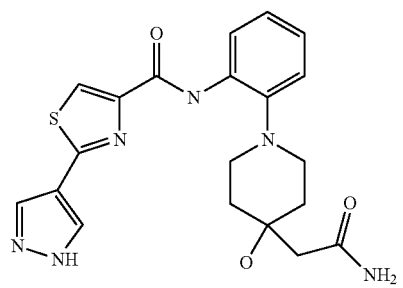 [SMILES: NC(=O)CC1(O)CCN(c2ccccc2NC(=O)c2csc(-c3cn[nH]c3)n2)CC1] |
and pharmaceutically acceptable salts, solvates, esters, prodrugs and stereoisomers thereof.
In one embodiment, the present invention provides the following compounds:
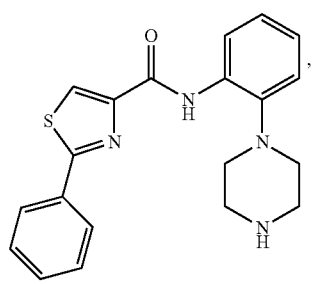
-continued
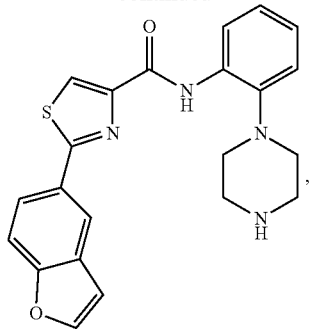
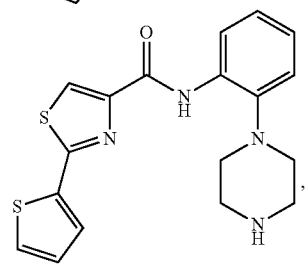
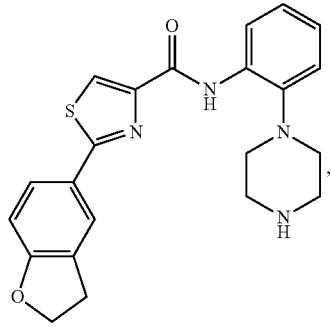
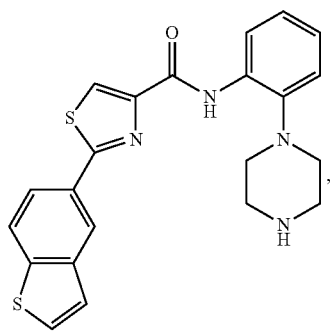
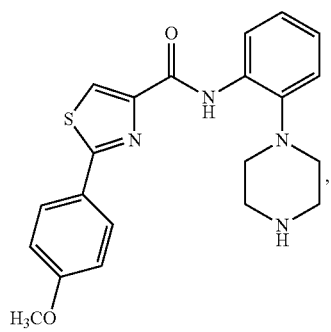

149
-continued
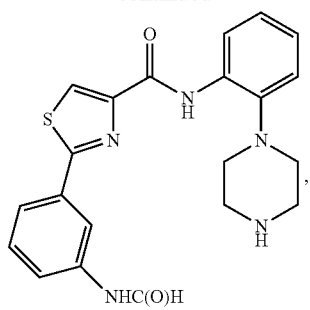
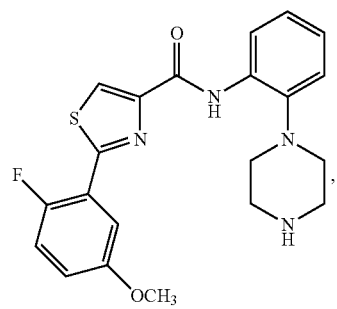
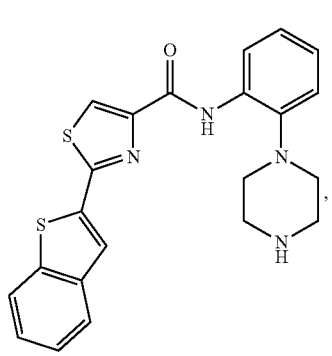
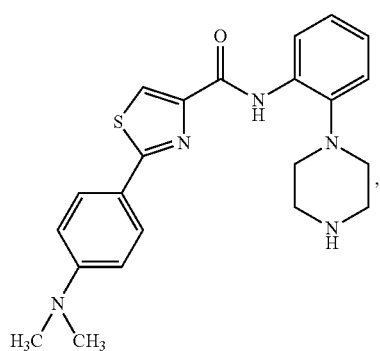
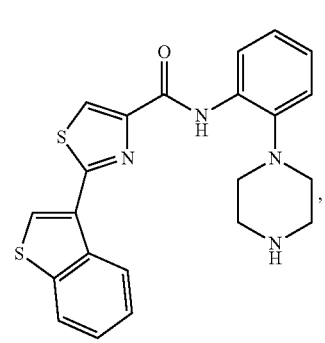
150
-continued
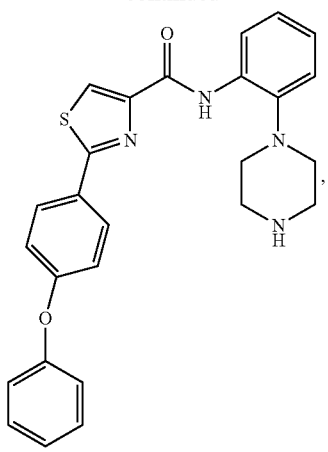
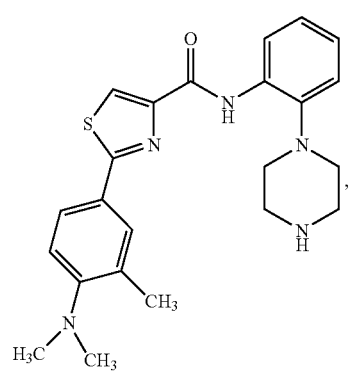
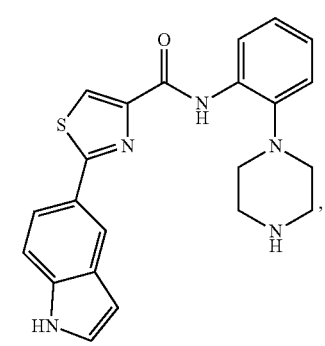
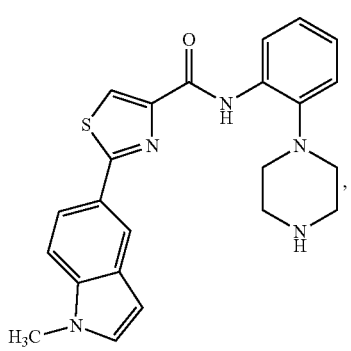

151
-continued
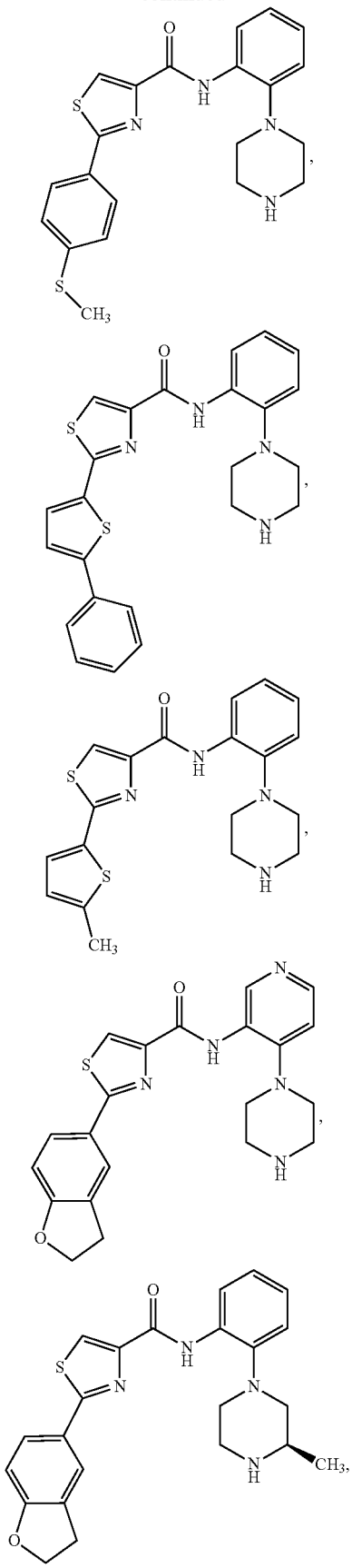
152
-continued
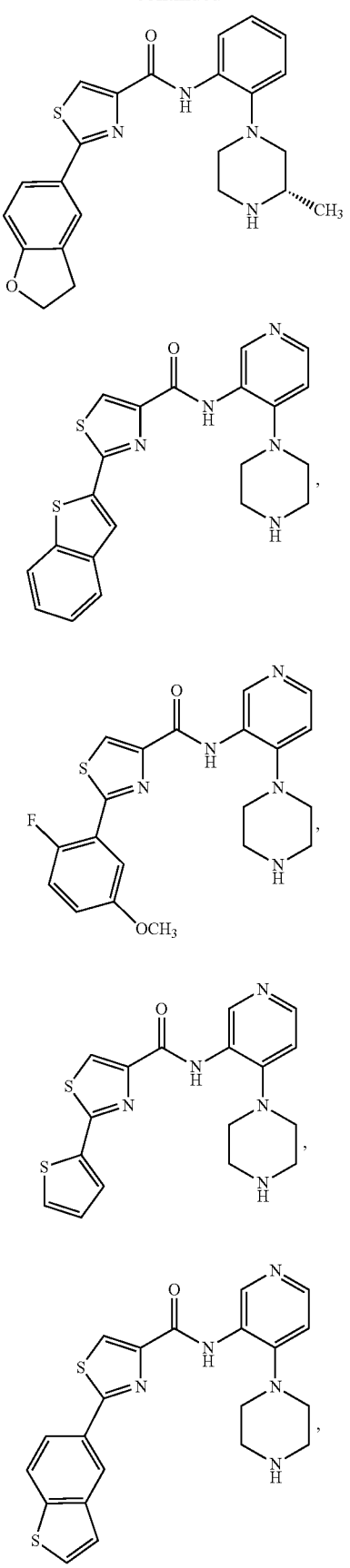

153
-continued
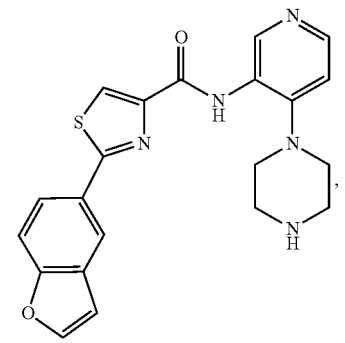
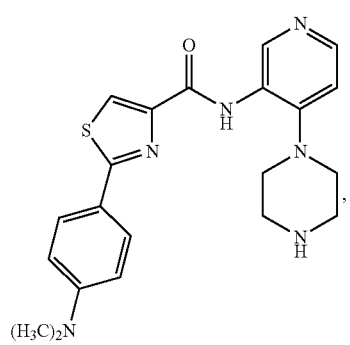
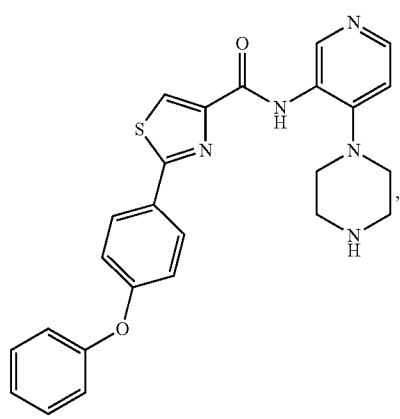
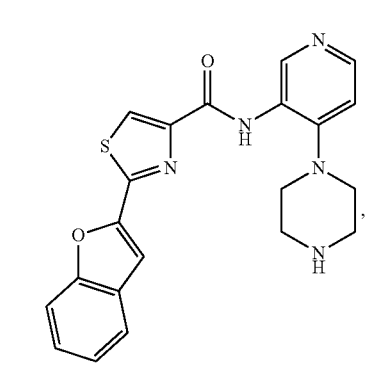
154
-continued
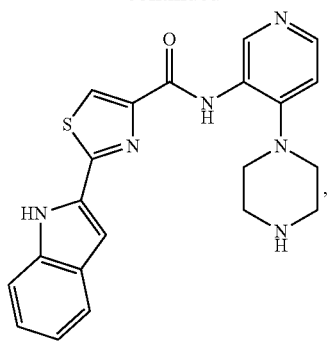
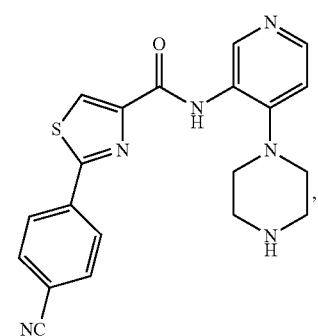
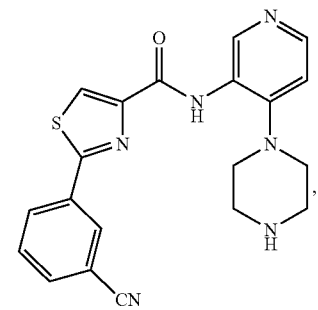
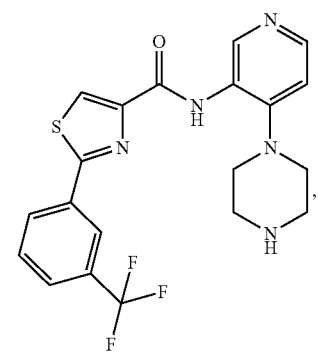
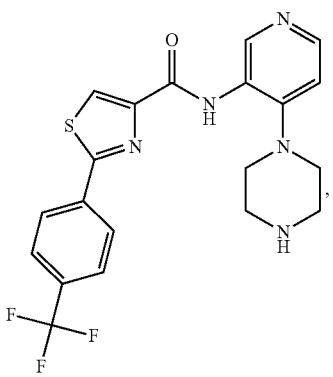

155
-continued
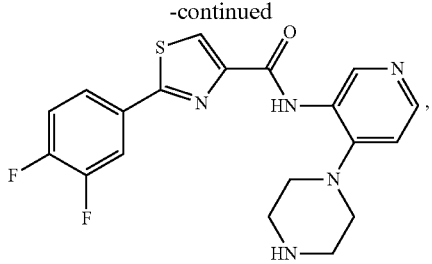
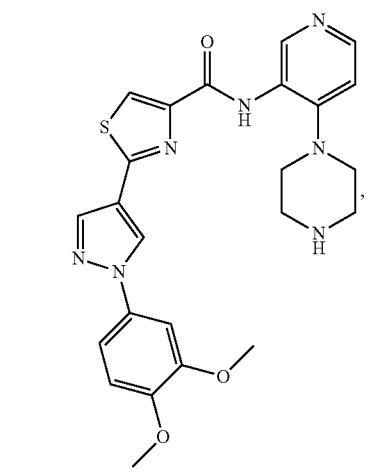
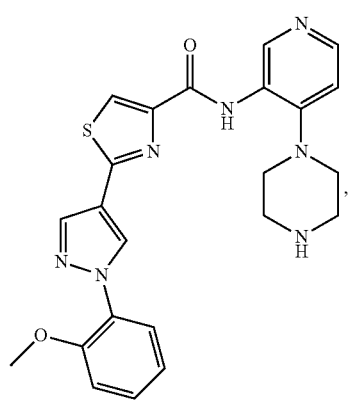
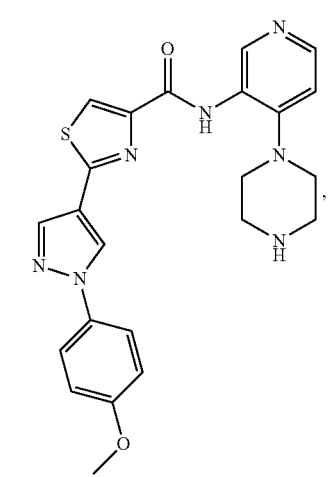
156
-continued
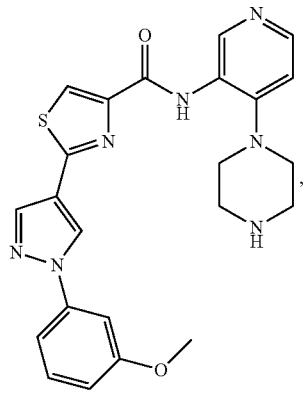
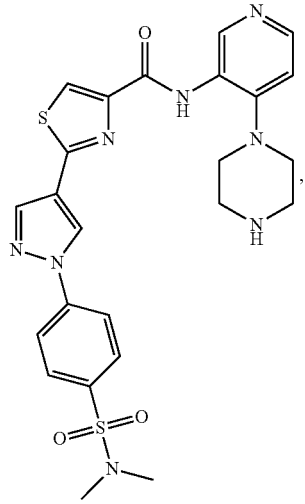
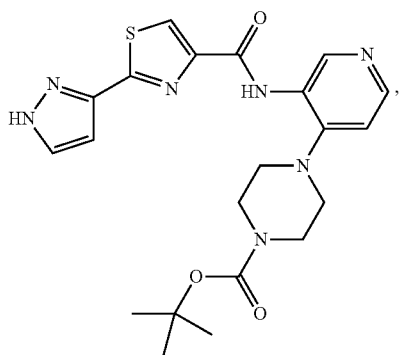
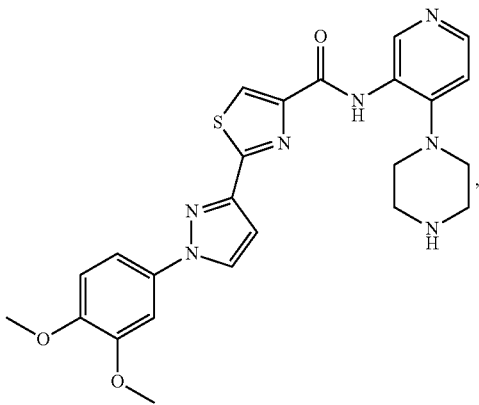

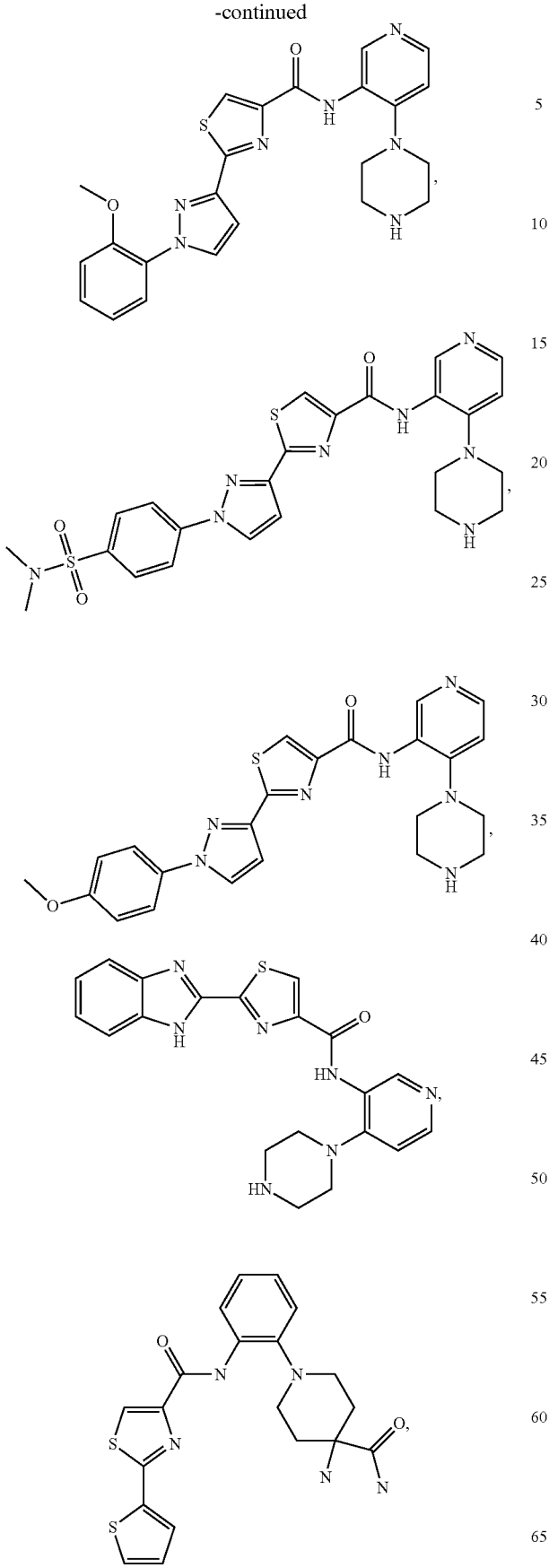
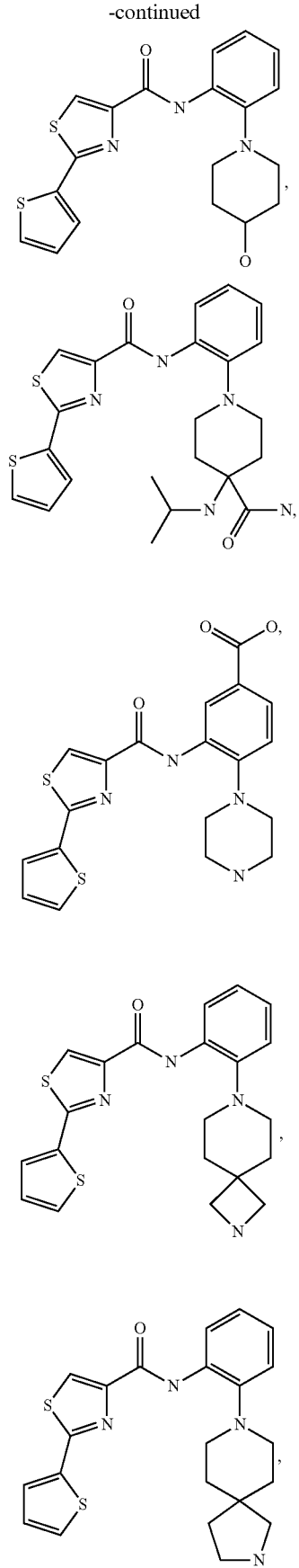

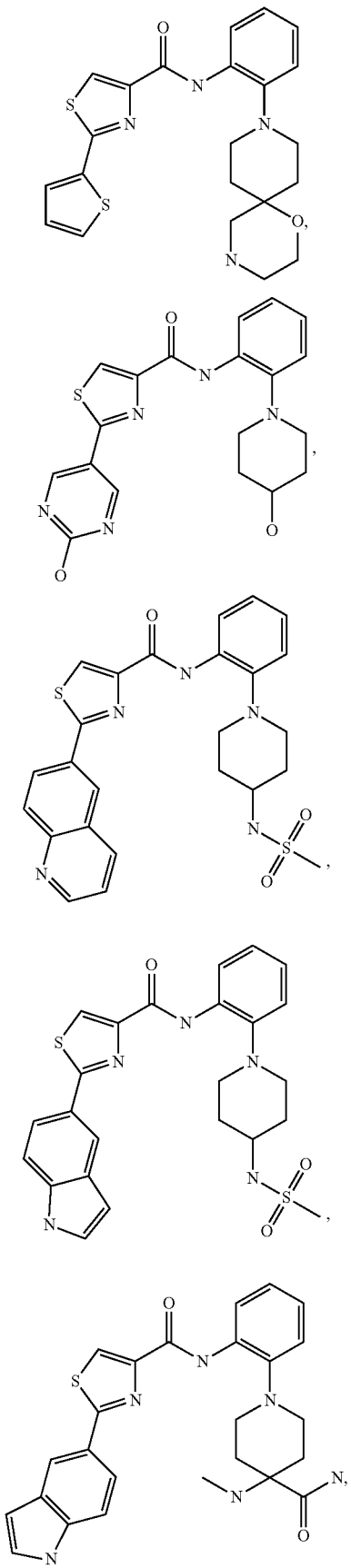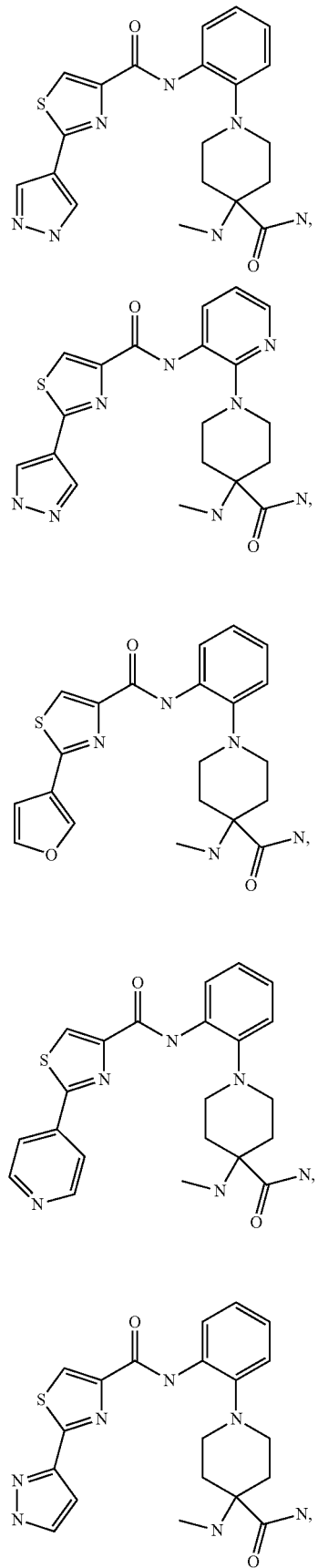

161
-continued
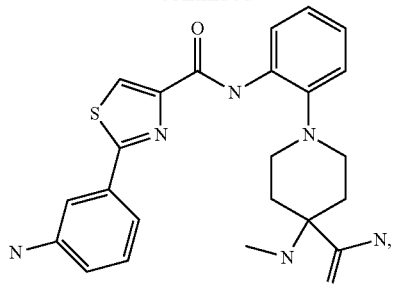
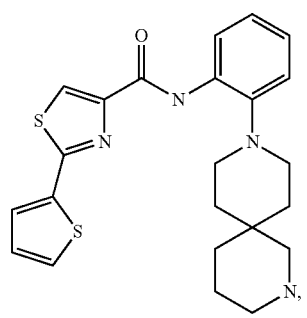
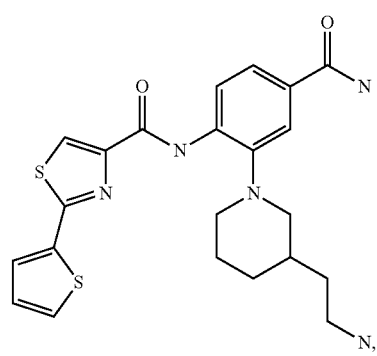
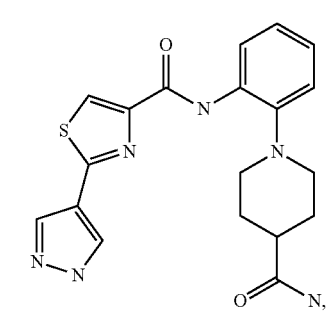
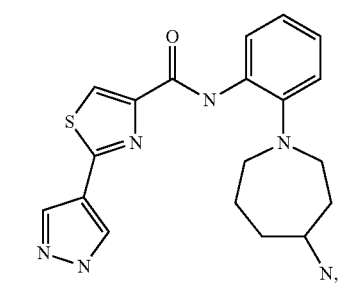
162
-continued
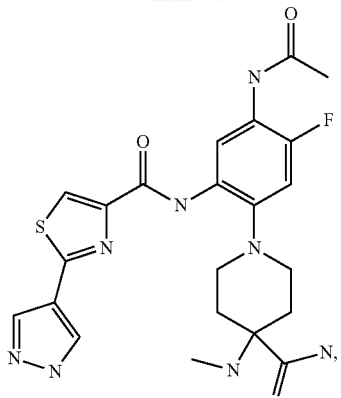
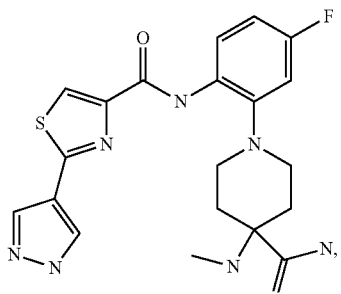
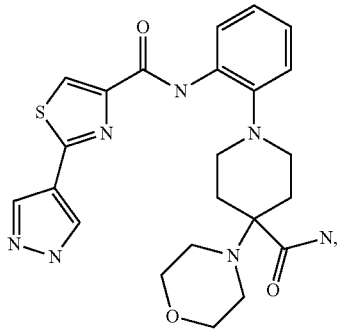
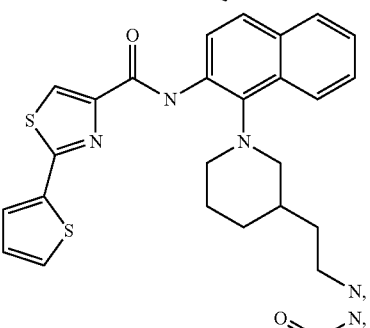
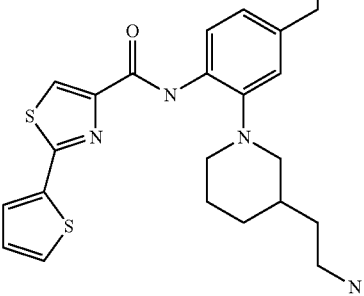

163
-continued
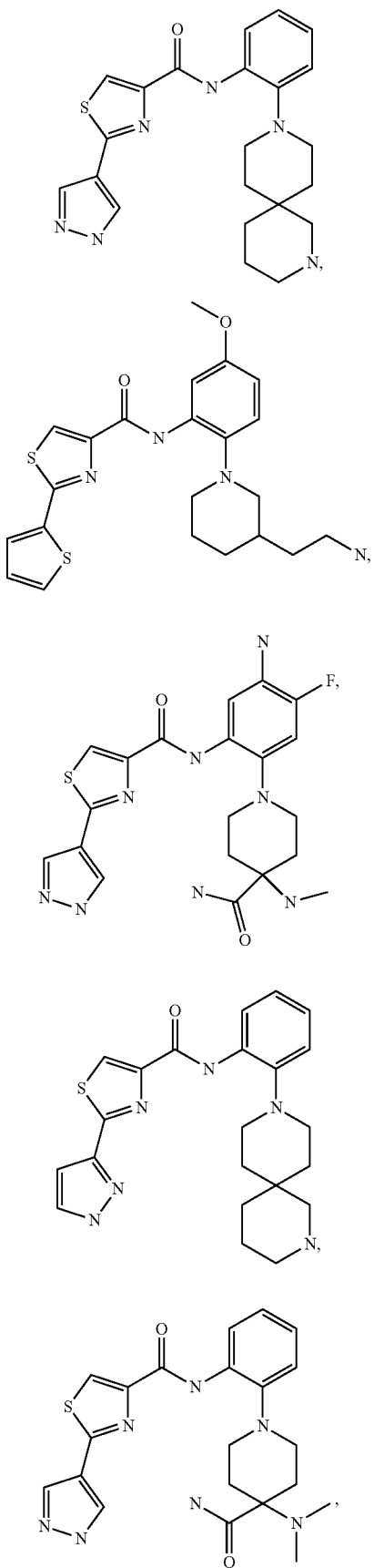
164
-continued
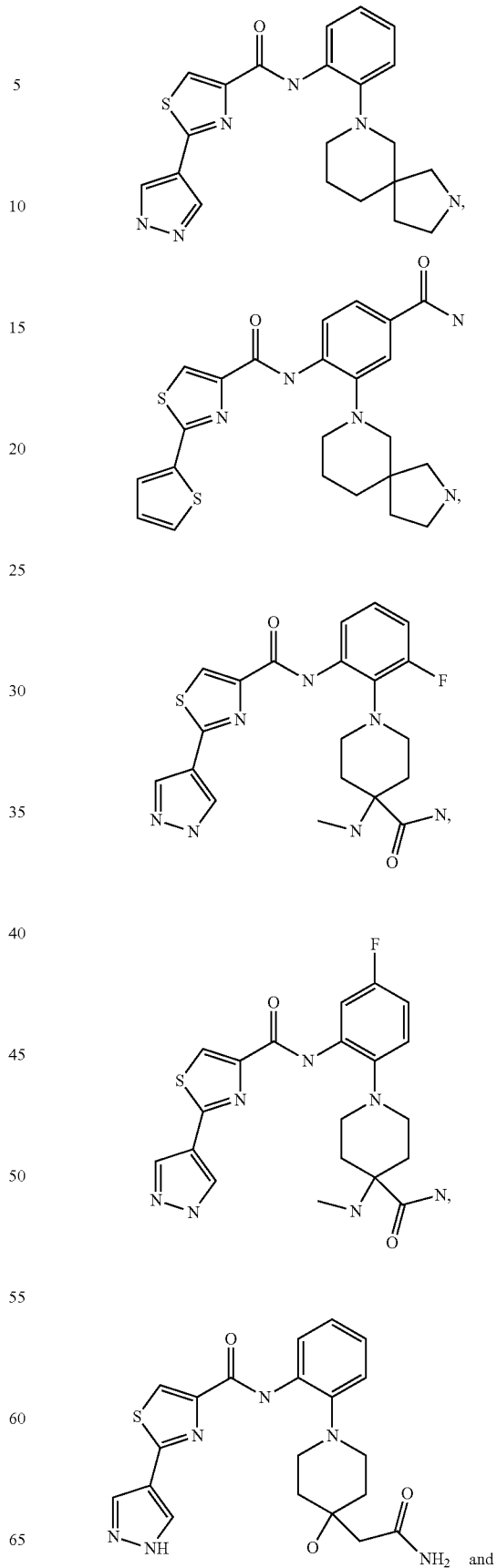

165
-continued
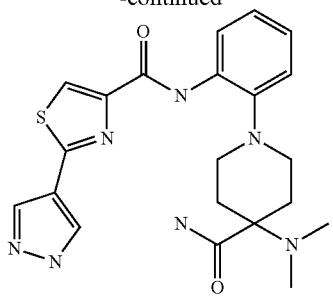
and pharmaceutically acceptable salts, solvates, esters, prodrugs and stereoisomers thereof.
In another embodiment, the present invention provides the following compounds:
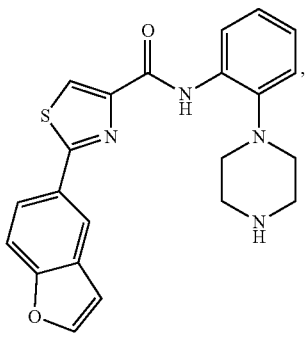
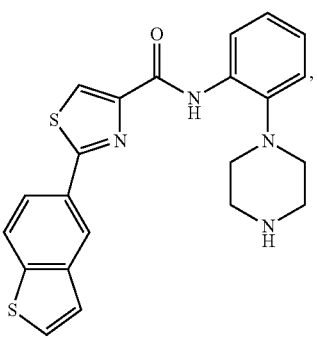
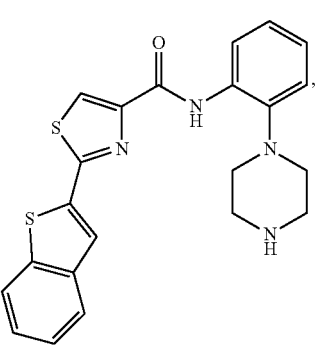
166
-continued
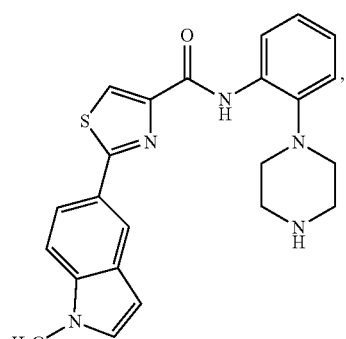
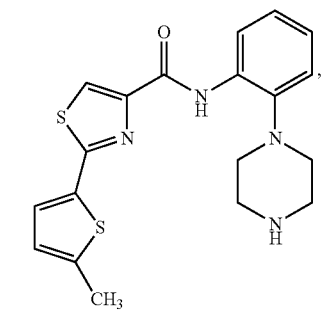
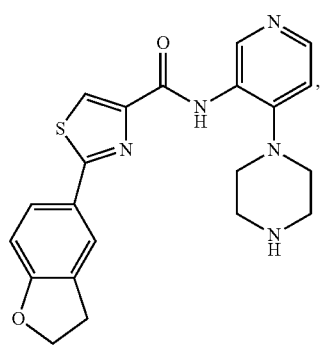
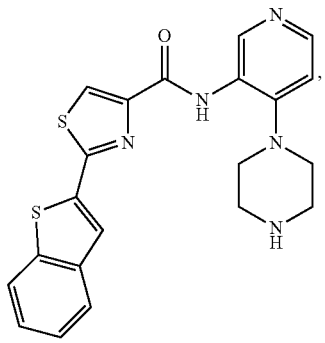
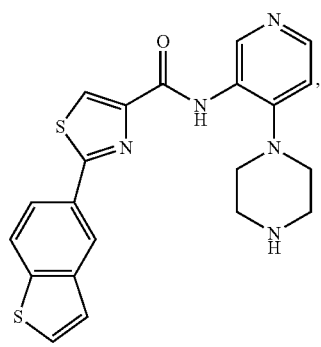

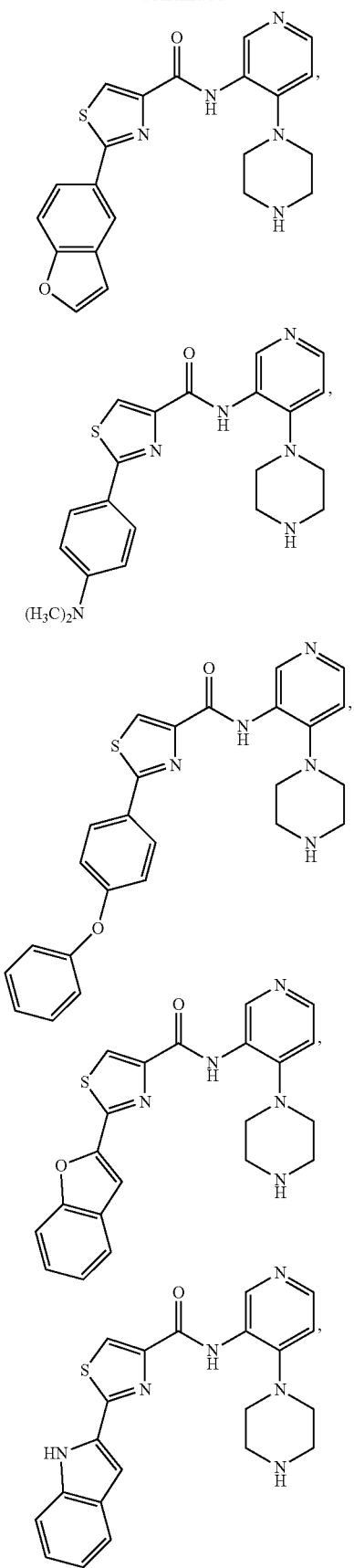
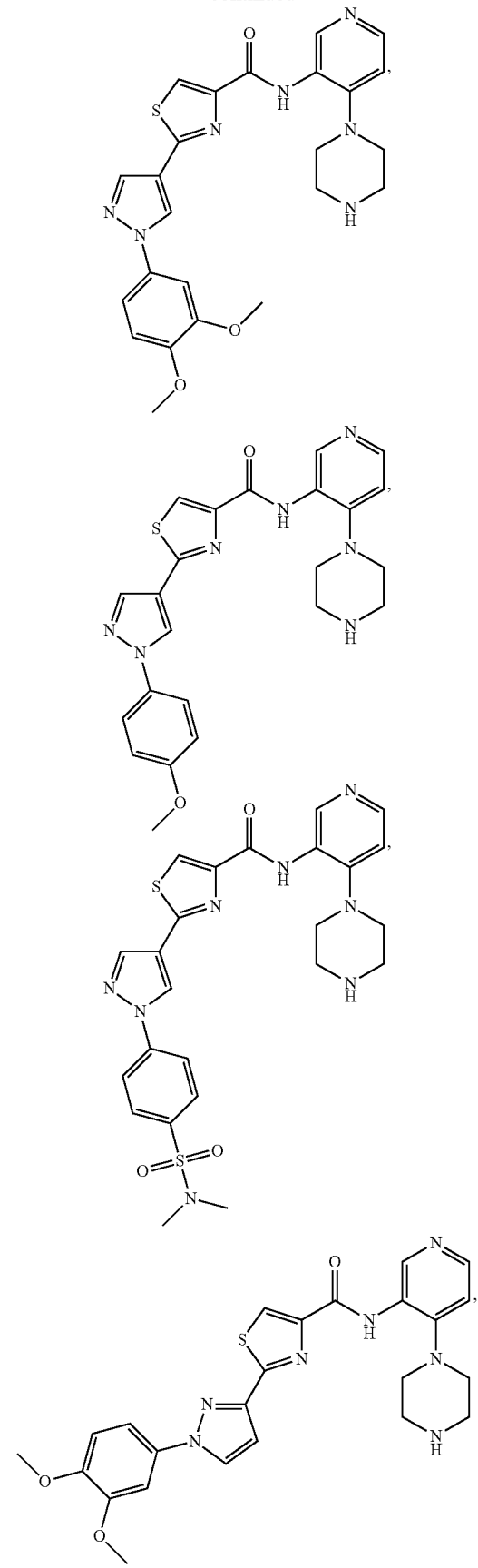

169
-continued
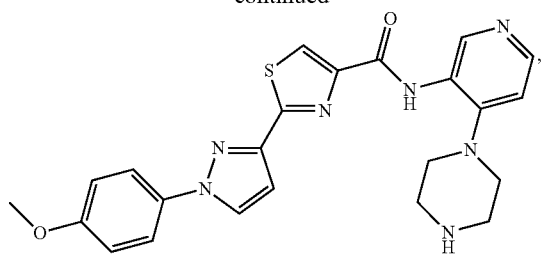
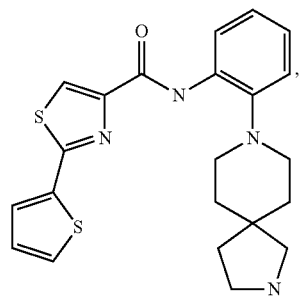
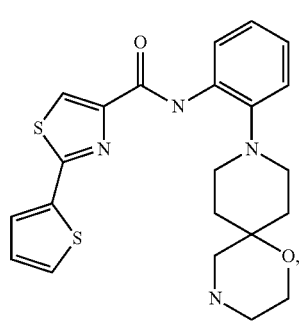
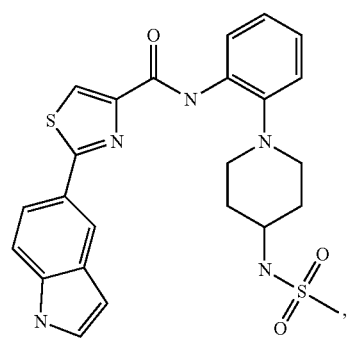
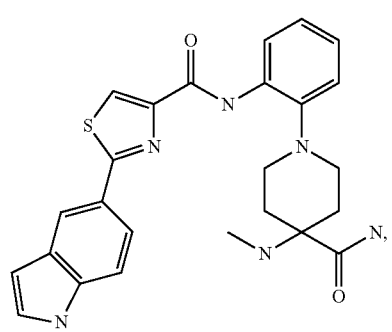
170
-continued
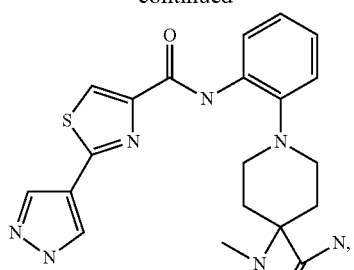
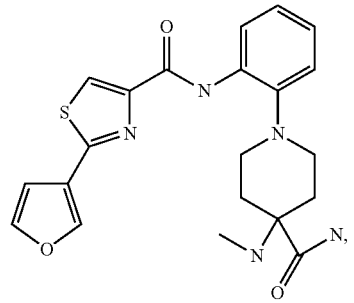
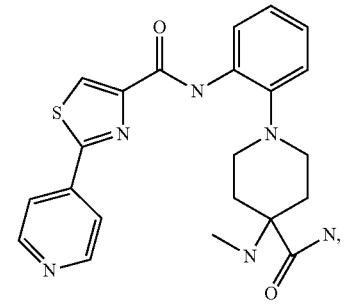
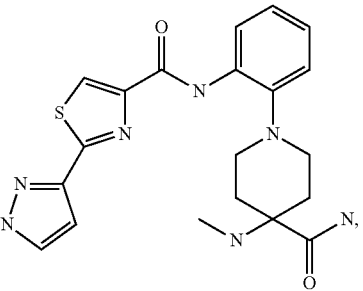
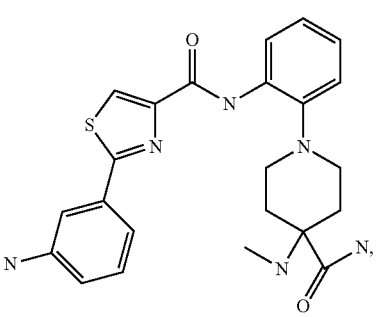

171
-continued
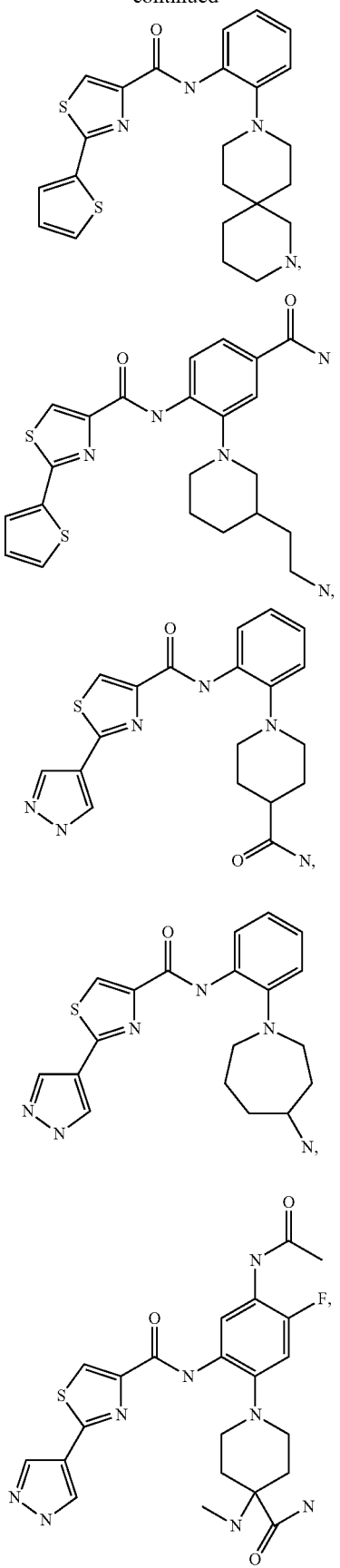
172
-continued
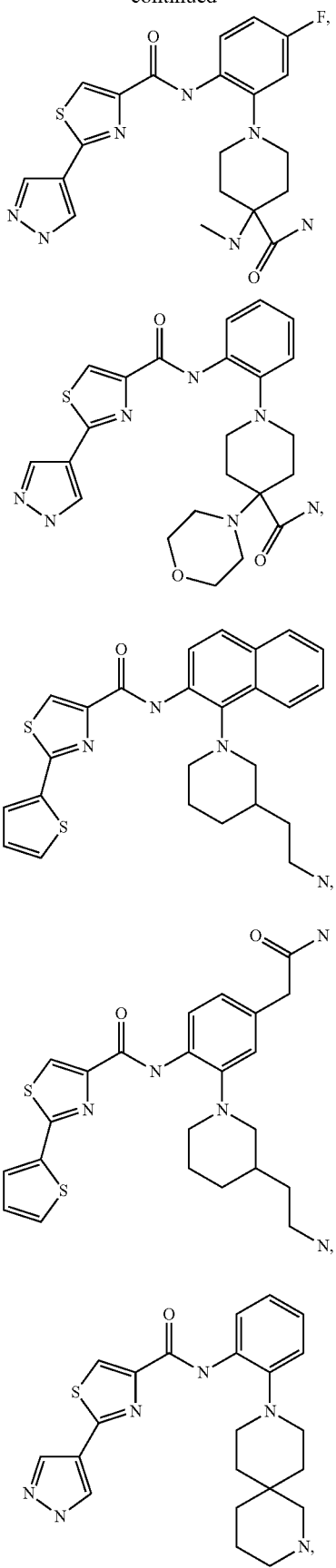

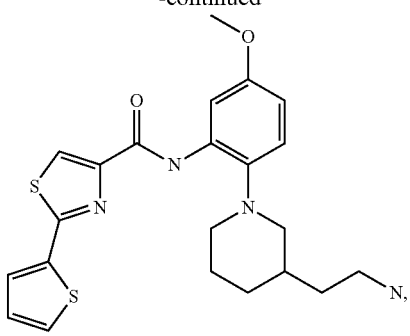

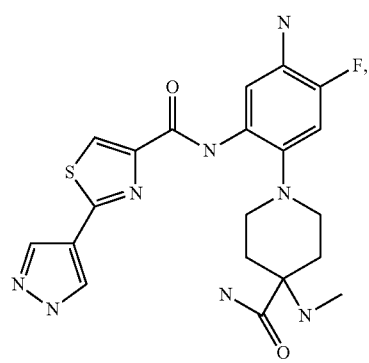

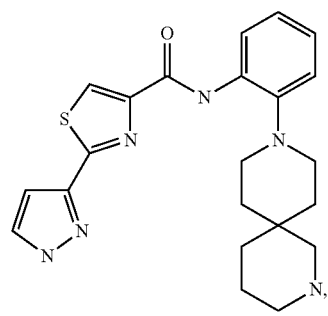

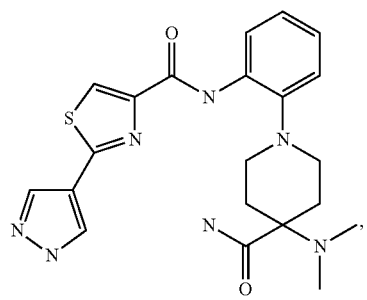

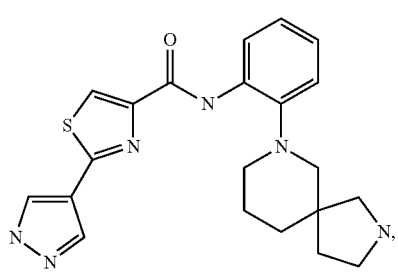

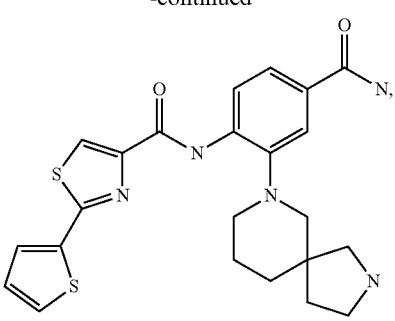

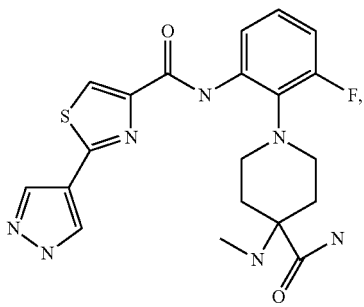

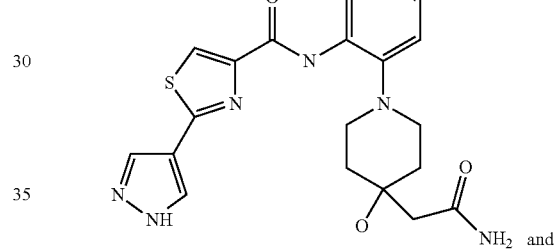

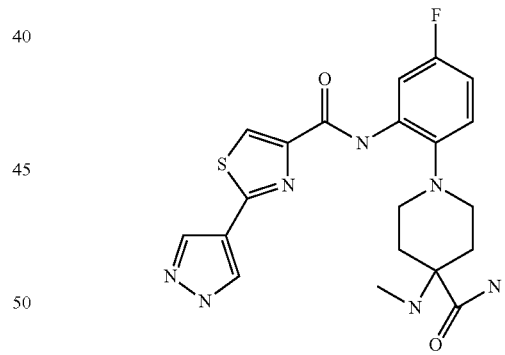

and pharmaceutically acceptable salts, solvates, esters, prodrugs and stereoisomers thereof.

Methods for Making the Anilinopiperazine Derivatives

Methods useful for making the Anilinopiperazine Derivatives of formula (I) are set forth below in Schemes 1-11. Alternative mechanistic pathways and analogous structures will be apparent to those skilled in the art.

Scheme 1 illustrates a method for making the intermediate amine compounds of formula iv.

Scheme 1

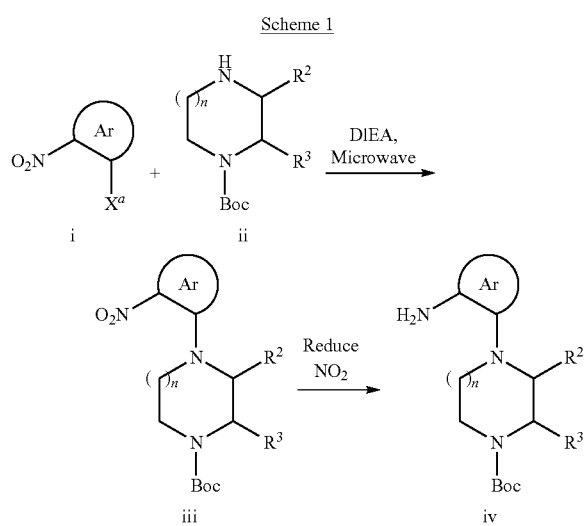

wherein $X^a$ is F or Cl, and $R^2$, $R^3$, Ar and n are as defined above for the compounds of formula (I).

A nitro-substituted aryl or heteroaryl derivative of formula i can be coupled with a piperizine compound of formula ii in the presence of diisopropylethylamine (DIEA) using a microwave-assisted process to provide the coupled compound iii. The nitro group of a compound of formula iii can then be reduced using an appropriate method to provide the intermediate amine compounds of formula iv.

Scheme 2 illustrates an alternative method for making the intermediate amine compounds of formula iv which are useful for making the Anilinopiperazine Derivatives of formula (I).

Scheme 2

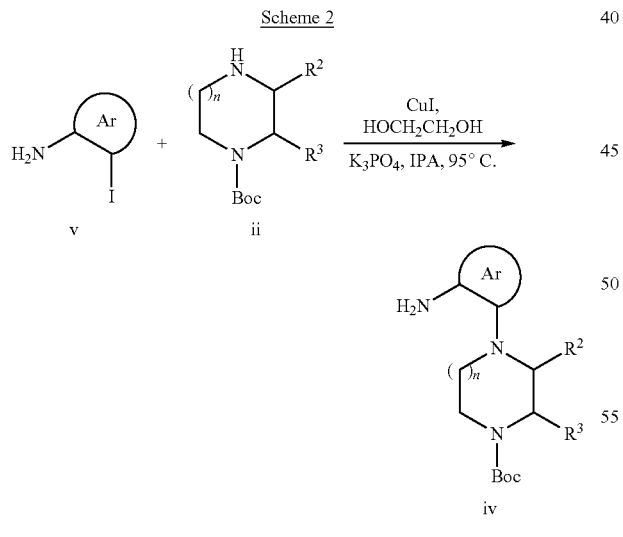

wherein $R^2$, $R^3$, Ar and n are as defined above for the compounds of formula (I).

An aryl iodide compound of formula v can be coupled with a piperazine compound of formula II using a copper iodide catalyzed process to provide the amine intermediate compounds of formula iv.

Scheme 3 illustrates a method for making the intermediate amine compounds of formula viii which are useful for making the Anilinopiperazine Derivatives of formula (I).

Scheme 3

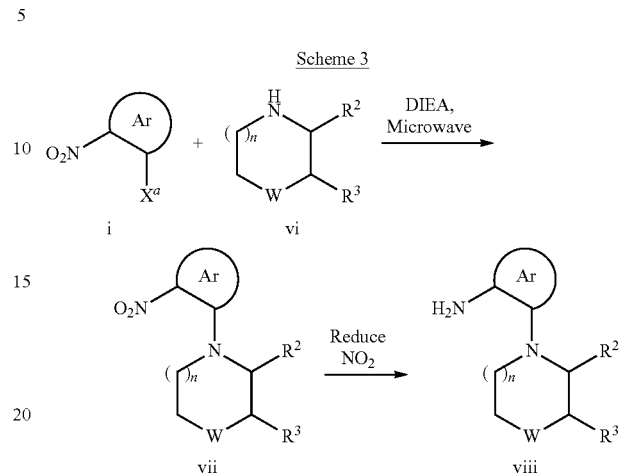

wherein $X^a$ is F or Cl, and $R^2$, $R^3$, W, Ar and n are as defined above for the compounds of formula (I).

A nitro-substituted aryl or heteroaryl derivative of formula i can be coupled with a cyclic amine of formula vi to provide the coupled compound vii, using the DIEA coupling method described in Scheme 1. The nitro group of a compound of formula vii can then be reduced using an appropriate method to provide the intermediate amine compounds of formula viii.

Scheme 4 illustrates a method for making the intermediate amine compounds of formula xii which are useful for making the Anilinopiperazine Derivatives of formula (I).

Scheme 4

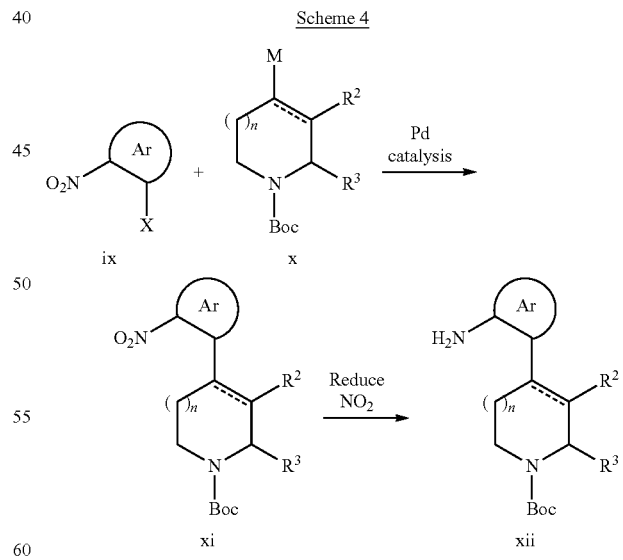

wherein X is Cl, Br or —OTf; M is $B(OH)_2$, ZnX or $SnBu_3$; and $R^2$, $R^3$, Ar and n are as defined above for the compounds of formula (I).

A nitro-substituted aryl or heteroaryl derivative of formula ix can be coupled with a piperidine compound of formula x using a Pd-catalyzed coupling method (e.g., a Suzuki coupling, a Negishi coupling or a Stille coupling) to provide the coupled compound xi. The nitro group of a compound of formula xi can then be reduced using an appropriate reduction method to provide the intermediate amine compounds of formula xii.

Scheme 5 illustrates a method for making the intermediate amine compounds of formula xv which are useful for making the Anilinopiperazine Derivatives of formula (I).

Scheme 5

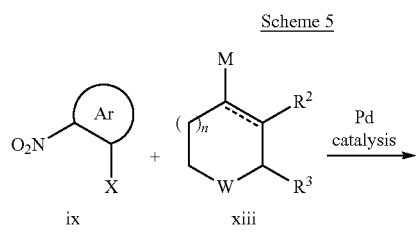

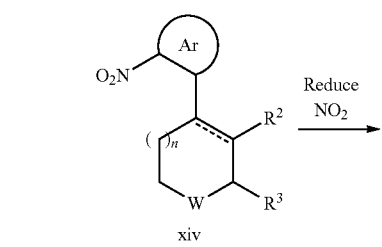

wherein X is —Cl, —Br or —OTf; M is B(OH)$_2$, ZnX or SnBu$_3$; and R$^2$, R$^3$, W, Ar and n are as defined above for the compounds of formula (I).

A nitro-substituted aryl or heteroaryl derivative of formula ix can be coupled with a compound of formula xiii to provide a compound of formula xiv, using the Pd coupling method described in Scheme 4. The nitro group of a compound of formula xiv can then be reduced using an appropriate method to provide the intermediate amine compounds of formula xv.

Scheme 6 illustrates methods useful for making 2-substituted-thiazole-5-carboxylic acid compounds which are useful intermediates for making the Anilinopiperazine Derivatives of formula (I).

Scheme 6

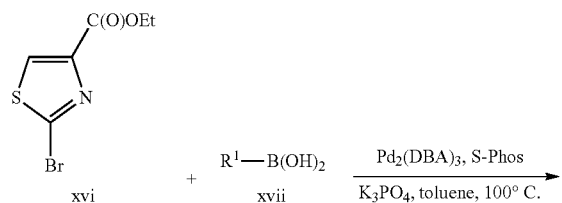

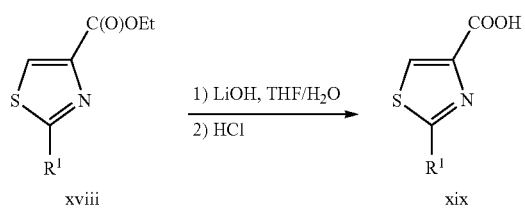

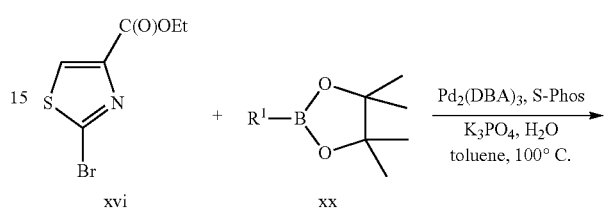

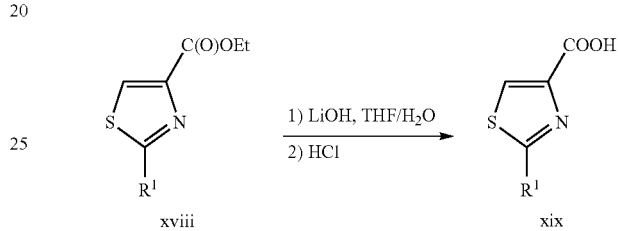

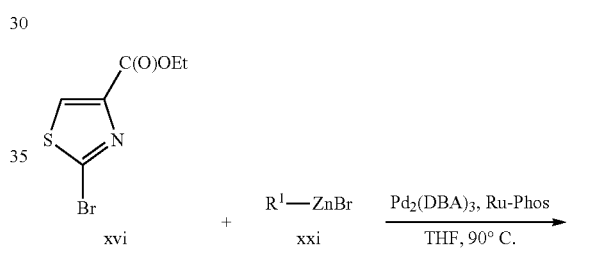

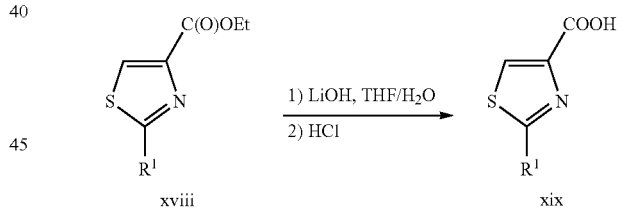

wherein R$^1$ is as defined above for the compounds of formula (I).

2-Bromothiazole-5-carboxylic acid ethyl ester (xvi) can be reacted with (i) a boronic acid compound of formula xvii, (ii) a boronic pinacol ester compound of formula xx, or (iii) a zinc bromide compound of formula xxi using appropriate palladium coupling conditions to make a 2-substituted thiazole ester intermediate of formula xviii. The compounds of formula xviii can then be hydrolyzed using LiOH, for example, to provide the 2-substituted thiazole-5-carboxylic acid compounds of formula xix.

Scheme 7 illustrates a method for making the Anilinopiperazine Derivatives of formula (I), wherein W is —NH— and Z is N.

Scheme 7

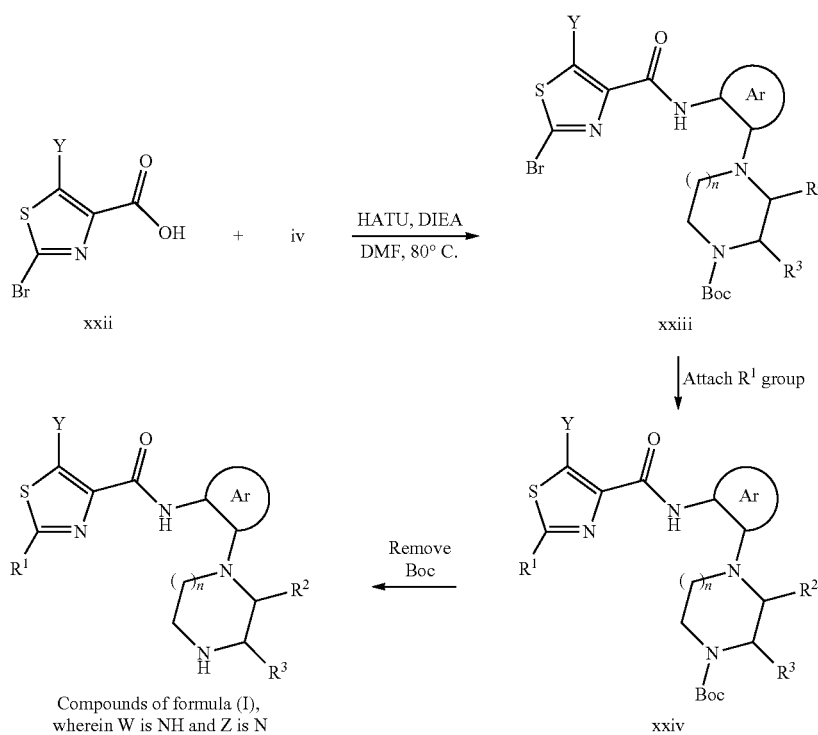

wherein $R^1$, $R^2$, $R^3$, Ar, n and Y are as defined above for the compounds of formula (I).

A 2-bromo-thiazole-4-carboxylic acid compound of formula xxii (prepared by hydrolyzing the ester moiety of a compound of formula xvi) can be coupled with an amine compound of formula iv using 2-(1H-7-azabenzotriazol-1-yl)-1,1,3,3-tetramethyl uronium hexafluorophosphate (HATU) in the presence of N,N-diisopropylethylamine to provide the amido intermediates of formula xxiii. A compound of formula xxiii can then be coupled with an $R^1$ group using a palladium-catalyzed process described in Scheme 6 to provide the compounds of formula xxiv. Removal of the Boc protecting group from a compound of formula xxiv using an acid, such as TFA or formic acid, provides the Anilinopiperazine Derivatives of formula (I), wherein W is —NH— and Z is N.

Scheme 8 illustrates a method for making the Anilinopiperazine Derivatives of formula (I), wherein W is —C(R$^4$)$_2$—; and Z is N.

Scheme 8

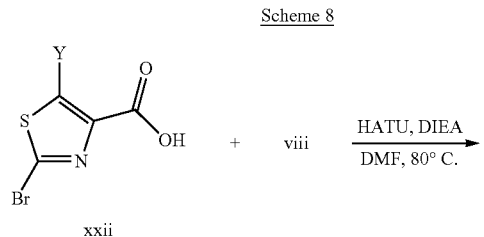

-continued

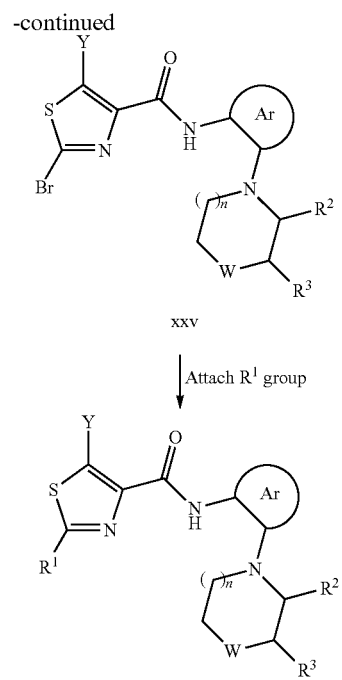

wherein $R^1$, $R^2$, $R^3$, Ar, W, Y and n are as defined above for the compounds of formula (I).

A 2-bromo-thiazole-4-carboxylic acid compound of formula xxii can be coupled with an amine intermediate of formula viii using the HATU coupling method set forth in Scheme 7 to provide the amido intermediates of formula xxv. A compound of formula xxv can then be coupled with an $R^1$ group using a palladium-catalyzed process described in Scheme 6 to provide the Anilinopiperazine Derivatives of formula (I), wherein W is —C($R^4$)$_2$—; and Z is N.

Scheme 9 illustrates a method for making the Anilinopiperazine Derivatives of formula (I), wherein W is —NH— and Z is $CR^7$.

Scheme 9

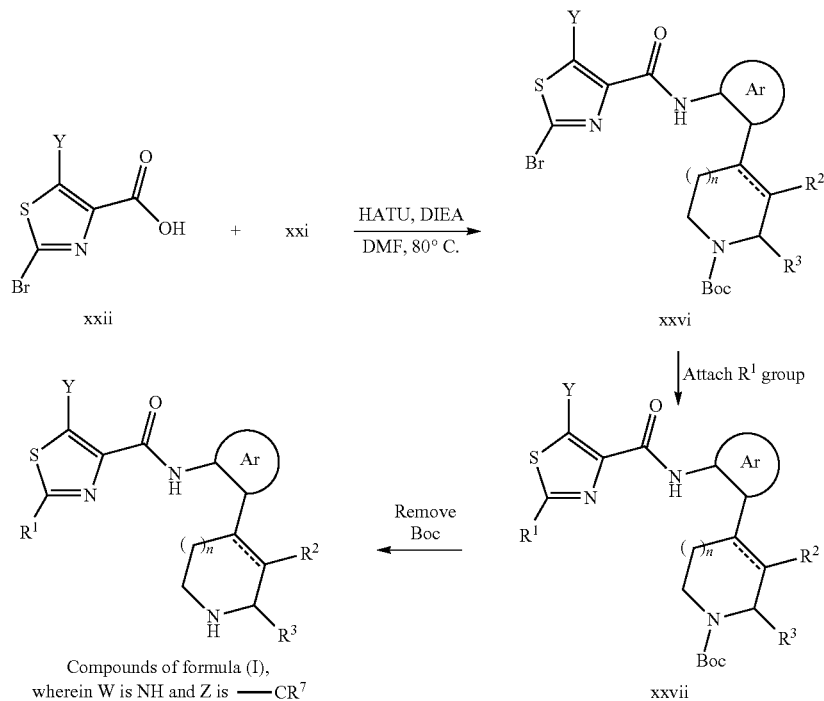

wherein $R^1$, $R^2$, $R^3$, Ar, Y and n are as defined above for the compounds of formula (I).

Using the method described in Scheme 7 and substituting intermediate amine compound xxii for intermediate amine compound xxi, the Anilinopiperazine Derivatives of formula (I) can be prepared, wherein W is —NH— and Z is $CR^7$.

Scheme 10 illustrates a method for making the Anilinopiperazine Derivatives of formula (I), wherein W is —C($R^4$)$_2$— and Z is —$CR^7$.

Scheme 10

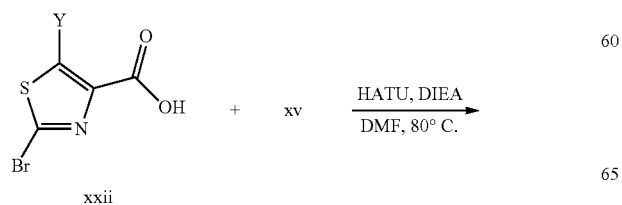

-continued

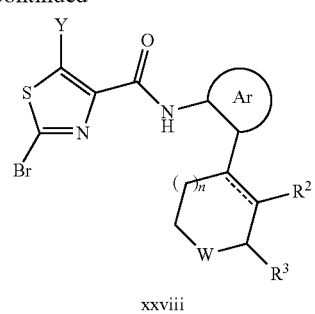

wherein $R^1$, $R^2$, $R^3$, Ar, Y and n are as defined above for the compounds of formula (I).

Using the method described in Scheme 8 and substituting intermediate amine compound xv for intermediate amine compound xxi, the Anilinopiperazine Derivatives of formula (I) can be prepared, wherein W is —$C(R^4)_2$— and Z is $CR^7$.

Scheme 11 illustrates an alternative method for making the Anilinopiperazine Derivatives of formula (I) comprising coupling an amine compound of formula xv with a 2-substituted-thiazole-5 carboxylic acid of formula xix.

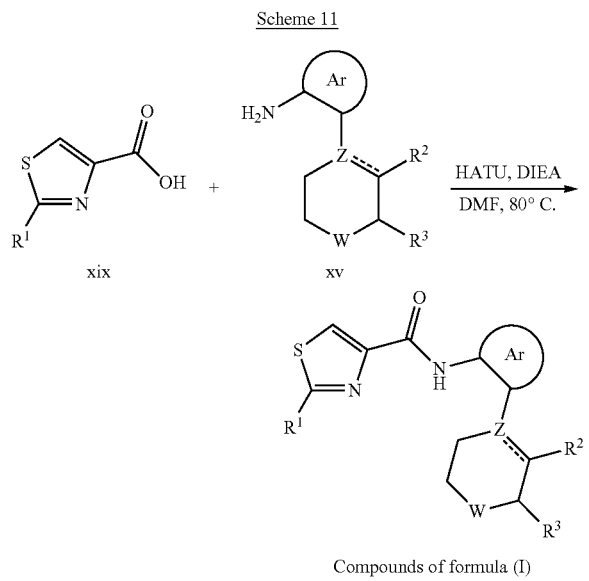

Scheme 11

Compounds of formula (I)

wherein $R^1$, $R^2$, $R^3$, Ar, W, Y, Z and n are as defined above for the compounds of formula (I).

An a 2-substituted-thiazole-5 carboxylic acid of formula xix can be coupled with an amine compound of formula xv using the HATU-mediated coupling method set forth in Scheme 7, then be further elaborated if necessary using the methods set forth above in Schemes 7 and 9 to provide the Anilinopiperazine Derivatives of formula (I).

EXAMPLES

General Methods

Solvents, reagents, and intermediates that are commercially available were used as received. Reagents and intermediates that are not commercially available were prepared in the manner as described below. $^1$H NMR spectra were obtained on a Varian AS-400 (400 MHz) and are reported as ppm down field from $Me_4Si$ with number of protons, multiplicities, and coupling constants in Hz indicated parenthetically. Where LC/MS data are presented, analyses were performed using an Applied Biosystems API-100 mass spectrometer and Shimadzu SCL-10A LC column: Altech platinum C18, 3 micron, 33 mm×7 mm ID; gradient flow: 0 minutes-10% $CH_3CN$, 5 minutes—95% $CH_3CN$, 7 minutes—95% $CH_3CN$, 7.5 minutes—10% $CH_3CN$, 9 minutes—stop. MS data were obtained using Agilent Technologies LC/MSD SL or 1100 series LC/MSD mass spectrometer. Final compounds were purified by PrepLC using the column of Varian Pursuit XRs C18 10 µm 250×21.2 mm and an eluent mixture of mobile phase A and B. The mobile phase A is composed of 0.1% TFA in $H_2O$ and the mobile phase B is composed of $CH_3CN$ (95%)/$H_2O$ (5%)/TFA (0.1%). The mixture of mobile phase A and B was eluted through the column at a flow rate of 20 mL/minutes at room temperature. The purity of all the final discrete compounds was checked by LCMS using a Higgins Haisil HL C18 5 µm 150×4.6 mm column and an eluent mixture of mobile phase A and B, wherein mobile phase A is composed of 0.1% TFA in $H_2O$ and the mobile phase B is composed of $CH_3CN$ (95%)/$H_2O$ (5%)/TFA (0.1%). The column was eluted at a flow rate of 3 mL/minutes at a temperature of 60° C. Intermediate compounds were characterized by LCMS using a Higgins Haisil HL C18 5 µm 50×4.6 mm column and an eluent mixture of mobile phase A and B, wherein mobile phase A is composed of 0.1% TFA in $H_2O$ and the mobile phase B is composed of $CH_3CN$ (95%)/$H_2O$ (5%)/TFA (0.1%). The column was eluted at a flow rate of 3 mL/minutes at a column temperature of 60° C.

Example 1

Preparation of Compound 10

Step 1—Synthesis of 2-(4-Methoxy-phenyl)-thiazole-4-carboxylic acid ethyl ester

2-Bromo-thiazole-4-carboxylic acid ethyl ester (1.00 mmol, 236 mg), 4-methoxyphenylboronic acid (1.50 mmol, 228 mg), $Pd_2(DBA)_3$ (0.020 mmol, 18 mg), S-Phos (0.060 mmol, 25 mg) and potassium phosphate tribasic monohydrate (1.5 mmol, 0.35 g) were loaded into a Schlenk tube containing a stir bar. The Schlenk tube was capped with a rubber septum, evacuated and refilled with nitrogen. Toluene (2 mL) was added through the septum via a syringe and the Schlenk tube was sealed with a Teflon screw cap under a flow of nitrogen, and put into an oil bath at 100° C. The reaction was allowed to stir at 100° C. for 15 hours, then the reaction mixture was cooled to room temperature and filtered through celite. The filtrate was concentrated in vacuo and the resultant crude residue was purified using column chromatography on silica gel (eluent: Hexane/EtOAc (4:1)) to provide 2-(4-Methoxy-phenyl)-thiazole-4-carboxylic acid ethyl ester as a yellowish solid.

Step 2—Synthesis of 2-(4-Methoxy-phenyl)-thiazole-4-carboxylic Acid

A mixture of 2-(4-Methoxy-phenyl)-thiazole-4-carboxylic acid ethyl ester and lithium hydroxide monohydrate (2.0 mmol, 84 mg) was diluted with a 2:1 mixture of THF:$H_2O$ (6 mL), and the resulting reaction was allowed to stir at room temperature for about 15 hours. The reaction mixture was then acidified using aqueous HCl (1 M, 10 mL), then dried via lyophilization to provide 2-(4-Methoxy-phenyl)-thiazole-4-carboxylic acid as an ammonium chloride salt. HPLC-MS RT. 1.37 minutes; mass calculated for formula $C_{11}H_9NO_3S$ 235.03, observed LCMS m/z 236.10 (M+H).

Step 3—Synthesis of Compound 10

To a solution of 2-(4-Methoxy-phenyl)-thiazole-4-carboxylic acid (0.1 mmol), N,N-diisopropylethylamine (0.50 mmol, 87 µL) and HATU (0.10 mmol, 38 mg) in DMF (1 mL) was added 4-(2-aminophenyl)-piperazine-1-carboxylic acid tert-butyl ester (0.10 mmol, 28 mg). The resulting reaction was heated to 80° C. and allowed to stir at this temperature for 15 h, after which time the reaction mixture was cooled to room temperature and concentrated in vacuo. The resulting residue was treated with TFA (0.5 mL) with stirring for 10 minutes then the reaction was concentrated in vacuo to provide a solute which was dissolved in DMSO/ACN (3:1), and the resulting solution was purified using reverse phase HPLC to provide Compound 10 as an ammonium salt.

Example 2

Preparation of Compound 2

To a solution of thiazole-5-carboxylic acid (0.050 mmol, 10 mg), N,N-diisopropylethylamine (0.20 mmol, 26 mg) and HATU (0.050 mmol, 19 mg) in DMF (1 mL) was added 4-(2-aminophenyl)-piperazine-1-carboxylic acid tert-butyl ester (0.10 mmol, 28 mg). The resulting reaction was heated to 80° C. and allowed to stir at this temperature for 15 h, after which time the reaction mixture was cooled to room temperature and concentrated in vacuo. The resulting residue was reacted with TFA (0.5 mL) for 10 minutes. The TFA solution was then concentrated in vacuo to provide a crude residue which was purified using reverse phase HPLC to provide Compound 2.

Example 3

Preparation of Compound 3

Using the method set forth in Example 1 above and substituting methylboronic acid for 4-methoxyphenylboronic acid in step 1, Compound 3 was prepared.

Example 4

Preparation of Compound 4

Using the method set forth in Example 1 above and substituting phenylboronic acid for 4-methoxyphenylboronic acid in step 1, Compound 4 was prepared.

Example 5

Preparation of Compound 5

To a solution of 2-bromo-thiazole-5-carboxylic acid (0.050 mmol, 10 mg), N,N-diisopropylethylamine (0.20 mmol, 26 mg) and HATU (0.050 mmol, 19 mg) in DMF (1 mL) was added 4-(2-aminophenyl)-piperazine-1-carboxylic acid tert-butyl ester (0.10 mmol, 28 mg). The resulting reaction was heated to 80° C. and allowed to stir at this temperature for 15 hours, after which time the reaction mixture was cooled to room temperature and concentrated in vacuo. The resulting residue was reacted with TFA (0.5 mL) for 10 minutes. The TFA solution was then concentrated in vacuo to provide a crude residue which was purified using reverse phase HPLC to provide Compound 5.

Example 6

Preparation of Compound 6

Using the method set forth in Example 1 above and substituting 3-pyridyl boronic acid for 4-methoxyphenylboronic acid in step 1, Compound 6 was prepared.

Example 7

Preparation of Compound 7

Using the method set forth in Example 1 above and substituting 4-pyridyl boronic acid for 4-methoxyphenylboronic acid in step 1, Compound 7 was prepared.

Example 8

Preparation of Compound 8

Using the method set forth in Example 1 above and substituting 2-thiophene boronic acid for 4-methoxyphenylboronic acid in step 1, Compound 8 was prepared.

Example 9

Preparation of Compound 9

Using the method set forth in Example 1 above and substituting 5-(4,4,5,5-tetramethyl-[1,3,2]dioxaborolan-2-yl)-benzofuran for 4-methoxyphenyl boronic acid in step 1, Compound 9 was prepared.

Example 10

Preparation of Compound 11

To a solution of 2-(2,3-dihydro-benzofuran-5-yl)-4-methyl-thiazole-5-carboxylic acid (0.10 mmol, 26 mg), N,N-diisopropylethylamine (0.50 mmol, 87 µL) and HATU (0.10 mmol, 38 mg) in DMF (1 mL) was added 4-(2-aminophenyl)-piperazine-1-carboxylic acid tert-butyl ester (0.10 mmol, 28 mg). The resulting reaction was heated to 80° C. and allowed to stir at this temperature for 15 h, after which time the reaction mixture was cooled to room temperature and concentrated in vacuo. The resulting residue was treated with TFA (0.5 mL) with stirring for 10 minutes, then the TFA solution was concentrated in vacuo. The resulting residue was dissolved in DMSO/ACN (3:1), and purified using reverse phase HPLC to provide Compound 11 as an ammonium salt.

Example 11

Preparation of Compound 12

Step 1—Synthesis of 2-(5-methyl-isoxazol-3-yl)-thiazole-4-carboxylic acid

A mixture of 2-(5-methyl-isoxazol-3-yl)-thiazole-4-carboxylic acid ethyl ester (0.24 g, 1.0 mmol) and lithium hydroxide monohydrate (84 mg, 2.0 mmol) was dissolved in THF/H$_2$O (2/1, 9 mL). The resulting reaction was allowed to stir at room temperature for about 15 hours, then acidified using 20% aqueous HCl. The solvent was removed by lyophilization to provide 2-(5-methyl-isoxazol-3-yl)-thiazole-4-carboxylic acid (21 mg).

Step 2—Synthesis of Compound 12

To a solution of 2-(5-methyl-isoxazol-3-yl)-thiazole-4-carboxylic acid (0.10 mmol, 21 mg) N,N-diisopropylethylamine (0.50 mmol, 87 µL) and HATU (0.10 mmol, 38 mg) in DMF (1 mL) was added 4-(2-aminophenyl)-piperazine-1-carboxylic acid tert-butyl ester (0.10 mmol, 28 mg). The resulting reaction was heated to 80° C. and allowed to stir at this temperature for 15 h, after which time the reaction mixture was cooled to room temperature and concentrated in vacuo. The resulting residue was treated with TFA (0.5 mL) with stirring for 10 minutes, then the TFA solution was concentrated in vacuo to provide Compound 12 as an ammonium salt.

Example 12

Preparation of Intermediate Compound A

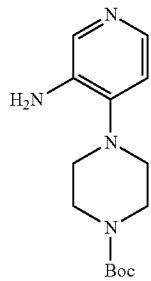

A

Step 1—Synthesis of 4-(3-nitro-pyridin-4-yl)-piperazine-1-carboxylic acid tert-butyl ester A solution of 4-chloro-3-nitro-pyridine (2.0 mmol, 0.32 g), triethylamine (3.0 mmol, 0.42 mL) and piperazine-1-carboxylic acid tert-butyl ester (2.5 mmol, 0.47 g) in dioxane (2 mL) was irradiated using microwave for 8 minutes at a temperature of 150° C. The reaction mixture was concentrated in vacuo, and the resulting residue was purified using flash column chromatography on silica gel (eluent: ethyl acetate) to provide 4-(3-nitro-pyridin-4-yl)-piperazine-1-carboxylic acid tert-butyl ester as a yellow solid (633 mg, quantitative yield). $^1$H NMR (400 MHz, CDCl$_3$) δ 8.87 (s, 1H), 8.40 (d, J=5.6 Hz, 1H), 6.87 (d, J=6.0 Hz, 1H), 3.68-3.56 (m, 4H), 3.32-3.18 (m, 4H), 1.48 (s, 9H).

Step 2—Synthesis of Compound A

To a solution of 4-(3-nitro-pyridin-4-yl)-piperazine-1-carboxylic acid tert-butyl ester (633 mg) in MeOH/EtOAc (1:1, 7 mL) was added Pd on carbon (5% Pd). The reaction mixture was stirred under a hydrogen atmosphere at room temperature for about 15 hours, then filtered through a pad of celite. The filtrate was concentrated in vacuo to provide Compound A as a solid. HPLC-MS RT=1.10 minutes, mass calculated for formula $C_{14}H_{22}N_4O_2$ 278.17, observed LCMS m/z 279.28 (M+H).

Example 13

Preparation of Intermediate Compound B

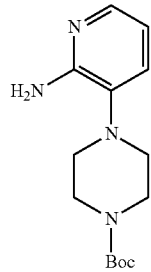

B

3-Iodo-pyridin-2-ylamine (1.0 mmol, 0.22 g), piperazine-1-carboxylic acid tert-butyl ester (1.2 mmol, 0.22 g), CuI (0.10 mmol, 19 mg) and K$_3$PO$_4$ (2.0 mmol, 0.42 g) were loaded into a Schlenk tube containing a stir bar. The tube was capped with a rubber septum, evacuated and refilled with nitrogen. Ethylene glycol (2.0 mmol, 0.11 mL) and 2-propanol (2 mL) were added through the septum via syringe. The tube was sealed with a Teflon screw cap under a flow of nitrogen and put into an oil bath at 95° C. The reaction was allowed to stir at this temperature for about 15 hours and was then cooled to room temperature and filtered through celite. The filtrate was concentrated in vacuo and the resulting residue was purified using flash column chromatography on silica gel (eluent: EtOAc/MeOH/Et$_3$N (90:5:5)) to provide Compound B (26 mg). HPLC-MS RT. 1.18 minutes, mass calculated for formula C14H$_{22}$N$_4$O$_2$ 278.17, observed LCMS m/z 279.25 (M+H).

Example 14

Preparation of Intermediate Compound C

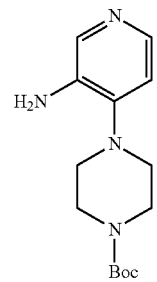

C

Using the method set forth in Example 13, and substituting 3-iodo-pyridin-4-ylamine for 3-iodo-pyridin-2-ylamine, intermediate Compound C was prepared as a solid (36 mg). HPLC-MS RT. 1.14 minutes, mass calculated for formula C$_{14}$H$_{22}$N$_4$O$_2$ 278.17, observed LCMS m/z 279.25 (M+H).

Example 15

Preparation of Intermediate Compound D

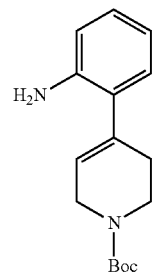

D

Step 1—Preparation of 4-(2-nitro-phenyl)-3,6-dihydro-2H-pyridine-1-carboxylic Acid tert-butyl ester 1-Chloro-2-nitrobenzene (3.00 mmol, 475 mg), Pd$_2$(DBA)$_3$ (0.060 mmol, 55 mg), S-Phos (0.18 mmol, 75 mg), 4-(4,4,5,5-Tetramethyl-[1,3,2]dioxaborolan-2-yl)-3,6-dihydro-2H-pyridine-1-carboxylic acid tert-butyl ester (4.0 mmol, 1.2 g) and $K_3PO_4$ (4.5 mmol, 1.0 g) were loaded into a Schlenk tube containing a stir bar. The tube was capped with a rubber septum, evacuated and refilled with nitrogen. Toluene (5 mL) was added through the septum via a syringe and the tube was sealed with a Teflon screw cap under a flow of nitrogen, and put into an oil bath at 100° C. The reaction was allowed to stir at this temperature for about 15 hours, then the reaction mixture was cooled to room temperature and filtered through celite. The filtrate was concentrated in vacuo and the resulting residue was purified using flash column chromatography on silica gel (eluent: 14% EtOAc in Hexane) to provide 4-(2-nitro-phenyl)-3,6-dihydro-2H-pyridine-1-carboxylic acid tert-butyl ester as a brown solid 660 mg, 72%). $^1$H NMR (400 MHz, $CDCl_3$) δ 7.90 (dd, J=8.0, 1.6 Hz, 1H), 7.58-7.53 (m, 1H), 7.44-7.39 (m, 1H), 7.30-7.27 (m, 1H), 5.62-5.58 (m, 1H), 4.04-4.01 (m, 2H), 3.64 (t, J=5.2 Hz, 2H), 2.36-2.30 (m, 2H), 1.49 (s, 9H).

Step 2—Synthesis of Compound D 0.15 g (0.50 mmol) of 4-(2-nitro-phenyl)-3,6-dihydro-2H-pyridine-1-carboxylic acid tert-butyl ester was mixed with sodium sulfide nonahydrate (0.31 g, 1.3 mmol) and a solution of $EtOH/H_2O$ (1/1, 2 mL). The reaction was heated to 60° C. and allowed to stir at this temperature for about 15 hours, after which time the reaction was quenched with water. The resulting solution was extracted with EtOAc/Ether (1/1) three times and the combined organics were washed sequentially with water and brine. Concentration of the organics in vacuo provided intermediate compound D as an oil (112 mg, 82%). $^1$H NMR (400 MHz, $CDCl_3$) δ 7.10-7.06 (m, 1H), 7.01-6.98 (m, 1H), 6.82-6.74 (m, 2H), 5.82-5.74 (m, 1H), 4.08-4.02 (m, 2H), 3.63 (t, J=5.6 Hz, 2H), 2.44-2.38 (m, 2H), 1.49 (s, 9H). HPLC-MS RT=1.69 minutes, mass calculated for formula $C_{16}H_{22}N_2O_2$ 274.17, observed LCMS m/z 297.20 (M+Na).

Example 16

Preparation of Intermediate Compound E

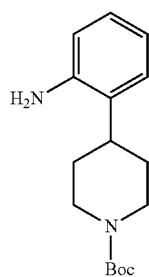

E

A solution of 4-(2-nitro-phenyl)-3,6-dihydro-2H-pyridine-1-carboxylic acid tert-butyl ester (500 mg) in MeOH/EtOAc (1:1, 10 mL) was mixed with Pd on carbon (5% Pd, 400 mg). The reaction was stirred under a hydrogen atmosphere at room temperature for about 15 hours, then the reaction mixture was filtered through a pad of Celite and the filtrate was concentrated in vacuo to provide intermediate compound E as an oil (424 mg, 93% yield). HPLC-MS RT=1.57 minutes, mass calculated for formula $C_{16}H_{24}N_2O_2$ 276.18, observed LCMS m/z 277.33 (M+H).

Example 17

Preparation of Intermediate Compound F

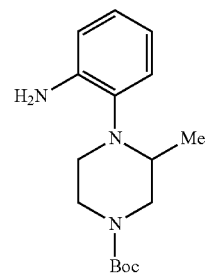

F

Step 1—Synthesis of
3-methyl-4-(2-nitro-phenyl)-piperazine-carboxylic acid tert-butyl ester 1-Bromo-2-nitrobenzene (2.00 mmol, 404 mg), $Pd(OAc)_2$ (0.100 mmol, 22.5 mg), Palucki-Phos (0.120 mmol, 45.8 mg) and $Cs_2CO_3$ (3 mmol, 1 g) were loaded into a Schlenk tube containing a stir bar. The tube was capped with a rubber septum, evacuated and refilled with nitrogen. 3-Methyl-piperazine-1-carboxylic acid tert-butyl ester (0.48 mL, 2.5 mmol) and toluene (3 mL) were added to the reaction through the septum via syringe and the tube was sealed with a Teflon screw cap under a flow of nitrogen, and put into an oil bath at 100° C. The reaction was allowed to stir at this temperature for about 15 hours and was then was cooled to room temperature and filtered through celite. The filtrate was concentrated in vacuo and the resulting residue was purified using flash column chromatography on silica gel (eluent: Hexane/EtOAc (5:1) to provide 3-methyl-4-(2-nitro-phenyl)-piperazine-carboxylic acid tert-butyl ester.

Step 2—Synthesis of Compound F

To a solution of 3-methyl-4-(2-nitro-phenyl)-piperazine-carboxylic acid tert-butyl ester in MeOH/EtOAc (1:1, 20 mL) was added Pd on carbon (5% Pd, 50 mg). The reaction mixture was stirred under a hydrogen atmosphere for about 15 hours, then filtered through a pad of celite. The filtrate was concentrated in vacuo to provide Compound F as a solid (30 mg). HPLC-MS RT=1.55 minutes, mass calculated for formula $C_{16}H_{25}N_3O_2$ 291.19, observed LCMS m/z 292.37 (M+H).

Example 18

Preparation of Compounds 14 and 15

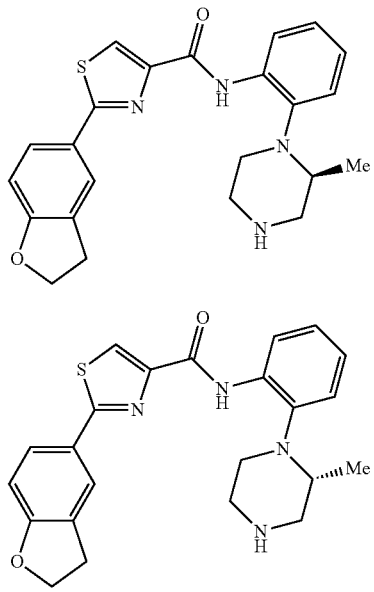

To a solution of 2-(2,3-Dihydro-benzofuran-5-yl)-thiazole-4-carboxylic acid (0.10 mmol, 25 mg), N,N-diisopropylethylamine (0.50 mmol, 87 µL) and HATU (0.10 mmol, 38 mg) in DMF (2 mL) was added 4-(2-aminophenyl)-3-methyl-piperazine-1-carboxylic acid tert-butyl ester (0.1 mmol, 30 mg). The reaction was heated to 80° C. and allowed to stir at this temperature for about 15 hours, then the reaction mixture was cooled to RT and concentrated in vacuo. The resulting residue was dissolved in DMSO/ACN (3:1), and the racemic product was purified using reverse phase HPLC to provide 2 enantiomers. Each enantiomer was then separately treated with TFA (0.5 mL) for 10 minutes, then each separate TFA solution was concentrated in vacuo. The resulting residues were separately dissolved in DMSO/ACN (3:1), and the solutions were then purified using reverse phase HPLC to provide Compounds 14 and 15 as their ammonium salts.

Example 19

Preparation of Compound 16

To a solution of 2-(2,3-Dihydro-benzofuran-5-yl)-thiazole-4-carboxylic acid (0.10 mmol, 25 mg), N,N-diisopropylethylamine (0.50 mmol, 87 µL) and HATU (0.10 mmol, 38 mg) in DMF (2 mL) was added 4-(2-amino-phenyl)-piperazine-1-carboxylic acid tert-butyl ester (0.1 mmol). The reaction mixture heated to 80° C. and allowed to stir at this temperature for about 15 hours, then concentrated in vacuo and the resulting residue was treated with TFA (0.5 mL) with stirring for 10 minutes. The TFA solution was then concentrated in vacuo and the resulting residue was dissolved in DMSO/ACN (3:1) and purified using reverse phase HPLC to provide Compound 16 as an ammonium salt.

Using the method described above and substituting the appropriate aniline coupling partner in place of 4-(2-aminophenyl)-piperazine-1-carboxylic acid tert-butyl ester, Compounds 17-28 were prepared. When a Boc group was not present in the aniline coupling partner, the residue resulting from concentration of the reaction mixture was not treated with TFA, but was instead dissolved in DMSO/ACN (3:1) and purified using reverse-phase HPLC to provide the desired product.

Example 20

Preparation of Compound 29

Step 1—Synthesis of Intermediate Compound A

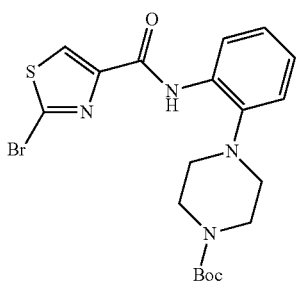

To a solution of 2-bromo-thiazole-4-carboxylic acid (2.0 mmol, 0.42 g), N,N-diisopropylethylamine (3.0 mmol, 0.52 mL) and HATU (2.0 mmol, 0.76 g) in DMF (10 mL) was added 4-(2-aminophenyl)-piperazine-1-carboxylic acid tert-butyl ester (2.0 mmol, 0.56 g). The reaction mixture was stirred at 80° C. for 3 h, and then concentrated in vacuo. Column chromatography on silica gel using Hexane/EtOAc (4.5/1) provided Compound A as a yellow solid (0.67 g, 72%). $^1$H NMR (400 MHz, CDCl$_3$) □ 10.38 (s, 1H), 8.49 (dd, J=8.0, 1.2 Hz, 1H), 8.14 (s, 1H), 7.23-7.10 (m, 3H), 3.72 (br s, 4H), 2.89-2.87 (m, 4H), 1.50 (s, 9H). HPLC-MS RT=2.39 minutes, mass calculated for formula $C_{19}H_{23}BrN_4O_3S$ 466.07, observed LCMS m/z 467.05 (M+H).

Step 1—Synthesis of Compound 29

Compound A (0.051 mmol, 24 mg), PdCl$_2$(CH$_3$CN)$_2$ (5.0 µmol, 2.0 mg), X-Phos (0.010 mmol, 4.8 mg) and Cs$_2$CO$_3$ (0.10 mmol, 33 mg) were loaded into a Schlenk tube containing a stir bar. Acetonitrile (0.25 mL) was added and the tube was flushed with nitrogen. Phenylacetylene (0.092 mmol, 10 µL) was added to the reaction mixture via a syringe under nitrogen and the tube was sealed and put into an oil bath at 85° C. The resulting reaction was allowed to stir at this temperature for about 15 hours, then the reaction mixture was cooled to room temperature and diluted with acetonitrile (5 mL). The resulting solution was then centrifuged for about 2 hours at about 1000 rpm. The resulting supernatant was collected, concentrated in vacuo, and the resulting residue was treated with TFA (0.5 mL) with stirring for 10 minutes. The TFA solution was concentrated in vacuo and the resulting residue was dissolved in DMSO/ACN (3:1), and purified using reverse phase HPLC to provide Compound 29 as an ammonium salt.

Example 21

Preparation of Compound 30

Compound A (0.051 mmol, 24 mg, prepared as described above), PdCl$_2$(CH$_3$CN)$_2$ (5.0 µmol, 2.0 mg), X-Phos (0.010 mmol, 4.8 mg) and Cs$_2$CO$_3$ (0.10 mmol, 33 mg) were loaded into a Schlenk tube containing a stir bar. The tube was capped with a rubber septum, evacuated and refilled with propyne gas. Acetonitrile (0.25 mL) was added through the septum via a syringe and the tube was sealed with a Teflon screw cap under a flow of propyne gas, and put into an oil bath at 80° C. The resulting reaction was allowed to stir at this temperature for about 15 hours, then the reaction mixture was cooled to room temperature and diluted with acetonitrile (5 mL). The resulting solution was then centrifuged for about 2 hours at about 1000 rpm. The resulting supernatant was collected, concentrated in vacuo, and the resulting residue was treated with TFA (0.5 mL) with stirring for 10 minutes. The TFA solution was concentrated in vacuo and the resulting residue was dissolved in DMSO/ACN (3:1), and purified using reverse phase HPLC to provide Compound 30 as an ammonium salt.

Example 22

Preparation of Compound 31

Step 1—Synthesis of 4-(2-{[2-(5-ethoxycarbonyl-thiophen-2-yl)-thiazole-4-carbonyl]-amino}-phenyl)-piperazine-1-carboxylic acid tert-butyl ester Compound A (0.40 mmol, 190 mg, prepared as described above), Pd$_2$(DBA)$_3$ (0.020 mmol, 18.3 mg), and Ru-Phos (0.050 mmol, 23.3 mg) were loaded into a Schlenk tube containing a stir bar. The tube was capped with a rubber septum, evacuated and refilled with nitrogen. A solution of 5-Ethoxycarbonyl-2-thienyl zinc bromide in THF (0.50 M, 2.0 mL) was added to the reaction mixture through the septum via a syringe, then the tube was sealed with a Teflon screw cap under a flow of nitrogen, and put into an oil bath at 90° C. The resulting reaction was allowed to stir at this temperature for about 15 hours, then the reaction mixture was cooled to room temperature and quenched with water. The resulting solution was extracted three times with EtOAc/Ether (1:1) and the combined organics were concentrated in vacuo. The resulting residue was purified using flash column chromatography on silica gel using Hexane/EtOAc (2:1) to provide 4-(2-{[2-(5-ethoxycarbonyl-thiophen-2-yl)-thiazole-4-carbonyl]-amino}-phenyl)-piperazine-1-carboxylic acid tert-butyl ester as a yellow solid (110 mg, 51%). LC/MS, HPLC-MS RT=2.56 minutes, mass calculated for formula C$_{26}$H$_{30}$N$_4$O$_5$S$_2$ 542.17, observed LCMS m/z 543.10 (M+H).

Step 2—Synthesis of Compound 31

4-(2-{[2-(5-ethoxycarbonyl-thiophen-2-yl)-thiazole-4-carbonyl]-amino}-phenyl)-piperazine-1-carboxylic acid tert-butyl ester (23 mg) of was dissolved in TFA (0.5 mL) and the resulting solution was stirred for 10 minutes at room temperature. The TFA solution was then concentrated in vacuo, the resulting residue was dissolved in DMSO/ACN (3:1), and the resulting solution was purified using reverse phase HPLC to provide Compound 31 as an ammonium salt.

Example 23

Preparation of Compound 32

4-(2-{[2-(5-ethoxycarbonyl-thiophen-2-yl)-thiazole-4-carbonyl]-amino}-phenyl)-piperazine-1-carboxylic acid tert-butyl ester (87 mg, 0.16 mmol, prepared as described in Example 22, step 1) was mixed with lithium hydroxide monohydrate (0.32 mmol) and the mixture was dissolved in a 2:1 mixture of THF:H$_2$O (6 mL). The resulting reaction was allowed to stir at room temperature for about 15 hours. The reaction mixture was then acidified using aqueous HCl (1 M, 1 mL), and the solvent was removed by lyophilization. The resulting residue was taken up in DMF (3 mL) and to the resulting solution was added HATU (60.8 mg, 0.16 mmol) and DIEA (87 µL, 0.5 mmol), followed by cyclopropylamine (11 µL, 0.16 mmol). The resulting reaction was heated to 80° C. and allowed to stir at this temperature for about 15 hours. The reaction mixture was then cooled to room temperature, concentrated in vacuo, and the resulting residue was treated with TFA (0.5 mL) with stirring for 10 minutes. The TFA solution was then concentrated in vacuo and the resulting residue was dissolved in DMSO/ACN (3:1) and purified using reverse phase HPLC to provide Compound 32 as an ammonium salt.

Example 24

Preparation of Compound 33

Using the method described in Example 23 and substituting azetidine for cyclopropylamine, Compound 33 was prepared.

Example 25

Preparation of Intermediate Compound G

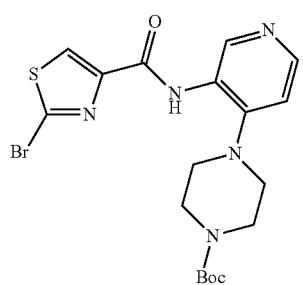

To a solution of 2-bromo-thiazole-4-carboxylic acid (0.78 mmol, 0.16 g), N,N-diisopropylethylamine (1.5 mmol, 0.26 mL) and HATU (0.78 mmol, 0.30 g) in DMF (10 mL) was added 4-(3-amino-pyridin-4-yl)-piperazine-1-carboxylic acid tert-butyl ester (0.78 mmol, 0.22 g). The reaction was heated to 80° C. and allowed to stir at this temperature for about 15 h, then the reaction mixture was cooled to room temperature and concentrated in vacuo. The resulting residue was purified using column chromatography on silica gel (eluent: EtOAc) to provide intermediate Compound G as a yellow solid. HPLC-MS RT=1.40 minutes, mass calculated for formula $C_{18}H_{22}BrN_5O_3S$ 467.06, observed LCMS m/z 468.05 (M+H).

Example 26

General Method for Boronic Acid/Ester Coupling with 2-Bromothiazole Derivatives

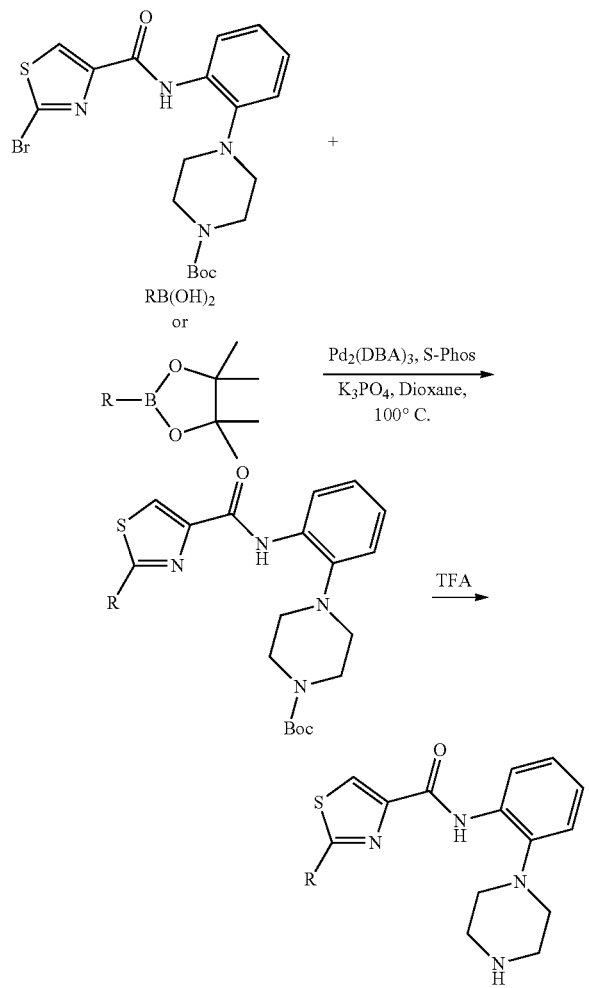

Boronic acid or pinacol ester (0.1 mmol) and $K_3PO_4$ (0.10 mmol, 21 mg) are loaded into a Schlenk tube containing a stir bar, and to the tube is added a solution of $Pd_2(DBA)_3$ (5.0 μmol, 4.6 mg), S-Phos (0.010 mmol, 4.1 mg) and a 2-bromothiazole derivative (0.050 mmol, 23 mg) in dioxane (0.5 mL). The tube is flushed with $N_2$ vigorously, sealed tightly and put into an oil bath at 100° C. The reaction is allowed to stir at this temperature for about 15 hours, then the reaction mixture is cooled to room temperature and diluted with acetonitrile (5 mL). The resulting solution is centrifuged at about 1000 rpm for about 2 hours. The resulting supernatant is collected and concentrated in vacuo, and, if the coupled product does not contain a Boc group, the resulting residue is dissolved in DMSO/ACN (3:1) and purified using reverse-phase HPLC. If the coupled product does contain a Boc group, the resulting residue is treated with TFA (0.5 mL) with stirring for 10 minutes. The TFA solution is then concentrated in vacuo and the resulting residue is dissolved in DMSO/ACN (3:1) and purified using reverse phase HPLC to provide the desired product as an ammonium salt.

Using the above method and the appropriate coupling partners, compounds 34-78 were prepared.

Example 27

Preparation of Compound 79

Using the method described in Example 26 and using benzothiophene-2-boronic acid (0.1 mmol) and Compound G (0.050 mmol, 23 mg) as coupling partners, Compound 79 was prepared.

Example 28

Preparation of Compound 80

Using the method described in Example 26 and using 2-fluoro-5-methoxy-phenyl boronic acid (0.1 mmol) and Compound G (0.050 mmol, 23 mg) as coupling partners, Compound 80 was prepared.

Example 29

Preparation of Compound 81

To a solution of 2-(2-thienyl)-1,3-thiazole-4-carboxylic acid (21 mg, 0.1 mmol), N,N-diisopropylethylamine (0.50 mmol, 87 μL) and HATU (0.10 mmol, 38 mg) in DMF (1 mL) was added 4-(3-amino-pyridin-4-yl)-piperazine-1-carboxylic acid tert-butyl ester (0.10 mmol, 28 mg). The reaction was heated to 80° C. and allowed to stir at this temperature for about 15 hours, then the reaction mixture was cooled to room temperature and concentrated in vacuo. The resulting residue was reacted with TFA (0.5 mL) for 10 minutes at room temperature, then the TFA solution was concentrated in vacuo. The resulting residue was purified using reverse phase HPLC to provide Compound 81.

LCMS data and HPLC retention times for Illustrative Anilinopiperazine Derivatives are provided in the table, Compound numbers in the table correspond to the compound numbering in the specification.

TABLE 1

| Compound | Observed LCMS m/z (M + H) | HPLC-MS retention time (minutes) |
|---|---|---|
| 2 | 289.23 | 2.67 |
| 3 | 303.25 | 2.95 |
| 4 | 365.28 | 3.84 |
| 5 | 367.06 | 3.06 |
| 6 | 366.17 | 2.87 |
| 7 | 366.15 | 2.46 |
| 8 | 371.14 | 3.63 |
| 9 | 405.37 | 4.03 |
| 10 | 395.22 | 3.95 |
| 11 | 421.29 | 3.9 |
| 12 | 370.78 | 3.42 |
| 13 | 393.33 | 3.79 |
| 14 | 421.33 | 4.10 |
| 15 | 421.31 | 4.11 |
| 16 | 407.22 | 3.86 |
| 17 | 408.26 | 3.69 |
| 18 | 408.26 | 2.85 |
| 19 | 408.25 | 2.52 |
| 20 | 408.32 | 2.73 |
| 21 | 421.25 | 4.1 |

TABLE 1-continued

| Compound | Observed LCMS m/z (M + H) | HPLC-MS retention time (minutes) |
|---|---|---|
| 22 | 421.27 | 4.11 |
| 23 | 420.16 | 3.95 |
| 24 | 448.16 | 5.26 |
| 25 | 406.32 | 3.69 |
| 26 | 404.27 | 3.71 |
| 27 | 421.28 | 4.16 |
| 29 | 389.22 | 4.25 |
| 30 | 327.26 | 3.36 |
| 31 | 443.19 | 4.28 |
| 32 | 454.26 | 3.82 |
| 33 | 454.25 | 3.84 |
| 34 | 458.25 | 3.51 |
| 35 | 458.25 | 3.61 |
| 36 | 458.24 | 3.60 |
| 37 | 408.30 | 2.99 |
| 38 | 408.26 | 3.69 |
| 39 | 422.28 | 3.81 |
| 40 | 355.26 | 3.09 |
| 41 | 421.20 | 4.34 |
| 42 | 415.21 | 3.62 |
| 43 | 425.26 | 4.22 |
| 44 | 413.26 | 4.17 |
| 45 | 413.25 | 4.17 |
| 46 | 329.29 | 3.42 |
| 47 | 409.33 | 3.85 |
| 48 | 421.29 | 4.32 |
| 49 | 371.27 | 3.64 |
| 50 | 409.25 | 4.34 |
| 51 | 355.26 | 3.07 |
| 52 | 425.29 | 3.88 |
| 53 | 355.29 | 3.56 |
| 54 | 409.22 | 3.86 |
| 55 | 408.31 | 4.12 |
| 56 | 441.31 | 4.77 |
| 57 | 457.29 | 4.73 |
| 58 | 421.23 | 4.3 |
| 59 | 396.24 | 3.70 |
| 60 | 472.28 | 3.53 |
| 61 | 472.28 | 3.84 |
| 62 | 472.25 | 3.82 |
| 63 | 395.29 | 3.42 |
| 64 | 500.29 | 3.98 |
| 65 | 411.29 | 4.21 |
| 66 | 408.30 | 3.55 |
| 67 | 422.32 | 3.06 |
| 68 | 422.36 | 2.49 |
| 69 | 422.31 | 2.85 |
| 70 | 385.28 | 4.03 |
| 71 | 354.29 | 3.33 |
| 72 | 354.29 | 3.33 |
| 73 | 418.31 | 4.25 |
| 74 | 404.27 | 3.96 |
| 75 | 447.26 | 4.74 |
| 76 | 409.27 | 3.20 |
| 77 | 391.16 | 3.22 |
| 78 | 367.18 | 2.81 |
| 79 | 422.21 | 2.90 |
| 80 | 414.30 | 2.57 |
| 81 | 372.21 | 2.13 |

Example 30

Preparation of compounds 83-88

Using the method described in Example 26, and utilizing the appropriate reactants, the following illustrative compounds of the invention were made and purified using reverse phase HPLC.

| Compound | Structure | LCMS m/z (M + H) |
|---|---|---|
| 83 | 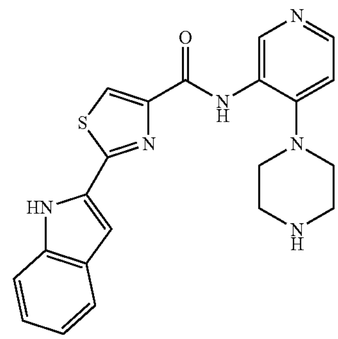 [SMILES: O=C(Nc1cnccc1N1CCNCC1)c1csc(-c2cc3ccccc3[nH]2)n1] | 405.20 |
| 84 | 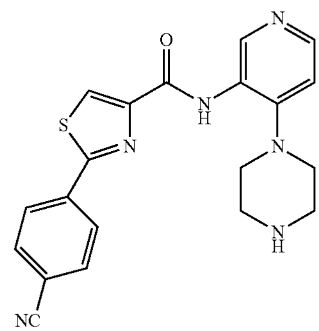 [SMILES: N#Cc1ccc(-c2nc(C(=O)Nc3cnccc3N3CCNCC3)cs2)cc1] | 391.20 |
| 85 | 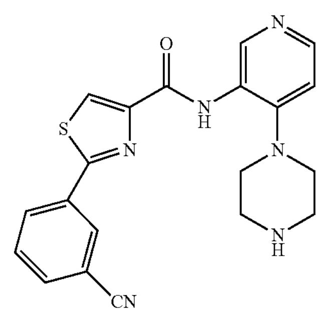 [SMILES: N#Cc1cccc(-c2nc(C(=O)Nc3cnccc3N3CCNCC3)cs2)c1] | 391.20 |
| 86 | 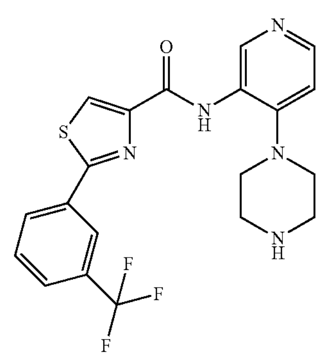 [SMILES: O=C(Nc1cnccc1N1CCNCC1)c1csc(-c2cccc(C(F)(F)F)c2)n1] | 434.20 |

-continued

| Compound | Structure | LCMS m/z (M + H) |
|---|---|---|
| 87 | 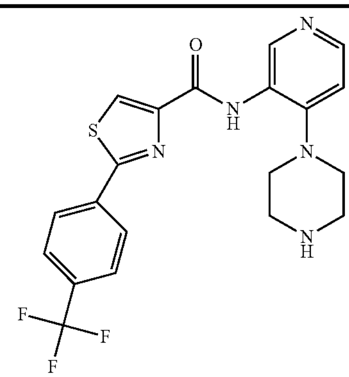 | 434.20 |
| 88 | 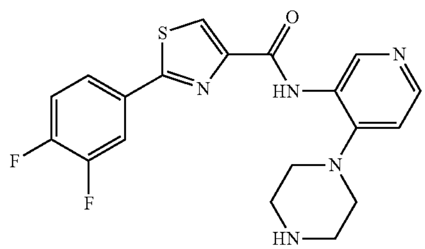 [SMILES: O=C(Nc1cnccc1N1CCNCC1)c1csc(-c2ccc(F)c(F)c2)n1] | 402.20 |

Example 31

Preparation of

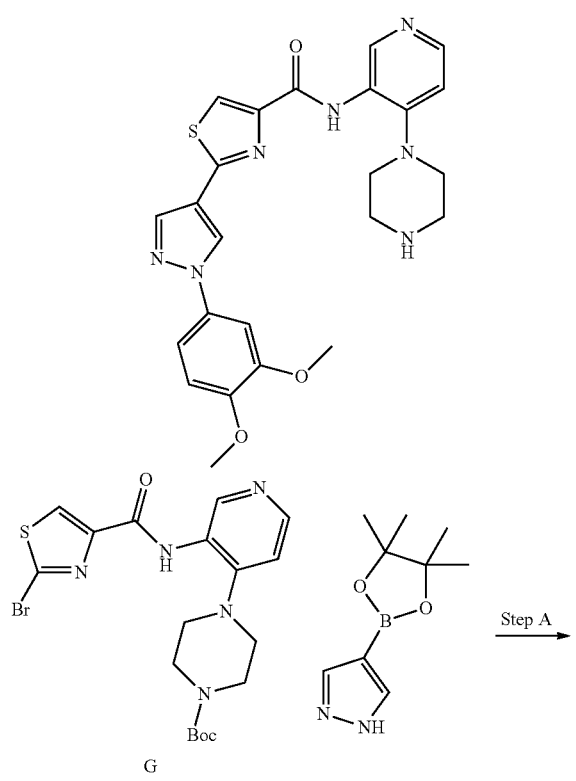

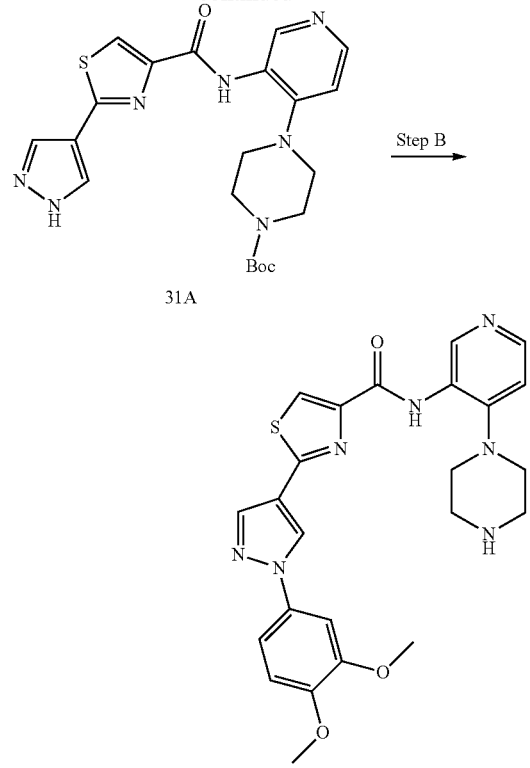

Step A—General Procedure

2-Bromothiazole compound (intermediate G described in Example 26) (0.1 mmol, 0.046 g.), 1-Boc-pyrazole-4-Boronic acid picolinic ester (0.2 mmol), PddppfCl$_2$ (10 mol %) and K$_3$PO$_4$ are taken up in dioxane. Degassed and flushed with Argon and heated to 80° C. for about 15 hours. Dioxane was removed and the residue was taken in ethylacetate, washed with water, brine and dried over anhydrous sodiumsulfate. Filtered and concentrated and purified by silica column. The desired product was obtained in good yield. Mass calculated formula C$_{21}$H$_{25}$N$_7$O$_3$S 455.11., observed LCMS m/z 456.20 (M+H)

Step B—Preparation of Title Compound

To a solution of the compound 31A (0.10 mmol, 0.045 g.) in toluene (0.5 mL) was added 3,4-dimethoxyphenyl bromide (0.11 mmol) CuI (0.004 g.), K$_2$CO$_3$ (0.21 mmol, 0.030 g), and trans-N,N-dimethylcyclohexane (10 µL). The mixture was degassed and flushed with argon and heated to 100° C. for 16 hours. The mixture was cooled to room temperature, and concentrated under reduced pressure. The crude product was taken up in EtOAc (2 mL), filtered and washed with water, brine and dried over anhydrous sodium sulfate. Filtered and concentrated to get crude product which was purified by prep LC. The product from prep LC was taken in 1 mL of dioxane and to it was added 1 mL of 4N HCl and stirred for 1 hr. The reaction mixture was concentrated and lyophilized to provide the title compound. Mass calculated formula C$_{24}$H$_{25}$N$_7$O$_3$S 491.17., observed LCMS m/z 492.20 (M+H)

Using the above method and utilizing the appropriate phenyl bromide in Step B, the following illustrative compounds of the invention were made.

| Compound | M + H Observed | Retention time |
|---|---|---|
| | 462.1 | 2.08 |
| | 462.1 | 2.16 |
| | 462.1 | 2.28 |
| | 539.1 | 2.7 |

-continued
| Compound | M + H Observed | Retention time |
|---|---|---|
| 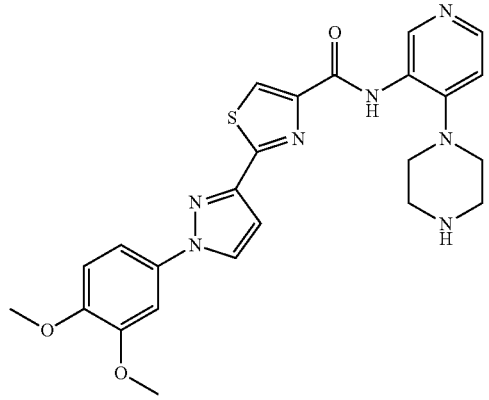 [SMILES: COc1ccc(-n2ccc(-c3nc(C(=O)Nc4cnccc4N4CCNCC4)cs3)n2)cc1OC] | 492.1 | 2.30 |
| 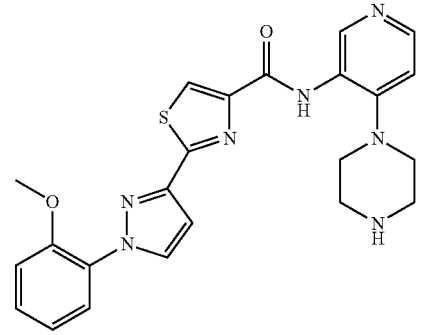 [SMILES: COc1ccccc1-n1ccc(-c2nc(C(=O)Nc3cnccc3N3CCNCC3)cs2)n1] | 462.1 | 2.38 |
| 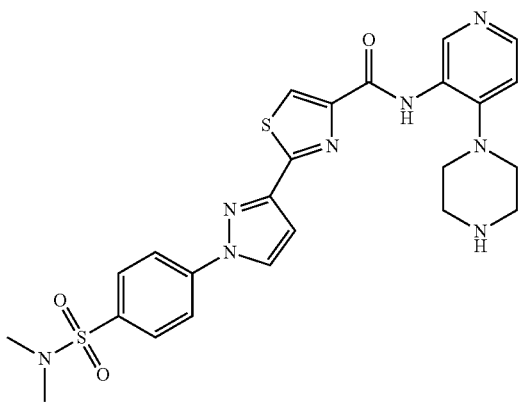 [SMILES: CN(C)S(=O)(=O)c1ccc(-n2ccc(-c3nc(C(=O)Nc4cnccc4N4CCNCC4)cs3)n2)cc1] | 539.1 | 2.37 |
| 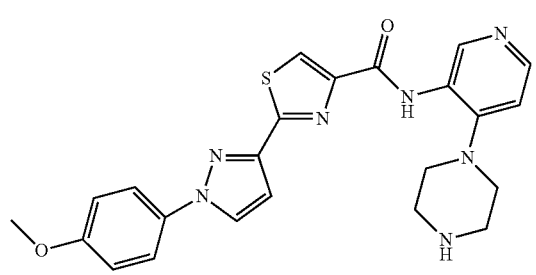 [SMILES: COc1ccc(-n2ccc(-c3nc(C(=O)Nc4cnccc4N4CCNCC4)cs3)n2)cc1] | 462.1 | 2.38 |

Example 32

Preparation of Intermediate Compound 32A

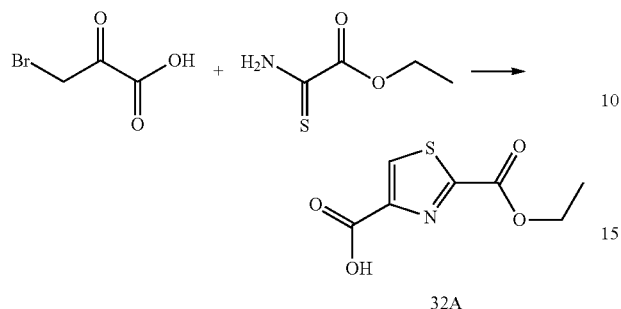

32A

A mixture of 3-bromopyruvic acid (16.37 g, 98.05 mmol) in anhydrous dioxane (90 mL) was treated with ethyl thioamidooxalate (13.08 g, 98.22 mmol) for 1.2 h at 50° C., and was then concentrated at 50° C. to yield a dry yellow solid. The crude product was dissolved in saturated sodium bicarbonate (150 mL) and water (150 mL). This solution was extracted with ethyl acetate (6×400 mL). The aqueous layer was then acidified to pH 2 with concentrated aqueous HCl (21 mL), resulting in the formation of a heavy precipitate. This suspension was extracted with ethyl acetate (5×500 mL). These extracts were pooled, dried with sodium sulfate, filtered, concentrated, and dried for about 15 hours under vacuum to yield compound 32A as a red-brown solid (14.36 g, 73% yield) which was used without further purification.

Example 33

Preparation of Intermediate Compound 33A

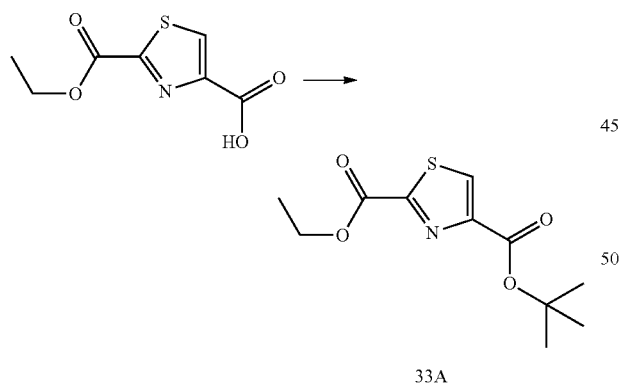

33A

A solution of 32A (2.03 g, 9.89 mmol) in tert-butyl alcohol (18.0 mL, 188 mmol) and pyridine (5.5 mL, 68 mmol) was cooled to 0° C. in an ice-water bath. p-toluenesulfonyl chloride (4.430 g, 23.24 mmol) was added in one portion, and the reaction was stirred for about 15 hours with gradual warming to room temperature. The reaction was diluted with water (20 mL) and saturated potassium carbonate solution (~6M, 20 mL) and stirred for 30 minutes, resulting in a dark brown biphasic solution. The aqueous layer was extracted with ether (3×100 mL). The ether extracts were combined and washed with 5% saturated aqueous potassium carbonate (2×100 mL) and 5% saturated aqueous potassium carbonate/95% brine (1×50 mL). The combined extracts were dried over sodium sulfate, filtered and concentrated at 35-50° C. to yield a dark brown oil which was redissolved in dichloromethane, and concentrated at 55° C. to provide compound 33A as a light brown solid (2.03 g, 80% yield).

Example 34

Preparation of Intermediate Compound 34A

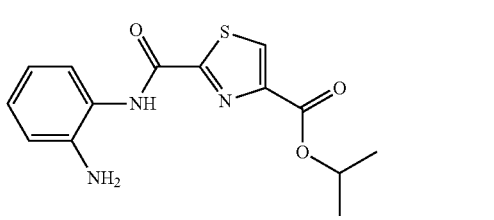

34A

A solution of compound 33A (0.777 g, 2.87 mmol) in ethanol (4.00 mL) and tetrahydrofuran (8.00 mL) was treated with 2M aqueous sodium hydroxide (2.00 mL). The resulting dark red-brown solution was heated at 50° C. for 2 h. The reaction mixture was cooled to room temperature and concentrated under vacuum. The residue was then dissolved in water (13 mL) to yield a solution with a pH of 9 which was acidified with 2N HCl (1.80 mL), resulting in the appearance of a white precipitate in the solution. The mixture was extracted with ethyl acetate (4×100 mL). The extracts were combined, washed with brine (10 mL), dried over anhydrous sodium sulfate, filtered and concentrated. The crude acid was dissolved in anhydrous DMF (4.0 mL) and was treated successively with PYBOP (0.809 g, 1.55 mmol), 4-methylmorpholine (0.500 mL, 4.55 mmol), and 1,2-benzenediamine (0.423 g, 3.91 mmol). The reaction was stirred 14 hours at 45-50° C. The reaction was diluted with water (50 mL) and was then extracted with ethyl acetate (2×50 mL). The extracts were combined, dried over sodium sulfate, filtered and concentrated at 55° C. to yield dark red-brown oil (0.628 g). This oil was dissolved in dichloromethane (8 mL) and purified by flash chromatography eluting with 0-3% dichloromethane-acetone to provide compound 34A as a yellow oil (0.138 g, 56% yield).

Example 35

Preparation of Intermediate Compound 35A

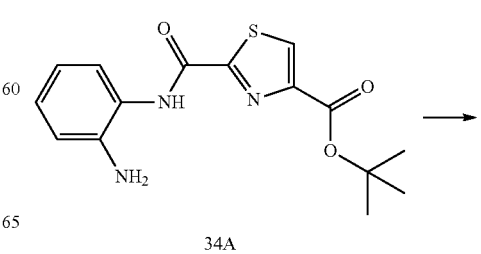

34A

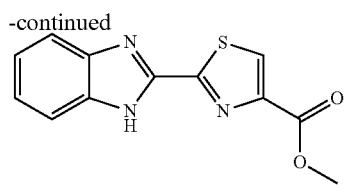

35A

A solution of compound 34A (0.059 g, 0.144 mmol) in 1.25 M hydrogen chloride in methanol (2.0 mL), in a sealed tube, was stirred 14 hours at room temperature. Additional 1.25M HCl-in-methanol (2.0 mL) was added and the reaction was stirred an additional three days at room temperature. The reaction solution was concentrated at 50° C. and dried under vacuum. The residue was redissolved in acetic acid (10.0 mL, 176 mmol) and heated for about 15 hours at 90° C. The reaction was then cooled to room temperature and concentrated at 65° C. to yield a yellow-orange oil, which was mixed with 5 mL of half-saturated potassium carbonate solution and then extracted with ethyl acetate (3×10 mL). The extracts were combined, washed with brine, dried over sodium sulfate, filtered and concentrated to provide compound 35A as an orange oil (0.030 g, 100% yield).

Example 36

Preparation of

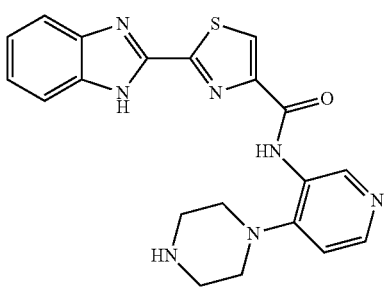 [SMILES: O=C(Nc1cnccc1N1CCNCC1)c1csc(-c2nc3ccccc3[nH]2)n1]

A solution of compound 35A (0.042 g, 0.117 mmol) in tetrahydrofuran (2.00 mL), methanol (2.00 mL) and water (1.00 mL) was treated with 2M aqueous sodium hydroxide (0.060 mL). The solution was stirred for about 15 hours at room temperature, then 5 hours at 50° C. The solution was then concentrated at 50° C. and dried under vacuum for 1.5 hours to provide an orange oily residue (0.049 g). This crude sodium carboxylate was redissolved in N,N-dimethylformamide (5.00 mL), and treated successively with PYBOP (0.124 g, 0.238 mmol), 4-methylmorpholine (0.100 mL, 0.910 mmol) and Preparative Example 2 (0.069 g, 0.246 mmol). The reaction mixture was stirred four days at 45° C. The reaction mixture was then cooled to room temperature and concentrated at 55-60° C. to yield a yellow-orange oil. 50% saturated aqueous potassium carbonate (15 mL) was added, and the mixture was extracted with dichloromethane (2×15 mL). The extracts were combined, dried over anhydrous sodium sulfate, filtered and concentrated to yield an orange oil (0.157 g). The oil was dissolved in chloroform (3.0 mL) and trifluoroacetic acid (3.0 mL) and was stirred for about 15 hours at room temperature. The reaction solution was then concentrated, and the residue was redissolved in 2.0 mL 1:1 formic acid-water and purified by reverse-phase chromatography on a Waters 25 mm PrepLC column to provide the title compound as a colorless oil (0.011 g, 21% yield). $^1$H NMR (DMSO) δ 9.86 (s, 1H), 9.00 (br s, 1H), 8.88 (br s, 2H), 8.72 (s, 1H), 8.41 (br s, 1H), 7.68 (br s, 2H), 7.30-7.34 (m, 3H), 3.46 (br s, 4H), 3.32 (br s, 4H); MH$^+$=406.

Example 37

Preparation of

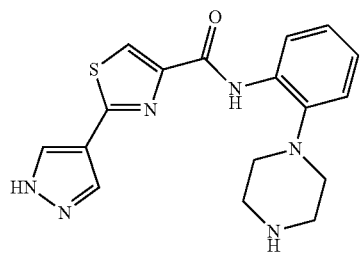 [SMILES: O=C(Nc1ccccc1N1CCNCC1)c1csc(-c2cn[nH]c2)n1]

$K_3PO_4$ (0.20 mmol, 42 mg), $Pd_2(dba)_3$ (7.0 μmol, 6.4 mg), X-Phos (0.020 mmol, 9.6 mg), 4-{2-[(2-Bromo-thiazole-4-carbonyl)-amino]-phenyl}-piperazine-1-carboxylic acid tert-butyl ester (0.10 mmol, 47 mg) and 4-pyrazoleboronic acid pinacol ester (0.20 mmol, 39 mg) were loaded into a Schlenk tube containing a stir bar. The tube was capped with a rubber septum, evacuated and refilled with nitrogen. Toluene (0.5 mL) was added to the reaction mixture through the septum via a syringe, and then the tube was sealed with a Teflon screw cap under a flow of nitrogen, and put into an oil bath at 110° C. The resulting reaction was allowed to stir at this temperature for 15 hours, and then the reaction mixture was cooled to room temperature. The reaction mixture was filtered through a pad of celite and the filtrate was concentrated in vacuo. The residue was reacted with TFA (0.5 mL) for 10 minutes. The TFA solution was concentrated in vacuo. The title compound was purified using reverse phase HPLC. HPLC-MS RT=2.95 minutes, observed LCMS m/z 355.28 (M+H).

Example 38

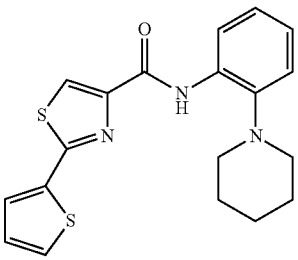 [SMILES: O=C(Nc1ccccc1N1CCCCC1)c1csc(-c2cccs2)n1]

A solution of 2-thiophen-2-yl-thiazole-4-carboxylic acid (0.10 mmol, 21 mg) and CDI (0.10 mmol, 16 mg) in DMF (0.5 mL) was stirred at room temperature for 1 hour. To this solution was added 2-piperidin-1-yl-phenylamine (0.10 mmol, 18 mg). The resulting reaction was heated to 80° C. and allowed to stir at this temperature for 15 hours. The reaction mixture was cooled to room temperature, and then dissolved in DMSO/acetonitrile (3:1), purified using reverse phase HPLC to provide the title compound. HPLC-MS RT=6.20 minutes, observed LCMS m/z 370.23 (M+H).

Using this method and utilizing the appropriate reactants, the following illustrative compounds of the present invention were made:

| Compound | LCMS m/z (M + H) |
|---|---|
|  | 356.12 |
|  | 353.05 |
|  | 384.11 |

Example 39

Preparation of

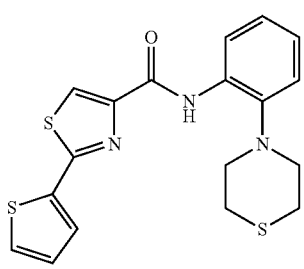 [SMILES: O=C(Nc1ccccc1N1CCSCC1)c1csc(-c2cccs2)n1]

Step A—Synthesis of Intermediate Compound 39A

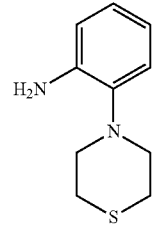

39A

A solution of 1-fluoro-2-nitro-benzene (2.0 mmol, 0.21 mL), triethylamine (3.0 mmol, 0.42 mL) and thiomorpholine (3.0 mmol, 0.30 mL) in dioxane (2 mL) was irradiated using microwave for 15 minutes at a temperature of 160° C. The solution was then cooled to room temperature and concentrated in vacuo and the resulting residue was purified using column chromatography on silica gel to provide 4-(2-Nitrophenyl)-thiomorpholine. To the solution of this nitro compound in MeOH (10 mL) was added Pd on carbon (5% Pd, 100 mg). The resulting reaction mixture was stirred under a hydrogen atmosphere at room temperature for about 15 hours. The reaction mixture was filtered through a pad of celite and the filtrate was concentrated in vacuo to provide compound 39A. HPLC-MS RT=1.06 minutes, mass calculated formula C10H14N2S 194.09, observed LCMS m/z 195.10 (M+H).

Step 2—Synthesis of Title Compound

Using the method described in Example 38 and substituting compound 39A as the amine coupling partner, the title compound was made. HPLC-MS RT=5.99 minutes, observed LCMS m/z 388.06 (M+H).

Using this method and utilizing the appropriate reactants, the following illustrative compounds of the present invention were made:

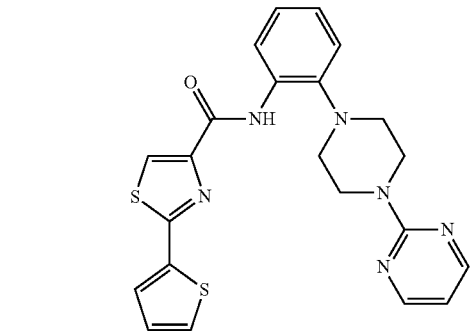

observed LCMS m/z 449.15 (M + H)

-continued

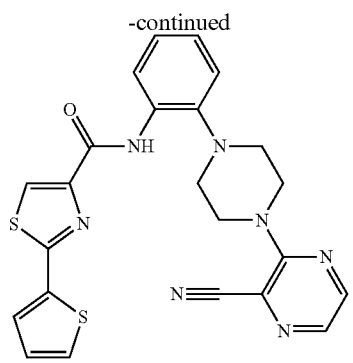

HPLC-MS RT = 5.74 minutes, observed LCMS m/z 474.13 (M + H)

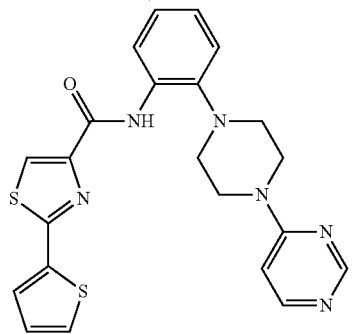

HPLC-MS RT = 4.13 minutes, observed LCMS m/z 449.20 (M + H)

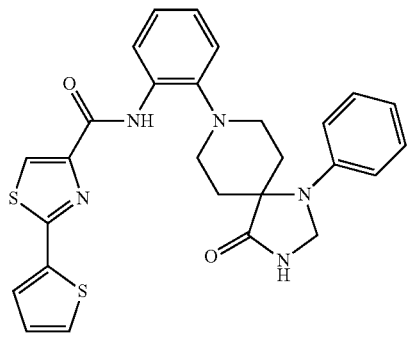

HPLC-MS RT = 5.35 minutes, observed LCMS m/z 516.21 (M + H)

Example 40

Preparation of

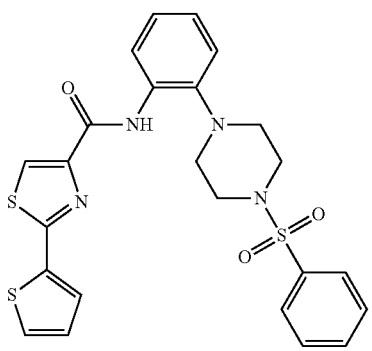 [SMILES: O=C(Nc1ccccc1N1CCN(S(=O)(=O)c2ccccc2)CC1)c1csc(-c2cccs2)n1]

Step 1—Preparation of Intermediate Compound 40A

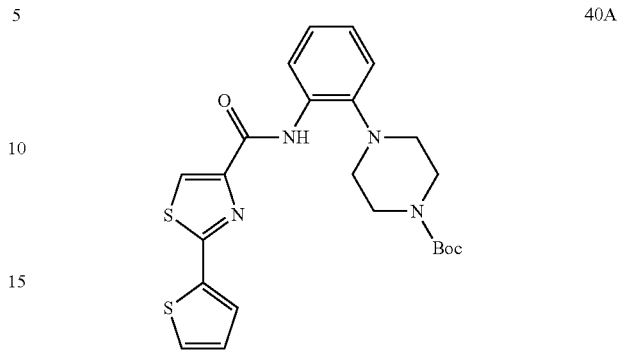

40A

A solution of 2-thiophen-2-yl-thiazole-4-carboxylic acid (4.0 mmol, 0.85 g) and CDI (4.0 mmol, 0.65 g) in DMF (10 mL) was stirred at room temperature for one hour. To the resulting solution was added 4-(2-amino-phenyl)-piperazine-1-carboxylic acid tert-butyl ester (4.0 mmol, 1.1 g) and the resulting reaction was heated to 80° C. and allowed to stir at this temperature for 3 hours, after which time the reaction mixture was cooled to room temperature, then concentrated in vacuo to provide a crude residue. The crude residue was purified using flash column chromatography on silica gel using Hexane/EtOAc/Toluene (4/1/2.5) as eluent to provide Compound 40A as a yellow solid.

Step 2—Preparation of Intermediate Compound 40B

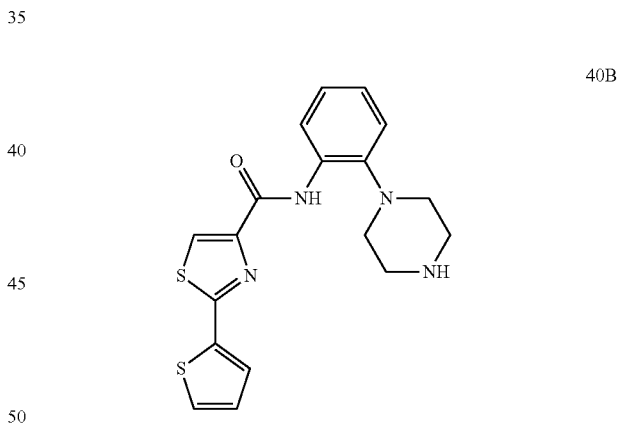

40B

A solution of Intermediate Compound 40A in TFA (5 mL) was stirred at room temperature for 10 minutes, then concentrated in vacuo. The resulting residue was dissolved in ACN/Water (1/1). The solution was lyophilized to give intermediate compound 40B as a TFA salt (2.2 g).

Step 3—Preparation of Title Compound

A solution of benzenesulfonyl chloride (8.8 mg, 0.050 mmol), N,N-diisopropylethylamine (44 µL, 0.25 mmol) and intermediate compound 40B as a TFA salt (24 mg, 0.050 mmol) in DMF (1 mL) was irradiated using microwave for 15 minutes at a temperature of 180° C. The reaction mixture was then dissolved in DMSO/Acetonitrile (3:1) and purified using reverse phase HPLC to provide the title compound. HPLC-MS RT=5.65 minutes, observed LCMS m/z 511.15 (M+H).

Using this method and utilizing the appropriate reactants, the following illustrative compounds of the present invention were made:
| Compound | LCMS m/z (M + H) | Retention Time (minutes) |
|---|---|---|
| | 568.21 | 5.02 minutes |
| 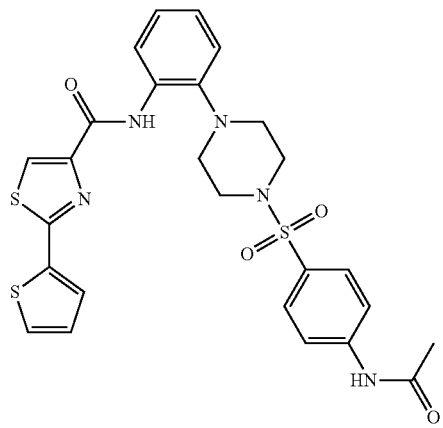 [SMILES: CC(=O)Nc1ccc(S(=O)(=O)N2CCN(c3ccccc3NC(=O)c3csc(-c4cccs4)n3)CC2)cc1] | 529.21 | 4.60 |
| 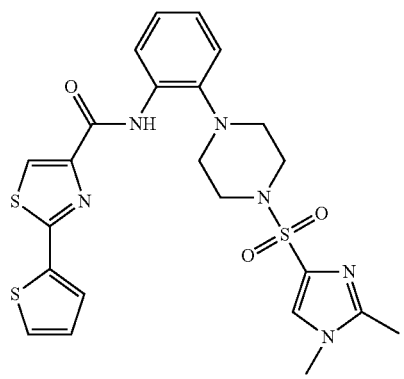 [SMILES: Cc1nc(S(=O)(=O)N2CCN(c3ccccc3NC(=O)c3csc(-c4cccs4)n3)CC2)cn1C] | 536.16 | |
| 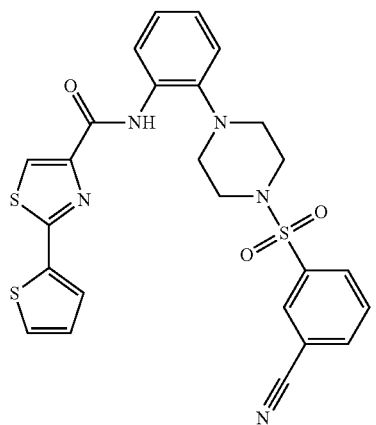 [SMILES: N#Cc1cccc(S(=O)(=O)N2CCN(c3ccccc3NC(=O)c3csc(-c4cccs4)n3)CC2)c1] | | |

-continued
| Compound | LCMS m/z (M + H) | Retention Time (minutes) |
|---|---|---|
| 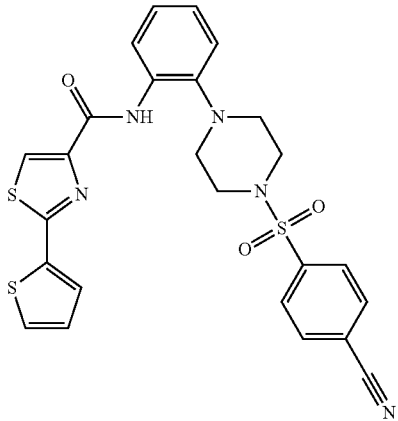 [SMILES: N#Cc1ccc(S(=O)(=O)N2CCN(c3ccccc3NC(=O)c3csc(-c4cccs4)n3)CC2)cc1] | 536.15 | |
| 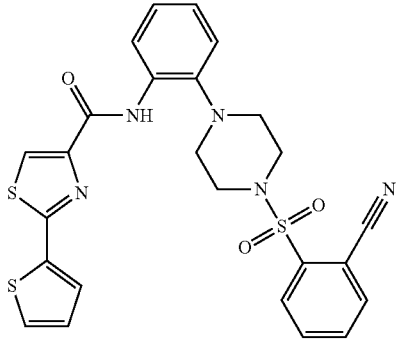 [SMILES: N#Cc1ccccc1S(=O)(=O)N1CCN(c2ccccc2NC(=O)c2csc(-c3cccs3)n2)CC1] | 536.17 | |
| 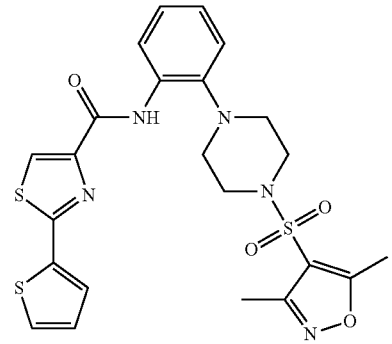 [SMILES: Cc1noc(C)c1S(=O)(=O)N1CCN(c2ccccc2NC(=O)c2csc(-c3cccs3)n2)CC1] | 530.21 | |
| 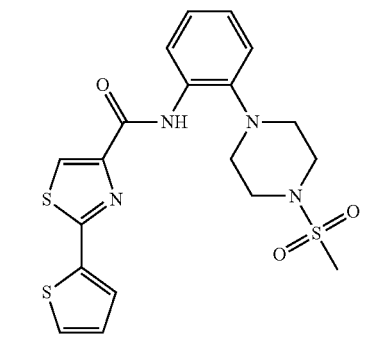 [SMILES: CS(=O)(=O)N1CCN(c2ccccc2NC(=O)c2csc(-c3cccs3)n2)CC1] | 449.09 | |

| Compound | LCMS m/z (M + H) | Retention Time (minutes) |
|---|---|---|
| 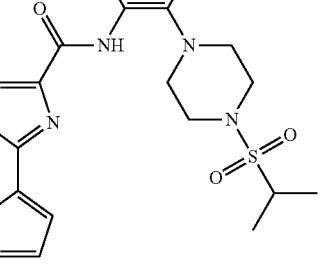 | 477.21 | |
| 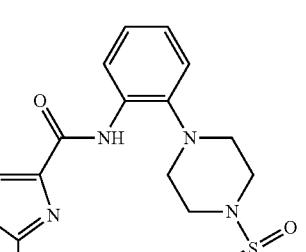 | 475.12 | |
| 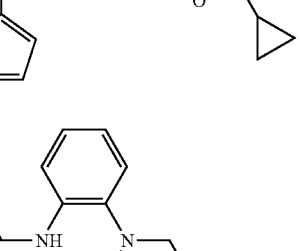 | 525.16 | |
| 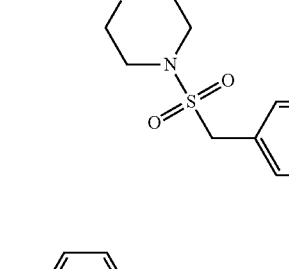 | 578.15 | |

| Compound | LCMS m/z (M + H) | Retention Time (minutes) |
|---|---|---|
| 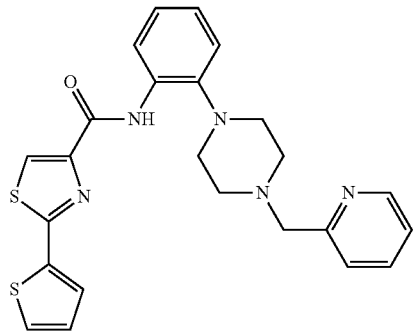 [SMILES: O=C(Nc1ccccc1N1CCN(Cc2ccccn2)CC1)c1csc(-c2cccs2)n1] | 462.26 | |
| 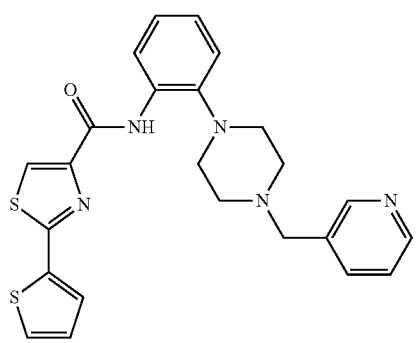 [SMILES: O=C(Nc1ccccc1N1CCN(Cc2cccnc2)CC1)c1csc(-c2cccs2)n1] | 462.23 | |
| 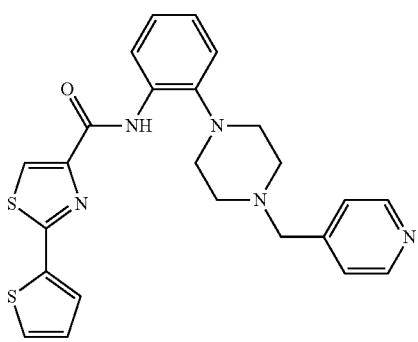 [SMILES: O=C(Nc1ccccc1N1CCN(Cc2ccncc2)CC1)c1csc(-c2cccs2)n1] | 462.26 | |
| 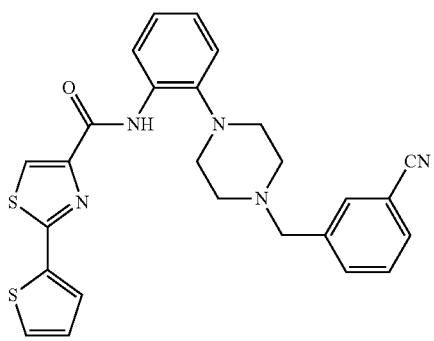 [SMILES: N#Cc1cccc(CN2CCN(c3ccccc3NC(=O)c3csc(-c4cccs4)n3)CC2)c1] | 486.22 | |

| Compound | LCMS m/z (M + H) | Retention Time (minutes) |
|---|---|---|
| 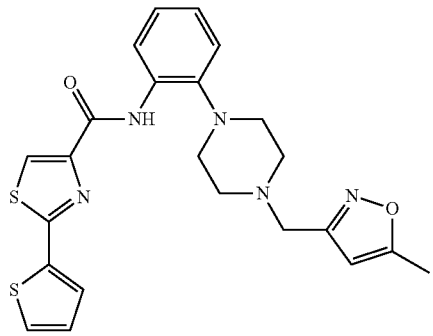 [SMILES: Cc1cc(CN2CCN(c3ccccc3NC(=O)c3csc(-c4cccs4)n3)CC2)no1] | 466.24 | |
| 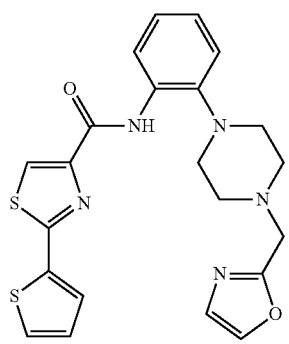 | 452.18 | |
| 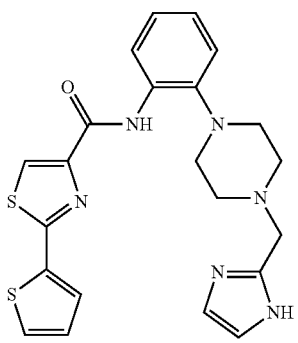 [SMILES: O=C(Nc1ccccc1N1CCN(Cc2ncc[nH]2)CC1)c1csc(-c2cccs2)n1] | 451.15 | |
| 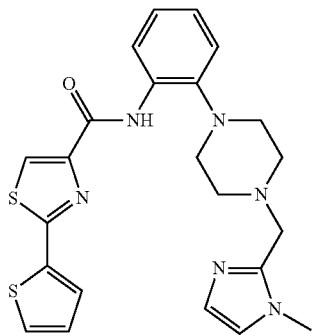 [SMILES: Cn1ccnc1CN1CCN(c2ccccc2NC(=O)c2csc(-c3cccs3)n2)CC1] | 465.17 | |

| Compound | LCMS m/z (M + H) | Retention Time (minutes) |
|---|---|---|
| 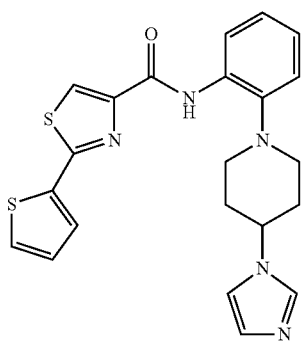 | 415.15 | |

Example 41

Preparation of

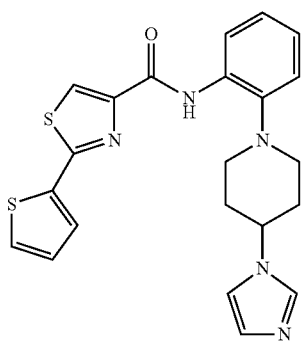

Step 1—Synthesis of Intermediate Compound 41A

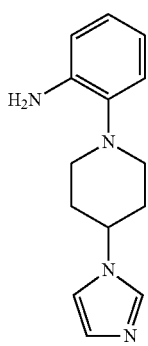

41A

A solution of 1-fluoro-2-nitro-benzene (0.32 mmol, 34 µL), N,N-diisopropylethylamine (1.6 mmol, 0.28 mL) and HCl salt of 4-Imidazol-1-yl-piperidine (0.53 mmol, 0.10 g) in ACN (2 mL) was irradiated using microwave for 10 minutes at a temperature of 180° C. The solution was then cooled to room temperature and concentrated in vacuo and the resulting residue was purified using column chromatography on silica gel to provide 4-Imidazol-1-yl-1-(2-nitro-phenyl)-piperidine (71 mg, 81% yield). To the solution of this nitro compound in EtOAc (15 mL) was added Pd on carbon (5% Pd, 55 mg). The resulting reaction mixture was stirred under a hydrogen atmosphere at room temperature for about 15 hours. The reaction mixture was filtered through a pad of celite and the filtrate was concentrated in vacuo to provide compound 41A (54 mg, 86% yield). HPLC-MS RT=0.63 minutes, mass calculated formula C14H18N4 242.15, observed LCMS m/z 243.30 (M+H).

Step 2—Synthesis of Title Compound

To a premixed solution of 2-thiophen-2-yl-thiazole-4-carboxylic acid (0.050 mmol, 11 mg) and HATU (0.050 mmol, 19 mg) in DMF (0.5 mL) was added N,N-diisopropylethylamine (0.25 mmol, 44 µL) and 41A (0.050 mmol, 12 mg). The resulting reaction was heated to 80° C. and allowed to stir at this temperature for 15 hours. The reaction mixture was dissolved in DMSO/acetonitrile (3:1), purified using reverse phase HPLC to provide the title compound. HPLC-MS RT=3.86 minutes, observed LCMS m/z 436.17 (M+H).

Using this method and substituting 4-imidazol-1-yl-piperidine for 4-[1,2,4]triazol-1-yl-piperidine, the following illustrative compound of the present invention was made:

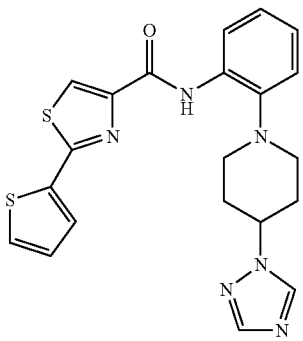

HPLC-MS RT = 4.82 minutes, observed LCMS m/z 437.16 (M + H)

Example 42

Preparation of

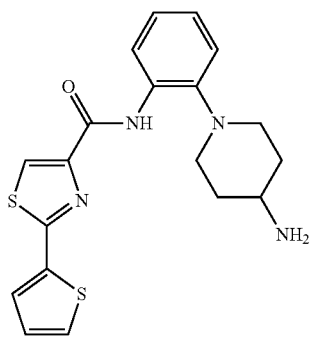 [SMILES: NC1CCN(c2ccccc2NC(=O)c2csc(-c3cccs3)n2)CC1]

Step 1—Synthesis of Intermediate Compound 42A

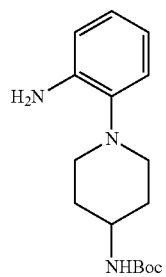

42A

A solution of 1-fluoro-2-nitro-benzene (0.50 mmol, 53 µL), N,N-diisopropylethylamine (0.50 mmol, 87 µL) and Piperidin-4-yl-carbamic acid tert-butyl ester (0.50 mmol, 0.10 g) in 1,4-dioxane (2 mL) was irradiated using microwave for 10 minutes at a temperature of 180° C. The solution was then cooled to room temperature and concentrated in vacuo and the resulting residue was purified using column chromatography on silica gel to provide [1-(2-Nitro-phenyl)-piperidin-4-yl]-carbamic acid tert-butyl ester (0.12 g, 77% yield). To the solution of this nitro compound in EtOAc (15 mL) was added Pd on carbon (5% Pd, 55 mg). The resulting reaction mixture was stirred under a hydrogen atmosphere at room temperature for about 15 hours. The reaction mixture was filtered through a pad of celite and the filtrate was concentrated in vacuo to provide Intermediate Compound 42A (97 mg, 86% yield).

Step 2—Synthesis of Title Compound

A solution of 2-thiophen-2-yl-thiazole-4-carboxylic acid (0.050 mmol, 11 mg) and CDI (0.050 mmol, 8.1 mg) in DMF (0.5 mL) was stirred at room temperature for 1 hour. To this solution was added Intermediate Compound 42A [1-(2-Amino-phenyl)-piperidin-4-yl]-carbamic acid tert-butyl ester (0.050 mmol, 15 mg). The resulting reaction was heated to 80° C. and allowed to stir at this temperature for 15 hours. The reaction mixture was cooled to room temperature and concentrated. The residue was reacted with TFA (0.5 mL) for 10 minutes. The TFA solution was concentrated in vacuo. The residue was dissolved in DMSO/acetonitrile (3:1), purified using reverse phase HPLC to provide the title compound. HPLC-MS RT. 3.67 minutes, observed LCMS m/z 385.12 (M+H).

Example 43

Preparation of

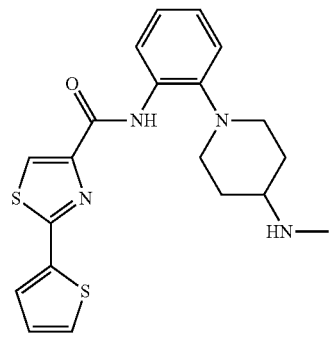 [SMILES: CNC1CCN(c2ccccc2NC(=O)c2csc(-c3cccs3)n2)CC1]

Using the method described in Example 42 and substituting Piperidin-4-yl-carbamic acid tert-butyl ester for Methyl-piperidin-4-yl-carbamic acid tert-butyl ester, the title compound was prepared. HPLC-MS RT=3.77 minutes, observed LCMS m/z 399.13 (M+H).

Example 44

Preparation of

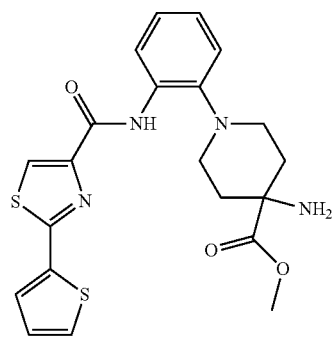 [SMILES: COC(=O)C1(N)CCN(c2ccccc2NC(=O)c2csc(-c3cccs3)n2)CC1]

Using the method described in Example 42 and substituting Piperidin-4-yl-carbamic acid tert-butyl ester for 4-tert-Butoxycarbonylamino-piperidine-4-carboxylic acid methyl ester, the title compound was prepared. HPLC-MS RT=3.93 minutes, observed LCMS m/z 443.20 (M+H).

Example 45

Preparation of

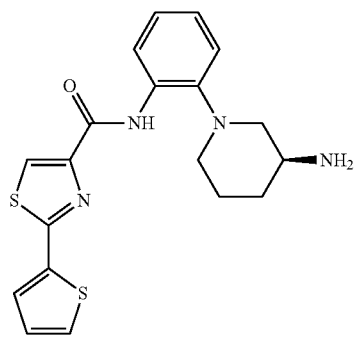 [SMILES: N[C@H]1CCCN(c2ccccc2NC(=O)c2csc(-c3cccs3)n2)C1]

Using the method described in Example 42 and substituting Piperidin-4-yl-carbamic acid tert-butyl ester for (S)-Piperidin-3-yl-carbamic acid tert-butyl ester, the title compound was prepared. HPLC-MS RT=3.85 minutes, observed LCMS m/z 385.18 (M+H).

Example 46

Preparation of

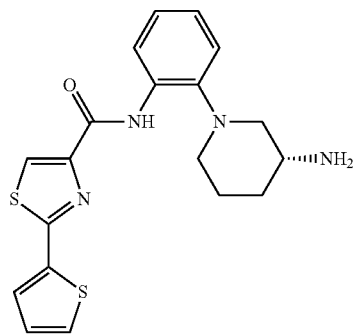 [SMILES: N[C@@H]1CCCN(c2ccccc2NC(=O)c2csc(-c3cccs3)n2)C1]

Using the method described in Example 42 and substituting Piperidin-4-yl-carbamic acid tert-butyl ester for (R)-Piperidin-3-yl-carbamic acid tert-butyl ester, the title compound was prepared. HPLC-MS RT=3.86 minutes, observed LCMS m/z 385.15 (M+H).

Example 47

Preparation of

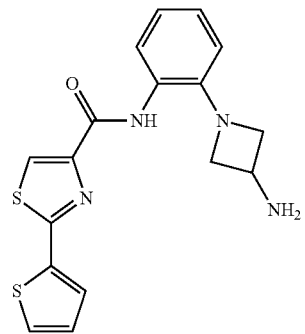 [SMILES: NC1CN(c2ccccc2NC(=O)c2csc(-c3cccs3)n2)C1]

Using the method described in Example 42 and substituting Piperidin-4-yl-carbamic acid tert-butyl ester for Azetidin-3-yl-carbamic acid tert-butyl ester, the title compound was prepared. HPLC-MS RT=3.11 minutes, observed LCMS m/z 357.17 (M+H).

Example 48

Preparation of

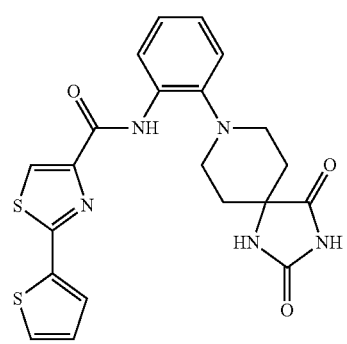 [SMILES: O=C1NC(=O)C2(CCN(c3ccccc3NC(=O)c3csc(-c4cccs4)n3)CC2)N1]

Step 1—Synthesis of Intermediate Compound 48A

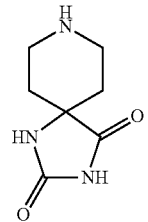

48A 1-t-Boc-piperidine-4-spiro-5'-hydantoin (1.9 mmol, 0.50 g) was reacted with TFA in water (90%, 5 mL) at room temperature for 1 hour. The solvent was removed by lyophilization to provide the intermediate compound 48A.

Step 2—Synthesis of Title Compound

Using the method described in Example 24 and substituting 48A for thiomorpholine, the title compound was prepared. HPLC-MS RT=4.51 minutes, observed LCMS m/z 454.18 (M+H).

Example 49

Preparation of

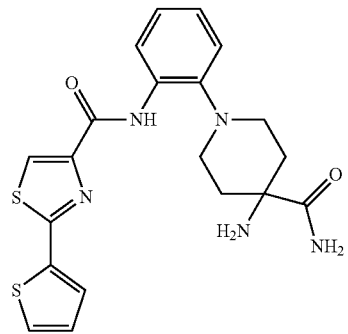 [SMILES: NC(=O)C1(N)CCN(c2ccccc2NC(=O)c2csc(-c3cccs3)n2)CC1]

Using the method described in Example 48 and substituting Piperidin-4-yl-carbamic acid tert-butyl ester for (4-Carbamoyl-piperidin-4-yl)-carbamic acid tert-butyl ester, Compound 152 was prepared. HPLC-MS RT=3.26 minutes, observed LCMS m/z 428.13 (M+H).

Example 50

Preparation of

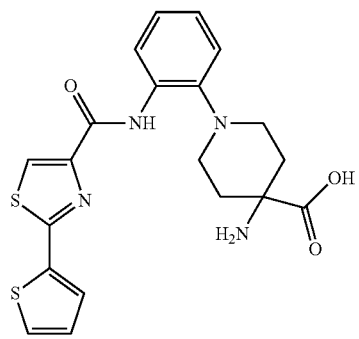 [SMILES: NC1(C(=O)O)CCN(c2ccccc2NC(=O)c2csc(-c3cccs3)n2)CC1]

A solution of the title compound from Example 49 (10 mg) in a 1:1 mixture of THF and water (1 mL) was stirred with lithium hydroxide (10 mg) at room temperature for about 15 hours. The reaction mixture was concentrated and the residue was dissolved in DMSO/acetonitrile (3:1) and purified using reverse phase HPLC to provide the title compound. HPLC-MS RT=3.58 minutes, observed LCMS m/z 429.20 (M+H).

Example 51

Preparation of

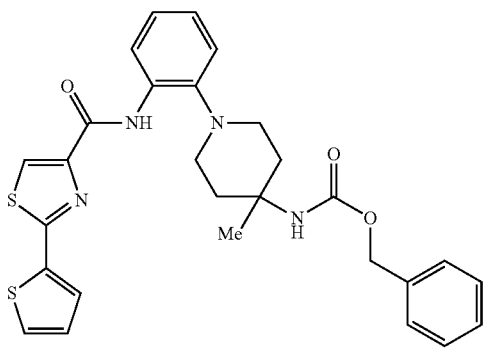 [SMILES: CC1(NC(=O)OCc2ccccc2)CCN(c2ccccc2NC(=O)c2csc(-c3cccs3)n2)CC1]

Step 1—Synthesis of Intermediate Compound 51A

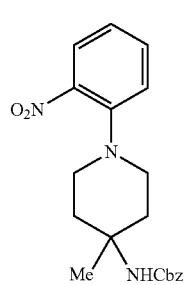

A solution of 1-fluoro-2-nitro-benzene (2.0 mmol, 0.21 mL), N,N-diisopropylethylamine (2.5 mmol, 0.44 mL) and (4-methyl-piperidin-4-yl)-carbamic acid benzyl ester (2.3 mmol, 0.57 g) in DMF (2 mL) was irradiated using microwave for 15 minutes at a temperature of 180° C. The solution was then cooled to room temperature and concentrated in vacuo. The resulting residue was purified using column chromatography on silica gel to provide Intermediate Compound 51A.

Step 2—Synthesis of Intermediate Compound 51B

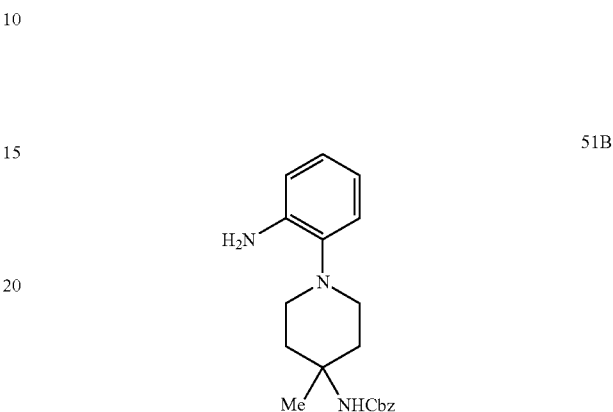

To the solution of Intermediate Compound 51A (2.0 mmol, 0.74 g) in EtOH (50 mL) was added zinc (78 mmol, 5.1 g) and calcium chloride (2.0 mmol, 0.22 g). The reaction mixture was stirred in refluxing ethanol for about 15 hours. The reaction mixture was filtered through a pad of celite and the filtrate was concentrated in vacuo to provide Intermediate Compound 51B. HPLC-MS 1.45 minutes, mass calculated formula C20H25N3O2 339.19, observed LCMS m/z 340.10 (M+H).

Step 2—Synthesis of Title Compound

Using the method described in Example 2 and substituting 2-piperidin-1-yl-phenylamine for Intermediate Compound 51B, the title compound was prepared. HPLC-MS RT=6.19 minutes, observed LCMS m/z 533.23 (M+H).

Example 52

Preparation of

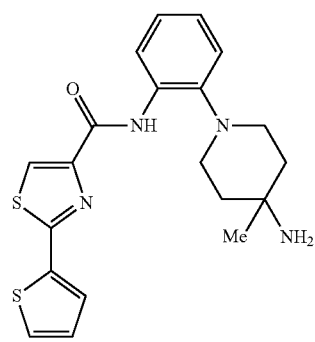 [SMILES: CC1(N)CCN(c2ccccc2NC(=O)c2csc(-c3cccs3)n2)CC1]

The title compound from Example 51 (10 mg) in a concentrated HCl aqueous solution (12 M, 10 mL) was refluxed for one hour. The reaction mixture was cooled to room temperature and concentrated. The residue was dissolved in DMSO/acetonitrile (3:1), purified using reverse phase HPLC to provide the title compound. HPLC-MS RT=3.85 minutes, observed LCMS m/z 399.18 (M+H).

Example 53

Preparation of

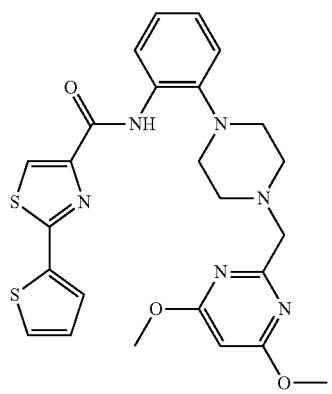 [SMILES: COc1cc(OC)nc(CN2CCN(c3ccccc3NC(=O)c3csc(-c4cccs4)n3)CC2)n1]

To a premixed solution of 2-thiophen-2-yl-thiazole-4-carboxylic acid (0.050 mmol, 11 mg) and HATU (0.050 mmol, 19 mg) in DMF (0.5 mL) was added N,N-diisopropylethylamine (0.25 mmol, 44 μL) and 4,6-Dimethoxy-2-piperazin-1-ylmethyl-pyrimidine (0.050 mmol, 17 mg). The resulting reaction was heated to 80° C. and allowed to stir at this temperature for 15 hours. The reaction mixture was dissolved in DMSO/acetonitrile (3:1), purified using reverse phase HPLC to provide the title compound. HPLC-MS RT=4.24 minutes, observed LCMS m/z 523.24 (M+H).

Example 54

Preparation of

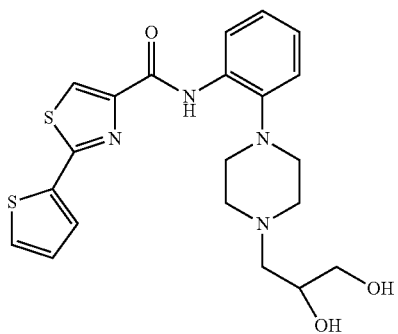 [SMILES: O=C(Nc1ccccc1N1CCN(CC(O)CO)CC1)c1csc(-c2cccs2)n1]

Step 1—Synthesis of Intermediate Compound 54A

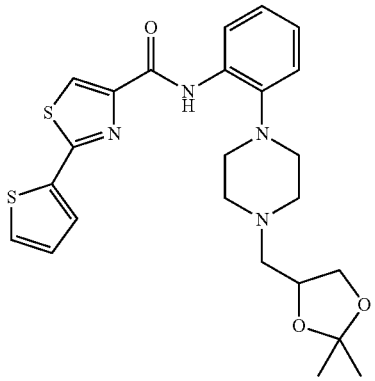

54A

Using the method described in Example 53 and substituting benzenesulfonyl chloride for 4-Chloromethyl-2,2-dimethyl-[1,3]dioxolane, Intermediate Compound 54 A was prepared. HPLC-MS RT=4.06 minutes, mass calculated formula C24H28N4O3S2 484.16, observed LCMS m/z 485.21 (M+H).

Step 2—Synthesis of Title Compound

Intermediate Compound 54A (10 mg) in an aqueous HCl solution (1 M, 5 mL) was stirred at room temperature for 1 hour. The reaction mixture was dissolved in DMSO/acetonitrile (3:1), purified using reverse phase HPLC to provide Compound 157. HPLC-MS RT=3.37 minutes, observed LCMS m/z 445.21 (M+H).

Example 55

Preparation of

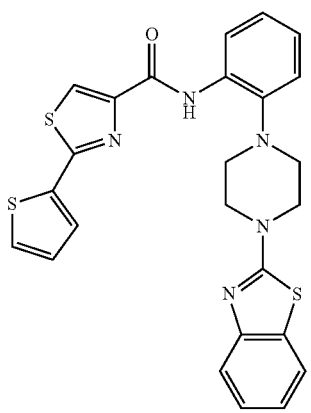 [SMILES: O=C(Nc1ccccc1N1CCN(c2nc3ccccc3s2)CC1)c1csc(-c2cccs2)n1]

Using the method described in Example 74 and substituting 4-Imidazol-1-yl-piperidine for 2-piperazin-1-yl-benzothiazole, the title compound was prepared. HPLC-MS RT=5.88 minutes, observed LCMS m/z 504.12 (M+H).

Example 56

Preparation of

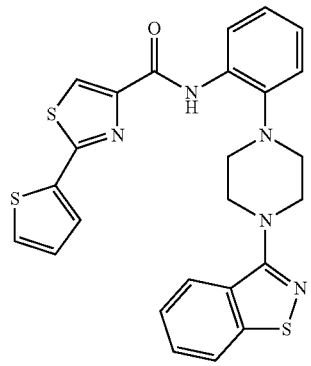 [SMILES: O=C(Nc1ccccc1N1CCN(c2nsc3ccccc23)CC1)c1csc(-c2cccs2)n1]

Using the method described in Example 74 and substituting 4-Imidazol-1-yl-piperidine for 3-piperazin-1-yl-benzo[d]isothiazole, the title compound was prepared. HPLC-MS RT=6.54 minutes, observed LCMS m/z 504.14 (M+H).

Example 57

Preparation of

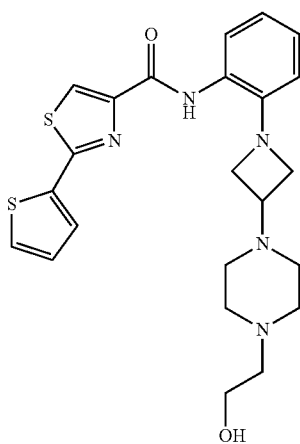 [SMILES: O=C(Nc1ccccc1N1CC(N2CCN(CCO)CC2)C1)c1csc(-c2cccs2)n1]

Step 1—Synthesis of Intermediate Compound 57A

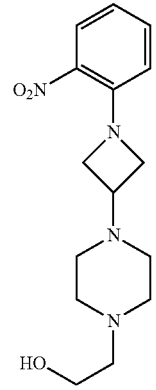

57A

A solution of 1-fluoro-2-nitro-benzene (0.60 mmol, 65 µL), N,N-diisopropylethylamine (1.0 mmol, 0.18 mL) and trihydrochloride salt of 2-(4-Azetidin-3-yl-piperazin-1-yl)-ethanol (1.0 mmol, 0.30 g) in ACN (2 mL) was irradiated using microwave for 10 minutes at a temperature of 180° C. The solution was then cooled to room temperature and concentrated in vacuo and the resulting residue was purified using column chromatography on silica gel to provide Intermediate Compound 57A (0.13 g, 72% yield).

Step 2—Synthesis of Intermediate Compound 57B

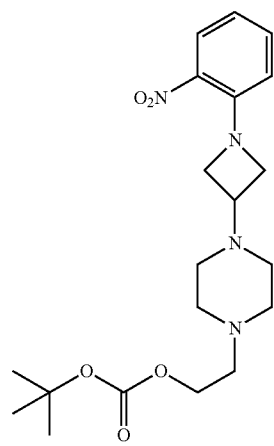

57B

To the solution of Intermediate Compound 57A (0.22 mmol, 66 mg) in THF (1 mL) was added Boc anhydride (0.32 mmol, 71 mg). The resulting reaction mixture was stirred at a temperature of 50° C. for 48 hours. The solution was then cooled to room temperature and concentrated in vacuo and the resulting residue was purified using column chromatography on silica gel to provide Intermediate Compound 57B (19 mg, 22% yield). HPLC-MS RT=1.26 minutes, mass calculated formula C20H30N4O5 406.22, observed LCMS m/z 407.20 (M+H).

Step 3—Synthesis of Intermediate Compound 57C

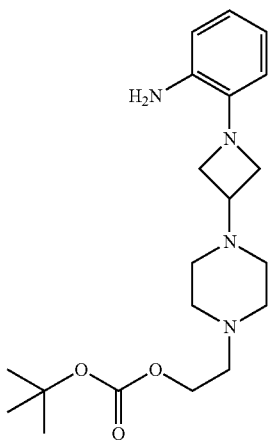

57C

To the solution of Intermediate Compound 57B (0.047 mmol, 19 mg) in EtOAc (15 mL) was added Pd on carbon (5% Pd, 10 mg). The resulting reaction mixture was stirred under a hydrogen atmosphere at room temperature for about 15 hours. The reaction mixture was filtered through a pad of celite and the filtrate was concentrated in vacuo to provide Intermediate Compound 57C (7.5 mg, 42% yield). HPLC-MS RT=0.97 minutes, mass calculated formula C20H32N4O3 376.25, observed LCMS m/z 377.20 (M+H).

Step 4—Synthesis of Title Compound

To a premixed solution of 2-thiophen-2-yl-thiazole-4-carboxylic acid (0.050 mmol, 11 mg) and HATU (0.050 mmol, 19 mg) in DMF (0.5 mL) was added N,N-diisopropylethylamine (0.25 mmol, 44 μL) and Intermediate Compound 57C (0.020 mmol, 7.5 mg). The resulting reaction was heated to 80° C. and allowed to stir at this temperature for 15 hours. The reaction mixture was cooled to room temperature and concentrated. The residue was reacted with TFA (0.5 mL) for 30 minutes. The TFA solution was concentrated in vacuo. The residue was dissolved in DMSO/acetonitrile (3:1), purified using reverse phase HPLC to provide the title compound. HPLC-MS RT=3.35 minutes, observed LCMS m/z 470.17 (M+H).

Example 58

Preparation of

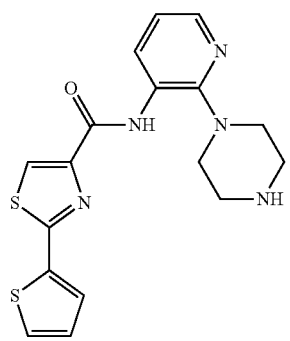 [SMILES: O=C(Nc1cccnc1N1CCNCC1)c1csc(-c2cccs2)n1]

Step 1—Synthesis of Intermediate Compound 58A

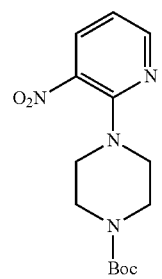

58A

A solution of 2-chloro-3-nitropyridine (6.3 mmol, 1.0 g), N,N-diisopropylethylamine (6.9 mmol, 1.2 mL) and 1-N-Boc-piperazine (7.0 mmol, 1.3 g) in ACN (10 mL) was irradiated using microwave for 15 minutes at a temperature of 160° C. The solution was then cooled to room temperature and concentrated in vacuo and the resulting residue was purified using column chromatography on silica gel with an eluent mixture of Hexane/EtOAc to provide Intermediate Compound 58A (1.98 g). $^1$H NMR (400 MHz, CDCl$_3$) δ8.35 (dd, J=1.6, 4.8 Hz, 1H), 8.16 (dd, J=1.6, 8.4 Hz, 1H), 6.80 (dd, J=4.8, 8.4 Hz, 1H), 3.60-3.54 (m, 4H), 3.48-3.38 (m, 4H), 1.48 (s, 9H).

Step 2—Synthesis of Intermediate Compound 58B

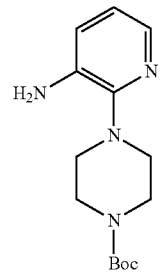

58B

To the solution of Intermediate Compound 58A (1 g) in EtOAc (20 mL) was added Pd on carbon (5% Pd, 0.2 g). The resulting reaction mixture was stirred under a hydrogen atmosphere at room temperature for about 15 hours. The reaction mixture was filtered through a pad of celite and the filtrate was concentrated in vacuo to provide Intermediate Compound 58B, 4-(3-Amino-pyridin-2-yl)-piperazine-1-carboxylic acid tert-butyl ester.

Step 3—Preparation of Title Compound

To a premixed solution of 2-thiophen-2-yl-thiazole-4-carboxylic acid (0.10 mmol, 21 mg) and HATU (0.10 mmol, 38 mg) in DMF (0.5 mL) was added N,N-diisopropylethylamine (0.50 mmol, 87 μL) and Intermediate Compound 58B (0.10 mmol, 28 mg). The resulting reaction was heated to 80° C. and allowed to stir at this temperature for 15 hours. The reaction mixture was cooled to room temperature and concentrated. The residue was reacted with TFA (1.0 mL) for 10 minutes. The TFA solution was concentrated in vacuo. The residue was dissolved in DMSO/acetonitrile (3:1), purified using reverse phase HPLC to provide the title compound. HPLC-MS RT=3.21 minutes, observed LCMS m/z 372.15 (M+H).

Example 59

Preparation of Intermediate Compound 59A

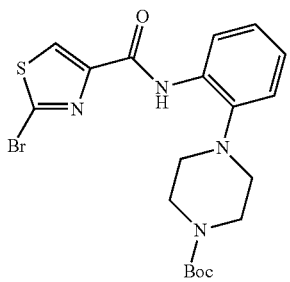

59A

To a premixed solution of 2-bromo-thiazole-4-carboxylic acid (2.0 mmol, 0.42 g), N,N-diisopropylethylamine (3.0 mmol, 0.52 mL) and HATU (2.0 mmol, 0.76 g) in DMF (10 mL) was added 4-(2-aminophenyl)-piperazine-1-carboxylic acid tert-butyl ester (2.0 mmol, 0.56 g). The reaction mixture was stirred at 80° C. for 3 h, and then concentrated in vacuo. The resulting residue was purified using column chromatography on silica gel (eluent: Hexane:EtOAc (4.5:1)) to provide Compound 59A as a yellow solid (0.67 g, 72%). $^1$H NMR (400 MHz, CDCl$_3$) δ 10.38 (s, 1H), 8.49 (dd, J=8.0, 1.2 Hz, 1H), 8.14 (s, 1H), 7.23-7.10 (m, 3H), 3.72 (br s, 4H), 2.89-2.87 (m, 4H), 1.50 (s, 9H). HPLC-MS RT=2.39 minutes, mass calculated formula C$_{19}$H$_{23}$BrN$_4$O$_3$S 466.07, observed LCMS m/z 467.05 (M+H).

Example 60

Preparation of

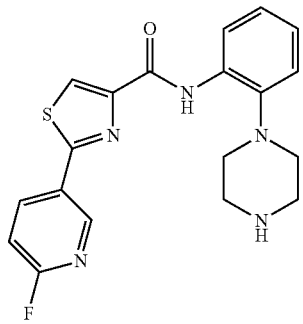 [SMILES: O=C(Nc1ccccc1N1CCNCC1)c1csc(-c2ccc(F)nc2)n1]

Compound 59A (0.050 mmol, 23 mg), K$_3$PO$_4$ (0.10 mmol, 21 mg), Pd$_2$(dba)$_3$ (5.0 µmol, 4.6 mg), S-Phos (0.010 mmol, 4.1 mg) and 2-Fluoropyridine-5-boronic acid pinacol ester (0.10 mmol, 22 mg) were loaded into a Schlenk tube containing a stir bar. The tube was capped with a rubber septum, evacuated and refilled with nitrogen. Toluene (0.5 mL) was added to the reaction mixture through the septum via a syringe. The tube was sealed with a Teflon screw cap under a flow of nitrogen, and put into an oil bath at 118° C. The resulting reaction was allowed to stir at this temperature for 15 hours. The reaction mixture was cooled to room temperature. The reaction mixture was filtered through a pad of celite and the filtrate was concentrated in vacuo. The residue was reacted with TFA (1.0 mL) for 10 minutes. The TFA solution was concentrated in vacuo. The residue was dissolved in DMSO/acetonitrile (3:1), purified using reverse phase HPLC to provide Compound 196. HPLC-MS RT=3.27 minutes, observed LCMS m/z 384.13 (M+H).

Example 61

Preparation of

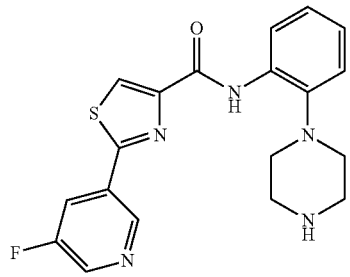 [SMILES: O=C(Nc1ccccc1N1CCNCC1)c1csc(-c2cncc(F)c2)n1]

Using the method described in Example 60 and substituting 2-Fluoropyridine-5-boronic acid pinacol ester for 3-Fluoropyridine-5-boronic acid pinacol ester, the title compound was prepared. HPLC-MS RT=3.25 minutes, observed LCMS m/z 384.22 (M+H).

Example 62

Preparation of Compound 198

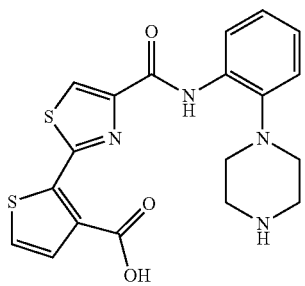 [SMILES: O=C(Nc1ccccc1N1CCNCC1)c1csc(-c2sccc2C(=O)O)n1]

Using the method described in Example 60 and substituting 2-Fluoropyridine-5-boronic acid pinacol ester for 3-carboxythiophene-2-boronic acid, the title compound was prepared. HPLC-MS RT=3.18 minutes, observed LCMS 415.14 (M+H).

Example 63

Preparation of

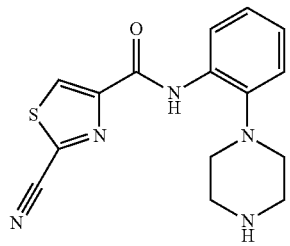 [SMILES: N#Cc1nc(C(=O)Nc2ccccc2N2CCNCC2)cs1]

Compound 59A (0.050 mmol, 23 mg), sodium cyanide (0.10 mmol, 5.0 mg), copper iodide (5.0 µmol, 1.0 mg) and potassium iodide (0.010 mmol, 1.7 mg) were loaded into a Schlenk tube containing a stir bar. The tube was capped with a rubber septum, evacuated and refilled with nitrogen. N,N'-Dimethyl-ethane-1,2-diamine (0.050 mmol, 5.4 µL) and toluene (0.5 mL) were added to the reaction mixture through the septum via a syringe. The tube was sealed with a Teflon screw cap under a flow of nitrogen, and put into an oil bath at 100° C. The resulting reaction was allowed to stir at this temperature for 15 hours. The reaction mixture was cooled to room temperature. The reaction mixture was filtered through a pad of celite and the filtrate was concentrated in vacuo. The residue was reacted with TFA (1.0 mL) for 10 minutes. The TFA solution was concentrated in vacuo. The residue was dissolved in DMSO/acetonitrile (3:1), purified using reverse phase HPLC to provide the title compound. HPLC-MS RT=2.65 minutes, observed LCMS m/z 314.18 (M+H).

Example 64

Preparation of Intermediate Compound 64A

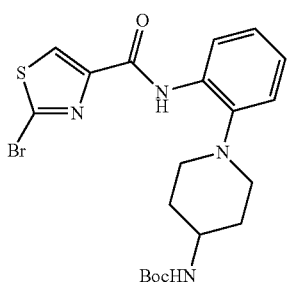

64A

To a premixed solution of 2-bromo-thiazole-4-carboxylic acid (2.0 mmol, 0.42 g), N,N-diisopropylethylamine (3.0 mmol, 0.52 mL) and HATU (2.0 mmol, 0.76 g) in DMF (3 mL) was added [1-(2-amino-phenyl)-piperidin-4-yl]-carbamic acid tert-butyl ester (2.0 mmol, 0.60 g). The reaction mixture was stirred at 80° C. for 3 h, and then concentrated in vacuo. The resulting residue was purified using column chromatography on silica gel (eluent: Hexane:EtOAc (4:1)) to provide Compound 64A as a yellow solid (0.27 g, 28%). HPLC-MS RT=2.30 minutes, mass calculated formula $C_{20}H_{25}BrN_4O_3S$ 480.08, observed LCMS m/z 481.00 (M+H).

Example 65

Preparation of

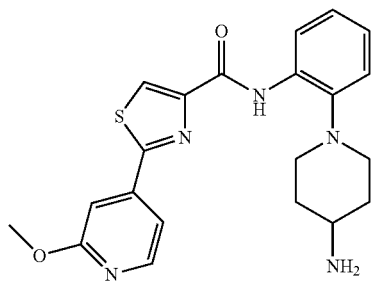 [SMILES: COc1cc(-c2nc(C(=O)Nc3ccccc3N3CCC(N)CC3)cs2)ccn1]

Using the method described in Example 60 and substituting compound 195 for compound 200 (example 102) and 2-fluoropyridine-5-boronic acid pinacol ester for 2-methoxy-4-pyridineboronic acid, compound 201 was prepared. HPLC-MS RT=3.57 minutes, observed LCMS m/z 410.18 (M+H).

Example 66

Preparation of

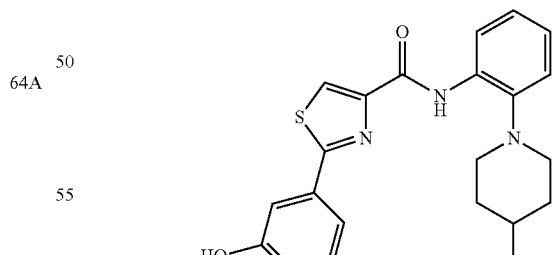

The title compound from Example 65 was reacted with iodotrimethylsilane in chloroform at room temperature for about 15 hours. The reaction mixture was concentrated and purified using reverse phase HPLC to provide the title compound. HPLC-MS RT=3.14 minutes, observed LCMS m/z 396.17 (M+H).

Example 67

Preparation of

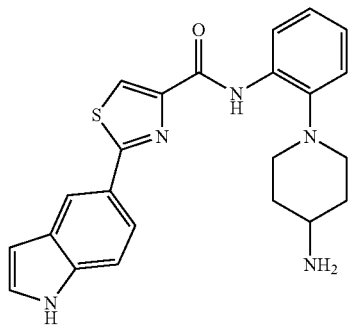 [SMILES: NC1CCN(c2ccccc2NC(=O)c2csc(-c3ccc4[nH]ccc4c3)n2)CC1]

Using the method described in Example 38 and substituting 4-{2-[(2-Bromo-thiazole-4-carbonyl)-amino]-phenyl}-piperazine-1-carboxylic acid tert-butyl ester for compound 200 and 4-(4,4,5,5-Tetramethyl-[1,3,2]dioxaborolan-2-yl)-1H-pyrazole for 7-azaindole-5-boronic acid pinacol ester, the title compound was prepared. HPLC-MS RT=1.99 minutes, observed LCMS m/z 419.17 (M+H).

Example 68

Preparation of

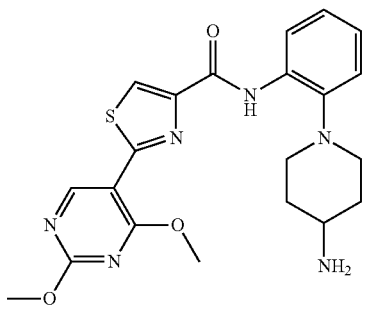 [SMILES: COc1ncc(-c2nc(C(=O)Nc3ccccc3N3CCC(N)CC3)cs2)c(OC)n1]

Using the method described in Example 98 and substituting compound 195 for compound 200 and 2-fluoropyridine-5-boronic acid pinacol ester for 2,4-dimethoxypyrimidine-5-boronic acid, the title compound was prepared. HPLC-MS RT=3.78 minutes, observed LCMS m/z 441.12 (M+H).

Example 69

Preparation of

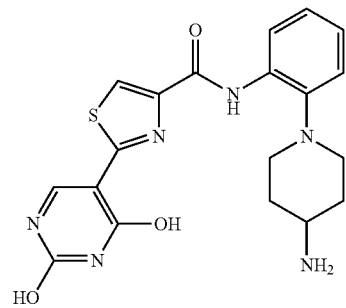 [SMILES: NC1CCN(c2ccccc2NC(=O)c2csc(-c3cnc(O)nc3O)n2)CC1]

[1-(2-{[2-(2,4-Dimethoxy-pyrimidin-5-yl)-thiazole-4-carbonyl]-amino}-phenyl)-piperidin-4-yl]-carbamic acid tert-butyl ester was reacted with iodotrimethylsilane in chloroform (1 mL) at room temperature for about 15 hours. The reaction mixture was concentrated and purified using reverse phase HPLC to provide the title compound. HPLC-MS RT=2.64 minutes, observed LCMS m/z 413.05 (M+H).

Example 70

Preparation of

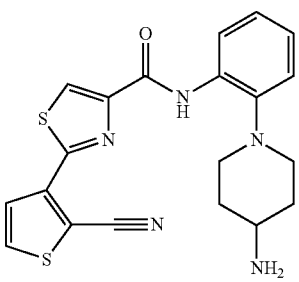 [SMILES: N#Cc1sccc1-c1nc(C(=O)Nc2ccccc2N2CCC(N)CC2)cs1]

Step 1—Synthesis of Intermediate Compound 70A

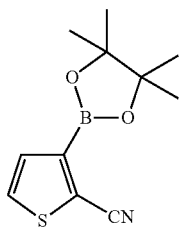

70A $K_3PO_4$ (3.5 mmol, 0.74 g), $Pd_2(dba)_3$ (0.080 mmol, 73 mg), S-Phos (0.20 mmol, 82 mg), bis(pinacolato)diborane (4 mmol, 1 g) and 3-bromo-thiophene-2-carbonitrile (2.0 mmol, 0.38 g) were loaded into a Schlenk tube containing a stir bar. The tube was capped with a rubber septum, evacuated and refilled with nitrogen. Toluene (3 mL) was added to the reaction mixture through the septum via a syringe, and then the tube was sealed with a Teflon screw cap under a flow of nitrogen, and put into an oil bath at 110° C. The resulting reaction was allowed to stir at this temperature for 12 hours, and then the reaction mixture was cooled to room temperature. The reaction mixture was filtered through a pad of celite and the filtrate was concentrated in vacuo. The resulting residue was purified using column chromatography on silica gel with an eluent mixture of Hexane:EtOAc (4:1) to provide intermediate compound 70A as a yellow solid (0.30 g, 64% yield). $^1$H NMR (400 MHz, CDCl$_3$) δ 7.71 (d, J=5.2 Hz, 1H), 7.65 (d, J=5.2 Hz, 1H), 1.26 (s, 12H).

Step 2—Preparation of Title Compound

Using the method described in Example 97 and substituting compound 200 for compound 195 and Intermediate Compound 7 for 2-fluoropyridine-5-boronic acid, the title compound was prepared. HPLC-MS RT=3.49 minutes, observed LCMS m/z 410.11 (M+H).

Example 71

Preparation of

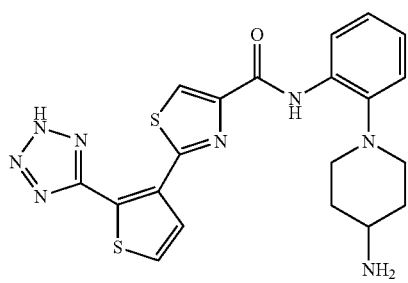 [SMILES: NC1CCN(c2ccccc2NC(=O)c2csc(-c3ccsc3-c3nn[nH]n3)n2)CC1]

[1-(2-{[2-(2-Cyano-thiophen-3-yl)-thiazole-4-carbonyl]-amino}-phenyl)-piperidin-4-yl]-carbamic acid tert-butyl ester was stirred with a mixture of sodium azide (0.10 mmol, 6.5 mg) and triethylamine hydrochloride (0.10 mmol, 14 mg) in toluene (1 mL) at room temperature for about 15 hours. The reaction mixture was filtered through a pad of celite and the filtrate was concentrated in vacuo. The residue was reacted with TFA (1.0 mL) for 10 minutes. The TFA solution was concentrated in vacuo. The residue was dissolved in DMSO/acetonitrile (3:1), purified using reverse phase HPLC to provide the title compound. HPLC-MS RT=3.01 minutes, observed LCMS m/z 453.18 (M+H).

Example 72

Preparation of

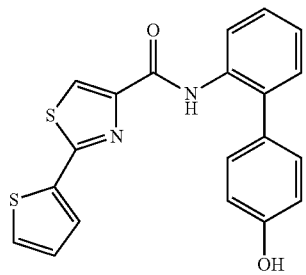 [SMILES: O=C(Nc1ccccc1-c1ccc(O)cc1)c1csc(-c2cccs2)n1]

Using the method described in Example 93 and replacing 4-aminomethylphenylboronic acid hydrochloride with 4-hydroxyphenylboronic acid pinacol ester, the title compound was prepared. HPLC-MS RT=5.12 minutes, observed LCMS m/z 379.05 (M+H).

Example 73

Preparation of

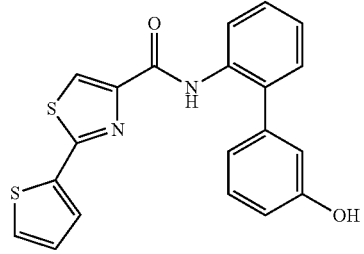 [SMILES: O=C(Nc1ccccc1-c1cccc(O)c1)c1csc(-c2cccs2)n1]

Using the method described in Example 93 and replacing 4-aminomethylphenylboronic acid hydrochloride with 3-hydroxyphenylboronic acid pinacol ester, the title compound was prepared. HPLC-MS RT=4.62 minutes, observed LCMS m/z 379.11 (M+H).

Example 74

Preparation of

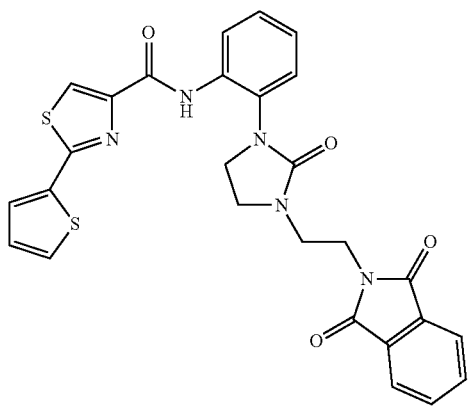 [SMILES: O=C(Nc1ccccc1N1CCN(CCN2C(=O)c3ccccc3C2=O)C1=O)c1csc(-c2cccs2)n1]

Step 1—Synthesis of Intermediate Compound 74A

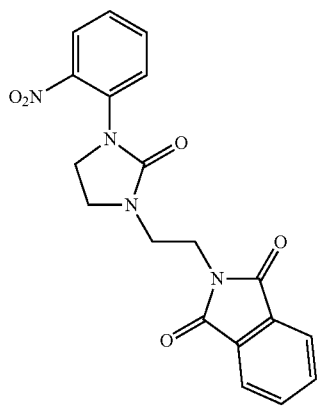

74A

A reaction mixture of 1-(2-nitro-phenyl)-imidazolidin-2-one (1.0 mmol, 0.21 g), sodium hydride (60% in mineral oil, 1.5 mmol, 60 mg) and N-(2-bromoethyl)phthalimide (1.5 mmol, 0.38 g) in DMA (2 mL) was stirred at a temperature of 60° C. for about 15 hours. The solution was then cooled to room temperature and concentrated in vacuo. The resulting residue was purified using column chromatography on silica gel with an eluent mixture of DCM/MeOH (1.5% MeOH) to provide Intermediate Compound 74A.

Step 2—Synthesis of Intermediate Compound 74B

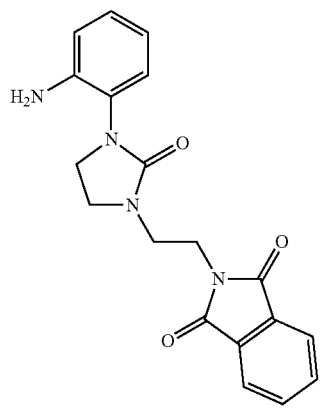

74B

To the solution of Intermediate Compound 74A in MeOH (15 mL) was added Pd on carbon (5% Pd, 55 mg). The resulting reaction mixture was stirred under a hydrogen atmosphere at room temperature for about 15 hours. The reaction mixture was filtered through a pad of celite and the filtrate was concentrated in vacuo to provide Intermediate Compound 74B.

Step 3—Preparation of Title Compound

Using the method described in Example 77 and replacing 2-imidazol-1-yl-phenylamine with Intermediate Compound 74B, the title compound was prepared. HPLC-MS RT=4.05 minutes, observed LCMS m/z 544.16 (M+H).

Example 78

Preparation of

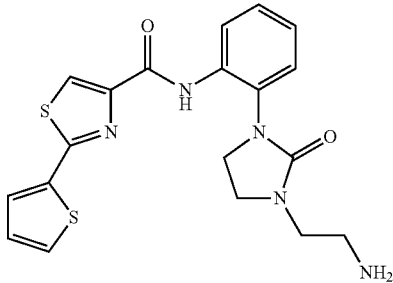 [SMILES: NCCN1CCN(c2ccccc2NC(=O)c2csc(-c3cccs3)n2)C1=O]

A mixture of the title compound from Example 77 and hydrazine monohydrate in DCM was stirred at room temperature for about 15 hours. The reaction mixture was concentrated in vacuo. The residue was dissolved in DMSO/aceto- nitrile (3:1), purified using reverse phase HPLC to provide the title compound. HPLC-MS RT=2.81 minutes, observed LCMS m/z 414.23 (M+H).

Example 79

Preparation of Compound 79A

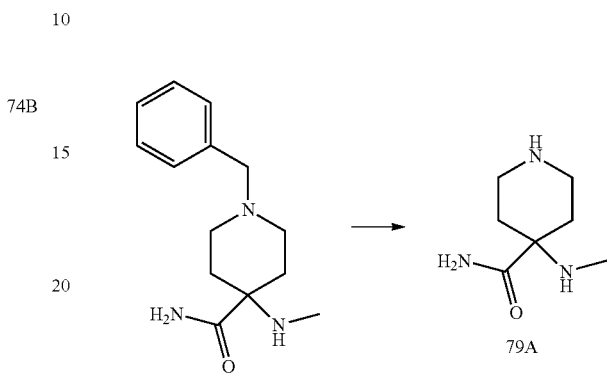

1-Benzyl-4-methylamino-4-piperidine carboxamide (3.03 mmol, 750 mg) was charged to a 100 mL roundbottom flask. To this was added 40 mL methanol followed by 300 mg 10% palladium on carbon. The flask was sealed with a septum and degassed under vacuum for 10 minutes. Hydrogen gas was added via balloon and the reaction was allowed to stir at room temperature for 18 hours. The mixture was filtered through celite with the assistance of dichloromethane. The solution was concentrated in vacuo to provide compound 79A, which was used without further purification.

Example 80

Preparation of Compound 80A

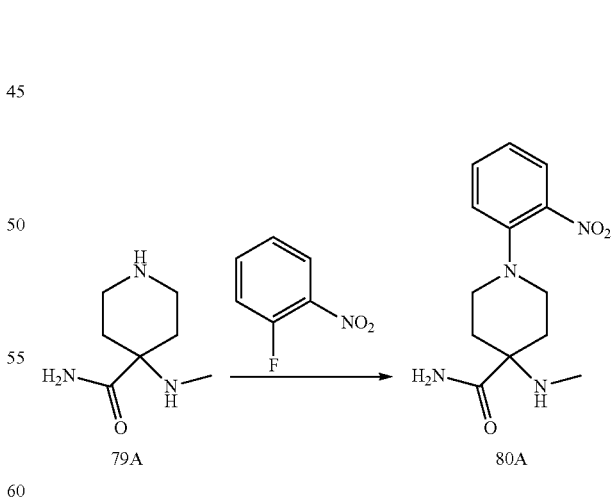

To a solution of compound 79A (8.65 mmol. 1.36 g) and DIEA (9.52 mmol, 1.66 mL) in acetonitrile (8 mL) and methanol (1 mL) was added 2-fluoronitrobenzene (9.52 mmol, 1.00 mL). The resulting reaction was heated to 180° C. in a Biotage Initiator microwave synthesizer and allowed to stir at this temperature for 30 minutes. The reaction mixture

Example 81

Preparation of Compound 81A

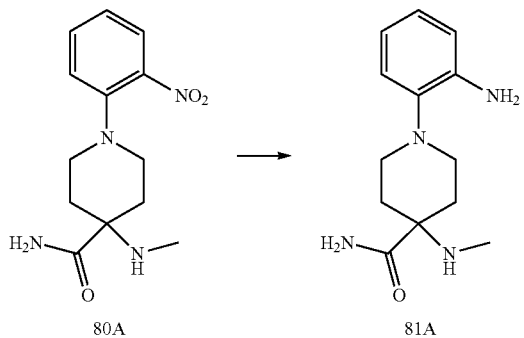 [SMILES: CNC1(C(N)=O)CCN(c2ccccc2[N+](=O)[O-])CC1 ; CNC1(C(N)=O)CCN(c2ccccc2N)CC1]

To a solution of compound 80A (7.19 mmol, 2.00 g) in methanol (50 mL) was added 10% palladium on carbon (800 mg). The flask was sealed with a septum and degassed under vacuum for 10 minutes. Hydrogen gas was added via balloon and the reaction was allowed to stir at room temperature for 18 hours. The mixture was filtered through celite with the assistance of dichloromethane. The solution was concentrated in vacuo. The desired product, 81A was used without further purification. $^1$H NMR (400 MHz, DMSO) δ 7.28-7.22 (s, 1H), 6.98-6.92 (s, 1H), 6.88-6.83 (d, J=7.6 Hz, 1H), 6.77-6.71 (t, J=7.4 Hz, 1H), 6.64-6.59 (d, J=7.6 Hz, 1H), 6.52-6.46 (t, J=7.4 Hz, 1H), 4.64 (s, 2H), 2.86-2.77 (t, J=10.0 Hz, 2H), 2.74-2.66 (m, 2H), 2.12-2.08 (d, J=5.0 Hz, 3H), 2.07-2.02 (t, J=5.4 Hz, 1H), 2.01-1.92 (m, 2H), 1.64-1.56 (d, J=13.0 Hz, 2H).

Example 82

Preparation of Compound 82A

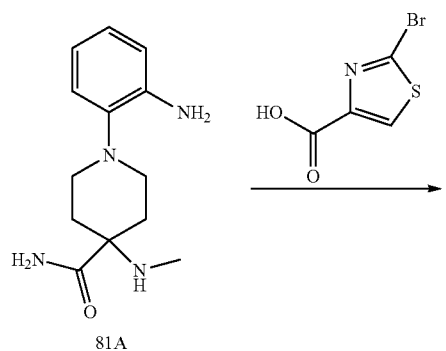

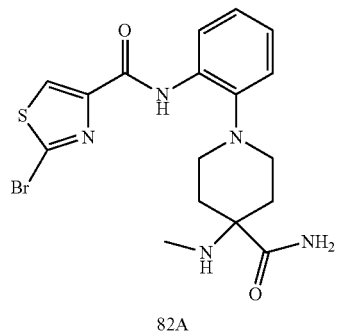

A solution of 2-bromothiazole-4-carboxylic acid (2.40 mmol, 500 mg), compound 81A (2.52 mmol, 627 mg) and HATU (2.52 mmol, 959 mg) in DMF (20 mL) was allowed to stir at room temperature for 18 hours. The mixture was concentrated in vacuo and purified via silica gel chromatography. Compound 82A was then recrystallized out of MeOH and Et$_2$O and filtered to afford an off-white solid. $^1$H NMR (400 MHz, DMSO) δ 10.03-10.00 (s, 1H), 8.48 (s, 1H), 8.34-8.30 (dd, J=7.8, 1.6 Hz, 1H), 7.27-7.22 (dd, J=7.4, 1.6 Hz, 1H), 7.20-7.11 (m, 2H), 3.13-3.04 (m, 2H), 2.90-2.82 (m, 2H), 2.54-2.45 (m, 5H), 2.15-2.06 (m, 2H).

Example 83

Preparation of

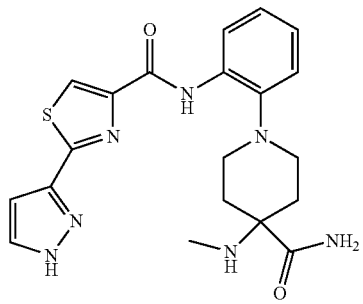 [SMILES: CNC1(C(N)=O)CCN(c2ccccc2NC(=O)c2csc(-c3cc[nH]n3)n2)CC1]

To a 20 mL scintillation vial was charged compound 82A (0.034 mmol, 15 mg), 1H-pyrazole-5-boronic acid (0.051 mmol, 5.8 mg), K$_3$PO$_4$ (0.068 mmol, 14.5 mg), palladium tetrakis (0.0034 mmol, 4 mg), and 3:1 1,4-dioxane:H$_2$O (1 mL). The vial was flushed with argon and sealed with Teflon tape. The reaction was allowed to shake at 100° C. for 18 hours. The mixture was concentrated in vacuo and the residue purified via reverse-phase HPLC in 3:1 DMSO:acetonitrile to provide the title compound. LC/MS (10 minutes TFA, retention time=2.48 minutes, visible mass was (M+H)=426.23).

Example 84

Preparation of Compound 217

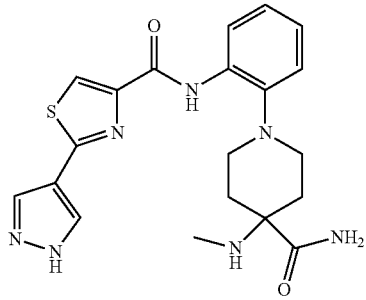 [SMILES: CNC1(C(N)=O)CCN(c2ccccc2NC(=O)c2csc(-c3cn[nH]c3)n2)CC1]

Using the method described in Example 83 and substituting 1H-pyrazole-4-boronic acid for 1H-pyrazole-5-boronic acid, the title compound was prepared. The final product was observed via LC/MS (10 minutes TFA, retention time=2.44 minutes, visible mass was (M+H)=426.25).

Example 85

Preparation of

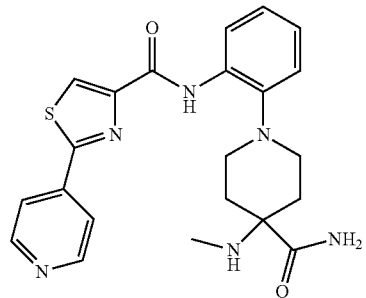 [SMILES: CNC1(C(N)=O)CCN(c2ccccc2NC(=O)c2csc(-c3ccncc3)n2)CC1]

Using the method described in Example 83 and substituting pyridine-4-boronic acid for 1H-pyrazole-5-boronic acid, the title compound was prepared. The final product was observed via LC/MS (10 minutes TFA, retention time=2.15 minutes, visible mass was (M+H)=437.22).

Example 86

Preparation of

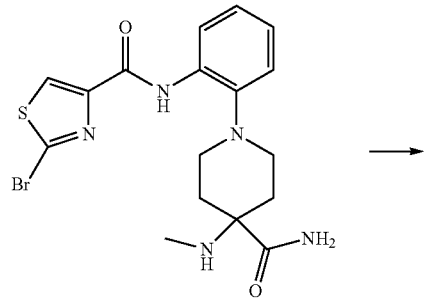

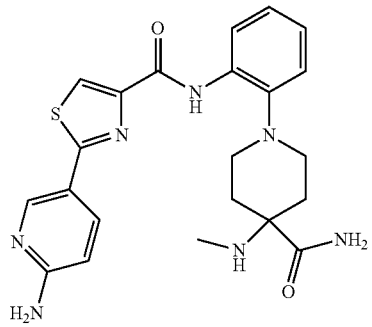

To a 20 mL scintillation vial was charged 1-{2-[(2-Bromo-thiazole-4-carbonyl)-amino]-phenyl}-4-methylamino-piperidine-4-carboxylic acid amide (0.034 mmol, 15 mg), [5-(4,4,5,5-Tetramethyl-[1,3,2]dioxaborolan-2-yl)-pyridin-2-yl]-carbamic acid tert-butyl ester (0.051 mmol, 16.4 mg), $K_3PO_4$ (0.068 mmol, 14.5 mg), palladium tetrakis (0.0034 mmol, 4 mg), and 3:1 1,4-dioxane:$H_2O$ (1 mL). The vial was flushed with argon and sealed with Teflon tape. The reaction was allowed to shake at 100° C. for 18 hours. The reaction mixture was then concentrated in vacuo and taken up in 1 mL 4N HCl in 1,4-dioxane plus 25 μL $H_2O$ and stirred at room temperature for 1 hour. The mixture was concentrated in vacuo, taken up in 3:1 DMSO:acetonitrile, and the title compound was purified via reverse-phase HPLC. The final product was observed via LC/MS (10 minutes TFA, retention time=2.04 minutes, visible mass was (M+H)=452.23).

Example 87

Preparation of

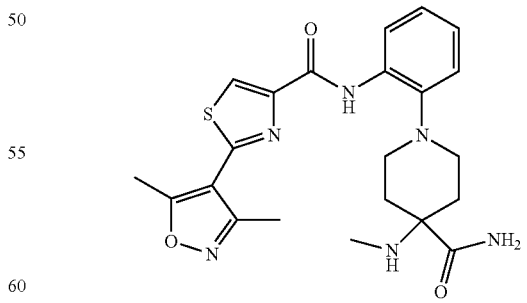

Using the method described in Example 86 and substituting 3,5-Dimethyl-isoxazole-4-boronic acid for 1H-pyrazole-5-boronic acid, the title compound was prepared. The final product was observed via LC/MS (10 minutes TFA, retention time=2.86 minutes, visible mass was=455.23).

Example 88

Preparation of

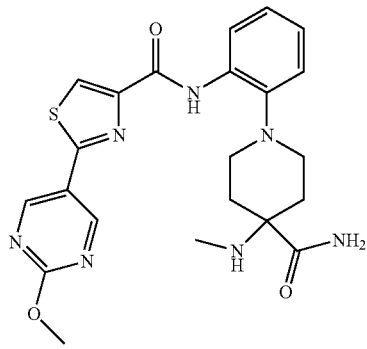 [SMILES: CNC1(C(N)=O)CCN(c2ccccc2NC(=O)c2csc(-c3cnc(OC)nc3)n2)CC1]

Using the method described in Example 86 and 2-methoxypyridine-5-boronic acid substituted for 1H-pyrazole-5-boronic acid, the title compound was prepared. The final product was observed via LC/MS (10 minutes TFA, retention time=2.77 minutes, visible mass was (M+H)=468.21).

Example 89

Preparation of

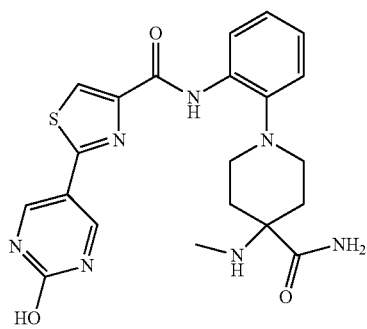 [SMILES: CNC1(C(N)=O)CCN(c2ccccc2NC(=O)c2csc(-c3cnc(O)nc3)n2)CC1]

To the title compound of Example 88 (0.034 mmol, 16 mg) was added 2 mL 2:1 THF:H$_2$O, followed by 1 N LiOH$_{(aq)}$ (0.068 mmol, 68 µL). This solution was heated to 180° C. for 20 minutes in Biotage Initiator microwave synthesizer. The mixture was concentrated in vacuo, taken up in 3:1 DMSO:acetonitrile, and the title compound purified via reversephase HPLC. The final product was observed via LC/MS (10 minutes TFA, retention time=2.15 minutes, visible mass was (M+H)=454.20).

Example 90

Preparation of

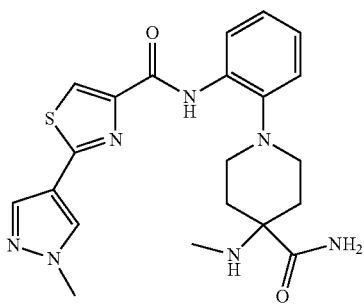 [SMILES: CNC1(C(N)=O)CCN(c2ccccc2NC(=O)c2csc(-c3cnn(C)c3)n2)CC1]

Using the method described in Example 86 and substituting 1-methylpyrazole-4-boronic acid pinacol ester for 1H-pyrazole-5-boronic acid, the title compound was prepared. The final product was observed via LC/MS (10 minutes TFA, retention time=2.65 minutes, visible mass was (M+H)=440.21).

Example 91

Preparation of

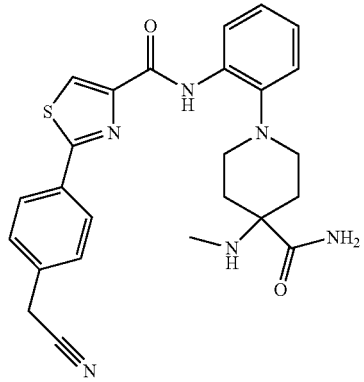 [SMILES: CNC1(C(N)=O)CCN(c2ccccc2NC(=O)c2csc(-c3ccc(CC#N)cc3)n2)CC1]

Using the method described in Example 86 and 4-(cyanomethyl)benzene boronic acid pinacol ester substituted for 1H-pyrazole-5-boronic acid, Compound 224 was prepared. The final product was observed via LC/MS (10 minutes TFA, retention time=3.09 minutes, visible mass was (M+H)=475.23).

Example 92

Preparation of

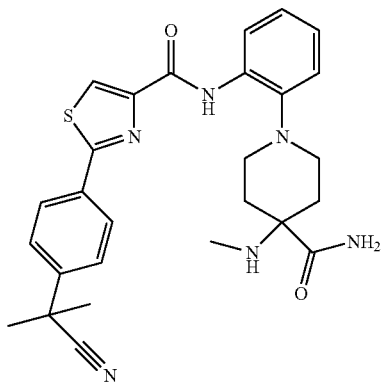 [SMILES: CNC1(C(N)=O)CCN(c2ccccc2NC(=O)c2csc(-c3ccc(C(C)(C)C#N)cc3)n2)CC1]

Using the method described in Example 86 and substituting 4-(2-cyanopropan-2-yl)phenyl boronic acid for 1H-pyrazole-5-boronic acid, the title compound was prepared. The final product was observed via LC/MS (10 minutes TFA, retention time=3.46 minutes, visible mass was (M+H)=503.30).

Example 93

Preparation of

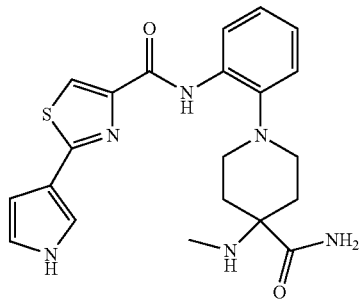 [SMILES: CNC1(C(N)=O)CCN(c2ccccc2NC(=O)c2csc(-c3cc[nH]c3)n2)CC1]

Using the method described in Example 86 and substituting 1-(tri-isopropylsilyl)-1H-pyrrole-3-boronic acid for 1H-pyrazole-5-boronic acid, the title compound was prepared. The final product was observed via LC/MS (10 minutes TFA, retention time=2.70 minutes, visible mass was (M+H)=425.26).

Example 94

Preparation of

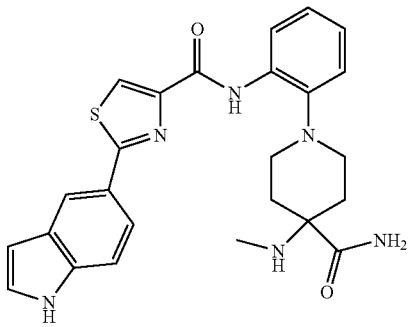 [SMILES: CNC1(C(N)=O)CCN(c2ccccc2NC(=O)c2csc(-c3ccc4[nH]ccc4c3)n2)CC1]

Using the method described in Example 86 and substituting 1H-Indole-5-boronic acid pinacol ester for 1H-pyrazole-5-boronic acid, the title compound was prepared. The final product was observed via LC/MS (10 minutes TFA, retention time=3.25 minutes, visible mass was (M+H)=475.22).

Example 95

Preparation of

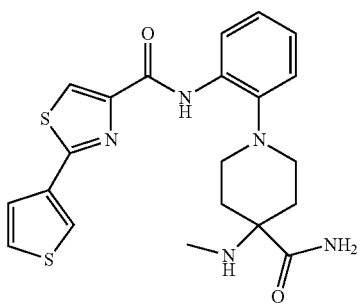 [SMILES: CNC1(C(N)=O)CCN(c2ccccc2NC(=O)c2csc(-c3ccsc3)n2)CC1]

Using the method described in Example 86 and substituting thiophene-3-boronic acid for 1H-pyrazole-5-boronic acid, the title compound was prepared. The final product was observed via LC/MS (10 minutes TFA, retention time=2.94 minutes, visible mass was (M+H)=442.18).

Example 96

Preparation of

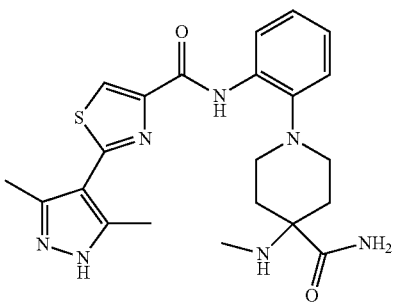 [SMILES: CNC1(C(N)=O)CCN(c2ccccc2NC(=O)c2csc(-c3c(C)n[nH]c3C)n2)CC1]

Using the method described in Example 86 and substituting 3,5-dimethylpyrazole-4-boronic acid pinacol ester for 1H-pyrazole-5-boronic acid, the title compound was prepared. The final product was observed via LC/MS (10 minutes TFA, retention time=2.77 minutes, visible mass was (M+H)=454.23).

Example 97

Preparation of

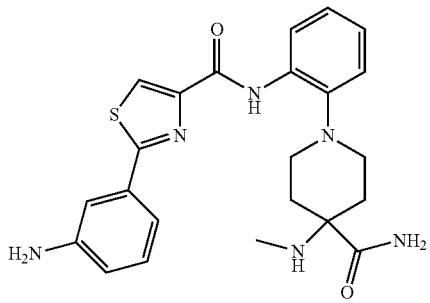 [SMILES: CNC1(C(N)=O)CCN(c2ccccc2NC(=O)c2csc(-c3cccc(N)c3)n2)CC1]

Using the method described in Example 86 and substituting 3-aminophenylboronic acid monohydrate for 1H-pyrazole-5-boronic acid, the title compound was prepared. The final product was observed via LC/MS (10 minutes TFA, retention time=2.51 minutes, visible mass was (M+H)=451.23).

Example 98

Preparation of

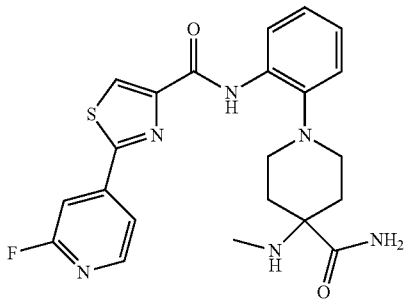 [SMILES: CNC1(C(N)=O)CCN(c2ccccc2NC(=O)c2csc(-c3ccnc(F)c3)n2)CC1]

Using the method described in Example 86 and substituting 2-fluoropyridine-4-boronic acid for 1H-pyrazole-5-boronic acid, the title compound was prepared. The final product was observed via LC/MS (10 minutes TFA, retention time=2.84 minutes, visible mass was (M+H)=455.23).

Example 99

Preparation of

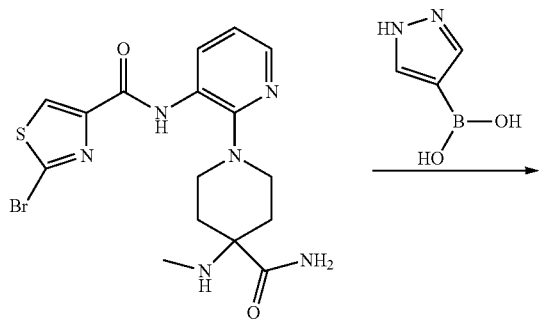

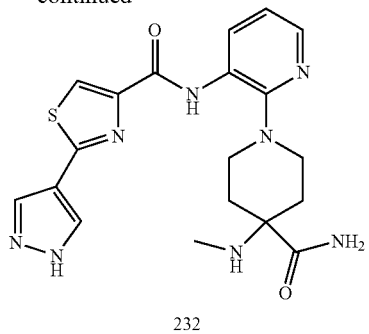

232

To a 20 mL scintillation vial was charged 3'-[(2-bromo-thiazole-4-carbonyl)-amino]-4-methylamino-3,4,5,6-tetrahydro-2H-[1,2']bipyridinyl-4-carboxylic acid amide (0.034 mmol, 15 mg), 1H-pyrazole-4-boronic acid (0.051 mmol, 5.8 mg), $K_3PO_4$ (0.068 mmol, 14.5 mg), palladium tetrakis (0.0034 mmol, 4 mg), and 3:1 1,4-dioxane:$H_2O$ (1 mL). The vial was flushed with argon and sealed with Teflon tape. The reaction was allowed to shake at 100° C. for 18 hours. The mixture was concentrated in vacuo and compound 232 was purified via reverse-phase HPLC in 3:1 DMSO:acetonitrile. The final product was observed via LC/MS (10 minutes TFA, retention time=2.06 minutes, visible mass was (M+H)=427.17).

Example 100

Preparation of

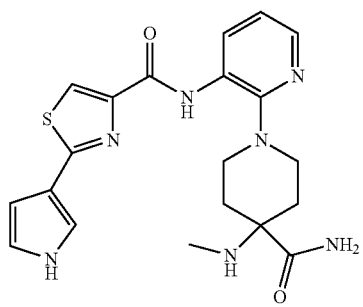 [SMILES: CNC1(C(N)=O)CCN(c2ncccc2NC(=O)c2csc(-c3cc[nH]c3)n2)CC1]

Using the method described in Example 99 and substituting 1-(tri-isopropylsilyl)-1H-pyrrole-3-boronic acid for 1H-pyrazole-4-boronic acid, the title compound was prepared. The final product was observed via LC/MS (10 minutes TFA, retention time=2.36 minutes, visible mass was (M+H)=426.25).

Example 101

Preparation of

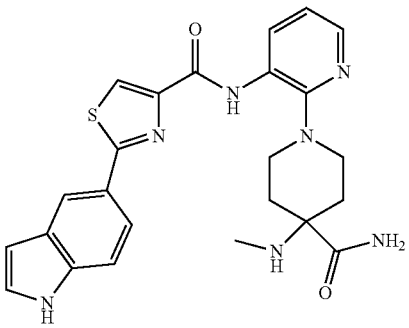 [SMILES: CNC1(C(N)=O)CCN(c2ncccc2NC(=O)c2csc(-c3ccc4[nH]ccc4c3)n2)CC1]

Using the method described in Example 99 and substituting 1H-Indole-5-boronic acid pinacol ester for 1H-pyrazole-4-boronic acid, the title compound was prepared. The final product was observed via LC/MS (10 minutes TFA, retention time=2.99 minutes, visible mass was (M+H)=476.21).

Example 102

Preparation of

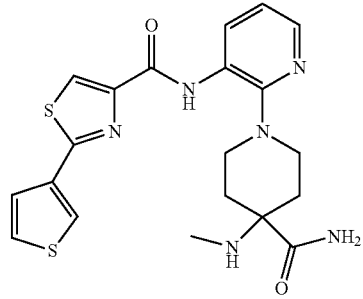 [SMILES: CNC1(C(N)=O)CCN(c2ncccc2NC(=O)c2csc(-c3ccsc3)n2)CC1]

Using the method described in Example 99 and substituting thiophene-3-boronic acid for 1H-pyrazole-4-boronic acid, the title compound was prepared. The final product was observed via LC/MS (10 minutes TFA, retention time=2.65 minutes, visible mass was (M+H)=443.17).

Example 103

Preparation of

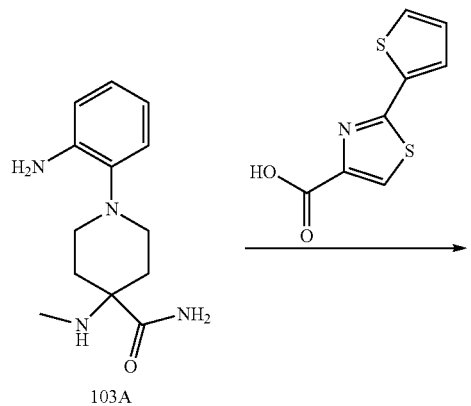

103A

A solution of 1-(2-amino-phenyl)-4-methylamino-piperidine-4-carboxylic acid amide (0.156 mmol, 38.8 mg), 2-thiophen-2-yl-thiazole-4-carboxylic acid (0.142 mmol, 30 mg), and HATU (0.156 mmol, 59.3 mg) in 3 mL DMF was allowed to stir at room temperature for 18 hours. The reaction mixture was then concentrated in vacuo, taken up in 3:1 DMSO:acetonitrile, and the title compound was purified via reverse-phase HPLC. The final product was observed via LC/MS (10 minutes TFA, retention time=3.30 minutes, visible mass was (M+H)=442.12).

Example 104

Preparation of

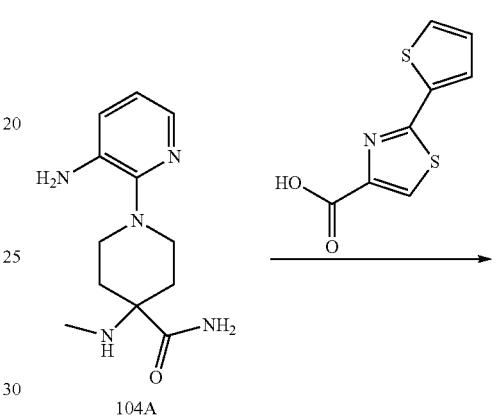

104A

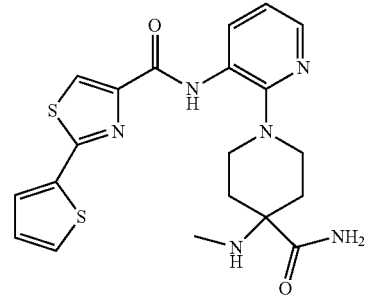

Using the method described in Example 103 and substituting compound 104A for 103A, the title compound was prepared. The final product was observed via LC/MS (10 minutes TFA, retention time=2.74 minutes, visible mass was (M+H)=443.17).

Example 105

Preparation of Compound 105A

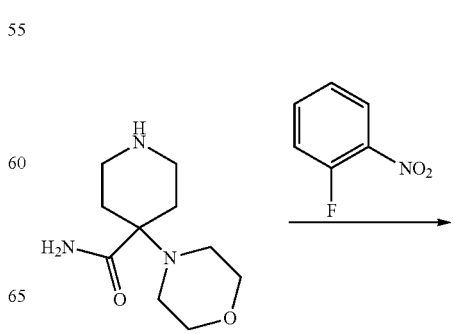

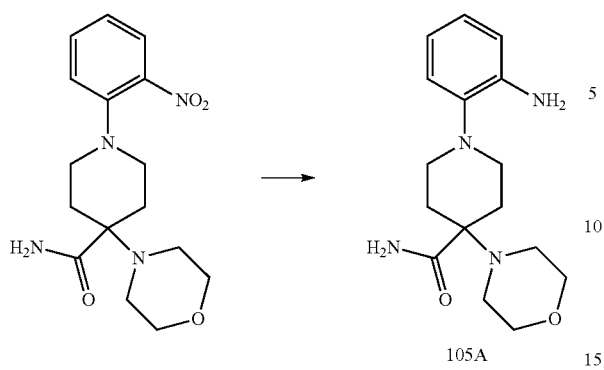

105A

Using the methods described in Examples 80 and 81 and utilizing the indicated reactants, compound 105A was prepared. $^1$H NMR (400 MHz, CDCl$_3$) δ 7.05-7.01 (dd, J=1.6, 8.2 Hz, 1H), 6.94-6.89 (td, J=1.6, 7.6 Hz, 1H), 6.75-6.70 (m, 2H), 4.0-3.9 (br s, 2H), 3.75-3.70 (t, J=4.6 Hz, 4H), 3.10-2.95 (m, 4H), 2.67-2.63 (t, J=4.6 Hz, 4H), 2.02-1.95 (m, 4H).

Example 106

Preparation of

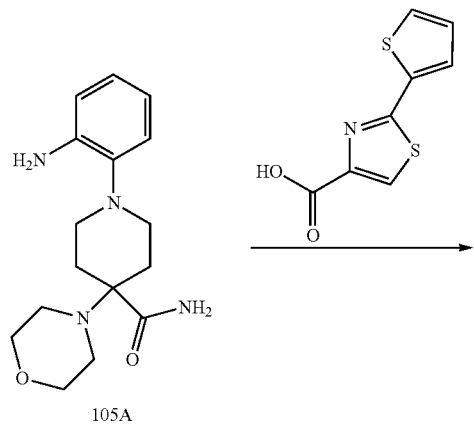

105A

Using the method described in Example 103 and substituting compound 105A for compound 103A, the title compound was prepared. The final product was observed via LC/MS (10 minutes TFA, retention time=3.60 minutes, visible mass was (M+H)=498.29).

Example 107

Preparation of Compound 107A

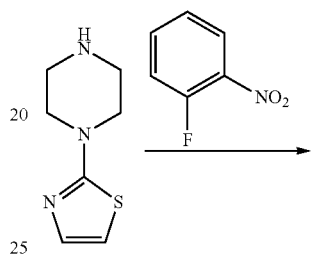

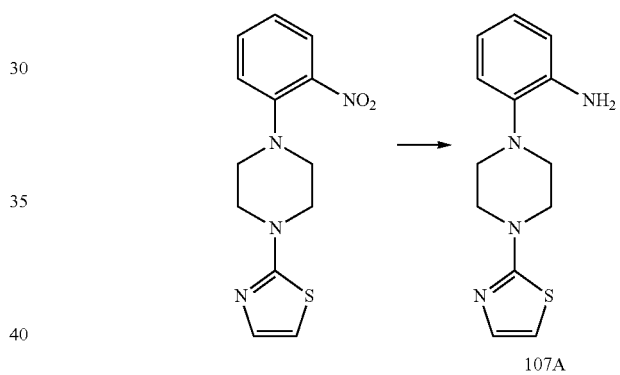

107A

Using the methods described in Examples 80 and 81 and utilizing the indicated reactants, compound 107A was prepared.

Example 108

Preparation of Compound 108A

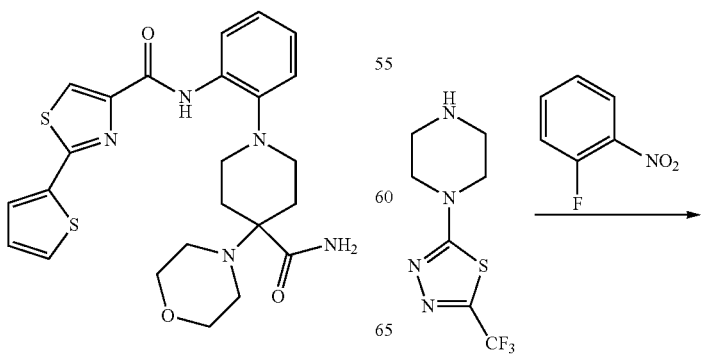

261
-continued

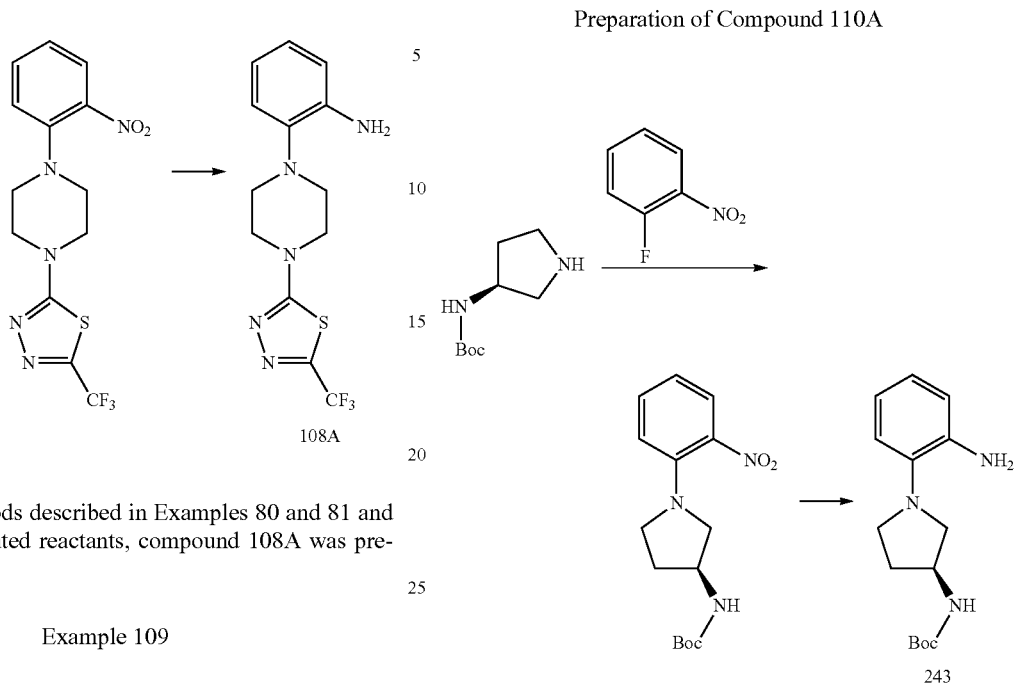

108A

Using the methods described in Examples 80 and 81 and utilizing the indicated reactants, compound 108A was prepared.

Example 109

Preparation of Compound 109A

109A

Using the methods described in Examples 80 and 81 and utilizing the indicated reactants, compound 109A was prepared.

262

Example 110

Preparation of Compound 110A

243

Using the methods described in Examples 80 and 81 and utilizing the indicated reactants, compound 110A was prepared.

Example 111

Preparation of Compound 111A

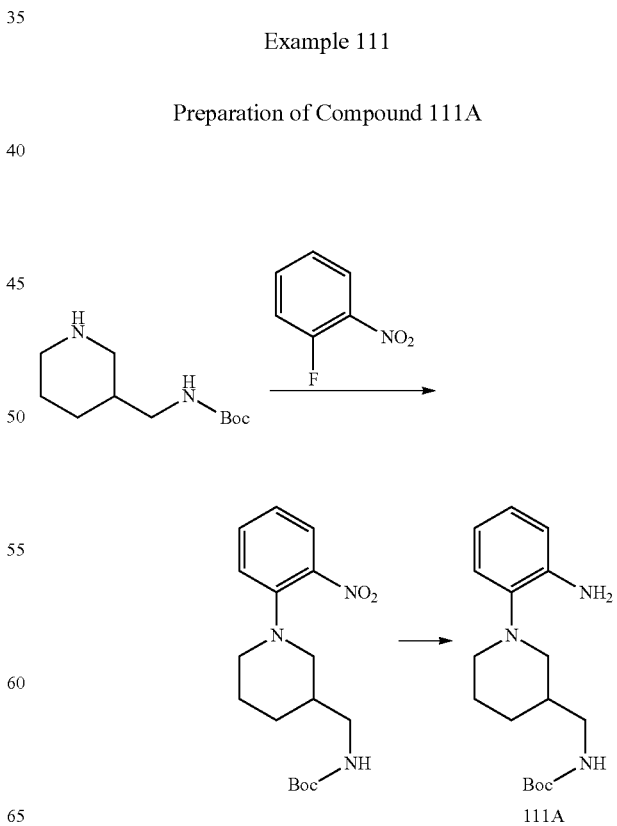

111A

Using the methods described in Examples 80 and 81 and utilizing the indicated reactants, compound 111A was prepared.

Example 112

Preparation of Compound 112A

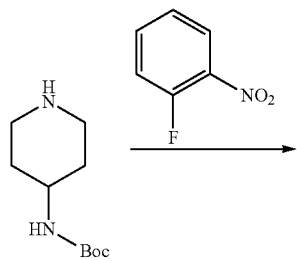

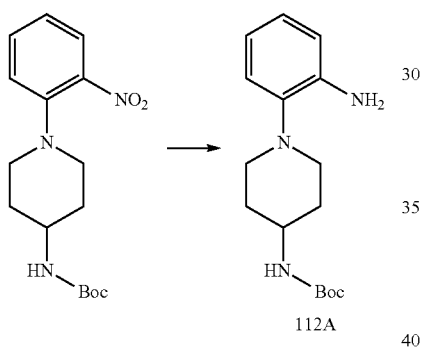

112A

Using the methods described in Examples 80 and 81 and utilizing the indicated reactants, compound 112A was prepared.

Example 113

Preparation of Compound 113A

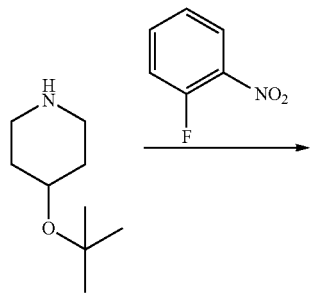

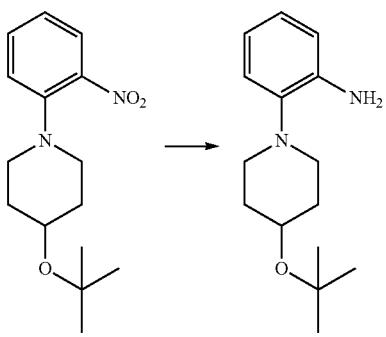

113A

Using the methods described in Examples 80 and 81 and utilizing the indicated reactants, compound 113A was prepared.

Example 114

Preparation of Compound 114A

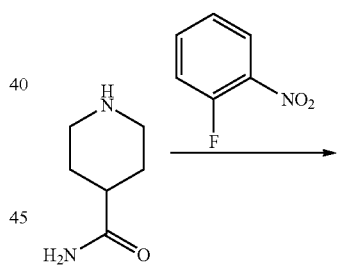

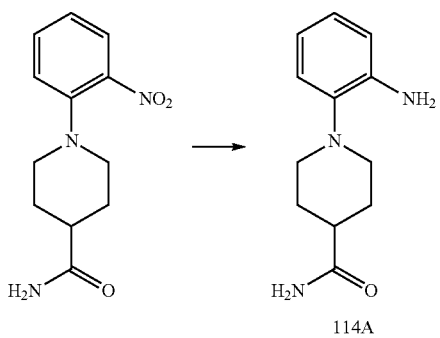

114A

Using the methods described in Examples 80 and 81 and utilizing the indicated reactants, compound 114A was prepared.

Example 115

Preparation of Compound 115A

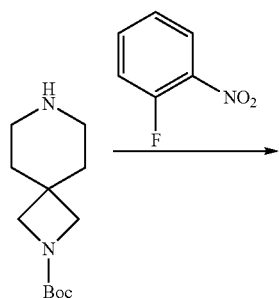

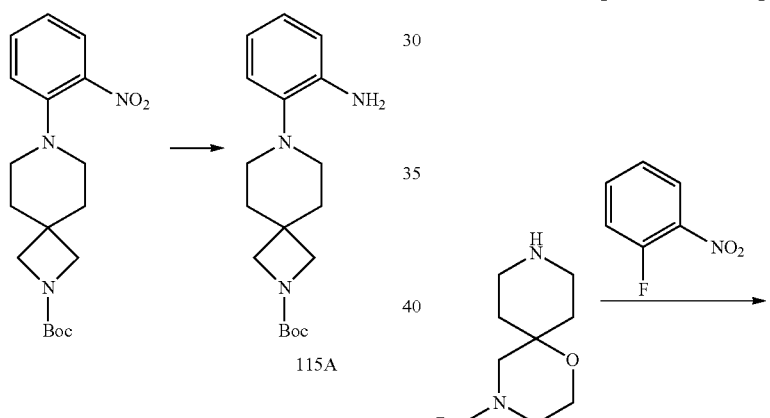

Using the methods described in Examples 80 and 81 and utilizing the indicated reactants, compound 115A was prepared.

Example 116

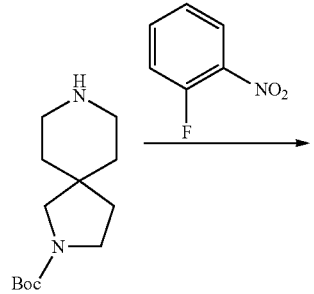

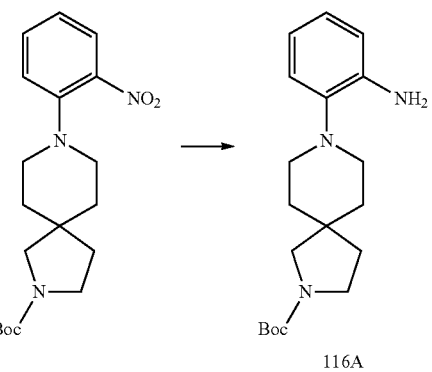

Using the methods described in Examples 80 and 81 and utilizing the indicated reactants, compound 116A was prepared.

Example 117

Preparation of Compound 117A

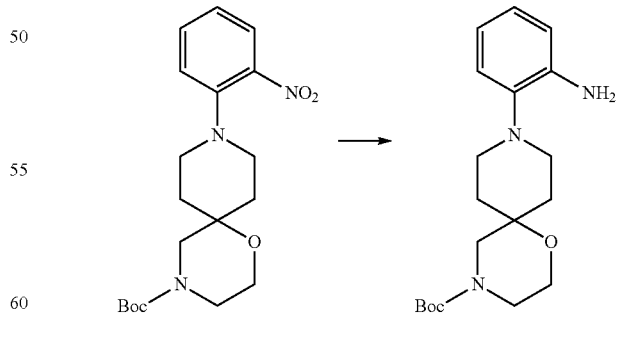

Using the methods described in Examples 80 and 81 and utilizing the indicated reactants, compound 117A was prepared.

Example 118

Preparation of Compound 118A

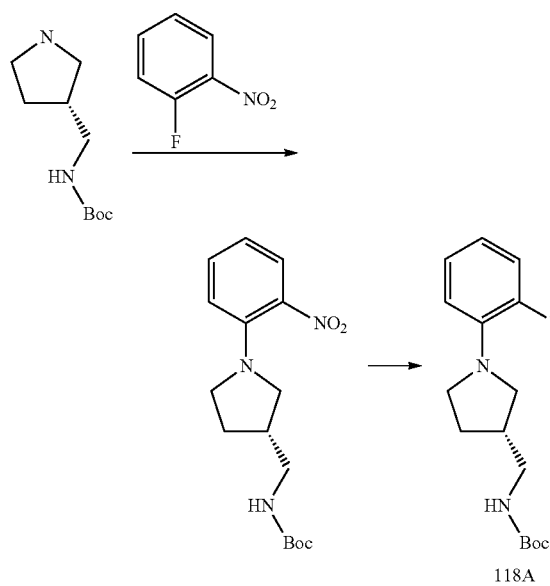

Using the methods described in Examples 80 and 81 and utilizing the indicated reactants, compound 118A was prepared.

Example 119

Preparation of Compound 119A

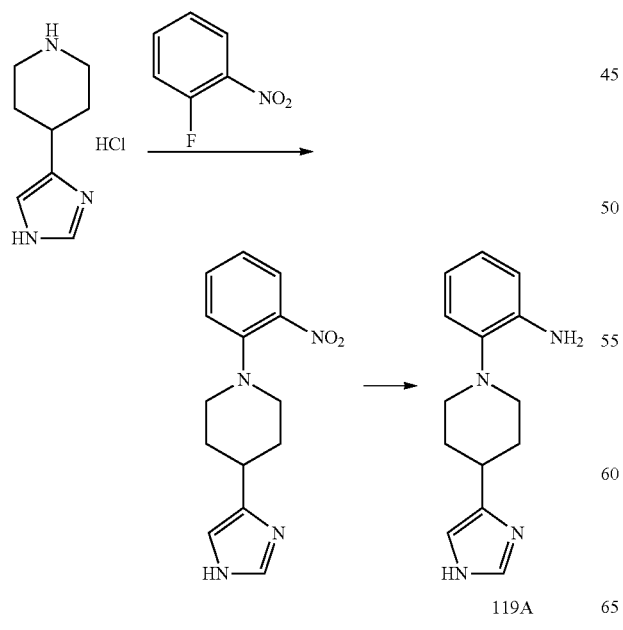

Using the methods described in Examples 80 and 81, utilizing the indicated reactants and an additional 1.1 equivalents DIEA, compound 116A was prepared.

Example 120

Preparation of Compound 120C

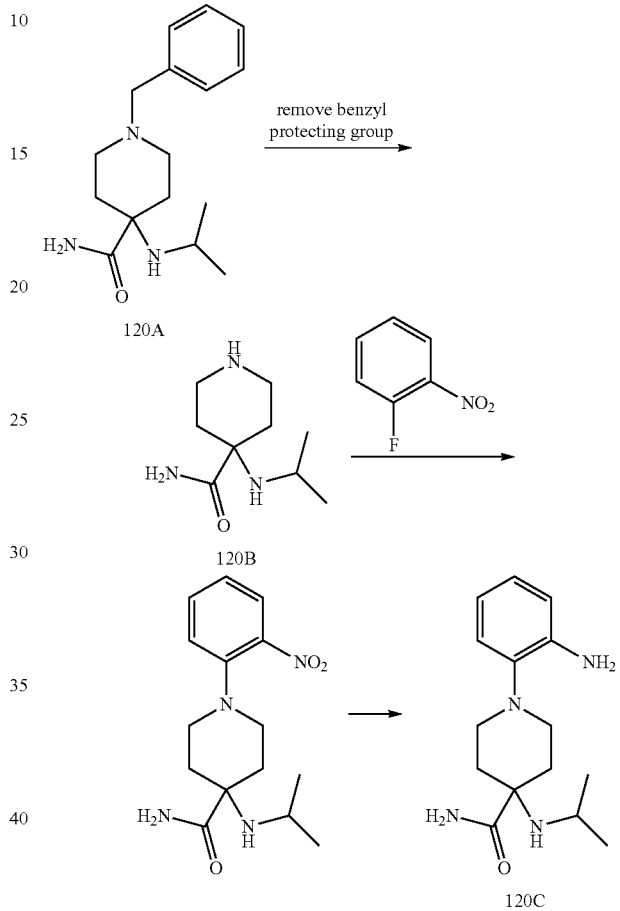

Compound 120A was deprotected using catalytic hydrogenation to provide compound 120B. Then, using the methods described in Examples 80 and 81 and utilizing the indicated reactants, compound 120B was converted to compound 120C.

Example 121

Preparation of Compound 121A

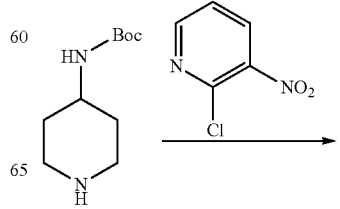

-continued

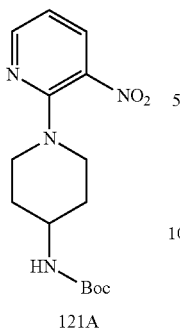

121A

To a solution of 4-N-Boc-aminopiperidine (10 mmol. 2.00 g) and DIEA (11 mmol, 1.92 mL) in acetonitrile (10 mL) was added 2-chloro-3-nitropyridine (10 mmol, 1.58 g). The resulting reaction was heated to 150° C. in a Biotage Initiator microwave synthesizer and allowed to stir at this temperature for 15 minutes. The reaction mixture was cooled to room temperature, and then purified via silica gel chromatography to provide Compound 121A.

Example 122

Preparation of Compound 122A

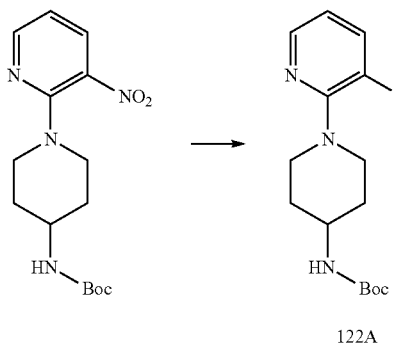

122A

Using the method described in Example 3 and (3'-nitro-3,4,5,6-tetrahydro-2H-[1,2']bipyridinyl-4-yl)-carbamic acid tert-butyl substituted for 4-Methylamino-1-(2-nitro-phenyl)-piperidine-4-carboxylic acid amide, Compound 122A was prepared.

Example 123

Preparation of Compound 123A

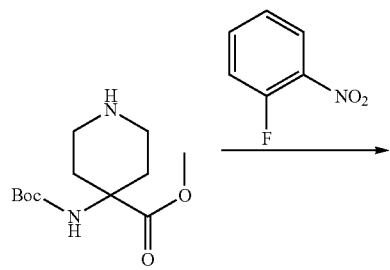

-continued

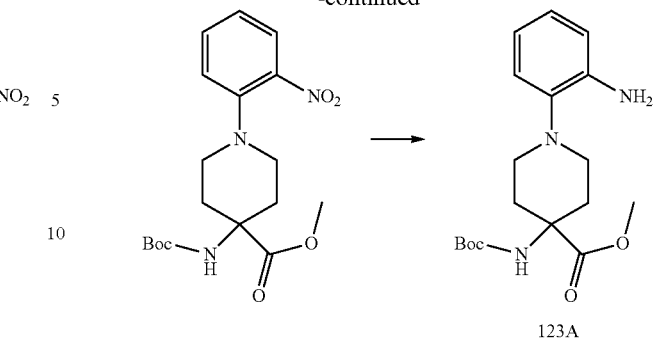

123A

Using the methods described in Example 103 and utilizing the indicated reactants, compound 123A was prepared.

Example 124

Preparation of Compound 124A

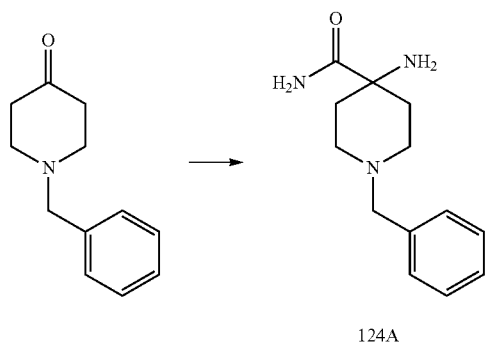 [SMILES: O=C1CCN(Cc2ccccc2)CC1 ; NC(=O)C1(N)CCN(Cc2ccccc2)CC1]

124A

Using the methods described by Metwally, Kamel A, et al., *J. Med. Chem.* 1998, vol 41(25), 5084-5093, Compound 124A was prepared.

Example 125

Preparation of Compound 125A

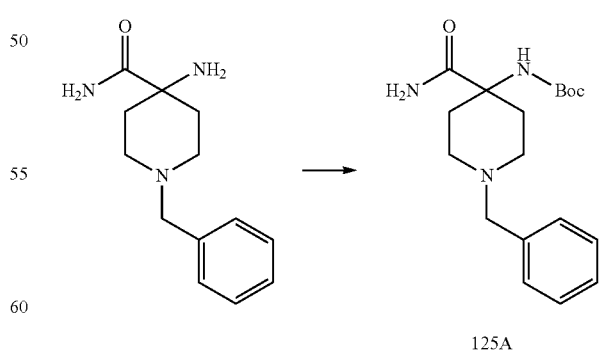

125A

To a solution of 4-amino-1-benzyl-piperidine-4-carboxylic acid amide (8.27 mmol, 1.93 g) in DCM (80 mL) was added di-tert-butyl-dicarbonate (75 mmol, 16.2 g). This solution was allowed to stir at room temperature for 40 hours. The

Example 126

Preparation of Compound 126A

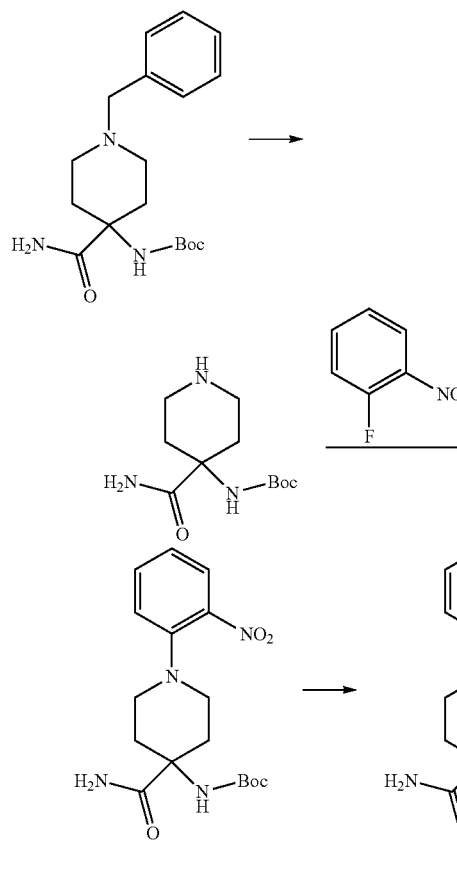

126A

Using the methods described in Example 1, Example 115 and Example 116 and (1-benzyl-4-carbamoyl-piperidin-4-yl)-carbamic acid tert-butyl ester substituted for 1-benzyl-4-methylamino-piperidine-4-carboxylic acid amide, Compound 263 was prepared.

Example 127

Preparation of Compound 127A

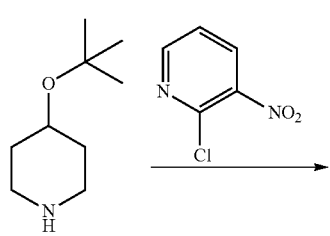

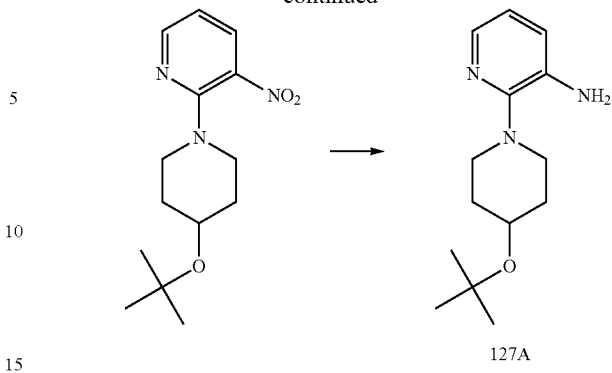

127A

Using the methods described in Example 103 and 4-tert-butoxy-piperidine substituted for 4-N-Boc-aminopiperidine, Compound 264 was prepared.

Example 128

Preparation of Compound 128A

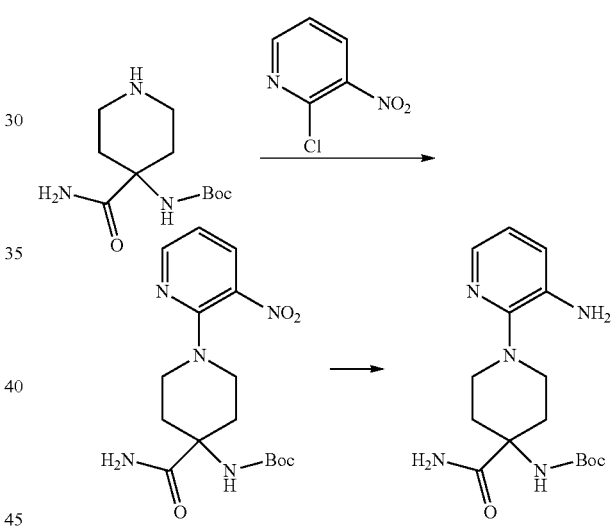

Using the methods described in Example 159 and Example 160 and (4-carbamoyl-piperidin-4-yl)-carbamic acid tert-butyl ester substituted for 4-N-Boc-aminopiperidine, compound 128A was prepared.

Example 129

Preparation of Compound 129A

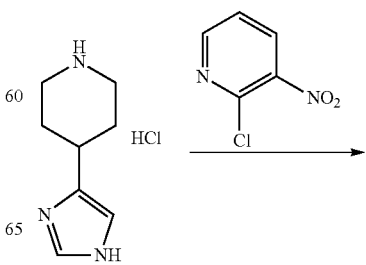

-continued

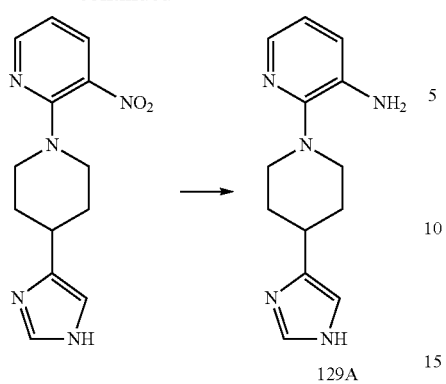

129A

Using the methods described in Example 103 and utilizing the indicated reactants and 1.1 additional equivalents of DIEA, compound 129A was prepared.

Example 130

Preparation of

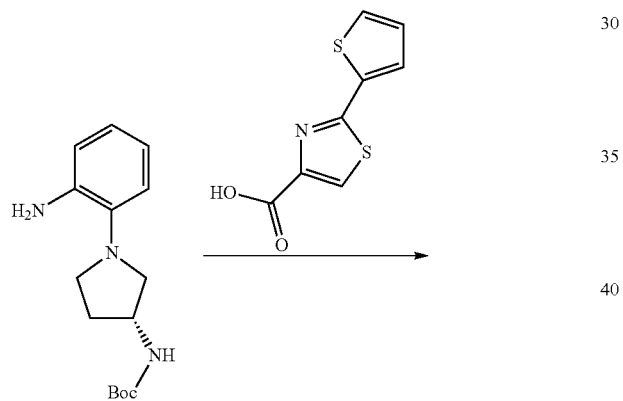

A solution of (R)-[1-(2-amino-phenyl)-pyrrolidin-3-yl]-carbamic acid tert-butyl ester (0.047 mmol, 13.1 mg), 2-thiophen-2-yl-thiazole-4-carboxylic acid (0.047 mmol, 10 mg), and HATU (0.047 mmol, 17.9 mg) in 1 mL DMF was allowed to stir at room temperature for 18 hours. The reaction mixture was then concentrated in vacuo. The residue was taken up in 4 N HCl in 1,4-dioxane and stirred for 1 hour at room temperature, then reduced in vacuo. This residue was taken up in 1.5 mL 3:1 DMSO:acetonitrile and the title compound was purified via reverse-phase HPLC. The final product was observed via LC/MS (10 minutes TFA, retention time=3.46 minutes, visible mass was (M+H)=371.14).

Example 131

Preparation of

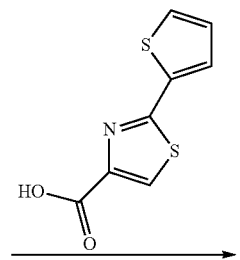

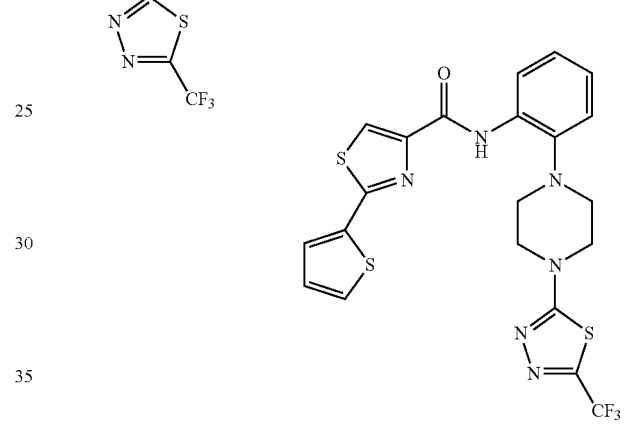

Using the method described in Example 103 and 2-[4-(5-trifluoromethyl-[1,3,4]thiadiazol-2-yl)-piperazin-1-yl]-phenylamine substituted for 1-(2-amino-phenyl)-4-methylamino-piperidine-4-carboxylic acid amide, the title compound was prepared. The final product was observed via LC/MS (10 minutes TFA, retention time=6.00 minutes, visible mass was (M+H)=523.10).

Example 132

Preparation of

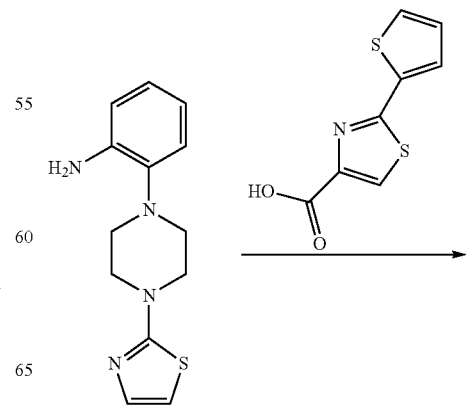

-continued

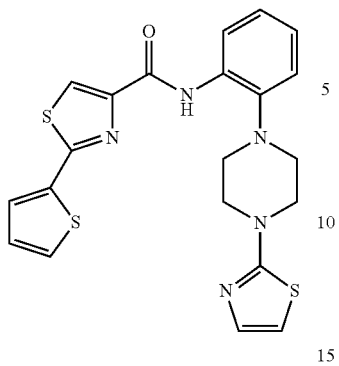

Using the method described in Example 36 and 2-(4-thiazol-2-yl-piperazin-1-yl)-phenylamine substituted for 1-(2-amino-phenyl)-4-methylamino-piperidine-4-carboxylic acid amide, the title compound was prepared. The final product was observed via LC/MS (10 minutes TFA, retention time=4.46 minutes, visible mass was (M+H)=454.17).

Example 133

Preparation of

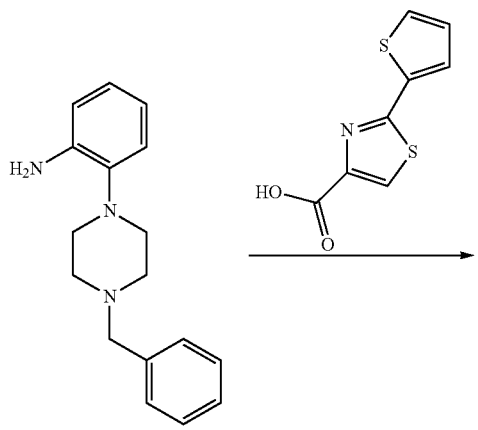

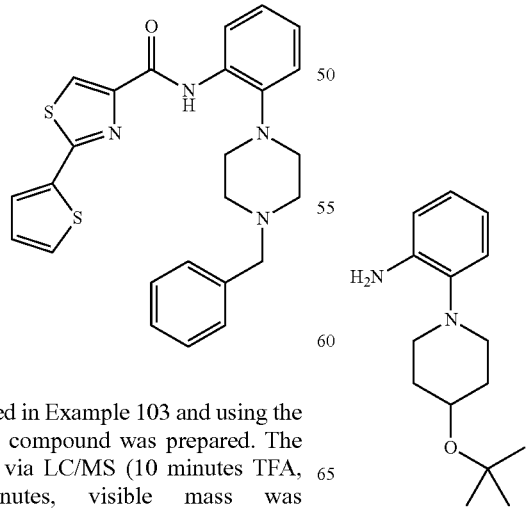

Using the method described in Example 103 and using the indicated reactants, the title compound was prepared. The final product was observed via LC/MS (10 minutes TFA, retention time=4.20 minutes, visible mass was (M+H)=461.18).

Example 134

Preparation of

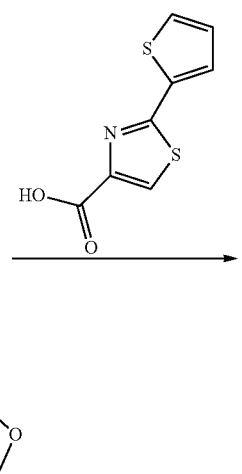

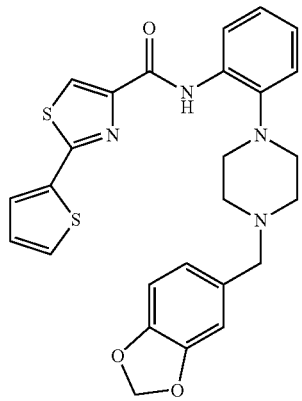

Using the method described in Example 103 and using the indicated reactants, the title compound was prepared. The final product was observed via LC/MS (10 minutes TFA, retention time=4.19 minutes, visible mass was (M+H)=505.24).

Example 135

Preparation of

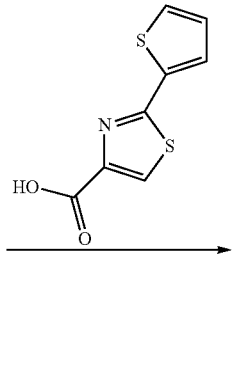

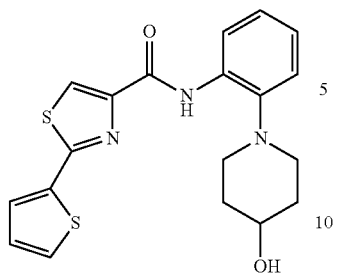

Using the method described in Example 103 and using the indicated reactants, the title compound was prepared. The final product was observed via LC/MS (10 minutes TFA, retention time=4.59 minutes, visible mass was (M+H)=386.14).

Example 136

Preparation of

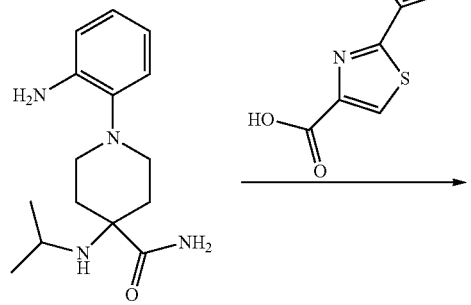

Using the method described in Example 103 and using the indicated reactants, the title compound was prepared. The final product was observed via LC/MS (10 minutes TFA, retention time=3.43 minutes, visible mass was (M+H)=470.09).

Example 137

Preparation of

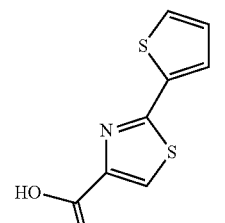

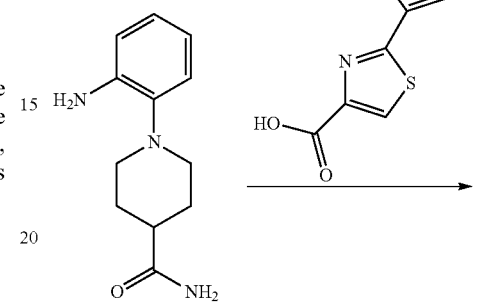

Using the method described in Example 103 and using the indicated reactants, the title compound was prepared. The final product was observed via LC/MS (10 minutes TFA, retention time=4.34 minutes, visible mass was (M+H)=413.16).

Example 138

Preparation of

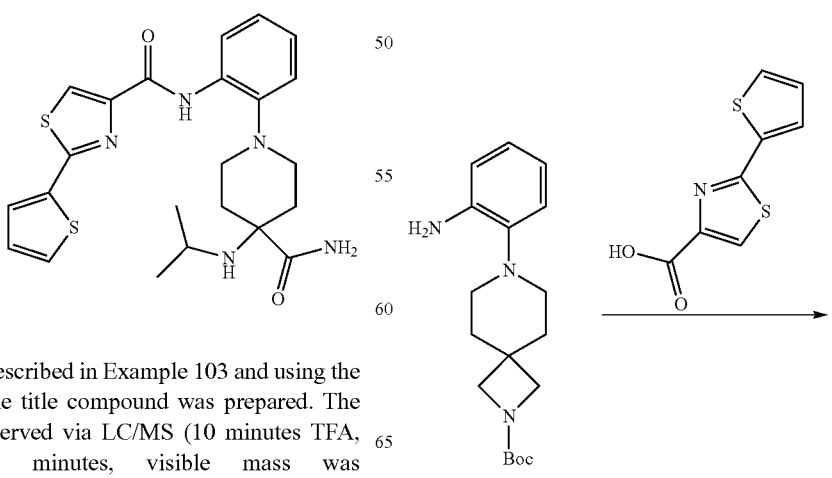

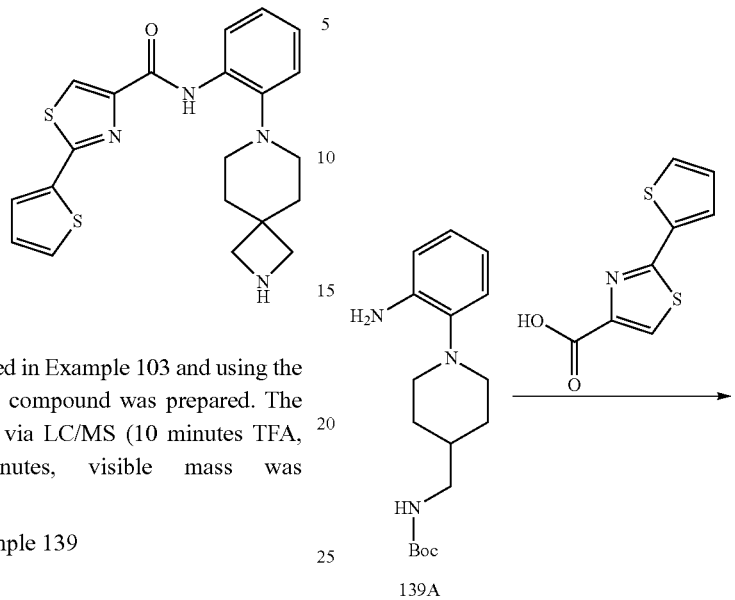

Using the method described in Example 103 and using the indicated reactants, the title compound was prepared. The final product was observed via LC/MS (10 minutes TFA, retention time=3.75 minutes, visible mass was (M+H)=411.19).

Example 139

Preparation of Compound 139A

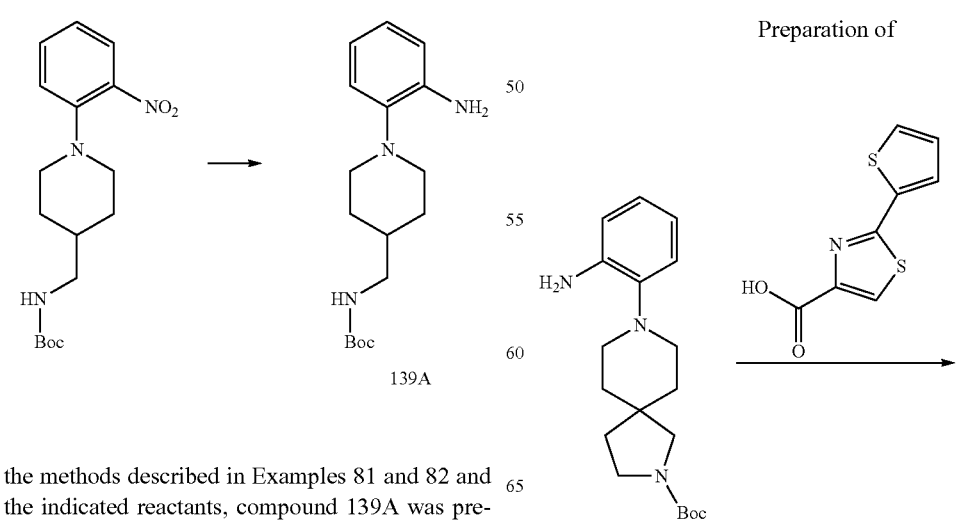

Using the methods described in Examples 81 and 82 and utilizing the indicated reactants, compound 139A was prepared.

Example 140

Preparation of

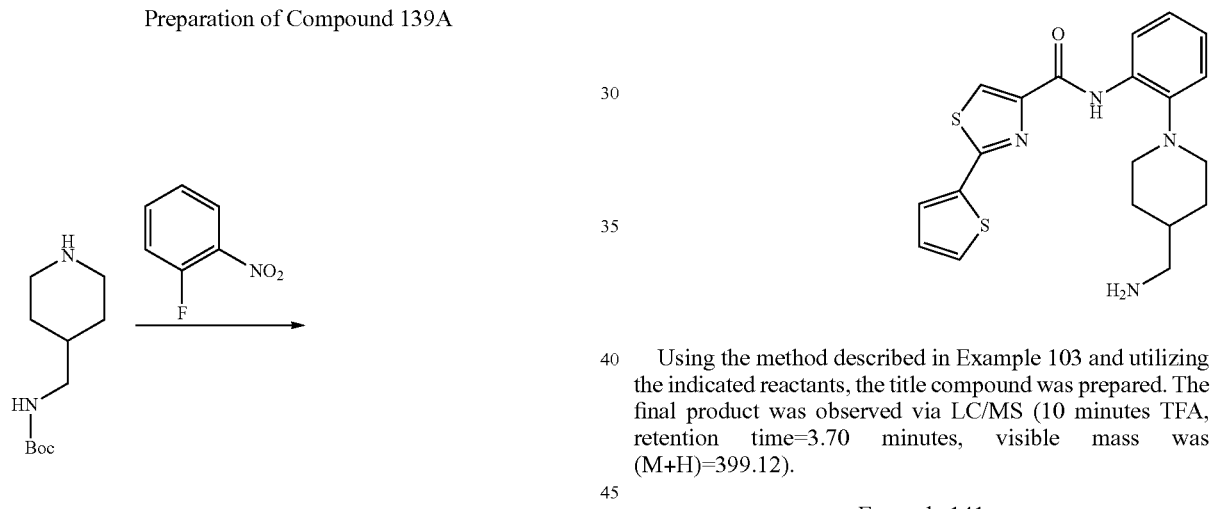

Using the method described in Example 103 and utilizing the indicated reactants, the title compound was prepared. The final product was observed via LC/MS (10 minutes TFA, retention time=3.70 minutes, visible mass was (M+H)=399.12).

Example 141

Preparation of

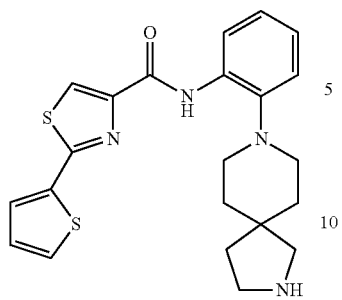

Using the method described in Example 103 and utilizing the indicated reactants, the title compound was prepared. The final product was observed via LC/MS (10 minutes TFA, retention time=3.90 minutes, visible mass was (M+H)=425.12).

Example 142

Preparation of

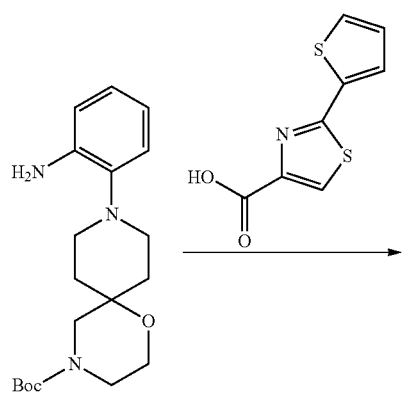

Using the method described in Example 103 and utilizing the indicated reactants, the title compound was prepared. The final product was observed via LC/MS (10 minutes TFA, retention time=3.82 minutes, visible mass was (M+H)=441.11).

Example 143

Preparation of

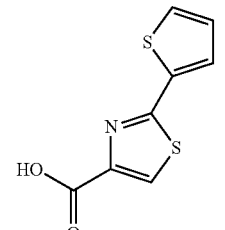

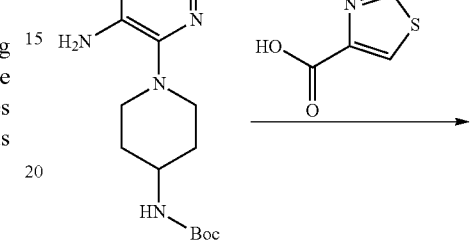

Using the method described in Example 103 and utilizing the indicated reactants, the title compound was prepared. The final product was observed via LC/MS (10 minutes TFA, retention time=2.88 minutes, visible mass was (M+H)=386.12).

Example 144

Preparation of

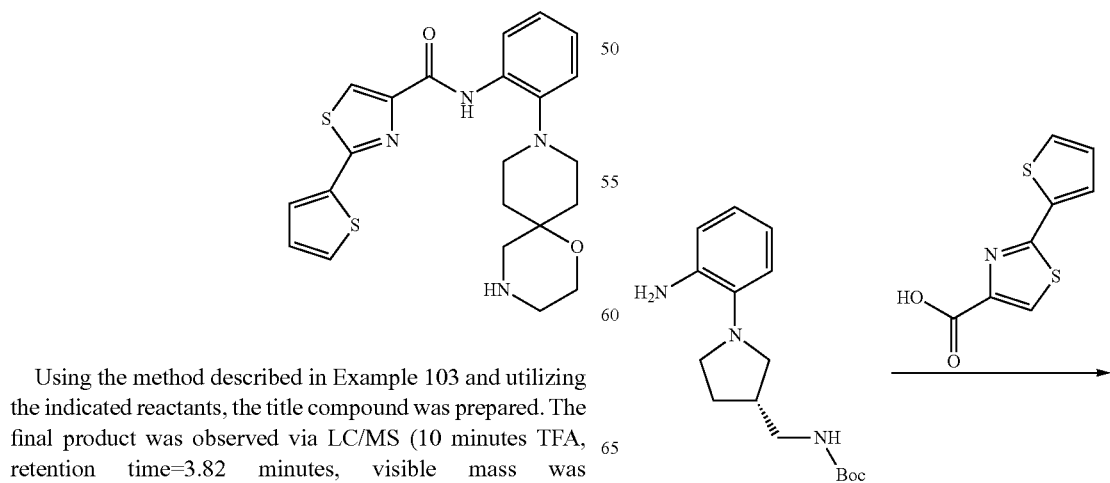

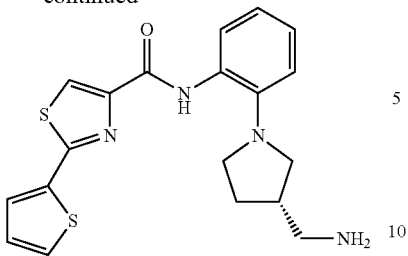

Using the method described in Example 103 and utilizing the indicated reactants, the title compound was prepared. The final product was observed via LC/MS (10 minutes TFA, retention time=3.48 minutes, visible mass was (M+H)=384.14).

Example 145

Preparation of

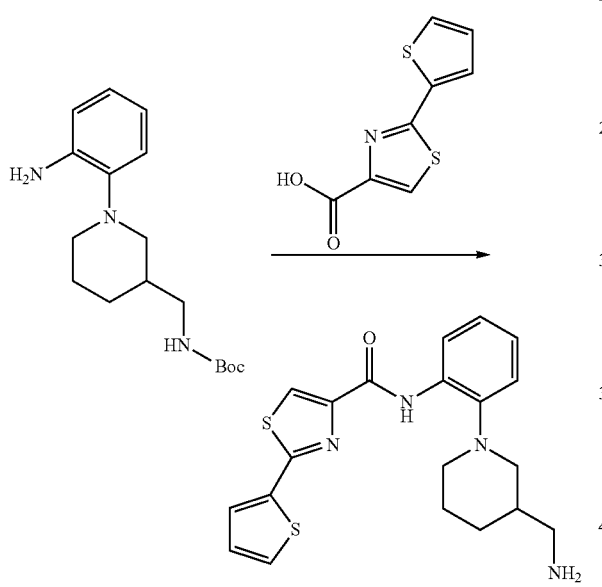

Using the method described in Example 103 and utilizing the indicated reactants, the title compound was prepared. The final product was observed via LC/MS (10 minutes TFA, retention time=3.95 minutes, visible mass was (M+H)=399.16).

Example 146

Preparation of

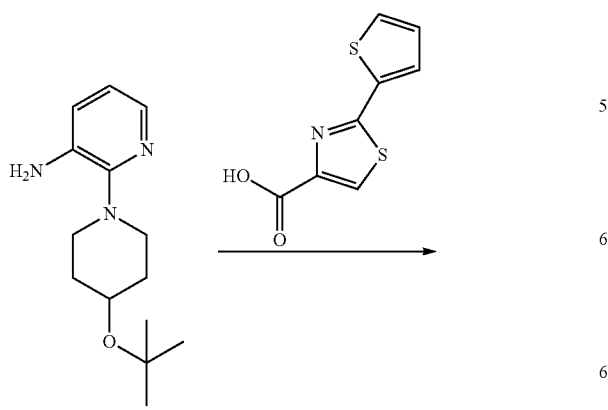

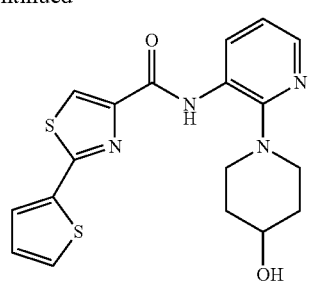

Using the method described in Example 103 and utilizing the indicated reactants, the title compound was prepared. The final product was observed via LC/MS (10 minutes TFA, retention time=3.28 minutes, visible mass was (M+H)=387.54).

Example 147

Preparation of

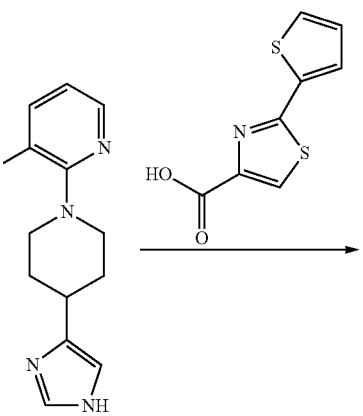

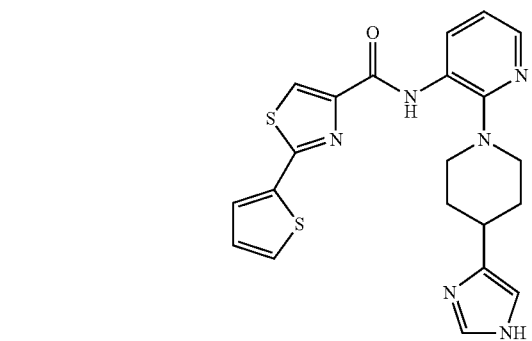

Using the method described in Example 103 and utilizing the indicated reactants, the title compound was prepared. The final product was observed via LC/MS (10 minutes TFA, retention time=3.07 minutes, visible mass was (M+H)=437.55).

Example 148

Preparation of

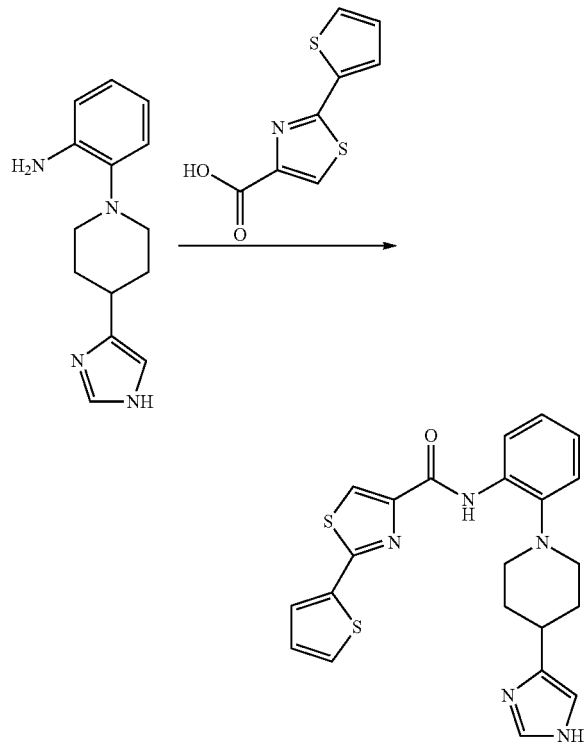 [SMILES: Nc1ccccc1N1CCC(c2c[nH]cn2)CC1 ; O=C(O)c1csc(-c2cccs2)n1 ; O=C(Nc1ccccc1N1CCC(c2c[nH]cn2)CC1)c1csc(-c2cccs2)n1]

Using the method described in Example 103 and utilizing the indicated reactants, the title compound was prepared. The final product was observed via LC/MS (10 minutes TFA, retention time=3.88 minutes, visible mass was (M+H)=436.17).

Example 149

Preparation of Compound 149A

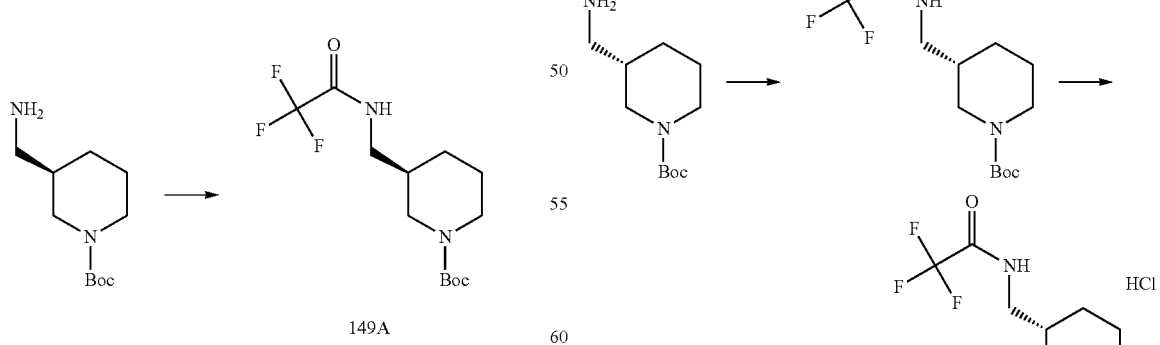

149A

A solution of (R)-1-N-Boc-piperidine-3-methylamine (1.0 mmol, 214 mg) in pyridine (4 mL) was cooled to 0° C. in an ice bath. To this was added trifluoroacetic acid anhydride (3.0 mmol, 418 µL). The resulting solution was allowed to warm to room temperature and stirred for 40 hours. After 40 hours, the reaction was diluted in 25 mL ethyl acetate and washed with 1 N HCl$_{(aq)}$ (×3), brine, and then dried over Na$_2$SO$_4$. Compound 149A was used without further purification.

Example 150

Preparation of Compound 150A

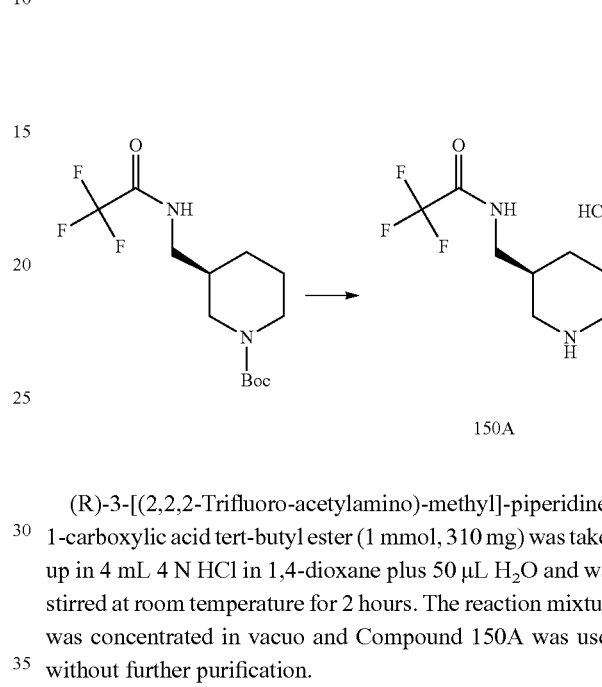

150A (R)-3-[(2,2,2-Trifluoro-acetylamino)-methyl]-piperidine-1-carboxylic acid tert-butyl ester (1 mmol, 310 mg) was taken up in 4 mL 4 N HCl in 1,4-dioxane plus 50 µL H$_2$O and was stirred at room temperature for 2 hours. The reaction mixture was concentrated in vacuo and Compound 150A was used without further purification.

Example 151

Preparation of Compound 151A

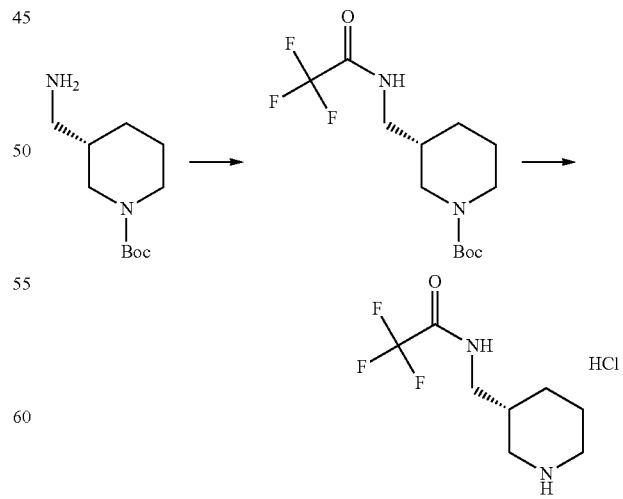

151A

Using the methods described in Examples 149 and 150 and substituting (S)-1-N-Boc-piperidine-3-methylamine substituted for (R)-1-N-Boc-piperidine-3-methylamine, Compound 151A was prepared.

Example 152

Preparation of Compound 152A

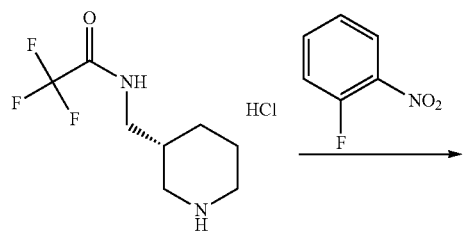

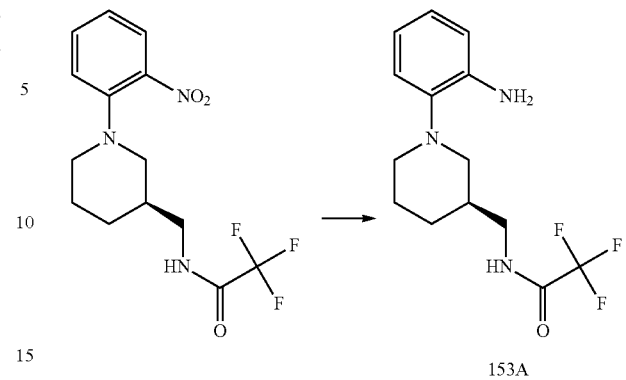

153A

Using the methods described in Examples 103 and utilizing the indicated reactants, compound 153A was prepared.

Example 154

Preparation of Compound 154A

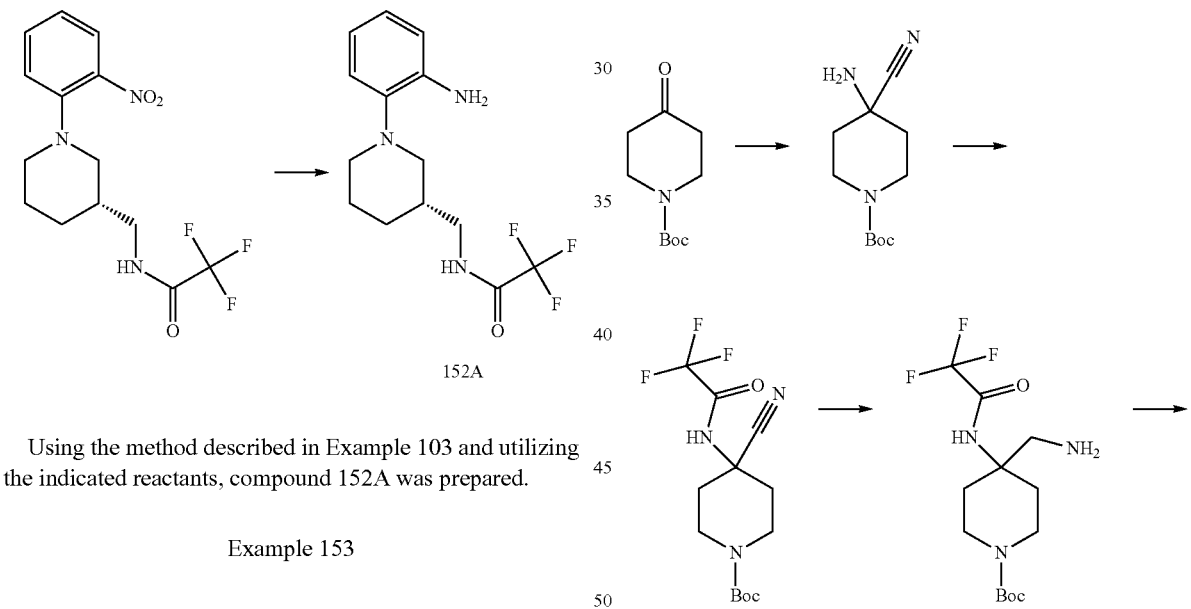

152A

Using the method described in Example 103 and utilizing the indicated reactants, compound 152A was prepared.

Example 153

Preparation of Compound 153A

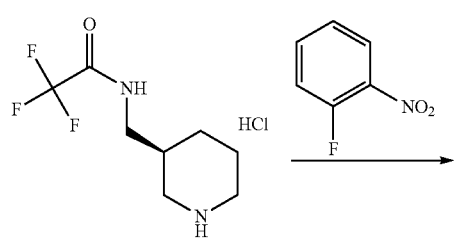

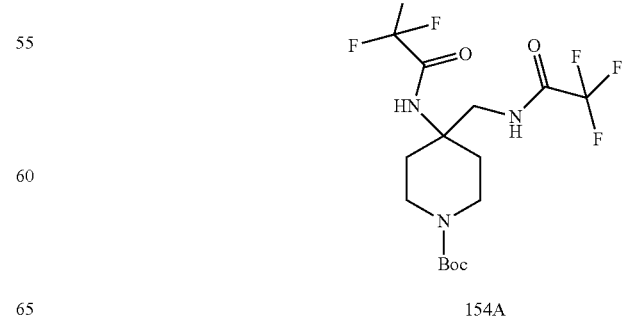

154A

Using the methods described by Kim, In Ho, et al., *Bioorganic and Medicinal Chemistry Letters*, 2007, vol 17(5), 1181-1184, Compound 154A was prepared.

Example 155

Preparation of Compound 155A

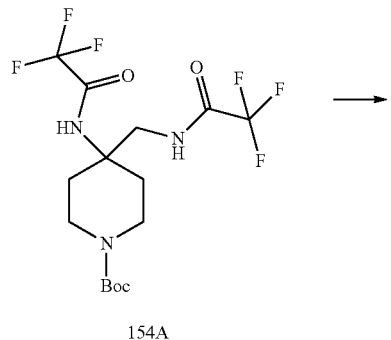

154A

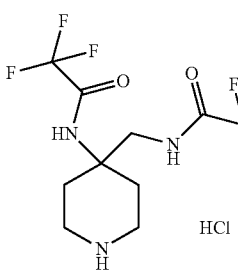

155A

Compound 154A (2.12 mmol, 895 mg) was taken up in 1,4-dioxane (15 mL). To this solution was added 4 N HCl in 1,4-dioxane (5 mL). The resulting solution was stirred at room temperature for 2 hours, then concentrated in vacuo to provide Compound 155A, which was used without further purification.

Example 156

Preparation of Compound 156A

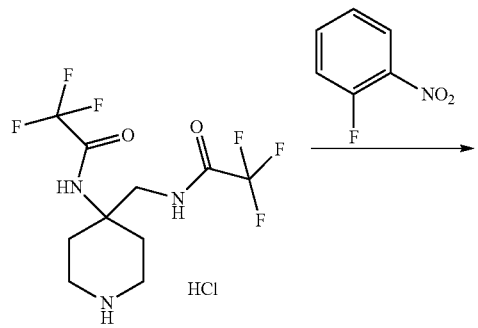

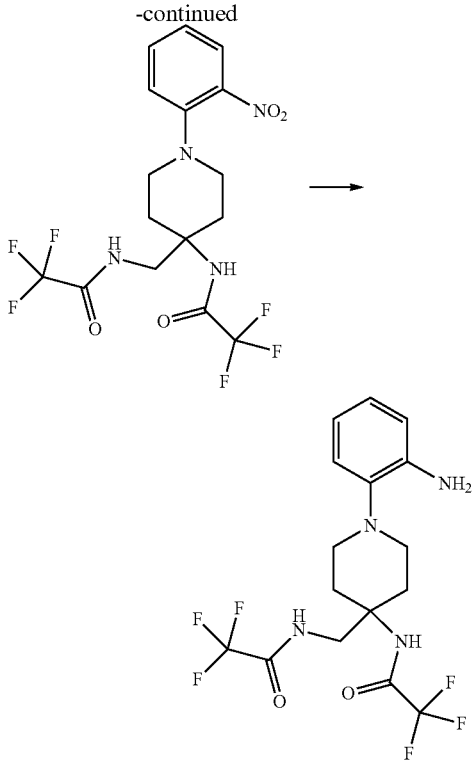

156A

Using the method described in Example 103 and utilizing the indicated reactants and 1.1 additional equivalents of DIEA added, compound 156A was prepared.

Example 157

Preparation of Compound 157A

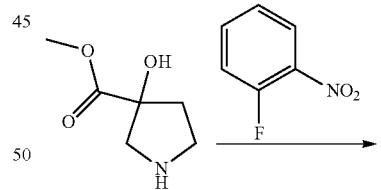

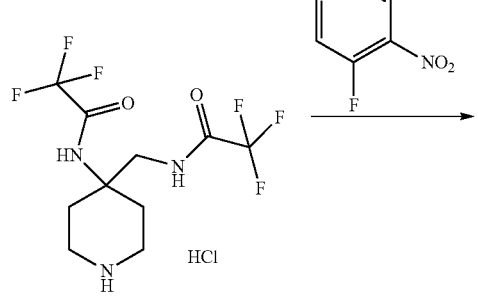

157A

Using the methods described in Examples 103 and utilizing the indicated reactants, compound 157A was prepared.

Example 158

Preparation of Compound 158A

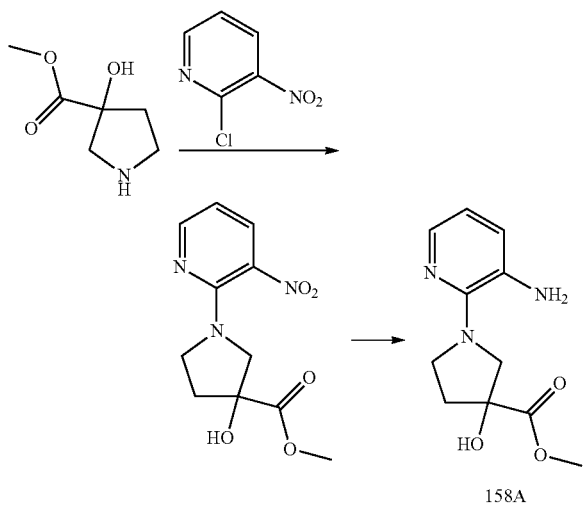

Using the methods described in Examples 80 and 81 and utilizing the indicated reactants, compound 158A was prepared.

Example 159

Preparation of Compound 159A

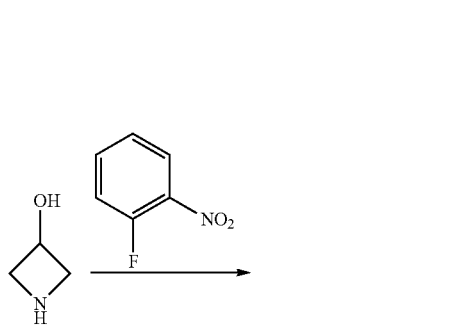

Using the methods described in Examples 80 and 81 and utilizing the indicated reactants, compound 159A was prepared.

Example 160

Preparation of Compound 160A

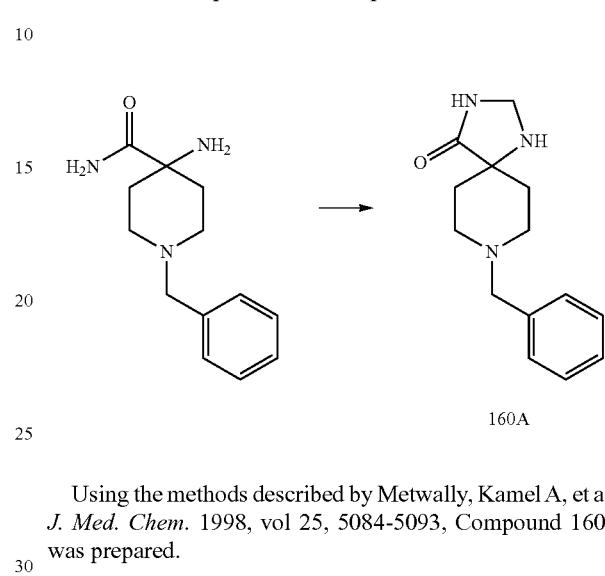

Using the methods described by Metwally, Kamel A, et al., *J. Med. Chem.* 1998, vol 25, 5084-5093, Compound 160A was prepared.

Example 161

Preparation of Compound 161A

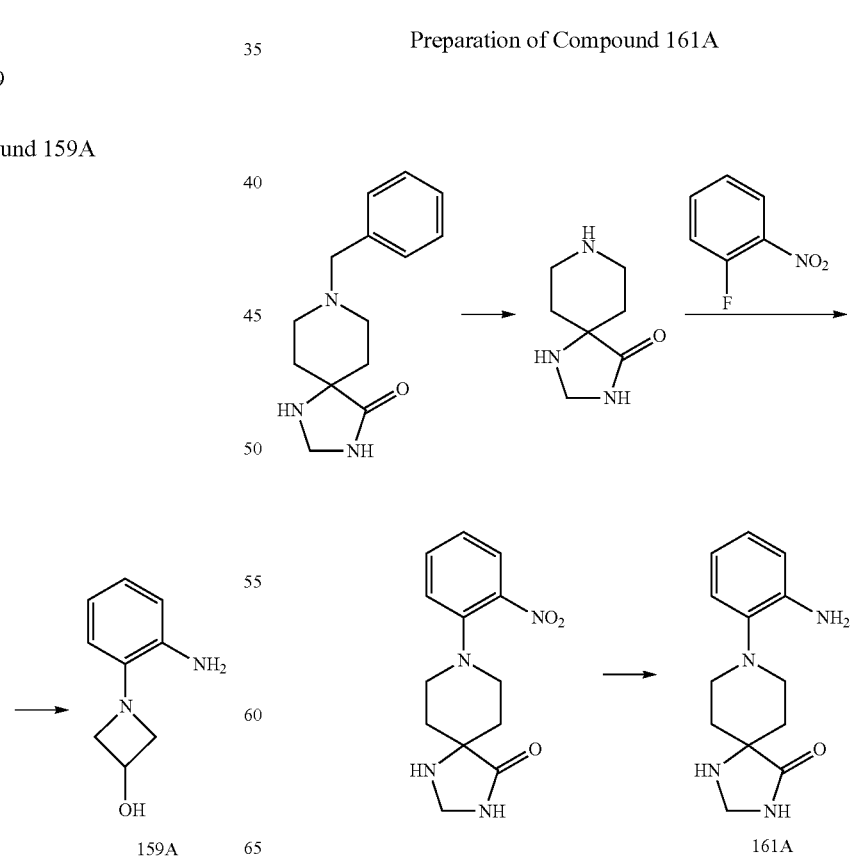

Using the methods described in Examples 80 and 81 and utilizing the indicated reactants, compound 161A was prepared.

Example 162

Preparation of Compound 162A

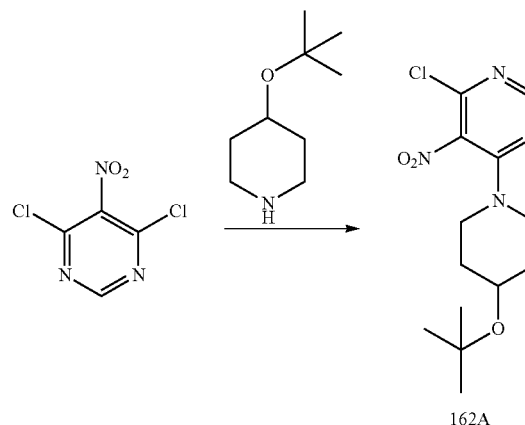

162A

To a solution of 4,6-dichloro-5-nitropyrimidine (5.15 mmol, 1.00 g) in dichloromethane (30 mL) was added diisopropylethylamine (6.70 mmol, 1.17 mL). This solution was cooled to −78° C. in a dry ice/isopropanol bath. To this solution was added dropwise a solution of 4-tert-butoxy-piperidine (5.20 mmol, 817 mg) in DCM (10 mL). Stir at −78° C. for 18 hours. This solution was concentrated in vacuo and Compound 162A was purified via silica gel chromatography.

Example 163

Preparation of Compound 163A

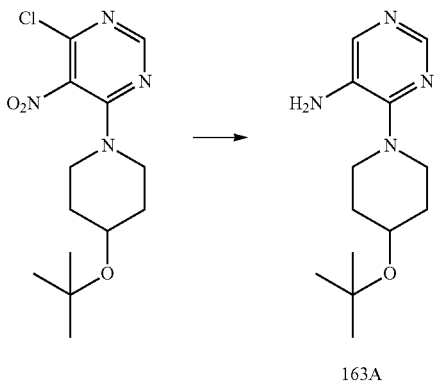 [SMILES: CC(C)(C)OC1CCN(c2ncnc(Cl)c2[N+](=O)[O-])CC1 ; CC(C)(C)OC1CCN(c2ncncc2N)CC1]

163A

To a solution of 4-(4-tert-butoxy-piperidin-1-yl)-6-chloro-5-nitro-pyrimidine (4.48 mmol, 1.41 g) in ethanol (200 mL) was added triethylamine (5.83 mmol, 820 µL). This solution was run through an H-cube hydrogenator at 50 bar and 60° C. This solution was then reduced to 40 mL in vacuo and diluted with 200 mL ethyl acetate. This was washed with a concentrated aqueous sodium bicarbonate solution (×1), then with a concentrated saline solution (×1), and dried over anhydrous sodium sulfate. This solution was concentrated in vacuo to yield Compound 163A as a fine, off-white powder. $^1$H NMR (400 MHz, DMSO) δ 8.07 (s, 1H), 7.83 (s, 1H), 4.75-4.72 (s, 2H), 3.68-3.55 (m, 3H), 2.87-2.78 (m, 2H), 1.77-1.69 (m, 2H), 1.56-1.45 (m, 2H), 1.13 (s, 9H)

Example 164

Preparation of Compound 164A

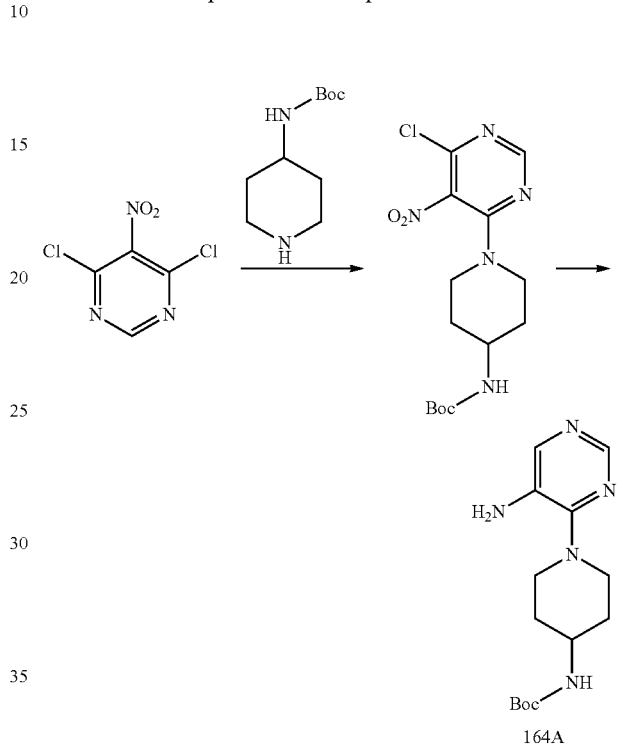

164A

Using the methods described in Examples 162 and 163, and utilizing the indicated starting materials, compound 164A was prepared.

Example 165

Preparation of Compound 165A

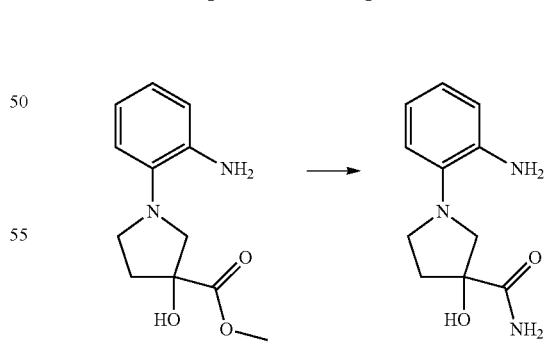

165A 1-(2-Amino-phenyl)-3-hydroxy-pyrrolidine-3-carboxylic acid methyl ester (0.317 mmol, 75 mg) was taken up in ~7N NH$_3$ in methanol (4 mL). To this solution was added potassium cyanide (0.032 mmol, 2 mg). The vial was sealed and the solution was heated to 55° C. for 18 hours. The reaction was then diluted with ethyl acetate (15 mL) and washed with concentrated aqueous sodium bicarbonate and then dried over sodium sulfate. The solution was then reduced in vacuo and Compound 165A used without further purification.

Example 166

Preparation of Compound 166A

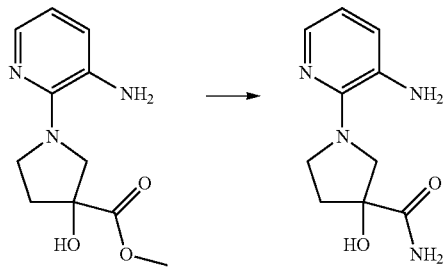

166A

Using the method described in Example 166, and 1-(3-amino-pyridin-2-yl)-3-hydroxy-pyrrolidine-3-carboxylic acid methyl ester substituted for 1-(2-Amino-phenyl)-3-hydroxy-pyrrolidine-3-carboxylic acid methyl ester, Compound 166A was prepared.

Example 167

Preparation of Compound 167A

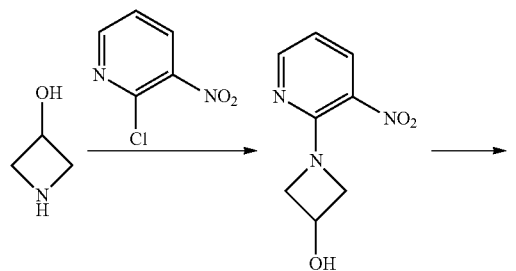

167A

Using the methods described in Example 80 and Example 81, and 3-hydroxyazetidine substituted for 4-N-Boc-aminopiperidine, Compound 167A was prepared.

Example 168

Preparation of Compound 168A

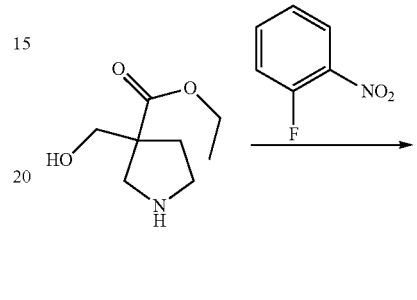

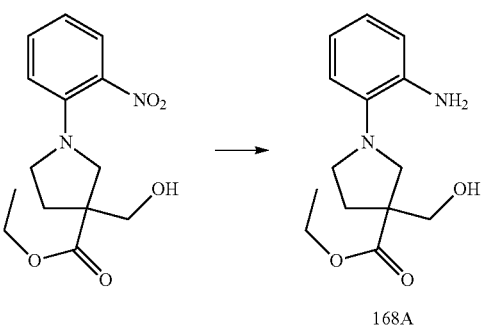

168A

Using the methods described in Example 80 and Example 81, and 3-Hydroxymethyl-pyrrolidine-3-carboxylic acid ethyl ester substituted for 4-methylamino-piperidine-4-carboxylic acid amide, Compound 168A was prepared.

Example 169

Preparation of

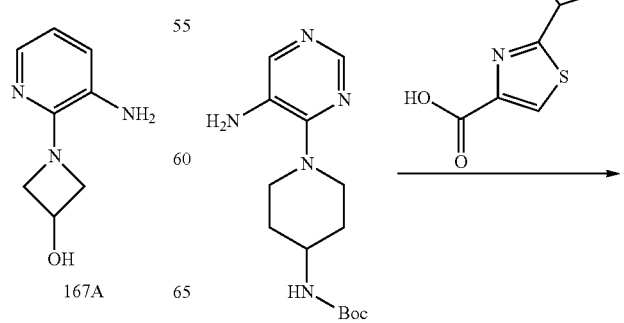

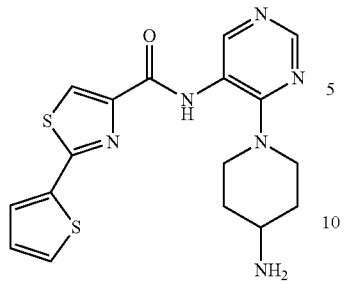

Using the method described in Example 103 and [1-(5-amino-pyrimidin-4-yl)-piperidin-4-yl]-carbamic acid tert-butyl ester substituted for (R)-[1-(2-amino-phenyl)-pyrrolidin-3-yl]-carbamic acid tert-butyl ester, Compound 316 was prepared. The final product was observed via LC/MS (10 minutes TFA, retention time=1.89 minutes, visible mass was (M+H)=387.16).

Example 170

Preparation of

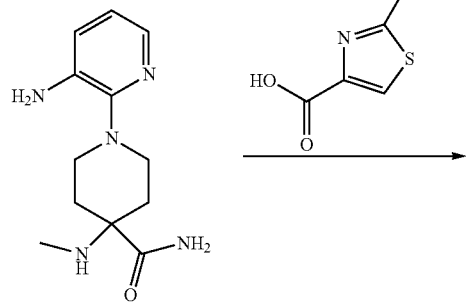

Using the method described in Example 103 and (3'-nitro-3,4,5,6-tetrahydro-2H-[1,2']bipyridinyl-4-yl)-carbamic acid tert-butyl ester substituted for 1-(2-amino-phenyl)-4-methylamino-piperidine-4-carboxylic acid amide, Compound 318 was prepared. The final product was observed via LC/MS (10 minutes TFA, retention time=2.74 minutes, visible mass was (M+H)=429.19).

Example 171

Preparation of

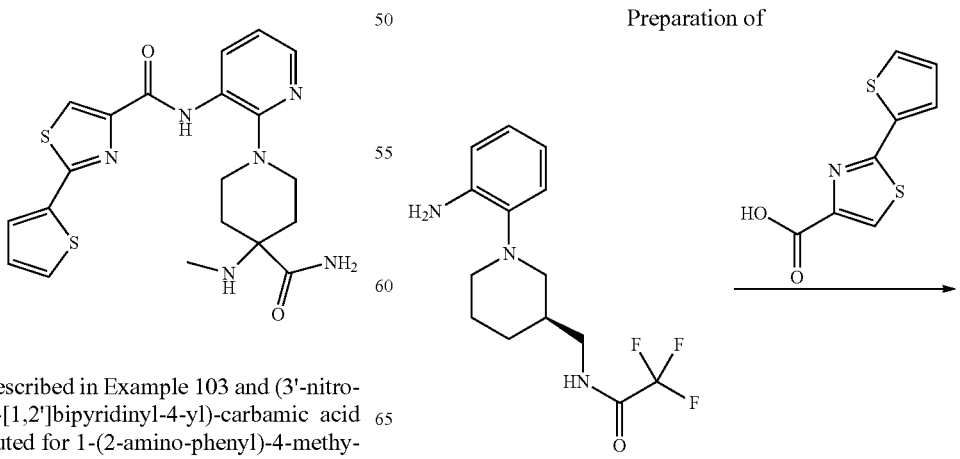

Using the method described in Example 103 and (S)-2,2,2-trifluoro-N-piperidin-3-ylmethyl-acetamide hydrochloride substituted for 1-(2-amino-phenyl)-4-methylamino-piperidine-4-carboxylic acid amide, the title compound was prepared. The final product was observed via LC/MS (10 minutes TFA, retention time=5.17 minutes, visible mass was (M+H)=495.57).

Example 172

Preparation of

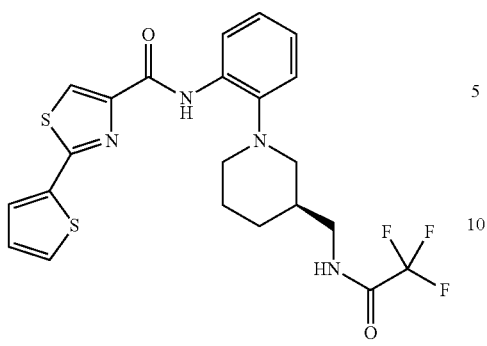

Using the method described in Example 103 and (R)-2,2,2-trifluoro-N-piperidin-3-ylmethyl-acetamide hydrochloride substituted for 1-(2-amino-phenyl)-4-methylamino-piperidine-4-carboxylic acid amide, the title compound was prepared. The final product was observed via LC/MS (10 minutes TFA, retention time=5.17 minutes, visible mass was (M+H)=495.59).

Example 173

Preparation of

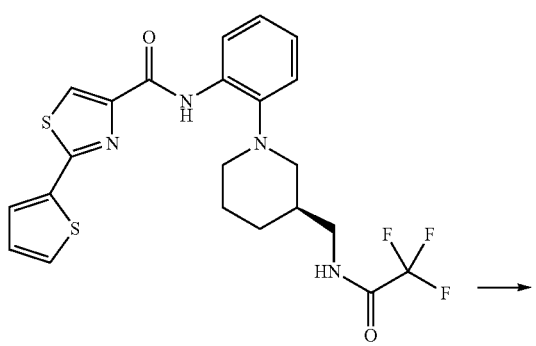

322

Using the method described in Example 178 and 2-thiophen-2-yl-thiazole-4-carboxylic acid (2-{3-[(2,2,2-trifluoro-acetylamino)-(R)-methyl]-piperidin-1-yl}-phenyl)-amide substituted for 2-thiophen-2-yl-thiazole-4-carboxylic acid (2-{3-[(2,2,2-trifluoro-acetylamino)-(S)-methyl]-piperidin-1-yl}-phenyl)-amide, the title compound was prepared. The final product was observed via LC/MS (10 minutes TFA, retention time=3.77 minutes, visible mass was (M+H)=399.60).

Example 174

Preparation of

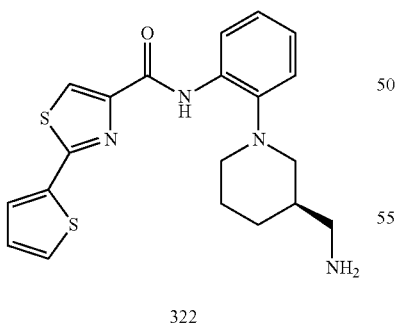

Using the method described in Example 103 and 1-(3-amino-pyridin-2-yl)-3-hydroxy-pyrrolidine-3-carboxylic acid amide substituted for 1-(2-amino-phenyl)-4-methylamino-piperidine-4-carboxylic acid amide, the title compound was prepared. The final product was observed via LC/MS (10 minutes TFA, retention time=2.35 minutes, visible mass was (M+H)=416.13).

Example 175

Preparation of

301
-continued

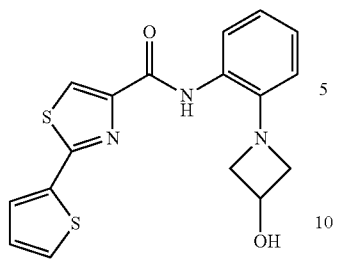

Using the method described in Example 103 and 1-(2-Amino-phenyl)-azetidin-3-ol substituted for (R)-[1-(2-amino-phenyl)-pyrrolidin-3-yl]-carbamic acid tert-butyl ester, the title compound was prepared. The final product was observed via LC/MS (10 minutes TFA, retention time=4.68 minutes, visible mass was (M+H)=358.10).

Example 176

Preparation of

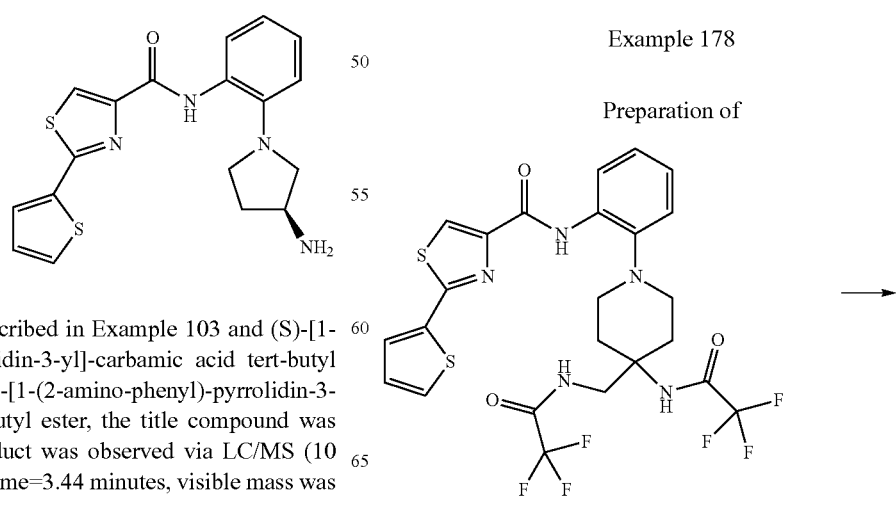

Using the method described in Example 103 and (S)-[1-(2-amino-phenyl)-pyrrolidin-3-yl]-carbamic acid tert-butyl ester substituted for (R)-[1-(2-amino-phenyl)-pyrrolidin-3-yl]-carbamic acid tert-butyl ester, the title compound was prepared. The final product was observed via LC/MS (10 minutes TFA, retention time=3.44 minutes, visible mass was (M+H)=371.12).

302

Example 177

Preparation of

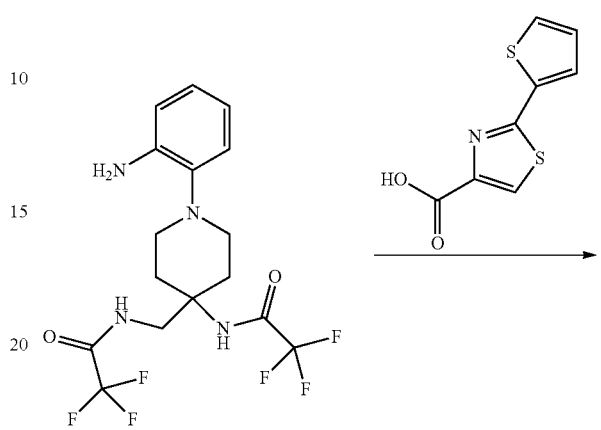

Using the method described in Example 103 and N-{1-(2-amino-phenyl)-4-[(2,2,2-trifluoro-acetylamino)-methyl]-piperidin-4-yl}-2,2,2-trifluoro-acetamide substituted for 1-(2-amino-phenyl)-4-methylamino-piperidine-4-carboxylic acid amide, the title compound was prepared. The final product was purified via silica gel chromatography.

Example 178

Preparation of

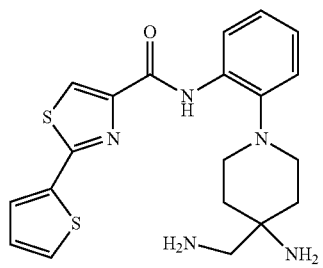

To a solution of 2-thiophen-2-yl-thiazole-4-carboxylic acid (2-{4-(2,2,2-trifluoro-acetylamino)-4-[(2,2,2-trifluoro-acetylamino)-methyl]-piperidin-1-yl}-phenyl)-amide (0.065 mmol, 40 mg) in 2:1 THF:H$_2$O (3 mL) added 1 N LiOH$_{(aq)}$ (0.20 mmol, 200 μL). The resulting solution was allowed to stir at room temperature for 18 hours. The solution was concentrated in vacuo, taken up in 3:1 DMSO:acetonitrile, and the title compound purified via reverse-phase HPLC. The final product was observed via LC/MS (10 minutes TFA, retention time=2.94 minutes, visible mass was (M+H)=414.14).

Example 179

Preparation of

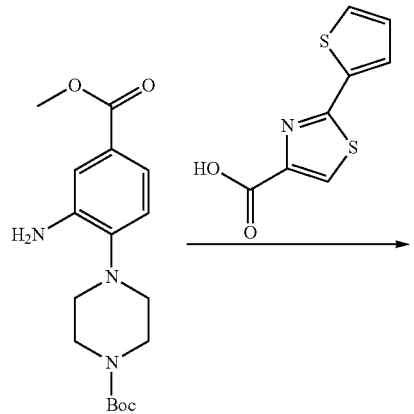

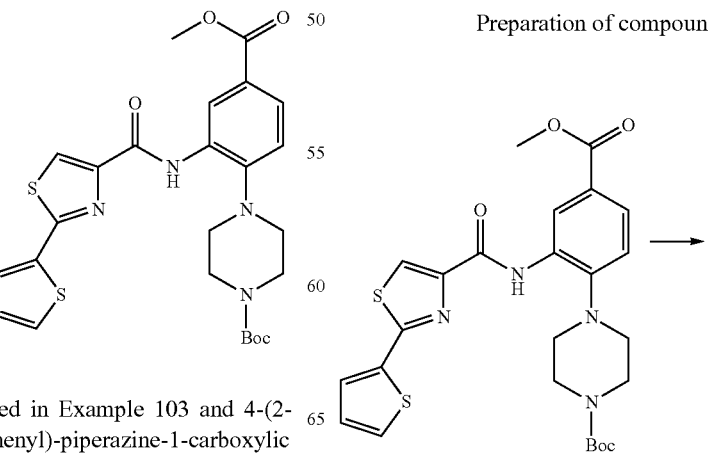

Using the method described in Example 103 and 4-(2-amino-4-methoxycarbonyl-phenyl)-piperazine-1-carboxylic acid tert-butyl ester substituted for 1-(2-amino-phenyl)-4-methylamino-piperidine-4-carboxylic acid amide, the title compound was prepared. The final product was purified via silica gel chromatography.

Example 180

Preparation of

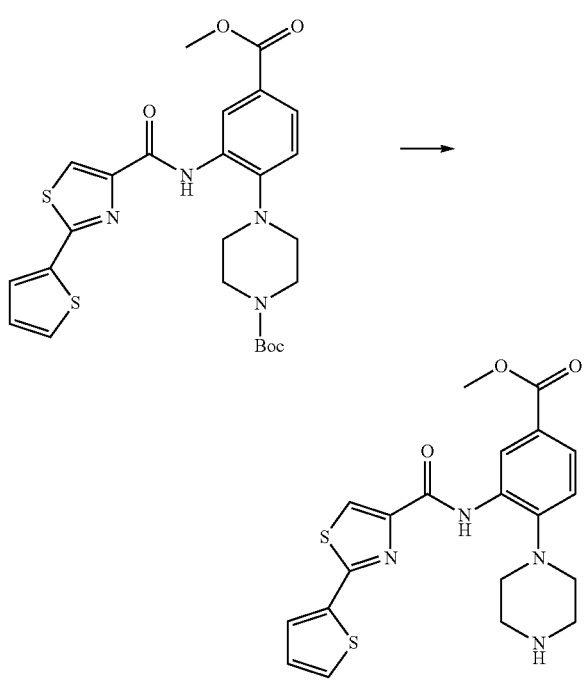

4-{4-Methoxycarbonyl-2-[(2-thiophen-2-yl-thiazole-4-carbonyl)-amino]-phenyl}-piperazine-1-carboxylic acid tert-butyl ester (0.076 mmol, 40 mg) was stirred at room temperature in a solution of 9:1 trifluoroacetic acid:H$_2$O (2 mL) for 2 hours. The solution was concentrated in vacuo, taken up in 3:1 DMSO:acetonitrile, and the title compound purified via reverse-phase HPLC. The final product was observed via LC/MS (10 minutes TFA, retention time=3.54 minutes, visible mass was (M+H)=429.09).

Example 181

Preparation of compound 181A

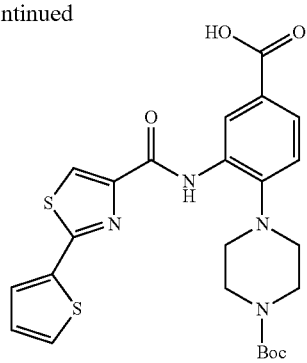

181A

To a solution of 4-{4-methoxycarbonyl-2-[(2-thiophen-2-yl-thiazole-4-carbonyl)-amino]-phenyl}-piperazine-1-carboxylic acid tert-butyl ester (0.152 mmol, 80 mg) in 2:1 THF:H$_2$O (3 mL) was added 1 N LiOH$_{(aq)}$ (0.20 mmol, 200 μL). The resulting solution was stirred at room temperature for 18 hours. After 18 hours, the reaction was acidified to pH=4 with IR-120H+ strong acid resin and then filtered to remove resin. The solvent was removed in vacuo and Compound 181A was used without further purification.

Example 182

Preparation of

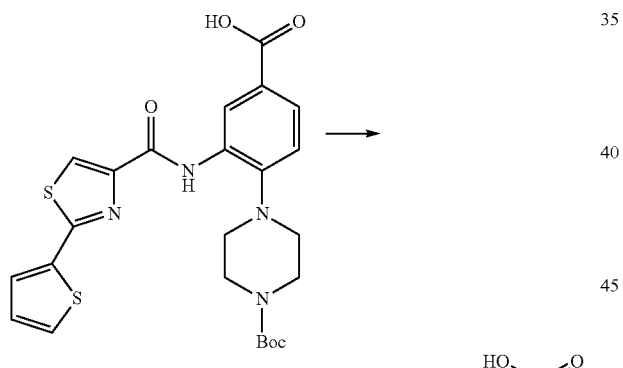

Using the method described in Example 180 and 4-{4-carboxy-2-[(2-thiophen-2-yl-thiazole-4-carbonyl)-amino]-phenyl}-piperazine-1-carboxylic acid tert-butyl ester substituted for 4-{4-methoxycarbonyl-2-[(2-thiophen-2-yl-thiazole-4-carbonyl)-amino]-phenyl}-piperazine-1-carboxylic acid tert-butyl ester, the title compound was prepared. The final product was observed via LC/MS (10 minutes TFA, retention time=2.69 minutes, visible mass was (M+H)=4151.15).

Example 183

Preparation of

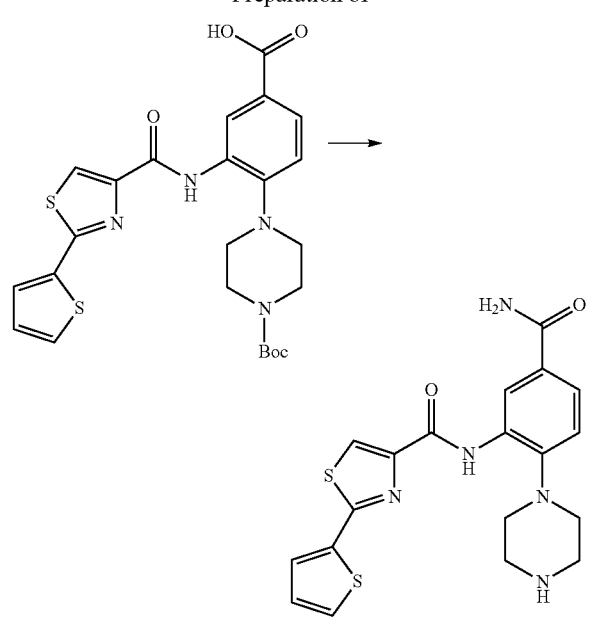

To a solution of 4-{4-carboxy-2-[(2-thiophen-2-yl-thiazole-4-carbonyl)-amino]-phenyl}-piperazine-1-carboxylic acid tert-butyl ester (0.082 mmol, 42.2 mg) in DMF (2 mL) was added ammonium chloride (0.164 mmol, 8.8 mg), EDC (0.180 mmol, 34.4 mg), HOBt (0.180 mmol, 24.3 mg) and DIEA (0.25 mmol, 44 μL). The reaction was allowed to stir at room temperature for 18 hours, at which time the DMF was removed in vacuo. The residue was taken up in 2 mL 9:1 TFA:H$_2$O and stirred at room temperature for two hours. The solution was concentrated in vacuo, taken up in 3:1 DMSO:acetonitrile, and the title compound purified via reverse-phase HPLC. The final product was observed via LC/MS (10 minutes TFA, retention time=2.78 minutes, visible mass was (M+H)=414.10).

Example 184

Preparation of

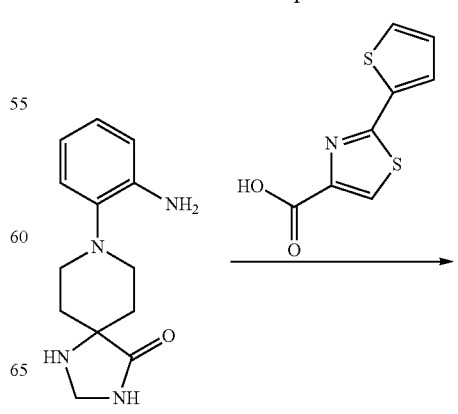

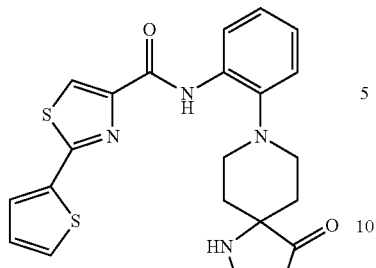

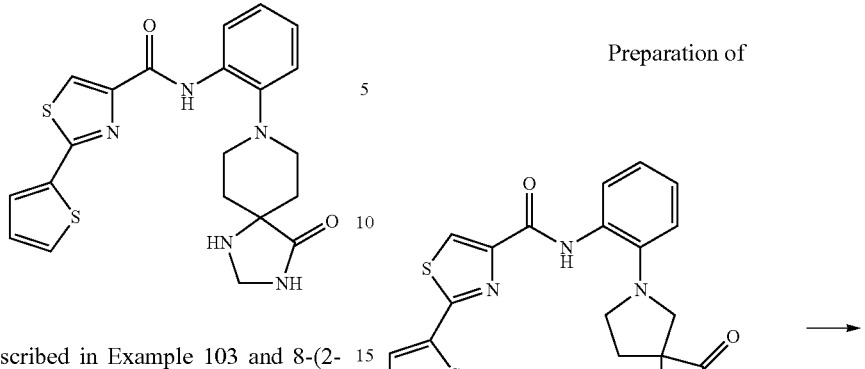

Using the method described in Example 103 and 8-(2-amino-phenyl)-1,3,8-triaza-spiro[4.5]decan-4-one substituted for 1-(2-amino-phenyl)-4-methylamino-piperidine-4-carboxylic acid amide, the title compound was prepared. The final product was observed via LC/MS (10 minutes TFA, retention time=3.62 minutes, visible mass was (M+H)=440.16).

Example 185

Preparation of

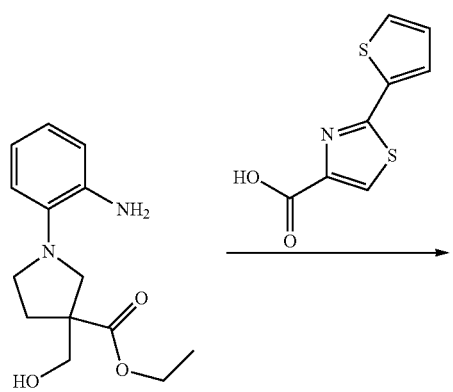

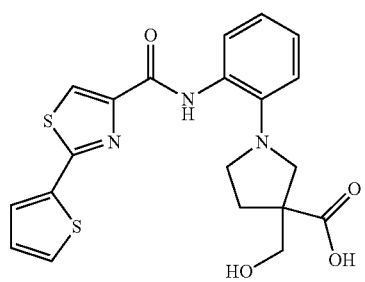

Using the method described in Example 103 and 1-(2-amino-phenyl)-3-hydroxymethyl-pyrrolidine-3-carboxylic acid ethyl ester substituted for 1-(2-amino-phenyl)-4-methylamino-piperidine-4-carboxylic acid amide, the title compound was prepared. The final product was purified via silica gel chromatography.

Example 186

Preparation of

3-Hydroxymethyl-1-{2-[(2-thiophen-2-yl-thiazole-4-carbonyl)-amino]-phenyl}-pyrrolidine-3-carboxylic acid ethyl ester (0.05 mmol, 23 mg) was charged to a 20 mL scintillation vial. To this vial was also charged 2:1 THF:H$_2$O (3 mL) followed by 1 N LiOH$_{(aq)}$ (0.06 mmol, 60 µL). This solution was allowed to stir at room temperature for 70 hours. The reaction was then brought to pH=4 with IR-120+ strong acid resin. The resin was filtered out, the solvent removed in vacuo, the residue taken up in 3:1 DMSO:acetonitrile, and the title compound was purified via reverse-phase HPLC. The final product was observed via LC/MS (10 minutes TFA, retention time=4.10 minutes, visible mass was (M+H)=430.13).

Example 187

Preparation of

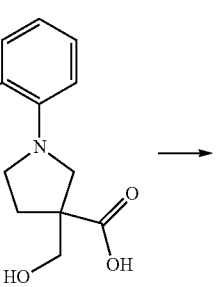

-continued

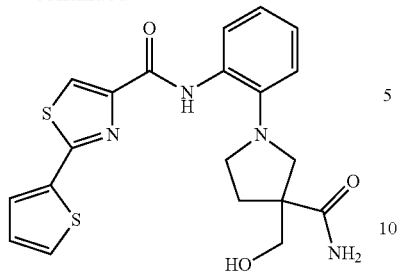

To a solution of 3-hydroxymethyl-1-{2-[(2-thiophen-2-yl-thiazole-4-carbonyl)-amino]-phenyl}-pyrrolidine-3-carboxylic acid (0.04 mmol, 17.2 mg) in DMF (2 mL) was added ammonium chloride (0.1 mmol, 5.4 mg), diisopropylethylamine (0.12 mmol, 21 µL), EDC (0.06 mmol, 11.5 mg), and HOBt (0.06 mmol, 8.1 mg). The reaction was stirred at room temperature for 18 hours. The solution was concentrated in vacuo, taken up in 3:1 DMSO:acetonitrile, and the title compound was purified via reverse-phase HPLC. The final product was observed via LC/MS (10 minutes TFA, retention time=3.83 minutes, visible mass was (M+H)=429.16).

Example 188

Preparation of

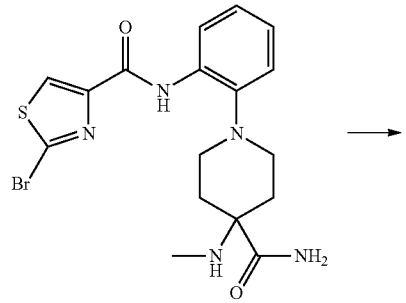

Using the method described in Example 99 and furan-3-boronic acid substituted for 1H-pyrazole-5-boronic acid, the title compound was prepared. The final product was observed via LC/MS (10 minutes TFA, retention time=2.79 minutes, visible mass was (M+H)=426.20).

Example 189

Preparation of

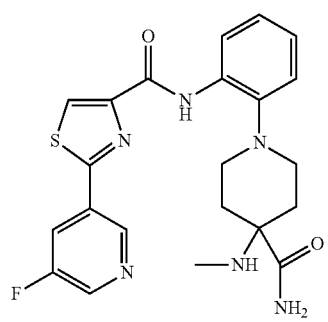

Using the method set forth in Example 99 above and substituting 3-pyridine-boronic acid for 5-fluoro3-pyridine-boronic acid, the title compound was prepared. HPLC-MS RT=2.79 minutes, mass calculated for formula $C_{22}H_{23}FN_6O_2S$ 454.16, observed LCMS m/z 455.17 (M+H).

Example 190

Preparation of

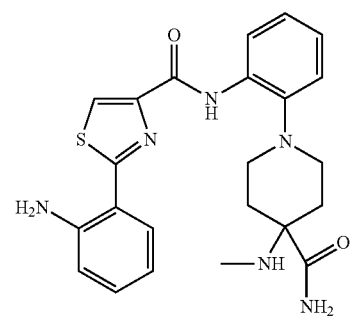 [SMILES: CNC1(C(N)=O)CCN(c2ccccc2NC(=O)c2csc(-c3ccccc3N)n2)CC1]

Using the method set forth in Example 99 above and substituting 3-pyridine-boronic acid for (2-amino)benzene-boronic acid, the title compound was prepared. HPLC-MS RT=2.97 minutes, mass calculated for formula $C_{22}H_{23}FN_6O_2S$ 454.16, observed LCMS m/z 455.17 (M+H).

Example 191

Preparation of

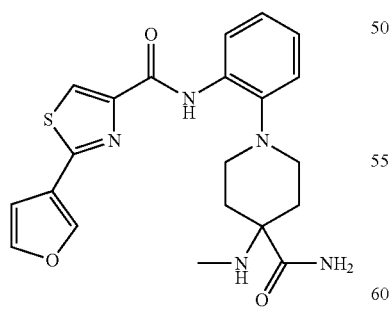

Using the method set forth in Example 99 above and substituting 3-pyridine-boronic acid for pyrrole-2-boronic acid, the title compound was prepared. HPLC-MS RT=2.59 minutes, mass calculated for formula $C_{23}H_{26}N_6O_2S$ 424.17, observed LCMS m/z 425.18 (M+H).

Example 192

Preparation of

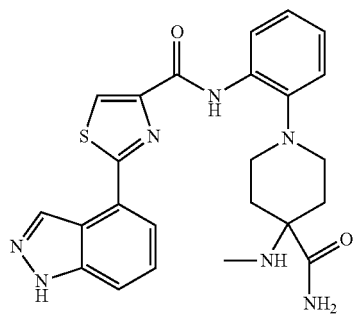

Using the method set forth in Example 99 above and substituting 3-pyridine-boronic acid for indazole-4-boronic acid, the title compound was prepared. HPLC-MS RT=2.98 minutes, mass calculated for formula $C_{24}H_{25}N_7O_2S$ 475.18, observed LCMS m/z 476.18 (M+H).

Example 193

Preparation of

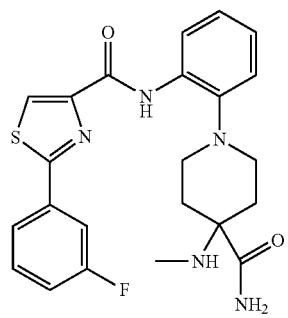 [SMILES: CNC1(C(N)=O)CCN(c2ccccc2NC(=O)c2csc(-c3cccc(F)c3)n2)CC1]

Using the method set forth in Example 99 above and substituting 3-pyridine-boronic acid for 3-fluoro-benzene-boronic acid, the title compound was prepared. HPLC-MS RT=3.19 minutes, mass calculated for formula $C_{23}H_{24}FN_5O_2S$ 453.16, observed LCMS m/z 454.16 (M+H).

Example 194

Preparation of

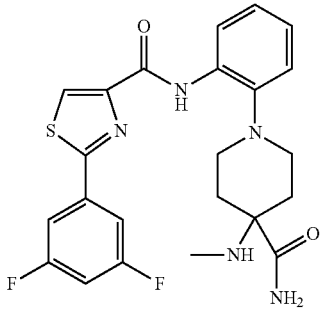 [SMILES: CNC1(C(N)=O)CCN(c2ccccc2NC(=O)c2csc(-c3cc(F)cc(F)c3)n2)CC1]

Using the method set forth in Example 99 above and substituting 3-pyridine-boronic acid for 3,5-difluoro-benzene-boronic acid, the title compound was prepared. HPLC-MS RT=3.27 minutes, mass calculated for formula $C_{23}H_{23}F_2N_5O_2S$ 471.15, observed LCMS m/z 472.16 (M+H).

Example 195

Preparation of

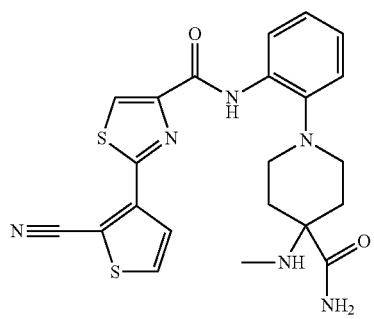 [SMILES: CNC1(C(N)=O)CCN(c2ccccc2NC(=O)c2csc(-c3ccsc3C#N)n2)CC1]

Using the method set forth in Example 99 above and substituting 3-pyridine-boronic acid for 2-cyano-thiophene-3-boronic acid, the title compound was prepared. HPLC-MS RT=3.01 minutes, mass calculated for formula $C_{22}H_{22}N_6O_2S_2$ 466.12, observed LCMS m/z 467.13 (M+H).

Example 196

Preparation of

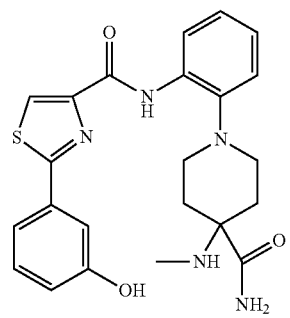 [SMILES: CNC1(C(N)=O)CCN(c2ccccc2NC(=O)c2csc(-c3cccc(O)c3)n2)CC1]

Using the method set forth in Example 99 above and substituting 3-pyridine-boronic acid for 3-hydroxy-benzene-boronic acid, the title compound was prepared. HPLC-MS RT=2.86 minutes, mass calculated for formula $C_{23}H_{25}N_5O_3S$ 451.17, observed LCMS m/z 452.17 (M+H).

Example 197

Preparation of

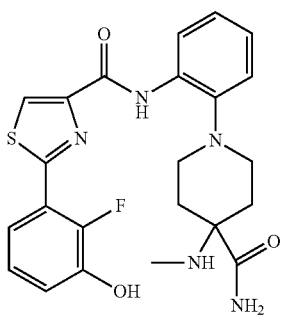 [SMILES: CNC1(C(N)=O)CCN(c2ccccc2NC(=O)c2csc(-c3cccc(O)c3F)n2)CC1]

Using the method set forth in Example 99 above and substituting 3-pyridine-boronic acid for 2-fluoro-3-hydroxy-benzene-boronic acid, the title compound was prepared. HPLC-MS RT=2.98 minutes, mass calculated for formula $C_{23}H_{24}FN_5O_3S$ 469.16, observed LCMS m/z 470.17 (M+H).

Example 198

Preparation of

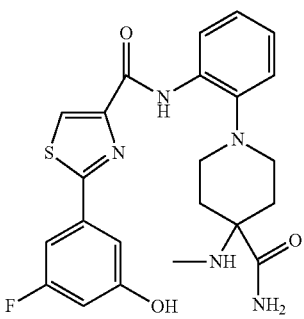 [SMILES: CNC1(C(N)=O)CCN(c2ccccc2NC(=O)c2csc(-c3cc(O)cc(F)c3)n2)CC1]

Using the method set forth in Example 99 above and substituting 3-pyridine-boronic acid for 5-fluoro-3-hydroxy-benzene-boronic acid, the title compound was prepared. HPLC-MS RT=2.88 minutes, mass calculated for formula $C_{23}H_{24}FN_5O_3S$ 469.16, observed LCMS m/z 470.17 (M+H).

Example 199

Preparation of

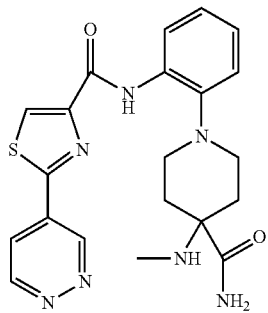 [SMILES: CNC1(C(N)=O)CCN(c2ccccc2NC(=O)c2csc(-c3ccnnc3)n2)CC1]

Step 1—Synthesis of Compound 199A

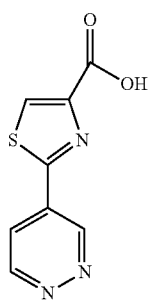

199A

A mixture of 4-tributylstannanyl-pyridazine (200 mg, 0.55 mmol), 2-bromo-thiazole-4-carboxylic acid ethyl ester (120 mg, 0.50 mmol), Pd(Ph$_3$P)$_4$ (60 mg) in toluene (3 mL) was degassed and heated under argon for 12 h at 110° C. The mixture was concentrated and purified by column flash chromatography (silica gel, CH$_2$Cl$_2$/EtOAc, 1:1) to provide compound 199A as light tan solid: $^1$H NMR 8.55 (s, 1H), 9.39 (dd, 1H, J=7.8 Hz, 1.2 Hz), 8.80 (s, 1H), 8.18 (m, 2H), 4.34 (q, 2H, J=6.8 Hz), 1.34 (3H, J=6.8 Hz).

Step 2—Synthesis of Compound 199B

199B

A mixture of compound 199A (360 mg, 1.53 mmol) and lithium hydroxide monohydrate (160 mg, 2.5 eq) in THF/H$_2$O (2:1, 15 mL) was stirred at rt for 12 h. THF was removed by vacuum and the resulting aqueous mixture was neutralized by 1 N HCl. The resulting solid product was collected by filtration and dried under vacuum to provide compound 199B. $^1$H NMR 10.57 (s, 1H, OH), 9.40 (d, 1H, J=7.8 Hz, 1.2 Hz), 8.75 (s, 1H), 8.09 (m, 2H).

Step 3—Synthesis of Title Compound

A mixture of compound 199B (42 mg, 0.20 mmol), compound 81A (50 mg, 0.2 mmol), EDCI (80 mg, 0.4 mmol) in pyridine (2.0 mL) was stirred at rt for 2 h, concentrated and purified by preparative LC to provide the title compound (42 mg, 0.20 mmol), as TFA salt. HPLC-MS RT=2.37 minutes, mass calculated for formula $C_{21}H_{23}N_7O_2S$ 437.16, observed LCMS m/z 438.17 (M+H).

Example 200

Preparation of

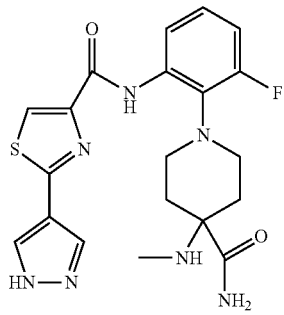 [SMILES: CNC1(C(N)=O)CCN(c2c(F)cccc2NC(=O)c2csc(-c3cn[nH]c3)n2)CC1]

Step 1—Synthesis of Compound 200A

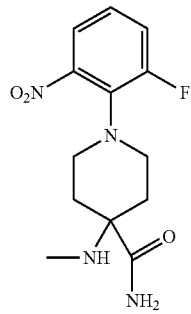
200A

A mixture of 4-methylamino-piperidine-4-carboxylic acid amide (200 mg, 0.55 mmol), 1,2-difluoro-3-nitro-benzene (120 mg, 0.75 mmol), triethylamine (0.10 mL, 0.55 mmol) in 4/1 $CH_3CN/MeOH$ (5.0 mL) toluene (3 mL) was degassed and heated under argon for 30 minutes at 150° C. by microwave. The mixture was concentrated and purified by column flash chromatography (silica gel, $CH_2Cl_2$/EtOAc, 1:1) to give Compound 200A as yellow solid.

Step 2—Synthesis of Compound 200B

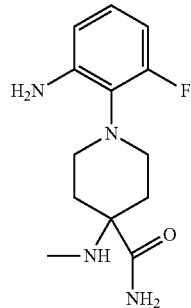
200B

A mixture of Compound 200A (100 mg, 0.33 mmol) and 10% Pd/C (10 mg) in EtOAc/MeOH (1:1, 5 mL) was degassed and stirred under hydrogen at rt for 4 h. The mixture was filtered and concentrated for next step without further purification.

Step 3—Synthesis of Compound 200C

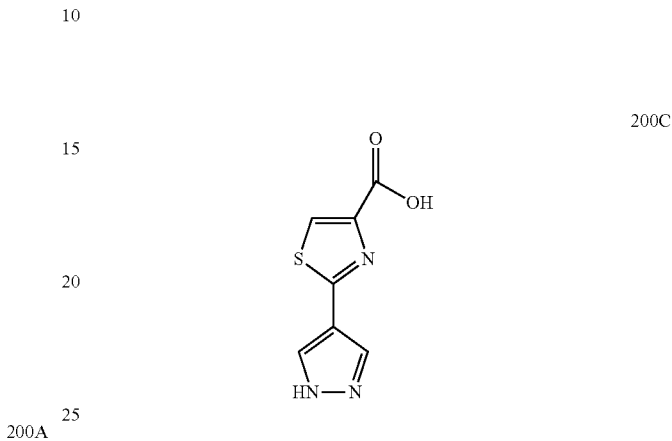
200C

A mixture of Compound 200C (62 mg, 0.32 mmol), Compound 200B (86 mg, 0.32 mmol), EDCl (125 mg, 0.64 mmol) in pyridine (5.0 mL) was stirred at rt for 2 h, concentrated and purified by preparative LC to provide the title compound as TFA salt. HPLC-MS RT=2.46 minutes, mass calculated for formula $C_{20}H_{22}N_7O_2S$ 443.15, observed LCMS m/z 444.16 (M+H).

Example 201

Preparation of

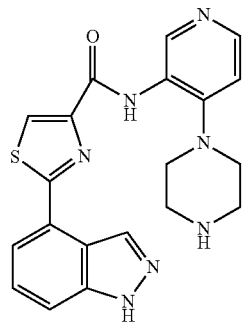 [SMILES: O=C(Nc1cnccc1N1CCNCC1)c1csc(-c2cccc3[nH]ncc23)n1]

A mixture of 4-indazole-boronic acid (17 mg, 0.07 mmol), (24 mg, 0.05 mmol), $Pd(Ph_3P)_4$, $K_2CO_3$ (22 mg) in a 3:1 mixture of dioxane/$H_2O$ (1 mL) was heated at 150° C. for 30 minutes by microwave. The mixture was cooled, concentrated and then treated with a 9:1 mixture of TFA/$H_2O$ at rt for 2 h and then concentrated. The residue was taken up into 3:1 mixture of DMSO/$CH_3CN$ and purified by preparative LC to provide the title compound as TFA salt. HPLC-MS RT=1.72 minutes, mass calculated for formula $C_{20}H_{13}N_7OS$ 405.14, observed LCMS m/z 406.15 (M+H).

Example 202

Preparation of

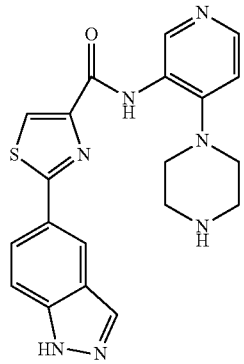 [SMILES: O=C(Nc1cnccc1N1CCNCC1)c1csc(-c2ccc3[nH]ncc3c2)n1]

Using the method set forth in Example 201 above and substituting 4-indazole-boronic acid for 5-indazole-boronic acid, the title compound was prepared. HPLC-MS RT=1.62 minutes, mass calculated for formula $C_{20}H_{13}N_7OS$ 405.14, observed LCMS m/z 406.15 (M+H).

Example 203

Preparation of

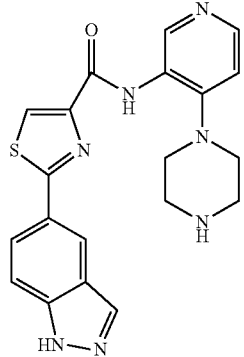 [SMILES: O=C(Nc1cnccc1N1CCNCC1)c1csc(-c2ccc3[nH]ncc3c2)n1]

Using the method set forth in Example 201 above and substituting 4-indazole-boronic acid for 7-indazole-boronic acid, the title compound was prepared. HPLC-MS RT=1.82 minutes, mass calculated for formula $C_{20}H_{19}N_7OS$ 405.14, observed LCMS m/z 406.15 (M+H).

Example 204

Preparation of

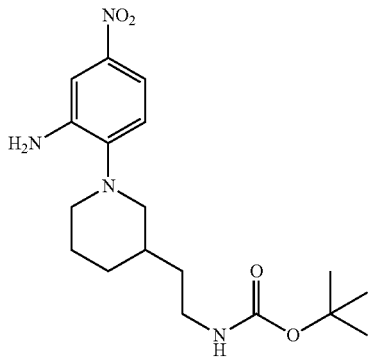 [SMILES: CC(C)(C)OC(=O)NCCC1CCCN(c2ccc([N+](=O)[O-])cc2N)C1]

To a solution of 2-fluoro-5-nitro-phenylamine (1.0 g, 6.4 mmol) and (2-piperidin-3-yl-ethyl)-carbamic acid tert-butyl ester (1.9 g, 8.3 mmol) in anhydrous 1,4-dioxane (5 mL) was added N,N-diisopropyl ethylamine (1.11 ml, 6.4 mmol). The mixture was heated at 100° C. for 16 h. The reaction mixture was cooled down, concentrated and purified with flash column chromatography (30%-50% EtOAc/hexanes) to provide the title compound (1.44 g, 62%). HPLC-MS RT=2.13 minutes, mass calculated for formula C18H28N4O4 364.21, observed LCMS m/z 365.91 (M+H).

Example 205

Preparation of

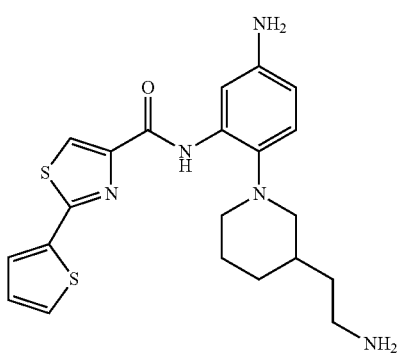

To a solution of {2-[1-(2-amino-4-nitro-phenyl)-piperidin-3-yl]-ethyl}-carbamic acid tert-butyl ester (1.0 g, 2.75 mmol) and 2-thiophen-2-yl-thiazole-4-carbonyl chloride (0.76 g, 3.30 mmol) in anhydrous dichloromethane (7 mL) and 1,4-dioxane (7 mL) was added triethylamine (0.77 ml, 5.5 mmol). The mixture was heated at 50° C. for 16 h. The reaction mixture was cooled down and concentrated. The residue was dissolved in ethanol (10 mL) and stirred in the presence of Pd/C (10%, 120 mg) and $H_2$ at atmospheric pressure for 6 h. The reaction mixture was filtered and concentrated. The crude residue was treated with 2.0 N HCl solution in 1,4-dioxane (2 mL) at rt for 2 h and then concentrated. The residue was taken up into 3:1 mixture of DMSO/CH₃CN and purified by preparative LC to provide the title compound as its TFA salt. HPLC-MS RT=2.62 minutes, mass calculated for formula C21H25N5OS2 427.15, observed LCMS m/z 428.15 (M+H).

Example 206

Preparation of

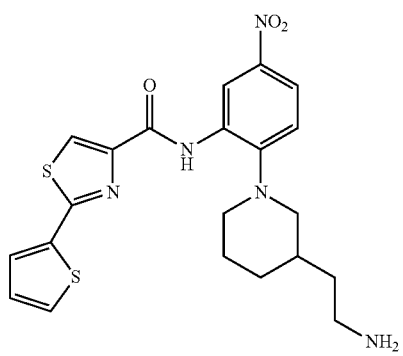

[2-(1-{4-Nitro-2-[(2-thiophen-2-yl-thiazole-4-carbonyl)-amino]-phenyl}-piperidin-3-yl)-ethyl]-carbamic acid tert-butyl ester (100 mg, 0.18 mmol) was treated with 2.0 N HCl solution in 1,4-dioxane (2 mL) at rt for 2 h and then concentrated. The residue was taken up into 3:1 mixture of DMSO/CH₃CN and purified by preparative LC to provide the title compound as its TFA salt. HPLC-MS RT=3.93 minutes, mass calculated for formula $C_{21}H_{23}N_5O_3S_2$ 457.12, observed LCMS m/z 458.13 (M+H).

Example 207

Preparation of

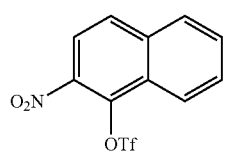 [SMILES: O=[N+]([O-])c1ccc2ccccc2c1OS(=O)(=O)C(F)(F)F]

To a solution of 2-Nitro-naphthalen-1-ol (1.0 g, 5.3 mmol) and N,N-diisopropyl ethylamine (1.11 ml, 6.4 mmol) in anhydrous dichloromethane (5 mL) was added triflic anhydride (1.5 g, 5.3 mmol). The mixture was stirred at room temp for 16 h. The reaction mixture was concentrated and purified with flash column chromatography (20%-30% EtOAc/hexanes) to provide the title compound. HPLC-MS RT=2.18 minutes, mass calculated for formula C11H6F3NO5S 320.99, observed LCMS m/z 321.99 (M+H).

Example 208

Preparation of

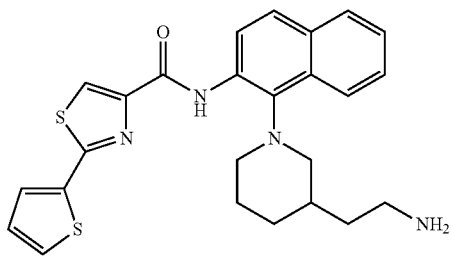 [SMILES: NCCC1CCCN(c2c(NC(=O)c3csc(-c4cccs4)n3)ccc3ccccc23)C1]

To a solution of trifluoro-methanesulfonic acid 2-nitro-naphthalen-1-yl ester (1.7 g, 5.3 mmol) and (2-Piperidin-3-yl-ethyl)-carbamic acid tert-butyl ester (1.21 g, 5.30 mmol) in anhydrous 1,4-dioxane (4 mL) was added N,N-diisopropyl ethylamine (0.77 ml, 5.5 mmol). The mixture was heated at 160° C. for 2 h. The reaction mixture was cooled down and concentrated. The residue was dissolved in ethanol (10 mL) and stirred in the presence of Pd/C (10%, 120 mg) and H₂ at atmospheric pressure for 6 h. The reaction mixture was filtered and concentrated. To a solution of the crude residue (110 mg) and 2-thiophen-2-yl-thiazole-4-carbonyl chloride (90 mg, 0.387 mmol) in anhydrous dichloromethane (1 mL) was added triethylamine (0.08 mL). The reaction mixture was stirred for 16 h and concentrated. The crude residue was treated with 2.0 N HCl solution in 1,4-dioxane (2 mL) at rt for 2 h and then concentrated. The residue was taken up into 3:1 mixture of DMSO/CH₃CN and purified by preparative LC to provide the title compound as its TFA salt. HPLC-MS RT=4.56 minutes, mass calculated for formula C25H26N4OS2 462.15, observed LCMS m/z 463.16 (M+H).

Example 209

Preparation of

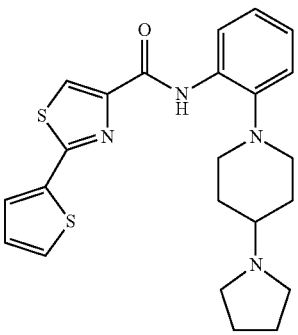 [SMILES: O=C(Nc1ccccc1N1CCC(N2CCCC2)CC1)c1csc(-c2cccs2)n1]

Step 1—Synthesis of Intermediate 209A

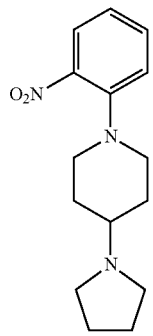

209A

A solution of 4-(1-pyrrolidinyl)piperidine (1.29 mmol, 0.20 g), N,N-diisopropylethylamine (1.0 eq, 1.29 mmol, 224.7 µL) and 1-fluoro-2-nitrobenzene (0.60 eq, 82 µL) in ACN (2 mL) was irradiated using microwave for 10 minutes at a temperature of 180° C. The solution was then cooled to room temperature and concentrated in vacuo to provide compound 209A. HPLC-MS RT=1.00 min, mass calculated for formula $C_{15}H_{21}N_3O_2$ 275.35, observed LCMS m/z 276.18 (M+H).

Step 2—Synthesis Compound 209B

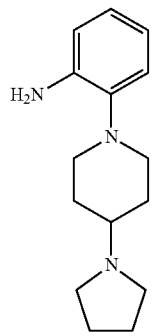

209B

Remove 50 mg from the reaction vial and place into 4 mL vial. Add 2 scoops of Amberlite resin and 2 scoops of isocyanate resin and DCM (1 mL) and DMF (1 mL). Shake solution and resin at room temperature for 24 hours. Filter out resin and evaporate solvent. Add 10% Pd/Carbon (15 mg) and ethyl acetate (15 mL), degass solution and then add $H_2$ balloon. Stir solution at room temperature for about 30 min (or until yellow was gone) and filter out Pd/C through Celite to provide compound 209B. HPLC-MS RT=0.702 min, mass calculated for formula $C_{15}H_{23}N_3$ 245.36, observed LCMS m/z 246.23 (M+H).

Step 3—Synthesis of Title Compound

To the solution of compound 209B (0.095 mmol) was added 2-thiophen-2-yl-thiazole-4-carboxylic acid (0.095 mmol, 0.020 g) in DMF (1 mL). Then, a solution of N,N-diisopropylethylamine (1 eq, 0.095 mmol, 16.5 µL) HOBT (1 eq, 0.095 mmol, 0.013 g), EDC (1 eq, 0.095 mmol, 0.018 g) was added. The resulting reaction was stirred at 50° C. for 15 hours. The reaction mixture was concentrated and purified using reverse phase HPLC to provide the title compound. HPLC-MS RT=3.85 minutes, mass calculated for formula $C_{23}H_{26}N_4OS_2$ 438.15, observed LCMS m/z 439.15 (M+H).

Example 210

Preparation of

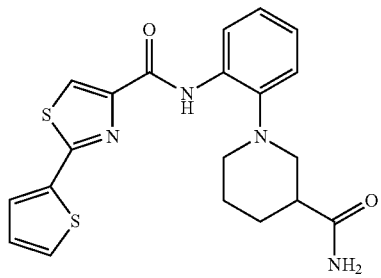 [SMILES: NC(=O)C1CCCN(c2ccccc2NC(=O)c2csc(-c3cccs3)n2)C1]

Using the method described in Example 209 and utilizing the appropriate reactants, the title compound was made. HPLC-MS RT=4.31 min, mass calculated for formula $C_{20}H_{20}N_4O_2S_2$ 412.10, observed LCMS m/z 413.12 (M+H).

Example 211

Preparation of

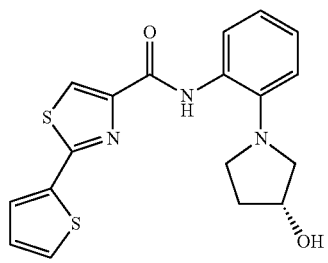 [SMILES: O=C(Nc1ccccc1N1CC[C@@H](O)C1)c1csc(-c2cccs2)n1]

Using the method described in Example 209 and utilizing the appropriate reactants, the title compound was made. HPLC-MS RT=3.83 min, mass calculated for formula $C_{18}H_{17}N_3O_2S_2$ 371.08, observed LCMS m/z 372.09 (M+H).

Example 212

Preparation of

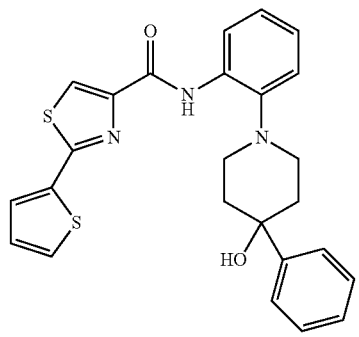 [SMILES: O=C(Nc1ccccc1N1CCC(O)(c2ccccc2)CC1)c1csc(-c2cccs2)n1]

Using the method described in Example 209 and utilizing the appropriate reactants, the title compound was made.

HPLC-MS RT=5.40 min, mass calculated for formula $C_{25}H_{23}N_3O_2S_2$ 461.12, observed LCMS m/z 462.14 (M+H).

Example 213

Preparation of

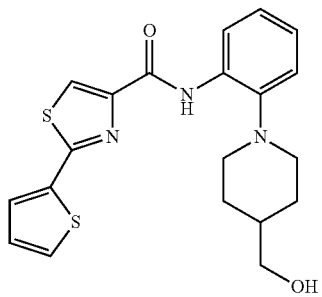 [SMILES: O=C(Nc1ccccc1N1CCC(CO)CC1)c1csc(-c2cccs2)n1]

Using the method described in Example 209 and utilizing the appropriate reactants, the title compound was made. HPLC-MS RT=4.55 min, mass calculated for formula $C_{20}H_{21}N_3O_2S_2$ 399.53, observed LCMS m/z 400.14 (M+H).

Example 214

Preparation of

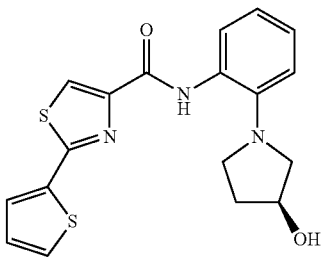 [SMILES: O=C(Nc1ccccc1N1CC[C@H](O)C1)c1csc(-c2cccs2)n1]

Using the method described in Example 209 and utilizing the appropriate reactants, the title compound was made. HPLC-MS RT=3.82 min, mass calculated for formula $C_{18}H_{17}N_3O_2S_2$ 371.08, observed LCMS m/z 372.08 (M+H).

Example 215

Preparation of

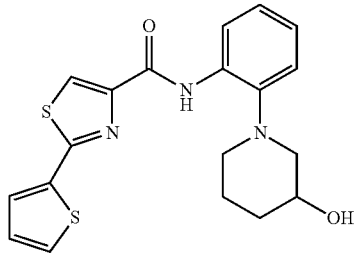 [SMILES: O=C(Nc1ccccc1N1CCCC(O)C1)c1csc(-c2cccs2)n1]

Using the method described in Example 209 and utilizing the appropriate reactants, the title compound was made. HPLC-MS RT=4.56 min, mass calculated for formula $C_{19}H_{19}N_3O_2S_2$ 385.09, observed LCMS m/z 386.10 (M+H).

Example 216

Preparation of

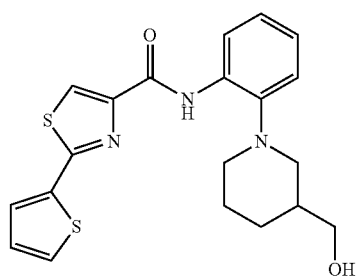 [SMILES: O=C(Nc1ccccc1N1CCCC(CO)C1)c1csc(-c2cccs2)n1]

Using the method described in Example 209 and utilizing the appropriate reactants, the title compound was made. HPLC-MS RT=4.68 min, mass calculated for formula $C_{20}H_{21}N_3O_2S_2$ 399.11, observed LCMS m/z 400.07 (M+H).

Example 217

Preparation of

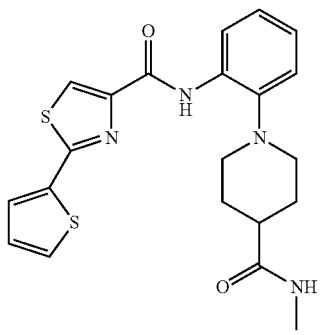 [SMILES: CNC(=O)C1CCN(c2ccccc2NC(=O)c2csc(-c3cccs3)n2)CC1]

Using the method described in Example 209 and utilizing the appropriate reactants, the title compound was made. HPLC-MS RT=4.41 min, mass calculated for formula $C_{21}H_{22}N_4O_2S_2$ 426.12, observed LCMS m/z 427.14 (M+H).

Example 218

Preparation of

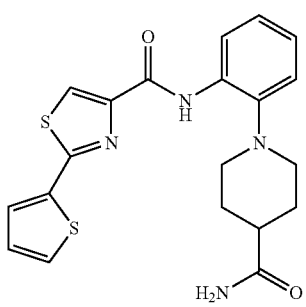 [SMILES: NC(=O)C1CCN(c2ccccc2NC(=O)c2csc(-c3cccs3)n2)CC1]

Using the method described in Example 209 and utilizing the appropriate reactants, the title compound was made. HPLC-MS RT=4.31 min, mass calculated for formula $C_{20}H_{20}N_4O_2S_2$ 412.10, observed LCMS m/z 413.12 (M+H).

Example 219

Preparation of

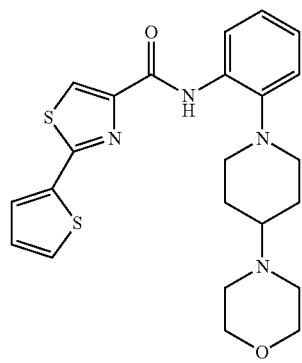 [SMILES: O=C(Nc1ccccc1N1CCC(N2CCOCC2)CC1)c1csc(-c2cccs2)n1]

Using the method described in Example 209 and utilizing the appropriate reactants, the title compound was made. HPLC-MS RT=3.69 min, mass calculated for formula $C_{23}H_{26}N_4O_2S_2$ 454.15, observed LCMS m/z 455.13 (M+H).

Example 220

Preparation of

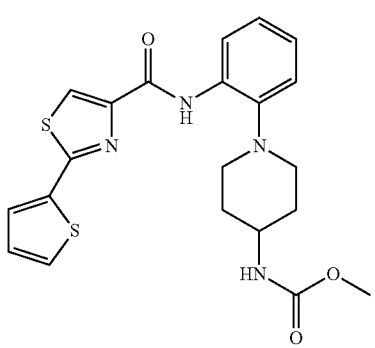 [SMILES: COC(=O)NC1CCN(c2ccccc2NC(=O)c2csc(-c3cccs3)n2)CC1]

Using the method described in Example 209 and utilizing the appropriate reactants, the title compound was made. HPLC-MS RT=4.95 min, mass calculated for formula $C_{21}H_{22}N_4O_2S_2$ 442.11, observed LCMS m/z 443.12 (M+H).

Example 221

Preparation of

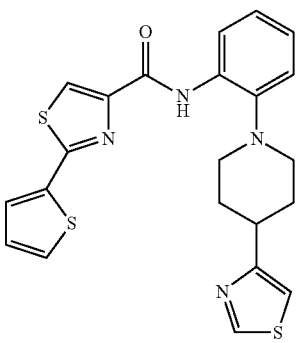 [SMILES: O=C(Nc1ccccc1N1CCC(c2cscn2)CC1)c1csc(-c2cccs2)n1]

Using the method described in Example 209 and utilizing the appropriate reactants, the title compound was made. HPLC-MS RT=5.49 min, mass calculated for formula $C_{22}H_{20}N_4OS_3$ 452.08, observed LCMS m/z 453.08 (M+H).

Example 222

Preparation of

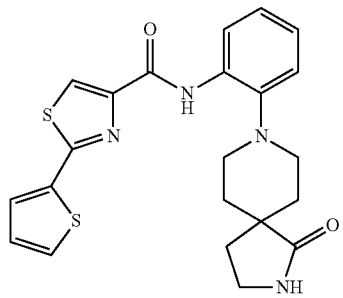 [SMILES: O=C(Nc1ccccc1N1CCC2(CCNC2=O)CC1)c1csc(-c2cccs2)n1]

Using the method described in Example 209 and utilizing the appropriate reactants, the title compound was made. HPLC-MS RT=4.66 min, mass calculated for formula $C_{22}H_{22}N_4O_2S_2$ 438.12, observed LCMS m/z 439.14 (M+H).

Example 223

Preparation of

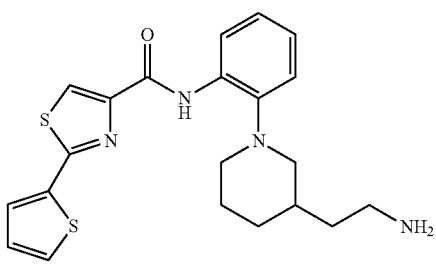 [SMILES: NCCC1CCCN(c2ccccc2NC(=O)c2csc(-c3cccs3)n2)C1]

Step 1—Synthesis of Compound 223A

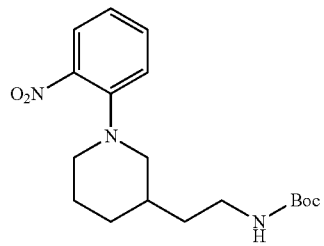

223A

A solution of 3-(N-Boc-aminoethyl)piperidine (1.31 mmol, 0.300 g),N,N-diisopropylethylamine (1.2 eq, 1.57 mmol, 274 µL) and 1-fluoro-2-nitrobenzene (0.98 eq, 135 µL) in ACN (2 mL) was irradiated using microwave for 20 minutes at a temperature of 200° C. The solution was then cooled to room temperature and concentrated in vacuo and the resulting residue was purified using column chromatography on silica gel with an eluent mixture of Hexane/EtOAc and concentrated to provide compound 223A (0.353 g). HPLC-MS RT=2.37 min, mass calculated for formula $C_{18}H_{27}N_3O_4$ 349.20, observed LCMS m/z 350.20 (M+H).

Step 2—Synthesis of Compound 223B

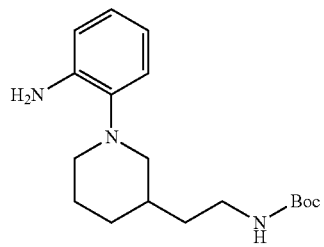

223B

A solution of Intermediate compound 223A (0.353 g) in EtOAc (40 mL) was hydrogenated in the H-Cube using a 10% Pd/C cartridge with the following settings:

| H-Cube Settings | |
|---|---|
| Pressure Regulator: | 20 bar |
| Column Heater: | 40° C. |
| Hydrogen: | Controlled |
| HPLC Pump: | 0.7 mL/min |

The resulting reaction mixture was concentrated in vacuo to provide compound 223B (0.302 g). HPLC-MS RT=1.40 min, mass calculated for formula $C_{18}H_{29}N_3O_2$ 319.23, observed LCMS m/z 320.20 (M+H).

Step 3—Preparation of Title Compound

To a solution of compound 223B (0.31 mmol, 0.1 g) in DMF (2 mL) was added N,N-diisopropylethylamine (1.2 eq, 0.37 mmol, 48 µL) HATU (1.2 eq, 0.37 mmol, 143 mg) and 2-thiophen-2-yl-thiazole-4-carboxylic acid (0.31 mmol, 65 mg). The resulting reaction was stirred at room temperature for 15 hours. The reaction mixture was concentrated. The residue was reacted with TFA:H2O (90:10), (1.0 mL) for 30 minutes. The TFA solution was concentrated in vacuo. The residue was dissolved in DMSO/acetonitrile (3:1), purified using reverse phase HPLC to provide the title compound (0.113 g). HPLC-MS RT=3.71 min, mass calculated for formula $C_{21}H_{24}N_4OS_2$ 412.14, observed LCMS m/z 413.18 (M+H).

Example 224

Preparation of

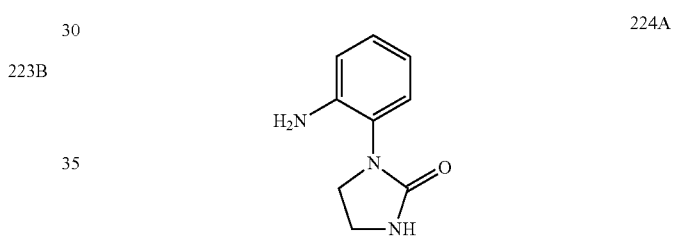

Step 1—Synthesis of Compound 224A

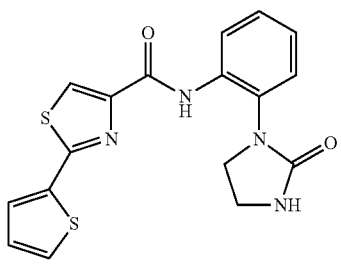 [SMILES: O=C(Nc1ccccc1N1CCNC1=O)c1csc(-c2cccs2)n1]

224A

A solution of 1-(2-nitro-phenyl) imidazolidin-2-one (0.070 g) in methanol (10 mL) was hydrogenated in the H-Cube using a 10% Pd/C cartridge with the following settings:

| H-Cube Settings | |
|---|---|
| Pressure Regulator: | 30 bar |
| Column Heater: | 50° C. |
| Hydrogen: | Controlled |
| HPLC Pump: | 0.7 mL/min |

The resulting reaction mixture was concentrated in vacuo to provide compound 224A (0.055 g). HPLC-MS RT=0.219 min, mass calculated for formula $C_9H_{11}N_3O$ 177.09, observed LCMS m/z 178.10 (M+H).

Step 2—Preparation of Title Compound

To a solution of compound 224A (0.31 mmol, 0.055 g) in DMF (2 mL) was added N,N-diisopropylethylamine (1.2 eq, 0.37 mmol, 64.8 µL) HATU (1.2 eq, 0.37 mmol, 0.141 g) and 2-thiophen-2-yl-thiazole-4-carboxylic acid (0.31 mmol, 0.065 mg). The resulting reaction was stirred at room temperature for 15 hours. The reaction mixture was concentrated. The residue was dissolved in DMSO/acetonitrile (3:1), and purified using reverse phase HPLC to provide 2-Thiophen-2-yl-thiazole-4-carboxylic acid [2-(2-oxo-imidazolidin-1-yl)- phenyl]-amide (0.087 g). HPLC-MS RT=3.32 min, mass calculated for formula $C_{17}H_{14}N_4O_2S_2$ 370.06, observed LCMS m/z 371.17 (M+H).

Example 225

Preparation of

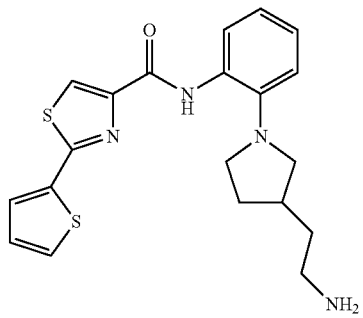 [SMILES: NCCC1CCN(c2ccccc2NC(=O)c2csc(-c3cccs3)n2)C1]

Using the method described in Example 233, and utilizing the appropriate reactants, the title compound was made. HPLC-MS RT=3.05 min, mass calculated for formula $C_{20}H_{22}N_3OS_2$ 398.12, observed LCMS m/z 399.23 (M+H).

Example 226

Preparation of

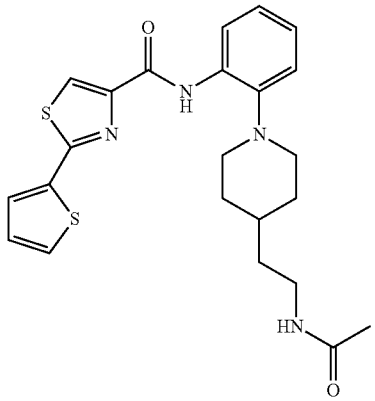 [SMILES: CC(=O)NCCC1CCN(c2ccccc2NC(=O)c2csc(-c3cccs3)n2)CC1]

Using the method described in Example 233, and utilizing the appropriate reactants, the title compound was made. HPLC-MS RT=4.48 min, mass calculated for formula $C_{23}H_{26}N_4O_2S_2$ 454.15, observed LCMS m/z 455.19 (M+H).

Example 227

Preparation of

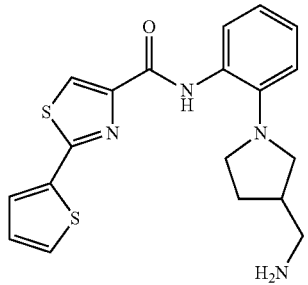 [SMILES: NCC1CCN(c2ccccc2NC(=O)c2csc(-c3cccs3)n2)C1]

Using the method described in Example 233 (except 10% Pd on carbon powder was used at room temperature overnight instead of the H-Cube for Step 2), and utilizing the appropriate reactants, the title compound was made. HPLC-MS RT=3.40 min, mass calculated for formula $C_{19}H_{20}N_4OS_2$ 384.11, observed LCMS m/z 385.17 (M+H).

Example 228

Preparation of

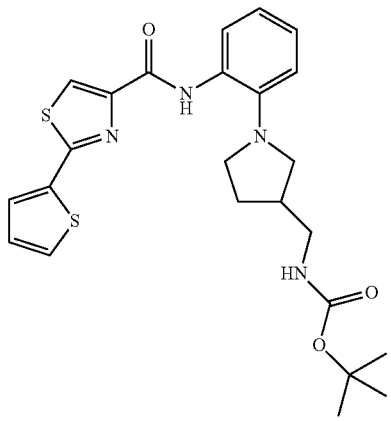 [SMILES: CC(C)(C)OC(=O)NCC1CCN(c2ccccc2NC(=O)c2csc(-c3cccs3)n2)C1]

Using the method described in Example 233 (except the Boc group was not removed with 90:10 TFA:$H_2O$ in the final step), and utilizing the appropriate reactants, the title compound was made. HPLC-MS RT=5.11 min, mass calculated for formula $C_{24}H_{28}N_4O_3S_2$ 484.16, observed LCMS m/z 485.60 (M+H).

Example 229

Preparation of

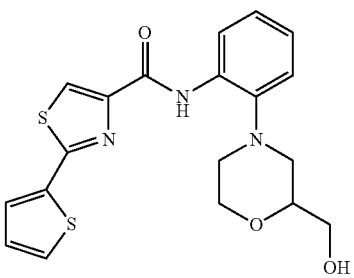 [SMILES: O=C(Nc1ccccc1N1CCOC(CO)C1)c1csc(-c2cccs2)n1]

The procedure follows the same steps as Example 17 except after Step 1 a Boc group was placed on the hydroxy group using the following method:

Add 2 mL of THF, N,N-diisopropylethylamine (2 eq) and di-t-butyl-dicarbonate (0.5 eq), and DMAP. Heat the solution to 100° C. overnight. Evaporate solvent and then column in 50:50 ethyl acetate:hexane. Also note:

| H-Cube Settings | |
|---|---|
| Pressure Regulator: | 0 bar |
| Column Heater: | 35° C. |
| Hydrogen: | Full H$_2$ |
| HPLC Pump: | 1.0 mL/min |

HPLC-MS RT=4.24 min, mass calculated for formula C$_{19}$H$_{19}$N$_3$O$_3$S$_2$ 401.09, observed LCMS m/z 402.10 (M+H).

Example 230

Preparation of

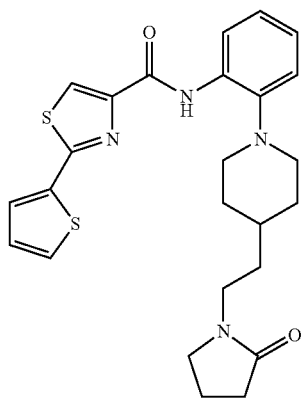 [SMILES: O=C(Nc1ccccc1N1CCC(CCN2CCCC2=O)CC1)c1csc(-c2cccs2)n1]

Using the method described in Example 233, and utilizing the appropriate reactants, the title compound was made. HPLC-MS RT=4.88 min, mass calculated for formula C$_{25}$H$_{28}$N$_4$O$_2$S$_2$ 480.17, observed LCMS m/z 481.21 (M+H).

Example 231

Preparation of

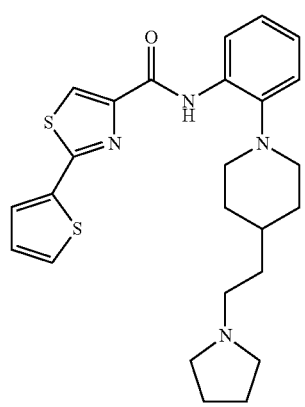 [SMILES: O=C(Nc1ccccc1N1CCC(CCN2CCCC2)CC1)c1csc(-c2cccs2)n1]

Using the method described in Example 233, and utilizing the appropriate reactants, the title compound was made. HPLC-MS RT=3.51 min, mass calculated for formula C$_{25}$H$_{30}$N$_4$OS$_2$ 466.19, observed LCMS m/z 467.22 (M+H).

Example 232

Preparation of

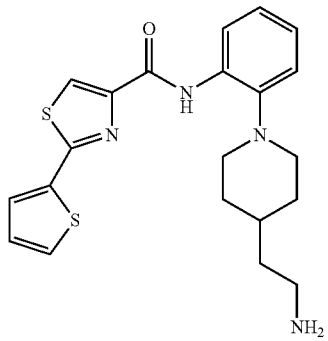 [SMILES: NCCC1CCN(c2ccccc2NC(=O)c2csc(-c3cccs3)n2)CC1]

Using the method described in Example 233, and utilizing the appropriate reactants, the title compound was made. HPLC-MS RT=3.44 min, mass calculated for formula C$_{21}$H$_{24}$N$_4$OS$_2$ 412.14, observed LCMS m/z 413.15 (M+H).

Example 233

Preparation of

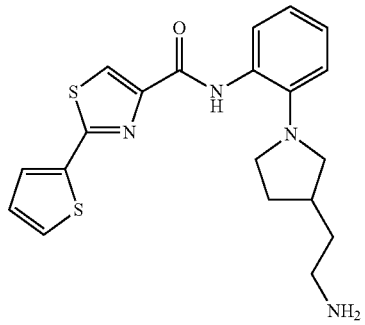 [SMILES: NCCC1CCN(c2ccccc2NC(=O)c2csc(-c3cccs3)n2)C1]

Using the method described in Example 233, and utilizing the appropriate reactants, the title compound was made. HPLC-MS RT=3.05 min, mass calculated for formula C$_{20}$H$_{22}$N$_4$OS$_2$ 398.12, observed LCMS m/z 399.23 (M+H).

Example 234

Preparation of

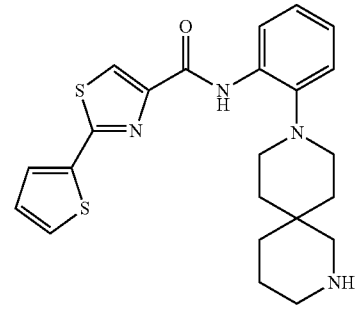 [SMILES: O=C(Nc1ccccc1N1CCC2(CCCNC2)CC1)c1csc(-c2cccs2)n1]

Using the method described in Example 233, and utilizing the appropriate reactants, the title compound was made.

HPLC-MS RT=3.64 min, mass calculated for formula $C_{23}H_{26}N_4OS_2$ 438.15, observed LCMS m/z 439.20 (M+H).

Example 235

Preparation of

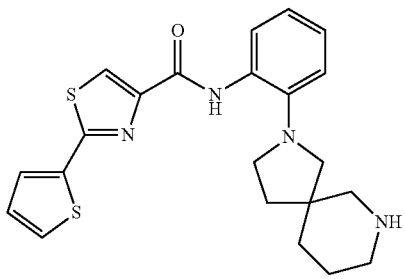 [SMILES: O=C(Nc1ccccc1N1CCC2(CCCNC2)C1)c1csc(-c2cccs2)n1]

Using the method described in Example 233, and utilizing the appropriate reactants, the title compound was made. HPLC-MS RT=3.48 min, mass calculated for formula $C_{22}H_{24}N_4OS_2$ 424.14, observed LCMS m/z 425.22 (M+H).

Example 236

Preparation of

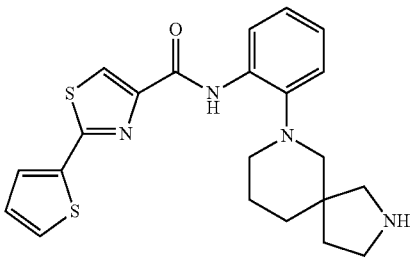 [SMILES: O=C(Nc1ccccc1N1CCCC2(CCNC2)C1)c1csc(-c2cccs2)n1]

Using the method described in Example 233, and utilizing the appropriate reactants, the title compound was made. HPLC-MS RT=3.58 min, mass calculated for formula $C_{22}H_{24}N_4OS_2$ 424.14, observed LCMS m/z 425.27 (M+H).

Example 237

Preparation of

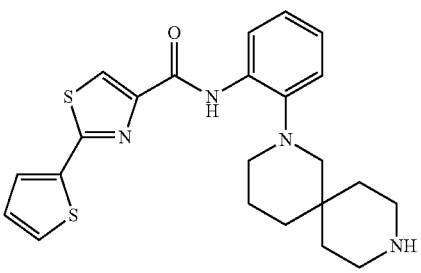 [SMILES: O=C(Nc1ccccc1N1CCCC2(CCNCC2)C1)c1csc(-c2cccs2)n1]

Using the method described in Example 233, and utilizing the appropriate reactants, the title compound was made.

HPLC-MS RT=3.72 min, mass calculated for formula $C_{23}H_{26}N_4OS_2$ 438.15, observed LCMS m/z 439.27 (M+H).

Example 238

Preparation of

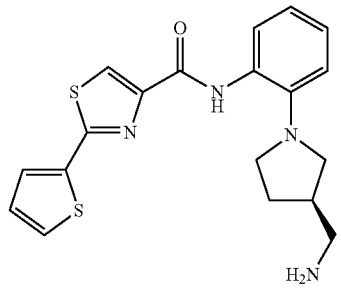 [SMILES: NC[C@H]1CCN(c2ccccc2NC(=O)c2csc(-c3cccs3)n2)C1]

Using the method described in Example 233, and utilizing the appropriate reactants, the title compound was made. HPLC-MS RT=3.12 min, mass calculated for formula $C_{19}H_{20}N_4OS_2$ 384.11, observed LCMS m/z 385.21 (M+H).

Example 239

Preparation of

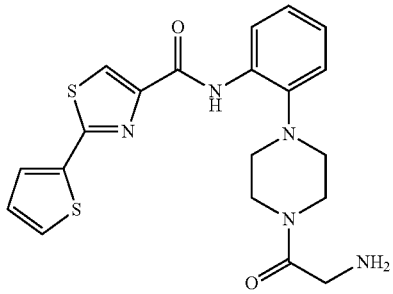 [SMILES: NCC(=O)N1CCN(c2ccccc2NC(=O)c2csc(-c3cccs3)n2)CC1]

Using the method described in Example 233, and utilizing the appropriate reactants, the title compound was made. HPLC-MS RT=3.16 min, mass calculated for formula $C_{20}H_{21}N_5O_2S_2$ 427.11, observed LCMS m/z 428.14 (M+H).

Example 240

Preparation of

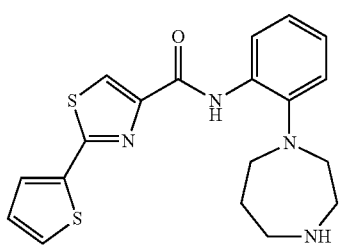 [SMILES: O=C(Nc1ccccc1N1CCCNCC1)c1csc(-c2cccs2)n1]

Using the method described in Example 233, and utilizing the appropriate reactants, the title compound was made.

HPLC-MS RT=3.11 min, mass calculated for formula $C_{19}H_{20}N_4OS_2$ 384.11, observed LCMS m/z 385.23 (M+H).

Example 241

Preparation of

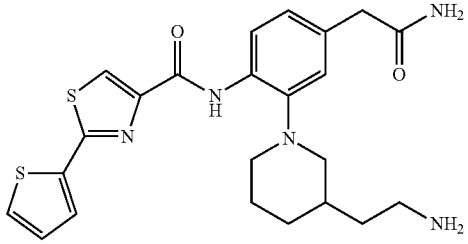 [SMILES: NCCC1CCCN(c2cc(CC(N)=O)ccc2NC(=O)c2csc(-c3cccs3)n2)C1]

Step 1—Synthesis of Compound 241A

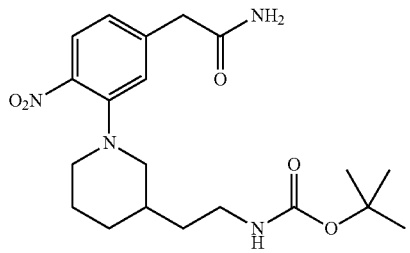 [SMILES: CC(C)(C)OC(=O)NCCC1CCCN(c2cc(CC(N)=O)ccc2N)C1]

241A

A solution of 2-(3-Chloro-4-nitro-phenyl)-acetamide (0.14 mmol, 0.030 g), N,N-diisopropylethylamine (1.2 eq, 0.17 mmol, 22.0 μL) and (2-Piperidin-3-yl-ethyl)-carbamic acid tert-butyl ester (1.0 eq, 32.0 mg) in ACN (2 mL) was irradiated using microwave for 18 minutes at a temperature of 180° C. The solution was then cooled to room temperature and concentrated in vacuo to provide compound 241A (0.020 g). HPLC-MS RT=1.72 min, mass calculated for formula $C_{20}H_{30}N_4O_5$ 406.22, observed LCMS m/z 407.20 (M+H).

Step 2—Synthesis of Compound 241B

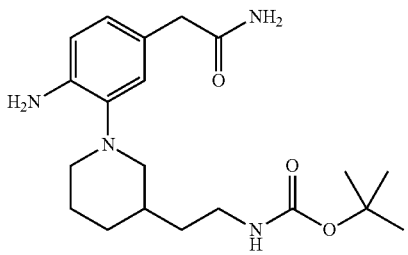

A solution of compound 241A in methanol (5.0 mL) was hydrogenated in the H-Cube using a 5% Pd/C cartridge with the following settings:

| H-Cube Settings | |
|---|---|
| Pressure Regulator: | 20 bar |
| Column Heater: | 45° C. |
| Hydrogen: | Controlled |
| HPLC Pump: | 1 mL/min |

The resulting reaction mixture was concentrated in vacuo to provide compound 241B (0.017 g). HPLC-MS RT=1.19 min, mass calculated for formula $C_{20}H_{32}N_4O_3$ 376.25, observed LCMS m/z 377.20 (M+H).

Step 3—Synthesis of Title Compound

To a solution of compound 241B (17 mg) in DMF (1 mL) was added 2-thiophen-2-yl-thiazole-4-carboxylic acid (0.98 eq, 9 mg). This mixture was heated to 50° C. Then, a solution of N,N-diisopropylethylamine (1.5 eq, 11.7 μL) and HATU (1.5 eq, 0.026 g) was added. The resulting reaction was stirred at room temperature for 15 hours. The resulting solution was concentrated and treated with 1 mL of (90:10) TFA:$H_2O$. The reaction mixture was concentrated and purified using reverse phase HPLC to the title compound. HPLC-MS RT=3.20 min, mass calculated for formula $C_{23}H_{27}N_5O_2S_2$ 469.16, observed LCMS m/z 470.30 (M+H).

Example 242

Preparation of

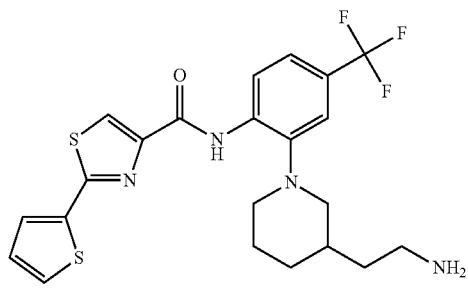 [SMILES: NCCC1CCCN(c2cc(C(F)(F)F)ccc2NC(=O)c2csc(-c3cccs3)n2)C1]

Using the method described in Example 241, and substituting 3-chloro-4-nitrobenzene trifluoride for 2-(3-chloro-4-nitro-phenyl)-acetamide in step 1, the title compound was made. HPLC-MS RT=4.31 min, mass calculated for formula $C_{22}H_{23}F_3N_4OS_2$ 480.13, observed LCMS m/z 481.27 (M+H).

Note

| H-Cube Settings | |
|---|---|
| Pressure Regulator: | 20 bar |
| Column Heater: | 40° C. |
| Hydrogen: | Controlled $H_2$ |
| HPLC Pump: | 0.8 mL/min |

Example 243

Preparation of

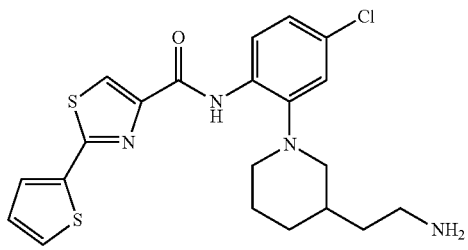 [SMILES: NCCC1CCCN(c2cc(Cl)ccc2NC(=O)c2csc(-c3cccs3)n2)C1]

Using the method described in Example 241, and substituting 4-chloro-2-fluoronitrobenzene for 2-(3-chloro-4-nitrophenyl)-acetamide in step 1, the title compound was made. HPLC-MS RT=4.12 min, mass calculated for formula $C_{21}H_{23}ClN_4OS_2$ 446.10, observed LCMS m/z 447.24 (M+H).

Note

| H-Cube Settings | |
|---|---|
| Pressure Regulator: | 0 bar |
| Column Heater: | 30° C. |
| Hydrogen: | Controlled $H_2$ |
| HPLC Pump: | 0.8 mL/min |

Example 244

Preparation of

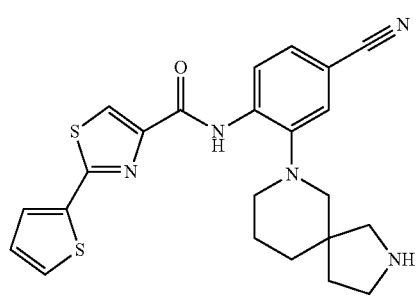 [SMILES: N#Cc1ccc(NC(=O)c2csc(-c3cccs3)n2)c(N2CCCC3(CCNC3)C2)c1]

Using the method described in Example 241, and substituting 3-fluoro-4-nitrobenzonitrile for 2-(3-chloro-4-nitrophenyl)-acetamide in step 1, the title compound was made. HPLC-MS RT=3.62 min, mass calculated for formula $C_{23}H_{23}N_5OS_2$ 449.13, observed LCMS m/z 450.21 (M+H).

Example 245

Preparation of

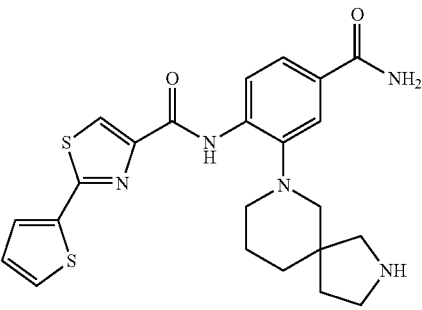 [SMILES: NC(=O)c1ccc(NC(=O)c2csc(-c3cccs3)n2)c(N2CCCC3(CCNC3)C2)c1]

Using the method described in Example 244, and replacing step 3 with the procedure listed below, the title compound was made:

To the solution of 7-(2-Amino-5-cyano-phenyl)-2,7-diaza-spiro[4.5]decane-2-carboxylic acid tert-butyl ester was added 2-thiophen-2-yl-thiazole-4-carboxylic acid (product of step 2, 0.98 eq,) in DMF (1 mL). Then, a solution of N,N-diisopropylethylamine (1.5 eq) HATU (1.5 eq) was added. The resulting reaction was stirred at room temperature for 15 hours and then concentrated and treated with 3 mL of (4:1) TFA:$H_2SO_4$. The reaction mixture was concentrated and purified using reverse phase HPLC to provide 2-Thiophen-2-yl-thiazole-4-carboxylic acid {2-[3-(2-amino-ethyl)-piperidin-1-yl]-4-carbamoylmethyl-phenyl}-amide. HPLC-MS RT=3.13 min, mass calculated for formula $C_{23}H_{25}N_5O_2S_2$ 467.14, observed LCMS m/z 468.21 (M+H).

Example 246

Preparation of

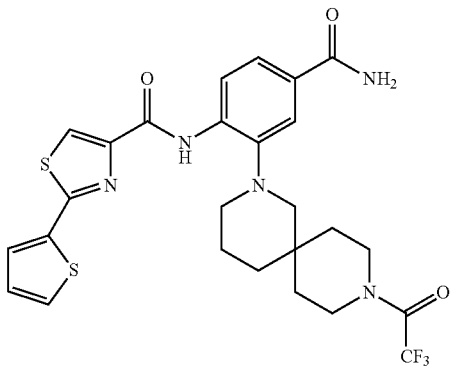 [SMILES: NC(=O)c1ccc(NC(=O)c2csc(-c3cccs3)n2)c(N2CCCC3(CCN(C(=O)C(F)(F)F)CC3)C2)c1]

Using the method described in Example 244, and replacing step 3 with the procedure listed below, the title compound was made:

To Intermediate 4-Amino-3-[9-(2,2,2-trifluoro-acetyl)-2,9-diaza-spiro[5.5]undec-2-yl]-benzonitrile was added 2-thiophen-2-yl-thiazole-4-carboxylic acid (098 eq) in DMF (1 mL). Then, a solution of N,N-diisopropylethylamine (1.5 eq) HATU (1.5 eq) was added. The resulting reaction was stirred at room temperature for 15 hours and then concentrated and treated with 3 mL of (4:1) TFA:H$_2$SO$_4$. The reaction mixture was concentrated and purified using reverse phase HPLC to provide 2-Thiophen-2-yl-thiazole-4-carboxylic acid {4-carbamoyl-2-[9-(2,2,2-trifluoro-acetyl)-2,9-diaza-spiro[5.5]undec-2-yl]-phenyl}-amide. HPLC-MS RT=4.46 min, mass calculated for formula C$_{26}$H$_{26}$F$_3$N$_5$O$_3$S$_2$ 577.14, observed LCMS m/z 578.21 (M+H).

Example 247

Preparation of

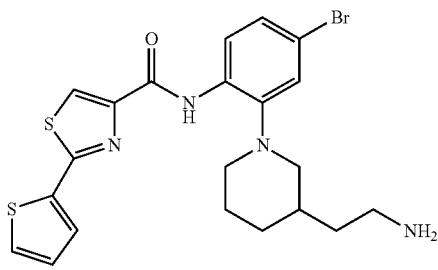 [SMILES: NCCC1CCCN(c2cc(Br)ccc2NC(=O)c2csc(-c3cccs3)n2)C1]

Step 1—Synthesis of Compound 247A

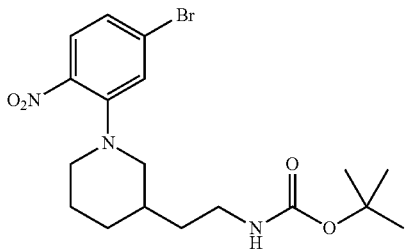 [SMILES: CC(C)(C)OC(=O)NCCC1CCCN(c2cc(Br)ccc2[N+](=O)[O-])C1]

A solution of (2-Piperidin-3-yl-ethyl)-carbamic acid tert-butyl ester (0.087 mmol, 0.020 g) and 4-Bromo-2-fluoronitrobenzene (1.0 eq, 0.019 g), N,N-diisopropylethylamine (1.2 eq, 13.5 µL) in ACN (2 mL) was irradiated using microwave for 18 minutes at a temperature of 130° C. The solution was then cooled to room temperature and concentrated in vacuo to provide {2-[1-(5-Bromo-2-nitro-phenyl)-piperidin-3-yl]-ethyl}-carbamic acid tert-butyl ester. HPLC-MS RT=2.37 min, mass calculated for formula C$_{18}$H$_{26}$BrN$_3$O$_4$ 427.11, observed LCMS m/z 428.22 and 430.11 (M+H).

Step 2—Synthesis of Compound 247B

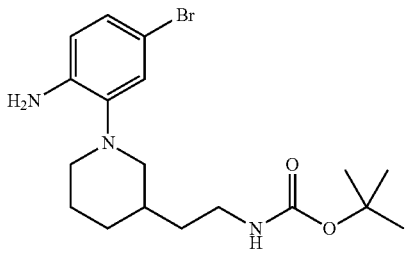

To the solution of compound 247A in ethyl acetate (10 mL) was added 5% Pd/C powder, degassed with argon, and an H$_2$ balloon. The solution was stirred at room temperature for 1 hour or until the yellow disappeared. The resulting reaction mixture was concentrated in vacuo to provide Intermediate {2-[1-(2-Amino-5-bromo-phenyl)-piperidin-3-yl]-ethyl}-carbamic acid tert-butyl ester (0.037 g). HPLC-MS RT=2.06 min, mass calculated for formula C$_{18}$H$_{28}$BrN$_3$O$_2$ 397.14, observed LCMS m/z 398.15 and 400.15 (M+H).

Step 3—Synthesis of Title Compound

To a solution of compound 247B in DMF (2 mL) was added 2-thiophen-2-yl-thiazole-4-carboxylic acid (098 eq, 0.019 g). Then, a solution of N,N-diisopropylethylamine (1.5 eq, 24.3 µL) HATU (1.5 eq, 0.042 g) was added. The resulting reaction was stirred at room temperature for 15 hours. The resulting solution was concentrated and treated with 1 mL of (90:10) TFA:H$_2$O. The reaction mixture was concentrated and purified using reverse phase HPLC to provide the title compound. HPLC-MS RT=4.18 min, mass calculated for formula C$_{21}$H$_{23}$BrN$_4$OS$_2$ 490.05, observed LCMS m/z 491.09 and 492.97 (M+H).

Example 248

Preparation of

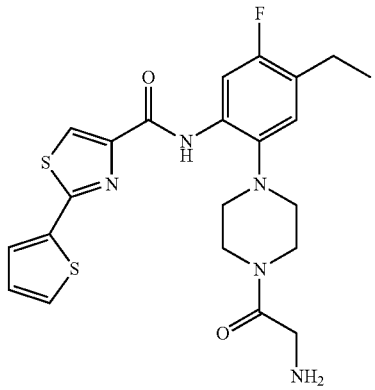 [SMILES: CCc1cc(N2CCN(C(=O)CN)CC2)c(NC(=O)c2csc(-c3cccs3)n2)cc1F]

Step 1—Synthesis of Compound 248A

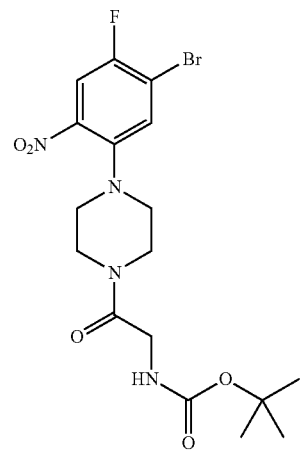 [SMILES: CC(C)(C)OC(=O)NCC(=O)N1CCN(c2cc(Br)c(F)cc2[N+](=O)[O-])CC1]

A solution of (2-Oxo-2-piperazin-1-yl-ethyl)-carbamic acid tert-butyl ester (1.23 mmol, 0.300 g), 1-Bromo-2,5-difluoro-4-nitro-benzene (0.98 eq, 0.287 g), and N,N-diisopropylethylamine (1.2 eq, 257 μL) in ACN (2 mL) was irradiated using microwave for 20 minutes at a temperature of 200° C. The solution was then cooled to room temperature and concentrated in vacuo. After dissolving the intermediate in DCM, the solution was columned in 50:50 Ethyl Acetate:Hexane and concentrated to compound 248A (0.306 g). HPLC-MS RT=2.14 min, mass calculated for formula $C_{17}H_{22}BrFN_4O_5$ 460.08, observed LCMS m/z 405.10 (t-butyl removed during LCMS) (M+H).

Step 2—Synthesis of Compound 248B

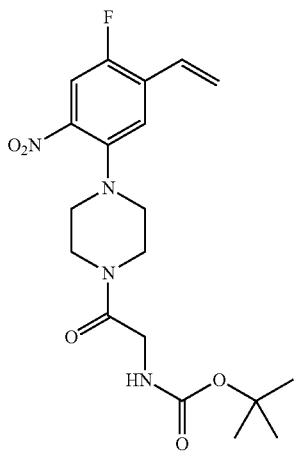 [SMILES: C=Cc1cc(N2CCN(C(=O)CNC(=O)OC(C)(C)C)CC2)c([N+](=O)[O-])cc1F]

To a solution of compound 248A in THF was added 4,4,5,5-Tetramethyl-2-vinyl-[1,3,2]dioxaborolane (1.5 eq), $Pd_2(DBA)_3$ (0.05 eq), S-Phos (0.15 eq) and $K_3PO_4$ (2 eq) at 80° C. overnight. The solution was washed and extracted with ethyl acetate, ethyl ether, and brine, and then filtered through a 0.45 μm pore size Whatman filter to provide compound 248B. HPLC-MS RT=2.18 min, mass calculated for formula $C_{19}H_{25}FN_4O_5$ 408.18, observed LCMS m/z 409.15 (M+H).

Step 3—Synthesis of Compound 248C

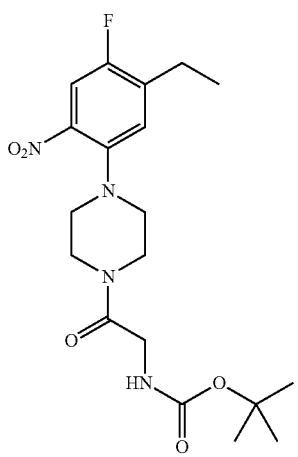 [SMILES: CCc1cc(N2CCN(C(=O)CNC(=O)OC(C)(C)C)CC2)c([N+](=O)[O-])cc1F]

Compound 248B was hydrogenated using the H-Cube with a 10% Pd/C cartridge with the following settings:

| H-Cube Settings | |
| --- | --- |
| Pressure Regulator: | 30 bar |
| Column Heater: | 50° C. |
| Hydrogen: | Controlled |
| HPLC Pump: | 0.8 mL/min |

The resulting reaction mixture was concentrated in vacuo to provide compound 248C (0.017 g). HPLC-MS RT=1.72 min, mass calculated for formula $C_{19}H_{29}FN_4O_3$ 380.22, observed LCMS m/z 381.25 (M+H).

Step 4—Synthesis of Title Compound

To a solution of compound 248C in DMF (2 mL) was added N,N-diisopropylethylamine (1.2 eq, 43.4 μL) HATU (1.2 eq, 0.091 g) 2-thiophen-2-yl-thiazole-4-carboxylic acid (0.98 eq, 0.042 g). The resulting reaction was stirred at room temperature for 15 hours. The resulting solution was concentrated and treated with 1 mL of (90:10) TFA:$H_2O$. Then, the reaction mixture was concentrated and purified using reverse phase HPLC to provide the title compound. HPLC-MS RT=3.83 min, mass calculated for formula $C_{22}H_{24}FN_5O_2S_2$ 473.14, observed LCMS m/z 474.24 (M+H).

Example 249

Preparation of

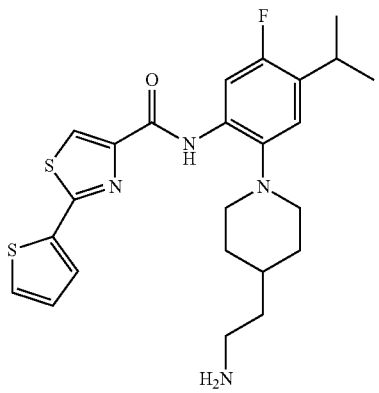 [SMILES: CC(C)c1cc(N2CCC(CCN)CC2)c(NC(=O)c2csc(-c3cccs3)n2)cc1F]

Step 1—Synthesis of Compound 249A

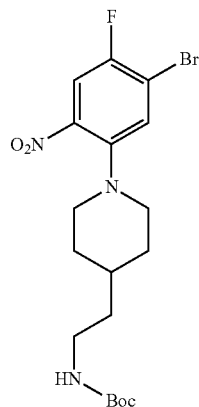

A solution of 1-bromo-2,5-difluoro-4-nitrobenzene (0.42 mmol, 0.1 g), N,N-diisopropylethylamine (1.2 eq, 0.54 mmol, 73 µL) and (2-Piperidin-4-yl-ethyl)-carbamic acid tert-butyl ester (1.2 eq, 0.50 mmol, 0.115 g) in ACN (2 mL) was irradiated using microwave for 20 minutes at a temperature of 200° C. The solution was then cooled to room temperature and concentrated in vacuo and the resulting residue was purified using column chromatography on silica gel with an eluent mixture of Hexane/EtOAc to provide compound 249A (0.353 g). HPLC-MS RT=2.37 minutes, mass calculated for formula $C_{18}H_{25}BrFN_3O_4$ 445.10, observed LCMS m/z 446.05 (M+H).

Step 2—Synthesis of Compound 249B

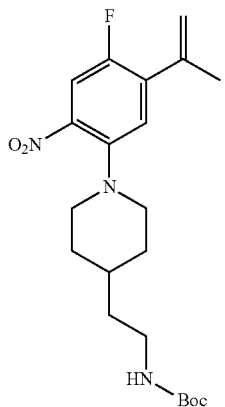 [SMILES: C=C(C)c1cc(N2CCC(CCNC(=O)OC(C)(C)C)CC2)c([N+](=O)[O-])cc1F]

A solution of isopropenylmagnesium bromide in THF (0.50 M, 3.0 mL) was added to a solution of zinc chloride in THF (0.50 M, 3.0 mL). The reaction mixture was stirred at room temperature under an atmosphere of nitrogen for one hour, and then added to a Schlenk tube containing $Pd_2(DBA)_3$ (0.035 mmol, 32 mg), S-Phos (0.10 mmol, 41 mg) and compound 249A (0.45 mmol, 0.20 g). The reaction mixture was stirred at a temperature of 65° C. for overnight. The reaction mixture was cooled to room temperature and then concentrated. The residue was diluted with a mixture of ethyl acetate and ether (1:1). The organics were washed with brine twice. Concentrate organic layer then filter through Whatman 0.45 µm cartridge with ethyl acetate. The filtrate was concentrated to provide compound 249B. HPLC-MS RT=2.67 minutes, mass calculated for formula $C_{21}H_{30}FN_3O_4$ 407.22, observed LCMS m/z 408.30 (M+H).

Step 3—Synthesis of Compound 249C

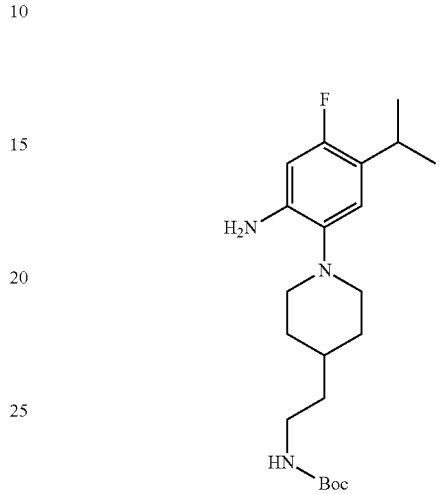

A solution of compound 249B (crude, 0.112 g) in EtOAc (30 mL) was hydrogenated in the H-Cube using a 10% Pd/C cartridge with the following settings:

| H-Cube Settings | |
| --- | --- |
| Pressure Regulator: | 40 bar |
| Column Heater: | 50° C. |
| Hydrogen: | Controlled |
| HPLC Pump: | 0.7 mL/min |

The resulting reaction mixture was concentrated in vacuo and the residue was dissolved in DMSO/acetonitrile (3:1), purified using reverse phase HPLC to provide compound 249C (0.8 mg). HPLC-MS RT=2.10 minutes, mass calculated for formula $C_{21}H_{34}FN_3O_2$ 379.26, observed LCMS m/z 380.20 (M+H).

Step 4—Synthesis of Title Compound

To a solution of compound 249C (0.8 mg, 0.002 mmol) in DMF (1 mL) was added N,N-diisopropylethylamine (1.2 eq, 0.31 mmol, 0.42 µL) HATU (1.2 eq, 0.91 mg) and 2-thiophen-2-yl-thiazole-4-carboxylic acid (1 eq, 0.42 mg). The resulting reaction was stirred at room temperature for 15 hours. The reaction mixture was concentrated. The residue was reacted with TFA:H2O (90:10), (1.0 mL) for 30 minutes. The TFA solution was concentrated in vacuo. The residue was dissolved in DMSO/acetonitrile (3:1), purified using reverse phase HPLC to provide 2-Thiophen-2-yl-thiazole-4-carboxylic acid {2-[4-(2-amino-ethyl)-piperidin-1-yl]-5-fluoro-4-isopropyl-phenyl}-amide (0.36 mg). HPLC-MS RT=4.40

Example 250

Preparation of

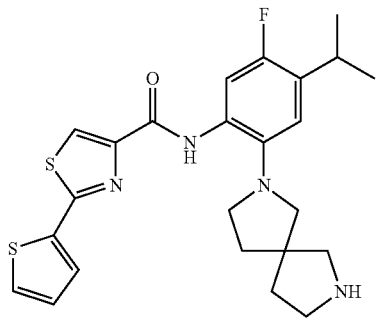 [SMILES: CC(C)c1cc(N2CCC3(CCNC3)C2)c(NC(=O)c2csc(-c3cccs3)n2)cc1F]

The procedure follows the same steps as Example 249. HPLC-MS RT=4.26 minutes, mass calculated for formula $C_{24}H_{27}FN_4OS_2$ 470.16, observed LCMS m/z 471.42 (M+H).

Example 251

Preparation of

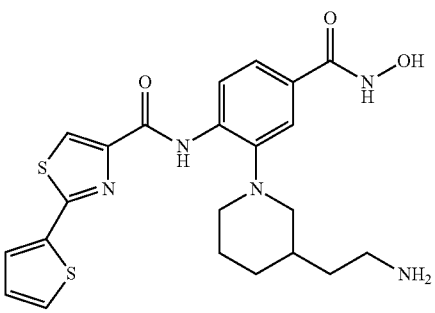 [SMILES: NCCC1CCCN(c2cc(C(=O)NO)ccc2NC(=O)c2csc(-c3cccs3)n2)C1]

Step 1—Synthesis of Compound 251A

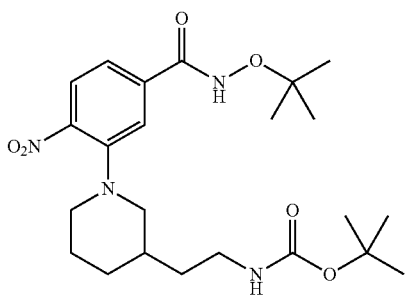

A solution of 3-Fluoro-4-nitro-benzoic acid methyl ester (0.50 mmol, 0.106 g), N,N-diisopropylethylamine (3.0 eq, 1.5 mmol, 261 μL) and (2-Piperidin-3-yl-ethyl)-carbamic acid tert-butyl ester (1.0 eq, 0.50 mmol, 0.114 g) in DMA (2 mL) was irradiated using microwave for 18 minutes at a temperature of 180° C. The solution was then cooled to room temperature and concentrated in vacuo to provide compound 251A.

Step 2—Synthesis of Compound 251B minutes, mass calculated for formula $C_{24}H_{29}FN_4OS_2$ 472.18, observed LCMS m/z 473.21 (M+H).

A solution of compound 251A, O-t-butyl hydroxylamine hydrochloride salt (2.0 eq,) and KOH in DMA (2 mL) was irradiated using microwave for 18 minutes at a temperature of 180° C. The solution was then cooled to room temperature and concentrated in vacuo to provide compound 251B.

Step 3—Synthesis of Compound 251C

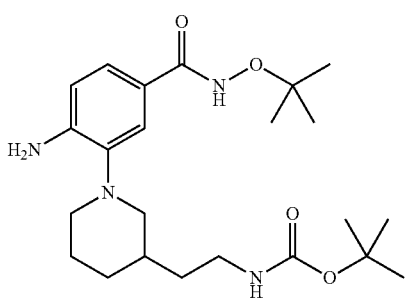 [SMILES: CC(C)(C)ONC(=O)c1ccc([N+](=O)[O-])c(N2CCCC(CCNC(=O)OC(C)(C)C)C2)c1]

A solution of compound 251B in 25 mL of methanol was hydrogenated using the H-Cube using a 10% Pd/C cartridge with the following settings:

| H-Cube Settings | |
|---|---|
| Pressure Regulator: | 30 bar |
| Column Heater: | 35° C. |
| Hydrogen: | Controlled |
| HPLC Pump: | 1.0 mL/min |

The hydrogenated solution was then concentrated in vacuo to provide compound 251C. HPLC-MS RT=3.41 minutes, mass calculated for formula $C_{23}H_{38}N_4O_4$ 434.29, observed LCMS m/z 435.38 (M+H).

Step 3—Synthesis of Title Compound

To the solution of compound 251C (0.006 mmol, 0.0026 g) in DMF (1 mL) was added N,N-diisopropylethylamine (1.2 eq, 0.007 mmol, 1.2 µL) HATU (1.2 eq, 0.007 mmol, 0.0027 g) and 2-Thiophen-2-yl-thiazole-4-carboxylic acid (1 eq, 0.0013 g). The resulting reaction was stirred at 50° C. for 15 hours and then concentrated. Then the mixture was deprotected with 1 mL of (90:10) TFA:H$_2$O and then an additional 200 µL of formic acid. The reaction mixture was concentrated and purified using reverse phase HPLC to provide the title compound. HPLC-MS RT=3.11 minutes, mass calculated for formula C$_{22}$H$_{25}$N$_5$O$_3$S$_2$ 471.14, observed LCMS m/z 472.20 (M+H).

Example 252

Preparation of

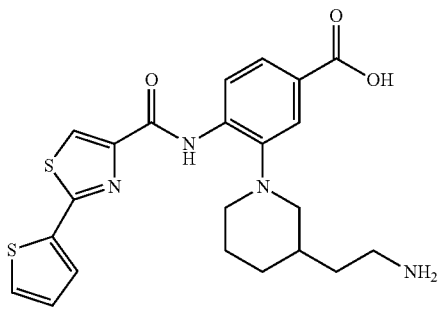 [SMILES: NCCC1CCCN(c2cc(C(=O)O)ccc2NC(=O)c2csc(-c3cccs3)n2)C1]

The procedure follows the same steps as Example 251. HPLC-MS RT=3.49 minutes, mass calculated for formula C$_{22}$H$_{24}$N$_4$O$_3$S$_2$ 456.13, observed LCMS m/z 457.22 (M+H).

Example 253

Preparation of

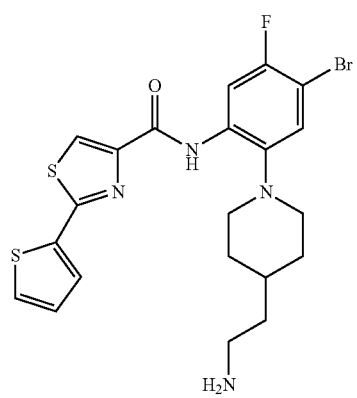 [SMILES: NCCC1CCN(c2cc(Br)c(F)cc2NC(=O)c2csc(-c3cccs3)n2)CC1]

Step 1—Synthesis of Compound 253A

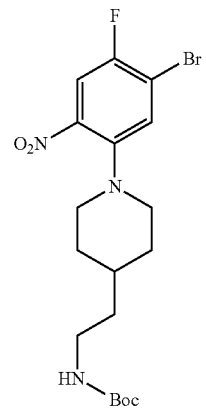 [SMILES: CC(C)(C)OC(=O)NCCC1CCN(c2cc(Br)c(F)cc2[N+](=O)[O-])CC1]

A solution of 1-bromo-2,5-difluoro-4-nitrobenzene (0.42 mmol, 0.1 g), N,N-diisopropylethylamine (1.2 eq, 0.54 mmol, 73 µL) and (2-Piperidin-4-yl-ethyl)-carbamic acid tert-butyl ester (1.2 eq, 0.50 mmol, 0.115 g) in ACN (2 mL) was irradiated using microwave for 20 minutes at a temperature of 200° C. The solution was then cooled to room temperature and concentrated in vacuo and the resulting residue was purified using column chromatography on silica gel with an eluent mixture of Hexane/EtOAc to provide compound 253A (0.353 g). HPLC-MS RT=2.37 minutes, mass calculated for formula C$_{18}$H$_{25}$BrFN$_3$O$_4$ 445.10, observed LCMS m/z 446.05 and 448.15 (M+H).

Step 2—Synthesis of Compound 253B

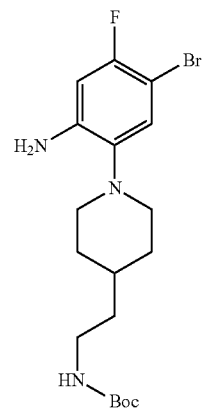

The solution of compound 253A (Crude 0.112 g) in EtOAc (30 mL) was hydrogenated in the H-Cube using a 10% Pd/C cartridge with the following settings:

| H-Cube Settings | |
| --- | --- |
| Pressure Regulator: | 40 bar |
| Column Heater: | 50° C. |
| Hydrogen: | Controlled |
| HPLC Pump: | 0.7 mL/min |

The resulting reaction mixture was concentrated in vacuo and the residue was dissolved in DMSO/acetonitrile (3:1), purified using reverse phase HPLC to provide compound 253B (0.8 mg). HPLC-MS RT=4.42 minutes, mass calculated for formula $C_{18}H_{27}BrFN_3O_2$ 415.13, observed LCMS m/z 416.11 (M+H).

Step 3—Synthesis of Title Compound

To compound 253B (0.8 mg, 0.002 mmol) was added N,N-diisopropylethylamine (1.2 eq, 0.31 mmol, 0.42 µL) HATU (1.2 eq, 0.91 mg) and 2-thiophen-2-yl-thiazole-4-carboxylic acid (1 eq, 0.42 mg) in DMF (1 mL). The resulting reaction was stirred at room temperature for 15 hours. The reaction mixture was concentrated. The residue was reacted with TFA:$H_2O$ (90:10), (1.0 mL) for 30 minutes. The TFA solution was concentrated in vacuo. The residue was dissolved in DMSO/acetonitrile (3:1), purified using reverse phase HPLC to provide the title compound (0.25 mg). HPLC-MS RT=4.25 minutes, mass calculated for formula $C_{21}H_{22}BrFN_4OS_2$ 508.04, observed LCMS m/z 509.11 (M+H).

Example 254

Preparation of

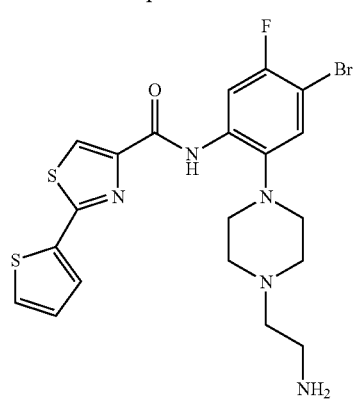

The procedure follows the same steps as Example 249, except that the isopropyl group was not installed. HPLC-MS RT=3.26 minutes, mass calculated for formula $C_{20}H_{21}BrFN_5OS_2$ 509.04, observed LCMS m/z 510.12 (M+H).

Example 255

Preparation of

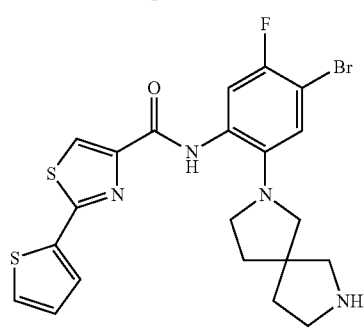 [SMILES: O=C(Nc1cc(F)c(Br)cc1N1CCC2(CCNC2)C1)c1csc(-c2cccs2)n1]

The procedure follows the same steps as Example 249, except that the isopropyl group was not installed. HPLC-MS RT=3.99 minutes, mass calculated for formula $C_{21}H_{20}BrFN_4OS_2$ 506.02, observed LCMS m/z 507.06 (M+H).

Example 256

Preparation of

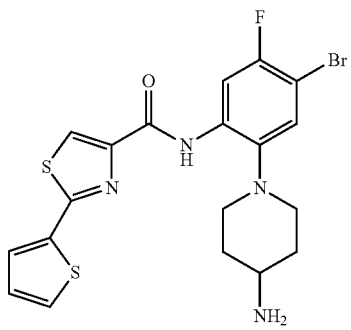 [SMILES: NC1CCN(c2cc(Br)c(F)cc2NC(=O)c2csc(-c3cccs3)n2)CC1]

The procedure follows the same steps as Example 249, except that the isopropyl group was not installed. HPLC-MS RT=3.81 minutes, mass calculated for formula $C_{19}H_{18}BrFN_4OS_2$ 480.01, observed LCMS m/z 481.06 (M+H).

Example 257

Preparation of

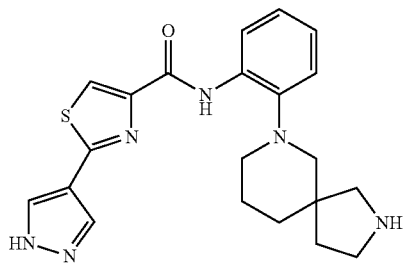 [SMILES: O=C(Nc1ccccc1N1CCCC2(CCNC2)C1)c1csc(-c2cn[nH]c2)n1]

Step 1—Synthesis of Compound 257A

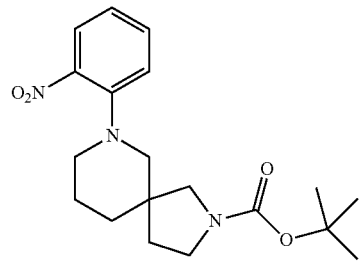 [SMILES: CC(C)(C)OC(=O)N1CCC2(CCCN(c3ccccc3[N+](=O)[O-])C2)C1]

A solution of t-butyl 2,8-diazaspiro[4.5]decane-2 carboxylate (1.99 mmol, 0.478 g), N,N-diisopropylethylamine (1.5 eq, 519 µL) and 1-Fluoro-2-nitrobenzene(1.0 eq, 207 µL) in ACN (2 mL) was irradiated using microwave for 20 minutes at a temperature of 200° C. The solution was then cooled to room temperature and concentrated in vacuo to provide compound 257A (0.603 g). HPLC-MS RT=2.26 min, mass calculated for formula $C_{19}H_{27}N_3O_4$ 361.20, observed LCMS m/z 362.20 (M+H).

Step 2—Synthesis of Compound 257B

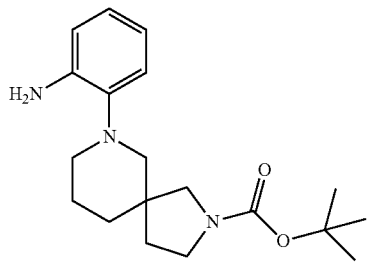 [SMILES: CC(C)(C)OC(=O)N1CCC2(CCCN(c3ccccc3N)C2)C1]

The solution of compound 257A in methanol (50.0 mL) was hydrogenated in the H-Cube using a 10% Pd/C cartridge with the following settings:

| H-Cube Settings | |
|---|---|
| Pressure Regulator: | 30 bar |
| Column Heater: | 50° C. |
| Hydrogen: | Controlled |
| HPLC Pump: | 1 mL/min |

The resulting reaction mixture was concentrated in vacuo to provide compound 257B (0.500 g). HPLC-MS RT=1.74 min, mass calculated for formula $C_{19}H_{29}N_3O_2$ 331.23, observed LCMS m/z 332.20 (M+H).

Step 3—Synthesis of Compound 257C

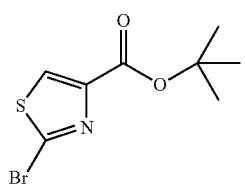

To a solution of compound 257B (1.00 g, 4.81 mmol) in DCM (25 mL) was added 2-tert-butyl-1,3-diisopropylisourea (29 mmol, 8.8 g). The resulting solution was heated to reflux and stirred at reflux for 18 hours. After 18 hours, the precipitate was filtered out via a fine frit and the solute reduced in vacuo. The residue was taken up in DCM and compound 257C was purified via silica gel chromatography. $^1$H NMR (400 MHz, DMSO) δ 8.40 (s, 1H), 1.51 (s, 9H).

Step 4—Synthesis of Compound 257D

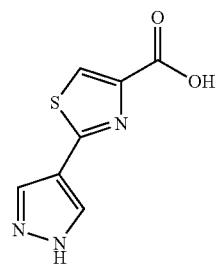 [SMILES: O=C(O)c1csc(-c2cn[nH]c2)n1]

To a 40 mL scintillation vial was charged compound 257C (500 mg, 1.90 mmol), 4-pyrazoleboronic acid pinacol ester (551 mg, 2.84 mmol), $K_3PO_4$ (807 mg, 3.80 mmol), and tetrakis(triphenylphosphine)palladium (219 mg, 190 mmol). To this was added a 3:1 1,4-dioxane:$H_2O$ solution (16 mL). The vial was flushed with argon and sealed with Teflon tape. The reaction was heated to 100° C. for 18 hours. It was then cooled to room temperature, diluted with DCM (80 mL) and washed with 1N $HCl_{(aq)}$. The organic layer was then dried over $Na_2SO_4$ and reduced in vacuo. The residue was then purified on 0% to 15% MeOH:DCM gradient to yield 2-(1H-pyrazol-4-yl)-thiazole-4-carboxylic acid tert-butyl ester (354 mg). This product was treated with 4N HCl in 1,4-dioxane (20 mL) plus $H_2O$ (1 mL) and stirred at room temperature. The solution was concentrated in vacuo to yield compound 257D.

Step 5—Synthesis of Title Compound

To the solution of compound 257D (0.077 mmol, 0.025 g) was added N,N-diisopropylethylamine (1.5 eq, 20 µL) HATU (1.5 eq, 0.029 g), and 2-(1H-Pyrazol-4-yl)-thiazole-4-carboxylic acid (1.0 eq, 0.015 g) in DMF (1 mL). The resulting reaction was stirred at room temperature for 15 hours and the resulting solution was concentrated and treated with 1 mL of (90:10) TFA:$H_2O$. The reaction mixture was concentrated and purified using reverse phase HPLC to provide 2-(1H-Pyrazol-4-yl)-thiazole-4-carboxylic acid [2-(2,7-diaza-spiro [4.5]dec-7-yl)-phenyl]amide. HPLC-MS RT=2.87 min, mass calculated for formula $C_{21}H_{24}N_6OS$ 408.17, observed LCMS m/z 409.28 (M+H).

Example 258

Preparation of

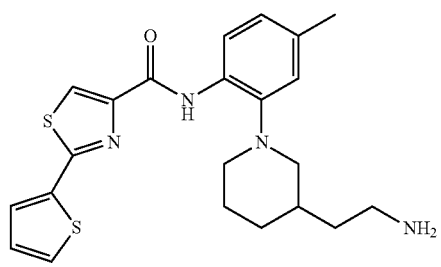 [SMILES: Cc1ccc(NC(=O)c2csc(-c3cccs3)n2)c(N2CCCC(CCN)C2)c1]

Step 1—Synthesis of Compound 258A

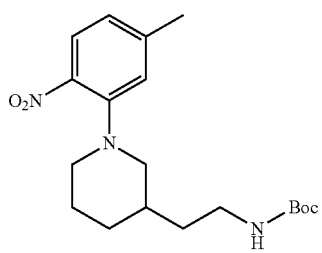 [SMILES: Cc1ccc([N+](=O)[O-])c(N2CCCC(CCNC(=O)OC(C)(C)C)C2)c1]

A solution of 3-(N-Boc-aminoethyl)-piperidine (0.09 mmol, 0.020 g), N,N-diisopropylethylamine (1.2 eq, 0.014 mmol, 18.8 µL) and 3-fluoro-4-nitrotoluene (0.98 eq, 0.014 g) in ACN (2 mL) was irradiated using microwave for 20 minutes at a temperature of 200° C. The solution was then cooled to room temperature and concentrated in vacuo to provide compound 258A (0.040 g). HPLC-MS RT=2.48 min, mass calculated for formula $C_{19}H_{29}N_3O_4$ 363.22, observed LCMS m/z 364.30 (M+H).

Step 2—Synthesis of Compound 258B

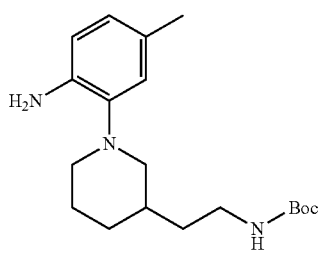 [SMILES: Cc1ccc(N)c(N2CCCC(CCNC(=O)OC(C)(C)C)C2)c1]

The solution of compound 258A (0.040 g) in methanol (10 mL) was hydrogenated in the H-Cube using a 10% Pd/C cartridge with the following settings:

| H-Cube Settings | |
|---|---|
| Pressure Regulator: | 30 bar |
| Column Heater: | 40° C. |
| Hydrogen: | Controlled |
| HPLC Pump: | 0.8 mL/min |

The resulting reaction mixture was concentrated in vacuo to provide compound 258B (0.032 g). HPLC-MS RT=1.48 min, mass calculated for formula $C_{19}H_{31}N_3O_2$ 333.24, observed LCMS m/z 334.30 (M+H).

Step 3—Synthesis of Title Compound

To compound 258B (0.097 mmol, 0.032 g) was added N,N-diisopropylethylamine (1.2 eq, 0.12 mmol, 20.3 µL) HATU (1.2 eq, 0.12 mmol, 0.044 g) and 2-thiophen-2-yl-thiazole-4-carboxylic acid (0.98 eq, 20 mg) in DMF (2 mL). The resulting reaction was stirred at room temperature for 15 hours. The reaction mixture was concentrated. The residue was reacted with 1 mL TFA:H2O (90:10) for 30 minutes. The TFA solution was concentrated in vacuo. The residue was dissolved in DMSO/acetonitrile (3:1), purified using reverse phase HPLC to provide the title compound (0.018 g). HPLC-MS RT=3.85 min, mass calculated for formula $C_{22}H_{26}N_4OS_2$ 426.15, observed LCMS m/z 427.25 (M+H).

Example 259

Preparation of

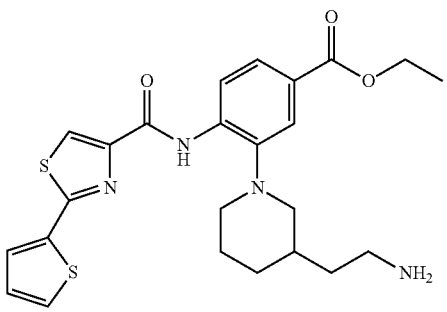 [SMILES: CCOC(=O)c1ccc(NC(=O)c2csc(-c3cccs3)n2)c(N2CCCC(CCN)C2)c1]

Step 1—Synthesis of Compound 259A

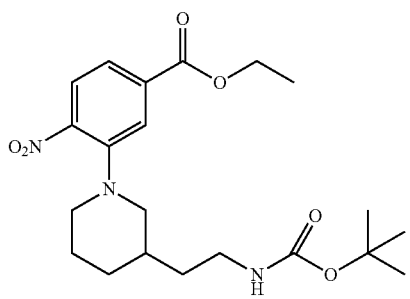 [SMILES: CCOC(=O)c1ccc([N+](=O)[O-])c(N2CCCC(CCNC(=O)OC(C)(C)C)C2)c1]

A solution of 3-(N-Boc-aminoethyl)-piperidine (0.098 mmol, 0.020 g), N,N-diisopropylethylamine (1.2 eq, 0.12 mmol, 20.5 µL) and ethyl 3-fluoro-nitrobenzene (0.98 eq, 0.020 g) in ACN (2 mL) was irradiated using microwave for 20 minutes at a temperature of 200° C. The solution was then cooled to room temperature and concentrated in vacuo to provide compound 259A (0.047 g). HPLC-MS RT=2.54 min, mass calculated for formula $C_{21}H_{31}N_3O_6$ 421.22, observed LCMS m/z 422.20 (M+H).

Step 2—Synthesis of Compound 259B

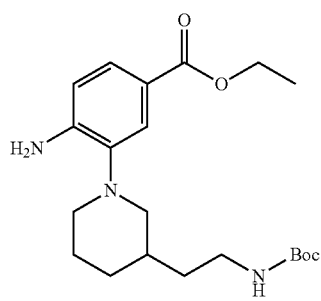 [SMILES: CCOC(=O)c1ccc(N)c(N2CCCC(CCNC(=O)OC(C)(C)C)C2)c1]

The solution of compound 259A (0.047 g) in methanol (10 mL) was hydrogenated in the H-Cube using a 10% Pd/C cartridge with the following settings:

| H-Cube Settings | |
|---|---|
| Pressure Regulator: | 30 bar |
| Column Heater: | 40° C. |
| Hydrogen: | Controlled |
| HPLC Pump: | 0.8 mL/min |

The resulting reaction mixture was concentrated in vacuo to provide compound 259B (Crude 0.038 g). HPLC-MS RT=2.00 min, mass calculated for formula $C_{21}H_{33}N_3O_4$ 391.25, observed LCMS m/z 392.20 (M+H).

Step 3—Synthesis of Title Compound

To Intermediate compound 259B (0.098 mmol, 0.038 g) was added N,N-diisopropylethylamine (1.2 eq, 0.12 mmol, 20.5 µL) HATU (1.2 eq, 0.12 mmol, 0.045 g) and 2-thiophen-2-yl-thiazole-4-carboxylic acid (0.98 eq, 20 mg) in DMF (2 mL). The resulting reaction was stirred at room temperature for 15 hours and then at 50° C. for 3 hours. The reaction mixture was concentrated. The residue was reacted with 1 mL TFA:H2O (90:10) for 30 minutes. The TFA solution was concentrated in vacuo. The residue was dissolved in DMSO/acetonitrile (3:1), and purified using reverse phase HPLC to provide the title compound (0.006 g). HPLC-MS RT=4.14 min, mass calculated for formula $C_{24}H_{28}N_4O_3S_2$ 484.16, observed LCMS m/z 485.29 (M+H).

Example 260

Preparation of

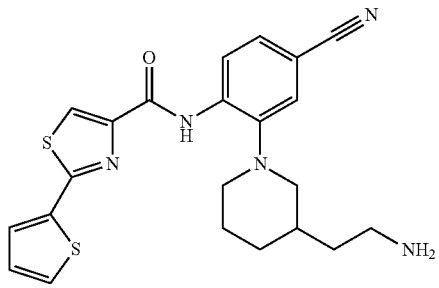 [SMILES: N#Cc1ccc(NC(=O)c2csc(-c3cccs3)n2)c(N2CCCC(CCN)C2)c1]

Step 1—Synthesis of Compound 260A

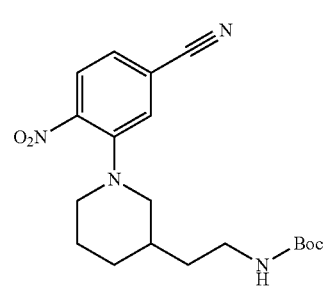 [SMILES: CC(C)(C)OC(=O)NCCC1CCCN(c2cc(C#N)ccc2[N+](=O)[O-])C1]

A solution of 3-Fluoro-4-nitro-benzonitrile (0.5 mmol, 83 mg), DIEA (1.5 mmol, 0.26 mL) and (2-Piperidin-3-yl-ethyl)-carbamic acid tert-butyl ester (0.60 mmol, 0.14 g) in DMA (2 mL) was irradiated using microwave for 20 minutes at a temperature of 200° C. The solution was then cooled to room temperature and concentrated in vacuo to provide compound 260A, which was used in the next step without further purification.

Step 2—Synthesis of Compound 260B

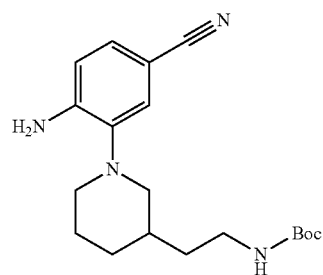

Compound 260A in methanol (30 mL) was hydrogenated in the H-Cube using a 10% Pd/C cartridge with the following settings:

| H-Cube Settings | |
|---|---|
| Pressure Regulator: | 30 bar |
| Column Heater: | 40° C. |
| Hydrogen: | Controlled |
| HPLC Pump: | 0.8 mL/min |

The resulting reaction mixture was concentrated in vacuo to provide compound 260B. The intermediate was dissolved in DMSO/acetonitrile (3:1), and purified using reverse phase HPLC (0.119 g). HPLC-MS RT=3.91 min, mass calculated for formula $C_{19}H_{25}N_4O_2$ 344.22, observed LCMS m/z 345.34 (M+H).

Step 3—Synthesis of Title Compound

To compound 260B (0.34 mmol, 0.119 g) was added N,N-diisopropylethylamine (1.2 eq, 0.41 mmol, 72.1 µL) HATU (1.2 eq, 0.41 mmol, 0.157 g) and 2-thiophen-2-yl-thiazole-4-carboxylic acid (0.98 eq, 0.071 mg) in DMF (2 mL). The resulting reaction was stirred at room temperature for 15 hours and then at 50° C. for 3 hours. The reaction mixture was concentrated. The residue was reacted with 1 mL TFA:H₂O (90:10) for 30 minutes. The TFA solution was concentrated in vacuo. The residue was dissolved in DMSO/acetonitrile (3:1), and purified using reverse phase HPLC to provide the title compound (0.024 g). HPLC-MS RT=3.76 min, mass calculated for formula $C_{22}H_{23}N_5OS_2$ 437.13, observed LCMS m/z 438.21 (M+H).

Example 261

Preparation of

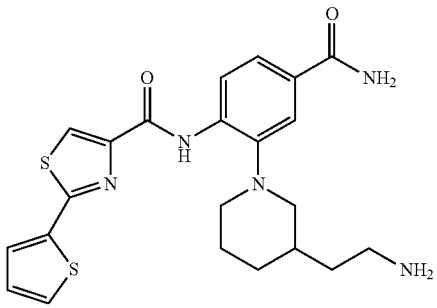 [SMILES: NCCC1CCCN(c2cc(C(N)=O)ccc2NC(=O)c2csc(-c3cccs3)n2)C1]

Step 1—Synthesis of Compound 261A

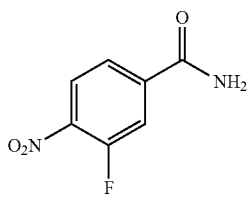 [SMILES: NC(=O)c1ccc([N+](=O)[O-])c(F)c1]

A solution of 3-Fluoro-4-nitro-benzonitrile (5.0 mmol, 0.83 g) in a ca. 7.0 mL mixture of TFA-H2SO4 (4:1, v/v) was stirred at room temperature for overnight. After completion of the reaction, the reaction mixture was poured into ice-cold water. The reaction mixture was extracted with ethyl acetate, and the organic solution was concentrated in vacuo to provide compound 261A, which was used in the next step without further purification.

Step 2—Synthesis of Compound 261B

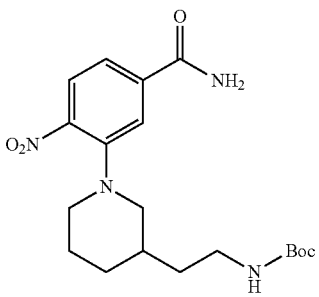 [SMILES: CC(C)(C)OC(=O)NCCC1CCCN(c2cc(C(N)=O)ccc2[N+](=O)[O-])C1]

A solution of 3-Fluoro-4-nitro-benzamide (0.5 mmol), DIEA (1.5 mmol, 0.26 mL) and compound 261A (0.60 mmol, 0.14 g) in DMA (2 mL) was irradiated using microwave for 20 minutes at a temperature of 200° C. The solution was then cooled to room temperature and concentrated in vacuo to provide compound 261B, which was used in the next step without further purification. HPLC-MS RT=1.77 minutes, mass calculated for formula C19H28N4O5 392.21, observed LCMS m/z 393.25 (M+H).

Step 3—Synthesis of Compound 261C

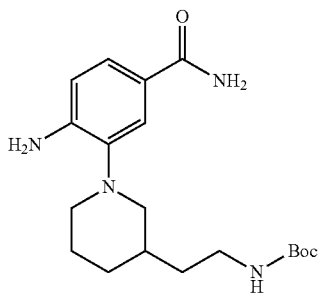

Compound 258A in methanol (30 mL) was hydrogenated in the H-Cube using a 10% Pd/C cartridge with the following settings:

| H-Cube Settings | |
|---|---|
| Pressure Regulator: | 30 bar |
| Column Heater: | 40° C. |
| Hydrogen: | Controlled |
| HPLC Pump: | 0.8 mL/min |

The resulting reaction mixture was concentrated in vacuo to provide compound 261C. The intermediate was dissolved in DMSO/acetonitrile (3:1), and purified using reverse phase HPLC (0.016 g). HPLC-MS RT=2.43 min, mass calculated for formula $C_{19}H_{30}N_4O_3$ 362.23, observed LCMS m/z 363.36 (M+H).

Step 4—Synthesis of Title Compound

To compound 261C was added N,N-diisopropylethylamine (1.2 eq, 0.053 mmol, 9.2 µL) HATU (1.2 eq, 0.053 mmol, 0.020 g) and 2-thiophen-2-yl-thiazole-4-carboxylic acid (0.98 eq, 0.0091 mg) in DMF (2 mL). The resulting reaction was stirred at room temperature for 15 hours. The reaction mixture was concentrated. The residue was reacted with 1 mL TFA:H2O (90:10) for 30 minutes. The TFA solution was concentrated in vacuo. The residue was dissolved in DMSO/acetonitrile (3:1), and purified using reverse phase HPLC to provide 2-Thiophen-2-yl-thiazole-4-carboxylic acid {2-[3-(2-amino-ethyl)-piperidin-1-yl]-4-carbamoyl-phenyl}-amide (0.013 g). HPLC-MS RT=3.23 min, mass calculated for formula $C_{22}H_{25}N_5O_2S_2$ 455.14, observed LCMS m/z 456.25 (M+H).

Example 262

Preparation of

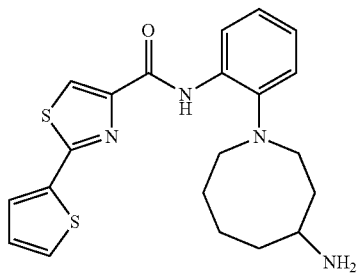 [SMILES: NC1CCCCN(c2ccccc2NC(=O)c2csc(-c3cccs3)n2)CC1]

Step 1—Synthesis of Compound 262A

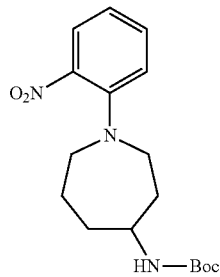 [SMILES: CC(C)(C)OC(=O)NC1CCCN(c2ccccc2[N+](=O)[O-])CC1]

A solution of Boc-4-aminohexahydro-4H-azepine (0.93 mmol, 0.20 g), N,N-diisopropylethylamine (1.1 eq, 1.02 mmol, 179 µL) and 1-fluoro-2-nitrobenzene (1.0 eq, 98.3 µL) in acetonitrile (4 mL) was irradiated using microwave for 20 minutes at a temperature of 170° C. The solution was then cooled to room temperature and concentrated in vacuo and the resulting residue was purified using column chromatography on silica gel with an eluent mixture of Hexane/EtOAc to provide compound 262A. HPLC-MS RT=2.09 min, mass calculated for formula $C_{17}H_{25}N_3O_4$ 335.18, observed LCMS m/z 336.20 (M+H).

Step 2—Synthesis of Compound 262B

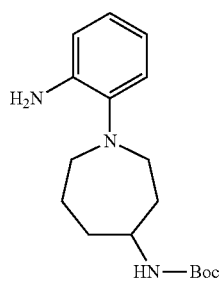

The solution of compound 262A in EtOAc (50 mL) was hydrogenated by adding 5% Pd/C (0.1 g) sealed and degassed under vacuum and then adding a H2 filled balloon. The solution stirred for 1 hour at room temperature, then filtered through celite and concentrated in vacuo to provide compound 262B. HPLC-MS RT=1.74 min, mass calculated for formula $C_{17}H_{27}N_3O_2$ 305.21, observed LCMS m/z 306.25 (M+H).

Step 3—Synthesis of Title Compound

To compound 262B (0.05 mmol, 0.016 g) was added N,N-diisopropylethylamine (1.2 eq, 0.072 mmol, 10.5 µL) HATU (1.2 eq, 0.072 mmol, 0.023 g) and 2-thiophen-2-yl-thiazole-4-carboxylic acid (0.98 eq, 0.058 mmol, 0.010 g) in DMF (1 mL). The resulting reaction was stirred at room temperature for 15 hours. The reaction mixture was concentrated and the residue was reacted with 1 mL TFA:H₂O (90:10), for 30 minutes at room temperature. The TFA solution was concentrated in vacuo and the residue was dissolved in DMSO/acetonitrile (3:1), purified using reverse phase HPLC to provide the title compound (0.023 g). HPLC-MS RT=3.30 min, mass calculated for formula $C_{20}H_{22}N_4OS_2$ 398.12, observed LCMS m/z 399.24 (M+H).

Example 263

Preparation of

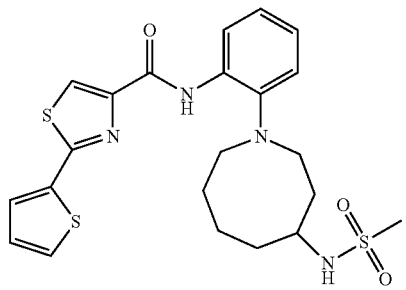 [SMILES: CS(=O)(=O)NC1CCCCN(c2ccccc2NC(=O)c2csc(-c3cccs3)n2)CC1]

To a solution of 2-Thiophen-2-yl-thiazole-4-carboxylic acid [2-(4-amino-azocan-1-yl)-phenyl]-amide (0.06 mmol, 0.018 g, which is the product of Example 262) in DCM (2 mL), was added N,N-diisopropylethylamine (4.0 eq, 0.024 mmol, 41.8 µL) and mesyl chloride (4.0 eq, 0.024 mmol, 18.6 µL). The resulting reaction was stirred at room temperature for 15 hours. The reaction mixture was concentrated and the residue was dissolved in DMSO/acetonitrile (3:1), purified using reverse phase HPLC to provide the title compound (0.015 g). HPLC-MS RT=4.24 min, mass calculated for formula $C_{21}H_{24}N_4O_3S_3$ 476.10, observed LCMS m/z 477.20 (M+H).

Example 264

Preparation of

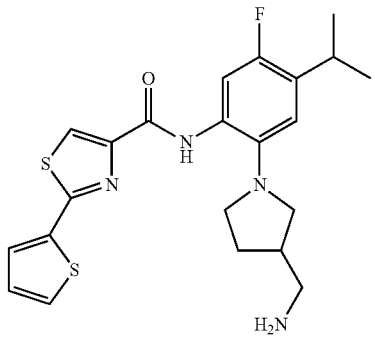 [SMILES: CC(C)c1cc(N2CCC(CN)C2)c(NC(=O)c2csc(-c3cccs3)n2)cc1F]

The procedure follows the same steps as Example 249. HPLC-MS RT=4.11 min, mass calculated for formula $C_{22}H_{25}FN_4OS_2$ 444.15, observed LCMS m/z 445.20 (M+H).

Example 265

Preparation of

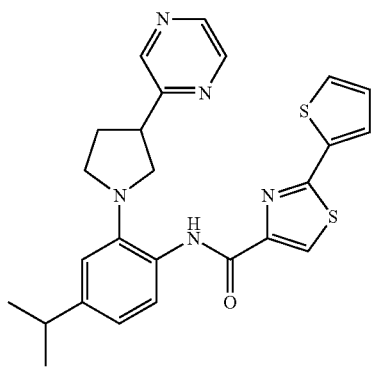 [SMILES: CC(C)c1ccc(NC(=O)c2csc(-c3cccs3)n2)c(N2CCC(c3cnccn3)C2)c1]

Step 1—Synthesis of Compound 265A

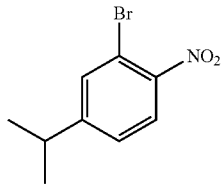

To intermediate 2-Bromo-4-isopropyl-phenylamine (20 mmol, 4.28 g) in toluene (150 mL) was added m-CPBA (25 g) portion wise (exothermic) slowly. The mixture was brought to reflux and stirred overnight, then cooled to room temperature and filtered. The filtrate was basified with NaOH (10%), extracted with ether and washed with brine. Then the solution was concentrated and chromatography on silica gel with Hexane:DCM (4:1) to provide compound 265A.

Step 2—Synthesis of Compound 265B

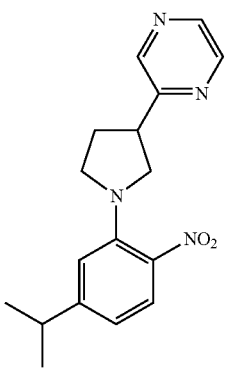 [SMILES: CC(C)c1ccc([N+](=O)[O-])c(N2CCC(c3cnccn3)C2)c1]

To compound 265A (0.5 mmol, 122 mg) in DMF (5 mL) was added 2-Pyrrolidin-3-yl-pyrazine 3HCl (0.5 mmol, 130 mg) and added N,N-diisopropylethylamine (3.0 mmol, 500 µL). The solution was irradiated for 20 minutes at 200° C. Chromatography on silica gel with 30% ethyl acetate in hexane gave compound 265B as a yellow product. HPLC-MS RT=2.08 min, mass calculated for formula $C_{17}H_{20}N_4O_2$ 312.16, observed LCMS m/z 313.15 (M+H).

Step 3—Synthesis of Compound 265C

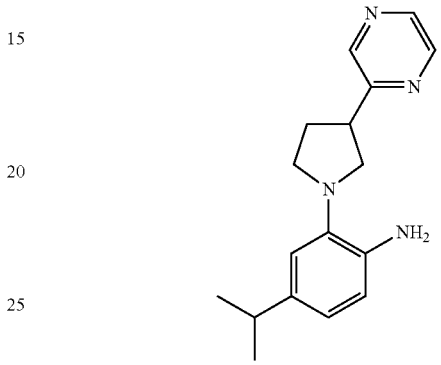

To compound 265B (0.4 mmol) was added Zn (16 mmol, 1.0 g) and $CaCl_2$ (0.4 mmol, 44 mg). The mixture was refluxed in ethanol (25 mL) for 4 hours and worked up to provide compound 265C, which was used without further purification. HPLC-MS RT=1.27 min, mass calculated for formula $C_{17}H_{22}N_4$ 282.18, observed LCMS m/z 283.20 (M+H).

Step 4—Synthesis of Title Compound

To compound 265C (0.11 mmol, 30.0 mg) was added 2-Thiophen-2-yl-thiazole-4-carboxylic acid (1 eq, 22.4 mg), N,N-diisopropylethylamine (1.2 eq, 22.0 µL), HATU (1.2 eq, 48.0 mg) in DMF (2 mL). The solution was stirred overnight at room temperature and then concentrated. The residue was dissolved in DMSO/acetonitrile (3:1), purified using reverse phase HPLC to provide the title compound. HPLC-MS RT=5.01 min, mass calculated for formula $C_{25}H_{25}N_5OS_2$ 475.15, observed LCMS m/z 476.23 (M+H).

Example 266

Preparation of

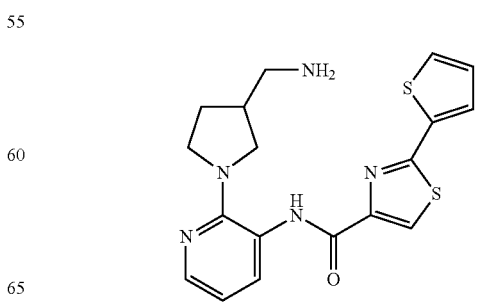

Step 1—Synthesis of Compound 266A

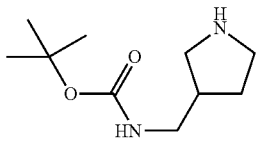
266A

1-Benzyl-pyrrolidin-3-ylmethyl carbamic acid tert-butyl ester (300 mg) was dissolved in ethyl acetate (30 mL). The solution was hydrogenated on the H-Cube with the following settings to provide compound 266A:

| H-Cube Settings | |
|---|---|
| Pressure Regulator: | 0 bar |
| Column Heater: | 60° C. |
| Hydrogen: | Full H$_2$ |
| HPLC Pump: | 1.0 mL/min |

HPLC-MS RT=0.57 min, mass calculated for formula $C_{10}H_{20}N_2O_2$ 200.15, observed LCMS m/z 201.15 (M+H).

Step 2—Synthesis of Compound 266B

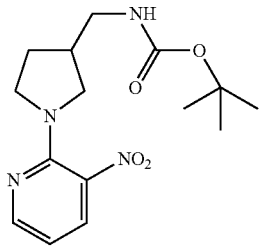 [SMILES: CC(C)(C)OC(=O)NCC1CCN(c2ncccc2[N+](=O)[O-])C1]

A solution of compound 266A (0.10 mmol, 0.200 g), N,N-diisopropylethylamine (1.0 eq, 17.4 µL) and 1 2-Chloro-3-nitro-pyridine (0.80 eq, 2.7 mg) in DMF (2 mL) was irradiated using microwave for 10 minutes at a temperature of 150° C. The solution was then cooled to room temperature and concentrated in vacuo and the resulting residue was purified using column chromatography on silica gel with an eluent mixture of Hexane/EtOAc (50:50) and concentrated to provide compound 266B (0.088 g). HPLC-MS RT=1.85 min, mass calculated for formula $C_{15}H_{22}N_4O_4$ 322.16, observed LCMS m/z 323.20 (M+H).

Step 3—Synthesis of Compound 266C

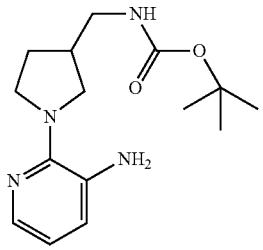

To the compound 266B, add 10% Pd/Carbon (15 mg) and ethyl acetate (10 mL), degas solution and then hydrogenate using an H$_2$-filled balloon. Stir solution at room temperature for about 30 minutes (or until yellow was gone) and filter out Pd/C through Celite to provide compound 266C. HPLC-MS RT=0.89 min, mass calculated for formula $C_{15}H_{24}N_4O_2$ 292.19, observed LCMS m/z 293.20 (M+H).

Step 3—Synthesis of Title Compound

To compound 266C (0.22 mmol, 0.066 g) was added N,N-diisopropylethylamine (1.0 eq, 38 µL) HATU (1.0 eq, 83.6 mg) and 2-thiophen-2-yl-thiazole-4-carboxylic acid (1.0 eq, 46 mg) in DMF (2 mL). The resulting reaction was stirred at room temperature for 15 hours. The reaction mixture was concentrated and the residue was reacted with TFA:H2O (90:10), (1.0 mL) for 30 minutes. The TFA solution was concentrated in vacuo. The residue was dissolved in DMSO/acetonitrile (3:1), purified using reverse phase HPLC to provide the title compound. HPLC-MS RT=2.07 min, mass calculated for formula $C_{18}H_{19}N_5OS_2$ 385.10, observed LCMS m/z 386.13 (M+H).

Example 267

CHK1 SPA Assay

An in vitro assay was developed that utilizes recombinant His-CHK1 expressed in the baculovirus expression system as an enzyme source and a biotinylated peptide based on CDC25C as substrate (biotin-RSGLYRSPSMPENLNRPR).
Materials and Reagents:
1) CDC25C Ser 216 C-term Biotinylated peptide substrate (25 mg), stored at −20° C., Custom Synthesis by Research Genetics: biotin-RSGLYRSPSMPENLNRPR 2595.4 MW
2) His-CHK1 In House lot P976, 235 µg/mL, stored at −80° C.
3) D-PBS (without CaCl and MgCl): GIBCO, Cat. #14190-144
4) SPA beads: Amersham, Cat. #SPQ0032: 500 mg/vial
  Add 10 mL of D-PBS to 500 mg of SPA beads to make a working concentration of 50 mg/mL. Store at 4° C. Use within 2 week after hydration.
5) 96-Well White Microplate with Bonded GF/B filter: Packard, Cat. #6005177
6) Top seal-A 96 well Adhesive Film: Perkin Elmer, Cat. #6005185
7) 96-well Non-Binding White Polystyrene Plate: Corning, Cat. #6005177
8) MgCl$_2$: Sigma, Cat. #M-8266
9) DTT: Promega, Cat. #V3155
10) ATP, stored at 4° C.: Sigma, Cat. #A-5394
11) $\gamma^{33}$P-ATP, 1000-3000 Ci/mMol: Amersham, Cat. #AH9968
12) NaCl: Fisher Scientific, Cat. #BP358-212
13) H$_3$PO$_4$ 85% Fisher, Cat. #A242-500
14) Tris-HCL pH 8.0: Bio-Whittaker, Cat. #16-015V
15) Staurosporine, 100 µg: CALBIOCHEM, Cat. #569397
16) Hypure Cell Culture Grade Water, 500 mL: HyClone, Cat. #SH30529.02
Reaction Mixtures:
1) Kinase Buffer: 50 mM Tris pH 8.0; 10 mM MgCl$_2$; 1 mM DTT
2) His-CHK1, In House Lot P976, MW ~30 KDa, stored at −80° C.
  6 nM is required to yield positive controls of ~5,000 CPM. For 1 plate (100 rxn): dilute 8 µL of 235 µg/mL (7.83 µM) stock in 2 mL Kinase Buffer. This makes a 31 nM mixture. Add 20 µL/well. This makes a final reaction concentration of 6 nM.

3) CDC25C Biotinylated peptide.

Dilute CDC25C to 1 mg/mL (385 µM) stock and store at −200C. For 1 plate (100 rxn): dilute 10 µL of 1 mg/mL peptide stock in 2 mL Kinase Buffer. This gives a 1.925 µM mix. Add 20 µL/rxn. This makes a final reaction concentration of 385 nM.

4) ATP Mix.

For 1 plate (100 rxn): dilute 10 µL of 1 mM ATP (cold) stock and 2 µL fresh P33-ATP (20 µCi) in 5 mL Kinase Buffer. This gives a 2 µM ATP (cold) solution; add 50 µL/well to start the reaction. Final volume is 100 µL/rxn so the final reaction concentrations will be 1 µM ATP (cold) and 0.2 µCi/rxn.

5) Stop Solution:

For 1 plate add: To 10 mL Wash Buffer 2 (2M NaCl 1% $H_3PO_4$): 1 mL SPA bead slurry (50 mg); Add 100 µL/well 6) Wash buffer 1: 2 M NaCl 7) Wash buffer 2: 2 M NaCl, 1% $H_3PO_4$ Assay Procedure:

| Assay Component | Final Concentration | Volume |
|---|---|---|
| CHK1 | 6 nM | 20 µl/rxn |
| Compound (10% DMSO) | — | 10 µl/rxn |
| CDC25C | 0.385 µM | 20 µl/rxn |
| $\gamma^{33}$P-ATP | 0.2 µCi/rxn | 50 µl/rxn |
| Cold ATP | 1 µM | |
| Stop solution | | 100 µl/rxn* |
| SPA beads | 0.5 mg/rxn | |
| | | 200 µl/rxn** |

*Total reaction volume for assay.
**Final reaction volume at termination of reaction (after addition of stop solution).

1) Dilute compounds to desired concentrations in water/10% DMSO—this will give a final DMSO concentration of 1% in the rxn. Dispense 10 µL/rxn to appropriate wells. Add 10 µL 10% DMSO to positive (CHK1+CDC25C+ATP) and negative (CHK1+ATP only) control wells.

2) Thaw enzyme on ice—dilute enzyme to proper concentration in kinase buffer (see Reaction Mixtures) and dispense 20 µL to each well.

3) Thaw the Biotinylated substrate on ice and dilute in kinase buffer (see Reaction Mixtures). Add 20 µL/well except to negative control wells. Instead, add 20 µL Kinase Buffer to these wells.

4) Dilute ATP (cold) and P33-ATP in kinase buffer (see Reaction Mixtures). Add 50 µL/well to start the reaction.

5) Allow the reaction to run for 2 hours at room temperature.

6) Stop reaction by adding 100 µL of the SPA beads/stop solution (see Reaction Mixtures) and leave to incubate for 15 minutes before harvest 7) Place a blank Packard GF/B filter plate into the vacuum filter device (Packard plate harvester) and aspirate 200 mL water through to wet the system.

8) Take out the blank and put in the Packard GF/B filter plate.

9) Aspirate the reaction through the filter plate.

10) Wash: 200 mL each wash; 1× with 2M NaCl; 1× with 2M NaCl/1% $H_3PO_4$

11) Allow filter plate to dry 15 minutes.

12) Put TopSeal-A adhesive on top of filter plate.

13) Run filter plate in Top Count
 Settings: Data mode: CPM
 Radio nuclide: Manual SPA:P33
 Scintillator: Liq/plast
 Energy Range Low $IC_{50}$ Determinations:

Dose-response curves were plotted from inhibition data generated, each in duplicate, from 8 point serial dilutions of inhibitory compounds. Concentration of compound was plotted against % kinase activity, calculated by CPM of treated samples divided by CPM of untreated samples. To generate $IC_{50}$ values, the dose-response curves were then fitted to a standard sigmoidal curve and $IC_{50}$ values were derived by nonlinear regression analysis.

Selected Anilinopiperazine Derivatives of the present invention, when tested using this assay provided $IC_{50}$ values ranging from about 1 nM to about 10 µM.

Example 268

CDK2 ASSAY

Baculovirus Constructions:

Cyclin E was cloned into pVL1393 (Pharmingen, La Jolla, Calif.) by PCR, with the addition of 5 histidine residues at the amino-terminal end to allow purification on nickel resin. The expressed protein was approximately 45 kDa. CDK2 was cloned into pVL1393 by PCR, with the addition of a haemaglutinin epitope tag at the carboxy-terminal end (YDVPD-YAS). The expressed protein was approximately 34 kDa in size.

Enzyme Production:

Recombinant baculoviruses expressing cyclin E and CDK2 were co-infected into SF9 cells at an equal multiplicity of infection (MOI=5), for 48 hrs. Cells were harvested by centrifugation at 1000 RPM for 10 minutes, then pellets lysed on ice for 30 minutes in five times the pellet volume of lysis buffer containing 50 mM Tris pH 8.0, 150 mM NaCl, 1% NP40, 1 mM DTT and protease inhibitors (Roche Diagnostics GmbH, Mannheim, Germany). Lysates were spun down at 15000 RPM for 10 minutes and the supernatant retained. 5 mL of nickel beads (for one liter of SF9 cells) were washed three times in lysis buffer (Qiagen GmbH, Germany). Imidazole was added to the baculovirus supernatant to a final concentration of 20 mM, then incubated with the nickel beads for 45 minutes at 4° C. Proteins were eluted with lysis buffer containing 250 mM imidazole. Eluate was dialyzed overnight in 2 liters of kinase buffer containing 50 mM Tris pH 8.0, 1 mM DTT, 10 mM $MgCl_2$, 100 µM sodium orthovanadate and 20% glycerol. Enzyme was stored in aliquots at −70° C.

Example 269

In Vitro Cyclin E/CDK2 Kinase Assays

Cyclin E/CDK2 kinase assays were performed in low protein binding 96-well plates (Corning Inc, Corning, N.Y.). Enzyme was diluted to a final concentration of 50 µg/mL in kinase buffer containing 50 mM Tris pH 8.0, 10 mM $MgCl_2$, 1 mM DTT, and 0.1 mM sodium orthovanadate. The substrate used in these reactions was a biotinylated peptide derived from Histone H1 (from Amersham, UK). The substrate was thawed on ice and diluted to 2 µM in kinase buffer. Compounds were diluted in 10% DMSO to desirable concentrations. For each kinase reaction, 20 µL of the 50 µg/mL enzyme solution (1 µg of enzyme) and 20 µl of the 2 µM substrate solution were mixed, then combined with 10 µL of diluted compound in each well for testing. The kinase reaction was started by addition of 50 µL of 2 µM ATP and 0.1 µCi of 33P-ATP (from Amersham, UK). The reaction was allowed to run for 1 hour at room temperature. The reaction was stopped by adding 200 µL of stop buffer containing 0.1%

Triton X-100, 1 mM ATP, 5 mM EDTA, and 5 mg/mL streptavidine coated SPA beads (from Amersham, UK) for 15 minutes. The SPA beads were then captured onto a 96-well GF/B filter plate (Packard/Perkin Elmer Life Sciences) using a Filtermate universal harvester (Packard/Perkin Elmer Life Sciences.). Non-specific signals were eliminated by washing the beads twice with 2M NaCl then twice with 2 M NaCl with 1% phosphoric acid. The radioactive signal was then measured using a TopCount 96 well liquid scintillation counter (from Packard/Perkin Elmer Life Sciences).

$IC_{50}$ Determinations:

Dose-response curves were plotted from inhibition data generated, each in duplicate, from 8 point serial dilutions of inhibitory compounds. Concentration of compound was plotted against % kinase activity, calculated by CPM of treated samples divided by CPM of untreated samples. To generate $IC_{50}$ values, the dose-response curves were then fitted to a standard sigmoidal curve and $IC_{50}$ values were derived by nonlinear regression analysis.

Example 270

MEK1 Kinase Assay

Full-length active phosphorylated MEK1 was expressed as a 6× histidine tagged protein ($His_6$-MEK1) by baculovirus infection of Hi-Five cells co-infected with a baculovirus expressing untagged constitutively active Raf-1. Several milligrams of active $His_6$-MEK1 was then purified by Ni-NTA affinity chromatography followed by gel filtration chromatography. Full-length murine catalytically inactive ERK2KR, which had the lysine in subdomain II mutated to arginine was used as a substrate. ERK2KR was expressed from vector pET32aRC in IPTG-induced BL21D3 *E. coli* as a biotinylated, 6× histidine and thioredoxin tagged fusion protein and purified by Ni-NTA affinity chromatography followed by Mono Q ion exchange chromatography. Kinase reactions were performed in duplicate in a 96-well plate, 33 µL per well at 25° C. for 15 mins, and consisted of 20 nM $His_6$-MEK1, 2 µM ERK2KR, 2 µM ATP, 10 µCi/µL [$\gamma$-$^{33}$P]-ATP, 10 mM $MgCl_2$, 0.01% β-octylglucoside, 1 mM DTT, 20 mM HEPES pH 7.5, 3% DMSO and test compounds ranging from 20 µM down to 0.08 nM. Kinase reactions were stopped by addition of 30 µL of 1.5% o-phosphoric acid, transferred to Millipore Multiscreen-PH plates and incubated for 5 minutes to allow ERK2KR binding. Non-specific activity was estimated from pre-inactivated reactions wherein 30 µL of 1.5% o-phosphoric acid was added per well before addition of enzyme. Stopped plates were washed three times by vacuum filtration with 0.75% o-phosphoric acid followed by two washes with 100% ethanol and air dried. 50 µL of scintillation cocktail was added to each well and $^{33}$P incorporated into ERK2KR was detected using a Wallac Microbeta 1450 JET scintillation counter. Percentage inhibition, $IC_{50}$ and Hill slope values were calculated using ActivityBase software.

Selected Anilinopiperazine Derivatives of the present invention, when tested using this assay, provided $IC_{50}$ values ranging from about 10 nM to about 100 µM.

Example 271

General Procedure for MEK1 TdF Assays

1 µM protein was mixed with micromolar concentrations (usually 1-50 µM) of compounds in 20 µl of assay buffer (25 mM HEPES, pH 7.4, 300 mM NaCl, 1 mM DTT, 2% DMSO, Sypro Orange 5×) in a white 96-well PCR plate. The plate is sealed by clear strips and placed in a thermocycler (Chromo4, BioRad). The fluorescence intensities are monitored at every 0.5° C. increment during melting from 25° C. to 95° C. The data are exported into an excel sheet and subject to a custom curve fitting algorithm to derive TdF Kd values. All TdF Kd values have an error margin of ~50% due to uncertainty with the enthalpy change of binding.

Selected Anilinopiperazine Derivatives of the present invention, when tested using this assay, provided $K_d$ values ranging from about 1 µM to about 100 µM.

Example 272

General Procedure for MEK1 Delfia Enzyme Activity Assay

The inhibitory effect of compounds was determined with a DELFIA (Perkin-Elmer) based enzyme assay in which both compound individual percent inhibitions and dose response curves (IC50 determinations) were run. Activated recombinant human MEK1 (5 nanomolar final concentration) in buffer containing Hepes, magnesium chloride, dithiothreitol and ATP (2 micromolar final concentration) was preincubated for 10 minutes, before starting the reaction by addition of the recombinant MEK1 substrate ERK (1 micromolar final concentration), which contains a biotin label. The reaction was run at 20 degrees centigrade for 60 minutes, at which time the reaction was stopped by transfer of reaction aliquots to ROCHE streptavidin microplates (Perkin-Elmer #11734776001) containing DELFIA assay buffer (Perkin-Elmer #4002-0010). After one hour of binding at room temperature with agitation the plates were washed with DELFIA wash buffer (Perkin-Elmer #4010-0010) following which DELFIA assay buffer containing a phosphotyrosine specific antibody (Perkin Elmer #AD0040) was added to the plate and incubated as above for one hour. After a second wash, the plates were developed by addition of Perkin-Elmer enhancement solution (#4001-0010), followed by a 10 minute incubation with agitation. Europium fluorescence was read on a Victor 1420 fluorescent plate reader. Percent inhibition and IC50 determinations were made by comparison of compound containing assays to reaction controls.

Selected Anilinopiperazine Derivatives of the present invention, when tested using this assay, provided $IC_{50}$ values ranging from about 10 nM to about 100 µM.

Example 273

In Vitro Aurora TdF Assays

Aurora A Assay

Aurora A kinase assays were performed in low protein binding 384-well plates (Corning Inc). All reagents were thawed on ice. Test compounds were diluted in 100% DMSO to desirable concentrations. Each reaction consisted of 8 nM enzyme (Aurora A, Upstate cat #14-511), 100 nM Tamra-PKAtide (Molecular Devices, 5TAMRA-GRTGRRNSI-COOH), 25 µM ATP (Roche), 1 mM DTT (Pierce), and kinase buffer (10 mM Tris, 10 mM MgCl2, 0.01% Tween 20). For each reaction, 14 µl containing TAMRA-PKAtide, ATP, DTT and kianse buffer were combined with 1 µl diluted compound. The kinase reaction was started by the addition of 5 µl diluted enzyme. The reaction was allowed to run for 2 hours at room temperature. The reaction was stopped by adding 60 µl IMAP beads (1:400 beads in progressive (94.7% buffer A: 5.3% buffer B) 1× buffer, 24 mM NaCl). After an additional 2 hours, fluorescent polarization was measured using an Analyst AD (Molecular devices).

Aurora B Assay

Aurora A kinase assays were performed in low protein binding 384-well plates (Corning Inc). All reagents were thawed on ice. Compounds were diluted in 100% DMSO to desirable concentrations. Each reaction consisted of 26 nM enzyme (Aurora B, Invitrogen cat #pv3970), 100 nM Tamra-PKAtide (Molecular Devices, 5TAMRA-GRTGRRNSI-COOH), 50 µM ATP (Roche), 1 mM DTT (Pierce), and kinase buffer (10 mM Tris, 10 mM $MgCl_2$, 0.01% Tween 20). For each reaction, 14 µl containing TAMRA-PKAtide, ATP, DTT and kianse buffer were combined with 1 µl diluted compound. The kinase reaction was started by the addition of 5 µl diluted enzyme. The reaction was allowed to run for 2 hours at room temperature. The reaction was stopped by adding 60 µl IMAP beads (1:400 beads in progressive (94.7% buffer A: 5.3% buffer B) 1× buffer, 24 mM NaCl). After an additional 2 hours, fluorescent polarization was measured using an Analyst AD (Molecular devices).

$IC_{50}$ Determinations

Dose-response curves were plotted from inhibition data generated each in duplicate, from 8-point serial dilutions of test compounds. Concentration of compound was plotted against kinase activity, calculated by degree of fluorescent polarization. To generate $IC_{50}$ values, the dose-response curves were then fitted to a standard sigmoidal curve and $IC_{50}$ values were derived by nonlinear regression analysis.

Selected Anilinopiperazine Derivatives of the present invention, when tested using the Aurora A and Aurora B assays, provided $K_d$ values ranging from about 1 nM to about 100 µM.

Uses of the Anilinopiperazine Derivatives

The Anilinopiperazine Derivatives can be useful for treating or preventing a Condition in a patient.

Specific diseases and disorders treatable by administration of an effective amount of at least one Anilinopiperazine Derivative include, but are not limited to, those disclosed in U.S. Pat. No. 6,413,974, which is incorporated by reference herein.

Treatment or Prevention of a Cardiovascular Disease

The Anilinopiperazine Derivatives are useful for treating or preventing a cardiovascular disease in a patient.

Accordingly, in one embodiment, the present invention provides a method for treating a cardiovascular disease in a patient, comprising administering to the patient an effective amount of one or more Anilinopiperazine Derivatives.

Illustrative examples of cardiovascular diseases treatable or preventable using the present methods, include, but are not limited to atherosclerosis, congestive heart failure, cardiac arrhythmia, myocardial infarction, atrial fibrillation, atrial flutter, circulatory shock, left ventricular hypertrophy, ventricular tachycardia, supraventricular tachycardia, coronary artery disease, angina, infective endocarditis, non-infective endocarditis, cardiomyopathy, peripheral artery disease, Reynaud's phenomenon, deep venous thrombosis, aortic stenosis, mitral stenosis, pulmonic stenosis and tricuspid stenosis.

In one embodiment, the cardiovascular disease is atherosclerosis.

In another embodiment, the cardiovascular disease is congestive heart failure.

In another embodiment, the cardiovascular disease is coronary artery disease.

Treatment or Prevention of a CNS Disorder

The Anilinopiperazine Derivatives are useful for treating or preventing a central nervous system (CNS) disorder in a patient.

Accordingly, in one embodiment, the present invention provides a method for treating a CNS disorder in a patient, comprising administering to the patient an effective amount of one or more Anilinopiperazine Derivatives.

Illustrative examples of CNS disorders treatable or preventable using the present methods, include, but are not limited to hypoactivity of the central nervous system, hyperactivity of the central nervous system, a neurodegenerative disease, Alzheimer's disease, amyotrophic lateral sclerosis (ALS), Creutzfeldt-Jakob disease, Huntington disease, multiple sclerosis, Lewy body disorder, a tic disorder, Tourette's Syndrome, Parkinson disease, Pick's disease, a prion disease or schizophrenia, epilepsy, migraine, anxiety, bipolar disorder, depression, attention deficit hyperactivity disorder (ADHD) and dementia.

In one embodiment, the CNS disorder is Alzheimer's disease.

In another embodiment, the CNS disorder is Parkinson disease.

In another embodiment, the CNS disorder is ALS.

Treatment or Prevention of a Viral Disease

The Anilinopiperazine Derivatives are useful for treating or preventing a viral disease in a patient.

Accordingly, in one embodiment, the present invention provides a method for treating a viral disease in a patient, comprising administering to the patient an effective amount of one or more Anilinopiperazine Derivatives.

Illustrative examples of viral diseases treatable or preventable using the present methods include, but are not limited to, HIV, human papilloma virus (HPV), herpesvirus, poxvirus, Epstein-Barr virus, Sindbis virus and adenovirus.

In one embodiment the viral disease is HIV.

In another embodiment the viral disease is HPV.

Treatment or Prevention of a Fungal Infection

The Anilinopiperazine Derivatives are useful for treating or preventing a fungal infection in a patient.

Accordingly, in one embodiment, the present invention provides a method for treating a fungal infection in a patient, comprising administering to the patient an effective amount of one or more Anilinopiperazine Derivatives.

Illustrative examples of fungal infections treatable or preventable using the present methods include, but are not limited to, aspergillosis, blastomycosis, candidiasis, coccidioidomycosis, cryptococcosis, histomplamosis, an opportunistic fungi (including yeasts and molds), mucormycosis, mycetoma, paracoccidioidomycosis and sporotrichosis.

In one embodiment the fungal infection is candidiasis.

Treating or Preventing a Disease Related to the Activity of a Protein Kinase The Anilinopiperazine Derivatives can be inibitors, regulators or modulators of protein kinases and are useful for treating or preventing a disease related to the activity of a protein kinase in a patient.

Accordingly, in one embodiment, the present invention provides a method for treating a disease related to the activity of a protein kinase in a patient, comprising administering to the patient an effective amount of one or more Anilinopiperazine Derivatives.

Illustrative examples of diseases related to the activity of a protein kinase that are treatable or preventable using the present methods include, but are not limited to, cyclin-dependent kinases (CDKs) such as CDK1, CDK2, CDK3, CDK4, CDK5, CDK6 and CDK7, CDK8; aurora kinases such as Aurora-A, Aurora-B and Aurora-C; mitogen activated protein kinase (MAPK/ERK); glycogen synthase kinase 3 (GSK3beta); c-Met kinases, such as c-Met; Pim-1 kinases; checkpoint kinases, such as Chk1 and Chk2; tyrosine kinases, such as the HER subfamily (including, for example, EGFR (HER1), HER2, HER3 and HER4), the insulin subfamily (including, for example, INS-R, IGF-IR, IR, and IR-R), the PDGF subfamily (including, for example, PDGF-alpha and beta receptors, CSFIR, c-kit and FLK-II), the FLK family (including, for example, kinase insert domain receptor (KDR), fetal liver kinase-1(FLK-1), fetal liver kinase-4 (FLK-4) and the fms-like tyrosine kinase-1 (flt-1)); non-receptor protein tyrosine kinases, for example LCK, Src, Frk, Btk, Csk, Abl, Zap70, Fes/Fps, Fak, Jak, Ack, and LIMK; and growth factor receptor tyrosine kinases such as VEGF-R2, FGF-R, TEK, Akt kinases and the like.

In one embodiment, the present invention provides a method of inhibiting one or more Checkpoint kinases in a patient in need thereof, comprising administering to the patient a therapeutically effective amount of at least one Anilinopiperazine Derivative or a pharmaceutically acceptable salt, solvate, ester, prodrug or stereoisomer thereof.

In another embodiment, the present invention provides a method of treating, or slowing the progression of, a disease associated with one or more Checkpoint kinases in a patient in need thereof, comprising administering a therapeutically effective amount of at least one Anilinopiperazine Derivative or a pharmaceutically acceptable salt, solvate, ester, prodrug or stereoisomer thereof.

In another embodiment, the present invention provides a method of treating one or more diseases associated with Checkpoint kinase, comprising administering to a patient in need of such treatment at least one Anilinopiperazine Derivative, or a pharmaceutically acceptable salt, solvate, ester, prodrug or stereoisomer thereof; and at least one additional anticancer agent, wherein the amounts of the at least one Anilinopiperazine Derivative and the at least one anticancer agent result in a therapeutic effect.

In still another embodiment, the present invention provides a method of treating, or slowing the progression of, a disease associated with one or more Checkpoint kinases in a patient in need thereof, comprising administering a therapeutically effective amount of a pharmaceutical composition comprising in combination at least one pharmaceutically acceptable carrier and at least one Anilinopiperazine Derivative, or a pharmaceutically acceptable salt, solvate, ester, prodrug or stereoisomer thereof.

In one embodiment, the checkpoint kinase to be inhibited, modulated or regulated is Chk1. In another embodiment, the checkpoint kinase to be inhibited, modulated or regulated is Chk2.

In one embodiment, the present invention provides a method of inhibiting one or more tyrosine kinases in a patient in need thereof, comprising administering to the patient a therapeutically effective amount of at least one Anilinopiperazine Derivative or a pharmaceutically acceptable salt, solvate, ester, prodrug or stereoisomer thereof.

In another embodiment, the present invention provides a method of treating, or slowing the progression of, a disease associated with one or more tyrosine kinases in a patient in need thereof, comprising administering a therapeutically effective amount of at least one Anilinopiperazine Derivative or a pharmaceutically acceptable salt, solvate, ester, prodrug or stereoisomer thereof.

In another embodiment, the present invention provides a method of treating one or more diseases associated with tyrosine kinase, comprising administering to a patient in need of such treatment at least one Anilinopiperazine Derivative, or a pharmaceutically acceptable salt, solvate, ester, prodrug or stereoisomer thereof; and at least one additional anticancer agent, wherein the amounts of the at least one Anilinopiperazine Derivative and the at least one anticancer agent result in a therapeutic effect.

In still another embodiment, the present invention provides a method of treating, or slowing the progression of, a disease associated with one or more tyrosine kinases in a patient in need thereof, comprising administering a therapeutically effective amount of a pharmaceutical composition comprising in combination at least one pharmaceutically acceptable carrier and at least one Anilinopiperazine Derivative or a pharmaceutically acceptable salt, solvate, ester, prodrug or stereoisomer thereof.

In specific embodiments, the tyrosine kinase being inhibited, modulated or regulated is VEGFR (VEGF-R2), EGFR, HER2, SRC, JAK or TEK, or a combination thereof.

In one embodiment, the present invention provides a method of inhibiting one or more Pim-1 kinases in a patient in need thereof, comprising administering to the patient a therapeutically effective amount of at least one Anilinopiperazine Derivative or a pharmaceutically acceptable salt, solvate, ester, prodrug or stereoisomer thereof.

In another embodiment, the present invention provides a method of treating, or slowing the progression of, a disease associated with one or more Pim-1 kinases in a patient in need thereof, comprising administering a therapeutically effective amount of at least one Anilinopiperazine Derivative or a pharmaceutically acceptable salt, solvate, ester, prodrug or stereoisomer thereof.

In another embodiment, the present invention provides a method of treating one or more diseases associated with Pim-1 kinase, comprising administering to a patient in need of such treatment at least one Anilinopiperazine Derivative, or a pharmaceutically acceptable salt, solvate, ester, prodrug or stereoisomer thereof; and at least one additional anticancer agent, wherein the amounts of the at least one Anilinopiperazine Derivative and the at least one anticancer agent result in a therapeutic effect.

In still another embodiment, the present invention provides a method of treating, or slowing the progression of, a disease associated with one or more Pim-1 kinases in a patient in need thereof, comprising administering a therapeutically effective amount of a pharmaceutical composition comprising in combination at least one pharmaceutically acceptable carrier and at least one Anilinopiperazine Derivative or a pharmaceutically acceptable salt, solvate, ester, prodrug or stereoisomer thereof.

In one embodiment, the present invention provides a method of treating one or more diseases associated with an Aurora kinase, comprising administering to a patient in need of such treatment at least one Anilinopiperazine Derivative, or a pharmaceutically acceptable salt, solvate, ester, prodrug or stereoisomer thereof; and at least one additional anticancer agent, wherein the amounts of the at least one Anilinopiperazine Derivative and the at least one anticancer agent result in a therapeutic effect.

In another embodiment, the present invention provides a method of treating, or slowing the progression of, a disease associated with one or more Aurora kinases in a patient in need thereof, comprising administering a therapeutically effective amount of a pharmaceutical composition comprising in combination at least one pharmaceutically acceptable carrier and at least one Anilinopiperazine Derivative or a pharmaceutically acceptable salt, solvate, ester, prodrug or stereoisomer thereof.

In one embodiment, the present invention provides a method of treating one or more diseases associated with a cyclin dependent kinase, comprising administering to a patient in need of such treatment an amount of a first compound, which is an Anilinopiperazine Derivative, or a pharmaceutically acceptable salt, solvate, ester, prodrug or stereoisomer thereof; and an amount of at least one second compound, the second compound being an anticancer agent different from the Anilinopiperazine Derivative, wherein the amounts of the first compound and the second compound result in a therapeutic effect.

The Anilinopiperazine Derivatives can also be useful for inhibiting oncogenes that encode for protein kinases. Non-limiting examples of such oncogenes include C-Met.

Treatment or Prevention of a Proliferative Disorder

The Anilinopiperazine Derivatives are useful for treating or preventing a proliferative disorder in a patient.

Accordingly, in one embodiment, the present invention provides a method for treating a proliferative disorder in a patient, comprising administering to the patient an effective amount of one or more Anilinopiperazine Derivatives.

Illustrative examples of proliferative disorders treatable or preventable using the present methods include, but are not limited to, cancer, atherosclerosis, benign prostate hyperplasia, familial adenomatosis polyposis, neuro-fibromatosis, atherosclerosis, pulmonary fibrosis, arthritis, psoriasis, glomerulonephritis, restenosis following angioplasty or vascular surgery, hypertrophic scar formation, inflammatory bowel disease, transplantation rejection, endotoxic shock, idiopathic pulmonary fibrosis, scleroderma and cirrhosis of the liver.

Induction or Inhibition of Apoptosis

The Anilinopiperazine Derivatives are useful for inducing or inhibiting apoptosis in a patient.

Accordingly, in one embodiment, the present invention provides a method for inducing or inhibiting apoptosis in a patient, comprising administering to the patient an effective amount of one or more Anilinopiperazine Derivatives.

The apoptotic response is aberrant in a variety of human diseases and the Anilinopiperazine Derivatives, as modulators of apoptosis, can be useful for the treatment of cancer, a viral infection, prevention of AIDS development in HIV-infected individuals, an autoimmune disease (including but not limited to systemic lupus, erythematosus, autoimmune mediated glomerulonephritis, rheumatoid arthritis, psoriasis, inflammatory bowel disease, and autoimmune diabetes mellitus), a neurodegenerative disorders (including but not limited to Alzheimer's disease, AIDS-related dementia, Parkinson's disease, amyotrophic lateral sclerosis, retinitis pigmentosa, spinal muscular atrophy and cerebellar degeneration), a myelodysplastic syndrome, aplastic anemia, an ischemic injury associated with myocardial infarction, stroke and reperfusion injury, arrhythmia, atherosclerosis, toxin-induced or alcohol related liver diseases, hematological diseases (including but not limited to chronic anemia and aplastic anemia), degenerative diseases of the musculoskeletal system (including but not limited to osteoporosis and arthritis) aspirin-sensitive rhinosinusitis, cystic fibrosis, multiple sclerosis, kidney diseases and cancer pain.

Treatment or Prevention of Cancer

The Anilinopiperazine Derivatives are useful for treating or preventing cancer in a patient.

Accordingly, in one embodiment, the present invention provides a method for treating cancer in a patient, comprising administering to the patient an effective amount of one or more Anilinopiperazine Derivatives.

Illustrative examples of cancers treatable or preventable using the present methods include, but are not limited to cancers of the bladder, breast, colon, rectum, kidney, liver, lung (including small cell lung cancer, non-small cell lung cancer, mesothelioma, and giant cell cancer), head and neck, esophagus, gall bladder, ovary, pancreas, stomach, cervix, thyroid, prostate or skin (including squamous cell carcinoma and melanoma); hematopoietic tumors of lymphoid lineage (including but not limited to, a leukemia such as acute lymphocytic leukemia, chronic lymphocytic leukemia or acute lymphoblastic leukemia; a lymphoma, such as B-cell lymphoma, T-cell lymphoma, Hodgkins lymphoma, non-Hodgkins lymphoma, hairy cell lymphoma, mantle cell lymphoma, myeloma or Burkett's lymphoma); a cancer of unknown origin; hematopoietic tumors of myeloid lineage, including but not limited to, acute and chronic myelogenous leukemias, myelodysplastic syndrome and promyelocytic leukemia; tumors of mesenchymal origin, including but not limited to, fibrosarcoma and rhabdomyosarcoma; tumors of the central and peripheral nervous system, including but not limited to brain tumors such as an astrocytoma, a neuroblastoma, a glioma (such as glioblastoma multiforme) or a schwannoma; and other tumors, including seminoma, teratocarcinoma, osteosarcoma, xenoderma pigmentosum, keratoctanthoma, thyroid follicular cancer and Kaposi's sarcoma. The Anilinopiperazine Derivatives are useful for treating primary and/or metastatic cancers.

The Anilinopiperazine Derivatives may also be useful in the chemoprevention of cancer. Chemoprevention is defined as inhibiting the development of invasive cancer by either blocking the initiating mutagenic event or by blocking the progression of pre-malignant cells that have already suffered an insult or inhibiting tumor relapse.

The Anilinopiperazine Derivatives may also be useful in inhibiting tumor angiogenesis and metastasis.

In one embodiment, the cancer treated or prevented is selected from: breast cancer, colorectal cancer, lung cancer, prostate cancer, ovarian cancer, pancreatic cancer, skin cancer, a leukemia and a lymphoma.

In another embodiment, the cancer treated or prevented is selected from: breast cancer, colorectal cancer, lung cancer and prostate cancer.

In one embodiment, the cancer treated or prevented is breast cancer.

In another embodiment, the cancer treated or prevented is lung cancer.

In another embodiment, the cancer treated or prevented is colorectal cancer.

In still another embodiment, the cancer treated or prevented is prostate cancer.

In still another embodiment, the cancer treated or prevented is a leukemia.

In still another embodiment, the cancer treated or prevented is a lymphoma.

In one embodiment, the cancer treated or prevented is a solid tumor.

In another embodiment, the cancer treated or prevented is a cancer of the blood or lymph.

In one embodiment, the cancer treated or prevented is a primary cancer.

In another embodiment, the cancer treated or prevented is a metastatic cancer.

In a further embodiment, the patient is being treated for both primary and metastatic cancer.

Combination Therapy

In one embodiment, the present invention provides methods for treating a Condition in a patient, the method comprising administering to the patient one or more Anilinopiperazine Derivatives, or a pharmaceutically acceptable salt, solvate, ester or prodrug thereof and at least one additional therapeutic agent that is not an Anilinopiperazine Derivative, wherein the amounts administered are together effective to treat or prevent a Condition.

Additional therapeutic agents useful in the present methods include, but are not limited to, an anticancer agent, an agent useful for treating a cardiovascular disease, an agent useful for treating a CNS disorder, an antiviral agent, an antifungal agent, an anti-proliferative agent, an anti-alopecia agent, an anti-inflammatory agent, an agent useful for the treatment of a protein kinase-related disorder, an anti-ischemic agent or any combination of two or more of these agents.

In another embodiment, the other therapeutic agent is an agent useful for reducing any potential side effect of an Anilinopiperazine Derivative. Such potential side effects include, but are not limited to, nausea, vomiting, headache, fever, lethargy, muscle aches, diarrhea, general pain, and pain at an injection site.

When administering a combination therapy to a patient in need of such administration, the therapeutic agents in the combination, or a composition or compositions comprising the therapeutic agents, may be administered in any order such as, for example, sequentially, concurrently, together, simultaneously and the like. The amounts of the various actives in such combination therapy may be different amounts (different dosage amounts) or same amounts (same dosage amounts).

In one embodiment, the one or more Anilinopiperazine Derivatives are administered during a time when the additional therapeutic agent(s) exert their prophylactic or therapeutic effect, or vice versa.

In another embodiment, the one or more Anilinopiperazine Derivatives and the additional therapeutic agent(s) are administered in doses commonly employed when such agents are used as monotherapy for treating a Condition.

In another embodiment, the one or more Anilinopiperazine Derivatives and the additional therapeutic agent(s) are administered in doses lower than the doses commonly employed when such agents are used as monotherapy for treating a Condition.

In still another embodiment, the one or more Anilinopiperazine Derivatives and the additional therapeutic agent(s) act synergistically and are administered in doses lower than the doses commonly employed when such agents are used as monotherapy for treating a Condition.

In one embodiment, the one or more Anilinopiperazine Derivatives and the additional therapeutic agent(s) are present in the same composition. In one embodiment, this composition is suitable for oral administration. In another embodiment, this composition is suitable for intravenous administration.

The one or more Anilinopiperazine Derivatives and the additional therapeutic agent(s) can act additively or synergistically. A synergistic combination may allow the use of lower dosages of one or more agents and/or less frequent administration of one or more agents of a combination therapy. A lower dosage or less frequent administration of one or more agents may lower toxicity of the therapy without reducing the efficacy of the therapy.

In one embodiment, the administration of one or more Anilinopiperazine Derivatives and the additional therapeutic agent(s) may inhibit the resistance of a Condition to one or more of these agents.

In one embodiment, the additional therapeutic agent is used at its known therapeutically effective dose. In another embodiment, the additional therapeutic agent is used at its normally prescribed dosage. In another embodiment, the additional therapeutic agent is used at less than its normally prescribed dosage or its known therapeutically effective dose.

The doses and dosage regimen of the other agents used in the combination therapies of the present invention for the treatment or prevention of a Condition can be determined by the attending clinician, taking into consideration the approved doses and dosage regimen in the package insert; the age, sex and general health of the patient; and the type and severity of the viral infection or related disease or disorder. When administered in combination, the Anilinopiperazine Derivative(s) and the other agent(s) for treating diseases or conditions listed above can be administered simultaneously or sequentially. This particularly useful when the components of the combination are given on different dosing schedules, e.g., one component is administered once daily and another every six hours, or when the compositions are different, e.g. one is a tablet and one is a capsule. A kit comprising the separate dosage forms is therefore advantageous.

Generally, a total daily dosage of the one or more Anilinopiperazine Derivatives and the additional therapeutic agent(s) can when administered as combination therapy, range from about 0.1 to about 2000 mg per day, although variations will necessarily occur depending on the target of the therapy, the patient and the route of administration. In one embodiment, the dosage is from about 0.2 to about 100 mg/day, administered in a single dose or in 2-4 divided doses. In another embodiment, the dosage is from about 1 to about 500 mg/day, administered in a single dose or in 2-4 divided doses. In another embodiment, the dosage is from about 1 to about 200 mg/day, administered in a single dose or in 2-4 divided doses. In still another embodiment, the dosage is from about 1 to about 100 mg/day, administered in a single dose or in 2-4 divided doses. In yet another embodiment, the dosage is from about 1 to about 50 mg/day, administered in a single dose or in 2-4 divided doses. In a further embodiment, the dosage is from about 1 to about 20 mg/day, administered in a single dose or in 2-4 divided doses.

Combination Therapy for the Treatment of Cancer

The compounds of this invention may also be useful in combination (administered together or sequentially in any order) with one or more separate anticancer treatments such as surgery, radiation therapy, biological therapy (e.g., anticancer vaccine therapy) and/or the administration of at least one additional anticancer agent different from the Anilinopiperazine Derivatives, in order to treat or prevent cancer in a patient. The compounds of the present invention can be present in the same dosage unit as the additional anticancer agent(s) or in separate dosage units.

Non-limiting examples of additional anticancer agents (also known as anti-neoplastic agents) suitable for use in combination with the compounds of the present invention include cytostatic agents, cytotoxic agents (such as for example, but not limited to, DNA interactive agents (such as cisplatin or doxorubicin)); taxanes (e.g. taxotere, taxol); topoisomerase II inhibitors (such as etoposide or teniposide); topoisomerase I inhibitors (such as irinotecan (or CPT-11), camptostar, or topotecan); tubulin interacting agents (such as paclitaxel, docetaxel or the epothilones); hormonal agents (such as tamoxifen); thymidylate synthase inhibitors (such as 5-fluorouracil); anti-metabolites (such as methoxtrexate); alkylating agents (such as temozolomide (TEMODAR™ from Schering-Plough Corporation, Kenilworth, N.J.), cyclophosphamide); Farnesyl protein transferase inhibitors (such as, SARASAR™ (4-[2-[4-[(11R)-3,10-dibromo-8-chloro-6,11-dihydro-5H-benzo[5,6]cyclohepta[1,2-b]pyridin-11-yl-]-1-piperidinyl]-2-oxoethyl]-1-piperidinecarboxamide, or SCH 66336 from Schering-Plough Corporation, Kenilworth, N.J.), tipifarnib (Zarnestra® or R115777 from Janssen Pharmaceuticals), L778,123 (a farnesyl protein transferase inhibitor from Merck & Company, Whitehouse Station, N.J.), BMS 214662 (a farnesyl protein transferase inhibitor from Bristol-Myers Squibb Pharmaceuticals, Princeton, N.J.); signal transduction inhibitors (such as, Iressa (from Astra Zeneca Pharmaceuticals, England), Tarceva (EGFR kinase inhibitors), antibodies to EGFR (e.g., C225), GLEEVEC™ (C-abl kinase inhibitor from Novartis Pharmaceuticals, East Hanover, N.J.); interferons such as, for example, intron (from Schering-Plough Corporation), Peg-Intron (from Schering-Plough Corporation); hormonal therapy combinations; aromatase combinations; ara-C, adriamycin, cytoxan, and gemcitabine.

Other useful additional anticancer agents include but are not limited to Uracil mustard, Chlormethine, Ifosfamide, Melphalan, Chlorambucil, Pipobroman, Triethylenemelamine, ara-C, adriamycin, cytoxan, Clofarabine (Clolar® from Genzyme Oncology, Cambridge, Mass.), cladribine (Leustat® from Janssen-Cilag Ltd.), aphidicolon, rituxan (from Genentech/Biogen Idec), sunitinib (Sutent® from Pfizer), dasatinib (or BMS-354825 from Bristol-Myers Squibb), tezacitabine (from Aventis Pharma), Sml1, fludarabine (from Trigan Oncology Associates), pentostatin (from BC Cancer Agency), triapine (from Vion Pharmaceuticals), didox (from Bioseeker Group), trimidox (from ALS Therapy Development Foundation), amidox, 3-AP (3-aminopyridine-2-carboxaldehyde thiosemicarbazone), MDL-101,731 ((E)-2'-deoxy-2'-(fluoromethylene)cytidine) and gemcitabine.

Other useful additional anticancer agents include but are not limited to Triethylenethiophosphoramine, Busulfan, Carmustine, Lomustine, Streptozocin, Dacarbazine, Floxuridine, Cytarabine, 6-Mercaptopurine, 6-Thioguanine, Fludarabine phosphate, oxaliplatin, leucovirin, oxaliplatin (ELOXATIN™ from Sanofi-Synthelabo Pharmaceuticals, France), Pentostatine, Vinblastine, Vincristine, Vindesine, Bleomycin, Dactinomycin, Daunorubicin, Doxorubicin, Epirubicin, Idarubicin, Mithramycin, Deoxycoformycin, Mitomycin-C, L-Asparaginase, Teniposide 17α-Ethinylestradiol, Diethylstilbestrol, Testosterone, Prednisone, Fluoxymesterone, Dromostanolone propionate, Testolactone, Megestrolacetate, Methylprednisolone, Methyltestosterone, Prednisolone, Triamcinolone, Chlorotrianisene, Hydroxyprogesterone, Aminoglutethimide, Estramustine, Medroxyprogesteroneacetate, Leuprolide, Flutamide, Toremifene, goserelin, Cisplatin, Carboplatin, Oxaliplatin, Aroplatin, Hydroxyurea, Amsacrine, Procarbazine, Mitotane, Mitoxantrone, Levamisole, Navelbene, Anastrazole, Letrazole, Capecitabine, Reloxafine, Droloxafine, Hexamethylmelamine, Avastin, Herceptin, Bexxar, Velcade, Zevalin, Trisenox, Xeloda, Vinorelbine, Profimer, Erbitux, Liposomal, Thiotepa, Altretamine, Melphalan, Trastuzumab, Lerozole, Fulvestrant, Exemestane, Fulvestrant, Ifosfomide, Rituximab, C225 and Campath.

In one embodiment, the other anticancer agent is selected from: a cytostatic agent, cisplatin, doxorubicin, taxotere, taxol, etoposide, irinotecan, camptostar, topotecan, paclitaxel, docetaxel, epothilones, tamoxifen, 5-fluorouracil, methoxtrexate, temozolomide, cyclophosphamide, SCH 66336, R115777, L778,123, BMS 214662, Iressa, Tarceva, antibodies to EGFR, Gleevec, intron, ara-C, adriamycin, cytoxan, gemcitabine, Uracil mustard, Chlormethine, Ifosfamide, Melphalan, Chlorambucil, Pipobroman, Triethylenemelamine, Triethylenethiophosphoramine, Busulfan, Carmustine, Lomustine, Streptozocin, Dacarbazine, Floxuridine, Cytarabine, 6-Mercaptopurine, 6-Thioguanine, Fludarabine phosphate, Pentostatine, Vinblastine, Vincristine, Vindesine, Bleomycin, Dactinomycin, Daunorubicin, Doxorubicin, Epirubicin, Idarubicin, Mithramycin, Deoxycoformycin, Mitomycin-C, L-Asparaginase, Teniposide 17α-Ethinylestradiol, Diethylstilbestrol, Testosterone, Prednisone, Fluoxymesterone, Dromostanolone propionate, Testolactone, Megestrolacetate, Methylprednisolone, Methyltestosterone, Prednisolone, Triamcinolone, Chlorotrianisene, Hydroxyprogesterone, Aminoglutethimide, Estramustine, Medroxyprogesteroneacetate, Leuprolide, Flutamide, Toremifene, goserelin, Carboplatin, Hydroxyurea, Amsacrine, Procarbazine, Mitotane, Mitoxantrone, Levamisole, Navelbene, Anastrazole, Letrazole, Capecitabine, Reloxafine, Droloxafine, Hexamethylmelamine, Avastin, Herceptin, Bexxar, Velcade, Zevalin, Trisenox, Xeloda, Vinorelbine, Profimer, Erbitux, Liposomal, Thiotepa, Altretamine, Melphalan, Trastuzumab, Lerozole, Fulvestrant, Exemestane, Ifosfomide, Rituximab, C225, Doxil, Ontak, Deposyt, Mylotarg, Campath, Celebrex, Sutent, Aranesp, Neupogen, Neulasta, Kepivance, SU11248, and PTK787.

In one embodiment, the other anticancer agent is a platinum-based agent, such as cisplatin, carboplatin or oxaliplatin.

In another embodiment, the other anticancer agent is an alkylating agent.

In another embodiment, the other anticancer agent is a vinca alkaloid, such as vincristine or vinblastine.

In still another embodiment, the other anticancer agent is a topoisomerase I inhibitor.

In another embodiment, the other anticancer agent is a topoisomerase II inhibitor.

In a further embodiment, the other anticancer agent is an antimetabolite.

In another embodiment, the other anticancer agent is a spindle poison.

In another embodiment, the other anticancer agent is an antitumor antibiotic.

If formulated as a fixed dose, such combination products employ the compounds of this invention within the dosage range described herein and the other pharmaceutically active agent or treatment within its dosage range. For example, the CDC2 inhibitor olomucine has been found to act synergistically with known cytotoxic agents in inducing apoptosis (*J. Cell Sci.*, (1995) 108, 2897. Anilinopiperazine Derivatives may also be administered sequentially with known anticancer or cytotoxic agents when a combination formulation is inappropriate. The invention is not limited in the sequence of administration; Anilinopiperazine Derivatives may be administered either prior to or after administration of the known anticancer or cytotoxic agent. For example, the cytotoxic activity of the cyclin-dependent kinase inhibitor flavopiridol is affected by the sequence of administration with anticancer agents. *Cancer Research*, (1997) 57, 3375. Such techniques are within the skills of persons skilled in the art as well as attending physicians.

Accordingly, in an aspect, this invention includes methods for treating cancer in a patient, comprising administering to the patient an amount of at least one Anilinopiperazine Derivative, or a pharmaceutically acceptable salt, solvate, ester, prodrug or stereoisomer thereof, and one or more other anticancer treatment modalities, wherein the amounts of the Anilinopiperazine Derivative(s)/other treatment modality result in the desired therapeutic effect. In one embodiment, the at least one Anilinopiperazine Derivative and the one or more other treatment modalities act synergistically. In another embodiment, the at least one Anilinopiperazine Derivative and the one or more other treatment modalities act additively.

In one embodiment, the other treatment modality is surgery.

In another embodiment, the other treatment modality is radiation therapy.

In another embodiment, the other treatment modality is biological therapy, such as hormonal therapy or anticancer vaccine therapy.

The pharmacological properties of the compounds of this invention may be confirmed by a number of pharmacological assays. The exemplified pharmacological assays which are described herein below have been carried out with compounds according to the invention and their salts, solvates, esters or prodrugs.

Compositions and Administration

This invention is also directed to pharmaceutical compositions which comprise at least one Anilinopiperazine Derivative, or a pharmaceutically acceptable salt, solvate, ester or prodrug of said compound and at least one pharmaceutically acceptable carrier.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g., magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), *Remington's Pharmaceutical Sciences*, 18th Edition, (1990), Mack Publishing Co., Easton, Pa.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations that are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

The compounds of this invention may also be delivered subcutaneously.

Preferably the compound is administered orally or intravenously or intrathecally or some suitable combination(s) thereof.

Preferably, the pharmaceutical preparation is in a unit dosage form. In such form, the preparation is subdivided into suitably sized unit doses containing appropriate quantities of the active component, e.g., an effective amount to achieve the desired purpose.

The quantity of active compound in a unit dose of preparation may be varied or adjusted from about 0.001 mg to about 500 mg. In one embodiment, the quantity of active compound in a unit dose of preparation is from about 0.01 mg to about 250 mg. In another embodiment, the quantity of active compound in a unit dose of preparation is from about 0.1 mg to about 100 mg. In another embodiment, the quantity of active compound in a unit dose of preparation is from about 1.0 mg to about 100 mg. In another embodiment, the quantity of active compound in a unit dose of preparation is from about 1.0 mg to about 50 mg. In still another embodiment, the quantity of active compound in a unit dose of preparation is from about 1.0 mg to about 25 mg.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 0.01 mg/day to about 2000 mg/day of the Anilinopiperazine Derivatives. In one embodiment, a daily dosage regimen for oral administration is from about 1 mg/day to 1000 mg/day. In another embodiment, a daily dosage regimen for oral administration is from about 1 mg/day to 500 mg/day. In another embodiment, a daily dosage regimen for oral administration is from about 100 mg/day to 500 mg/day. In another embodiment, a daily dosage regimen for oral administration is from about 1 mg/day to 250 mg/day. In another embodiment, a daily dosage regimen for oral administration is from about 100 mg/day to 250 mg/day. In still another embodiment, a daily dosage regimen for oral administration is from about 1 mg/day to 100 mg/day. In still another embodiment, a daily dosage regimen for oral administration is from about 50 mg/day to 100 mg/day. In a further embodiment, a daily dosage regimen for oral administration is from about 1 mg/day to 50 mg/day. In another embodiment, a daily dosage regimen for oral administration is from about 25 mg/day to 50 mg/day. In a further embodiment, a daily dosage regimen for oral administration is from about 1 mg/day to 25 mg/day. The daily dosage may be administered in a single dosage or can be divided into from two to four divided doses.

Kits

In one aspect, the present invention provides a kit comprising an effective amount of one or more Anilinopiperazine Derivatives, or a pharmaceutically acceptable salt, solvate, ester or prodrug thereof, and a pharmaceutically acceptable carrier.

In another aspect the present invention provides a kit comprising an amount of one or more Anilinopiperazine Derivatives, or a pharmaceutically acceptable salt, solvate, ester or prodrug thereof, and an amount of at least one additional therapeutic agent listed above, wherein the combined amounts are effective for treating or preventing a Condition in a patient.

When the components of a combination therapy regimen are to be administered in more than one composition, they can be provided in a kit comprising a single package containing one or more containers, wherein one container contains one or more Anilinopiperazine Derivatives in a pharmaceutically acceptable carrier, and a second, separate container comprises an additional therapeutic agent in a pharmaceutically acceptable carrier, with the active components of each composition being present in amounts such that the combination is therapeutically effective.

In another aspect the present invention provides a kit comprising an amount of at least one Anilinopiperazine Derivative, or a pharmaceutically acceptable salt, solvate, ester or prodrug of said compound and an amount of at least one anticancer therapy and/or additional anticancer agent listed above, wherein the amounts of the two or more ingredients result in the desired therapeutic effect.

The present invention is not to be limited in scope by the specific embodiments disclosed in the examples which are intended as illustrations of a few aspects of the invention and any embodiments that are functionally equivalent are within the scope of this invention. Indeed, various modifications of the invention in addition to those shown and described herein will become apparent to those skilled in the relevant art and are intended to fall within the scope of the appended claims.

A number of references have been cited, the entire disclosures of which have been incorporated herein in their entirety.

What is claimed is:

1. A compound having the formula:

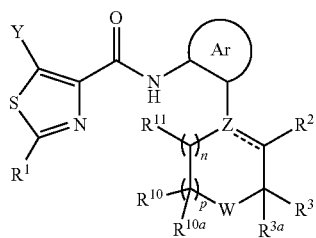

(I)

or a pharmaceutically acceptable salt thereof, wherein the dashed line indicates an optional and additional bond and wherein:

$R^1$ is H, alkyl, alkenyl, alkynyl, halo, -(alkylene)$_m$-aryl, -alkenylene-aryl, -alkynylene-aryl, -(alkylene)$_m$-cycloalkyl, -(alkylene)$_m$-heteroaryl, -(alkylene)$_m$-heterocyclenyl, wherein any aryl, cycloalkyl, heteroaryl, or heterocyclenyl group can be optionally substituted with up to 5 substituents, which may be the same or different, and are independently selected from halo, alkyl, cycloalkyl, -(alkylene)$_m$-N(R$^9$)$_2$, -(alkylene)$_m$-O-alkyl, —O-aryl, —C(O)R$^8$, —S-alkyl, —O-alkyl, -(alkylene)$_m$-CN, alkynyl, alkenyl, hydroxyalkyl, haloalkyl, —O-haloalkyl, —C(O)OR$^7$, —NHC(O)R$^7$, —C(O)N(R$^7$)$_2$, —S(O)$_2$N(R$^8$)$_2$, —NHS(O)$_2$R$^8$, -(alkylene)$_m$-heteroaryl, -(alkylene)$_m$-heterocyclyl and -(alkylene)$_m$-aryl; wherein an alkyl, alkenyl or alkynyl group can be substituted with one or more substituents, which may be the same or different, and are independently selected from halo, alkyl, —N(R$^7$)$_2$, —C(O)OH, aryl, and —O-alkyl; wherein any cyclic R$^1$ group can be optionally fused to a cycloalkyl, aryl, heteroaryl or heterocyclyl group; such that when R$^1$ is heteroaryl, heterocyclyl or heterocyclenyl, these groups are attached to the rest of the compound of formula (I) by a ring carbon atom;

$R^2$ is H, alkyl, haloalkyl, hydroxyalkyl, -(alkylene)$_m$-C(O)N(R$^8$)$_2$, -(alkylene)$_m$-NHC(O)—R$^9$ or -(alkylene)$_m$-N(R$^9$)$_2$, or R$^2$ and the ring carbon atom to which it is attached, form a carbonyl group;

$R^3$ is H, -alkyl, haloalkyl, hydroxyalkyl, -(alkylene)$_m$-C(O)N(R$^8$)$_2$, -(alkylene)$_m$-NHC(O)—R$^9$ or -(alkylene)$_m$-N(R$^9$)$_2$, or R$^3$ and R$^{3a}$, together with the common carbon atom to which each are attached, join to form a carbonyl, cycloalkyl or heterocyclyl group;

$R^{3a}$ is H, -alkyl, haloalkyl, hydroxyalkyl, -(alkylene)$_m$-C(O)N(R$^8$)$_2$, -(alkylene)$_m$-NHC(O)—R$^9$ or -(alkylene)$_m$-N(R$^9$)$_2$;

each occurrence of R$^4$ is independently H, -alkyl, -(alkylene)$_m$-aryl, -(alkylene)$_m$-heteroaryl, -(alkylene)$_m$-heterocyclyl, -(alkylene)$_m$-N(R$^8$)$_2$, -(alkylene)$_m$-OH, -(alkylene)$_m$-NHC(O)R$^8$, hydroxyalkyl, haloalkyl, —CH$_2$NH$_2$, —C(O)R$^5$, —C(O)OR$^8$, —C(O)-(alkylene)$_m$-N(R$^8$)$_2$, —C(O)NH-alkyl, —C(O)N(alkyl)$_2$, -(alkylene)$_m$-NHC(O)R$^6$, —NHC(O)OR$^8$, —CR$^2$C(O)NH$_2$, —CR$^2$C(O)NH(alkyl), —CR$^2$C(O)NH(alkyl)$_2$ or —NHS(O)$_2$R$^6$;

$R^5$ is H, alkyl, aryl,-heteroaryl or —NHOH;

each occurrence of R$^6$ is independently H, alkyl, aryl or haloalkyl;

each occurrence of R$^7$ is H, —OH, alkyl, —O-alkyl, cycloalkyl or haloalkyl;

each occurrence of R$^8$ is independently H, alkyl, -(alkylene)$_m$-aryl, -(alkylene)$_m$-heterocyclyl, -(alkylene)$_m$-heteroaryl or -(alkylene)$_m$-cycloalkyl;

each occurrence of R$^9$ is H, alkyl, haloalkyl, hydroxyalkyl, -(alkylene)$_m$-aryl, -(alkylene)$_m$-heterocyclyl, -(alkylene)$_m$-heteroaryl or -(alkylene)$_m$-cycloalkyl;

$R^{10}$ is H, -alkyl, haloalkyl, hydroxyalkyl, -(alkylene)$_m$-C(O)N(R$^8$)$_2$, -(alkylene)$_m$-NHC(O)—R$^9$ or -(alkylene)$_m$-N(R$^9$)$_2$, or R$^{10}$ and R$^{10a}$, together with the common carbon atom to which each are attached, join to form a carbonyl, cycloalkyl or heterocyclyl group;

$R^{10a}$ is H, -alkyl, haloalkyl, hydroxyalkyl, -(alkylene)$_m$-C(O)N(R$^8$)$_2$, -(alkylene)$_m$-NHC(O)—R$^9$ or -(alkylene)$_m$-N(R$^9$)$_2$;

each occurrence of R$^{11}$ is independently H, alkyl, haloalkyl, hydroxyalkyl, -(alkylene)$_m$-C(O)N(R$^8$)$_2$, -(alkylene)$_m$-NHC(O)—R$^9$ or -(alkylene)$_m$-N(R$^9$)$_2$, or any R$^{11}$ and the ring carbon atom to which it is attached, form a carbonyl group;

each occurrence of R$^{12}$ is independently H, alkyl, -(alkylene)$_m$-aryl, -(alkylene)$_m$-heteroaryl, -(alkylene)$_m$-heterocyclyl, —S(O)$_2$-alkyl, —S(O)$_2$-aryl, —S(O)$_2$-heteroaryl, hydroxyalkyl, —C(O)R$^8$, or —C(O)OR$^8$;

Ar is arylene or heteroarylene, wherein the arylene or heteroarylene is joined via any 2 of its adjacent ring carbon atoms, and wherein the arylene or heteroarylene group can be optionally substituted with up to 4 substituents, which may be the same or different, and are independently selected from halo, alkyl, —OH, —OR⁹, -(alkylene)$_m$-N(R⁶)₂, —N(alkyl)₂, —SR⁹, —S(O)R⁸, —S(O)₂R⁸, —S(O)₂NHR⁹, —C(O)R⁸, —C(O)OR⁹, -(alkylene)$_m$-C(O)N(R⁸)₂, —NHC(O)R⁹, haloalkyl, hydroxyalkyl, —CN and NO₂, such that when Ar is tetrahydronaphthylene, R² and R³ are each other than hydrogen;

W is —N(R¹²)—, —S—, —O— or —C(R⁴)₂—, wherein both R⁴ groups and the common carbon atom to which they are attached can combine to form a cycloalkyl or heterocyclyl group, each of which can be further substituted;

Y is H, halo, alkyl or —CN;

Z is —C(R⁷)— or —N—, such that when the optional additional bond is present, Z is —C(R⁷)—;

each occurrence of m is independently 0 or 1;

n is an integer ranging from 0 to 2; and p is 0 or 1.

2. The compound of claim 1, wherein R¹ is -aryl, -arylalkyl, benzofused cycloalkyl, heteroaryl, benzofused heteroaryl or benzofused heterocyclenyl.

3. The compound of claim 1, wherein R¹ is phenyl, pyridyl, thiophenyl, benzothiophenyl, benzofuranyl, 2,3-dihydrobenzofuranyl, isoxazolyl, pyrazolyl, pyrimidinyl, biphenyl, phenyl-O-phenyl, furanyl, pyrrolyl, indolyl, N-alkyl indolyl or

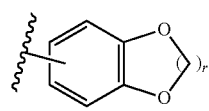

wherein r is 1, 2 or 3.

4. The compound of claim 1, wherein R¹ is:

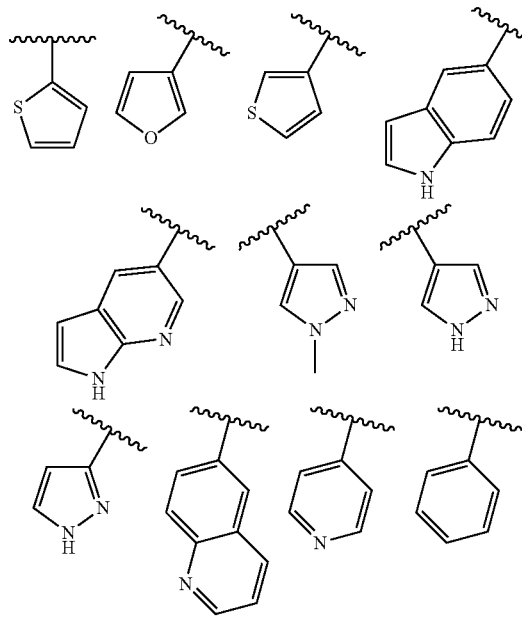

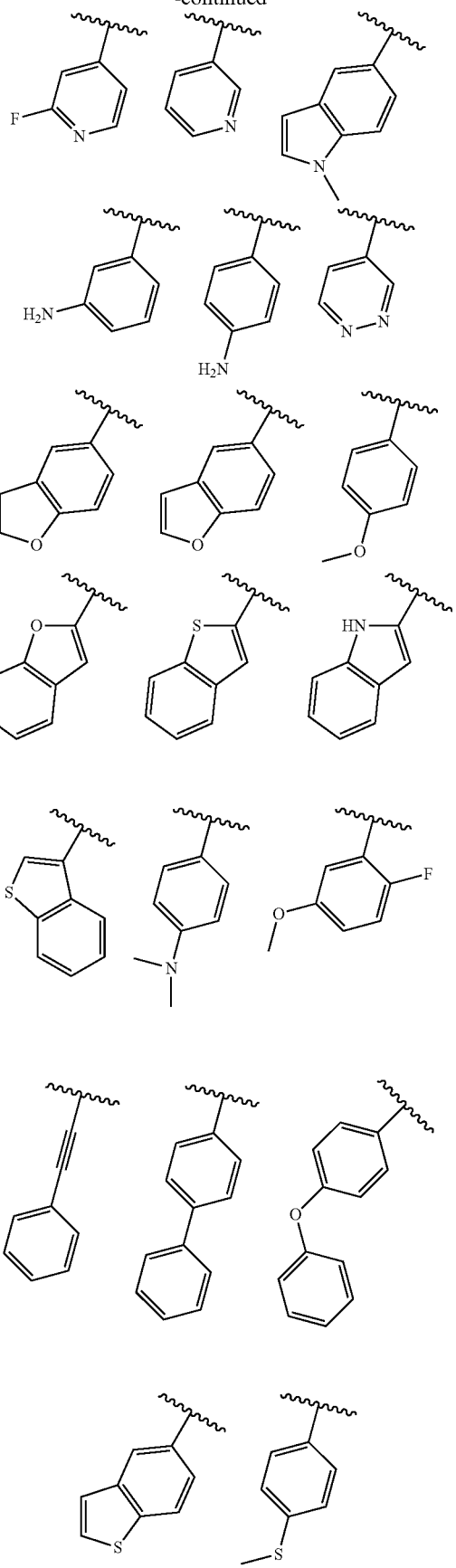

-continued
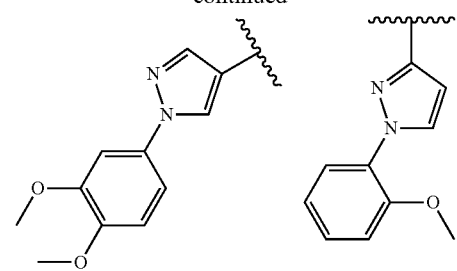
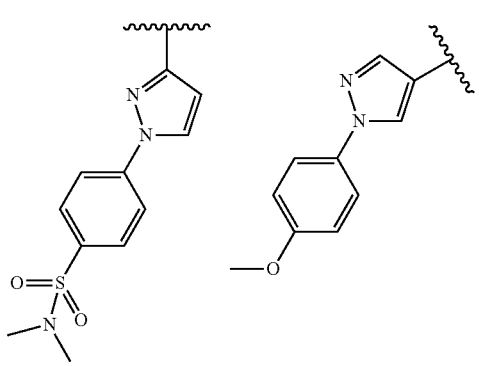
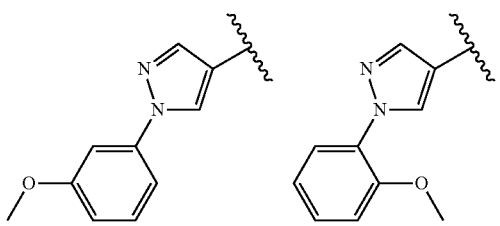
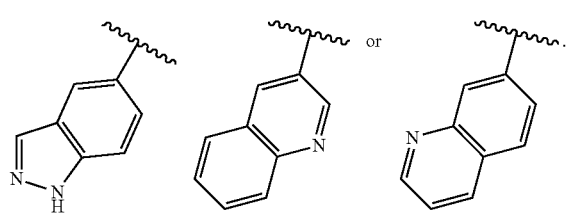
5. The compound of claim 1, wherein Ar is:
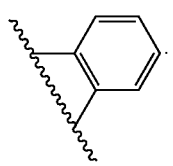
6. The compound of claim 5, wherein n is 1 and Y is H.
7. The compound of claim 6, wherein Z is N and $R^2$ and $R^3$ are each —H.
8. The compound of claim 6, wherein W is NH.
9. The compound of claim 1, wherein the group
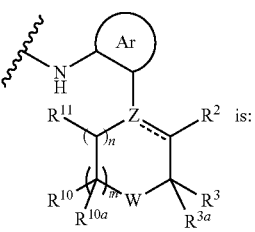
is:
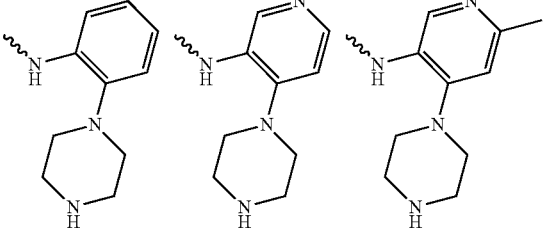
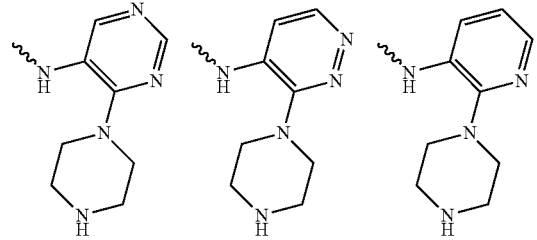
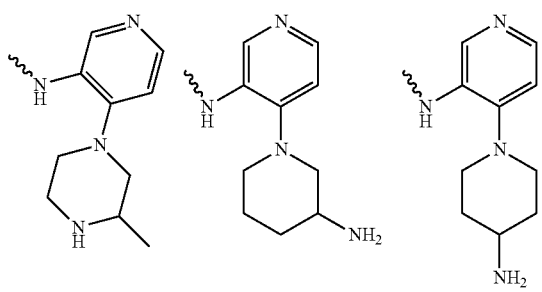
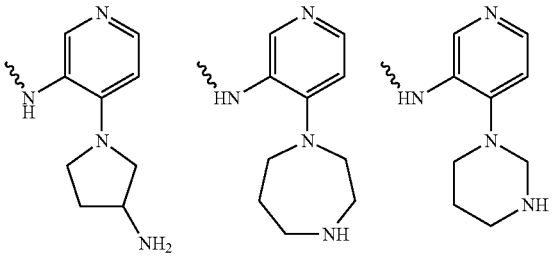
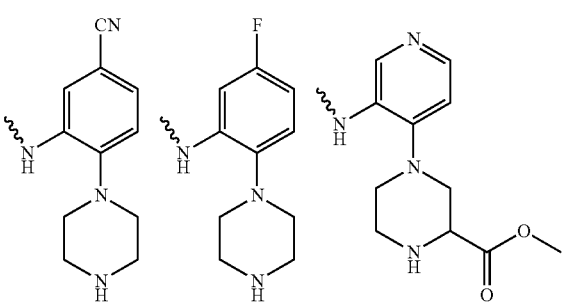

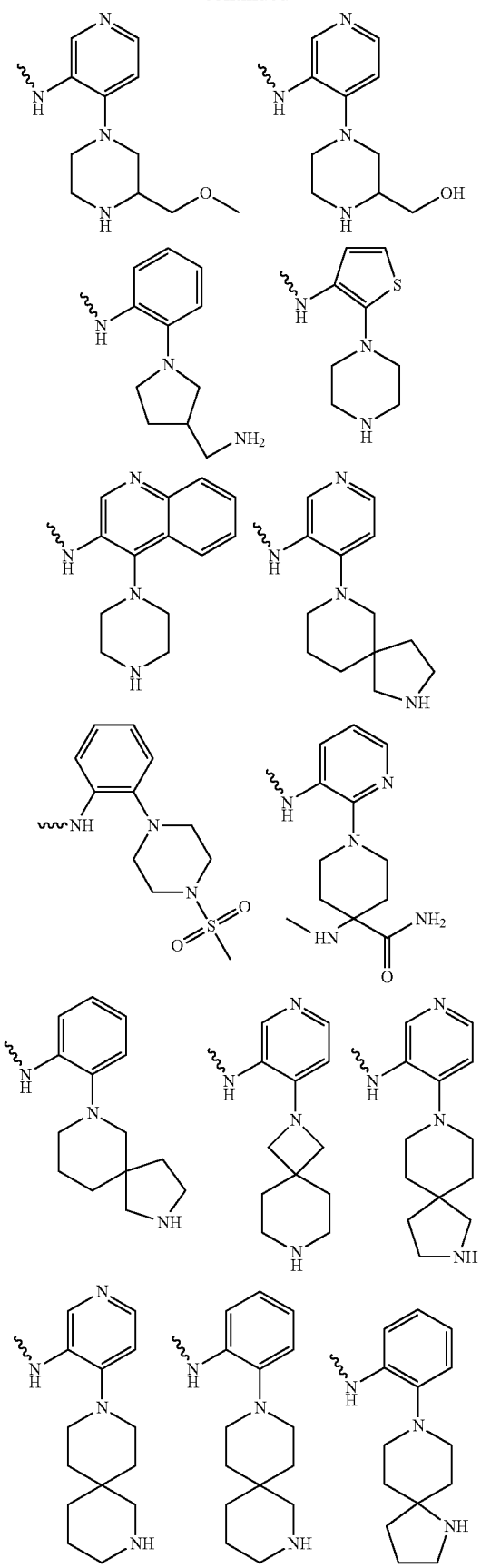
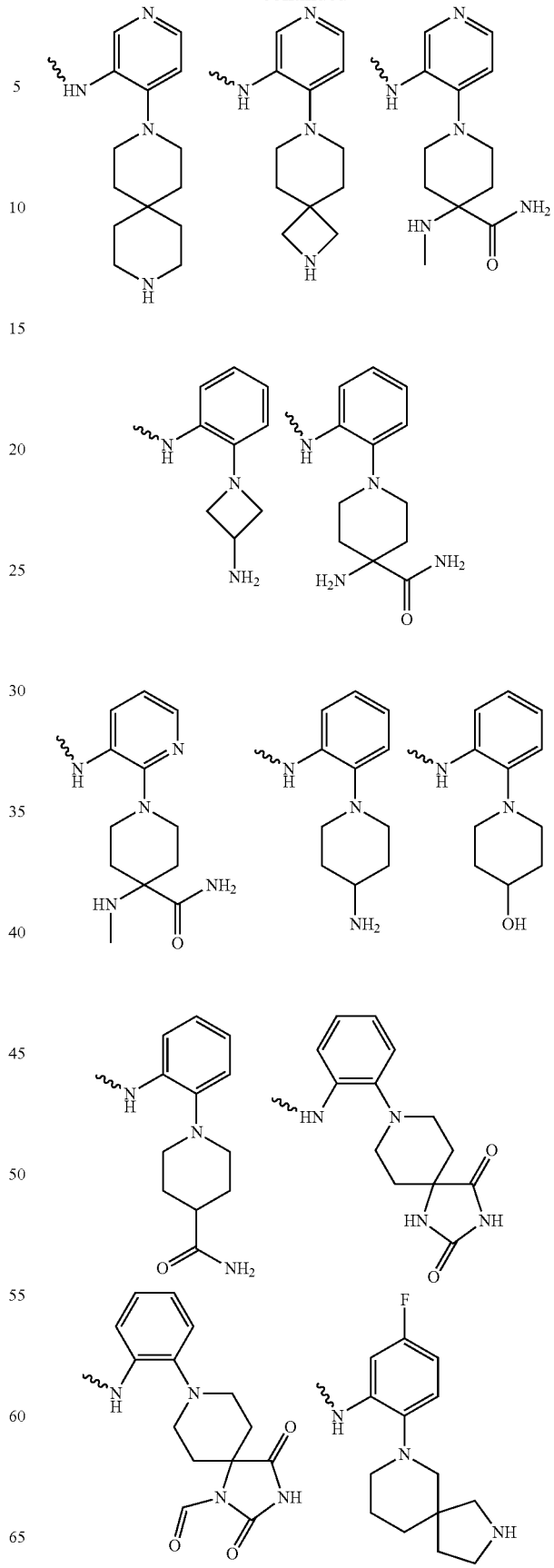

-continued
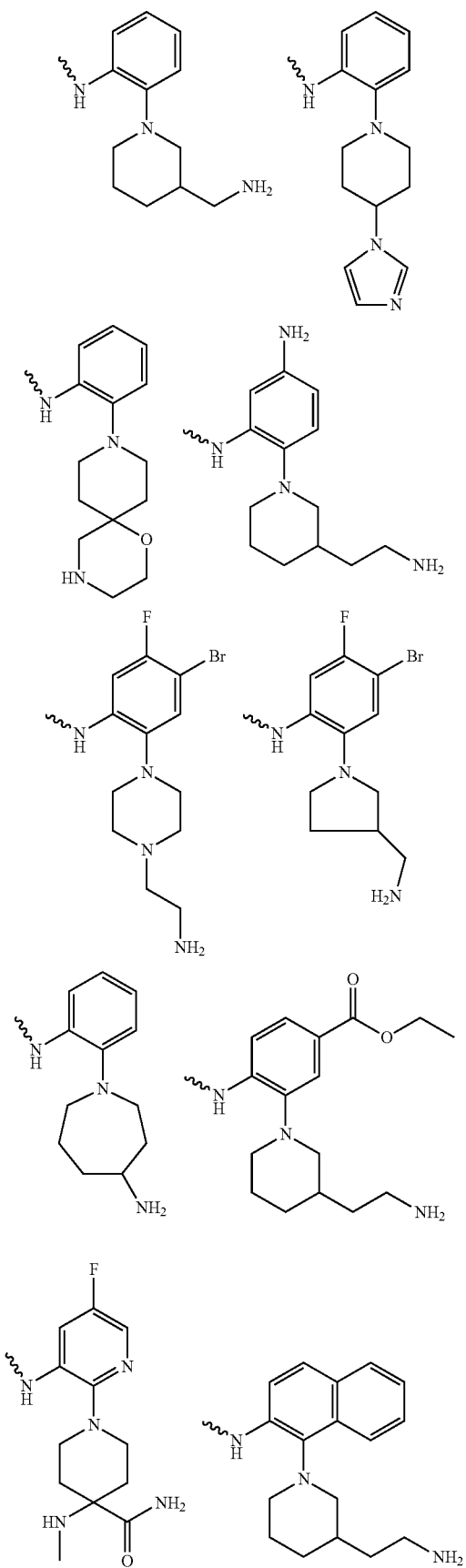
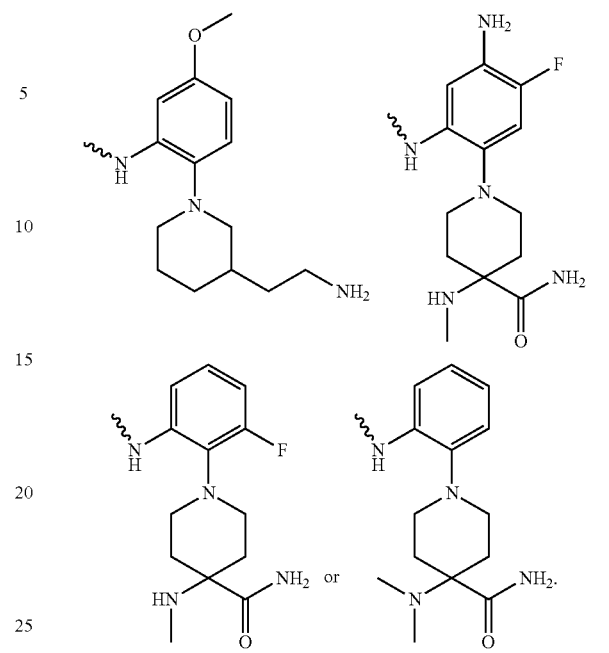
10. The compound of claim 9, wherein R¹ is:
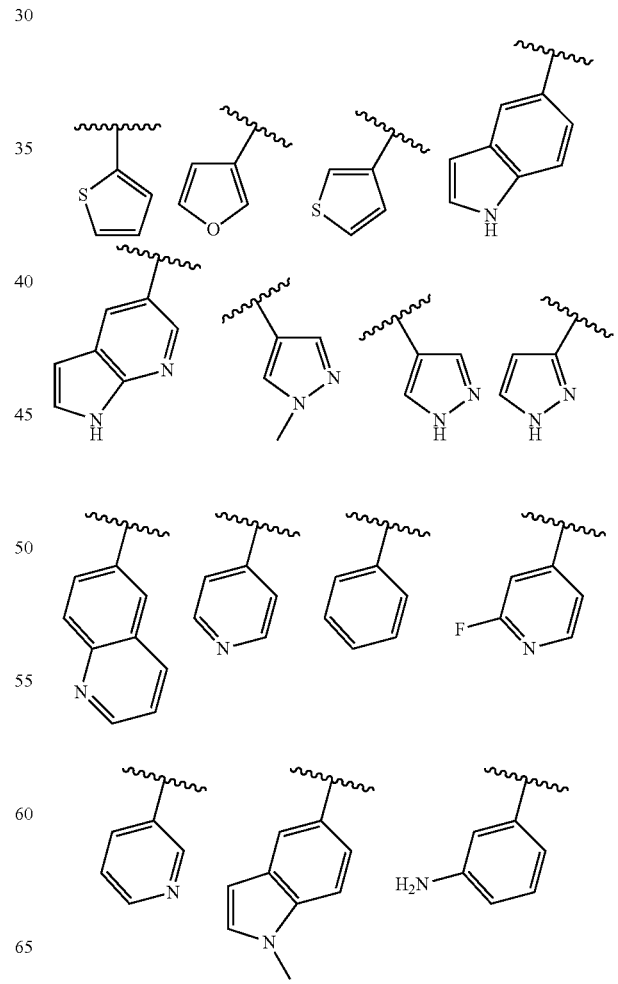

391

-continued

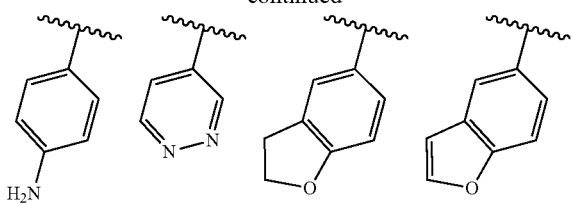

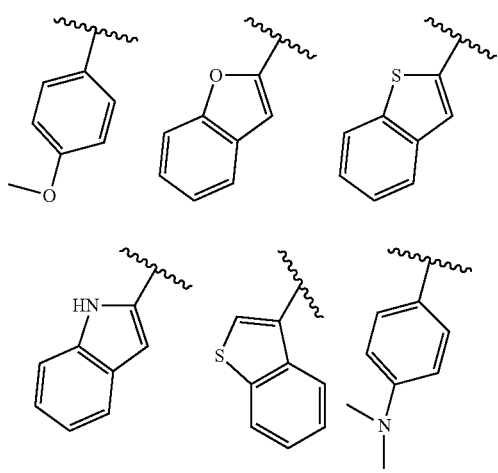

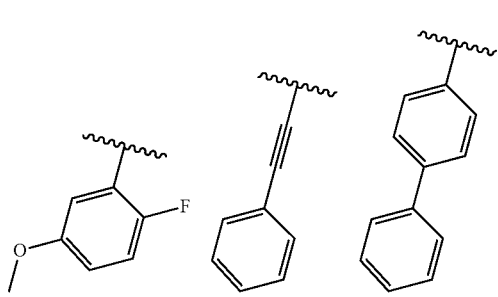

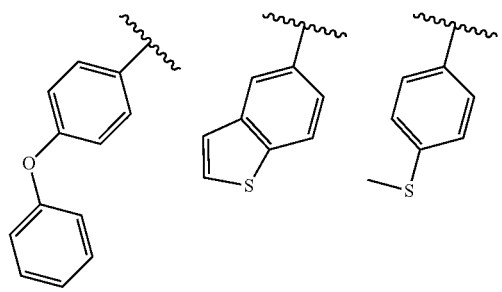

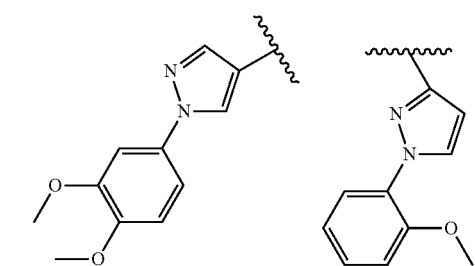

392

-continued

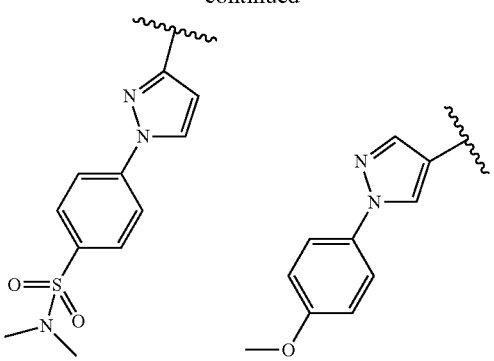

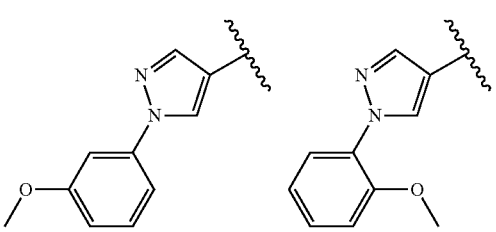

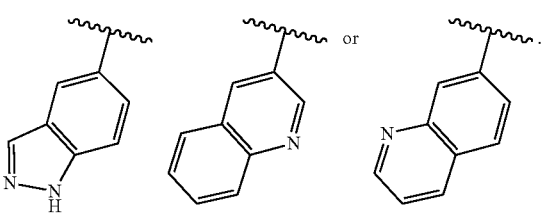

11. The compound of claim 1 having the formula:

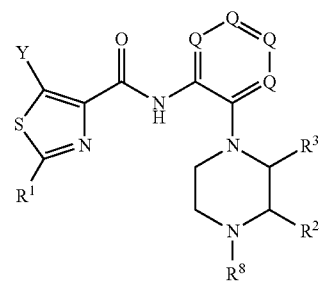

wherein

R$^1$, R$^2$, and R$^3$ are as defined in claim 1;

each Q is independently CH or N, such at least three occurrences of Q must be CH; and R$^8$ is H or alkyl.

12. The compound of claim 11, wherein each occurrence of Q is CH, and R$^2$, R$^3$, R$^8$ and Y are each —H.

13. The compound of claim 12, wherein R$^1$ is -aryl, -benzofused cycloalkyl, -heteroaryl, -benzofused heteroaryl or -benzofused heterocyclenyl.

14. A compound having the structure:
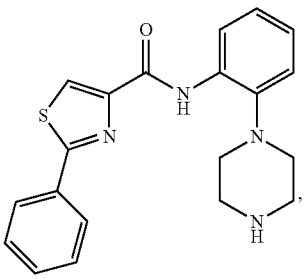
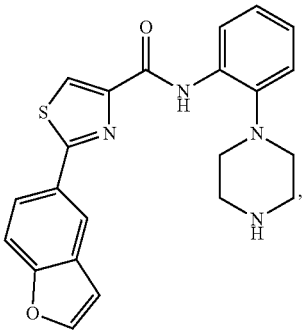
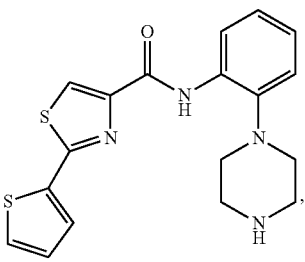
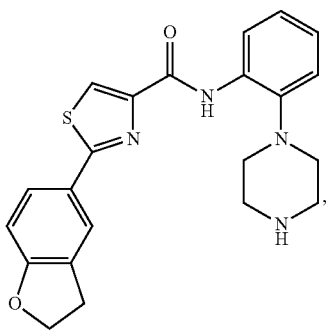
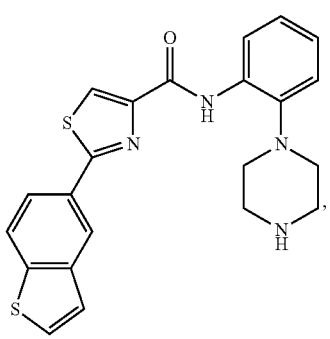
-continued
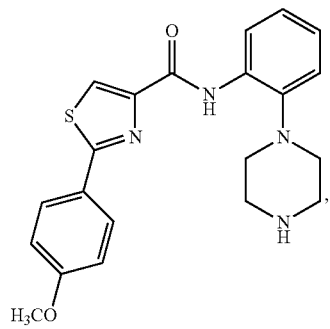
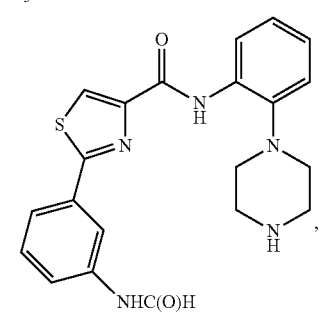
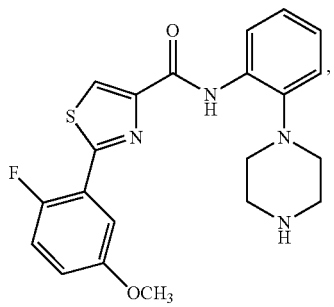
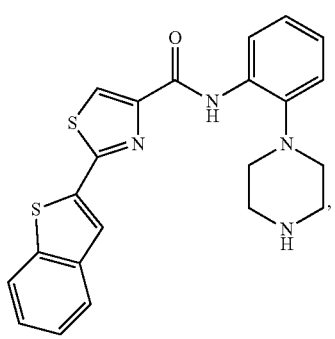
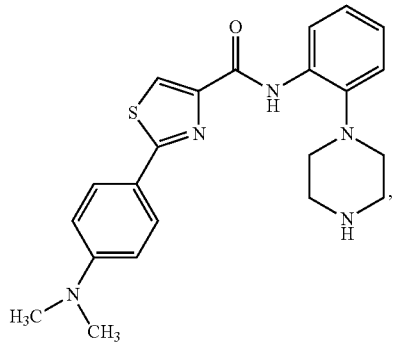

-continued
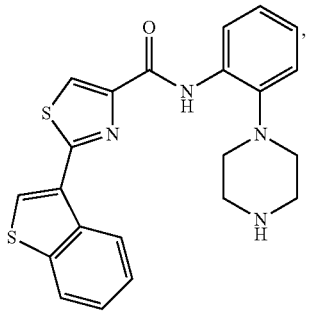
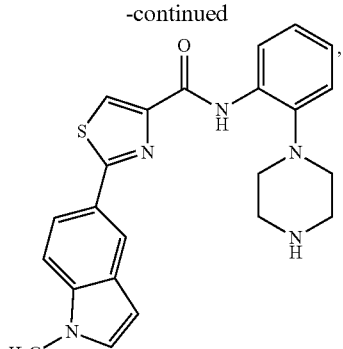
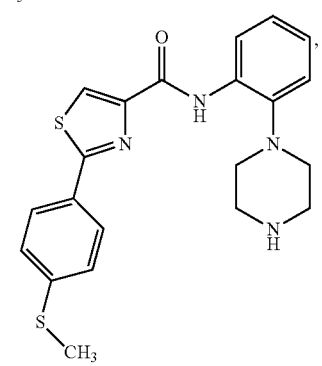
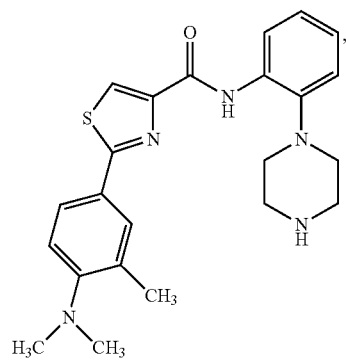
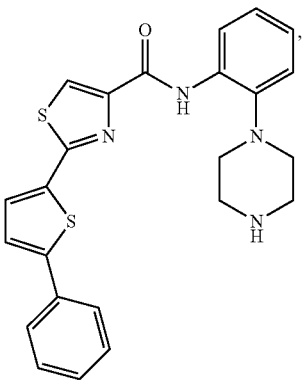
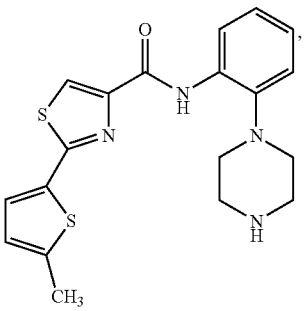
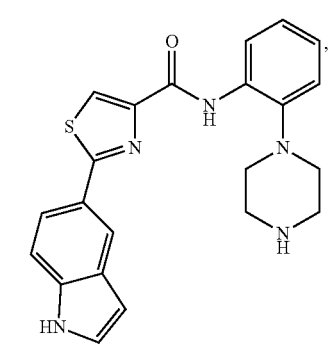
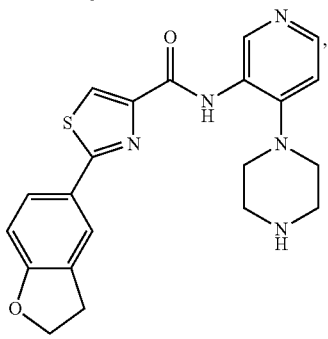

397
-continued
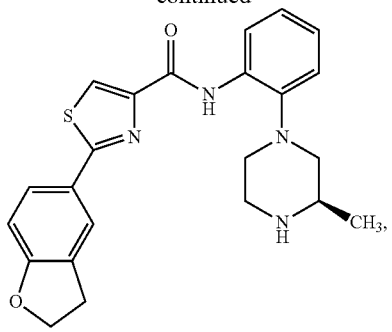
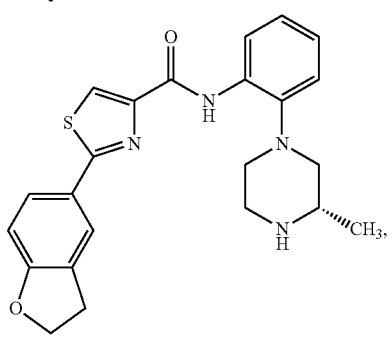
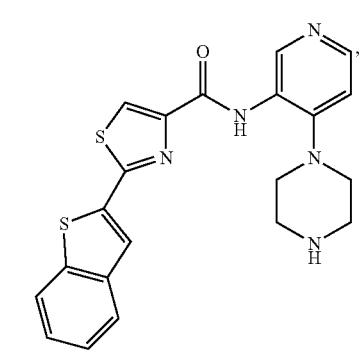
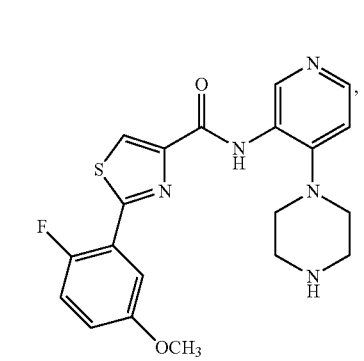
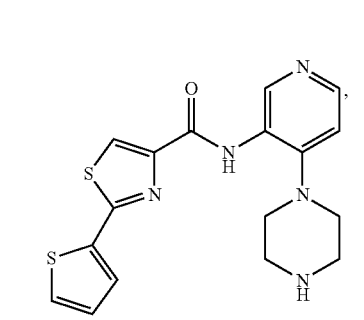
398
-continued
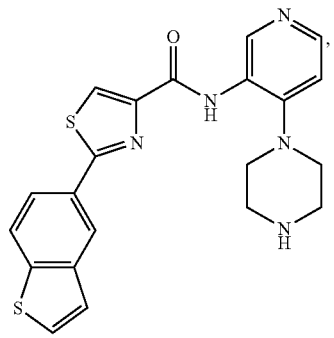
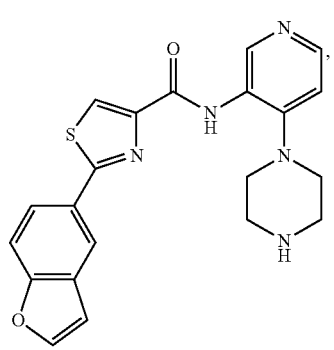
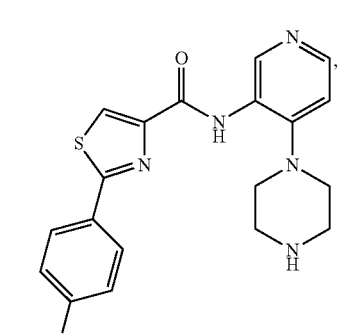
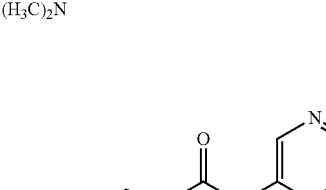
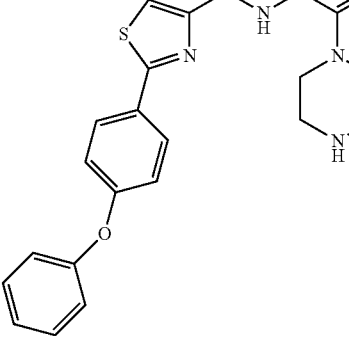

-continued
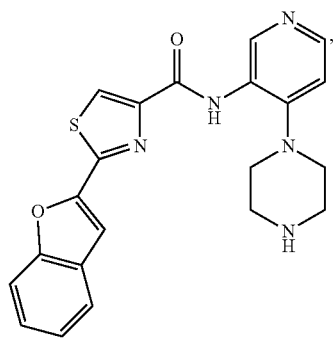
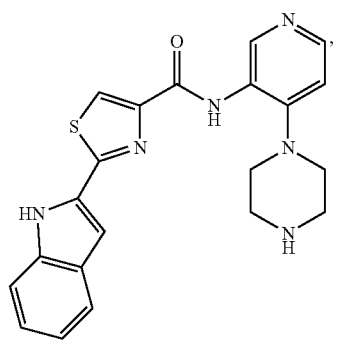
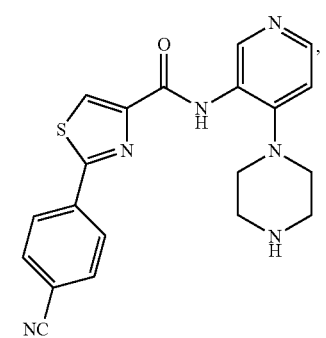
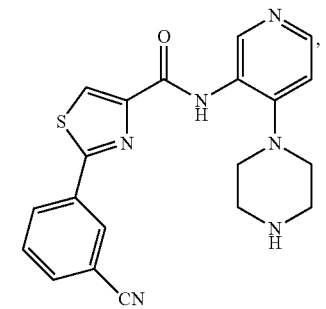
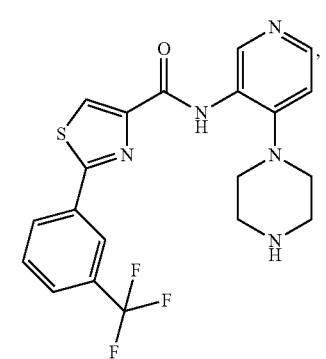
-continued
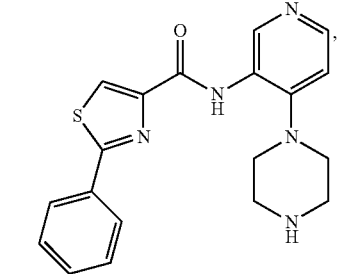
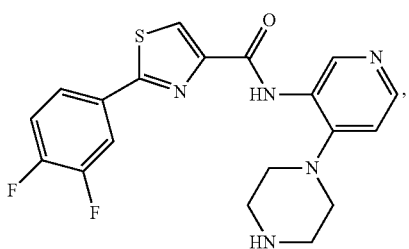
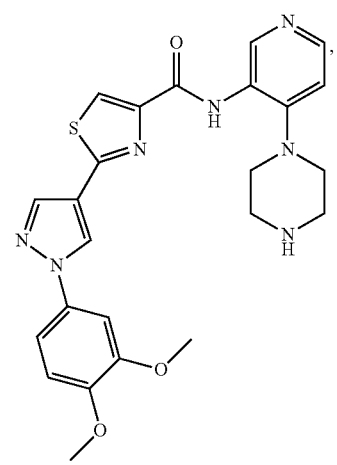
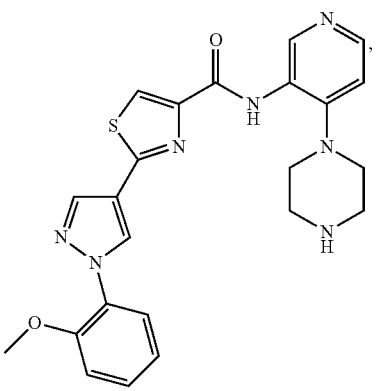

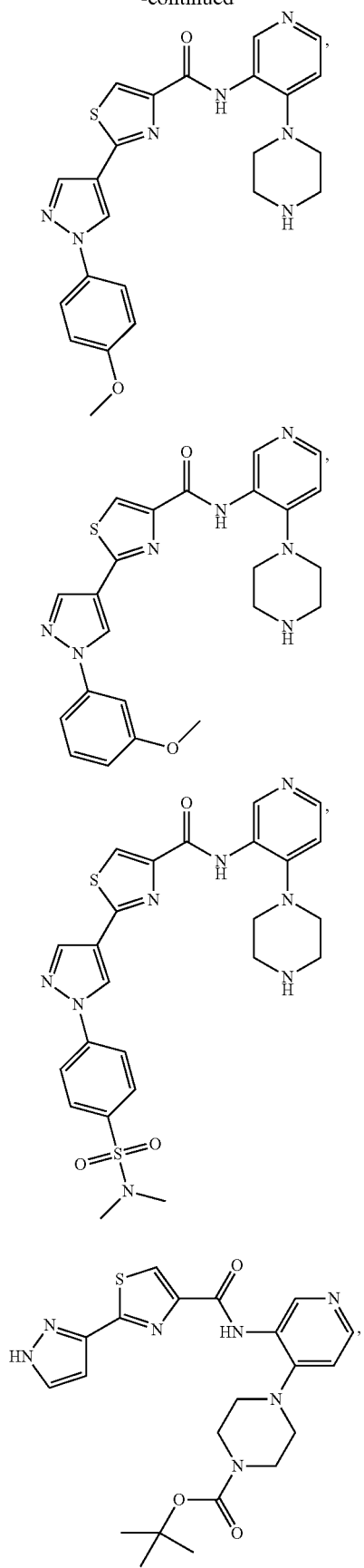

-continued
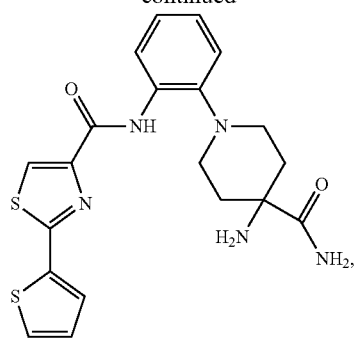
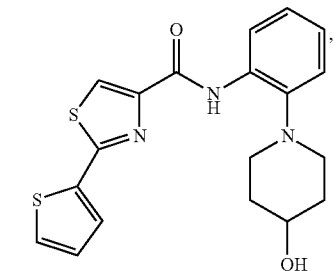
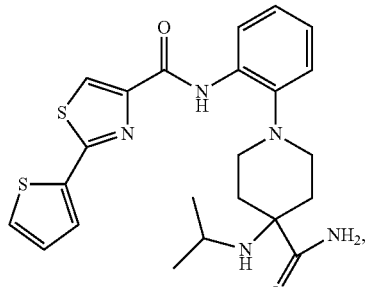
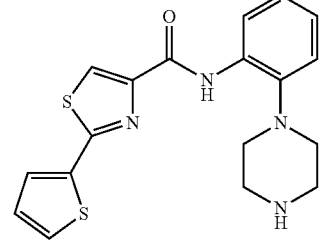
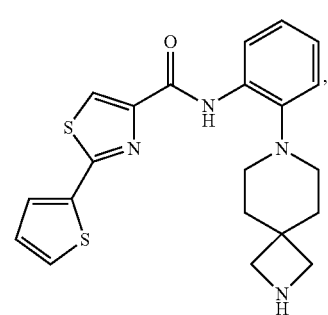
-continued
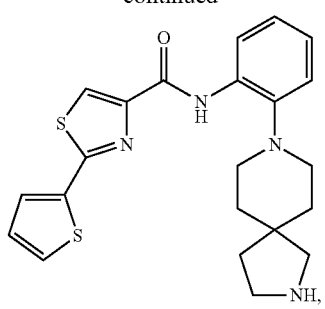
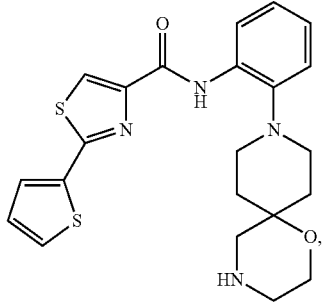
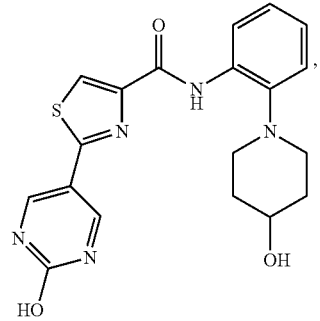
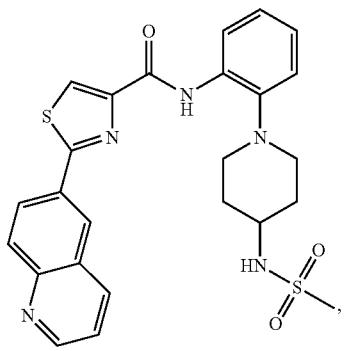
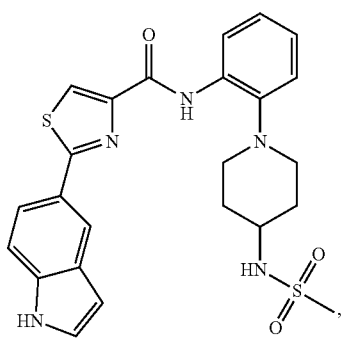

405
-continued
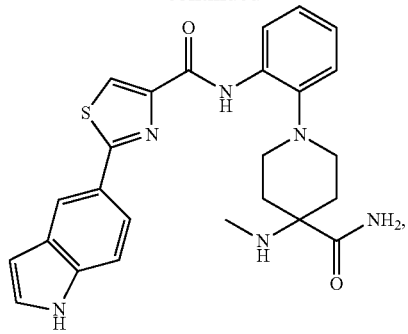
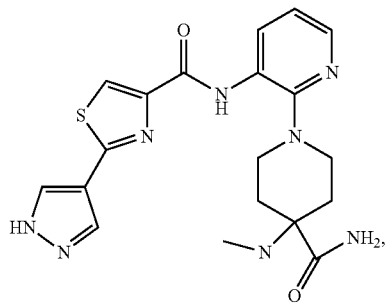
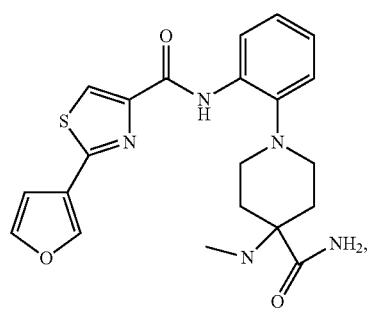
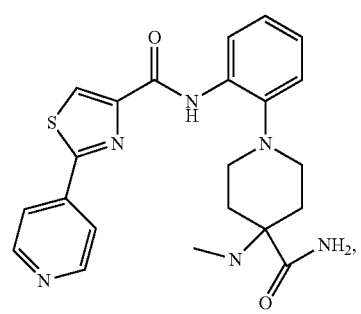
406
-continued
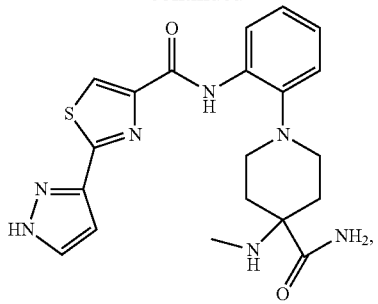
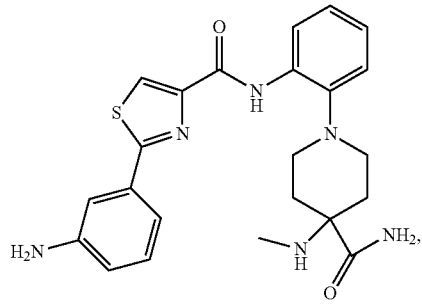
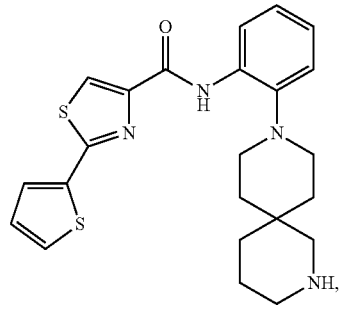

407
-continued
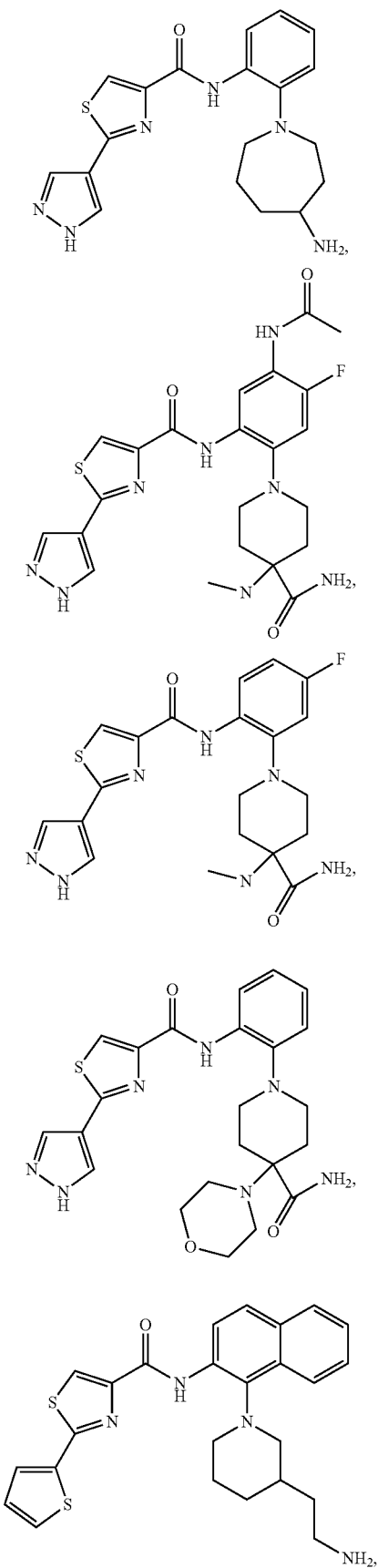
408
-continued
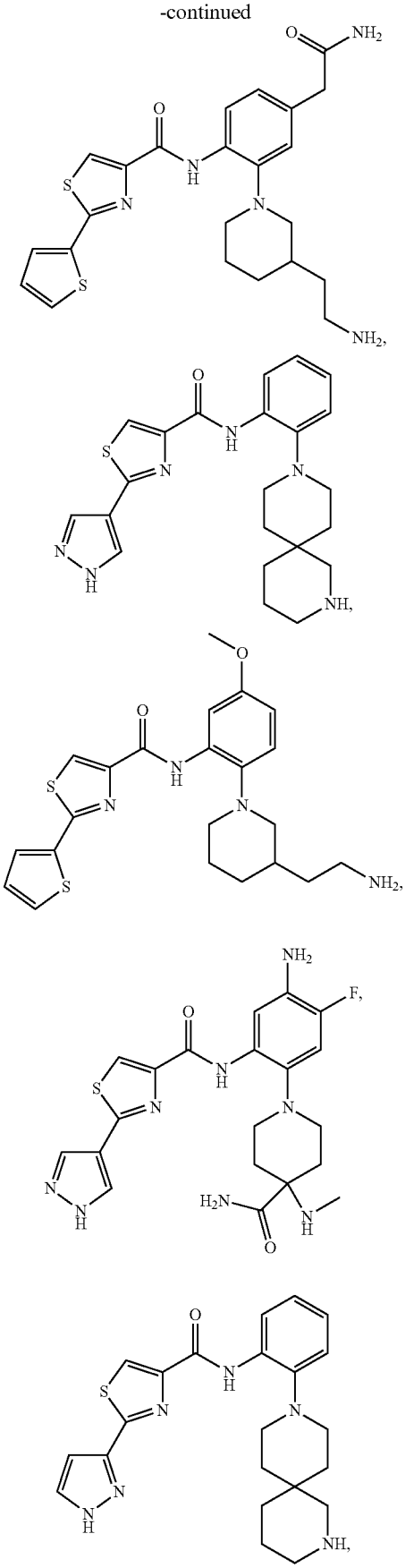

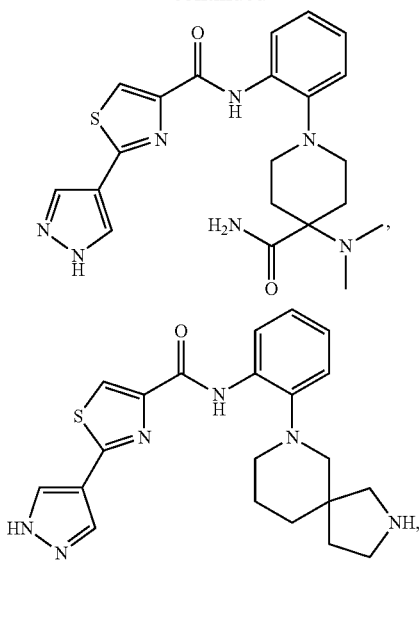

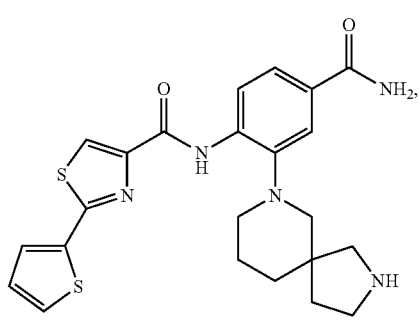

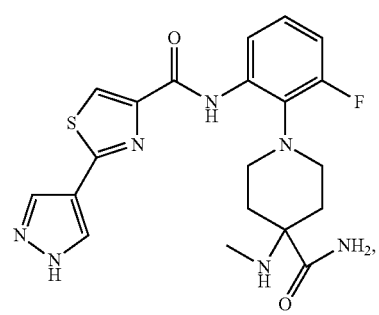

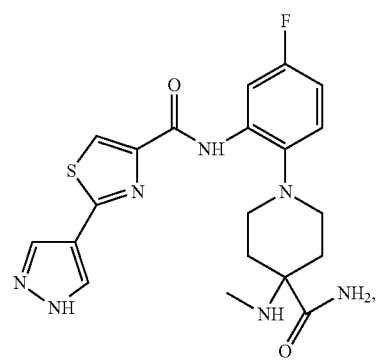

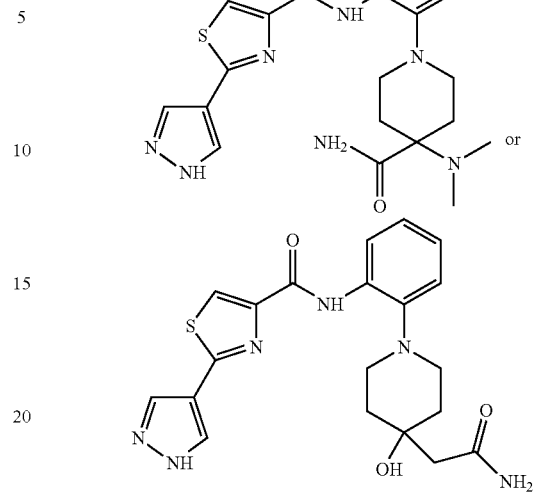

or a pharmaceutically acceptable salt thereof.

15. A compound of claim 1 in purified form.

16. A pharmaceutical composition comprising an effective amount of at least one compound of claim 1 or a pharmaceutically acceptable salt thereof, and a pharmaceutically acceptable carrier.

17. The composition of claim 16, further comprising at least one additional anticancer agent.

18. The composition of claim 17, wherein the at least one additional anticancer agents are selected from the group consisting of cytostatic agent, cisplatin, doxorubicin, taxotere, taxol, etoposide, irinotecan, camptostar, topotecan, paclitaxel, docetaxel, epothilones, tamoxifen, 5-fluorouracil, methoxtrexate, temozolomide, cyclophosphamide, SCH 66336, R115777, L778,123, BMS 214662, Iressa, Tarceva, antibodies to EGFR, Gleevec, intron, ara-C, adriamycin, cytoxan, gemcitabine, Uracil mustard, Chlormethine, Ifosfamide, Melphalan, Chlorambucil, Pipobroman, Triethylenemelamine, Triethylenethiophosphoramine, Busulfan, Carmustine, Lomustine, Streptozocin, Dacarbazine, Floxuridine, Cytarabine, 6-Mercaptopurine, 6-Thioguanine, Fludarabine phosphate, Pentostatine, Vinblastine, Vincristine, Vindesine, Bleomycin, Dactinomycin, Daunorubicin, Doxorubicin, Epirubicin, Idarubicin, Mithramycin, Deoxycoformycin, Mitomycin-C, L-Asparaginase, Teniposide 17α-Ethinylestradiol, Diethylstilbestrol, Testosterone, Prednisone, Fluoxymesterone, Dromostanolone propionate, Testolactone, Megestrolacetate, Methylprednisolone, Methyltestosterone, Prednisolone, Triamcinolone, Chlorotrianisene, Hydroxyprogesterone, Aminoglutethimide, Estramustine, Medroxyprogesteroneacetate, Leuprolide, Flutamide, Toremifene, goserelin, Carboplatin, Hydroxyurea, Amsacrine, Procarbazine, Mitotane, Mitoxantrone, Levamisole, Navelbene, Anastrazole, Letrazole, Capecitabine, Reloxafine, Droloxafine, Hexamethylmelamine, Avastin, Herceptin, Bexxar, Velcade, Zevalin, Trisenox, Xeloda, Vinorelbine, Profimer, Erbitux, Liposomal, Thiotepa, Altretamine, Melphalan, Trastuzumab, Lerozole, Fulvestrant, Exemestane, Ifosfomide, Rituximab, C225, Doxil, Ontak, Deposyt, Mylotarg, Campath, Celebrex, Sutent, Aranesp, Neupogen, Neulasta, Kepivance, SU11248, and PTK787.

19. A pharmaceutical composition comprising an effective amount of at least one compound of claim 14 or a pharmaceutically acceptable salt thereof, and a pharmaceutically acceptable carrier.

20. The composition of claim 19, further comprising at least one additional anticancer agent.

21. The composition of claim 20, wherein the at least one additional anticancer agents are selected from the group consisting of cytostatic agent, cisplatin, doxorubicin, taxotere, taxol, etoposide, irinotecan, camptostar, topotecan, paclitaxel, docetaxel, epothilones, tamoxifen, 5-fluorouracil, methoxtrexate, temozolomide, cyclophosphamide, SCH 66336, R115777, L778,123, BMS 214662, Iressa, Tarceva, antibodies to EGFR, Gleevec, intron, ara-C, adriamycin, cytoxan, gemcitabine, Uracil mustard, Chlormethine, Ifosfamide, Melphalan, Chlorambucil, Pipobroman, Triethylenemelamine, Triethylenethiophosphoramine, Busulfan, Carmustine, Lomustine, Streptozocin, Dacarbazine, Floxuridine, Cytarabine, 6-Mercaptopurine, 6-Thioguanine, Fludarabine phosphate, Pentostatine, Vinblastine, Vincristine, Vindesine, Bleomycin, Dactinomycin, Daunorubicin, Doxorubicin, Epirubicin, Idarubicin, Mithramycin, Deoxycoformycin, Mitomycin-C, L-Asparaginase, Teniposide 17α-Ethinylestradiol, Diethylstilbestrol, Testosterone, Prednisone, Fluoxymesterone, Dromostanolone propionate, Testolactone, Megestrolacetate, Methylprednisolone, Methyltestosterone, Prednisolone, Triamcinolone, Chlorotrianisene, Hydroxyprogesterone, Aminoglutethimide, Estramustine, Medroxyprogesteroneacetate, Leuprolide, Flutamide, Toremifene, goserelin, Carboplatin, Hydroxyurea, Amsacrine, Procarbazine, Mitotane, Mitoxantrone, Levamisole, Navelbene, Anastrazole, Letrazole, Capecitabine, Reloxafine, Droloxafine, Hexamethylmelamine, Avastin, Herceptin, Bexxar, Velcade, Zevalin, Trisenox, Xeloda, Vinorelbine, Profimer, Erbitux, Liposomal, Thiotepa, Altretamine, Melphalan, Trastuzumab, Lerozole, Fulvestrant, Exemestane, Ifosfomide, Rituximab, C225, Doxil, Ontak, Deposyt, Mylotarg, Campath, Celebrex, Sutent, Aranesp, Neupogen, Neulasta, Kepivance, SU11248, and PTK787.

* * * * *